United States Patent
Ishibuchi et al.

(10) Patent No.: US 10,407,408 B2
(45) Date of Patent: Sep. 10, 2019

(54) IMIDE DERIVATIVES AND USE THEREOF AS MEDICINE

(71) Applicant: MITSUBISHI TANABE PHARMA CORPORATION, Osaka-shi, Osaka (JP)

(72) Inventors: Seigo Ishibuchi, Osaka (JP); Kunio Saruta, Osaka (JP); Maiko Hamada, Osaka (JP); Nobuatsu Matoba, Osaka (JP); Tetsuji Matsudaira, Osaka (JP); Maki Seki, Osaka (JP); Akiko Tarao, Osaka (JP); Takashi Honjo, Osaka (JP); Shingo Ogata, Osaka (JP); Atsushi Kawata, Osaka (JP); Kenji Morokuma, Osaka (JP); Naoto Fujie, Osaka (JP); Yukio Aoyama, Osaka (JP)

(73) Assignee: MITSUBISHI TANABE PHARMA CORPORATION, Osaka (JP)

(*) Notice: Subject to any disclaimer, the term of this patent is extended or adjusted under 35 U.S.C. 154(b) by 0 days.

(21) Appl. No.: 15/743,091

(22) PCT Filed: Jul. 8, 2016

(86) PCT No.: PCT/JP2016/070214
§ 371 (c)(1),
(2) Date: Jan. 9, 2018

(87) PCT Pub. No.: WO2017/007008
PCT Pub. Date: Jan. 12, 2017

(65) Prior Publication Data
US 2019/0077787 A1   Mar. 14, 2019

(30) Foreign Application Priority Data
Jul. 9, 2015   (JP) ................ 2015-138105

(51) Int. Cl.
| | |
|---|---|
| *C07D 401/14* | (2006.01) |
| *A61K 31/496* | (2006.01) |
| *C07D 405/14* | (2006.01) |
| *C07D 413/14* | (2006.01) |
| *A61K 31/4178* | (2006.01) |
| *A61K 31/437* | (2006.01) |
| *A61K 31/4439* | (2006.01) |
| *A61K 31/454* | (2006.01) |
| *A61K 31/4545* | (2006.01) |
| *A61K 31/497* | (2006.01) |
| *A61K 31/501* | (2006.01) |
| *C07D 233/78* | (2006.01) |
| *C07D 401/10* | (2006.01) |
| *C07D 401/12* | (2006.01) |
| *C07D 403/10* | (2006.01) |
| *C07D 403/14* | (2006.01) |
| *C07D 409/14* | (2006.01) |

(Continued)

(52) U.S. Cl.
CPC ........ *C07D 401/14* (2013.01); *A61K 31/4178* (2013.01); *A61K 31/437* (2013.01); *A61K 31/4439* (2013.01); *A61K 31/454* (2013.01); *A61K 31/4545* (2013.01); *A61K 31/496* (2013.01); *A61K 31/497* (2013.01); *A61K 31/501* (2013.01); *A61P 1/00* (2018.01); *A61P 19/02* (2018.01); *A61P 25/00* (2018.01); *C07D 233/78* (2013.01); *C07D 401/10* (2013.01); *C07D 401/12* (2013.01); *C07D 403/10* (2013.01); *C07D 403/14* (2013.01); *C07D 405/14* (2013.01); *C07D 409/14* (2013.01); *C07D 413/14* (2013.01); *C07D 417/14* (2013.01); *C07D 471/04* (2013.01); *C07D 498/04* (2013.01); *C07D 513/04* (2013.01)

(58) Field of Classification Search
CPC .. C07D 401/14; C07D 401/10; A61K 31/496; A61K 31/4545
USPC ................... 544/360; 514/252, 318; 546/194
See application file for complete search history.

(56) References Cited

U.S. PATENT DOCUMENTS 7,041,693 B2 * 5/2006 Sheppeck ............ C07D 401/12
514/306

OTHER PUBLICATIONS

Ainiala et al., "Increased Serum Matrix Metalloproteinase 9 Levels in Systemic Lupus Erythematosus Patients With Neuropsychiatric Manifestations and Brain Magnetic Resonance Imaging Abnormalities," *Arthritis Rheum.*, 50(3): 858-865 (2004).

(Continued)

*Primary Examiner* — Charanjit Aulakh
(74) *Attorney, Agent, or Firm* — Leydig, Voit & Mayer, Ltd.

(57) ABSTRACT

Provided is a novel low-molecular-weight compound that suppresses production of induction type MMPs, particularly MMP-9, rather than production of hemostatic type MMP-2. The present invention relates to a compound represented by the following formula (I):

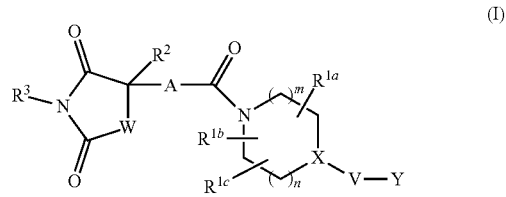

wherein each symbol is as described in the DESCRIPTION. The compound has a selective MMP-9 production suppressive action, and is useful as a drug for the prophylaxis and/or treatment of autoimmune diseases such as rheumatoid arthritis and the like, inflammatory bowel diseases (ulcerative colitis, Crohn's disease) or osteoarthritis.

21 Claims, No Drawings

(51) Int. Cl.
  *C07D 417/14*  (2006.01)
  *C07D 471/04*  (2006.01)
  *C07D 498/04*  (2006.01)
  *C07D 513/04*  (2006.01)
  *A61P 19/02*  (2006.01)
  *A61P 1/00*  (2006.01)
  *A61P 25/00*  (2006.01)

(56) References Cited

OTHER PUBLICATIONS

Itoh et al., "The Role of Matrix Metalloproteinase-2 and Matrix Metalloproteinase-9 in Antibody-Induced Arthritis," *J. Immunol.*, 169(5): 2643-2647 (2002).

Konttinen et al., "Analysis of 16 different matrix metalloproteinases (MMP-1 to MMP-20) in the synovial membrane: different profiles in trauma and rheumatoid arthritis," *Ann. Rheum. Dis.*, 58(11): 691-697 (1999).

Opdenakker et al., "Functional roles and therapeutic targeting of gelatinase B and chemokines in multiple sclerosis," *Lancet Neurol.*, 2(12): 747-756 (2003).

Japanese Patent Office, International Search Report in International Patent Application No. PCT/JP2016/070214 (dated Sep. 20, 2016).

\* cited by examiner

IMIDE DERIVATIVES AND USE THEREOF AS MEDICINE

CROSS-REFERENCE TO RELATED APPLICATIONS

This patent application is the U.S. national phase of International Patent Application No. PCT/JP2016/070214, filed Jul. 8, 2016, which claims the benefit of Japanese Patent Application No. 2015-138105, filed on Jul. 9, 2015, which are incorporated by reference in their entireties herein.

TECHNICAL FIELD

The present invention relates to a novel imide derivative showing a selective MMP-9 production suppressive action and pharmaceutical use thereof.

BACKGROUND ART

Matrix metalloprotease (MMPs) is an enzyme group playing a key role in the binding tissue degradation in living organisms. The activity of MMPs is controlled by each step of 1) production of latent enzyme (proMMP) by gene expression, 2) activation of proMMP, 3) activity inhibition by TIMP which is an inhibitor of active enzymes. MMPs includes two types of hemostatic type and induction type, the former includes MMP-2 and MMP-14, and the latter includes many MMPs such as MMP-1, 3, 9, 13 etc. Particularly, promoted production or expression in rheumatoid arthritis, osteoarthritis, multiple sclerosis, systemic lupus erythematosus and inflammatory bowel diseases (ulcerative colitis, Crohn's disease) by MMP-9 has been acknowledged, and the involvement of MMP-9 in these pathologies has been suggested [Ann. Rheum. Dis., vol. 58, pages 691-697 (1999) (non-patent document 1), J. Clin. Invest., vol. 92, pages 179-185 (1993) (non-patent document 2), Arthritis Rheum., vol. 46, pages 2625-2631 (2002) (non-patent document 3), Lancet Neurol., vol. 2, pages 747-756 (2003) (non-patent document 4), Arthritis Rheum., vol. 50, pages 858-865 (2004) (non-patent document 5), Journal of Leukocyte Biology, vol. 79, pages 954-962 (2006) (non-patent document 9)].

In addition, it has been suggest from the studies of MMP knockout mouse that MMP-9 is involved in the formation and progression of cancer, MMP-9 plays an important role in the progression of arthritis and articular destruction [J. Natl. Cancer Inst., vol. 94, 1134-1142 (2002) (non-patent document 6), J. Immunol., vol. 169, 2643-2647 (2002) (non-patent document 7)]. On the other hand, MMP-2 shows an anti-inflammatory action and the action mechanism thereof is considered to be degradation of MCP-3 and the like [Science, vol. 289, pages 1202-1206 (2000) (non-patent document 8)]. Therefore, a medicament that does not influence MMP-2 production and selectively suppresses MMP-9 production can be expected as a novel therapeutic drug.

JP-A-2004-359657 (patent document 1) discloses leptomycin B, which is a medicament that inhibits MMP-9 production, and a derivative thereof.

Furthermore, WO 2010/050461 (patent document 2) and WO 2011/136292 (patent document 3) disclose compounds that inhibit MMP-9 production. However, the ring having an imide structure of the formula (I) of the present application binds to substituent A via a carbon atom, whereas the compounds disclosed in patent documents 2 and 3 bind to substituents A and W via a nitrogen atom, and the structures are different.

DOCUMENT LIST

Patent Documents patent document 1: JP-A-2004-359657
patent document 2: WO 2010/050461
patent document 3: WO 2011/136292

Non-Patent Document non-patent document 1: Ann. Rheum. Dis., vol. 58, pages 691-697 (1999)
non-patent document 2: J. Clin. Invest., vol. 92, pages 179-185 (1993)
non-patent document 3: Arthritis Rheum., vol. 46, pages 2625-2631 (2002)
non-patent document 4: Lancet Neurol., vol. 2, pages 747-756 (2003)
non-patent document 5: Arthritis Rheum., vol. 50, pages 858-865 (2004)
non-patent document 6: J. Natl. Cancer Inst., vol. 94, pages 1134-1142 (2002)
non-patent document 7: J. Immunol., vol. 169, pages 2643-2647 (2002)
non-patent document 8: Science, vol. 289, pages 1202-1206 (2000)
non-patent document 9: Journal of Leukocyte Biology, vol. 79, pages 954-962 (2006)

SUMMARY OF THE INVENTION

Problems to be Solved by the Invention

The problem of the present invention is to provide a novel low-molecular-weight compound that suppresses production of induction type MMPs, particularly MMP-9, rather than production of hemostatic type MMP-2.

Means of Solving the Problems

In view of the above-mentioned problems, the present inventors have conducted intensive studies in an attempt to find a low-molecular-weight compound showing an MMP-9 production suppressive action. As a result, they have found that the imide derivative of the present invention suppresses production of induction type MMPs, particularly MMP-9, rather than production of hemostatic type MMP-2, which resulted in the completion of the present invention.

Therefore, the present invention is as described below.

[1] An imide derivative represented by the following formula (I)

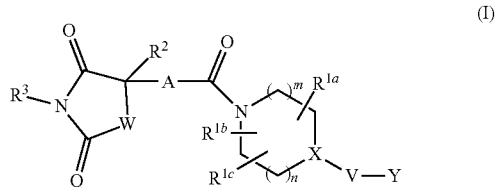

wherein A is a 5-membered heteroarylene containing 1-3 atoms selected from a nitrogen atom, an oxygen atom and a sulfur atom or phenylene or a 6-membered heteroarylene represented by the following formula,

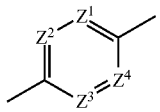

wherein $Z^1$, $Z^2$, $Z^3$ and $Z^4$ are the same or different and each is a carbon atom or a nitrogen atom,
these phenylene and heteroarylene are optionally substituted by one or the same or different 2 or 3 substituents selected from a halogen atom; hydroxyl group; nitro; cyano; $C_1$-$C_6$ alkyl optionally substituted by amino optionally mono- or di-substituted by $C_1$-$C_6$ alkyl, a halogen atom, a hydroxyl group or $C_1$-$C_6$ alkoxy; $C_3$-$C_6$ cycloalkyl optionally substituted by amino optionally mono- or di-substituted by $C_1$-$C_6$ alkyl, a halogen atom, a hydroxyl group or $C_1$-$C_6$ alkoxy; amino optionally mono- or di-substituted by $C_1$-$C_6$ alkyl; and $C_1$-$C_6$ alkoxy optionally substituted by amino optionally mono- or di-substituted by $C_1$-$C_6$ alkyl, a halogen atom, a hydroxyl group or $C_1$-$C_6$ alkoxy, the right bond is linked to carbonyl and the left bond is linked to quaternary carbon bonded to $R^2$, $R^{1a}$, $R^{1b}$ and $R^{1c}$ are the same or different and each is a hydrogen atom; a halogen atom; a hydroxyl group; cyano; oxo; carboxy; $C_1$-$C_6$ alkyl optionally substituted by amino optionally mono- or di-substituted by $C_1$-$C_6$ alkyl, a halogen atom, a hydroxyl group or $C_1$-$C_6$ alkoxy; $C_1$-$C_6$ alkoxy optionally substituted by amino optionally mono- or di-substituted by $C_1$-$C_6$ alkyl, a halogen atom, a hydroxyl group or $C_1$-$C_6$ alkoxy; $C_2$-$C_7$ alkoxycarbonyl; or aminocarbonyl optionally mono- or di-substituted by $C_1$-$C_6$ alkyl; or two of $R^{1a}$, $R^{1b}$ and $R^{1c}$ are joined to show $C_3$-$C_6$ cycloalkyl; or two of $R^{1a}$, $R^{1b}$ and $R^{1c}$ are joined to show a saturated nonaromatic heterocyclic group containing 1-4 atoms selected from a nitrogen atom, an oxygen atom and a sulfur atom and having 3-7 ring-constituting atoms, $R^2$ is $C_1$-$C_6$ alkyl optionally substituted by amino optionally mono- or di-substituted by $C_1$-$C_6$ alkyl, $C_3$-$C_6$ cycloalkyl, a halogen atom, a hydroxyl group or $C_1$-$C_6$ alkoxy; $C_3$-$C_6$ cycloalkyl optionally substituted by a halogen atom, a hydroxyl group, $C_1$-$C_6$ alkoxy or amino; a saturated nonaromatic heterocyclic group containing 1-4 atoms selected from a nitrogen atom, an oxygen atom and a sulfur atom and having 3-7 ring-constituting atoms; $C_6$-$C_{10}$ aryl optionally substituted by substituent B shown below; or heteroaryl containing 1-6 atoms selected from a nitrogen atom, an oxygen atom and a sulfur atom, having 5-10 ring-constituting atoms, and optionally substituted by substituent B shown below, $R^3$ is a hydrogen atom; $C_1$-$C_6$ alkyl optionally substituted by amino optionally mono- or di-substituted by $C_1$-$C_6$ alkyl, a halogen atom, a hydroxyl group, $C_1$-$C_6$ alkoxy or $C_2$-$C_7$ acyloxy; $C_3$-$C_6$ cycloalkyl; arylalkyl wherein the $C_6$-$C_{10}$ aryl moiety is optionally substituted by a halogen atom, a hydroxyl group, $C_1$-$C_6$ alkoxy, $C_1$-$C_6$ alkyl or amino, and the alkyl moiety has a carbon number of 1-6; or heteroarylalkyl wherein the heteroaryl moiety containing 1-6 atoms selected from a nitrogen atom, an oxygen atom and a sulfur atom and having 5 to 10 ring-constituting atoms is optionally substituted by a halogen atom, a hydroxyl group, $C_1$-$C_6$ alkoxy, $C_1$-$C_6$ alkyl or amino and the alkyl moiety has a carbon number of 1-6, W is —N($R^x$)— wherein $R^x$ is a hydrogen atom or $C_1$-$C_6$ alkyl optionally substituted by a halogen atom, a hydroxyl group, $C_1$-$C_6$ alkoxy or $C_2$-$C_7$ acyloxy or methylene optionally substituted by a halogen atom, a hydroxyl group, $C_1$-$C_6$ alkyl or $C_1$-$C_6$ alkoxy, m+n is 0, 1, 2 or 3, X is a carbon atom (any one of $R^{1a}$, $R^{1b}$ and $R^{1c}$ may be bonded to the carbon atom but the carbon atom is not substituted by oxo) or a nitrogen atom (when V is a bond, the nitrogen atom may be oxidized to form N-oxide), V is a bond; carbonyl; $C_1$-$C_6$ alkylene optionally substituted by a halogen atom, a hydroxyl group or $C_1$-$C_6$ alkoxy; an oxygen atom; or —N($R^Y$)— wherein $R^Y$ is a hydrogen atom, $C_1$-$C_6$ alkyl or $C_2$-$C_7$ acyl, Y is a 5-membered ring group, a 6-membered ring group, a 5-membered ring group substituted by a 5-membered ring group, a 5-membered ring group substituted by a 6-membered ring group, a 6-membered ring group substituted by a 5-membered ring group, a 6-membered ring group substituted by a 6-membered ring group, a fused ring group of a 5-membered ring and a 5-membered ring, a fused ring group of a 5-membered ring and a 6-membered ring or a fused ring group of a 6-membered ring and a 6-membered ring (wherein the 5-membered ring and the 5-membered ring group contain 0-4 atoms selected from a nitrogen atom, an oxygen atom and a sulfur atom, and the rest is constituted a carbon atom, the 6-membered ring and the 6-membered ring group contain 0-4 atoms selected from a nitrogen atom, an oxygen atom and a sulfur atom, and the rest is constituted of a carbon atom), and these ring groups are optionally substituted by a halogen atom; a hydroxyl group; $C_1$-$C_6$ alkyl optionally substituted by amino optionally mono- or di-substituted by $C_1$-$C_6$ alkyl, a halogen atom, a hydroxyl group or $C_1$-$C_6$ alkoxy; $C_3$-$C_6$ cycloalkyl optionally substituted by a halogen atom, a hydroxyl group, amino or $C_1$-$C_6$ alkyl; or $C_1$-$C_6$ alkoxy optionally substituted by amino optionally mono- or di-substituted by $C_1$-$C_6$ alkyl, a halogen atom, a hydroxyl group, $C_1$-$C_6$ alkyl or $C_1$-$C_6$ alkoxy:

Substituent B a halogen atom; a hydroxyl group; cyano; $C_1$-$C_6$ alkyl optionally substituted by amino optionally mono- or di-substituted by $C_1$-$C_6$ alkyl, a halogen atom, a hydroxyl group or $C_1$-$C_6$ alkoxy; $C_3$-$C_6$ cycloalkyl optionally substituted by a halogen atom, a hydroxyl group or amino; $C_1$-$C_6$ alkoxy optionally substituted by amino optionally mono- or di-substituted by $C_1$-$C_6$ alkyl, a halogen atom, a hydroxyl group or $C_1$-$C_6$ alkoxy; amino optionally mono- or di-substituted by $C_1$-$C_6$ alkyl or $C_3$-$C_6$ cycloalkyl, or a pharmacologically acceptable salt thereof (sometimes to be abbreviated as "compound (I)" in the present specification).

[2] The imide derivative of [1] wherein A is phenylene or 6-membered heteroarylene shown below:

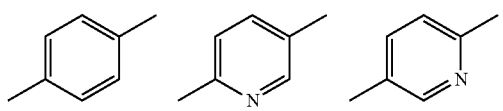

or a pharmacologically acceptable salt thereof.

[3] The imide derivative of [1] or [2] wherein Y is phenyl, pyridyl, pyrazinyl, pyridazinyl, naphthyl, quinolyl or a ring group shown below

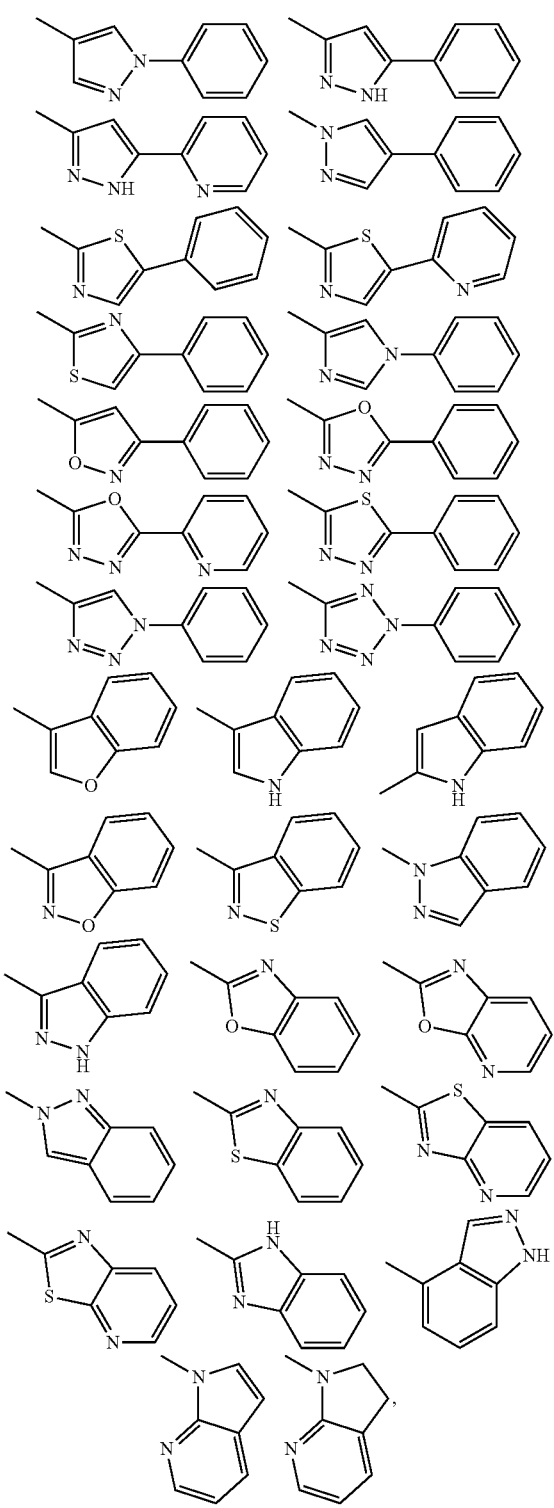

and
these ring groups are optionally substituted by a halogen atom; a hydroxyl group; $C_1$-$C_6$ alkyl optionally substituted by amino optionally mono- or di-substituted by $C_1$-$C_6$ alkyl, a halogen atom, a hydroxyl group or $C_1$-$C_6$ alkoxy; $C_3$-$C_6$ cycloalkyl optionally substituted by a halogen atom, a hydroxyl group, amino or $C_1$-$C_6$ alkyl; or $C_1$-$C_6$ alkoxy optionally substituted by amino optionally mono- or di-substituted by $C_1$-$C_6$ alkyl, a halogen atom, a hydroxyl group, $C_1$-$C_6$ alkyl or $C_1$-$C_6$ alkoxy, or a pharmacologically acceptable salt thereof.

[4] The imide derivative of any one of [1] to [3] wherein Y is phenyl or pyridyl represented by the following formula

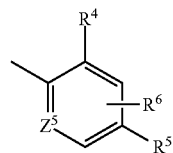

wherein $Z^5$ is a carbon atom or a nitrogen atom,
$R^4$ and $R^5$ are the same or different and each is $C_1$-$C_6$ alkyl optionally substituted by a halogen atom; or $C_3$-$C_6$ cycloalkyl optionally substituted by a halogen atom, and
$R^6$ is a hydrogen atom; $C_1$-$C_6$ alkyl optionally substituted by a halogen atom; or $C_3$-$C_6$ cycloalkyl optionally substituted by a halogen atom, or
a ring group represented by the following formula

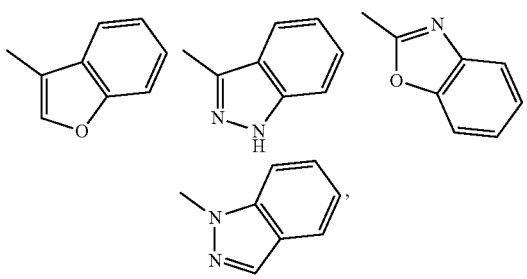

these ring groups being optionally substituted by a halogen atom or $C_1$-$C_6$ alkyl,
or a pharmacologically acceptable salt thereof.

[5] The imide derivative of any one of [1] to [4] wherein Y is phenyl or pyridyl represented by the following formula

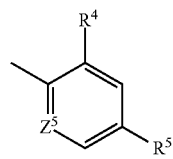

wherein $Z^5$ is a carbon atom or a nitrogen atom, and
$R^4$ and $R^5$ are the same or different and each is $C_1$-$C_6$ alkyl; or $C_3$-$C_6$ cycloalkyl, or a pharmacologically acceptable salt thereof.

[6] The imide derivative of any one of [1] to [5] wherein Y is pyridyl represented by the following formula

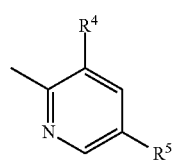

wherein $R^4$ and $R^5$ are the same or different and each is $C_1$-$C_6$ alkyl; or $C_3$-$C_6$ cycloalkyl, or a pharmacologically acceptable salt thereof.

[7] The imide derivative of any one of [1] to [6] wherein V is a bond, or a pharmacologically acceptable salt thereof.
[8] The imide derivative of any one of [1] to [7] wherein X is a nitrogen atom, or a pharmacologically acceptable salt thereof.
[9] The imide derivative of any one of [1] to [8] wherein $R^{1a}$, $R^{1b}$ and $R^{1c}$ are each a hydrogen atom, or a pharmacologically acceptable salt thereof.
[10] The imide derivative of any one of [1] to [9] wherein $R^2$ is $C_1$-$C_6$ alkyl and $R^3$ is a hydrogen atom, or a pharmacologically acceptable salt thereof.
[11] The imide derivative of any one of [1] to [10] wherein W is —NH— or methylene, or a pharmacologically acceptable salt thereof.
[12] The imide derivative of any one of [1] to [11] wherein W is —NH—, or a pharmacologically acceptable salt thereof.
[13] (R)-5-{4-[4-(3,5-dimethylpyridin-2-yl)piperazine-1-carbonyl]phenyl}-5-methylimidazolidine-2,4-dione,
(R)-5-{4-[4-(3,5-dimethylpyridin-2-yl)piperazine-1-carbonyl]-3-fluorophenyl}-5-methylimidazolidine-2,4-dione,
(R)-5-{4-[4-(5-cyclopropyl-3-methylpyridin-2-yl)piperazine-1-carbonyl]phenyl}-5-methylimidazolidine-2,4-dione,
(R)-5-methyl-5-{4-[4-(3,5,6-trimethylpyridin-2-yl)piperazine-1-carbonyl]phenyl}imidazolidine-2,4-dione,
(R)-5-{4-[4-(3,5-dimethylpyridin-2-yl)piperazine-1-carbonyl]phenyl}-5-isopropylimidazolidine-2,4-dione,
5-isopropyl-5-{2-methoxy-4-[4-(3,5,6-trimethylpyridin-2-yl)piperazine-1-carbonyl]phenyl}imidazolidine-2,4-dione,
(R)-5-{4-[(S)-3-(3,5-dimethylpyridin-2-ylamino)pyrrolidine-1-carbonyl]phenyl}-5-isopropylimidazolidine-2,4-dione,
(R)-5-{4-[(S)-3-(3,5-dimethylpyridin-2-ylamino)pyrrolidine-1-carbonyl]phenyl}-5-ethylimidazolidine-2,4-dione,
(R)-5-{4-[4-(3,5-dimethylpyridin-2-yl)-2,2-dimethylpiperazine-1-carbonyl]phenyl}-5-isopropylimidazolidine-2,4-dione,
(R)-5-{4-[(S)-4-(3,5-dimethylpyridin-2-yl)-3-methylpiperazine-1-carbonyl]phenyl}-5-isopropylimidazolidine-2,4-dione,
5-tert-butyl-5-{4-[4-(5-cyclopropyl-3-methylpyridin-2-yl)piperazine-1-carbonyl]phenyl}imidazolidine-2,4-dione,
(R)-5-{4-[4-(3,5-dimethylpyridin-2-yl)piperazine-1-carbonyl]phenyl}-5-ethylimidazolidine-2,4-dione,
(R)-5-methyl-5-{4-[4-(4-methylbenzoyl)piperidine-1-carbonyl]phenyl}imidazolidine-2,4-dione,
(R)-5-methyl-5-[4-(4-p-tolyloxypiperidine-1-carbonyl]phenyl}imidazolidine-2,4-dione,
(R)-5-isopropyl-5-{4-[4-(5-methylpyridine-2-carbonyl)piperidine-1-carbonyl]phenyl}imidazolidine-2,4-dione,
(R)-5-isopropyl-5-{4-[4-(6-methylbenzofuran-3-yl)piperidine-1-carbonyl]phenyl}imidazolidine-2,4-dione,
(R)-5-{4-[4-(4,6-dimethylbenzofuran-3-yl)piperidine-1-carbonyl]phenyl}-5-methylimidazolidine-2,4-dione,
(R)-5-isopropyl-5-{4-[4-(6-methylbenzoxazol-2-yl)piperidine-1-carbonyl]phenyl}imidazolidine-2,4-dione,
(R)-5-{4-[4-(5,7-dimethylindazol-1-yl)piperidine-1-carbonyl]phenyl}-5-isopropylimidazolidine-2,4-dione,
(R)-5-{4-[4-(4,6-dimethyl-1H-indazol-3-yl)piperidine-1-carbonyl]phenyl}-5-methyl-imidazolidine-2,4-dione,
(R)-5-methyl-5-{4-[4-(1,4,6-trimethyl-1H-indazol-3-yl)piperidine-1-carbonyl]phenyl}imidazolidine-2,4-dione,
(R)-5-{4-[4-(4-fluoro-6-methyl-1H-indazol-3-yl)piperidine-1-carbonyl]phenyl}-5-methylimidazolidine-2,4-dione,
5-{4-[4-(5-cyclopropyl-3-methylpyridin-2-yl)piperazine-1-carbonyl]phenyl}-5-(tetrahydropyran-4-yl)imidazolidine-2,4-dione, or
5-{4-[4-(5-cyclopropyl-3-methylpyridin-2-yl)piperazine-1-carbonyl]phenyl}-5-isopropylimidazolidine-2,4-dione.
[14] A pharmaceutical composition comprising the imide derivative of any one of [1] to [13], or a pharmacologically acceptable salt thereof, and a pharmaceutically acceptable additive.
[15] An agent for suppressing MMP-9 production, comprising the imide derivative of any one of [1] to [13], or a pharmacologically acceptable salt thereof.
[16] A medicament for the prophylaxis and/or treatment of an autoimmune disease or inflammatory bowel disease comprising the imide derivative of any one of [1] to [13], or a pharmacologically acceptable salt thereof.
[17]. The medicament of [16], wherein the autoimmune disease is rheumatoid arthritis, multiple sclerosis or systemic lupus erythematosus.
[18] The medicament of [16], wherein the inflammatory bowel disease is Crohn's disease or ulcerative colitis.
[19] A medicament for the prophylaxis and/or treatment of osteoarthritis, comprising the imide derivative of any one of [1] to [13], or a pharmacologically acceptable salt thereof.
[20] A method of preventing and/or treating an autoimmune disease or an inflammatory bowel disease, comprising administering the imide derivative of any one of [1] to [13], or a pharmacologically acceptable salt thereof.
[21] The method of [20] wherein the autoimmune disease is rheumatoid arthritis, multiple sclerosis or systemic lupus erythematosus.
[22] The method of [20] wherein the inflammatory bowel disease is Crohn's disease or ulcerative colitis.
[23] A method of preventing and/or treating osteoarthritis, comprising administering the imide derivative of any one of [1] to [13], or a pharmacologically acceptable salt thereof.

Effect of the Invention

Since the compound of the present invention selectively suppresses production of induction type MMPs, particularly MMP-9, rather than production of hemostatic type MMP-2, it is useful as a medicament for the prophylaxis and/or treatment of autoimmune diseases such as rheumatoid arthritis and the like, inflammatory bowel diseases (ulcerative colitis, Crohn's disease) and osteoarthritis.

DESCRIPTION OF EMBODIMENTS

The compound of the present invention is the above-mentioned imide derivative represented by the formula (I), a pharmacologically acceptable salt thereof or a hydrate or solvate thereof. In the following, the meanings of the terms used in the present specification are described, and the present invention is explained in more detail. The explanation of the following terms does not limit the present invention in any way.

The halogen atom is a fluorine atom, a chlorine atom, a bromine atom or an iodine atom.

The $C_1$-$C_6$ alkyl is straight chain or branched chain alkyl, and methyl, ethyl, propyl, isopropyl, butyl, isobutyl, secondary butyl, tertiary butyl, pentyl, 3-methylbutyl, neopentyl, hexyl, 2-ethylbutyl and the like can be mentioned.

The $C_1$-$C_3$ alkyl is straight chain or branched chain alkyl, and methyl, ethyl, propyl, isopropyl and the like can be mentioned.

Examples of the $C_3$-$C_6$ cycloalkyl include cyclopropyl, cyclobutyl, cyclopentyl, cyclohexyl, methylcyclopropyl, ethylcyclopropyl, methylcyclobutyl, ethylcyclobutyl, methylcyclopentyl and the like can be mentioned.

Examples of the $C_6$-$C_{10}$ aryl include phenyl, naphthyl and the like.

The arylalkyl is the aforementioned $C_1$-$C_6$ alkyl substituted by the aforementioned $C_6$-$C_{10}$ aryl, and benzyl, phenethyl, phenylpropyl, naphthylmethyl, naphthylethyl and the like can be mentioned.

The heteroaryl containing 1-6 atoms selected from a nitrogen atom, an oxygen atom and a sulfur atom and having 5-10 ring-constituting atoms is a monovalent group induced from a monocyclic aromatic heterocycle containing 1 to 3 nitrogen atoms, oxygen atoms and sulfur atoms and having 5 or 6 ring-constituting atoms, a fused ring of this monocyclic aromatic heterocycle and benzene and a fused ring of the same or different these two monocyclic aromatic heterocycles. Specific examples include pyrrolyl, furyl, thienyl, pyrazolyl, imidazolyl, triazolyl, tetrazolyl, oxazolyl, isoxazolyl, oxadiazolyl, thiazolyl, isothiazolyl, thiadiazolyl, furazanyl, pyridyl, pyranyl, thiopyranyl, pyridazinyl, pyrimidinyl, pyrazinyl, triazinyl, tetrazinyl, indolyl, isoindolyl, benzofuryl, benzothienyl, indazolyl, benzoxazolyl, benzimidazolyl, benzothiazolyl, pyrrolopyridyl, pyrazolopyridyl, imidazopyridyl, pyrrolopyrimidinyl, pyrazolopyrimidinyl, quinolyl, isoquinolyl, quinoxalyl, quinazolyl and the like.

The 5-membered heteroarylene containing 1-3 atoms selected from a nitrogen atom, an oxygen atom and a sulfur atom is a divalent group induced from pyrrole, pyrazole, imidazole, triazole, thiophene, furan, oxazole, isoxazole, thiazole, isothiazole and furazan.

The heteroarylalkyl is the aforementioned $C_1$-$C_6$ alkyl substituted by the aforementioned heteroaryl containing 1-6 nitrogen atoms, oxygen atoms and sulfur atoms, and having 5-10 ring-constituting atoms.

The saturated nonaromatic heterocyclic group containing 1-4 atoms selected from a nitrogen atom, an oxygen atom and a sulfur atom and having 3-7 ring-constituting atoms is a monovalent group derived from a saturated monocyclic heterocycle containing 1 to 4 nitrogen atoms, oxygen atoms and sulfur atoms and having 3-7 ring-constituting atoms. Specific examples include aziridinyl, azetidinyl, pyrrolidinyl, tetrahydrofuryl, tetrahydrothienyl, imidazolidinyl, pyrazolidinyl, oxazolidinyl, isoxazolidinyl, thiazolidinyl, isothiazolidinyl, piperidinyl, tetrahydropyranyl, tetrahydrothiopyranyl, piperazinyl, morpholinyl, thiomorpholinyl and the like can be mentioned.

The $C_1$-$C_6$ alkoxy is straight chain or branched chain alkoxy, and methoxy, ethoxy, propoxy, isopropoxy, butoxy, isobutoxy, secondary butoxy, tertiary butoxy, pentoxy, 3-methylbutoxy, neopentoxy, hexyloxy, 2-ethylbutoxy or the like.

The $C_2$-$C_7$ acyl is carbonyl substituted by the aforementioned $C_1$-$C_6$ alkyl, carbonyl substituted by the aforementioned $C_3$-$C_6$ cycloalkyl, or carbonyl substituted by phenyl. Examples thereof include acetyl, propionyl, butyryl, isobutyryl, valeryl, isovaleryl, hexanoyl, cyclopropylcarbonyl, cyclopentylcarbonyl, cyclohexylcarbonyl, benzoyl and the like.

Examples of the $C_2$-$C_7$ acyloxy include acetoxy, ethylcarbonyloxy, propylcarbonyloxy, isopropylcarbonyloxy, butylcarbonyloxy, isobutylcarbonyloxy, secondary butylcarbonyloxy, tertiary butylcarbonyloxy, pentylcarbonyloxy, neopentylcarbonyloxy, hexylcarbonyloxy, cyclopropylcarbonyloxy, cyclobutylcarbonyloxy, cyclopentylcarbonyloxy, cyclohexylcarbonyloxy, benzoyloxy and the like.

Examples of the $C_2$-$C_7$ alkoxycarbonyl include a group wherein the aforementioned $C_1$-$C_6$ alkoxy is bonded to carbonyl, and methoxycarbonyl, ethoxycarbonyl, propoxycarbonyl, isopropoxycarbonyl, butoxycarbonyl, isobutoxycarbonyl, secondary butoxycarbonyl, tertiary butoxycarbonyl, pentoxycarbonyl, 3-methylbutoxycarbonyl, neopentoxycarbonyl, hexyloxycarbonyl, 2-ethylbutoxycarbonyl and the like.

Examples of the amino optionally mono- or di-substituted by $C_1$-$C_6$ alkyl include amino, methylamino, ethylamino, propylamino, isopropylamino, butylamino, isobutylamino, secondary butylamino, tertiary butylamino, pentylamino, 3-methylbutylamino, neopentylamino, hexylamino, 2-ethylbutylamino, dimethylamino, ethylmethylamino, diethylamino, methylpropylamino, ethylpropylamino, dipropylamino and the like.

The aminocarbonyl optionally mono- or di-substituted by $C_1$-$C_6$ alkyl is carbonyl wherein the amino moiety is substituted by the aforementioned amino optionally mono- or di-substituted by $C_1$-$C_6$ alkyl. Specific examples thereof include aminocarbonyl, methylaminocarbonyl, dimethylaminocarbonyl, ethylmethylaminocarbonyl and the like.

The $C_1$-$C_6$ alkylene is straight chain or branched chain alkylene. Examples thereof include methylene, ethylene, trimethylene, tetramethylene, pentamethylene, hexamethylene, propylene, ethylethylene and the like.

The 5-membered ring containing 0-4 atoms selected from a nitrogen atom, an oxygen atom and a sulfur atom, and the rest constituted of a carbon atom is 5-membered carbocycle or 5-membered heterocycle, and the 5-membered ring group containing 0-4 atoms selected from a nitrogen atom, an oxygen atom and a sulfur atom, and the rest constituted of a carbon atom is a 5-membered carbocyclic group or a 5-membered heterocyclic group. Examples of the 5-membered carbocycle include cyclopentane, cyclopentene, cyclopentadiene and the like and examples of the 5-membered carbocyclic group include a monovalent group induced from the aforementioned 5-membered carbocycle. The 5-membered heterocycle includes 5-membered aromatic heterocycle and 5-membered nonaromatic heterocycle. The same applies to the 5-membered heterocyclic group. Examples of the 5-membered heterocycle include pyrrole, pyrazole, imidazole, triazole, tetrazole, furan, thiophene, oxazole, isoxazole, thiazole, isothiazole, oxadiazole, thiadiazole, oxathiol, oxathiazole and these rings partly or entirely reduced and the like, and examples of the 5-membered heterocyclic group include a monovalent group induced from the aforementioned 5-membered heterocycle.

The 6-membered ring containing 0-4 atoms selected from a nitrogen atom, an oxygen atom and a sulfur atom, and the rest constituted of a carbon atom is 6-membered carbocycle or 6-membered heterocycle, and the 6-membered ring group containing 0-4 atoms selected from a nitrogen atom, an oxygen atom and a sulfur atom, and the rest constituted of a carbon atom is a 6-membered carbocyclic group or a 6-membered heterocyclic group. Examples of the 6-membered carbocycle include benzene, cyclohexane and the like and examples of the 6-membered carbocyclic group include a monovalent group induced from the aforementioned 6-membered carbocycle. The 6-membered heterocycle includes 6-membered aromatic heterocycle and 6-membered nonaromatic heterocycle. The same applies to the 6-membered heterocyclic group. Examples of the 6-membered heterocycle include pyran, thiopyran, pyridine, pyridazine, pyrimidine, pyrazine, triazine, tetrazine, oxazine, thioxazine, these rings partly or entirely reduced and the like, and examples of the 6-membered heterocyclic group include a monovalent group induced from the aforementioned 6-membered heterocycle.

In the present specification, the number of the substituents when "optionally substituted" is one or more unless particularly specified, and the kind of the substituents may be the same or different.

Preferable embodiments of the above-mentioned formula (I) are explained below. A is preferably thienylene or phenylene or 6-membered heteroarylene represented by

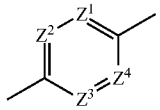

wherein $Z^1$, $Z^2$, $Z^3$ and $Z^4$ are the same or different and each is a carbon atom or a nitrogen atom, and more preferably phenylene or 6-membered heteroarylene. More specifically

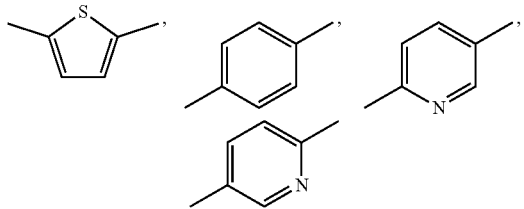

are preferable, and

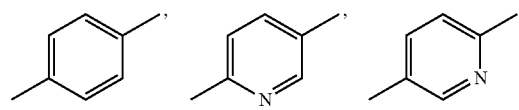

are further preferable. As a particularly preferable example of A,

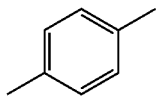

can be mentioned.

The substituent when A has a substituent is preferably one or the same or different 2 or 3 substituents selected from a halogen atom; a hydroxyl group; $C_1$-$C_6$ alkyl optionally substituted by amino optionally mono- or di-substituted by $C_1$-$C_6$ alkyl, a halogen atom, a hydroxyl group or $C_1$-$C_6$ alkoxy; and $C_1$-$C_6$ alkoxy optionally substituted by amino optionally mono- or di-substituted by $C_1$-$C_6$ alkyl, a halogen atom, a hydroxyl group or $C_1$-$C_6$ alkoxy, more preferably one or the same or different 2 or 3 substituents selected from a halogen atom; a hydroxyl group; $C_1$-$C_6$ alkyl; and $C_1$-$C_6$ alkoxy; further preferably a halogen atom or $C_1$-$C_6$ alkoxy.

The substituent when A has a substituent is as mentioned above, and unsubstituted A is also a preferable embodiment.

$R^{1a}$, $R^{1b}$ and $R^{1c}$ are the same or different and each is preferably a hydrogen atom; hydroxyl group; cyano; $C_1$-$C_6$ alkyl optionally substituted by amino optionally mono- or di-substituted by $C_1$-$C_6$ alkyl, a halogen atom, a hydroxyl group or $C_1$-$C_6$ alkoxy; $C_2$-$C_7$ alkoxycarbonyl; aminocarbonyl optionally mono- or di-substituted by $C_1$-$C_6$ alkyl; or two of $R^{1a}$, $R^{1b}$ and $R^{1c}$ are joined to show cycloalkyl having 3 to 6 ring-constituting atoms, more preferably a hydrogen atom; a hydroxyl group; cyano; $C_1$-$C_6$ alkyl optionally substituted by a hydroxyl group or $C_1$-$C_6$ alkoxy; $C_2$-$C_7$ alkoxycarbonyl; or two of $R^{1a}$, $R^{1b}$ and $R^{1c}$ are joined to show cycloalkyl ring having 3 to 6 ring-constituting atoms. When two of $R^{1a}$, $R^{1b}$ and $R^{1c}$ are joined to constitute a ring, it is preferably a spiro ring. A particularly preferable example of $R^{1a}$ is a hydrogen atom or $C_1$-$C_3$ alkyl, a particularly preferable example of $R^{1b}$ is a hydrogen atom or $C_1$-$C_3$ alkyl, and a particularly preferable example of $R^{1c}$ is a hydrogen atom. In a most preferable example, $R^{1a}$, $R^{1b}$ and $R^{1c}$ are each a hydrogen atom.

$R^2$ is preferably $C_1$-$C_6$ alkyl optionally substituted by amino optionally mono- or di-substituted by $C_1$-$C_6$ alkyl, $C_3$-$C_6$ cycloalkyl, a halogen atom, a hydroxyl group or $C_1$-$C_6$ alkoxy; $C_3$-$C_6$ cycloalkyl optionally substituted by a halogen atom, a hydroxyl group, $C_1$-$C_6$ alkoxy or amino; a saturated nonaromatic heterocyclic group containing 1-4 atoms selected from a nitrogen atom, an oxygen atom and a sulfur atom and having 3-7 ring-constituting atoms; $C_6$-$C_{10}$ aryl; or heteroaryl containing 1-6 atoms selected from a nitrogen atom, an oxygen atom and a sulfur atom and having 5-10 ring-constituting atoms, more preferably $C_1$-$C_6$ alkyl optionally substituted amino optionally mono- or di-substituted by $C_1$-$C_6$ alkyl, $C_3$-$C_6$ cycloalkyl, a halogen atom, a hydroxyl group or $C_1$-$C_6$ alkoxy; $C_3$-$C_6$ cycloalkyl optionally substituted by a halogen atom, a hydroxyl group, $C_1$-$C_6$ alkoxy or amino; a saturated nonaromatic heterocyclic group containing 1-4 atoms selected from a nitrogen atom, an oxygen atom and a sulfur atom and having 3-7 ring-constituting atoms; or $C_6$-$C_{10}$ aryl, further preferably $C_1$-$C_6$ alkyl optionally substituted by a halogen atom or $C_1$-$C_6$ alkoxy; $C_3$-$C_6$ cycloalkyl optionally substituted by $C_1$-$C_6$ alkoxy; tetrahydropyranyl; or phenyl. Particularly preferable examples of $R^2$ include $C_1$-$C_6$ alkyl and tetrahydropyranyl, and a most preferably example thereof is $C_1$-$C_6$ alkyl. The $C_1$-$C_6$ alkyl in the most preferably example of $R^2$ is specifically methyl, ethyl or isopropyl.

$R^3$ is preferably a hydrogen atom; $C_1$-$C_6$ alkyl optionally substituted by amino optionally mono- or di-substituted by $C_1$-$C_6$ alkyl, a halogen atom, a hydroxyl group, $C_1$-$C_6$ alkoxy or $C_2$-$C_7$ acyloxy; or arylalkyl wherein the $C_6$-$C_{10}$ aryl moiety is optionally substituted by a halogen atom, a hydroxyl group, $C_1$-$C_6$ alkoxy, $C_1$-$C_6$ alkyl or amino, and the alkyl moiety has a carbon number of 1-6, more preferably a hydrogen atom; or $C_1$-$C_6$ alkyl optionally substituted by a hydroxyl group or $C_2$-$C_7$ acyloxy, further preferably a hydrogen atom.

In another embodiment of the present invention, $R^2$ is preferably $C_1$-$C_6$ alkyl (e.g., methyl, ethyl, propyl, isopropyl, butyl, isobutyl, tert-butyl), and $R^3$ is preferably a hydrogen atom.

W is preferably —N($R^x$)— wherein $R^x$ is a hydrogen atom or $C_1$-$C_6$ alkyl optionally substituted by a hydroxyl group, or methylene, more preferably —NH— or methylene. A particularly preferable example of W is —N($R^x$)— wherein $R^x$ is a hydrogen atom or $C_1$-$C_6$ alkyl optionally substituted by a hydroxyl group, and —NH— is the most preferable example.

m+n is preferably 0, 1 or 2, more preferably 1 or 2, further preferably 2. More specifically, m is preferably 0 or 1, and n is preferably 0 or 1. A preferable combination of m and n is more specifically (0,0), (0,1) or (1,1) as (m,n), more preferably (0,1) or (1,1), particularly preferably (1,1).

X is preferably a carbon atom or a nitrogen atom. More specifically, when m+n is 0 or 1, a carbon atom is preferable. When m+n is 2, both a carbon atom and a nitrogen atom are preferable, and a nitrogen atom is particularly preferable.

Specific preferable combinations of m, n and X are

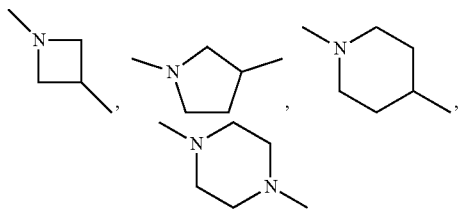

more specific preferable examples are

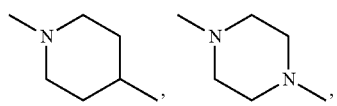

and
particularly specific preferable example is

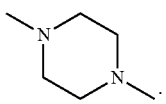

V is preferably a bond, carbonyl, $C_1$-$C_6$ alkylene, an oxygen atom or —NH—, more preferably a bond, carbonyl, methylene, an oxygen atom or —NH—, further preferably a bond, carbonyl, an oxygen atom or —NH—. Particularly preferable examples of V include a bond and carbonyl, and the most preferable example is a bond.

The 5-membered ring group for Y is preferably pyrrolyl, dihydropyrrolyl, pyrazolyl, imidazolyl, triazolyl, tetrazolyl, thiazolyl, oxazolyl, isoxazolyl, thiazolyl, isothiazolyl, oxadiazolyl, thiadiazolyl or furyl.

The 6-membered ring group for Y is preferably phenyl, pyridyl, pyrazinyl or pyridazinyl.

Y is preferably phenyl, pyridyl, pyrazinyl, pyridazinyl, naphthyl, quinolyl or a ring group shown below

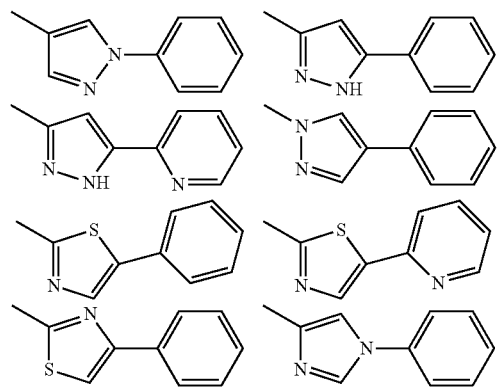

more preferably phenyl, pyridyl or a ring group shown below

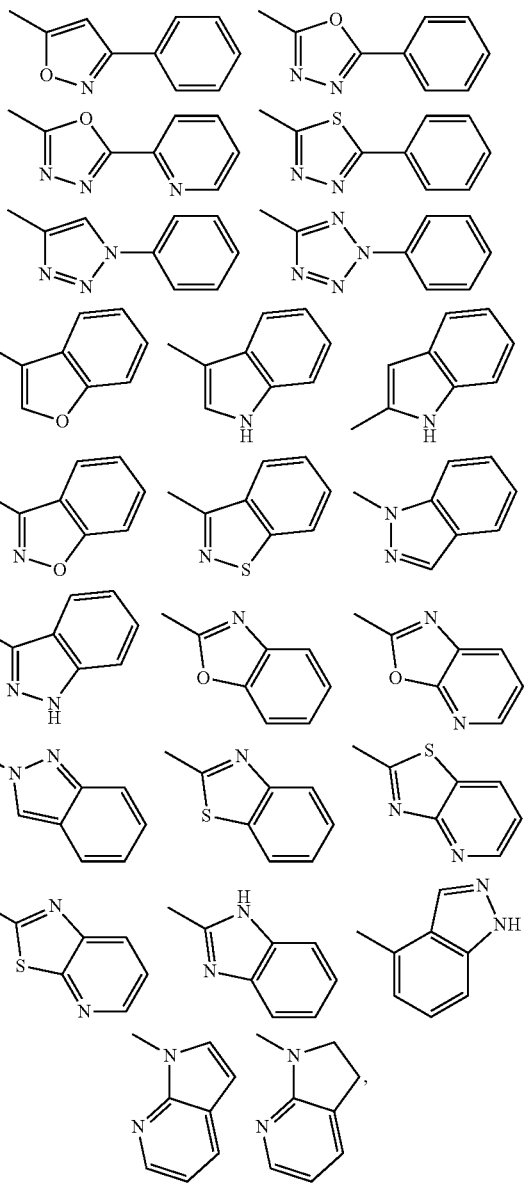

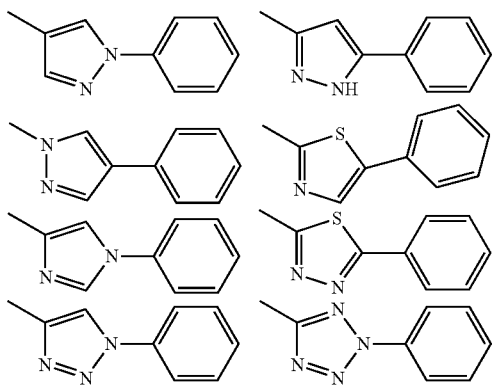

-continued

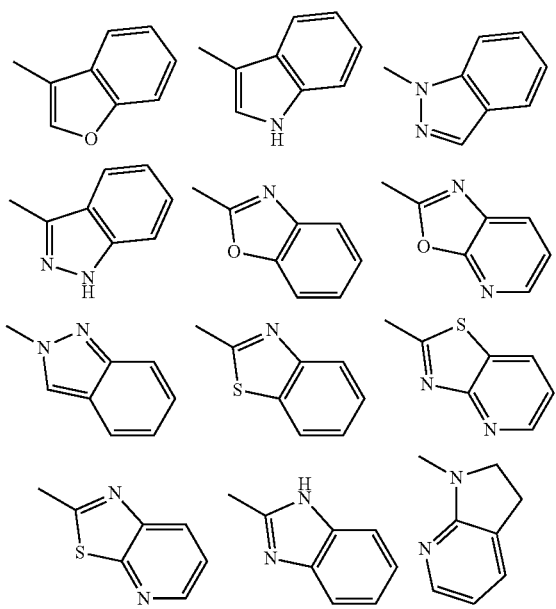

further preferably phenyl, pyridyl or a ring group shown below

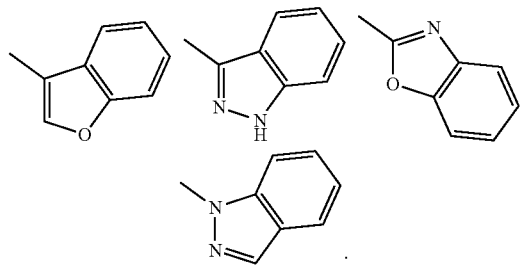

A particularly preferable example of Y is pyridyl, more specifically

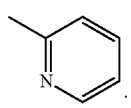

When Y has a substituent, the substituent is preferably a halogen atom; $C_1$-$C_6$ alkyl optionally substituted by amino optionally mono- or di-substituted by $C_1$-$C_6$ alkyl, a halogen atom, a hydroxyl group or $C_1$-$C_6$ alkoxy; $C_3$-$C_6$ cycloalkyl optionally substituted by a halogen atom, a hydroxyl group, amino or $C_1$-$C_6$ alkyl; or $C_1$-$C_6$ alkoxy optionally substituted by amino optionally mono- or di-substituted by $C_1$-$C_6$ alkyl, a halogen atom, a hydroxyl group, $C_1$-$C_6$ alkyl or $C_1$-$C_6$ alkoxy, more preferably a halogen atom; $C_1$-$C_6$ alkyl optionally substituted by a halogen atom; $C_3$-$C_6$ cycloalkyl; or $C_1$-$C_6$ alkoxy, further preferably $C_1$-$C_6$ alkyl; or $C_3$-$C_6$ cycloalkyl. A particularly preferable example of the substituent for Y is $C_1$-$C_6$ alkyl, specifically methyl. The number of the substituents is preferably 2 or 3.

Particularly preferable examples of Y specifically include

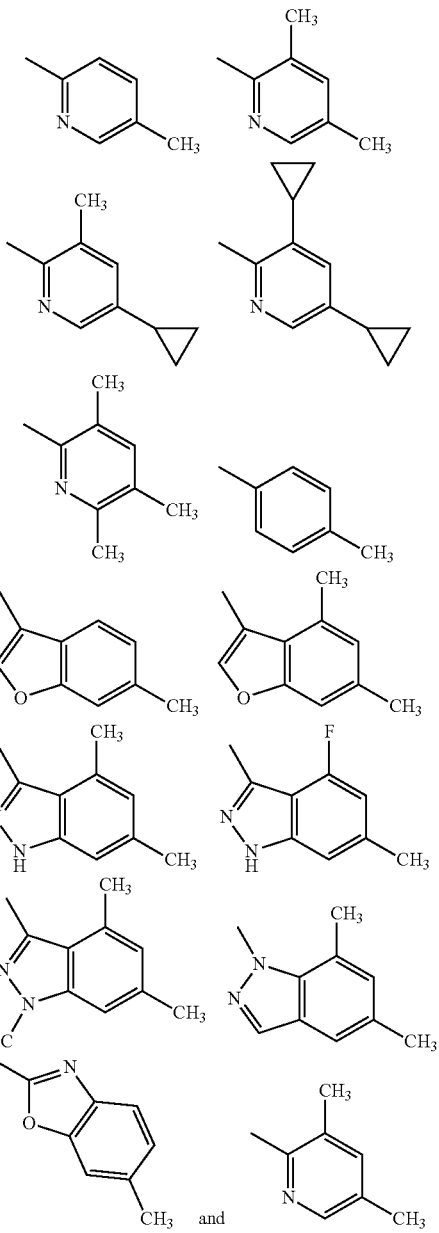

and

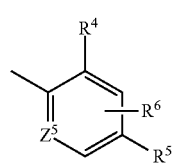

is most preferable.

In another embodiment of the present invention, Y is preferably phenyl or pyridyl represented by the following formula wherein $Z^5$ is a carbon atom or a nitrogen atom,
$R^4$ and $R^5$ are the same or different and each is $C_1$-$C_6$ alkyl (e.g., methyl, ethyl) optionally substituted by a halogen atom; or $C_3$-$C_6$ cycloalkyl (e.g., cyclopropyl) optionally substituted by a halogen atom, $R^6$ is a hydrogen atom; $C_1$-$C_6$ alkyl (e.g., methyl) optionally substituted by a halogen atom; or $C_3$-$C_6$ cycloalkyl optionally substituted by a halogen atom or a ring group represented by the following formula

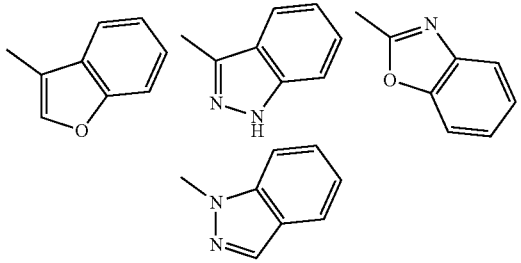

(these ring groups are optionally substituted by a halogen atom (e.g., fluorine atom, chlorine atom, bromine atom) or $C_1$-$C_6$ alkyl (e.g., methyl)), more preferably, phenyl or pyridyl represented by the following formula

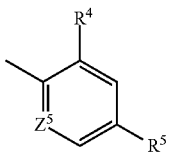

wherein $Z^5$ is a carbon atom or a nitrogen atom,
$R^4$ and $R^5$ are the same or different and each is $C_1$-$C_6$ alkyl (e.g., methyl, ethyl); or $C_3$-$C_6$ cycloalkyl (e.g., cyclopropyl), more preferably, pyridyl represented by the following formula

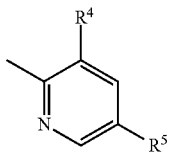

wherein $R^4$ and $R^5$ are the same or different and each is $C_1$-$C_6$ alkyl (e.g., methyl, ethyl); or $C_3$-$C_6$ cycloalkyl (e.g., cyclopropyl).

Preferable examples of compound (I) include the following compounds.

[Compound I-A]

Compound (I) wherein A is 5-membered heteroarylene (e.g., thienylene) containing 1-3 atoms selected from a nitrogen atom, an oxygen atom and a sulfur atom or phenylene or 6-membered heteroarylene represented by the following formula

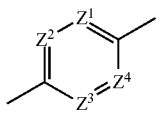

wherein $Z^1=Z^2=Z^3=Z^4$=carbon atom; $Z^1=Z^2=Z^4$=carbon atom and $Z^3$=nitrogen atom; or $Z^1=Z^2=Z^3$=carbon atom and $Z^4$=nitrogen atom, and these phenylene and heteroarylene are optionally substituted by one or the same or different 2 or 3 substituents selected from a halogen atom (e.g., fluorine atom, bromine atom); a hydroxyl group; $C_1$-$C_6$ alkyl (e.g., methyl) optionally substituted by 1 to 3 halogen atoms (e.g., fluorine atom); and $C_1$-$C_6$ alkoxy (e.g., methoxy, ethoxy), the right bond is linked to carbonyl, and the left bond is linked to quaternary carbon bonded to $R^2$, $R^{1a}$, $R^{1b}$ and $R^{1c}$ are the same or different and each is a hydrogen atom; a hydroxyl group; cyano; $C_1$-$C_6$ alkyl (e.g., methyl, ethyl, isopropyl) optionally substituted by one or the same or different 2 or 3 substituents selected from a hydroxyl group and $C_1$-$C_6$ alkoxy (e.g., methoxy); $C_2$-$C_7$ alkoxycarbonyl (e.g., methoxycarbonyl); aminocarbonyl; or two of $R^{1a}$, Rib and $R^{1c}$ are joined to show $C_3$-$C_6$ cycloalkyl (e.g., cyclobutyl), $R^2$ is $C_1$-$C_6$ alkyl (e.g., methyl, ethyl, propyl, isopropyl, butyl, isobutyl, tert-butyl) optionally substituted by one or the same or different 2 or 3 substituents selected from a halogen atom (e.g., fluorine atom), a hydroxyl group and $C_1$-$C_6$ alkoxy (e.g., methoxy, ethoxy); $C_3$-$C_6$ cycloalkyl (e.g., cyclopropyl, cyclobutyl) optionally substituted by $C_1$-$C_6$ alkoxy (e.g., methoxy); a saturated nonaromatic heterocyclic group containing 1-4 atoms selected from a nitrogen atom, an oxygen atom and a sulfur atom and having 3-7 ring-constituting atoms (e.g., tetrahydropyranyl); or $C_6$-$C_{10}$ aryl (e.g., phenyl), $R^3$ is $C_1$-$C_6$ alkyl (e.g., methyl, ethyl) optionally substituted by one or the same or different 2 or 3 substituents selected from a hydrogen atom; a hydroxyl group and $C_2$-$C_7$ acyloxy (e.g., acetoxy, propylcarbonyloxy, tert-butylcarbonyloxy); or arylalkyl wherein the $C_6$-$C_{10}$ aryl moiety is optionally substituted by $C_1$-$C_6$ alkoxy (e.g., methoxy) and the alkyl moiety has a carbon number of 1-6 (e.g., benzyl), W is —N($R^x$)— wherein $R^x$ is a hydrogen atom or $C_1$-$C_6$ alkyl (e.g., methyl, ethyl) optionally substituted by a hydroxyl group, or methylene, m+n is 0, 1 or 2, X is a carbon atom or a nitrogen atom, V is a bond; carbonyl; alkylene (e.g., methylene) having 1-6 carbon atoms; oxygen atom; or —N($R^Y$)— wherein $R^Y$ is a hydrogen atom, and Y is a 6-membered ring group (e.g., phenyl, pyridyl, pyrazinyl, pyridazinyl), a 5-membered ring group (e.g., pyrazolyl, imidazolyl, isoxazolyl, thiazolyl, oxadiazolyl, triazolyl, thiadiazolyl, tetrazolyl) substituted by a 6-membered ring group (e.g., phenyl, pyridyl), a fused ring group of a 5-membered ring and a 6-membered ring (e.g., benzoxazolyl, benzoisoxazolyl, benzimidazolyl, benzothiazolyl, benzoisothiazolyl, benzofuryl, oxazolopyridinyl, thiazolopyridyl, pyrrolopyridyl, dihydropyrrolopyridyl, indazolyl, indolyl) or a fused ring group of a 6-membered ring and a 6-membered ring (e.g., naphthyl, quinolyl) (wherein the 5-membered ring and the 5-membered ring group contain 0-4 atoms selected from a nitrogen atom, an oxygen atom and a sulfur atom, and the rest is constituted of a carbon atom, the 6-membered ring and the 6-membered ring group contain 0-4 atoms selected from a nitrogen atom, an oxygen atom and a sulfur atom, and the rest is constituted of a carbon atom), these ring groups are optionally substituted one or the same or different 2 or 3 substituents selected from a halogen atom (e.g., fluorine atom, chlorine atom, bromine atom); $C_1$-$C_6$ alkyl (e.g., methyl, ethyl) optionally substituted by 1 to 3 halogen atoms (e.g., fluorine atom); $C_3$-$C_6$ cycloalkyl (e.g., cyclopropyl); and $C_1$-$C_6$ alkoxy (e.g., methoxy).

[Compound I-B]

Compound (I) wherein A is 5-membered heteroarylene (e.g., thienylene) containing 1-3 atoms selected from a nitrogen atom, an oxygen atom and a sulfur atom or phenylene or 6-membered heteroarylene represented by the following formula

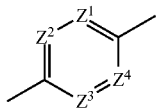

wherein $Z^1=Z^2=Z^3=Z^4$=carbon atom; or $Z^1=Z^2=Z^4$=carbon atom and $Z^3$=nitrogen atom,
these phenylene and heteroarylene are optionally substituted by one or the same or different 2 or 3 substituents selected from a halogen atom (e.g., fluorine atom); a hydroxyl group; and $C_1$-$C_6$ alkyl (e.g., methyl), the right bond is linked to carbonyl, and the left bond is linked to quaternary carbon bonded to $R^2$, $R^{1a}$, $R^{1b}$ and $R^{1c}$ are the same or different and each is a hydrogen atom; a hydroxyl group; cyano; $C_1$-$C_6$ alkyl (e.g., methyl) optionally substituted by one or the same or different 2 or 3 substituents selected from $C_1$-$C_6$ alkoxy (e.g., methoxy); $C_2$-$C_7$ alkoxycarbonyl (e.g., methoxycarbonyl); or two of $R^{1a}$, $R^{1b}$ and $R^{1c}$ are joined to show $C_3$-$C_6$ cycloalkyl (e.g., cyclobutyl), $R^2$ is $C_1$-$C_6$ alkyl (e.g., methyl, ethyl, isopropyl, tert-butyl) optionally substituted by one or the same or different 2 or 3 substituents selected from a halogen atom (e.g., fluorine atom) and $C_1$-$C_6$ alkoxy (e.g., methoxy); $C_3$-$C_6$ cycloalkyl (e.g., cyclopropyl, cyclobutyl) optionally substituted by $C_1$-$C_6$ alkoxy (e.g., methoxy); a saturated nonaromatic heterocyclic group containing 1-4 atoms selected from a nitrogen atom, an oxygen atom and a sulfur atom and having 3-7 ring-constituting atoms (e.g., tetrahydropyranyl); or $C_6$-$C_{10}$ aryl (e.g., phenyl), $R^3$ is a hydrogen atom; or $C_1$-$C_6$ alkyl (e.g., methyl) optionally substituted by one or the same or different 2 or 3 substituents selected from $C_2$-$C_7$ acyloxy (e.g., acetoxy), W is —N($R^x$)— wherein $R^x$ is a hydrogen atom or $C_1$-$C_6$ alkyl (e.g., methyl), m+n is 0, 1 or 2, X is a carbon atom or a nitrogen atom, V is a bond; carbonyl; an oxygen atom; or —N($R^Y$)— wherein $R^Y$ is a hydrogen atom, and Y is a 6-membered ring group (e.g., phenyl, pyridyl, pyrazinyl, pyridazinyl), a 5-membered ring group (e.g., pyrazolyl, imidazolyl, thiazolyl, triazolyl, thiadiazolyl, tetrazolyl) substituted by a 6-membered ring group (e.g., phenyl), a fused ring group of a 5-membered ring and a 6-membered ring (e.g., benzoxazolyl, benzimidazolyl, benzothiazolyl, benzofuryl, oxazolopyridyl, thiazolopyridyl, dihydropyrrolopyridyl, indazolyl, indolyl) (wherein the 5-membered ring and the 5-membered ring group contain 0-4 atoms selected from a nitrogen atom, an oxygen atom and a sulfur atom, and the rest is constituted of a carbon atom, the 6-membered ring and the 6-membered ring group contain 0-4 atoms selected from a nitrogen atom, an oxygen atom and a sulfur atom, and the rest is constituted of a carbon atom), these ring groups are optionally substituted one or the same or different 2 or 3 substituents selected from a halogen atom (e.g., fluorine atom); $C_1$-$C_6$ alkyl (e.g., methyl) optionally substituted by 1 to 3 halogen atoms (e.g., fluorine atom); and $C_3$-$C_6$ cycloalkyl (e.g., cyclopropyl).

[Compound I-C]

Compound (I) wherein A is phenylene represented by the following formula

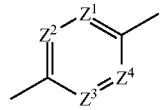

wherein $Z^1=Z^2=Z^3=Z^4$=carbon atom,
phenylene is optionally substituted by one or the same or different 2 or 3 substituents selected from a halogen atom (e.g., fluorine); and $C_1$-$C_6$ alkoxy (e.g., methoxy), the right bond is linked to carbonyl, and the left bond is linked to quaternary carbon bonded to $R^2$, $R^{1a}$, $R^{1b}$ and $R^{1c}$ are the same or different and each is a hydrogen atom; or $C_1$-$C_6$ alkyl (e.g., methyl), $R^2$ is $C_1$-$C_6$ alkyl (e.g., methyl, ethyl, isopropyl, tert-butyl); or a saturated nonaromatic heterocyclic group containing 1-4 atoms selected from a nitrogen atom, an oxygen atom and a sulfur atom and having 3-7 ring-constituting atoms (e.g., tetrahydropyranyl), $R^3$ is a hydrogen atom, W is —N($R^x$)— wherein $R^x$ is a hydrogen atom, m+n is 1 or 2, X is a carbon atom or a nitrogen atom, V is a bond; carbonyl; an oxygen atom; or —N($R^Y$)— wherein $R^Y$ is a hydrogen atom, and Y is a 6-membered ring group (e.g., phenyl, pyridyl) or a fused ring group of a 5-membered ring and a 6-membered ring (e.g., benzoxazolyl, benzofuryl, indazolyl) (wherein the 5-membered ring contains 0-4 atoms selected from a nitrogen atom, an oxygen atom and a sulfur atom, and the rest is constituted of a carbon atom, the 6-membered ring and the 6-membered ring group contain 0-4 atoms selected from a nitrogen atom, an oxygen atom and a sulfur atom, and the rest is constituted of a carbon atom), these ring groups are optionally substituted one or the same or different 2 or 3 substituents selected from a halogen atom (e.g., fluorine atom); $C_1$-$C_6$ alkyl (e.g., methyl); and $C_3$-$C_6$ cycloalkyl (e.g., cyclopropyl).

Examples of preferable compounds of the compound of the present invention include the compounds of Examples 1-355, more preferably the compounds of Examples 1, 3, 5, 6, 8, 22, 49, 50, 59, 80, 91, 124, 150, 152, 186, 240, 245, 257, 272, 276, 278, 280, 325 and 329.

In the present invention, the "pharmacologically acceptable salt" is not particularly limited as long as it is acceptable as a medicament, and salt with inorganic acid, salt with organic acid, salt with alkali metal, salt with alkaline earth metal, salt with inorganic base, and salt with organic base can be mentioned. In the present specification, the salt also includes hydrate and solvate.

The "pharmacologically acceptable" in the present specification means being generally safe and harmless, and may be biologically undesirable but preferable in other aspects, and include those useful for the preparation of pharmaceutical compositions usable as medicament for human as well as veterinary medicine.

While the compound of the present invention can be produced by the following methods, the production methods are not limited.

The compound (I) of the present invention can be produced by the following Method A, B, C, D, E or F.

(Method A)

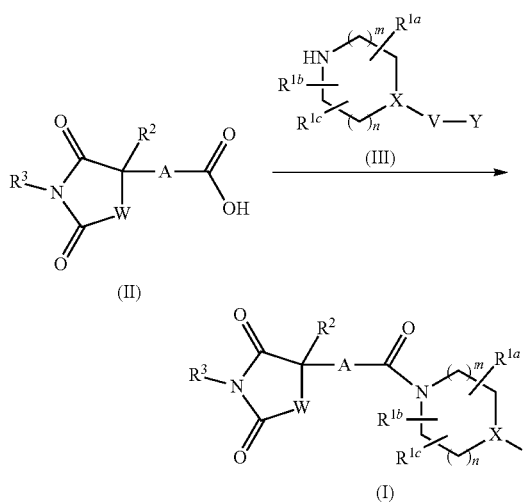

wherein the symbols are as defined above.

By reacting a compound represented by the formula (II) with a compound represented by the formula (III), the corresponding compound represented by the formula (I) can be obtained. The reaction proceeds using a condensing agent in a suitable solvent at 0° C.—room temperature. Examples of the condensing agent include 4-(4,6-dimethoxy[1.3.5]triazin-2-yl)-4-methylmorpholinium chloride hydrate (DMT-MM), 1-ethyl-3-(3'-dimethylaminopropyl)carbodiimide hydrochloride (WSC HCl) and the like. Examples of the solvent include methanol, N,N-dimethylformamide, chloroform, tetrahydrofuran and the like. The reaction may be promoted by the addition of 1-hydroxybenzotriazole (HOBt). When a compound represented by the formula (III) forms a salt with an acid, the reaction proceeds by neutralization by the addition of a base.

(Method B)

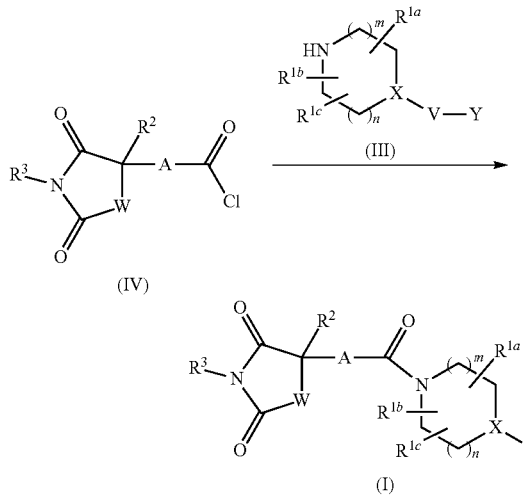

wherein the symbols are as defined above.

By reacting a compound represented by the formula (IV) with a compound represented by the formula (III), the corresponding compound represented by the formula (I) is obtained. The reaction proceeds by using a base in a suitable solvent at 0° C.—room temperature. Examples of the base include aqueous sodium hydroxide solution, triethylamine, N-methylmorpholine, pyridine and the like. Examples of the solvent include tetrahydrofuran, dimethoxyethane, ethyl acetate, pyridine and the like.

(Method C)
Step 1

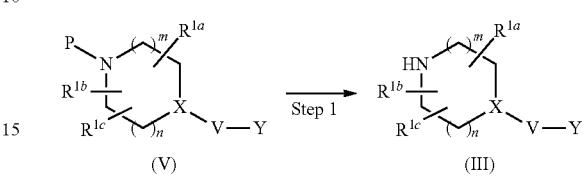

wherein P is an amino-protecting group, and other symbols are as defined above.

By subjecting protecting group P of a compound represented by the formula (V) to deprotection, a compound represented by the formula (III) is obtained. When, for example, P in the formula is Boc group, the reaction proceeds using an acid in a suitable solvent at 0° C.—room temperature. Examples of the acid include hydrogen chloride/ethyl acetate, hydrogen chloride/1,4-dioxane and the like. Examples of the solvent include chloroform, ethyl acetate, 1,4-dioxane, ethanol, methanol and the like.

Step 2

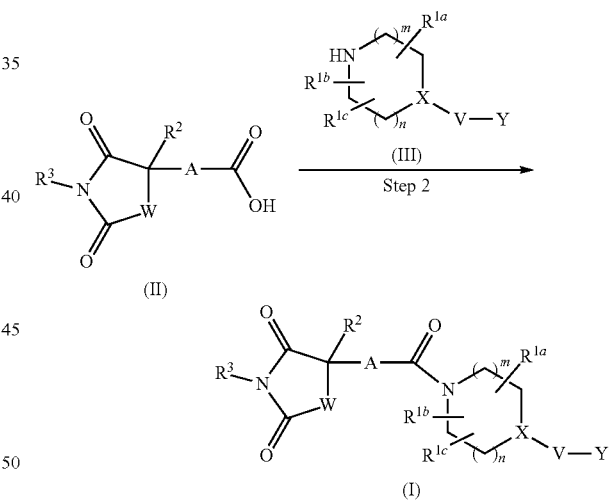

wherein the symbols are as defined above.

By reacting a compound represented by the formula (II) with a compound represented by the formula (III), the corresponding compound represented by the formula (I) can be obtained. The reaction proceeds using a condensing agent in a suitable solvent at 0° C.—room temperature. Examples of the condensing agent include 4-(4,6-dimethoxy[1.3.5]triazin-2-yl)-4-methylmorpholinium chloride hydrate (DMT-MM), 1-ethyl-3-(3'-dimethylaminopropyl)carbodiimide hydrochloride (WSC HCl) and the like. Examples of the solvent include methanol, N,N-dimethylformamide, chloroform, tetrahydrofuran and the like. The reaction may be promoted by the addition of 1-hydroxybenzotriazole (HOBt). When a compound represented by the formula (III)

forms a salt with an acid, the reaction proceeds by neutralization by the addition of a base.

(Method D: The Formula (I) Wherein R³ is a Group Other than a Hydrogen Atom)

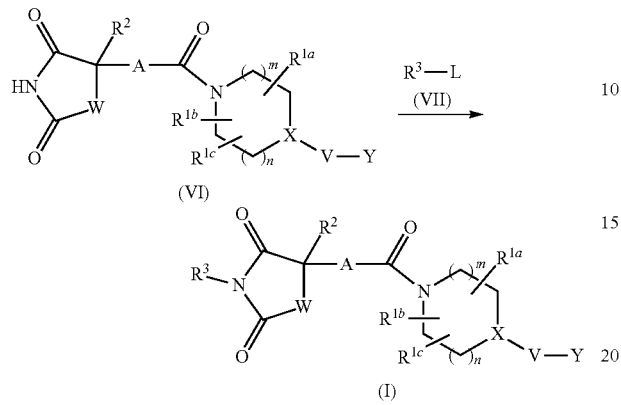

wherein L is a leaving group such as a halogen atom and the like, R³ is C₁-C₆ alkyl optionally substituted by amino optionally mono- or di-substituted by C₁-C₆ alkyl, a halogen atom, a hydroxyl group, C₁-C₆ alkoxy or C₂-C₇ acyloxy; C₃-C₆ cycloalkyl; arylalkyl wherein the C₆-C₁₀ aryl moiety is optionally substituted by a halogen atom, a hydroxyl group, C₁-C₆ alkoxy, C₁-C₆ alkyl or amino, and the alkyl moiety has a carbon number of 1-6; or heteroarylalkyl wherein the heteroaryl moiety containing 1-6 atoms selected from a nitrogen atom, an oxygen atom and a sulfur atom and having 5 to ring-constituting atoms is optionally substituted by a halogen atom, a hydroxyl group, C₁-C₆ alkoxy, C₁-C₆ alkyl or amino and the alkyl moiety has a carbon number of 1-6, and other symbols are as defined above.

By reacting a compound represented by the formula (VI) with a compound represented by the formula (VII), the corresponding compound represented by the formula (I) is obtained. The reaction proceeds using a base in a suitable solvent at 0° C.-100° C. Examples of the base include potassium carbonate, sodium hydrogen carbonate and the like. Examples of the solvent include N,N-dimethylformamide and the like.

When R³ is C₁-C₆ alkyl optionally substituted by amino optionally mono-substituted by C₁-C₆ alkyl, the above-mentioned reaction is performed using the formula (VII) protected by a suitable amino-protecting group and deprotection is performed to give the corresponding compound represented by the formula (I).

(Method E: the formula (I) wherein W is —N(Rˣ)— wherein Rˣ is C₁-C₆ alkyl optionally substituted by a substituent selected from a halogen atom, a hydroxyl group and C₁-C₆ alkoxy)

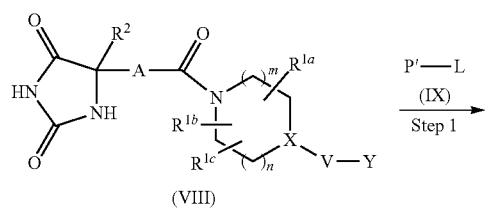

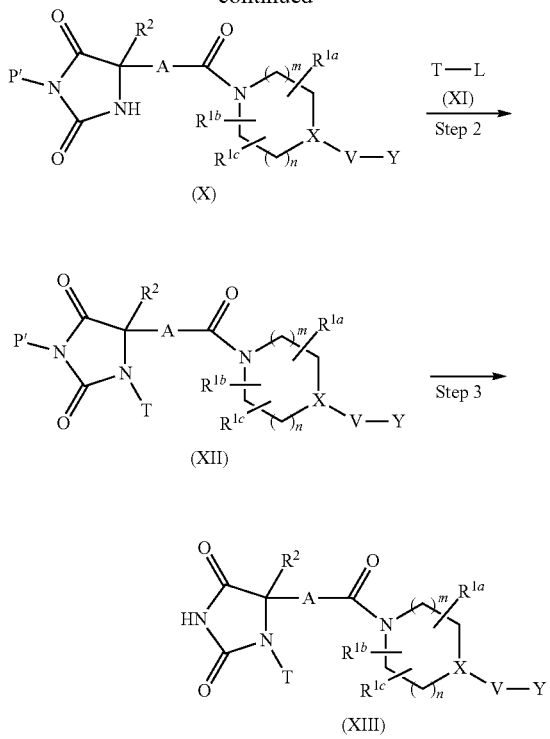

wherein P' is a protecting group, T is C₁-C₆ alkyl optionally substituted by a substituent selected from a halogen atom, a hydroxyl group and C₁-C₆ alkoxy, and other symbols are as defined above.

Step 1

By reacting a compound represented by the formula (VIII) with a compound represented by the formula (IX), the corresponding compound represented by the formula (X) is obtained. The reaction proceeds using a base in a suitable solvent at 0° C.-100° C. Examples of the base include potassium carbonate, sodium hydrogen carbonate and the like. Examples of the solvent include N,N-dimethylformamide, tetrahydrofuran and the like.

Step 2

By reacting a compound represented by the formula (X) with a compound represented by the formula (XI), the corresponding compound represented by the formula (XII) is obtained. The reaction proceeds using a base in a suitable solvent at 0° C.-100° C. Examples of the base include potassium carbonate, sodium hydride and the like. Examples of the solvent include N,N-dimethylformamide, tetrahydrofuran and the like.

Step 3

By subjecting protecting group P' of a compound represented by the formula (XII) to deprotection, a compound represented by the formula (XIII) is obtained. For example, when P' in the formula is a 4-methoxybenzyl group, the reaction proceeds using an acid in a suitable solvent at 0° C.-100° C. Examples of the acid include trifluoromethanesulfonic acid, trifluoromethanesulfonic anhydride and the like. Examples of the solvent include 1,2-dichloroethane and the like.

(F Method: The Formula (I) Wherein $R^{1a}$ is $C_1$-$C_6$ Alkyl Substituted by a Hydroxyl Group)

Step 1

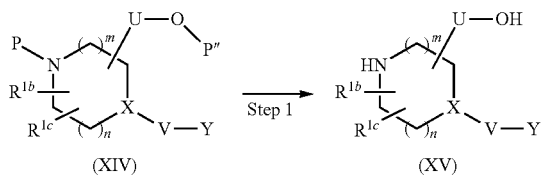

wherein P''' is a hydroxyl-protecting group, U is alkylene having 1-6 carbon atoms, and other symbols are as defined above.

By removing the protecting groups P, P''' of the compound represented by the formula (XIV), a compound represented by the formula (XV) is obtained. For example, when P in the formula is a Boc group and P''' in the formula is a TBS group, the reaction proceeds using an acid in a suitable solvent at 0° C.—room temperature. Examples of the acid include hydrogen chloride/ethyl acetate, hydrogen chloride/1,4-dioxane and the like. Examples of the solvent include chloroform, ethyl acetate, 1,4-dioxane, ethanol, methanol and the like.

Step 2

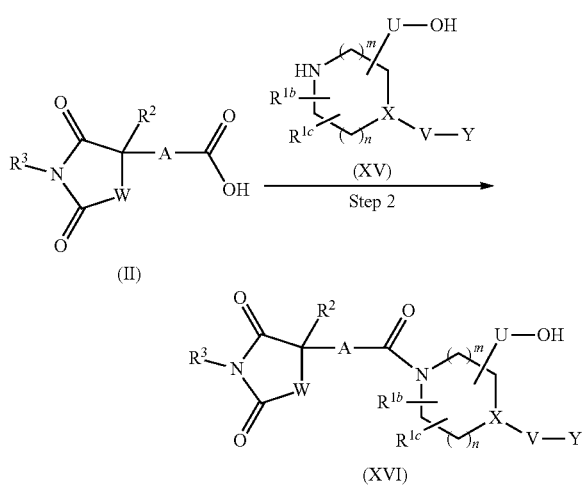

wherein $R^3$ is a hydrogen atom; $C_1$-$C_6$ alkyl optionally substituted by amino optionally mono- or di-substituted by $C_1$-$C_6$ alkyl, a halogen atom, a hydroxyl group, $C_1$-$C_6$ alkoxy or $C_2$-$C_7$ acyloxy; $C_3$-$C_6$ cycloalkyl; arylalkyl wherein the $C_6$-$C_{10}$ aryl moiety is optionally substituted by a halogen atom, a hydroxyl group, $C_1$-$C_6$ alkoxy, $C_1$-$C_6$ alkyl or amino, and the alkyl moiety has a carbon number of 1-6; or heteroarylalkyl wherein the heteroaryl moiety containing 1-6 atoms selected from a nitrogen atom, an oxygen atom and a sulfur atom and having 5 to 10 ring-constituting atoms is optionally substituted by a halogen atom, a hydroxyl group, $C_1$-$C_6$ alkoxy, $C_1$-$C_6$ alkyl or amino and the alkyl moiety has a carbon number of 1-6, and other symbols are as defined above.

By reacting a compound represented by the formula (II) with a compound represented by the formula (XV), the corresponding compound represented by the formula (XVI) can be obtained. The reaction proceeds using a condensing agent in a suitable solvent at 0° C.—room temperature. Examples of the condensing agent include 4-(4,6-dimethoxy[1.3.5]triazin-2-yl)-4-methylmorpholinium chloride hydrate (DMT-MM), 1-ethyl-3-(3'-dimethylaminopropyl)carbodiimide hydrochloride (WSC HCl) and the like. Examples of the solvent include methanol, N,N-dimethylformamide, chloroform, tetrahydrofuran and the like. The reaction may be promoted by the addition of 1-hydroxybenzotriazole (HOBt). When a compound represented by the formula (XV) forms a salt with an acid, the reaction proceeds by neutralization by the addition of a base.

The imide derivative of the formula (I), which was produced by the aforementioned method, can be purified to any purity by a conventionally-used purification means, for example, concentration, extraction, chromatography, reprecipitation, recrystallization and the like. In addition, it can be converted to a pharmacologically acceptable salt as necessary by treatment with an acid or base etc. in a suitable solvent (water, alcohol, ether etc.). Furthermore, the obtained compound of the present invention or a pharmacologically acceptable salt thereof can be converted to a hydrate or solvate thereof by treatment with water, water-containing solvent or other solvent (e.g., alcohol etc.).

The imide derivative and a pharmacologically acceptable salt thereof of the present invention include racemic compounds, stereoisomers, and mixture of these compounds, and includes isotope-labeled and radioactivity-labeled compounds. Such isomers can be isolated by a standard separation technique including fractional crystallization and chiral column chromatography. In addition, the compound of the present invention has an asymmetric carbon atom. Therefore, it includes enantiomer and diastereomer. A diastereomer mixture can be separated into each diastereomer based on their physical/chemical differences by a method well known in the art, for example, chromatography and/or fractional crystallization. Enantiomer can be separated by chiral column chromatography or by reacting an enantiomer compound with an appropriate optically active compound to give a diastereomer mixture, separating each diastereomer and converting each diastereomer to a corresponding enantiomer. All such isomers including diastereomer, enantiomer and a mixture thereof are a part of the compound of the present invention.

The compound of the present invention has a MMP-9 selective production suppressive action, and can be used as a prophylactic medicament or a therapeutic drug for autoimmune diseases represented by rheumatoid arthritis, multiple sclerosis, systemic lupus erythematosus and the like, inflammatory bowel diseases (ulcerative colitis, Crohn's disease) or osteoarthritis.

In the present invention, "prophylaxis" means an act of administering the compound of the present invention or a pharmaceutical composition containing the compound to an individual who has not developed a disease, condition or symptom. In addition, "treatment" means an act of administering the compound of the present invention or a pharmaceutical composition containing the compound to an individual who has developed a disease, condition or symptom. Therefore, an act of administration to an individual who has developed a disease, condition or symptom, for the prevention of aggravation of the symptom and the like, and for the prevention of attack and recurrence is one embodiment of the "treatment".

When the compound of the present invention is used as a medicament, the compound of the present invention is mixed with a pharmaceutically acceptable additive (excipient, binder, disintegrant, corrigent, flavor, emulsifier, diluent, solubilizing agents and the like) to give a pharmaceutical composition which can be orally or parenterally administered. A pharmaceutical composition can be formulated by a general method.

In the present specification, parenteral includes subcutaneous injection, intravenous injection, intramuscular injection, intraperitoneal injection, drip or topical administration (intraarticular administration, transdermal administration, transocular administration, transpulmonary or bronchial administration, transnasal administration, transrectal administration and the like) and the like.

The dose of the compound of the present invention is determined according to the age, body weight, general health condition, sex, diet, administration time, administration method, clearance rate, and the level of disease for which patients are undergoing treatments at that time, or further in consideration of other factors. While the daily dose of the compound of the present invention varies depending on the condition and body weight of patient, the kind of the compound, administration route and the like, it is parenterally administered at, for example, about 0.001 to 100 mg/patient/day by subcutaneous, intravenous, intramuscular, intraarticular, transdermal, transocular, transpulmonary or bronchial, transnasal or rectal administration, or about 0.01 to 1000 mg/patient/day by oral administration.

EXAMPLES

The present invention is explained in more detail in the following by referring to Preparation Examples, Examples and Experimental Examples, which do not limit the present invention in any way.

Preparation Example 1: Preparation of 4-(4-ethyl-2,5-dioxoimidazolidin-4-yl)benzoic acid

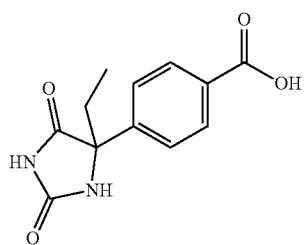 [SMILES: CCC1(c2ccc(C(=O)O)cc2)NC(=O)NC1=O]

To 5-ethyl-5-(4-methylphenyl)imidazolidine-2,4-dione (1.01 g) were added water (40 mL), 1N aqueous sodium hydroxide solution (7.7 mL) and potassium permanganate (2.26 g) and the mixture was stirred at room temperature for 30 min and at 80° C. for 1 hr 30 min. The reaction mixture was cooled to room temperature and poured into a mixture of ice and concentrated hydrochloric acid, and ethyl acetate and saturated brine were added. After filtration through celite, the filtrate was extracted with ethyl acetate. The organic layer was washed with saturated brine, and dried over sodium sulfate. After treatment with activated carbon, the filtrate was concentrated under reduced pressure. To the obtained residue was added hexane/ethyl acetate, and the precipitate was collected by filtration to give the title compound (989 mg).

MS (ESI) m/z: 249 (M+H)$^+$

Preparation Example 2: Preparation of 2-fluoro-4-(4-methyl-2,5-dioxoimidazolidin-4-yl)benzoic acid

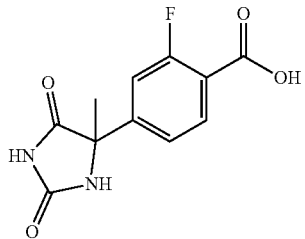

To 1-(3-fluoro-4-methylphenyl)ethanone (5.20 g) were added ethanol (20.6 mL) and 28% aqueous ammonia (15.5 mL), then ammonium carbonate (13.12 g), potassium carbonate (5.66 g) and trimethylsilyl cyanide (5.33 mL) and the mixture was stirred at room temperature for 4 days. The reaction mixture was ice-cooled and acidified by dropwise addition of concentrated hydrochloric acid. The precipitated solid was collected by filtration to give 5-(3-fluoro-4-methylphenyl)-5-methylimidazolidine-2,4-dione (7.02 g).

To be obtained 5-(3-fluoro-4-methylphenyl)-5-methylimidazolidine-2,4-dione (3.00 g) were added water (30 mL), 1N aqueous sodium hydroxide solution (27 mL) and potassium permanganate (6.61 g) and the mixture was stirred at room temperature for 30 min and 80° C. for 90 min. The reaction mixture was ice-cooled, ethanol (30 mL) was added slowly, and the mixture was stirred at the same temperature for 10 min and at room temperature for 1 hr. After filtration through celite, the filtrate was concentrated under reduced pressure, and ethanol was evaporated. The remaining aqueous solution was ice-cooled and acidified with concentrated hydrochloric acid. Sodium chloride was added and the mixture was extracted with ethyl acetate. The organic layer was washed with saturated brine and dried over sodium sulfate. The solvent was evaporated, acetic acid (50 mL) was added to the obtained residue and the mixture was stirred with heating under reflux for 2 hr. The reaction mixture was concentrated under reduced pressure. To the obtained residue was added hexane/ethyl acetate, and the precipitate was collected by filtration to give the title compound (2.05 g).

MS(ESI) m/z: 251 (M−H)$^−$

Preparation Example 3: Preparation of 2-bromo-4-(4-methyl-2,5-dioxoimidazolidin-4-yl)benzoic acid

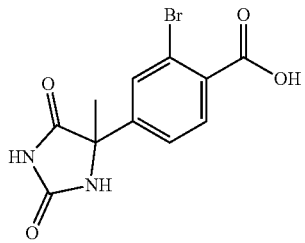 [SMILES: CC1(c2ccc(C(=O)O)c(Br)c2)NC(=O)NC1=O]

To a suspension of 1-(3-bromo-4-methylphenyl)ethanone (3.97 g), ethanol (7.5 mL), 28% aqueous ammonia (5.6 mL), ammonium carbonate (7.16 g) and potassium carbonate (3.08 g) was added trimethylsilyl cyanide (2.79 mL) and the mixture was stirred at room temperature for 16 hr and further at 60° C. for 6 hr. Water was added to the reaction mixture, and the precipitated crystal was collected by filtration to give 5-(3-bromo-4-methylphenyl)-5-methylimidazolidine-2,4-dione (4.4 g).

A mixed solution of the obtained 5-(3-bromo-4-methylphenyl)-5-methylimidazolidine-2,4-dione (4.0 g) and potassium permanganate (6.7 g) in 1N aqueous sodium hydroxide solution (28 mL) and water (113 mL) was stirred at 95° C. for 2 hr and at room temperature for 1.5 hr. To the reaction mixture was added ethanol (20 mL) and the mixture was stirred for 1 hr. After filtration through celite, the filtrate was concentrated under reduced pressure, and ethanol was evaporated. The resulting aqueous solution was acidified with 1N hydrochloric acid and extracted with ethyl acetate. The solvent was evaporated, to the obtained residue was added acetic acid (20 mL) and the mixture was stirred at 100° C. for 2 hr. The reaction mixture was concentrated under reduced pressure, to the obtained residue was added hexane/ethyl acetate, and the precipitate was collected by filtration to give the title compound (3.94 g).

MS (ESI) m/z: 313 (M+H)+

Preparation Example 4: Preparation of 5-(4-methyl-2,5-dioxoimidazolidin-4-yl)pyridine-2-carboxylic acid

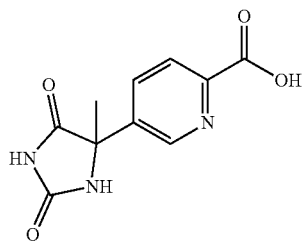 [SMILES: CC1(c2ccc(C(=O)O)nc2)NC(=O)NC1=O]

To 1-(6-methylpyridin-3-yl)ethanone (3.00 g) were added ethanol (12 mL) and 28% aqueous ammonia (9 mL) and then ammonium carbonate (8.53 g), potassium carbonate (3.68 g) and trimethylsilyl cyanide (3.46 mL) and the mixture was stirred at room temperature for 5 days. The reaction mixture was concentrated under reduced pressure, to the obtained residue was added water, and the mixture was neutralized with concentrated hydrochloric acid. Sodium chloride was added and the mixture was extracted with ethyl acetate/tetrahydrofuran. The organic layer was washed with saturated brine, dried over sodium sulfate, and the solvent was evaporated. The obtained residue was recrystallized from hexane/ethyl acetate to give 5-methyl-5-(6-methylpyridin-3-yl)imidazolidine-2,4-dione (4.18 g)

To the obtained 5-methyl-5-(6-methylpyridin-3-yl)imidazolidine-2,4-dione (3.67 g) were added water (50 mL), 1N aqueous sodium hydroxide solution (21.5 mL) and potassium permanganate (8.76 g) and the mixture was stirred at 60° C. for 2 hr and 80° C. for 3 hr. The reaction mixture was cooled to room temperature, ethanol (30 mL) was added, and the mixture was stirred at room temperature overnight. To the reaction mixture was added activated carbon and the mixture was filtered. The filtrate was concentrated under reduced pressure and ethanol was evaporated. To the residue was added water, and concentrated hydrochloric acid was added under ice-cooling (pH 4-5). The precipitate was collected by filtration to give the title compound (3.27 g).

MS(ESI) m/z: 236 (M+H)+

Preparation Example 5: Preparation of 4-(4-isopropyl-2,5-dioxoimidazolidin-4-yl)benzoic acid

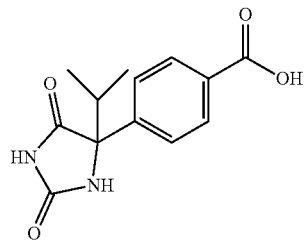 [SMILES: CC(C)C1(c2ccc(C(=O)O)cc2)NC(=O)NC1=O]

To 5-isopropyl-5-(p-tolyl)imidazolidine-2,4-dione (450 mg) were added 1N aqueous sodium hydroxide solution (4.0 mL) and potassium permanganate (920 mg) and the mixture was stirred at room temperature for 3 hr and at 70° C. for 2 hr. To the reaction mixture was added ethanol under ice-cooling, and the mixture was stirred at for 3 hr. After filtration through celite, the filtrate was concentrated under reduced pressure. To the obtained residue were added water and 1N hydrochloric acid, and the precipitate was collected by filtration to give the title compound (350 mg).

MS(ESI) m/z: 261 (M−H)−

Preparation Example 6: Preparation of 4-((R)-4-methyl-2,5-dioxoimidazolidin-4-yl)benzoic acid

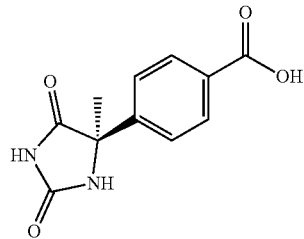

To (R)-5-methyl-5-(p-tolyl)imidazolidine-2,4-dione (2.21 g) synthesized according to the method described Chirality, 4, pages 400-403 (1992) were added potassium permanganate (6.84 g), 1N aqueous sodium hydroxide solution (21.6 mL), water (86 mL) and the mixture was stirred at 95° C. for 4 hr. At room temperature, ethanol (20 mL) was added, and the mixture was stirred for 1 hr. After filtration through celite, 1N hydrochloric acid was added to the filtrate (about pH 4), and the mixture was extracted with ethyl acetate. After washing with saturated brine, the solvent was evaporated under reduced pressure. To the residue was added acetic acid (50 mL) and the mixture was stirred at 110° C. for 1 hr. The insoluble material was removed by filtering hot, and the filtrate was concentrated under reduced pressure. To the obtained residue was added hexane/ethyl acetate, and the precipitate was collected by filtration to give the title compound (1.7 g).

MS(ESI) m/z: 235 (M+H)+

Preparation Example 7: Preparation of 4-(4-butyl-2,5-dioxoimidazolidin-4-yl)benzoic acid

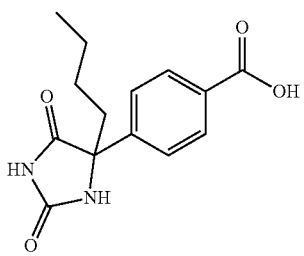 [SMILES: CCCCC1(c2ccc(C(=O)O)cc2)NC(=O)NC1=O]

To a mixture of 4-methylvalerophenone (1.00 g), ammonium carbonate (2.18 g), potassium carbonate (0.94 g) and 28% aqueous ammonia solution (1.98 mL) were successively added ethanol (2.84 mL) and trimethylsilyl cyanide (0.851 mL) and the mixture was stirred at 60° C. for 8 hr. Water was added to the reaction mixture, and the mixture was extracted with ethyl acetate. The organic layer was dried over anhydrous sodium sulfate and concentrated under reduced pressure. To the obtained residue was added hexane/ethyl acetate, and the precipitate was collected by filtration to give 5-butyl-5-(p-tolyl)imidazolidine-2,4-dione (0.449 g).

To the obtained 5-butyl-5-(p-tolyl)imidazolidine-2,4-dione (0.444 g) were added 1N aqueous sodium hydroxide solution (3.6 mL), potassium permanganate (0.853 g) and water (14.4 mL) and the mixture was stirred at 95° C. for 2 hr. The reaction mixture was allowed to cool to room temperature, ethanol (3.4 mL) was added and the mixture was stirred for 1 hr. After filtration through celite, to the filtrate was added 1N hydrochloric acid (7.5 mL) and the mixture was extracted with ethyl acetate. The organic layer was dried over anhydrous sodium sulfate and concentrated under reduced pressure to give the title compound (0.472 g).

MS(ESI) m/z: 277 (M+H)+

Preparation Example 8: Preparation of 2-methyl-4-(4-methyl-2,5-dioxoimidazolidin-4-yl)benzoic acid

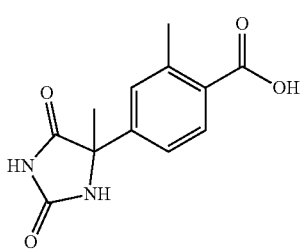 [SMILES: Cc1cc(C2(C)NC(=O)NC2=O)ccc1C(=O)O]

To 4-acetyl-2-methylbenzoic acid methyl ester (1 g) were added ethanol (4 mL), 28% aqueous ammonia solution (3 mL), ammonium carbonate (2 g), trimethylsilyl cyanide (0.774 mL) and potassium carbonate (0.863 g) and the mixture was stirred at 60° C. for 6 hr. A 28% aqueous ammonia solution (1.5 mL) was added, and the mixture was stirred at 60° C. for 1.5 hr. The reaction mixture was acidified by adding water and concentrated hydrochloric acid under ice-cooling, and the precipitate was collected by filtration. The obtained precipitate was suspended in hexane/ethyl acetate, and collected by filtration to give 2-methyl-4-(4-methyl-2,5-dioxoimidazolidin-4-yl)benzoic acid methyl ester (0.975 g).

The obtained 2-methyl-4-(4-methyl-2,5-dioxoimidazolidin-4-yl)benzoic acid methyl ester (0.872 g) was dissolved in acetic acid (13 mL), concentrated hydrochloric acid (13 mL) was added and the mixture was stirred at 80° C. for 15 hr. The reaction mixture was concentrated under reduced pressure, to the obtained residue was added water and the precipitate was collected by filtration to give the title compound (0.794 g).

MS(ESI) m/z: 247 (M−H)−

Preparation Example 9: Preparation of 4-(4-methoxymethyl-2,5-dioxoimidazolidin-4-yl)benzoic acid

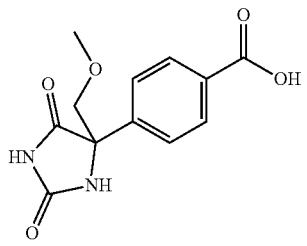 [SMILES: COCC1(c2ccc(C(=O)O)cc2)NC(=O)NC1=O]

Under a nitrogen stream, a solution of 4-(chloroformyl)benzoic acid methyl ester (2.17 g) in acetonitrile (20 mL) was ice-cooled, then a 0.6 M hexane solution (36.4 mL) of trimethylsilyldiazomethane was added dropwise, and the mixture was stirred at room temperature for 2 hr. The reaction mixture was ice-cooled, methanol (10 mL) and boron trifluoride diethyl ether (2.05 mL) were added, and the mixture was stirred for 2 hr. To the reaction mixture was added ethyl acetate, and the organic layer was washed with saturated brine and dried over sodium sulfate. The solvent was evaporated and the obtained residue was purified by column chromatography (hexane:ethyl acetate) to give 4-(2-methoxyacetyl)benzoic acid methyl ester (1.68 g).

To the obtained 4-(2-methoxyacetyl)benzoic acid methyl ester (916 mg) were added 28% ammonium water (2 mL) and ethanol (5 mL), then ammonium carbonate (1.69 g), potassium carbonate (1.22 g) and trimethylsilyl cyanide (1.14 mL) were added, and the mixture was stirred at room temperature for 8 days. The reaction mixture was ice-cooled, acidified by adding water (10 mL) and concentrated sulfuric acid (30 mL) and stirred at 100° C. for 2 hr and 120° C. for 3 hr. Under ice-cooling, to the reaction mixture was added saturated brine, and the mixture was extracted with ethyl acetate. The organic layer was washed with saturated brine and dried over sodium sulfate. The solvent was evaporated and to the obtained residue was added hexane/ethyl acetate, and the precipitate was collected by filtration to give the title compound (759 mg).

MS(ESI) m/z: 263 (M−H)−

Preparation Example 10: Preparation of 4-(2,5-dioxo-4-trifluoromethylimidazolidin-4-yl)benzoic acid

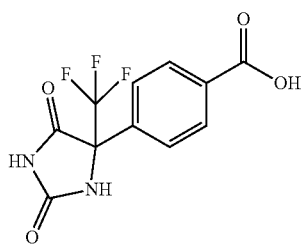 [SMILES: O=C1NC(=O)C(c2ccc(C(=O)O)cc2)(C(F)(F)F)N1]

To 4-(trifluoroacetyl)benzoic acid (218 mg) were added 28% aqueous ammonia (1 mL) and water (1 mL), then ammonium carbonate (768 mg), potassium carbonate (828 mg) and trimethylsilyl cyanide (0.52 mL) were added, and the mixture was stirred at room temperature for 4 hr and 80° C. for 8 hr. The reaction mixture was ice-cooled, acidified by adding concentrated hydrochloric acid, saturated brine was added, and the mixture was extracted with ethyl acetate. The organic layer was washed with saturated brine and dried over sodium sulfate. The solvent was evaporated and hexane/ethyl acetate was added to the obtained residue. The precipitate was collected by filtration to give the title compound (136 mg).

MS(ESI) m/z: 287 (M−H)⁻

Preparation Example 11: Preparation of 4-(4-cyclopropyl-2,5-dioxoimidazolidin-4-yl)benzoic acid

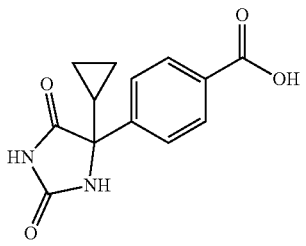 [SMILES: O=C1NC(=O)C(c2ccc(C(=O)O)cc2)(C2CC2)N1]

4-Cyclopropanecarbonylbenzoic acid methyl ester (488 mg) was dissolved in tetrahydrofuran (5 mL) and methanol (3 mL) and, under ice-cooling, 1N aqueous sodium hydroxide solution (3.59 mL) was added and the mixture was stirred for 30 min and at room temperature for 2 hr. The reaction mixture was ice-cooled, 1N hydrochloric acid (5 mL) was added, and the mixture was extracted with ethyl acetate. The organic layer was washed with saturated brine and dried over sodium sulfate. The solvent was evaporated to give 4-cyclopropanecarbonylbenzoic acid (441 mg).

To the obtained 4-cyclopropanecarbonylbenzoic acid (433 mg) were added 28% aqueous ammonia (6 mL), water (2 mL), ammonium carbonate (2.62 g), potassium carbonate (1.89 mg) and trimethylsilyl cyanide (1.69 mL) and the mixture was stirred at 80° C. for 34 hr. Under ice-cooling, the reaction mixture was acidified by adding water and concentrated hydrochloric acid, and extracted with ethyl acetate. The organic layer was washed with saturated brine, dried over anhydrous sodium sulfate, and the solvent was evaporated. To the obtained residue was added hexane/ethyl acetate, and the precipitate was collected by filtration to give the title compound (589 mg).

MS(ESI) m/z: 259 (M−H)⁻

Preparation Example 12: Preparation of 4-(4-ethyl-2,5-dioxoimidazolidin-4-yl)-2-fluorobenzoic acid

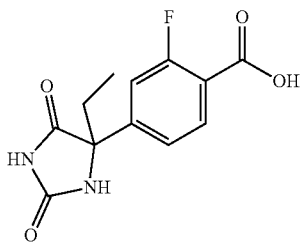 [SMILES: CCC1(c2ccc(C(=O)O)c(F)c2)NC(=O)NC1=O]

To 1-(3-fluoro-4-methylphenyl)propan-1-one (3.84 g) were added ethanol (30 mL), 28% aqueous ammonia (15 mL), ammonium carbonate (6.82 g), potassium carbonate (4.91 g) and trimethylsilyl cyanide (4.6 mL) and the mixture was stirred at room temperature for 20 hr and 80° C. for 20 hr. 28% Aqueous ammonia (15 mL), ammonium carbonate (6.82 g), potassium carbonate (4.91 g) and trimethylsilyl cyanide (4.6 mL) were added, and the mixture was stirred at room temperature for 4 days. The reaction mixture was acidified by adding water and concentrated hydrochloric acid and extracted with ethyl acetate. The organic layer was washed with saturated brine, dried over sodium sulfate, and the solvent was evaporated. To the obtained residue was added hexane/ethyl acetate, and the precipitate was collected by filtration to give 5-ethyl-5-(3-fluoro-4-methylphenyl)imidazolidine-2,4-dione (3.56 g).

To the obtained 5-ethyl-5-(3-fluoro-4-methylphenyl)imidazolidine-2,4-dione (1.59 g) were added water (16 mL), 12N aqueous sodium hydroxide solution (3.37 mL) and potassium permanganate (3.30 g) and the mixture was stirred at 80° C. for 2.5 hr. The reaction mixture was ice-cooled, ethanol (15 mL) was added, and the mixture was stirred at room temperature for 30 min. The reaction mixture was filtered through celite, and the filtrate was concentrated under reduced pressure. The remaining aqueous solution was acidified with concentrated hydrochloric acid under ice-cooling. Saturated brine was added and the mixture was extracted with ethyl acetate/tetrahydrofuran. The solvent was evaporated and acetic acid (20 mL) was added to the obtained residue. The mixture was stirred with heating under reflux for 1 hr. The reaction mixture was concentrated under reduced pressure to give the title compound (1.52 g).

MS(ESI) m/z: 265 (M−H)⁻

Preparation Example 13: Preparation of 4-(4-tert-butyl-2,5-dioxoimidazolidin-4-yl)benzoic acid

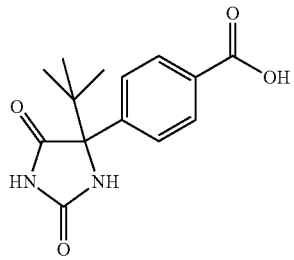 [SMILES: CC(C)(C)C1(c2ccc(C(=O)O)cc2)NC(=O)NC1=O]

To a mixture of 2,2-dimethyl-1-(4-methylphenyl)propan-1-one (9.85 g), tert-butanol (100 mL) and water (50 mL) were added 4N aqueous sodium hydroxide solution (27.9 mL) and potassium permanganate (30.91 g) and the mixture was stirred at 60° C. for 3 days. The reaction mixture was ice-cooled, ethanol (100 mL) was added, and the mixture was stirred at room temperature. To the reaction mixture was added activated carbon, and the mixture was filtered. The filtrate was acidified with concentrated hydrochloric acid, and the mixture was concentrated under reduced pressure (evaporation of ethanol). The precipitate was collected by filtration to give 4-(2,2-dimethylpropionyl)benzoic acid (10.2 g).

To 4-(2,2-dimethylpropionyl)benzoic acid (4 g) were added 28% aqueous ammonia (20 mL), ammonium carbonate (7.44 g), potassium carbonate (5.36 g) and trimethylsilyl cyanide (5.04 mL) and the mixture was stirred under microwave irradiation at 120° C. for 1 hr. The reaction mixture was acidified under ice-cooling by adding concentrated hydrochloric acid. The precipitate was collected by filtration to give the title compound (5.32 g).

MS(ESI) m/z: 275 (M−H)⁻

Preparation Example 14: Preparation of 4-((R)-4-ethyl-2,5-dioxoimidazolidin-4-yl)benzoic acid

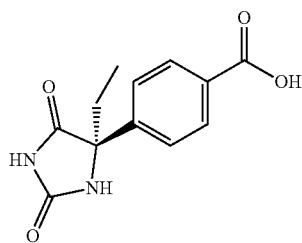 [SMILES: CC[C@]1(c2ccc(C(=O)O)cc2)NC(=O)NC1=O]

(2R)-2-amino-2-(4-methylphenyl)carboxylic acid. hydrochloride (965 mg) was dissolved in water (10 mL), sodium cyanide (812 mg) was added, and the mixture was stirred at room temperature for 16.5 hr and 100° C. for 2.5 hr. The reaction mixture was allowed to cool to room temperature, 1N hydrochloric acid was added, and the mixture was extracted with ethyl acetate. The organic layer was washed with saturated brine, dried over anhydrous magnesium sulfate and concentrated under reduced pressure. The obtained residue was dissolved in acetic acid and the mixture was stirred at 70° C. for 2.5 hr. The reaction mixture was concentrated under reduced pressure, to the obtained residue was added 1N hydrochloric acid, and the mixture was extracted with ethyl acetate. The organic layer was washed with saturated brine, dried over anhydrous magnesium sulfate and concentrated under reduced pressure. To the obtained residue was added hexane/ethyl acetate, and the precipitate was collected by filtration to give (R)-5-ethyl-5-(p-tolyl)imidazolidine-2,4-dione (720 mg).

To the obtained (R)-5-ethyl-5-(p-tolyl)imidazolidine-2,4-dione (550 mg) were added 1N aqueous sodium hydroxide solution (7.5 mL), potassium permanganate (996 mg) and water (2.5 mL) and the mixture was stirred at 70° C. for 2 hr. To the reaction mixture was added ethanol, and the mixture was stirred at room temperature for 20 min. After filtration through celite, the filtrate was concentrated under reduced pressure. To the remaining aqueous solution was added 1N hydrochloric acid (pH<2), and the precipitate was collected by filtration to give the title compound (560 mg).

MS(APCI) m/z: 247 (M−H)⁻

Preparation Example 15: Preparation of 2-fluoro-4-(4-isopropyl-2,5-dioxoimidazolidin-4-yl)benzoic acid

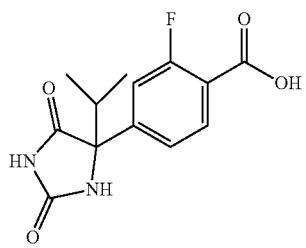 [SMILES: CC(C)C1(c2ccc(C(=O)O)c(F)c2)NC(=O)NC1=O]

To 1-(3-fluoro-4-methyl-phenyl)-2-methyl-propan-1-one (4360 mg) were added ethanol (5 mL), ammonium carbonate (768 mg), potassium carbonate (415 mg), 28% aqueous ammonia solution (5 mL) and trimethylsilyl cyanide (0.40 mL) and the mixture was stirred at 70° C. for 8 hr. To the reaction mixture was added 1N hydrochloric acid (pH<2), and the mixture was extracted with ethyl acetate. The organic layer was washed with saturated brine and dried over anhydrous magnesium sulfate. The solvent was evaporated and the obtained residue was purified by column chromatography (hexane:ethyl acetate) to give 5-(3-fluoro-4-methylphenyl)-5-isopropylimidazolidine-2,4-dione (390 mg).

The obtained 5-(3-fluoro-4-methylphenyl)-5-isopropylimidazolidine-2,4-dione (390 mg) was dissolved in 1N aqueous sodium hydroxide solution (2.8 mL), potassium permanganate (440 mg) and water (5 mL) were added and the mixture was stirred at room temperature for 9 hr. To the reaction mixture was added ethanol and the mixture was stirred at room temperature for 30 min. After filtration through celite, the filtrate was concentrated under reduced pressure. To the remaining aqueous solution was added 1N hydrochloric acid (pH<2), and the precipitate was collected by filtration to give the title compound (83 mg).

Preparation Example 16: Preparation of 4-(2,5-dioxo-4-propylimidazolidin-4-yl)benzoic acid

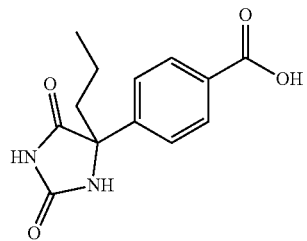 [SMILES: CCCC1(c2ccc(C(=O)O)cc2)NC(=O)NC1=O]

To a mixture of 1-(p-tolyl)butan-1-one (4.87 g), ammonium carbonate (11.5 g), potassium carbonate (4.98 g), 28% aqueous ammonia solution (10.5 mL) were successively added ethanol (15 mL) and trimethylsilyl cyanide (4.46 mL) and the mixture was stirred at 60° C. for 15 hr. The reaction mixture was allowed to cool to room temperature, water was added, and the precipitate was collected by filtration to give 5-propyl-5-(p-tolyl)imidazolidine-2,4-dione (5.58 g).

To the obtained 5-propyl-5-(p-tolyl)imidazolidine-2,4-dione (2.0 g) were added 1N aqueous sodium hydroxide solution (17.2 mL), water (69 mL) and potassium permanganate (4.08 g) and the mixture was stirred at 95° C. for 2 hr. To the reaction mixture was added ethanol, and the mixture was stirred at room temperature for 1 hr. After filtration through celite, the filtrate was concentrated under reduced pressure. To the remaining aqueous solution was added concentrated hydrochloric acid (about pH 1), and the precipitate was collected by filtration to give the title compound (2.32 g).

MS(ESI) m/z: 261 (M−H)⁻

Preparation Example 17: Preparation of 4-(2,5-dioxo-4-propylimidazolidin-4-yl)-2-fluorobenzoic acid

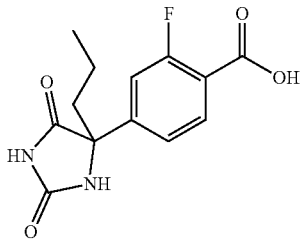 [SMILES: CCCC1(c2ccc(C(=O)O)c(F)c2)NC(=O)NC1=O]

To a solution of 1-(3-fluoro-4-methylphenyl)butan-1-one (997 mg) in ethanol (2.8 mL) were added ammonium carbonate (2.13 g), potassium carbonate (918 mg), 28% aqueous ammonia solution (1.94 mL) and trimethylsilyl cyanide (0.823 mL) and the mixture was stirred at 75° C. for 2 hr and 60° C. for 1 hr. The mixture was left standing at room temperature overnight, 28% aqueous ammonia solution (2 mL) was added, and the mixture was stirred at 60° C. for 6.5 hr. The reaction mixture was allowed to cool to room temperature, water was added, and the precipitate was collected by filtration to give 5-(3-fluoro-4-methylphenyl)-5-propylimidazolidine-2,4-dione (803 mg).

To the obtained 5-(3-fluoro-4-methylphenyl)-5-propylimidazolidine-2,4-dione (790 mg) were added 1N aqueous sodium hydroxide solution (6.31 mL), water (25.3 mL), potassium permanganate (1.50 g) and the mixture was stirred at 95° C. for 1 hr. To the reaction mixture was added ethanol, and the mixture was stirred at room temperature for 1 hr. After filtration through celite, the filtrate was concentrated under reduced pressure. The remaining aqueous solution was acidified with concentrated hydrochloric acid, and extracted with ethyl acetate. The solvent was evaporated and hexane/ethyl acetate was added to the obtained residue. The precipitate was collected by filtration to give the title compound (664 mg).

MS(ESI) m/z: 279 (M−H)−

Preparation Example 18: Preparation of 3-fluoro-4-(4-methyl-2,5-dioxoimidazolidin-4-yl)benzoic acid

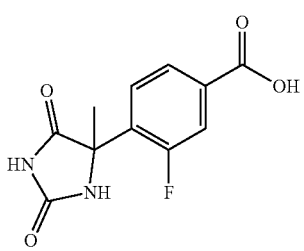 [SMILES: CC1(c2ccc(C(=O)O)cc2F)NC(=O)NC1=O]

To a suspension of 1-(2-fluoro-4-methylphenyl)ethanone (5.53 g), ethanol (14.5 mL), 28% aqueous ammonia (10 mL), ammonium carbonate (13.9 g), potassium carbonate (6.0 g) was added trimethylsilyl cyanide (5.4 mL) and the mixture was stirred at 60° C. for 2 hr and 80° C. for 1.5 hr. Water was added to the reaction mixture, and the precipitate was collected by filtration to give 5-(2-fluoro-4-methylphenyl)-5-methylimidazolidine-2,4-dione (4.69 g).

To the obtained 5-(2-fluoro-4-methylphenyl)-5-methylimidazolidine-2,4-dione (4.69 g) were added potassium permanganate (10.0 g), 1N aqueous sodium hydroxide solution (42 mL) and water (168 mL) and the mixture was stirred at 95° C. for 2.5 hr. To the reaction mixture was added ethanol (40 mL) and the mixture was stirred at room temperature. After filtration through celite, to the filtrate was added 1N hydrochloric acid (about pH 4), and the precipitate was collected by filtration to give the title compound (3.38 g).

MS(ESI) m/z: 251 (M−H)−

Preparation Example 19: Preparation of 4-(4-ethyl-2,5-dioxoimidazolidin-4-yl)-2-methylbenzoic acid

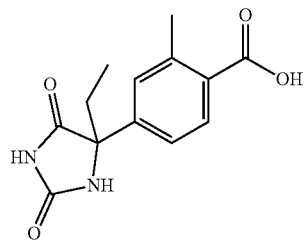 [SMILES: CCC1(c2ccc(C(=O)O)c(C)c2)NC(=O)NC1=O]

To a suspension of 1-(4-bromo-3-methylphenyl)propan-1-one (1.03 g), ethanol (4.5 mL), 28% aqueous ammonia (1.5 mL), ammonium carbonate (1.7 g), potassium carbonate (746 mg) was added trimethylsilyl cyanide (676 μL) and the mixture was stirred at room temperature for 2 hr and 60° C. for 2 hr. To the reaction mixture were added trimethylsilyl cyanide (169 μL) and potassium carbonate (186 mg) and the mixture was stirred at 60° C. for 1 hr. Water was added to the reaction mixture, and the precipitate was collected by filtration to give 5-(4-bromo-3-methylphenyl)-5-ethylimidazolidine-2,4-dione (990 mg).

A mixture of the obtained 5-(4-bromo-3-methylphenyl)-5-ethylimidazolidine-2,4-dione (985 mg), zinc cyanide (233 mg), zinc (26 mg), 1,1′-bis(diphenylphosphino)ferrocene (183 mg), tris(dibenzylideneacetone)dipalladium(0) chloroform adduct (171 mg) and N,N-dimethylacetamide (10 mL) was stirred at 130° C. for 6.5 hr. To the reaction mixture were added water and saturated aqueous sodium hydrogen carbonate solution and the mixture was filtered through celite. The filtrate was extracted with ethyl acetate, and the solvent was evaporated. The obtained residue was purified by column chromatography (hexane:ethyl acetate) to give 4-(4-ethyl-2,5-dioxoimidazolidin-4-yl)-2-methylbenzonitrile (360 mg). To the obtained 4-(4-ethyl-2,5-dioxoimidazolidin-4-yl)-2-methylbenzonitrile (360 mg) were added acetic acid (5 mL) and concentrated hydrochloric acid (5 mL) and the mixture was stirred at 80° C. for 2 days. To the reaction mixture was added concentrated sulfuric acid (2.0 mL) and the mixture was stirred at 100° C. for 1 day and 120° C. for 1 day. Water was added to the reaction mixture, and the mixture was extracted with ethyl acetate. The solvent was evaporated, water was added to the obtained residue, and the precipitate was collected by filtration to give the title compound as a crude product (270 mg).

MS(ESI) m/z: 263 (M+H)+

Preparation Example 20: Preparation of 4-(3-ethyl-2,5-dioxopyrrolidin-3-yl)benzoic acid

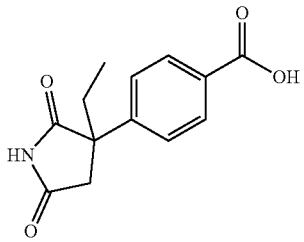 [SMILES: CCC1(c2ccc(C(=O)O)cc2)CC(=O)NC1=O]

To 3-ethyl-3-(4-methylphenyl)pyrrolidine-2,5-dione (2.0 g) were added water (40 mL), 1N aqueous sodium hydroxide solution (18.41 mL) and potassium permanganate (4.36 g) and the mixture was stirred at room temperature overnight. To the reaction mixture was added ethanol (20 mL) and the mixture was stirred for 1 hr and filtered through celite. The filtrate was concentrated under reduced pressure and acidified by adding concentrated hydrochloric acid. The precipitate was collected by filtration to give the title compound (1.63 g).

MS(ESI) m/z: 246 (M−H)$^-$

Preparation Example 21: Preparation of 3-iodo-4-(4-methyl-2,5-dioxoimidazolidin-4-yl)benzoic acid

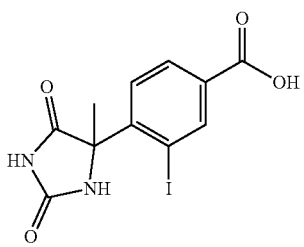 [SMILES: CC1(c2ccc(C(=O)O)cc2I)NC(=O)NC1=O]

To a suspension of 1-(2-iodo-4-methylphenyl)ethanone (3.9 g), ethanol (7.5 mL), 28% aqueous ammonia (5 mL), ammonium carbonate (5.7 g) and potassium carbonate (2.5 g) was added trimethylsilyl cyanide (2.81 mL) and the mixture was stirred at 60° C. for 4.5 hr. Water was added to the reaction mixture, and the precipitate was collected by filtration to give 5-(3-iodo-4-methylphenyl)-5-methylimidazolidine-2,4-dione (3.77 g).

To the obtained 5-(3-iodo-4-methylphenyl)-5-methylimidazolidine-2,4-dione (1.65 g) were added 1N aqueous sodium hydroxide solution (10 mL), water (40 mL) and potassium permanganate (2.37 g) and the mixture was stirred at 95° C. for 5 hr. To the reaction mixture was added ethanol (10 mL) and the mixture was stirred at room temperature and filtered through celite. The filtrate was acidified with 1N hydrochloric acid and extracted with ethyl acetate. The solvent was evaporated and acetic acid (20 mL) was added to the obtained residue, and the mixture was stirred at 80° C. for 3 hr. The mixture was concentrated under reduced pressure, hexane/ethyl acetate was added to the obtained residue, and the precipitate was collected by filtration to give the title compound (1.39 g).

MS(ESI) m/z: 361 (M+H)$^+$

Preparation Example 22: Preparation of 3-methoxy-4-(4-methyl-2,5-dioxoimidazolidin-4-yl)benzoic acid

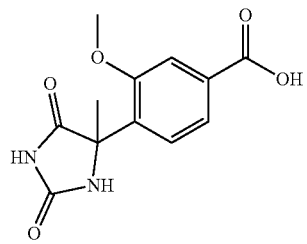 [SMILES: COc1cc(C(=O)O)ccc1C1(C)NC(=O)NC1=O]

To 4-acetyl-3-methoxybenzoic acid (0.5 g) were added water (2.3 mL), ammonium carbonate (0.99 g), potassium carbonate (1.07 g), 28% aqueous ammonia (2.3 mL) and trimethylsilyl cyanide (643 μL) and the mixture was stirred at room temperature overnight. The reaction mixture was acidified with 1N hydrochloric acid. The precipitate was collected by filtration to give the title compound (0.466 g).

MS(APCI) m/z: 265 (M+H)$^+$

Preparation Example 23: Preparation of 4-(4-hydroxymethyl-2,5-dioxoimidazolidin-4-yl)benzoic acid

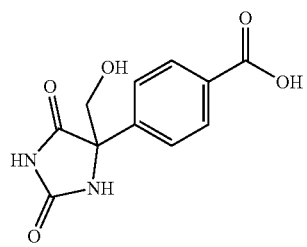 [SMILES: O=C1NC(=O)C(CO)(c2ccc(C(=O)O)cc2)N1]

To 4-(4-methoxymethyl-2,5-dioxoimidazolidin-4-yl)benzoic acid (200 mg) described in Preparation Example 9 was added 1 M boron tribromide/dichloromethane solution (7.57 mL) and the mixture was stirred at room temperature for 4 days. The reaction mixture was ice-cooled, water was added, and the insoluble material was filtered off. The filtrate was concentrated under reduced pressure, methanol was added to the obtained residue, and the mixture was concentrated under reduced pressure. To the obtained residue were added acetic acid (2 mL) and concentrated hydrochloric acid (2 mL) and the mixture was stirred at 80° C. for 5 hr. The reaction mixture was concentrated under reduced pressure to give the title compound (126 mg).

MS(ESI) m/z: 249 (M−H)$^-$, 251 (M+H)$^+$

Preparation Example 24: Preparation of 4-(4-ethoxymethyl-2,5-dioxoimidazolidin-4-yl)benzoic acid

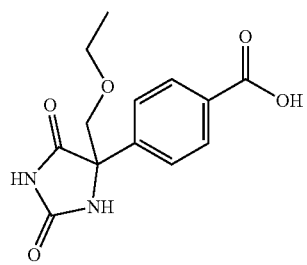 [SMILES: CCOCC1(c2ccc(C(=O)O)cc2)NC(=O)NC1=O]

A solution of methyl-4-(chloroformyl)benzoic acid (6.00 g) in acetonitrile (60 mL) was ice-cooled, 0.6 M trimethylsilyldiazomethane/hexane solution (75.5 mL) was added dropwise, and the mixture was stirred at the same temperature for 30 min and at room temperature for 2 hr. The reaction mixture was ice-cooled, ethanol (30 mL) was added dropwise, and the mixture was stirred at room temperature for 1 hr. The reaction mixture was extracted with ethyl acetate. The solvent was evaporated and the obtained residue was purified by column chromatography (hexane:chloroform) to give 4-(2-diazoacetyl)benzoic acid methyl ester (4.83 g).

4-(2-Diazoacetyl)benzoic acid methyl ester (4.82 g) was dissolved in tetrahydrofuran (50 mL) and methanol (30 mL) and, under ice-cooling, 1N aqueous sodium hydroxide solution (32.5 mL) was added, and the mixture was stirred at the same temperature for 30 min and at room temperature for 1.5 hr. To the reaction mixture was added 1N hydrochloric acid (50 mL) and the mixture was extracted with ethyl acetate. The solvent was evaporated and the obtained residue was dissolved in acetonitrile (50 mL) and ethanol (50 mL) and, under ice-cooling, boron trifluoride diethyl ether (7 mL) was added dropwise and the mixture was stirred at room temperature for 2 hr. The reaction mixture was ice-cooled, brine was added, and the mixture was extracted with ethyl acetate. After a treatment with activated carbon, the solvent was evaporated to give 4-(2-ethoxyacetyl)benzoic acid (4.25 g).

To 4-(2-ethoxyacetyl)benzoic acid (4.24 g) were added water (20 mL), 28% aqueous ammonia (20 mL), ammonium carbonate (7.83 g), potassium carbonate (8.44 g) and trimethylsilyl cyanide (5.29 mL) and the mixture was stirred at room temperature for 20 hr. The reaction mixture was acidified with concentrated hydrochloric acid and extracted with ethyl acetate. The solvent was evaporated, 2 M hydrogen chloride/ethanol solution (80 mL) was added to the obtained residue, and the mixture was stirred at room temperature for 2 days. The reaction mixture was concentrated under reduced pressure, and the obtained residue was extracted with ethyl acetate. The solvent was evaporated and the obtained residue was purified by column chromatography and NH column chromatography (chloroform:methanol) to give 4-(4-ethoxymethyl-2,5-dioxoimidazolidin-4-yl)benzoic acid ethyl ester (2.66 g).

To 4-(4-ethoxymethyl-2,5-dioxoimidazolidin-4-yl)benzoic acid ethyl ester (2.64 g) was added under ice-cooling 1N aqueous sodium hydroxide solution (26 mL) and the mixture was stirred for 2 hr. To the reaction mixture was added 1N hydrochloric acid (30 mL) and the precipitated solid was collected by filtration to give the title compound (2.28 g).

MS(ESI) m/z: 277 (M–H)⁻

Preparation Example 25: Preparation of 4-[4-(1-methoxy-1-methylethyl)-2,5-dioxoimidazolidin-4-yl]benzoic acid

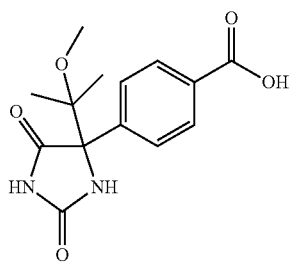 [SMILES: COC(C)(C)C1(c2ccc(C(=O)O)cc2)NC(=O)NC1=O]

Under a nitrogen stream, to a solution of 4-(2-hydroxy-2-methylpropionyl)benzoic acid methyl ester (222 mg) in tetrahydrofuran (3 mL) were added under ice-cooling methyl iodide (0.186 mL) and 60% sodium hydride (160 mg) and the mixture was stirred at room temperature overnight. Water (3 mL) was added and the mixture was stirred at room temperature for 1 hr. The mixture was acidified with 1N hydrochloric acid and extracted with ethyl acetate. After a treatment with activated carbon, the solvent was evaporated to give 4-(2-methoxy-2-methylpropionyl)benzoic acid methyl ester (234 mg).

To the obtained 4-(2-methoxy-2-methylpropionyl)benzoic acid methyl ester (225 mg) were added ammonium carbonate (481 mg), potassium carbonate (415 mg), trimethylsilyl cyanide (0.389 mL) and 28% aqueous ammonia (2 mL) and the mixture was stirred under microwave irradiation at 100° C. for 50 min. The reaction mixture was acidified by adding water and concentrated hydrochloric acid and extracted with ethyl acetate/tetrahydrofuran. The solvent was evaporated and hexane/ethyl acetate was added to the obtained residue. The precipitate was collected by filtration to give the title compound (101.5 mg).

MS(ESI) m/z: 291 (M–H)⁻

Preparation Example 26: Preparation of 2,3-difluoro-4-(4-methyl-2,5-dioxoimidazolidin-4-yl)benzoic acid

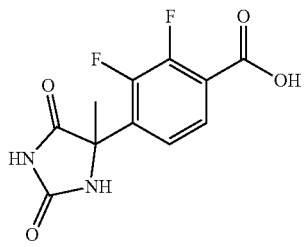 [SMILES: CC1(c2ccc(C(=O)O)c(F)c2F)NC(=O)NC1=O]

To 1-(2,3-difluoro-4-methylphenyl)ethanone (2 g) were added ethanol (6 mL), ammonium carbonate (4.52 g), potassium carbonate (1.95 g), 28% aqueous ammonia (4.1 mL) and trimethylsilyl cyanide (1.8 mL) and the mixture was stirred at 60° C. for 4 hr. 28% Aqueous ammonia (3 mL) and ammonium carbonate (2.2 g) were added and the mixture was stirred at 60° C. for 2 hr. Water was added to the reaction mixture and the mixture was stirred for 1 hr under ice-cooling. The precipitated solid was collected by filtration to give 5-(2,3-difluoro-4-methylphenyl)-5-methylimidazolidine-2,4-dione (2.2 g).

To the obtained 5-(2,3-difluoro-4-methylphenyl)-5-methylimidazolidine-2,4-dione (1 g) were added water (33 mL), 1N aqueous sodium hydroxide solution (8.3 mL) and potassium permanganate (1.97 g) and the mixture was stirred at 90° C. for 3 hr. To the reaction mixture was added ethanol (6 mL) and the mixture was stirred for 1 hr and filtered through celite. The filtrate was concentrated under reduced pressure, acidified with 1N hydrochloric acid, and the mixture was extracted with ethyl acetate. The solvent was evaporated, diisopropyl ether was added to the obtained residue, and the precipitate was collected by filtration to give the title compound (0.91 g).

MS(APCI) m/z: 269 (M–H)⁻

Preparation Example 27: Preparation of 4-(4-isobutyl-2,5-dioxoimidazolidin-4-yl)benzoic acid

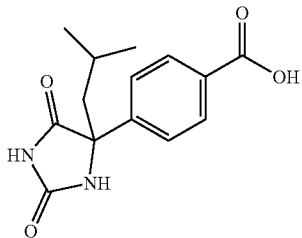 [SMILES: CC(C)CC1(c2ccc(C(=O)O)cc2)NC(=O)NC1=O]

To 4-(3-methylbutyryl)benzoic acid (1.68 g) were added ammonium carbonate (3.13 g), potassium carbonate (1.35 g), 28% aqueous ammonia solution (5.0 mL), ethanol (6.7 mL) and trimethylsilyl cyanide (1.21 mL) and the mixture was stirred at 60° C. for 17 hr. To the reaction mixture were added ammonium carbonate (1.565 g), potassium carbonate (1.35 g), 28% aqueous ammonia solution (1.0 mL), ethanol (1.5 mL) and trimethylsilyl cyanide (1.21 mL) and the mixture was stirred at 60° C. for 24 hr. Under ice-cooling, the reaction mixture acidified by adding water and concentrated hydrochloric acid, and the precipitate was collected by filtration. The obtained precipitate was suspended in hexane/ethyl acetate/ethanol and collected by filtration to give the title compound (1.91 g).

MS(ESI) m/z: 275 (M−H)⁻

Preparation Example 28: Preparation of 2-fluoro-4-(4-methoxymethyl-2,5-dioxoimidazolidin-4-yl)benzoic acid

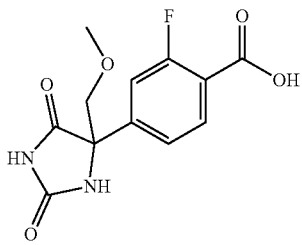 [SMILES: COCC1(c2ccc(C(=O)O)c(F)c2)NC(=O)NC1=O]

To a mixture of 1-(3-fluoro-4-methylphenyl)-2-methoxyethanone (2.11 g), ammonium carbonate (4.18 g), potassium carbonate (3.20 g), ethanol (8.4 mL) and 28% aqueous ammonia (6.3 mL) was added trimethylsilyl cyanide (3.10 mL) and the mixture was stirred at 60° C. for 1.5 hr. Ammonium carbonate (4.18 g), potassium carbonate (3.20 g), ethanol (8.4 mL), 28% aqueous ammonia (6.3 mL) and trimethylsilyl cyanide (3.10 mL) were added, and the mixture was stirred at 60° C. overnight. Under ice-cooling, the reaction mixture was acidified with concentrated hydrochloric acid. The precipitate was collected by filtration to give 5-(3-fluoro-4-methylphenyl)-5-methoxymethylimidazolidine-2,4-dione (2.74 g).

To the obtained 5-(3-fluoro-4-methylphenyl)-5-methoxymethylimidazolidine-2,4-dione (2.74 g) were added water (27.4 mL), 12N aqueous sodium hydroxide solution (1.81 mL) and potassium permanganate (3.60 g) and the mixture was stirred at room temperature for 6 hr. Potassium permanganate (3.42 g) was added, and the mixture was stirred at room temperature overnight. To the reaction mixture was added ethanol, and the mixture was filtered through celite. The filtrate was concentrated under reduced pressure, water and concentrated hydrochloric acid were added to the obtained residue, and the precipitate was collected by filtration to give 2-fluoro-4-(4-methoxymethyl-2,5-dioxoimidazolin-4-yl)benzoic acid as a crude product (1.50 g).

To a solution of the obtained crude product (1.03 g) of 2-fluoro-4-(4-methoxymethyl-2,5-dioxoimidazolin-4-yl)benzoic acid in methanol (15 mL) was added under ice-cooling concentrated sulfuric acid (5.15 mL) and the mixture was stirred at room temperature for 1 hr. Water was added to the reaction mixture, and the mixture was extracted with chloroform. The solvent was evaporated and the obtained residue was purified by column chromatography (hexane:ethyl acetate) to give methyl 2-fluoro-4-(4-methoxymethyl-2,5-dioxoimidazolin-4-yl)benzoate (293 mg).

To the obtained methyl 2-fluoro-4-(4-methoxymethyl-2,5-dioxoimidazolin-4-yl)benzoate (293 mg) was added 1N aqueous sodium hydroxide solution (2.96 mL) and the mixture was stirred at room temperature for 4 hr. To the reaction mixture was added 1N hydrochloric acid, and the precipitate was collected by filtration to give the title compound (230 mg).

MS(ESI) m/z: 281 (M−H)⁻

Preparation Example 29: Preparation of 2-fluoro-4-((R)-4-methyl-2,5-dioxoimidazolidin-4yl)benzoic acid

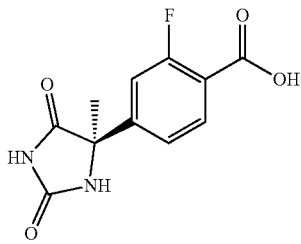 [SMILES: C[C@]1(c2ccc(C(=O)O)c(F)c2)NC(=O)NC1=O]

To a mixed solution of 5-(3-fluoro-4-methylphenyl)-5-methylimidazolidine-2,4-dione (6.77 g) described in Preparation Example 2, water (57.6 mL) and 1N aqueous sodium hydroxide solution (21.3 mL) was added (S)-1-phenylethylamine (11.8 mL). Water (49.4 mL) and ethanol (12.1 mL) were added, and the precipitate was dissolved by heating. The mixture was allowed to cool to room temperature, and the precipitate was collected by filtration to give (R)-5-(3-fluoro-4-methylphenyl)-5-methylimidazolidine-2,4-dione. (S)-1-phenylethylamine salt as a crude product (2.67 g). To the obtained crude product (2.67 g) was added water (40 mL) and the mixture was refluxed for 3 hr. The mixture was allowed to cool to room temperature, and the precipitate was collected by filtration to give (R)-5-(3-fluoro-4-methylphenyl)-5-methylimidazolidine-2,4-dione. (S)-1-phenylethylamine salt (2.23 g).

To (R)-5-(3-fluoro-4-methylphenyl)-5-methylimidazolidine-2,4-dione. (S)-1-phenylethylamine salt (2.58 g) were added water (77.4 mL) and 1N hydrochloric acid (77.4 mL) and the mixture was stirred at room temperature for 30 min. The precipitated solid was collected by filtration to give (R)-5-(3-fluoro-4-methylphenyl)-5-methylimidazolidine-2,4-dione (1.71 g).

To (R)-5-(3-fluoro-4-methylphenyl)-5-methylimidazolidine-2,4-dione (1.7 g) were added water (17 mL), 12N aqueous sodium hydroxide solution (1.12 mL) and potassium permanganate (2.24 g) and the mixture was stirred at room temperature for 48 hr. To the reaction mixture was added ethanol and the mixture was filtered through celite. The filtrate was concentrated under reduced pressure, to the obtained residue were added water and concentrated hydrochloric acid, and the precipitate was collected by filtration. The obtained precipitate was suspended in hexane/ethyl acetate, and collected by filtration to give the title compound (1.49 g).

MS(ESI) m/z: 251 (M–H)⁻

Preparation Example 30: Preparation of 4-(2,5-dioxo-4-propylimidazolidin-4-yl)-3-fluorobenzoic acid

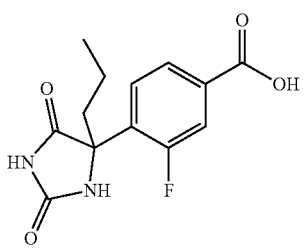 [SMILES: CCCC1(c2ccc(C(=O)O)cc2F)NC(=O)NC1=O]

Under ice-cooling, to a solution of 2-fluoro-N-methoxy-4,N-dimethylbenzamide (1.50 g) in tetrahydrofuran (20 mL) was added n-propylmagnesium bromide/tetrahydrofuran solution (1.02 M) (8.0 mL) and the mixture was stirred for 2 hr. To the reaction mixture was added 1N hydrochloric acid (20 mL) and the mixture was extracted with ethyl acetate. The obtained organic layer was dried over anhydrous sodium sulfate and concentrated under reduced pressure. The obtained residue was purified by column chromatography (hexane:ethyl acetate) to give 1-(2-fluoro-4-methylphenyl)butan-1-one (677 mg).

To a solution of 1-(2-fluoro-4-methylphenyl)butan-1-one (675 mg) in ethanol (1.89 mL) were added ammonium carbonate (1.44 g), potassium carbonate (621 mg), 28% aqueous ammonia solution (1.31 mL) and trimethylsilyl cyanide (0.557 mL) and the mixture was stirred at room temperature overnight. 28% Aqueous ammonia solution (1.00 mL), ammonium carbonate (1.00 g) and trimethylsilyl cyanide (0.20 mL) were added, and the mixture was stirred at 45° C. for 9 hr. The reaction mixture was allowed to cool to room temperature, water was added, and the precipitated solid was collected by filtration to give 5-(2-fluoro-4-methylphenyl)-5-propylimidazolidine-2,4-dione (572 mg)

To 5-(2-fluoro-4-methylphenyl)-5-propylimidazolidine-2,4-dione (569 mg) were added 1N aqueous sodium hydroxide solution (4.54 mL), water (18.2 mL) and potassium permanganate (1.08 g) and the mixture was stirred at room temperature for 15 hr and at 60° C. for 3 hr. The reaction mixture was allowed to cool to room temperature, ethanol was added and the mixture was stirred for 1 hr. After filtration through celite, the filtrate was concentrated under reduced pressure to evaporate ethanol. Under ice-cooling, to the remaining aqueous solution was added concentrated hydrochloric acid (about pH 1), and the precipitated solid was collected by filtration to give the title compound (352 mg).

MS(ESI) m/z: 279 (M–H)⁻

Preparation Example 31: Preparation of 4-[2,5-dioxo-4-(3,3,3-trifluoropropyl)imidazolidin-4-yl]benzoic acid

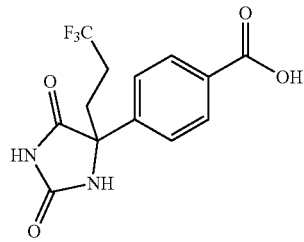 [SMILES: O=C1NC(=O)C(CCC(F)(F)F)(c2ccc(C(=O)O)cc2)N1]

To 4-(4,4,4-trifluorobutyryl)benzoic acid methyl ester (200 mg) were added methanol (0.5 mL) and 1N aqueous sodium hydroxide solution (1.55 mL) and the mixture was stirred at room temperature for 4 hr. To the reaction mixture was added 1N hydrochloric acid (pH<2) and the mixture was extracted with chloroform. The organic layer was washed with saturated brine, dried over anhydrous magnesium sulfate and concentrated under reduced pressure to give 4-(4,4,4-trifluorobutyryl)benzoic acid (183 mg).

To the obtained 4-(4,4,4-trifluorobutyryl)benzoic acid (180 mg) were added ammonium carbonate (280 mg), potassium carbonate (200 mg), 28% aqueous ammonia solution (2.5 mL), ethanol (2.5 mL) and trimethylsilyl cyanide (0.15 mL) and the mixture was stirred under microwave irradiation at 100° C. for 2 hr. The reaction mixture was allowed to cool to room temperature, 1N hydrochloric acid was added (pH<2), and the precipitate was collected by filtration to give the title compound (169 mg).

Preparation Example 32: Preparation of 4-[2,5-dioxo-4-(tetrahydropyran-4-yl)imidazolidin-4-yl]benzoic acid

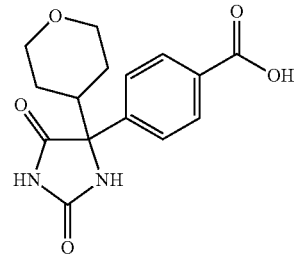 [SMILES: O=C1NC(=O)C(c2ccc(C(=O)O)cc2)(C2CCOCC2)N1]

To 4-(4-methylbenzoyl)oxane (0.2 g) were added ammonium carbonate (0.377 g), potassium carbonate (0.163 g), 28% aqueous ammonia solution (0.343 mL), ethanol (0.98 mL), water (0.98 mL) and trimethylsilyl cyanide (0.147 mL) and the mixture was stirred at 60° C. overnight. Ammonium carbonate (0.377 g), potassium carbonate (0.163 g), 28% aqueous ammonia solution (0.343 mL) and trimethylsilyl cyanide (0.147 mL) were added, and the mixture was stirred under microwave irradiation at 100° C. for 2.5 hr. Ammonium carbonate (0.377 g), potassium carbonate (0.163 g), 28% aqueous ammonia solution (0.343 mL) and trimethylsilyl cyanide (0.147 mL) were added, and the mixture was stirred under microwave irradiation at 100° C. for 1.5 hr. The reaction mixture was acidified with 1N hydrochloric acid and extracted with ethyl acetate. The organic layer was dried over anhydrous sodium sulfate and concentrated under reduced pressure. Hexane was added to the obtained residue and the precipitate was collected by filtration to give 5-(tetrahydropyran-4-yl)-5-(p-tolyl)imidazolidine-2,4-dione (0.186 g).

To the obtained 5-(tetrahydropyran-4-yl)-5-(p-tolyl)imidazolidine-2,4-dione (0.180 g) were added 1N aqueous sodium hydroxide solution (0.132 mL), potassium permanganate (0.332 g) and water (0.528 mL) and the mixture was stirred at room temperature for 11 hr. To the reaction mixture was added ethanol (1.32 mL) and the mixture was filtered through celite. The filtrate was concentrated under reduced pressure, acidified with 1N hydrochloric acid, and extracted with ethyl acetate. The organic layer was dried over anhydrous sodium sulfate and concentrated under reduced pressure to give the title compound (0.183 g).

MS(ESI) m/z: 303 (M−H)⁻

Preparation Example 33: Preparation of 4-(4-cyclobutyl-2,5-dioxoimidazolidin-4-yl)benzoic acid

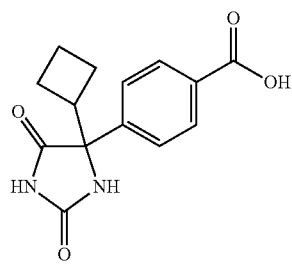 [SMILES: O=C1NC(=O)C(c2ccc(C(=O)O)cc2)(C2CCC2)N1]

To cyclobutyl(p-tolyl)methanone (4.75 g) were added ammonium carbonate (10.47 g), potassium carbonate (4.52 g), 28% aqueous ammonia solution (9.54 mL), ethanol (54.6 mL), water (27.3 mL) and trimethylsilyl cyanide (4.09 mL) and the mixture was stirred at 60° C. overnight. Under ice-cooling, water was added to the reaction mixture, and the precipitate was collected by filtration. The obtained precipitate was dissolved in ethyl acetate, the solution was washed with 1N hydrochloric acid and saturated brine, and dried over anhydrous magnesium sulfate. The solvent was evaporated and hexane was added to the obtained residue, and the precipitate was collected by filtration to give 5-cyclobutyl-5-p-tolylimidazolidine-2,4-dione (3.64 g).

To the obtained 5-cyclobutyl-5-p-tolylimidazolidine-2,4-dione (3.64 g) were added 1N aqueous sodium hydroxide solution (298 mL), potassium permanganate (4.94 g) and water (119 mL) and the mixture was stirred at room temperature for 16 hr and at 50° C. for 6 hr. To the reaction mixture was added dimethylsulfoxide (1.49 mL) and the mixture was filtered through celite. The filtrate was acidified with 1N hydrochloric acid, and the precipitate was collected by filtration to give the title compound (3.78 g).

MS(ESI) m/z: 273 (M−H)⁻

Preparation Example 34: Preparation of 4-(4-cyclopropyl-2,5-dioxoimidazolidin-4-yl)-2-fluorobenzoic acid

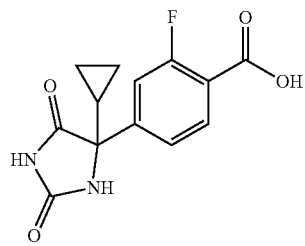 [SMILES: O=C1NC(=O)C(c2ccc(C(=O)O)c(F)c2)(C2CC2)N1]

To a solution of cyclopropyl(3-fluoro-4-methylphenyl)methanone (2.11 g) in ethanol (6.1 mL) were successively added ammonium carbonate (4.66 g), potassium carbonate (2 g), 28% aqueous ammonia solution (4.24 mL) and trimethylsilyl cyanide (1.8 mL) and the mixture was stirred at room temperature overnight and then at 60° C. for 4 hr. 28% Aqueous ammonia solution (4.24 mL), ammonium carbonate (4.66 g), trimethylsilyl cyanide (1.8 mL), potassium carbonate (2 g) and ethanol (6.1 mL) were added, and the mixture was stirred at 45° C. for 6 hr and at 60° C. for 7 hr. The reaction mixture was allowed to cool to room temperature, water was added, and the mixture was extracted with ethyl acetate. The obtained organic layer was dried over anhydrous sodium sulfate and concentrated under reduced pressure. The obtained residue was purified by silica gel column chromatography (hexane:ethyl acetate) to give 5-cyclopropyl-5-(3-fluoro-4-methylphenyl)imidazolidine-2,4-dione (1.1 g).

To the obtained 5-cyclopropyl-5-(3-fluoro-4-methylphenyl)imidazolidine-2,4-dione (1.08 g) were added 1N aqueous sodium hydroxide solution (9 mL), water (36 mL) and potassium permanganate (1.37 g) and the mixture was stirred at room temperature overnight. Potassium permanganate (500 mg) was added, and the mixture was stirred at room temperature overnight. The reaction mixture was filtered through celite, and the obtained filtrate was acidified with concentrated hydrochloric acid and partitioned with chloroform. The aqueous layer was concentrated under reduced pressure and the precipitated solid was collected by filtration to give the title compound (500 mg).

MS(ESI) m/z: 279 (M+H)⁺

Preparation Example 35: Preparation of 4-(4-isopropyl-2,5-dioxoimidazolidin-4-yl)-3-methoxybenzoic acid

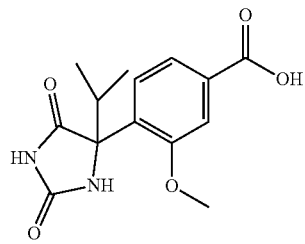 [SMILES: COc1cc(C(=O)O)ccc1C1(C(C)C)NC(=O)NC1=O]

1) Preparation of 4-isobutyryl-3-methoxybenzoic acid

To 1-(4-bromo-2-methoxyphenyl)-2-methylpropan-1-one (7.97 g) were added palladium acetate (0.674 g), 1,1'-bis (diphenylphosphino)ferrocene (0.832 g), methanol (24.3 mL), N,N-dimethylformamide (75 mL) and triethylamine (8.36 mL) and the mixture was stirred under carbon monoxide atmosphere at 80° C. for 5 hr. The reaction mixture was poured into cold water and the mixture was extracted with ethyl acetate. To the organic layer were added SH silica, activated carbon and anhydrous sodium sulfate, and the mixture was filtered. The filtrate was concentrated under reduced pressure, water was added to the obtained residue and the mixture was extracted with diethyl ether. To the organic layer were added SH silica, activated carbon and anhydrous sodium sulfate, and the mixture was filtered. The filtrate was concentrated under reduced pressure to give 4-isobutyryl-3-methoxybenzoic acid methyl ester (7.015 g).

To a solution of the obtained 4-isobutyryl-3-methoxybenzoic acid methyl ester (7.01 g) in tetrahydrofuran (148 mL) was added 2N aqueous sodium hydroxide solution (44.5 mL) and the mixture was stirred at room temperature for 15 hr. The reaction mixture was concentrated under reduced pressure, and the remaining aqueous solution was partitioned with hexane. The aqueous layer was acidified with 2N hydrochloric acid, and the mixture was extracted with ethyl acetate. The organic layer was washed with saturated brine, dried over anhydrous sodium sulfate and concentrated under reduced pressure. To the obtained residue was added hexane/diisopropyl ether, and the precipitate was collected by filtration to give 4-isobutyryl-3-methoxybenzoic acid (4.426 g).

2) Preparation of 4-(4-isopropyl-2,5-dioxoimidazolidin-4-yl)-3-methoxybenzoic acid To 4-isobutyryl-3-methoxybenzoic acid (0.571 g) described in the above-mentioned 1) were added water (2.3 mL), ammonium carbonate (1.98 g), potassium carbonate (1.07 g), 28% aqueous ammonia (4.6 mL) and trimethylsilyl cyanide (1.29 mL) and the mixture was stirred at 60° C. for 8 hr. The reaction mixture was acidified with 1N hydrochloric acid, and the precipitated solid was collected by filtration to give 4-(4-isopropyl-2,5-dioxoimidazolidin-4-yl)-3-methoxybenzoic acid (0.69 g).

MS(APCI) m/z: 293 (M+H)⁺

Preparation Example 36: Preparation of 4-[4-(2-methoxyethyl)-2,5-dioxoimidazolidin-4-yl]benzoic acid

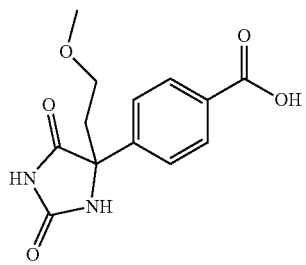 [SMILES: COCCC1(c2ccc(C(=O)O)cc2)NC(=O)NC1=O]

To 3-methoxy-1-(4-methylphenyl)propan-1-one (651 mg) and ammonium carbonate (1.24 g) were added potassium carbonate (0.949 g), ethanol (2.6 mL), 28% aqueous ammonia (2 mL) and trimethylsilyl cyanide (893 μL) and the mixture was stirred at 60° C. overnight. Under ice-cooling, the reaction mixture was acidified with concentrated hydrochloric acid. The precipitate was collected by filtration to give 5-(2-methoxyethyl)-5-(p-tolyl)imidazolidine-2,4-dione (690 mg).

To the obtained 5-(2-methoxyethyl)-5-(p-tolyl)imidazolidine-2,4-dione (670 mg) were added water (6.7 mL), 12N aqueous sodium hydroxide solution (0.45 mL) and potassium permanganate (0.9 g) and the mixture was stirred at room temperature for 30 hr. Potassium permanganate (0.86) was added, and the mixture was stirred at room temperature for 24 hr. The reaction mixture was ice-cooled, ethanol was added, and the mixture was stirred at room temperature for 30 min. The reaction mixture was filtered through celite and the filtrate was concentrated under reduced pressure.

To the obtained residue were added water and concentrated hydrochloric acid, and the mixture was filtered. The filtrate was extracted with a mixed solvent of chloroform and ethanol. The organic layer was dried over anhydrous magnesium sulfate, and the solvent was evaporated to give the title compound as a crude product (280 mg).

MS(ESI) m/z: 277 (M–H)⁻

Preparation Example 37: Preparation of 4-(2,5-dioxo-4-phenylimidazolidin-4-yl)benzoic acid

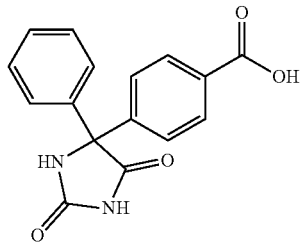 [SMILES: O=C1NC(=O)C(c2ccccc2)(c2ccc(C(=O)O)cc2)N1]

To p-benzoylbenzoic acid (2 g) were added ammonium carbonate (3.4 g), potassium carbonate (3.67 g), trimethylsilyl cyanide (2.3 mL), 28% aqueous ammonia (10 mL), water (10 mL) and methanol (20 mL) and the mixture was stirred at 60° C. overnight. Ammonium carbonate (3.4 g), potassium carbonate (3.67 g), trimethylsilyl cyanide (2.3 mL), 28% aqueous ammonia (10 mL) and methanol (10 mL) were added, and the mixture was stirred at 60° C. overnight. Furthermore, potassium carbonate (2.44 g) and trimethylsilyl cyanide (2.3 mL) were added, and the mixture was stirred at 60° C. overnight.

Under ice-cooling, the reaction mixture was acidified by adding water and concentrated hydrochloric acid and the mixture was extracted with ethyl acetate. The solvent was evaporated, hexane/ethyl acetate was added to the obtained residue, and the precipitate was collected by filtration to give the title compound (2.6 g).

MS (ESI) m/z: 295 (M–H)⁻

Preparation Example 38: Preparation of 4-[4-(2-methoxy-1,1-dimethylethyl)-2,5-dioxoimidazolidin-4-yl]benzoic acid

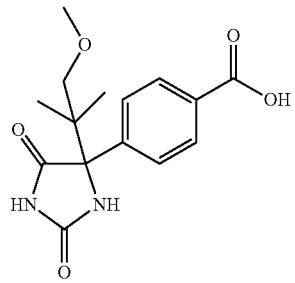 [SMILES: COCC(C)(C)C1(c2ccc(C(=O)O)cc2)NC(=O)NC1=O]

To a solution of 3-methoxy-2,2-dimethylpropanoic acid (2 g) in chloroform (20 mL) were added under ice-cooling oxalyl chloride (1.95 mL) and N,N-dimethylformamide (one drop), and the mixture was stirred at room temperature for 2 hr. The reaction mixture was concentrated under reduced pressure, to the obtained residue were added toluene (50 mL), 4-(methoxycarbonyl)phenylboric acid (2 g), tripotassium phosphate (4.72 g), bis(tricyclohexylphosphine)palladium(II) dichloride (390 mg) and water (0.6 mL) and the mixture was stirred under a nitrogen stream for 30 min with heating under reflux. The reaction mixture was cooled to room temperature, water was added, and the mixture was extracted with ethyl acetate. The organic layer was washed with saturated aqueous sodium hydrogen carbonate solution and saturated brine, dried over sodium sulfate, and the solvent was evaporated under reduced pressure. The obtained residue was purified by column chromatography (hexane:ethyl acetate) to give 4-(3-methoxy-2,2-dimethylpropionyl)benzoic acid methyl ester (570 mg). To the obtained 4-(3-methoxy-2,2-dimethylpropionyl)benzoic acid methyl ester (560 mg) were added methanol (5 mL), tetrahydrofuran (5 mL) and 1N aqueous sodium hydroxide solution (4.5 mL) and the mixture was stirred at room temperature for 3 hr. To the reaction mixture was added ethyl acetate, and back extraction was performed using water and aqueous potassium carbonate solution. The partitioned aqueous layer was combined, acidified with concentrated hydrochloric acid and extracted with ethyl acetate. The organic layer was washed with saturated brine, dried over sodium sulfate, and the solvent was evaporated under reduced pressure to give 4-(3-methoxy-2,2-dimethylpropionyl)benzoic acid (518 mg). To 4-(3-methoxy-2,2-dimethylpropionyl)benzoic acid (503 mg) were added ammonium carbonate (1.02 g), potassium carbonate (1.47 g), trimethylsilyl cyanide (831 µL), 28% aqueous ammonia (6 mL) and water (3 mL) and the mixture was stirred under microwave irradiation at 150° C. for 1 hr. Trimethylsilyl cyanide (831 µL) was added, and the mixture was stirred under microwave irradiation at 150° C. for 1 hr. Furthermore, potassium carbonate (1.47 g), trimethylsilyl cyanide (1662 µL) and 28% aqueous ammonia (3 mL) were added, and the mixture was stirred under microwave irradiation at 150° C. for 2 hr. To the reaction mixture were added water and ethyl acetate, and the mixture was acidified with concentrated hydrochloric acid and extracted with ethyl acetate. The organic layer was washed with saturated brine, dried over sodium sulfate, and the solvent was evaporated under reduced pressure. To the obtained residue was added hexane/ethyl acetate, and the precipitate was collected by filtration to give the title compound (552 mg).

MS(ESI) m/z: 307 (M+H)$^+$

Preparation Example 39: Preparation of 4-(4-isopropyl-2,5-dioxoimidazolidin-4-yl)-3-methylbenzoic acid

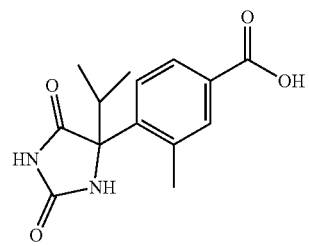

To 1-(4-bromo-2-hydroxyphenyl)-2-methylpropan-1-one (12.89 g) were added 1,1'-bis(diphenylphosphino)ferrocene (2.94 g), dipalladium(II) acetate (595 mg), N,N-dimethylformamide (133 mL), methanol (42.9 mL) and triethylamine (22.2 mL) and the mixture was stirred under carbon monoxide atmosphere at 80° C. for 14 hr. Water was added to the reaction mixture and the mixture was extracted with ethyl acetate. The extract was dried over anhydrous sodium sulfate and the solvent was evaporated under reduced pressure. The obtained residue was purified by column chromatography (hexane:ethyl acetate) to give 3-hydroxy-4-isobutyrylbenzoic acid methyl ester (10.14 g).

To a solution of the obtained 3-hydroxy-4-isobutyrylbenzoic acid methyl ester (5 g) in dichloromethane (225 mL) were added N,N-diisopropylethylamine (19.6 mL) and N-phenylbis(trifluoromethanesulfonimide) (16.1 g) and the mixture was stirred at room temperature for 20 hr. N-phenylbis(trifluoromethanesulfonimide) (9.0 g) was added, and the mixture was stirred at room temperature for 33 hr. Furthermore, N-phenylbis(trifluoromethanesulfonimide) (9.0 g) and N,N-diisopropylethylamine (5 mL) were added, and the mixture was stirred at room temperature for 3 days. The reaction mixture was washed with water and saturated brine, dried over sodium sulfate, and the solvent was evaporated under reduced pressure. The obtained residue was purified by silica gel column chromatography (hexane:ethyl acetate) to give 4-isobutyryl-3-trifluoromethanesulfonyloxybenzoic acid methyl ester (7.99 g).

To the obtained 4-isobutyryl-3-trifluoromethanesulfonyloxybenzoic acid methyl ester (7 g) were added [1,1'-bis(diphenylphosphino)ferrocene]palladium(II) dichloride.dichloromethane adduct (806 mg), potassium carbonate (6.82 g), 1,4-dioxane (132 mL) and 2,4,6-trimethylboroxine (5.5 mL) and the mixture was stirred under an argon atmosphere at 110° C. for 3 hr. At room temperature, to the reaction mixture were added activated carbon and heavy metal-free silica (SH Silica), and the mixture was filtered. The filtrate was concentrated under reduced pressure, and the obtained residue was purified by column chromatography (hexane:ethyl acetate) to give 4-isobutyryl-3-methylbenzoic acid methyl ester (3.97 g).

To the obtained 4-isobutyryl-3-methylbenzoic acid methyl ester (2.2 g) were added methanol (5 mL), 1N aqueous sodium hydroxide solution (15 mL) and tetrahydrofuran (8 mL) and the mixture was stirred at room temperature for 2 hr. The reaction mixture was poured into ice water and 1N hydrochloric acid was added. The precipitated solid was collected by filtration to give 4-isobutyryl-3-methylbenzoic acid. To the obtained 4-isobutyryl-3-methylbenzoic acid were added ethanol (5 mL), 28% aqueous ammonia (3.5 mL), ammonium carbonate (3.8 g), potassium carbonate (1.66 g) and trimethylsilyl cyanide (1.5 mL) and the mixture was stirred at 60° C. for 8 hr. Trimethylsilyl cyanide (3.75 mL) and potassium carbonate (6.9 g) were added, and the mixture was stirred at 80-100° C. for 1 day. Furthermore, trimethylsilyl cyanide (3.75 mL) and potassium carbonate (6.9 g) were added, and the mixture was stirred at 60° C. for 1 day. The reaction mixture was neutralized with concentrated hydrochloric acid and extracted with ethyl acetate. The solvent was evaporated under reduced pressure, to the obtained residue were added 1N hydrochloric acid, water and methanol, and the precipitate was collected by filtration to give the title compound as a crude product (943 mg).

MS(ESI) m/z: 275 (M−H)⁻

Preparation Example 40: Preparation of 4-(4-ethyl-2,5-dioxoimidazolidin-4-yl)-3-fluorobenzoic acid

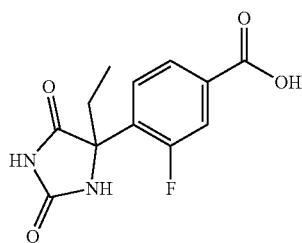 [SMILES: CCC1(c2ccc(C(=O)O)cc2F)NC(=O)NC1=O]

To 1-(4-bromo-2-fluorophenyl)propan-1-one (2.3 g) were added ethanol (5 mL), 28% aqueous ammonia (3.5 mL), ammonium carbonate (3.8 g), potassium carbonate (1.66 g) and trimethylsilyl cyanide (1.5 mL) and the mixture was stirred at 50° C. for about 5 hr. Trimethylsilyl cyanide (0.25 mL), potassium carbonate (830 mg) and 28% aqueous ammonia (1.5 mL) were added, and the mixture was stirred at 60° C. for 8 hr. Water was added to the reaction mixture, and the precipitate was collected by filtration. The obtained precipitate was suspended in diethyl ether/hexane and collected by filtration to give 5-(4-bromo-2-fluorophenyl)-5-ethylimidazolidine-2,4-dione (795 mg).

To the obtained 5-(4-bromo-2-fluorophenyl)-5-ethylimidazolidine-2,4-dione (789 mg) were added zinc cyanide (450 mg), zinc (25 mg), 1,1'-bis(diphenylphosphino)ferrocene (177 mg), tris(dibenzylideneacetone)dipalladium(0) (146 mg) and N,N-dimethylformamide (10 mL) and the mixture was stirred at 130° C. for 7 hr. The reaction mixture was purified by column chromatography (hexane:ethyl acetate). The solvent was evaporated and hexane/ethyl acetate was added to the obtained residue. The precipitate was collected by filtration to give 4-(4-ethyl-2,5-dioxoimidazolidin-4-yl)-3-fluorobenzonitrile (225 mg).

To the obtained 4-(4-ethyl-2,5-dioxoimidazolidin-4-yl)-3-fluorobenzonitrile (220 mg) were added acetic acid (1 mL), concentrated hydrochloric acid (1 mL) and concentrated sulfuric acid (1 mL) and the mixture was stirred at 120° C. for 8.5 hr. Water was added, and the precipitated solid was collected by filtration to give the title compound (211 mg).

MS(ESI) m/z: 265 (M−H)⁻

Preparation Example 41: Preparation of 4-(3-methyl-2,5-dioxopyrrolidin-3-yl)benzoic acid

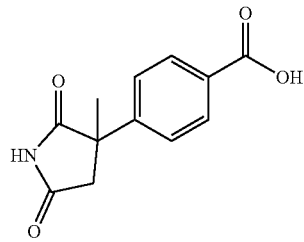 [SMILES: CC1(c2ccc(C(=O)O)cc2)CC(=O)NC1=O]

To 3-methyl-3-(4-methylphenyl)pyrrolidine-2,5-dione (698 mg) were added 1N aqueous sodium hydroxide solution (7.0 mL), water (28 mL) and potassium permanganate (1.09 g) and the mixture was stirred at room temperature overnight. Ethanol was added, and the mixture was stirred at room temperature for 2 hr and filtered through celite. The filtrate was concentrated under reduced pressure, to the obtained residue was added acetic acid (50 mL) and the mixture was stirred with heating under reflux for 6 hr. To the reaction mixture was added toluene (50 mL), a Dean-Stark trap was set, and the mixture was heated under reflux for 1 hr. The solvent was evaporated, acetic acid (50 mL) was added and the mixture was stirred with heating under reflux for 6 hr. The solvent was evaporated under reduced pressure, to the obtained residue were added water and saturated brine, and the mixture was extracted with tetrahydrofuran. The obtained organic layer was washed with saturated brine, dried over anhydrous sodium sulfate and concentrated under reduced pressure. The obtained residue was purified by column chromatography (ethyl acetate:methanol) to give the title compound (512 mg).

MS(ESI) m/z: 232 (M−H)⁻

Preparation Example 42: Preparation of 4-[4-(3-methoxypropyl)-2,5-dioxoimidazolidin-4-yl]benzoic acid

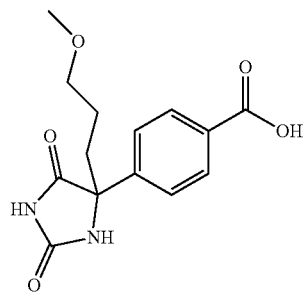 [SMILES: COCCCC1(c2ccc(C(=O)O)cc2)NC(=O)NC1=O]

To a solution of 4-methoxybutyric acid (2.0 g) in chloroform (20 mL) were added N,N-dimethylformamide (0.17 mL) and oxalyl chloride (2.41 mL) and the mixture was stirred at room temperature. After completion of the reaction, the reaction mixture was concentrated under reduced pressure. To the obtained residue were added tetrahydrofuran (30 mL), 4-(ethoxycarbonyl)phenylzinc bromide (0.5 M, tetrahydrofuran solution) (23.4 mL) and bis(triphenylphosphine)palladium(II) dichloride (0.41 g) and the mixture was stirred at room temperature for 2 hr and at 60° C. for 2 hr. To the reaction mixture was added 1N hydrochloric acid and the mixture was extracted with diethyl ether. The organic layer was washed with saturated brine, dried over anhydrous magnesium sulfate, and the solvent was evaporated under reduced pressure. The obtained residue was purified by column chromatography (hexane:ethyl acetate) to give ethyl 4-(4-methoxybutyryl)benzoate (830 mg).

To the obtained ethyl 4-(4-methoxybutyryl)benzoate (830 mg) were added ethanol (8 mL), tetrahydrofuran (8 mL) and 1N aqueous sodium hydroxide solution (6.6 mL) and the mixture was stirred at room temperature overnight. To the reaction mixture was added ethyl acetate and the mixture was subjected to back extraction with water and aqueous sodium hydrogen carbonate solution. The partitioned aqueous layers were combined and acidified with concentrated hydrochloric acid. The precipitate was collected by filtration to give 4-(4-methoxybutyryl)benzoic acid (490 mg).

To the obtained 4-(4-methoxybutyryl)benzoic acid (480 mg) were added ethanol (1.9 mL), ammonium carbonate (0.78 g), potassium carbonate (0.597 g), 28% aqueous ammonia (1.4 mL), trimethylsilyl cyanide (0.562 mL) and the mixture was stirred at 60° C. overnight. The reaction mixture was acidified with concentrated hydrochloric acid under ice-cooling, and the mixture was extracted with ethyl acetate. The organic layer was washed with saturated brine and dried over sodium sulfate. The solvent was evaporated and hexane/ethyl acetate was added to the obtained residue. The precipitate was collected by filtration to give the title compound (650 mg).

MS(ESI) m/z: 293 (M+H)$^+$

Preparation Example 43: Preparation of 5-(4-tert-butyl-2,5-dioxoimidazolidin-4-yl)pyridine-2-carboxylic acid

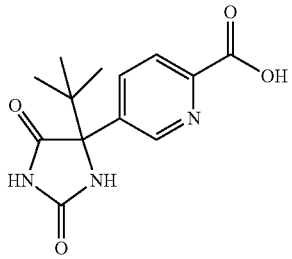 [SMILES: CC(C)(C)C1(c2ccc(C(=O)O)nc2)NC(=O)NC1=O]

To 2,2-dimethyl-1-(6-methylpyridin-3-yl)propan-1-one (674 mg) were added ethanol (5.4 mL), 28% aqueous ammonia (4 mL), ammonium carbonate (1.33 g), potassium carbonate (1.02 g), trimethylsilyl cyanide (0.959 mL) and the mixture was stirred under microwave irradiation at 130° C. for 1 hr. The reaction mixture was neutralized by adding water and concentrated hydrochloric acid, and the precipitate was collected by filtration to give 5-tert-butyl-5-(6-methylpyridin-3-yl)imidazodine-2,4-dione (403 mg).

To the obtained 5-tert-butyl-5-(6-methylpyridin-3-yl)imidazodine-2,4-dione (403 mg) were added water (4 mL), 12N aqueous sodium hydroxide solution (0.272 mL) and potassium permanganate (0.54 g) and the mixture was stirred at room temperature overnight. Potassium permanganate (128 mg) was added, and the mixture was stirred at room temperature for 2 hr, and at 50° C. overnight. Furthermore, potassium permanganate (128 mg) was added, and the mixture was stirred at 50° C. for 7 hr. To the reaction mixture was added ethanol and the mixture was filtered through celite. The filtrate was neutralized with concentrated hydrochloric acid, and concentrated under reduced pressure. Water was added to the obtained residue, and the mixture was extracted with a mixed solvent of ethyl acetate and tetrahydrofuran. The solvent was evaporated and hexane/ethyl acetate was added to the obtained residue. The precipitate was collected by filtration to give the title compound (247 mg).

MS(ESI) m/z: 278 (M+H)$^+$

Preparation Example 44: Preparation of 4-[4-(1-methoxycyclopropyl)-2,5-dioxoimidazolidin-4-yl]benzoic acid

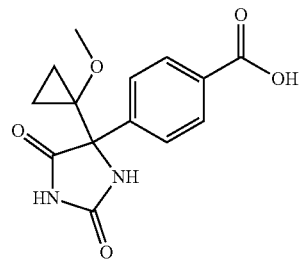 [SMILES: COC1(C2(c3ccc(C(=O)O)cc3)NC(=O)NC2=O)CC1]

Under a nitrogen stream, a solution of 1-hydroxycyclopropanecarboxylic acid (1.41 g) in chloroform (14 mL) was ice-cooled, oxalyl chloride (2.08 mL) and N,N-dimethylformamide (one drop) were added and the mixture was stirred at room temperature for 3 hr. The reaction mixture was concentrated under reduced pressure, to the obtained residue were added toluene (40 mL), 4-(methoxycarbonyl)phenylboric acid (2.18 g), tripotassium phosphate (5.59 g) and bis(tricyclohexylphosphine)palladium(II) dichloride (426 mg) and, under a nitrogen stream, the mixture was stirred at 60° C. for 1 hr and at 80° C. for 1 hr. Water was added to the reaction mixture, and the mixture was extracted with ethyl acetate. The organic layer was washed with saturated brine, dried over sodium sulfate, and the solvent was evaporated. The obtained residue was purified by column chromatography (hexane:ethyl acetate) to give 4-(1-methoxycyclopropanecarbonyl)benzoic acid methyl ester (325 mg).

To the obtained 4-(1-methoxycyclopropanecarbonyl)benzoic acid methyl ester (315 mg) were added methanol (3 mL), tetrahydrofuran (3 mL) and 1N aqueous sodium hydroxide solution (2.68 mL) and the mixture was stirred at room temperature for 3 hr. The reaction mixture was acidified with 1N hydrochloric acid, saturated brine was added, and the mixture was extracted with ethyl acetate, the extract was dried over sodium sulfate, and the solvent was evaporated to give 4-(1-methoxycyclopropanecarbonyl)benzoic acid (232 mg).

To the obtained 4-(1-methoxycyclopropanecarbonyl)benzoic acid (225 mg) were added ammonium carbonate (490 mg), potassium carbonate (423 mg), trimethylsilyl cyanide (0.398 mL) and 28% aqueous ammonia (2 mL) and the mixture was stirred under microwave irradiation at 80° C. for 30 min and at 100° C. for 1 hr. The reaction mixture was acidified with concentrated hydrochloric acid, water was added, and the mixture was extracted with a mixed solvent of ethyl acetate and tetrahydrofuran. The organic layer was washed with saturated brine, dried over sodium sulfate and concentrated under reduced pressure. To the obtained residue was added hexane/ethyl acetate, and the precipitate was collected by filtration to give the title compound (283 mg).

MS(ESI) m/z: 289 (M−H)$^-$

Preparation Example 45: Preparation of 4-((R)-4-isopropyl-2,5-dioxoimidazolidin-4-yl)benzoic acid

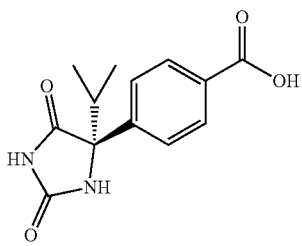 [SMILES: CC(C)[C@]1(c2ccc(C(=O)O)cc2)NC(=O)NC1=O]

1) Preparation of 4-((R)-4-isopropyl-2,5-dioxoimidazolidin-4-yl)benzoic acid. (R)-(+)-1-phenylethylamine salt To 4-(4-isopropyl-2,5-dioxoimidazolidin-4-yl)benzoic acid (200 mg) described in Preparation Example 5 were added water (8 mL), 1N aqueous sodium hydroxide solution (0.458 mL) and (R)-1-phenylethylamine (59 μL) and the mixture was stirred at 110° C. After confirmation of complete dissolution, the mixture was allowed to cool to room temperature, and the precipitated solid was collected by filtration to give 4-((R)-4-isopropyl-2,5-dioxoimidazolidin-4-yl)benzoic acid. (R)-(+)-1-phenylethylamine salt as a crude product (76.4 mg). To the obtained 4-((R)-4-isopropyl-2,5-dioxoimidazolidin-4-yl)benzoic acid. (R)-(+)-1-phenylethylamine salt as a crude product (76.3 mg) was added water (3 mL) and the mixture was stirred at 80° C. for 20 min. The mixture was allowed to cool to room temperature, and the precipitated solid was collected by filtration to give 4-((R)-4-isopropyl-2,5-dioxoimidazolidin-4-yl)benzoic acid. (R)-1-phenylethylamine salt (37.2 mg, 99.7% ee).

2) Preparation of 4-((R)-4-isopropyl-2,5-dioxoimidazolidin-4-yl)benzoic acid 4-((R)-4-isopropyl-2,5-dioxoimidazolidin-4-yl)benzoic acid. (R)-1-phenylethylamine salt (55.36 g, 97.1% ee) obtained by a method similar to the above-mentioned 1) was suspended in water (250 mL) and acidified (pH 1-2) with 1N hydrochloric acid (155 mL). The mixture was stirred at room temperature for 1 hr, and the precipitate was collected by filtration to give 4-((R)-4-isopropyl-2,5-dioxoimidazolidin-4-yl)benzoic acid (32.42 g, 98.7% ee).

MS(ESI) m/z: 263 (M+H)+

Preparation Example 46: Preparation of 6-(4-tert-butyl-2,5-dioxoimidazolidin-4-yl)nicotinic acid

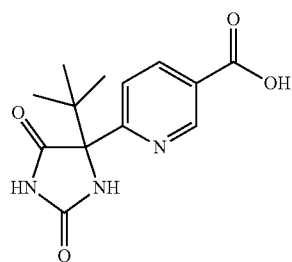 [SMILES: CC(C)(C)C1(c2ccc(C(=O)O)cn2)NC(=O)NC1=O]

To 2,2-dimethyl-1-(5-methylpyridin-2-yl)propan-1-one (0.3 g) were added water (1 mL), ethanol (1 mL), 28% aqueous ammonia solution (0.592 mL), ammonium carbonate (0.65 g), potassium carbonate (0.327 g) and trimethylsilyl cyanide (0.296 mL) and the mixture was stirred under microwave irradiation at 130° C. for 1 hr. The reaction mixture was neutralized with concentrated hydrochloric acid and water was added. The precipitate was collected by filtration to give 5-tert-butyl-5-(5-methylpyridin-2-yl)imidazolidine-2,4-dione (0.287 g).

To the obtained 5-tert-butyl-5-(5-methylpyridin-2-yl)imidazolidine-2,4-dione (0.281 g) were added 1N aqueous sodium hydroxide solution (2.28 mL), water (9.12 mL) and potassium permanganate (0.396 g) and the mixture was stirred at room temperature overnight. Potassium permanganate (54 mg) was added, and the mixture was stirred at 40° C. for 25 hr. To the reaction mixture was added dimethylsulfoxide (0.024 mL) and the mixture was filtered through celite. The filtrate was acidified with 1N hydrochloric acid (pH 4-5) and filtered. The filtrate was extracted with ethyl acetate/tetrahydrofuran. The organic layer was dried over anhydrous sodium sulfate and concentrated under reduced pressure to give the title compound as a crude product (74 mg).

MS(ESI) m/z: 276 (M−H)−

Preparation Example 47: Preparation of 4-(4-methyl-2,5-dioxoimidazolidin-4-yl)-2-trifluoromethylbenzoic acid

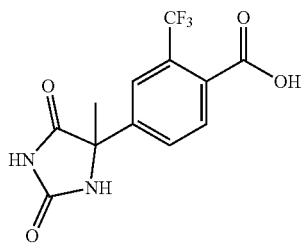

To 1-[4-bromo-3-(trifluoromethyl)phenyl]ethan-1-one (3.2 g) were added ethanol (12 mL), 28% aqueous ammonia (6 mL), ammonium carbonate (4.6 g), potassium carbonate (3.3 g) and trimethylsilyl cyanide (3 mL) and the mixture was stirred at room temperature for 1.5 hr and at 50° C. for 2 hr. Water (6 mL) was added, and the mixture was stirred at 50° C. for 1.5 hr. Furthermore, trimethylsilyl cyanide (1.5 mL), potassium carbonate (1.65 g), ammonium carbonate (2.3 g) and 28% aqueous ammonia (3 mL) were added, and the mixture was stirred at 50° C. for 4 hr. Water was added to the reaction mixture, and the precipitated solid was collected by filtration to give 5-(4-bromo-3-trifluoromethylphenyl)-5-methylimidazolidine-2,4-dione (3.2 g).

To the obtained 5-(4-bromo-3-trifluoromethylphenyl)-5-methylimidazolidine-2,4-dione (3.2 g) were added zinc cyanide (2.8 g), zinc (134 mg), 1,1'-bis(diphenylphosphino)ferrocene (526 mg), tris(dibenzylideneacetone)dipalladium (0) (430 mg) and N,N-dimethylformamide (32 mL) and the mixture was stirred at 130° C. for 7 hr. To the reaction mixture was added chloroform, and the mixture was filtered through celite. The filtrate was concentrated under reduced pressure, and the obtained residue was purified by column chromatography (hexane:ethyl acetate) to give 4-(4-methyl-2,5-dioxoimidazolidin-4-yl)-2-trifluoromethylbenzonitrile (1.36 g).

To the obtained 4-(4-methyl-2,5-dioxoimidazolidin-4-yl)-2-trifluoromethylbenzonitrile (1.36 g) were added acetic acid (5 mL), concentrated hydrochloric acid (5 mL) and concentrated sulfuric acid (3 mL) and the mixture was stirred at 120° C. for 6 hr. Acetic acid (1 mL) and concentrated sulfuric acid (2 mL) were added, and the mixture was stirred at 120° C. for 8 hr. Furthermore, acetic acid (2 mL) and concentrated hydrochloric acid (2 mL) were added, and the mixture was stirred at 120° C. Water was added to the reaction mixture, and the mixture was extracted with ethyl acetate and chloroform. The solvent was evaporated, to the obtained residue were added acetic acid (3 mL), concentrated hydrochloric acid (1 mL) and concentrated sulfuric acid (3 mL) and the mixture was stirred under microwave irradiation at 120° C. for 1.5 hr and at 150° C. for 3 hr. Water was added to the reaction mixture, and the mixture was extracted with ethyl acetate. The solvent was evaporated under reduced pressure to give the title compound as a crude product (410 mg).

MS (ESI) m/z: 301 (M–H)⁻

Preparation Example 48: Preparation of 2-hydroxy-4-(4-methyl-2,5-dioxoimidazolidin-4-yl)benzoic acid

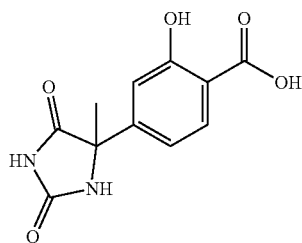

To 1-(4-bromo-3-methoxyphenyl)ethanone (1.36 g) were added ethanol (3 mL), 28% aqueous ammonia (3 mL), ammonium carbonate (2.26 g), potassium carbonate (1.63 g) and trimethylsilyl cyanide (1.48 mL) and the mixture was stirred at room temperature overnight. Water (3 mL) was added, and the mixture was stirred at room temperature for 4 hr and at 50° C. for 3 hr. Furthermore, 28% aqueous ammonia (3 mL), ammonium carbonate (1.13 g), potassium carbonate (815 mg) and trimethylsilyl cyanide (0.74 mL) were added, and the mixture was stirred at 50° C. for 3 hr. Water was added to the reaction mixture, and the mixture was concentrated under reduced pressure until a solid was precipitated. The precipitate was collected by filtration to give 5-(4-bromo-3-methoxyphenyl)-5-methylimidazolidine-2,4-dione (1.21 g).

To the obtained 5-(4-bromo-3-methoxyphenyl)-5-methylimidazolidine-2,4-dione (1.21 g) were added zinc cyanide (1.19 g), zinc (56 mg), 1,1'-bis(diphenylphosphino)ferrocene (222 mg), tris(dibenzylideneacetone)dipalladium(0) (183 mg) and N,N-dimethylformamide (13 mL) and the mixture was stirred at 130° C. for 8 hr. Zinc (280 mg), 1,1'-bis(diphenylphosphino)ferrocene (222 mg) and tris(dibenzylideneacetone)dipalladium(0) (183 mg) were added, and the mixture was stirred at 130° C. for 8 hr. Furthermore, 1,1'-bis(diphenylphosphino)ferrocene (222 mg) and tris(dibenzylideneacetone)dipalladium(0) (183 mg) were added, and the mixture was stirred at 150° C. for 8 hr. To the reaction mixture was added chloroform, and the mixture was filtered through celite. The filtrate was concentrated under reduced pressure and the obtained residue was purified by column chromatography (hexane:ethyl acetate) to give 2-methoxy-4-(4-methyl-2,5-dioxoimidazolidin-4-yl)benzonitrile (420 mg).

To the obtained 2-methoxy-4-(4-methyl-2,5-dioxoimidazolidin-4-yl)benzonitrile (420 mg) were added acetic acid (3 mL), concentrated hydrochloric acid (3 mL), concentrated sulfuric acid (3 mL) and the mixture was stirred under microwave irradiation at 150° C. for 2 hr. Water was added to the reaction mixture, and the mixture was extracted with ethyl acetate. The solvent was evaporated and water was added to the obtained residue, and the precipitate was collected by filtration to give the title compound (133 mg).

MS(ESI) m/z: 249 (M–H)⁻

Preparation Example 49: Preparation of 4-(3-isopropyl-2,5-dioxopyrrolidin-3-yl)benzoic acid

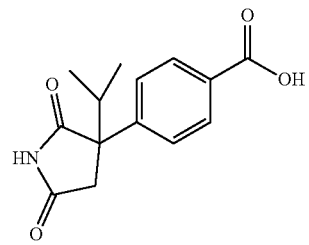 [SMILES: CC(C)C1(c2ccc(C(=O)O)cc2)CC(=O)NC1=O]

1) Preparation of 3-isopropyl-3-(p-tolyl)pyrrolidine-2,5-dione

To a solution of 3-methyl-2-(p-tolyl)butyric acid methyl ester (5.2 g) in tetrahydrofuran (94 mL) was added dropwise under cooling to –78° C. lithium diisopropylamide (2 M, heptane/tetrahydrofuran/ethylbenzene solution) (18.91 mL) and the mixture was stirred for 1 hr. A solution of bromoacetonitrile (5.04 mL) in tetrahydrofuran (10 mL) was added, and the mixture was stirred at –78° C. for 2 hr. To the reaction mixture was added aqueous ammonia chloride solution, and the mixture was extracted with ethyl acetate. The organic layer was washed with saturated brine, dried over anhydrous magnesium sulfate and concentrated under reduced pressure. The obtained residue was purified by column chromatography (hexane/ethyl acetate) to give 2-cyanomethyl-3-methyl-2-(p-tolyl)butyric acid methyl ester (5.81 g).

To the obtained 2-cyanomethyl-3-methyl-2-(p-tolyl)butyric acid methyl ester (500 mg) were added ethanol (5 mL), 30% hydrogen peroxide water (5.68 mL), 1N aqueous sodium hydroxide solution (5.56 mL) and the mixture was stirred at room temperature overnight. 30% Hydrogen peroxide water (5.68 mL) was added, and the mixture was stirred at room temperature overnight. Furthermore, 30% hydrogen peroxide water (5.68 mL) was added, and the mixture was stirred at room temperature overnight. Furthermore, ethanol (5 mL), 30% hydrogen peroxide water (5.68 mL) and 1N aqueous sodium hydroxide solution (5.56 mL) were added, and the mixture was stirred at room temperature overnight. Sodium bisulfite was added, and the mixture was acidified with concentrated hydrochloric acid. The precipitate was collected by filtration to give 3-isopropyl-3-(p-tolyl)pyrrolidine-2,5-dione (314 mg).

2) Preparation of 4-(3-isopropyl-2,5-dioxopyrrolidin-3-yl)benzoic acid

To 3-isopropyl-3-(p-tolyl)pyrrolidine-2,5-dione (720 mg, see the above-mentioned 1)) were added water (7.2 mL), 1N aqueous sodium hydroxide solution (6.23 mL) and potassium permanganate (1.42 g) and the mixture was stirred at room temperature overnight. Potassium permanganate (676 mg) was added, and the mixture was stirred at room temperature for 3.5 hr. To the reaction mixture was added ethanol (6 mL) and the mixture was stirred for 1 hr and filtered through celite. The filtrate was concentrated under reduced pressure to evaporate ethanol. The remaining aqueous solution was acidified with concentrated hydrochloric acid and extracted with a mixed solvent of chloroform and methanol. The solvent was evaporated and the obtained residue was purified by column chromatography (chloroform:methanol) to give the title compound (375 mg).

MS(ESI) m/z: 260 (M−H)⁻

Preparation Example 50: Preparation of 6-(3-methyl-2,5-dioxopyrrolidin-3-yl)nicotinic acid

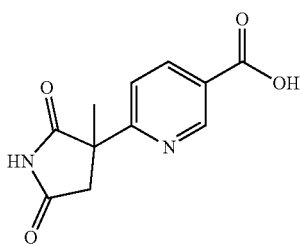 [SMILES: CC1(c2ccc(C(=O)O)cn2)CC(=O)NC1=O]

1) Preparation of 6-(tert-butoxycarbonylcyanomethyl)nicotinic acid ethyl ester To 6-chloronicotinic acid ethyl ester (11 g) were added tert-butyl cyanoacetate ester (8.88 mL), N,N-dimethylformamide (100 mL) and potassium carbonate (19.7 g) and the mixture was stirred at 95° C. for 11 hr. tert-Butyl cyanoacetate ester (4 mL) and potassium carbonate (10 g) were added, and the mixture was stirred at 95° C. for 4 hr. The reaction mixture was filtered through celite, and the filtrate was concentrated under reduced pressure. The obtained residue was diluted with water, under ice-cooling, 1N hydrochloric acid was added (about pH 4), and the precipitate was collected by filtration. The obtained precipitate was suspended in diethyl ether and collected by filtration to give 6-(tert-butoxycarbonylcyanomethyl)nicotinic acid ethyl ester (16.228 g)

2) Preparation of 6-(tert-butoxycarbonylcyanomethylmethyl)nicotinic acid ethyl ester To a mixed solution of 6-(tert-butoxycarbonylcyanomethyl)nicotinic acid ethyl ester (1 g) described in the above-mentioned 1) and potassium carbonate (1.43 g) in N,N-dimethylformamide (70 mL) was added methyl iodide (0.24 mL) and the mixture was stirred at room temperature overnight. Methyl iodide (0.11 mL) was added, and the mixture was stirred at room temperature overnight. Water was added to the reaction mixture, and the mixture was extracted with ethyl acetate. The obtained organic layer was concentrated under reduced pressure and the obtained residue was purified by column chromatography (hexane:ethyl acetate) to give 6-(tert-butoxycarbonylcyanomethylmethyl) nicotinic acid ethyl ester (951 mg).

3) Preparation of 6-(3-methyl-2,5-dioxopyrrolidin-3-yl)nicotinic acid

To 6-(tert-butoxycarbonylcyanomethylmethyl)nicotinic acid ethyl ester (300 mg) described in the above-mentioned 2) were added montmorillonite K10 (100 mg) and toluene (6 mL) and the mixture was stirred at 100° C. for 3 hr and refluxed for 2 hr. The reaction mixture was filtered through celite, and the filtrate was concentrated under reduced pressure to give 6-(cyanomethylmethyl)nicotinic acid ethyl ester (193 mg).

A solution of the obtained 6-(cyanomethylmethyl)nicotinic acid ethyl ester (189 mg) in tetrahydrofuran (3 mL) was added to a suspension of sodium hydride (40.8 mg, 60% in oil) in tetrahydrofuran (2 mL) at room temperature with stirring. Then, the reaction mixture was stirred at 90° C. for 30 min, and methyl bromoacetate ester (0.094 mL) was added at room temperature. The reaction mixture was stirred at 90° C. for 1 hr, and treated with a saturated aqueous ammonium chloride solution at room temperature. The mixture was extracted with ethyl acetate, and the obtained organic layer was dried over anhydrous sodium sulfate and concentrated under reduced pressure to give 6-(cyanomethoxycarbonylmethylmethylmethyl)nicotinic acid ethyl ester (220 mg).

To the obtained 6-(cyanomethoxycarbonylmethylmethylmethyl)nicotinic acid ethyl ester (216 mg) were added acetic acid (13 mL) and concentrated sulfuric acid (0.64 mL) and the mixture was stirred at 140° C. for 16 hr. After completion of the reaction, the reaction mixture was concentrated under reduced pressure, water was added to the obtained residue, and the mixture was extracted with ethyl acetate. The obtained organic layer was dried over anhydrous sodium sulfate and concentrated under reduced pressure to give 6-(3-methyl-2,5-dioxopyrrolidin-3-yl)nicotinic acid (85 mg).

MS (ESI) m/z: 235 (M+H)⁺

Preparation Example 51: Preparation of 6-(3-ethyl-2,5-dioxopyrrolidin-3-yl) nicotinic acid

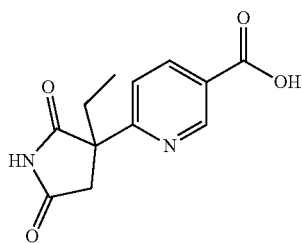 [SMILES: CCC1(c2ccc(C(=O)O)cn2)CC(=O)NC1=O]

Using 6-(tert-butoxycarbonylcyanomethyl)nicotinic acid ethyl ester (1.00 g) described in Preparation Example 50, 1) and ethyl iodide (0.608 mL), reactions and treatments similar to those in Preparation Example 50, 2) were performed to give 6-(l-tert-butoxycarbonyl-1-cyanopropyl)nicotinic acid ethyl ester (1.05 g).

Using the obtained 6-(1-tert-butoxycarbonyl-1-cyanopropyl)nicotinic acid ethyl ester (500 mg) and methyl bromoacetate ester (0.152 mL), reactions and treatments similar to those in Preparation Example 50, 3) were performed to give the title compound (155 mg).

MS(ESI) m/z: 249 (M+H)⁺, 247 (M−H)⁻

Preparation Example 52: Preparation of 6-(3-isopropyl-2,5-dioxopyrrolidin-3-yl) nicotinic acid

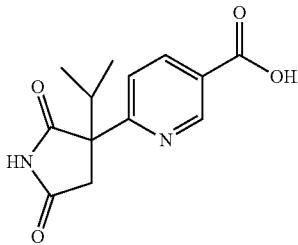 [SMILES: CC(C)C1(c2ccc(C(=O)O)cn2)CC(=O)NC1=O]

To a mixed solution of 6-(tert-butoxycarbonylcyanomethyl)nicotinic acid ethyl ester (1 g) described in Preparation Example 50, 1) and potassium carbonate (1.43 g) in N,N-dimethylformamide (70 mL) was added 2-iodopropane (0.376 mL) and the mixture was stirred at room temperature overnight. 2-Iodopropane (1.03 mL) was added, and the mixture was stirred at 70° C. for 28 hr. Water was added to the reaction mixture, and the mixture was extracted with ethyl acetate. The obtained organic layer was concentrated under reduced pressure and the obtained residue was purified by silica gel column chromatography (hexane:ethyl acetate) to give 6-(1-tert-butoxycarbonyl-1-cyano-2-methylpropyl)nicotinic acid ethyl ester (1.02 g).

Using the obtained 6-(1-tert-butoxycarbonyl-1-cyano-2-methylpropyl)nicotinic acid ethyl ester (500 mg) and methyl bromoacetate ester (0.151 mL), reactions and treatments similar to those in Preparation Example 50, 3) were performed to give the title compound (145 mg).

MS(ESI) m/z: 263 (M+H)⁺, 261 (M−H)⁻

Preparation Example 53: Preparation of 4-(4-ethyl-2,5-dioxoimidazolidin-4-yl)-3-methoxybenzoic acid

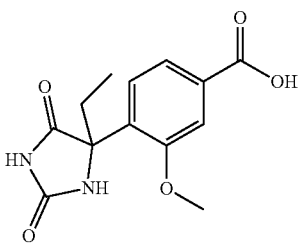 [SMILES: CCC1(c2ccc(C(=O)O)cc2OC)NC(=O)NC1=O]

To 1-(4-bromo-2-methoxyphenyl)propan-1-one (7.33 g) were added palladium acetate (0.339 g), 1,1'-bis(diphenylphosphino)ferrocene (1.672 g), ethanol (35.2 mL), N,N-dimethylformamide (125 mL) and triethylamine (8.4 mL) and the mixture was stirred under carbon monoxide atmosphere at 80° C. for 6 hr. To the reaction mixture were added water (150 mL) and ethyl acetate (150 mL) and the mixture was stirred at room temperature overnight. After filtration through celite, the filtrate was extracted with ethyl acetate. The organic layer was concentrated under reduced pressure, toluene was added to the obtained residue, and insoluble material was removed by filtration. The filtrate was concentrated under reduced pressure and the obtained residue was purified by column chromatography (hexane/ethyl acetate) to give 3-methoxy-4-propionylbenzoic acid ethyl ester (6.166 g).

The obtained 3-methoxy-4-propionylbenzoic acid ethyl ester (1.0 g) was dissolved in ethanol (10 mL) and tetrahydrofuran (10 mL), 1N aqueous sodium hydroxide solution (8.89 mL) was added, and the mixture was stirred at room temperature for 4.5 hr. To the reaction mixture was added 1N hydrochloric acid (10 mL) and the mixture was extracted with a mixed solvent of chloroform and methanol. The organic layer was washed with saturated brine, dried over anhydrous magnesium sulfate and concentrated under reduced pressure. To the obtained residue was added hexane/ethyl acetate, and the precipitate was collected by filtration to give 3-methoxy-4-propionylbenzoic acid (639 mg).

To the obtained 3-methoxy-4-propionylbenzoic acid (620 mg) were added ammonium carbonate (1.075 g), potassium carbonate (0.823 g), ethanol (1.5 mL), 28% aqueous ammonia (2.5 mL) and trimethylsilyl cyanide (0.774 mL) and the mixture was stirred under microwave irradiation at 120° C. for 1.5 hr. The reaction mixture was acidified by adding water and concentrated hydrochloric acid under ice-cooling (about pH 2). The precipitated solid was collected by filtration to give the title compound (825 mg).

MS(ESI) m/z: 277 (M−H)⁻

Preparation Example 54: Preparation of 4-(2,5-dioxo-4-propylimidazolidin-4-yl)-3-methoxybenzoic acid

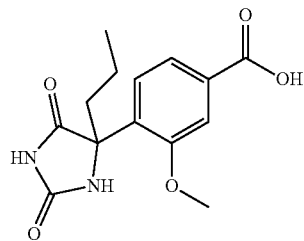 [SMILES: CCCC1(c2ccc(C(=O)O)cc2OC)NC(=O)NC1=O]

To 1-(4-bromo-2-methoxyphenyl)butan-1-one (5.7 g) were added palladium acetate (0.249 g), 1,1'-bis(diphenylphosphino)ferrocene (1.23 g), ethanol (25.9 mL), N,N-dimethylformamide (55 mL) and triethylamine (6.2 mL) and the mixture was stirred under carbon monoxide atmosphere at 80° C. for 2 hr. The reaction mixture was cooled to room temperature, ethyl acetate was added and the mixture was filtered through celite. The filtrate was washed with saturated brine, dried over anhydrous sodium sulfate and concentrated under reduced pressure. The obtained residue was purified by column chromatography (hexane:ethyl acetate) to give 4-butyryl-3-methoxybenzoic acid ethyl ester (4.662 g).

The obtained 4-butyryl-3-methoxybenzoic acid ethyl ester (1.0 g) was dissolved in ethanol (10 mL) and tetrahydrofuran (10 mL), 1N aqueous sodium hydroxide solution (8.39 mL) was added, and the mixture was stirred at room temperature for 4 hr. To the reaction mixture was added 1N hydrochloric acid (10 mL) and the mixture was extracted with a mixed solvent of chloroform and methanol. The organic layer was washed with saturated brine, dried over anhydrous magnesium sulfate and concentrated under reduced pressure. To the obtained residue was added hexane/ethyl acetate, and the precipitate was collected by filtration to give 4-butyryl-3-methoxybenzoic acid (636 mg).

To the obtained 4-butyryl-3-methoxybenzoic acid (620 mg) were added ammonium carbonate (1.007 g), potassium carbonate (0.771 g), ethanol (1.5 mL), 28% aqueous ammonia (2.5 mL) and trimethylsilyl cyanide (0.726 mL) and the mixture was stirred under microwave irradiation at 120° C. for 1.5 hr. The reaction mixture was acidified by adding water and concentrated hydrochloric acid under ice-cooling. The precipitated solid was collected by filtration to give the title compound (755 mg).

MS(ESI) m/z: 291 (M−H)⁻

Preparation Example 55: Preparation of 4-(4-difluoromethyl-2,5-dioxoimidazolidin-4-yl)-3-methoxybenzoic acid

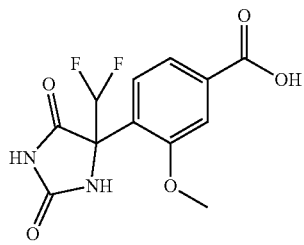 [SMILES: COc1cc(C(=O)O)ccc1C1(C(F)F)NC(=O)NC1=O]

To 1-(4-bromo-2-methoxyphenyl)ethanone (26.15 g) were added palladium acetate (1.28 g), 1,1'-bis(diphenylphosphino)ferrocene (6.32 g), ethanol (133 mL), N,N-dimethylformamide (290 mL) and triethylamine (31.8 mL) and the mixture was stirred under carbon monoxide atmosphere at 80° C. for 4 hr. The reaction mixture was cooled to room temperature and concentrated under reduced pressure. To the obtained residue were added ethyl acetate and SH silica gel and, after filtration through celite, the filtrate was concentrated under reduced pressure. The obtained residue was purified by column chromatography (hexane:ethyl acetate) to give 4-acetyl-3-methoxybenzoic acid ethyl ester (23.0 g).

To a solution of the obtained 4-acetyl-3-methoxybenzoic acid ethyl ester (5 g) in cyclohexane (45 mL) were added n-butylamine (4.45 mL), molecular sieve 4 A (5 g) and trifluoroacetic acid (catalytic amount), and the mixture was stirred under reflux for 18 hr. The reaction mixture was filtered through celite and the filtrate was concentrated under reduced pressure. To the obtained residue was added saturated aqueous sodium hydrogen carbonate solution and the mixture was extracted with diisopropyl ether. The organic layer was washed with saturated brine and dried over anhydrous sodium sulfate. The solvent was evaporated and the obtained residue (6.36 g) was dissolved in acetonitrile (110 mL). Sodium sulfate (2.25 g) and Selectfluor (21 g) were added, and the mixture was stirred under reflux for 4 hr. The reaction mixture was cooled to room temperature, 6N hydrochloric acid (20 mL) was added and the mixture was stirred for 15 min and extracted with ethyl acetate. The organic layer was washed with saturated aqueous sodium hydrogen carbonate solution and saturated brine, dried over anhydrous sodium sulfate and concentrated under reduced pressure. The obtained residue was purified by column chromatography (hexane:ethyl acetate) to give 4-(2,2-difluoroacetyl)-3-methoxybenzoic acid ethyl ester (3.39 g).

The obtained 4-(2,2-difluoroacetyl)-3-methoxybenzoic acid ethyl ester (1.0 g) was dissolved in ethanol (10 mL) and tetrahydrofuran (10 mL), 1N aqueous sodium hydroxide solution (8.13 mL) was added, and the mixture was stirred at room temperature for 3 hr. To the reaction mixture was added 1N hydrochloric acid (10 mL) and the mixture was extracted with a mixed solvent of chloroform and methanol. The organic layer was washed with saturated brine, dried over anhydrous magnesium sulfate and concentrated under reduced pressure. To the obtained residue was added hexane/ethyl acetate, and the precipitate was collected by filtration to give 4-(2,2-difluoroacetyl)-3-methoxybenzoic acid (667 mg).

To the obtained 4-(2,2-difluoroacetyl)-3-methoxybenzoic acid (620 mg) were added ammonium carbonate (0.973 g), potassium carbonate (0.745 g), 28% aqueous ammonia (2.5 mL) and trimethylsilyl cyanide (0.701 mL) and the mixture was stirred under microwave irradiation at 120° C. for 1.5 hr. The reaction mixture was acidified by adding water and concentrated hydrochloric acid under ice-cooling and the mixture was extracted with a mixed solvent of chloroform and methanol. The organic layer was washed with saturated brine, dried over anhydrous magnesium sulfate and concentrated under reduced pressure. To the obtained residue was added hexane/ethyl acetate, and the precipitate was collected by filtration to give the title compound (80 mg).

MS(ESI) m/z: 299 (M−H)⁻

Preparation Example 56: Preparation of 3-ethoxy-4-(4-isopropyl-2,5-dioxoimidazolidin-4-yl)benzoic acid

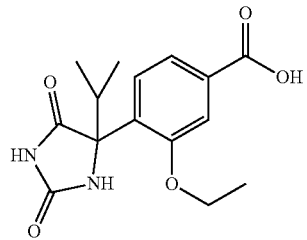 [SMILES: CCOc1cc(C(=O)O)ccc1C1(C(C)C)NC(=O)NC1=O]

1-(4-Bromo-2-hydroxyphenyl)-2-methylpropan-1-one (4.35 g) was dissolved in acetone (89.5 mL), potassium carbonate (11.13 g) and ethyl iodide (4.3 mL) were added, and the mixture was stirred at 60° C. overnight. The reaction mixture was filtered and the filtrate was concentrated under reduced pressure. To the obtained residue was added water, and the mixture was extracted with ethyl acetate. The organic layer was washed with saturated brine (50 mL), dried over anhydrous sodium sulfate, and concentrated under reduced pressure to give 1-(4-bromo-2-ethoxyphenyl)-2-methylpropan-1-one (5.23 g).

To the obtained 1-(4-bromo-2-ethoxyphenyl)-2-methylpropan-1-one (5.23 g) were added palladium acetate (0.25 g), 1,1'-bis(diphenylphosphino)ferrocene (1.13 g), ethanol (23.7 mL), N,N-dimethylformamide (40.6 mL) and triethylamine (5.7 mL) and the mixture was stirred under carbon monoxide atmosphere at 80° C. for 4 hr. To the reaction mixture was added water, and the mixture was extracted with diethyl ether. The organic layer was filtered through celite, and the filtrate was dried over anhydrous sodium sulfate and concentrated under reduced pressure. The obtained residue was purified by column chromatography (hexane:ethyl acetate) to give 3-ethoxy-4-isobutyrylbenzoic acid ethyl ester (3.94 g).

The obtained 3-ethoxy-4-isobutyrylbenzoic acid ethyl ester (680 mg) was dissolved in ethanol (6.8 mL) and tetrahydrofuran (6.8 mL), 1N aqueous sodium hydroxide solution (5.4 mL) was added, and the mixture was stirred at room temperature for 4 hr. To the reaction mixture was added 1N hydrochloric acid (10 mL) and the mixture was extracted with a mixed solvent of chloroform and methanol. The organic layer was washed with saturated brine, dried over anhydrous magnesium sulfate and concentrated under reduced pressure. To the obtained residue was added hexane/ethyl acetate, and the precipitate was collected by filtration to give 3-ethoxy-4-isobutyrylbenzoic acid (118 mg). The filtrate was concentrated under reduced pressure, to the obtained residue was added hexane/diisopropyl ether, and the precipitate was collected by filtration to give 3-ethoxy-4-isobutyrylbenzoic acid (403 mg).

To the obtained 3-ethoxy-4-isobutyrylbenzoic acid (495 mg) were added ammonium carbonate (0.756 g), potassium carbonate (0.579 g), 28% aqueous ammonia (2 mL), ethanol (1 mL) and trimethylsilyl cyanide (0.545 mL) and the mixture was stirred under microwave irradiation at 120° C. for 3.5 hr. The reaction mixture was acidified by adding water and concentrated hydrochloric acid under ice-cooling, and the precipitated solid was collected by filtration to give the title compound (615 mg).

MS(ESI) m/z: 305 (M−H)−

Preparation Example 57: Preparation of 4-(4-isopropyl-2,5-dioxoimidazolidin-4-yl)-5-methoxy-2-methylbenzoic acid

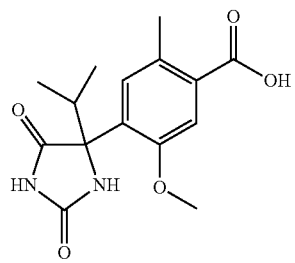 [SMILES: COc1cc(C(=O)O)c(C)cc1C1(C(C)C)NC(=O)NC1=O]

To a suspension of aluminum chloride (5.33 g) in dichloromethane (50 mL) was added a solution of 3-bromo-4-methylanisole (5.36 g) in dichloromethane (10 mL) under ice-cooling, and the mixture was stirred for 5 min. To the reaction mixture was added isobutyryl chloride, and the mixture was stirred under ice-cooling for 45 min. To the reaction mixture was added ice water, 6N hydrochloric acid was added and the mixture was extracted with chloroform. The organic layer was washed with saturated aqueous sodium hydrogen carbonate solution, dried over anhydrous sodium sulfate and concentrated under reduced pressure. The obtained residue was purified by column chromatography (hexane:ethyl acetate) to give 1-(4-bromo-2-methoxy-5-methylphenyl)-2-methylpropan-1-one (4.86 g).

To the obtained 1-(4-bromo-2-methoxy-5-methylphenyl)-2-methylpropan-1-one (500 mg) were added ammonium carbonate (0.666 g), potassium carbonate (0.51 g), 28% aqueous ammonia (4 mL), ethanol (5 mL) and trimethylsilyl cyanide (0.48 mL) and the mixture was stirred under microwave irradiation at 130° C. for 1.5 hr. Ammonium carbonate (0.666 g), potassium carbonate (0.51 g), 28% aqueous ammonia (2 mL) and trimethylsilyl cyanide (0.48 mL) were added, and the mixture was stirred under microwave irradiation at 130° C. for 2 hr. Furthermore, ammonium carbonate (0.666 g), potassium carbonate (0.51 g), 28% aqueous ammonia (2 mL) and trimethylsilyl cyanide (0.48 mL) were added, and the mixture was stirred under microwave irradiation at 130° C. for 1 hr. The reaction mixture was acidified by adding water and concentrated hydrochloric acid under ice-cooling (about pH 3), and the precipitate was collected by filtration. The obtained precipitate was suspended in hexane/ethyl acetate and collected by filtration to give 5-(4-bromo-2-methoxy-5-methylphenyl)-5-isopropylimidazolidine-2,4-dione (508 mg).

To the obtained 5-(4-bromo-2-methoxy-5-methylphenyl)-5-isopropylimidazolidine-2,4-dione (300 mg) were added zinc cyanide (124 mg), zinc (5.8 mg), 1,1'-bis(diphenylphosphino)ferrocene (49 mg), tris(dibenzylideneacetone)dipalladium(0) (40 mg) and N,N-dimethylformamide (3 mL) and the mixture was stirred under microwave irradiation at 150° C. for 1 hr. To the reaction mixture were added water and ethyl acetate, and the mixture was filtered through celite. The filtrate was extracted with ethyl acetate, and the organic layer was dried over anhydrous magnesium sulfate and concentrated under reduced pressure. The obtained residue was purified by column chromatography (hexane:ethyl acetate) to give 4-(4-isopropyl-2,5-dioxoimidazolidin-4-yl)-5-methoxy-2-methylbenzonitrile (250 mg)

To the obtained 4-(4-isopropyl-2,5-dioxoimidazolidin-4-yl)-5-methoxy-2-methylbenzonitrile (245 mg) were added 1,4-dioxane (1.47 mL) and 6N hydrochloric acid (1.42 mL) and the mixture was stirred under reflux overnight. The reaction mixture was concentrated under reduced pressure to evaporate 1,4-dioxane. To the obtained residue was added acetic acid (1.47 mL) and the mixture was stirred under microwave irradiation at 150° C. for 2 hr. Water was added to the reaction mixture, and the mixture was extracted with ethyl acetate. The organic layer was washed with saturated brine, dried over anhydrous magnesium sulfate and concentrated under reduced pressure. The obtained residue was purified by column chromatography (chloroform:methanol) to give the title compound (114 mg).

MS(ESI) m/z: 305 (M−H)−

Preparation Example 58: Preparation of 5-hydroxy-4-(4-isopropyl-2,5-dioxoimidazolidin-4-yl)-2-methylbenzoic acid

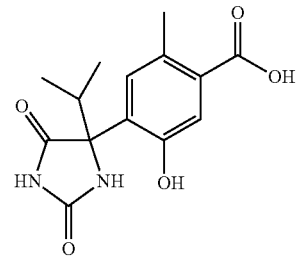 [SMILES: Cc1cc(C2(C(C)C)NC(=O)NC2=O)c(O)cc1C(=O)O]

The resultant product by-produced in Preparation Example 57 was purified by column chromatography (chloroform:methanol) to give the title compound (16.3 mg).

MS (ESI) m/z: 291 (M−H)⁻

Preparation Example 59: Preparation of 2-fluoro-4-(4-isopropyl-2,5-dioxoimidazolidin-4-yl)-5-methoxybenzoic acid

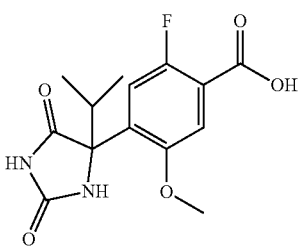 [SMILES: COc1cc(C(=O)O)c(F)cc1C1(C(C)C)NC(=O)NC1=O]

To 1-(4-bromo-5-fluoro-2-hydroxyphenyl)-2-methylpropan-1-one (6.63 g) were added acetone (130 mL), potassium carbonate (5.27 g) and methyl iodide (4.8 mL) and the mixture was stirred at 60° C. for 3 hr. The reaction mixture was filtered, and the filtrate was concentrated under reduced pressure. The obtained residue was purified by column chromatography (hexane:ethyl acetate) to give 1-(4-bromo-5-fluoro-2-methoxyphenyl)-2-methylpropan-1-one (5 g).

To the obtained 1-(4-bromo-5-fluoro-2-methoxyphenyl)-2-methylpropan-1-one (5 g) were added palladium acetate (0.204 g), 1,1'-bis(diphenylphosphino)ferrocene (1 g), methanol (14.7 mL), N,N-dimethylformamide (46 mL) and triethylamine (5.1 mL) and the mixture was stirred under carbon monoxide atmosphere at 80° C. for 17 hr. Water was added to the reaction mixture, and the mixture was extracted with ethyl acetate. Anhydrous sodium sulfate and SH silica gel were added to the organic layer and the mixture was filtered. The filtrate was concentrated under reduced pressure, and the obtained residue was purified by column chromatography (hexane:ethyl acetate) to give 2-fluoro-4-isobutyryl-5-methoxybenzoic acid methyl ester (2.3 g).

To the obtained 2-fluoro-4-isobutyryl-5-methoxybenzoic acid methyl ester (1 g) were added methanol (2 mL), tetrahydrofuran (3 mL) and 1N aqueous sodium hydroxide solution (6 mL) and the mixture was stirred at room temperature for 3.5 hr. To the reaction mixture was added 1N hydrochloric acid, and the precipitate was collected by filtration to give 2-fluoro-4-isobutyryl-5-methoxybenzoic acid (790 mg).

To the obtained 2-fluoro-4-isobutyryl-5-methoxybenzoic acid (786 mg) were added ammonium carbonate (1.57 g), potassium carbonate (1.37 g), 28% aqueous ammonia (1.7 mL), water (1.7 mL) and trimethylsilyl cyanide (1.23 mL) and the mixture was stirred under microwave irradiation at 100° C. for 1 hr. 28% Aqueous ammonia (0.5 mL) and trimethylsilyl cyanide (0.41 mL) were added, and the mixture was stirred under microwave irradiation at 120° C. for 1.5 hr. The reaction mixture was acidified with 3N hydrochloric acid and the precipitate was collected by filtration. The obtained precipitate was washed with water and diethyl ether to give the title compound (608 mg).

MS(ESI) m/z: 309 (M−H)⁻

Preparation Example 60: Preparation of 4-[4-(1,1-difluoroethyl)-2,5-dioxoimidazolidin-4-yl]-3-methoxybenzoic acid

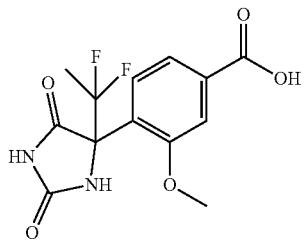 [SMILES: COc1cc(C(=O)O)ccc1C1(C(C)(F)F)NC(=O)NC1=O]

To 3-methoxy-4-propionylbenzoic acid ethyl ester (3.55 g) described in Preparation Example 53 were added n-butylamine (2.2 g), molecular sieves 4 A (3.55 g), cyclohexane (35 mL) and trifluoroacetic acid (catalytic amount), and the mixture was refluxed under an argon atmosphere with stirring for 20.5 hr. The reaction mixture was filtered and washed with diisopropyl ether. The organic layer was washed with saturated aqueous sodium hydrogen carbonate solution, dried over anhydrous magnesium sulfate and concentrated under reduced pressure. The obtained residue was dissolved in acetonitrile (50 mL), sodium sulfate (1.5 g) and Selectfluor (11.71 g) were added, and the mixture was stirred under reflux for 4 hr. The reaction mixture was cooled to room temperature, 6N hydrochloric acid (10 mL) was added, and the mixture was stirred at room temperature for 10 min and extracted with ethyl acetate. The organic layer was washed with saturated aqueous sodium hydrogen carbonate solution and saturated brine, dried over anhydrous magnesium sulfate and concentrated under reduced pressure. The obtained residue was purified by column chromatography (hexane:ethyl acetate) to give 4-(2,2-difluoropropionyl)-3-methoxybenzoic acid ethyl ester (3.284 g).

To the obtained 4-(2,2-difluoropropionyl)-3-methoxybenzoic acid ethyl ester (544 mg) were added ethanol (1 mL), tetrahydrofuran (2 mL) and 1N aqueous sodium hydroxide solution (3 mL) and the mixture was stirred at room temperature for 4 hr. To the reaction mixture was added 1N hydrochloric acid under ice-cooling, and the precipitated solid was collected by filtration to give 4-(2,2-difluoropropionyl)-3-methoxybenzoic acid (381 mg).

To the obtained 4-(2,2-difluoropropionyl)-3-methoxybenzoic acid (378 mg) were added ammonium carbonate (744 mg), potassium carbonate (642 g), 28% aqueous ammonia (0.75 mL), water (0.75 mL) and trimethylsilyl cyanide (0.581 mL) and the mixture was stirred under microwave irradiation at 100° C. for 1 hr. To the reaction mixture was added 3N hydrochloric acid under ice-cooling, and the precipitated solid was collected by filtration to give the title compound (423 mg).

MS(ESI) m/z: 313 (M−H)⁻

Preparation Example 61: Preparation of 4-(4-tert-butyl-2,5-dioxoimidazolidin-4-yl)-3-methoxybenzoic acid

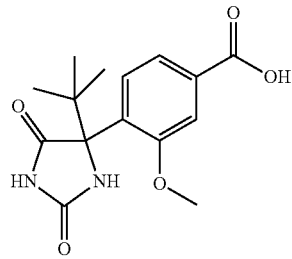 [SMILES: COc1cc(C(=O)O)ccc1C1(C(C)(C)C)NC(=O)NC1=O]

To a solution of 4-isobutyryl-3-methoxybenzoic acid (600 mg) described in Preparation Example 35, 1) and tert-butanol (60 mg) in tetrahydrofuran (12 mL) was added sodium hydride (432 mg, 60% in oil) under ice-cooling, and the mixture was stirred under a nitrogen atmosphere at room temperature for 3 hr. To the reaction mixture was added methyl iodide (0.336 mL) under ice-cooling, and the mixture was stirred at under a nitrogen atmosphere at room temperature for 1 hr. tert-Butanol (60 mg) and methyl iodide (0.336 mL) were added, and the mixture was stirred under a nitrogen atmosphere at 50° C. for 3 hr. To the reaction mixture was added 1N aqueous sodium hydroxide solution (3 mL) and the mixture was stirred at room temperature overnight and acidified with 1N hydrochloric acid. Sodium bisulfite and saturated brine were added, and the mixture was extracted with ethyl acetate. The organic layer was washed with saturated brine, dried over sodium sulfate and concentrated under reduced pressure. To the obtained residue were added ammonium carbonate (1.73 g), potassium carbonate (1.49 g), trimethylsilyl cyanide (1.4 mL) and 28% aqueous ammonia (10 mL) and the mixture was stirred under microwave irradiation at 100° C. for 1 hr and at 135° C. for 1 hr. Trimethylsilyl cyanide (2.8 mL) was added, and the mixture was stirred under microwave irradiation at 135° C. for 2 hr. Furthermore, trimethylsilyl cyanide (2.8 mL) was added, and the mixture was stirred under microwave irradiation at 135° C. for 2 hr. To the reaction mixture were added water, ethyl acetate and potassium carbonate, and the mixture was filtered through celite. The filtrate was acidified with concentrated hydrochloric acid under ice-cooling, and extracted with ethyl acetate. The organic layer was washed with saturated brine, dried over sodium sulfate, and treated with activated carbon. The solvent was evaporated and hexane/ethyl acetate was added to the obtained residue. The precipitate was collected by filtration to give the title compound (673 mg).

MS(ESI) m/z: 305 (M−H)⁻

Preparation Example 62: Preparation of 4-(4-difluoromethyl-2,5-dioxoimidazolidin-4-yl)benzoic acid

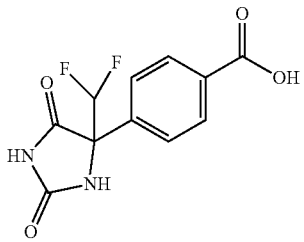 [SMILES: O=C1NC(=O)C(c2ccc(C(=O)O)cc2)(C(F)F)N1]

To 4-(2,2-difluoroacetyl)benzoic acid methyl ester (1.7 g) were added methanol (16 mL), tetrahydrofuran (5 mL) and 1N aqueous sodium hydroxide solution (24 mL) and the mixture was stirred at room temperature for 2 hr. The reaction mixture was concentrated under reduced pressure, water and 1N hydrochloric acid were added to the obtained aqueous solution, and the precipitate was collected by filtration to give 4-(2,2-difluoroacetyl)benzoic acid (496 mg).

To the obtained 4-(2,2-difluoroacetyl)benzoic acid (496 mg) were added ammonium carbonate (960 mg), potassium carbonate (691 mg), 28% aqueous ammonia (5 mL), water (5 mL) and trimethylsilyl cyanide (0.625 mL) and the mixture was stirred under microwave irradiation at 80° C. for 1 hr. Ammonium carbonate (480 mg), potassium carbonate (345 mg) and trimethylsilyl cyanide (0.312 mL) were added, and the mixture was stirred under microwave irradiation at 80° C. for 1.5 hr. To the reaction mixture were added water and concentrated hydrochloric acid (about pH 1), and the mixture was extracted with ethyl acetate and chloroform. The organic layer was dried over anhydrous magnesium sulfate and concentrated under reduced pressure. To the obtained residue was added hexane/ethyl acetate, and the precipitate was collected by filtration to give the title compound (72 mg).

MS(ESI) m/z: 271 (M+H)⁺, 269 (M−H)⁻

Preparation Example 63: Preparation of 4-(4-fluoromethyl-2,5-dioxoimidazolidin-4-yl)benzoic acid

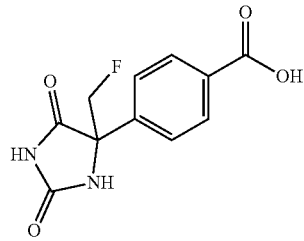 [SMILES: O=C1NC(=O)C(CF)(c2ccc(C(=O)O)cc2)N1]

To 4-acetylbenzoic acid methyl ester (6.3 g) were added methanol (170 mL) and Selectfluor (25 g) and the mixture was refluxed with stirring for 2 days. After filtration through celite, the filtrate was concentrated under reduced pressure. To the obtained residue was added chloroform, and the mixture was filtered (insoluble material was removed). The filtrate was concentrated under reduced pressure and the obtained residue was purified by column chromatography (hexane:ethyl acetate) to give 4-(2-fluoro-1,1-dimethoxyethyl)benzoic acid methyl ester (5.4 g).

The obtained 4-(2-fluoro-1,1-dimethoxyethyl)benzoic acid methyl ester (5.4 g) was dissolved in methanol (44 mL) and tetrahydrofuran (15 mL), 1N aqueous sodium hydroxide solution (67 mL) was added under ice-cooling, and the mixture was stirred at room temperature for 6 hr. Under ice-cooling, to the reaction mixture was added 2N hydrochloric acid, and the mixture was stirred for 1 hr and the precipitate was collected by filtration. To the obtained precipitate (4.8 g) were added dichloromethane (45 mL) and trifluoroacetic acid (10 mL) and the mixture was stirred at room temperature for 2 hr. The precipitate was collected by filtration to give 4-(2-fluoroacetyl)benzoic acid (3.68 g).

To the obtained 4-(2-fluoroacetyl)benzoic acid (910 mg) were added ammonium carbonate (1.2 g), potassium carbonate (2.07 g), 28% aqueous ammonia (9 mL), water (9 mL) and trimethylsilyl cyanide (1.8 mL) and the mixture was stirred under microwave irradiation at 80° C. for 1.5 hr. To the reaction mixture was added hydrochloric acid, and the precipitate was collected by filtration. The obtained precipitate was recrystallized from a mixed solvent of ethanol and water to give the title compound (730 mg).

MS(ESI) m/z: 251 (M−H)⁻

Preparation Example 64: Preparation of 6-(3-methoxymethyl-2,5-dioxopyrrolidin-3-yl) nicotinic acid

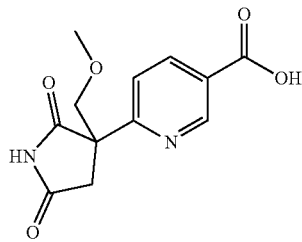 [SMILES: COCC1(c2ccc(C(=O)O)cn2)CC(=O)NC1=O]

To 6-(tert-butoxycarbonylcyanomethyl)nicotinic acid ethyl ester (6.1 g) described in Preparation Example 50, 1) were added N,N-dimethylformamide (400 mL), potassium carbonate (8.71 g) and ethyl bromoacetate (4.4 mL), and the mixture was stirred at 70° C. for 1 hr and at room temperature overnight. The reaction mixture was filtered through celite, to the filtrate was added saturated brine, and the mixture was extracted with ethyl acetate. The organic layer was dried over anhydrous sodium sulfate and concentrated under reduced pressure. The obtained residue was purified by column chromatography (hexane:ethyl acetate) to give 2-cyano-2-(5-ethoxycarbonylpyridin-2-yl)succinic acid 1-tert-butyl ester 4-ethyl ester (6.222 g).

To the obtained 2-cyano-2-(5-ethoxycarbonylpyridin-2-yl)succinic acid 1-tert-butyl ester 4-ethyl ester (6.2 g) were added toluene (50 mL) and montmorillonite K10 (2 g) and the mixture was stirred at 120° C. for 1.5 hr. The reaction mixture was filtered through celite and the filtrate was concentrated under reduced pressure. The obtained residue was purified by column chromatography (hexane:ethyl acetate) to give 6-[cyano(ethoxycarbonylmethyl)methyl] nicotinic acid ethyl ester (4.086 g).

To a solution of the obtained 6-[cyano(ethoxycarbonylmethyl)methyl]nicotinic acid ethyl ester (0.5 g) in N,N-dimethylformamide (9 mL) was added under ice-cooling sodium hydride (60% in oil) (0.145 g) and the mixture was stirred under ice-cooling for 30 min and at room temperature for 40 min. Under ice-cooling, chloromethyl methyl ether (0.272 mL) was added, and the mixture was stirred at room temperature for 8 hr. The reaction mixture was poured into ice water and the mixture was extracted with ethyl acetate. The organic layer was dried over anhydrous sodium sulfate and concentrated under reduced pressure. The obtained residue was purified by column chromatography (hexane: ethyl acetate) to give 6-[cyano(ethoxycarbonylmethyl) (methoxymethyl)methyl]nicotinic acid ethyl ester (0.335 g).

To the obtained 6-[cyano(ethoxycarbonylmethyl) (methoxymethyl)methyl]nicotinic acid ethyl ester (0.171 g) were added ethanol (3 mL), hydrogen peroxide water (0.982 mL) and 1N aqueous sodium hydroxide solution (1.6 mL) and the mixture was stirred at room temperature overnight. Under ice-cooling, to the reaction mixture was added 5% aqueous sodium bisulfite solution, and the mixture was stirred at room temperature for 1 hr. The reaction mixture was extracted with tetrahydrofuran. The solvent was evaporated and the obtained residue was purified by column chromatography (chloroform:methanol) to give the title compound (0.087 g).

MS(ESI) m/z: 265 (M+H)⁺

Preparation Example 65: Preparation of 4-[(R)-1-(2, 2-dimethylpropionyloxymethyl)-4-methyl-2,5-dioxoimidazolidin-4-yl]benzoic acid

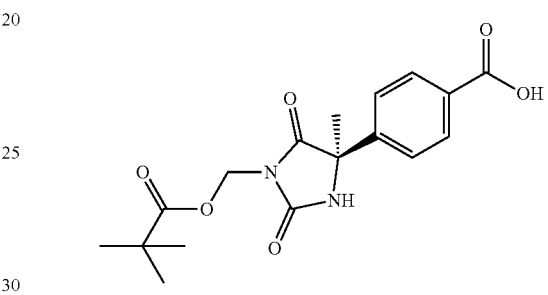

4-((R)-4-methyl-2,5-dioxoimidazolidin-4-yl)benzoic acid (1.5 g) of Preparation Example 6, 1-ethyl-3-(3'-dimethylaminopropyl) carbodiimide.hydrochloride (1.842 g) and 4-dimethylaminopyridine (0.156 g) were dissolved in dichloromethane (30 mL), benzyl alcohol (1.326 mL) was added, and the mixture was stirred at room temperature for 3 days. Water was added to the reaction mixture and the mixture was extracted with chloroform. The solvent was concentrated under reduced pressure and the obtained residue was purified by column chromatography (chloroform: methanol) to give 4-((R)-4-methyl-2,5-dioxoimidazolidin-4-yl)benzoate benzyl ester (0.903 g).

To a solution of the obtained 4-((R)-4-methyl-2,5-dioxoimidazolidin-4-yl)benzoate benzyl ester (450 mg) in N,N-dimethylformamide (5 mL) were added potassium carbonate (230 mg) and chloromethyl 2,2-dimethylpropionate (0.211 mL) and the mixture was stirred at room temperature overnight. Water was added to the reaction mixture, and the mixture was extracted with ethyl acetate. The solvent was evaporated and the obtained residue was purified by column chromatography (hexane:ethyl acetate) to give 4-[(R)-1-(2, 2-dimethylpropionyloxymethyl)-4-methyl-2,5-dioxoimidazolidin-4-yl]benzoate benzyl ester (512 mg).

To a solution of the obtained 4-[(R)-1-(2,2-dimethylpropionyloxymethyl)-4-methyl-2,5-dioxoimidazolidin-4-yl] benzoate benzyl ester (512 mg) in methanol (10 mL) was added 10% palladium carbon (100 mg) and the mixture was stirred under a hydrogen atmosphere at room temperature for 2 hr. The reaction mixture was filtered through celite and the filtrate was concentrated under reduced pressure to give the title compound (400 mg).

MS(ESI) m/z: 349 (M+H)⁺, 347 (M−H)⁻

Preparation Example 66: Preparation of 5-(4-isopropyl-2,5-dioxoimidazolidin-4-yl)thiophene-2-carboxylic acid

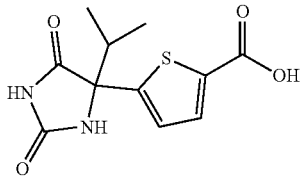 [SMILES: CC(C)C1(c2ccc(C(=O)O)s2)NC(=O)NC1=O]

To 5-isobutyrylthiophene-2-carboxylic acid (172 mg) were added ammonium carbonate (417 mg), potassium carbonate (240 mg), trimethylsilyl cyanide (0.226 mL) and 28% aqueous ammonia (2 mL) and the mixture was stirred under microwave irradiation at 100° C. for 2 hr. The reaction mixture was poured into ice water, acidified with concentrated hydrochloric acid and extracted with ethyl acetate. The organic layer was washed with saturated brine, dried over sodium sulfate and concentrated under reduced pressure. To the obtained residue was added hexane/ethyl acetate, and the precipitate was collected by filtration to give the title compound (207 mg).

MS(ESI) m/z: 267 (M−H)⁻

Preparation Example 67: Preparation of 2-(piperidin-4-yl)-2H-indazole.2 hydrochloride

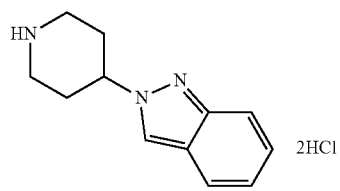 [SMILES: c1ccc2nn(C3CCNCC3)cc2c1]

To 2-nitrobenzaldehyde (377 mg) were added 4-aminopiperidine-1-carboxylic acid tert-butyl ester (500 mg), anhydrous magnesium sulfate (1 g) and ethanol (12 mL) and the mixture was stirred at 90° C. for 3.5 hr. The reaction mixture was filtered and the filtrate was concentrated under reduced pressure. To the obtained residue was added triethyl phosphite (4 mL) and the mixture was stirred under microwave irradiation at 150° C. for 40 min. The reaction mixture was purified by column chromatography (hexane:ethyl acetate) to give 4-(indazol-2-yl)piperidine-1-carboxylic acid tert-butyl ester (490 mg).

The obtained 4-(indazol-2-yl)piperidine-1-carboxylic acid tert-butyl ester (490 mg) was dissolved in 1,4-dioxane (2.5 mL), 4N hydrogen chloride/1,4-dioxane solution (2.5 mL) was added, and the mixture was stirred at room temperature. After completion of the reaction, the solvent was evaporated to give the title compound (439 mg).

MS(ESI) m/z: 202 (M+H)⁺

Preparation Example 68: Preparation of 5-chloro-2-(piperidin-4-yl)-2H-indazole.2 hydrochloride

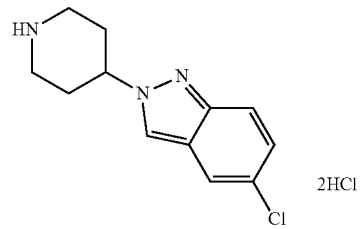 [SMILES: Clc1ccc2nn(C3CCNCC3)cc2c1]

To 5-chloro-2-nitrobenzaldehyde (465 mg) were added 4-aminopiperidine-1-carboxylic acid tert-butyl ester (500 mg) and acetonitrile (10 mL) and the mixture was stirred under microwave irradiation at 80° C. for 10 min. Triethyl phosphite (4.3 mL) was added, and the mixture was stirred under microwave irradiation at 130° C. for 1 hr. The reaction mixture was concentrated under reduced pressure and the obtained residue was purified by column chromatography (hexane:ethyl acetate) to give 4-(5-chloroindazol-2-yl)piperidine-1-carboxylic acid tert-butyl ester (495 mg).

The obtained 4-(5-chloroindazol-2-yl)piperidine-1-carboxylic acid tert-butyl ester (490 mg) was dissolved in 1,4-dioxane (2.4 mL), 4N hydrogen chloride/1,4-dioxane solution (2.4 mL) was added, and the mixture was stirred at room temperature. After completion of the reaction, the solvent was evaporated to give the title compound (432 mg).

MS(ESI) m/z: 236 (M+H)⁺

Preparation Example 69: Preparation of 5-bromo-2-(piperidin-4-yl)-2H-indazole.2 hydrochloride

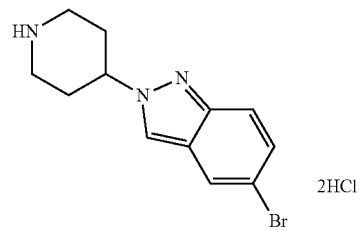 [SMILES: Brc1ccc2nn(C3CCNCC3)cc2c1]

To 5-bromo-2-nitrobenzaldehyde (1.15 g) were added 4-aminopiperidine-1-carboxylic acid tert-butyl ester (1 g) and acetonitrile (10 mL) and the mixture was stirred under microwave irradiation at 80° C. for 10 min. Triethyl phosphite (8.5 mL) was added, and the mixture was stirred under microwave irradiation at 130° C. for 1 hr. The reaction mixture was concentrated under reduced pressure and the obtained residue was purified by column chromatography (hexane:ethyl acetate) to give 4-(5-bromoindazol-2-yl)piperidine-1-carboxylic acid tert-butyl ester (1.22 g).

The obtained 4-(5-bromoindazol-2-yl)piperidine-1-carboxylic acid tert-butyl ester (150 mg) was dissolved in 1,4-dioxane (1.5 mL), 4N hydrogen chloride/1,4-dioxane solution (1.5 mL) was added, and the mixture was stirred at room temperature. After completion of the reaction, the solvent was evaporated to give the title compound (135 mg).

MS(ESI) m/z: 280 (M+H)⁺

Preparation Example 70: Preparation of 5-methyl-2-(piperidin-4-yl)-2H-indazole.2 hydrochloride

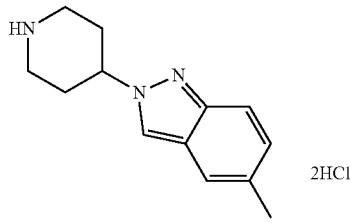 [SMILES: Cc1ccc2nn(C3CCNCC3)cc2c1]

Using 5-methyl-2-nitrobenzaldehyde (206 mg) and 4-aminopiperidine-1-carboxylic acid tert-butyl ester (250 mg), reactions and treatments similar to those in Preparation Example 68 were performed to give the title compound as a crude product (196 mg).

MS(ESI) m/z: 216 (M+H)+

Preparation Example 71: Preparation of 3,5-dichloro-2-(5-piperidin-4-yl[1,3,4]oxadiazol-2-yl)pyridine.2 hydrochloride

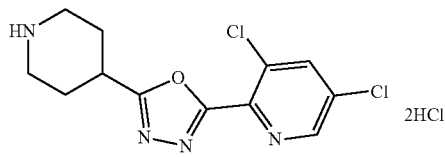 [SMILES: Clc1cnc(-c2nnc(C3CCNCC3)o2)c(Cl)c1]

To 4-hydrazinocarbonylpiperidine-1-carboxylic acid tert-butyl ester (500 mg) were added 3,5-dichloropyridine-2-carboxylic acid (475 mg), 1-hydroxybenzotriazole (420 mg), 1-ethyl-3-(3'-dimethylaminopropyl) carbodiimide.hydrochloride (590 mg), triethylamine (575 μL) and chloroform (10 mL) and the mixture was stirred at room temperature overnight. The reaction mixture was purified by column chromatography (chloroform:methanol) to give 4-[N'-(3,5-dichloropyridine-2-carbonyl)hydrazinocarbonyl]piperidine-1-carboxylic acid tert-butyl ester (525 mg).

To the obtained 4-[N'-(3,5-dichloropyridine-2-carbonyl)hydrazinocarbonyl]piperidine-1-carboxylic acid tert-butyl ester (520 mg) were added p-toluenesulfonyl chloride (356 mg), tetrahydrofuran (10 mL) and triethylamine (350 μL) and the mixture was stirred under microwave irradiation at 80° C. for 1 hr. The reaction mixture was purified by column chromatography (hexane:ethyl acetate) to give 4-[5-(3,5-dichloropyridin-2-yl) [1,3,4]oxadiazol-2-yl]piperidine-1-carboxylic acid tert-butyl ester (327 mg).

To the obtained 4-[5-(3,5-dichloropyridin-2-yl) [1,3,4] oxadiazol-2-yl]piperidine-1-carboxylic acid tert-butyl ester (300 mg) were added 1,4-dioxane (3 mL) and 4N hydrogen chloride/1,4-dioxane solution (3 mL) and the mixture was stirred at room temperature. After completion of the reaction, the solvent was evaporated to give the title compound (255 mg).

MS(ESI) m/z: 299 (M+H)+

Preparation Example 72: Preparation of 5-methyl-2-(2-piperidin-4-ylthiazol-5-yl)pyridine.hydrochloride

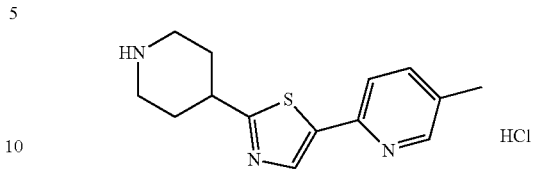

To 4-(4,4,5,5-tetramethyl[1,3,2]dioxaborolan-2-yl)-3,6-dihydro-2H-pyridine-1-carboxylic acid tert-butyl ester (1.5 g) were added tetrakis(triphenylphosphine)palladium(0) (280 mg), tetrahydrofuran (20 mL), 2-bromothiazole (955 mg) and 2 M aqueous sodium carbonate solution (1.65 mL) and the mixture was stirred under a nitrogen atmosphere at 100° C. for 6.5 hr. The reaction mixture was purified by column chromatography (hexane:ethyl acetate) to give 4-(thiazol-2-yl)-3,6-dihydro-2H-pyridine-1-carboxylic acid tert-butyl ester (557 mg).

To the obtained 4-(thiazol-2-yl)-3,6-dihydro-2H-pyridine-1-carboxylic acid tert-butyl ester (520 mg) were added ethanol (10 mL) and 10% palladium/carbon (wetted with 53.5% water) (260 mg) and the mixture was stirred under a hydrogen atmosphere at room temperature overnight. The reaction mixture was filtered and the filtrate was concentrated under reduced pressure. The obtained residue was purified by column chromatography (hexane:ethyl acetate) to give 4-(thiazol-2-yl)piperidine-1-carboxylic acid tert-butyl ester (480 mg).

Under a nitrogen atmosphere, to a solution of bis(pinacolato)diboron (535 mg), (1,5-cyclooctadiene) (methoxy) iridium(I) dimer (58 mg) and 4,4'-di-tert-butyl-2,2'-bipyridine (94 mg) in tetrahydrofuran (7 mL) was added a solution of 4-(thiazol-2-yl)piperidine-1-carboxylic acid tert-butyl ester (470 mg) in tetrahydrofuran (3 mL) and the mixture was stirred at 70° C. for 5 hr. The reaction mixture was concentrated under reduced pressure and the obtained residue was purified by column chromatography (hexane:ethyl acetate) to give 4-[5-(4,4,5,5-tetramethyl[1,3,2]dioxaborolan-2-yl)thiazol-2-yl]piperidine-1-carboxylic acid tert-butyl ester (407 mg).

To 4-[5-(4,4,5,5-tetramethyl[1,3,2]dioxaborolan-2-yl)thiazol-2-yl]piperidine-1-carboxylic acid tert-butyl ester (390 mg) were added 2-bromo-5-methylpyridine (222 mg), [1,1'-bis(diphenylphosphino)ferrocene]palladium(II) dichloride. dichloromethane adduct (41 mg), toluene (7.8 mL) and 2M aqueous sodium carbonate solution (1 mL) and the mixture was stirred under a nitrogen atmosphere at 90° C. for 1.5 hr. The reaction mixture was concentrated under reduced pressure and the obtained residue was purified by column chromatography (hexane:ethyl acetate) to give 4-[5-(5-methylpyridin-2-yl)thiazol-2-yl]piperidine-1-carboxylic acid tert-butyl ester (232 mg).

To the obtained 4-[5-(5-methylpyridin-2-yl)thiazol-2-yl] piperidine-1-carboxylic acid tert-butyl ester (225 mg) were added 1,4-dioxane (2.3 mL) and 4N hydrogen chloride/1,4-dioxane solution (2.3 mL) and the mixture was stirred at room temperature overnight. The solvent was evaporated and diisopropyl ether was added to the obtained residue, and the precipitate was collected by filtration to give the title compound (115 mg).

MS(ESI) m/z: 260 (M+H)+

Preparation Example 73: Preparation of (2S,4S)-2-(tert-butyldimethylsilanyloxymethyl)-4-(2,4-dimethylphenylamino) pyrrolidine-1-carboxylic acid tert-butyl ester

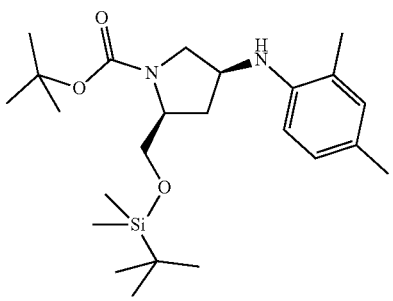 [SMILES: Cc1ccc(N[C@H]2C[C@@H](CO[Si](C)(C)C(C)(C)C)N(C(=O)OC(C)(C)C)C2)c(C)c1]

To (2S,4S)-4-amino-2-(tert-butyldimethylsilanyloxymethyl)pyrrolidine-1-carboxylic acid tert-butyl ester (200 mg) were added 2,4-dimethylbromobenzene (134 mg), tris(dibenzylideneacetone)dipalladium(0) (28 mg), 2,2'-bis(diphenylphosphino)-1,1'-binaphthyl (38 mg), sodium tert-butoxide (87 mg) and toluene (4 mL) and the mixture was stirred under a nitrogen atmosphere at 80° C. for 5 hr. The reaction mixture was purified by silica gel column chromatography (hexane:ethyl acetate) to give the title compound (220 mg).

MS (ESI) m/z: 435 (M+H)$^+$

Preparation Example 74: Preparation of 3,5-dimethyl-2',3',5',6'-tetrahydro-1'H-[2,4']bipyridinyl-4'-ol.2 hydrochloride

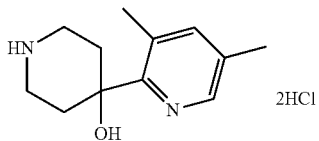

To a solution of 2-bromo-3,5-dimethylpyridine (2.0 g) in tetrahydrofuran (30 mL) was added under cooling at −78° C. 1.59 M n-butyllithium/hexane solution (7.04 mL) and the mixture was stirred for 1 hr. A solution of 1-(tert-butoxycarbonyl)-4-piperidone (2.23 g) in tetrahydrofuran (40 mL) was added, and the mixture was stirred at −78° C. for 30 min. The reaction mixture was heated to room temperature, saturated aqueous sodium carbonate solution was added, and the mixture was extracted with ethyl acetate. The organic layer was washed with saturated brine, dried over anhydrous sodium sulfate and concentrated under reduced pressure. The obtained residue was purified by column chromatography (hexane:ethyl acetate) and NH column chromatography (hexane:ethyl acetate) to give 4'-hydroxy-3,5-dimethyl-3',4',5',6'-tetrahydro-2'H-[2,4']bipyridinyl-1'-carboxylic acid tert-butyl ester (1.69 g).

To a solution of the obtained 4'-hydroxy-3,5-dimethyl-3',4',5',6'-tetrahydro-2'H-[2,4']bipyridinyl-1'-carboxylic acid tert-butyl ester (1.69 g) in ethyl acetate (10 mL) was added 4N hydrogen chloride/ethyl acetate solution (10 mL) and the mixture was stirred at room temperature for 3 hr. The precipitate was collected by filtration to give the title compound (1.384 g).

MS(ESI) m/z: 207 (M+H)$^+$

Preparation Example 75: Preparation of 4-[5-(2,4-dimethylphenyl) [1,3,4]oxadiazol-2-yl]piperidine.hydrochloride

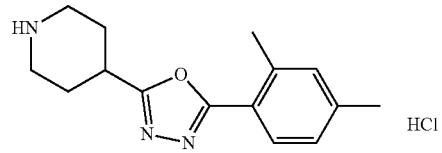 [SMILES: Cc1ccc(-c2nnc(C3CCNCC3)o2)c(C)c1 ; Cl]

To 4-(hydrazinocarbonyl)piperidine-1-carboxylic acid tert-butyl ester (1 g) were added 2,4-dimethylbenzoic acid (802 mg), 1-hydroxybenzotriazole (833 mg), 1-ethyl-3-(3'-dimethylaminopropyl)carbodiimide.hydrochloride (1.182 g) and N,N-dimethylformamide (10 mL) and the mixture was stirred at room temperature overnight. Water was added to the reaction mixture and the mixture was extracted with ethyl acetate. The organic layer was washed with saturated brine, dried over anhydrous sodium sulfate, and the solvent was concentrated under reduced pressure. The obtained residue was purified by column chromatography (hexane:ethyl acetate) to give 4-[N'-(2,4-dimethylbenzoyl)hydrazinocarbonyl]piperidine-1-carboxylic acid tert-butyl ester (979 mg).

To a solution of the obtained 4-[N'-(2,4-dimethylbenzoyl)hydrazinocarbonyl]piperidine-1-carboxylic acid tert-butyl ester (979 mg) in tetrahydrofuran (15 mL) was added Burgess reagent (1.243 g) and the mixture was stirred at room temperature overnight. Water was added to the reaction mixture and the mixture was extracted with chloroform. The organic layer was dried over anhydrous sodium sulfate and concentrated under reduced pressure. The obtained residue was purified by column chromatography (hexane:ethyl acetate) to give 4-[5-(2,4-dimethylphenyl) [1,3,4]oxadiazol-2-yl]piperidine-1-carboxylic acid tert-butyl ester (923 mg).

To a solution of the obtained 4-[5-(2,4-dimethylphenyl) [1,3,4]oxadiazol-2-yl]piperidine-1-carboxylic acid tert-butyl ester (923 mg) in 1,4-dioxane (10 mL) was added 4N hydrogen chloride/1,4-dioxane solution (6.46 mL) and the mixture was stirred at room temperature overnight. The precipitate was collected by filtration to give the title compound (688 mg).

MS(ESI) m/z: 258 (M+H)$^+$

Preparation Example 76: Preparation of 5-methyl-2-(5-piperidin-4-yl-2H-pyrazol-3-yl)pyridine.2 hydrochloride

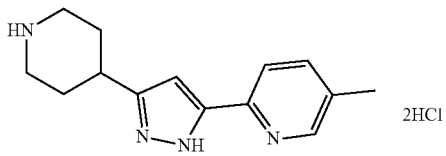 [SMILES: Cc1ccc(-c2cc(C3CCNCC3)n[nH]2)nc1]

4-Acetylpiperidine-1-carboxylic acid tert-butyl ester (1.353 g) was dissolved in tetrahydrofuran (10 mL) and N,N-dimethylformamide (5 mL) and sodium hydride (60% in oil) (524 mg) was added. The mixture was stirred at room temperature for 10 min, 5-methylpyridine-2-carboxylic acid methyl ester (900 mg) was added, and the mixture was stirred at 60° C. for 3 hr. To the reaction mixture was added aqueous ammonium chloride solution and the mixture was extracted with ethyl acetate. The organic layer was washed with saturated brine, dried over anhydrous sodium sulfate and concentrated under reduced pressure. The obtained residue was purified by column chromatography (hexane: ethyl acetate) to give 4-[3-(5-methylpyridin-2-yl)-3-oxopropionyl]piperidine-1-carboxylic acid tert-butyl ester (1.121 g).

The obtained 4-[3-(5-methylpyridin-2-yl)-3-oxopropionyl]piperidine-1-carboxylic acid tert-butyl ester (1.121 g) was dissolved in ethanol (10 mL) and methanol (10 mL), hydrazine.1 hydrate (0.394 mL) was added, and the mixture was stirred at room temperature for 3 days. The reaction mixture was concentrated under reduced pressure and the obtained residue was purified by column chromatography (hexane:ethyl acetate) to give 4-[5-(5-methylpyridin-2-yl)-1H-pyrazol-3-yl]piperidine-1-carboxylic acid tert-butyl ester (0.87 g).

To the obtained 4-[5-(5-methylpyridin-2-yl)-1H-pyrazol-3-yl]piperidine-1-carboxylic acid tert-butyl ester (870 mg) were added 1,4-dioxane (15 mL) and 4N hydrogen chloride/1,4-dioxane solution (6.35 mL) and the mixture was stirred at room temperature overnight. The precipitate was collected by filtration to give the title compound (826 mg).

MS(ESI) m/z: 243 (M+H)$^+$

Preparation Example 77: Preparation of 4-[5-(p-tolyl)-1H-pyrazol-3-yl]piperidine

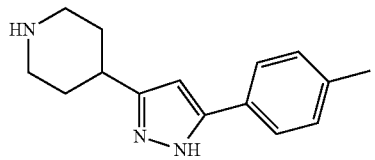 [SMILES: Cc1ccc(-c2cc(C3CCNCC3)n[nH]2)cc1]

To a solution of 1-[(benzyloxy)carbonyl]piperidine-4-carboxylic acid (4 g) in dichloromethane (20 mL) were added under ice-cooling oxalyl chloride (1.6 mL) and N,N-dimethylformamide (catalytic amount), and the mixture was stirred at room temperature for 2 hr. The reaction mixture was concentrated under reduced pressure to give 4-(chlorocarbonyl)piperidine-1-carboxylic acid benzyl ester.

To a solution of 4-methylacetophenone (3.1 g) in tetrahydrofuran (40 mL) was added under cooling at −78° C. lithium bis(trimethylsilyl)amide (about 0.5 mol/L, tetrahydrofuran solution) (45.6 mL) and the mixture was stirred for 30 min. To the reaction mixture was added a solution of the above-mentioned 4-(chlorocarbonyl)piperidine-1-carboxylic acid benzyl ester in tetrahydrofuran (40 mL) and the mixture was stirred for 3.5 hr. To the reaction mixture was added saturated aqueous ammonium chloride solution and the mixture was extracted with ethyl acetate. The organic layer was washed with saturated brine, dried over anhydrous magnesium sulfate and concentrated under reduced pressure. The obtained residue was purified by column chromatography (hexane:ethyl acetate) to give 4-[3-oxo-3-(p-tolyl)propionyl]piperidine-1-carboxylic acid benzyl ester (3.91 g).

To a solution of the obtained 4-[3-oxo-3-(p-tolyl)propionyl]piperidine-1-carboxylic acid benzyl ester (500 mg) in ethanol (5 mL) was added hydrazine.1 hydrate (0.32 mL) and the mixture was stirred at room temperature overnight. The reaction mixture was concentrated under reduced pressure, water was added to the obtained residue, and the precipitate was collected by filtration to give 4-[5-(p-tolyl)-1H-pyrazol-3-yl]piperidine-1-carboxylic acid benzyl ester (168 mg).

To the obtained 4-[5-(p-tolyl)-1H-pyrazol-3-yl]piperidine-1-carboxylic acid benzyl ester (160 mg) were added methanol (3 mL), tetrahydrofuran (3 mL) and 10% palladium carbon (32 mg) and the mixture was stirred under a hydrogen atmosphere at room temperature for 2 hr. The reaction mixture was filtered and the filtrate was concentrated under reduced pressure to give the title compound (100 mg).

MS(ESI) m/z: 242 (M+H)$^+$

Preparation Example 78: Preparation of 4-[2-(p-tolyl)-2H-tetrazol-5-yl]piperidine

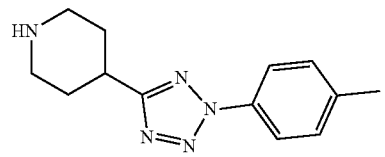 [SMILES: Cc1ccc(-n2nnc(C3CCNCC3)n2)cc1]

1) Preparation of 4-methylbenzenediazonium chloride

To a solution of 4-methylaniline (500 mg) and concentrated hydrochloric acid (0.6 mL) in 50% ethanol (5 mL) was added at not more than 5° C. a solution of sodium nitrite (321.9 mg) in water (1 mL) (preparation of 4-methylbenzenediazonium chloride solution).

2) Preparation of 4-[2-(p-tolyl)-2H-tetrazol-5-yl]piperidine

To a solution of 1-(tert-butoxycarbonyl)-4-piperidinecarboxaldehyde (2 g) in ethanol (30 mL) was added p-toluenesulfonylhydrazide (1.7 g) and the mixture was stirred at 30° C. for 16 hr. The reaction mixture was concentrated under reduced pressure, to the obtained residue were added diisopropyl ether (20 mL) and ethyl acetate (10 mL) and the precipitate was collected by filtration to give 4-(p-toluenesulfonylhydrazonomethyl)piperidine-1-carboxylic acid tert-butyl ester (3 g).

To a solution of the obtained 4-(p-toluenesulfonylhydrazonomethyl)piperidine-1-carboxylic acid tert-butyl ester (1.7 g) in pyridine (10 mL) was directly added dropwise under cooling at −10° C. to −15° C. the reaction solution of the above-mentioned 1) (solution of 4-methylbenzenediazonium chloride) over not less than 30 min. The mixture was stirred at 0° C. for 2 hr, poured into water, and extracted with dichloromethane. The organic layer was washed with saturated brine, dried over anhydrous sodium sulfate and concentrated under reduced pressure. The obtained residue was purified by column chromatography (diisopropyl ether:ethyl acetate) to give 4-[2-(p-tolyl)-2H-tetrazol-5-yl]piperidine-1-carboxylic acid tert-butyl ester (300 mg).

To a solution of the obtained 4-[2-(p-tolyl)-2H-tetrazol-5-yl]piperidine-1-carboxylic acid tert-butyl ester (100 mg) in 1,4-dioxane (5 mL) was added 4N hydrogen chloride/1, 4-dioxane solution (5 mL) and the mixture was stirred at 35° C. for 1 hr. The reaction mixture was concentrated under reduced pressure, the obtained residue was basified (pH 9) with 1N aqueous sodium hydroxide solution. The mixture was extracted with dichloromethane, and the organic layer was dried over anhydrous magnesium sulfate and concentrated under reduced pressure to give 4-[2-(p-tolyl)-2H-tetrazol-5-yl]piperidine (60 mg).

MS(APCI) m/z: 244 (M+H)+

Preparation Example 79: Preparation of 4-[1-(p-tolyl)-1H-[1,2,3]triazol-4-yl]piperidine.2 hydrochloride

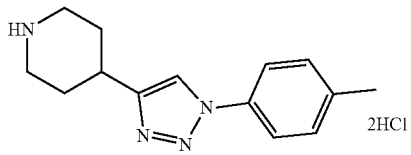 [SMILES: Cc1ccc(-n2cc(C3CCNCC3)nn2)cc1]

To 4-ethynylpiperidine-1-carboxylic acid tert-butyl ester (1.00 g) were added sodium ascorbate (0.757 g), copper sulfate. 5 hydrate (0.239 mg), tetrahydrofuran (30 mL), water (10 mL) and 1-azido-4-methylbenzene (10 mL) and the mixture was stirred at room temperature for 3 days. Water was added to the reaction mixture and the mixture was extracted with ethyl acetate. The organic layer was washed with saturated brine, dried over anhydrous sodium sulfate and concentrated under reduced pressure. The obtained residue was purified by column chromatography (hexane:ethyl acetate) to give 4-[1-(p-tolyl)-1H-[1,2,3]triazol-4-yl]piperidine-1-carboxylic acid tert-butyl ester (0.861 mg).

To the obtained 4-[1-(p-tolyl)-1H-[1,2,3]triazol-4-yl]piperidine-1-carboxylic acid tert-butyl ester (0.86 mg) were added 1,4-dioxane (7 mL), methanol (10 mL) and 4N hydrogen chloride/1,4-dioxane solution (3.14 mL) and the mixture was stirred at room temperature overnight. The reaction mixture was concentrated under reduced pressure, ethyl acetate was added to the obtained residue, and the precipitate was collected by filtration to give the title compound (0.807 g).

MS(ESI) m/z: 243 (M+H)+

Preparation Example 80: Preparation of 4-[1-(p-tolyl)-1H-imidazol-4-yl]piperidine.2 hydrochloride

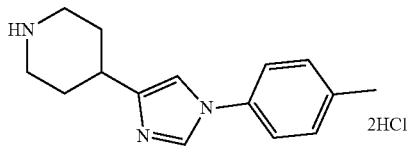 [SMILES: Cc1ccc(-n2cnc(C3CCNCC3)c2)cc1]

To 4-(1H-imidazol-4-yl)piperidine-1-carboxylic acid tert-butyl ester (370 mg) were added 4-iodotoluene (0.23 mL), potassium carbonate (407 mg), copper iodide (42 mg), 8-hydroxyquinoline (32 mg) and dimethyl sulfoxide (7 mL) and the mixture was stirred at 100° C. for 3 days. Water was added to the reaction mixture and the mixture was extracted with ethyl acetate. The organic layer was washed with saturated brine, dried over anhydrous sodium sulfate and concentrated under reduced pressure. The obtained residue was purified by column chromatography (hexane:ethyl acetate) to give 4-[1-(p-tolyl)-1H-imidazol-4-yl]piperidine-1-carboxylic acid tert-butyl ester (277 mg).

To the obtained 4-[1-(p-tolyl)-1H-imidazol-4-yl]piperidine-1-carboxylic acid tert-butyl ester (270 mg) were added 1,4-dioxane (3 mL), methanol (1 mL) and 4N hydrogen chloride/1,4-dioxane solution (0.99 mL) and the mixture was stirred at room temperature overnight. To the reaction mixture was added ethyl acetate and the precipitate was collected by filtration to give the title compound (253 mg).

MS(ESI) m/z: 242 (M+H)+

Preparation Example 81: Preparation of 3,5-dimethyl-1',2',3',4',5',6'-hexahydro[2,4']bipyridinyl.2 hydrochloride

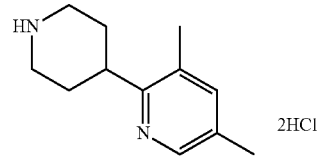

To 2-bromo-3,5-dimethylpyridine (6.62 g) were added N-Boc-1,2,3,6-tetrahydropyridine-4-boronic acid pinacol ester (10 g), sodium carbonate (7.54 g), 1,4-dioxane (50 mL), water (50 mL) and tetrakis(triphenylphosphine)palladium(0) (1.87 g) and the mixture was stirred under a nitrogen stream at 100° C. for 5 hr. Water was added to the reaction mixture and the mixture was extracted with ethyl acetate. The organic layer was washed with saturated brine, dried over sodium sulfate, and treated with activated carbon. The solvent was evaporated and the obtained residue was purified by column chromatography (hexane:ethyl acetate) to give 3,5-dimethyl-3',6'-dihydro-2'H-[2,4']bipyridinyl-1'-carboxylic acid tert-butyl ester (8.93 g).

The obtained 3,5-dimethyl-3',6'-dihydro-2'H-[2,4']bipyridinyl-1'-carboxylic acid tert-butyl ester (8.8 g) was dissolved in ethanol (100 mL), 10% palladium carbon was added and the mixture was stirred under a hydrogen atmosphere for 29 hr. The reaction mixture was filtered, the filtrate was concentrated under reduced pressure to give 3,5-dimethyl-3',4',5',6'-tetrahydro-2'H-[2,4']bipyridinyl-1'-carboxylic acid tert-butyl ester (8.58 g).

To 3,5-dimethyl-3',4',5',6'-tetrahydro-2'H-[2,4']bipyridinyl-1'-carboxylic acid tert-butyl ester (8.55 g) was added 2N hydrogen chloride/methanol solution (70 mL) and the mixture was stirred at room temperature for 20 hr. The reaction mixture was concentrated under reduced pressure, and a mixed solvent of methanol and ethyl acetate was added to the obtained residue. The precipitate was collected by filtration to give the title compound (7.9 g).

MS(ESI) m/z: 191 (M+H)+

Preparation Example 82: Preparation of 4-(2,4-dimethylphenyl)piperidine.hydrochloride

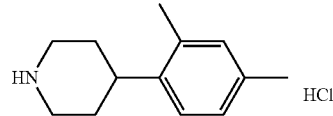

To 4-(2,4-dimethylphenyl)piperidin-4-ol (450 mg) was added trifluoroacetic acid (10 mL) and the mixture was stirred at room temperature for 1 hr. The reaction mixture was concentrated under reduced pressure and the obtained residue was dissolved in methanol (15 mL). 10% Palladium carbon (250 mg) was added and the mixture was stirred under a hydrogen atmosphere at room temperature for 5 hr. The reaction mixture was filtered and the filtrate was concentrated under reduced pressure. To the obtained residue was added 2N hydrogen chloride/methanol solution and the mixture was concentrated under reduced pressure. To the obtained residue was added hexane/ethyl acetate, and the precipitate was collected by filtration to give the title compound (211 mg).
MS(ESI) m/z: 190 (M+H)+

Preparation Example 83: Preparation of 3',5'-dimethyl-3,4,5,6-tetrahydro-2H-[1,2']bipyrazinyl

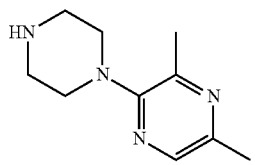

To 2-chloro-3,5-dimethylpyrazine (2.8 g) were added 1-(tert-butoxycarbonyl)piperazine (3.7 g), palladium(II) acetate (225 mg), 2-(dicyclohexylphosphino)-2',4',6'-triisopropylbiphenyl (953 mg), sodium tert-butoxide (2.7 g) and toluene (40 mL) and the mixture was stirred under reflux for 8 hr. Water was added to the reaction mixture and the mixture was extracted with ethyl acetate. The solvent was evaporated and the obtained residue was purified by column chromatography (hexane:ethyl acetate) to give 3',5'-dimethyl-2,3,5,6-tetrahydro-[1,2']bipyrazinyl-4-carboxylic acid tert-butyl ester (5 g).
The obtained 3',5'-dimethyl-2,3,5,6-tetrahydro-[1,2']bipyrazinyl-4-carboxylic acid tert-butyl ester (5 g) was dissolved in chloroform (15 mL), 4N hydrogen chloride/ethyl acetate solution (15 mL) was added, and the mixture was stirred at room temperature overnight. To the reaction mixture was added ethyl acetate (100 mL) and the precipitate was collected by filtration to give 3',5'-dimethyl-3,4,5,6-tetrahydro-2H-[1,2']bipyrazinyl.hydrochloride (3.3 g).
To the obtained 3',5'-dimethyl-3,4,5,6-tetrahydro-2H-[1,2']bipyrazinyl.hydrochloride (1.86 g) was added saturated sodium bicarbonate water and the mixture was extracted with chloroform. The solvent was evaporated and the obtained residue was purified by NH column chromatography (ethyl acetate:methanol) to give the title compound (960 mg).
MS(ESI) m/z: 193 (M+H)+

Preparation Example 84: Preparation of 3,4,5-trimethyl-6-piperazin-1-ylpyridazine

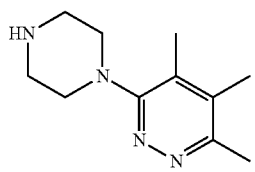

To 3-chloro-4,5,6-trimethylpyridazine (300 mg) were added 1-(tert-butoxycarbonyl)piperazine (428 mg), palladium acetate (22 mg), 2-(dicyclohexylphosphino)-2',4',6'-triisopropylbiphenyl (182.6 mg), sodium tert-butoxide (276 mg) and toluene (4 mL) and the mixture was stirred at 110° C. for 4 hr. Water was added to the reaction mixture and the mixture was extracted with ethyl acetate. The solvent was evaporated and the obtained residue was purified by column chromatography (chloroform:ethyl acetate) to give 4-(4,5,6-trimethylpyridazin-3-yl)piperazine-1-carboxylic acid tert-butyl ester (297 mg).
The obtained 4-(4,5,6-trimethylpyridazin-3-yl)piperazine-1-carboxylic acid tert-butyl ester (297 mg) was dissolved in ethyl acetate (3 mL) and 4N hydrogen chloride/ethyl acetate solution (2.6 mL) was added. The mixture was stirred at room temperature for 3 hr and the precipitate was collected by filtration. To the obtained precipitate was added saturated aqueous sodium hydrogen carbonate solution, and the mixture was extracted with chloroform/methanol. The organic layer was dried over anhydrous magnesium sulfate and concentrated under reduced pressure. The obtained residue was purified by NH column chromatography (ethyl acetate:methanol) to give the title compound (68.4 mg).
MS(ESI) m/z: 207 (M+H)+

Preparation Example 85: Preparation of (3,5-dimethylpyridin-2-yl)piperidin-4-ylamine

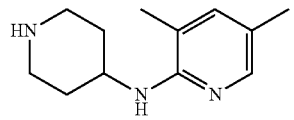

To 2-bromo-3,5-dimethylpyridine (1 g) were added 4-amino-1-(tert-butoxycarbonyl)piperidine (1.29 g), tris(dibenzylideneacetone)dipalladium(0) (250 mg), 2,2'-bis(diphenylphosphino)-1,1'-binaphthyl (330 mg), sodium tert-butoxide (770 mg) and toluene (8 mL) and the mixture was stirred at 120° C. overnight. The reaction mixture was filtered through celite and the filtrate was concentrated under reduced pressure. The obtained residue was purified by NH column chromatography (hexane:ethyl acetate) to give 4-(3,5-dimethylpyridin-2-ylamino)piperidine-1-carboxylic acid tert-butyl ester (1.499 g).
The obtained 4-(3,5-dimethylpyridin-2-ylamino)piperidine-1-carboxylic acid tert-butyl ester (610 mg) was dissolved in chloroform (3 mL), trifluoroacetic acid (2 mL) was added, and the mixture was stirred at room temperature for 3 hr. The reaction mixture was charged for ion exchange chromatography, washed with methanol, and eluted with 1N ammonia/methanol solution to give the title compound (317.8 mg).
MS(APCI) m/z: 206 (M+H)+

Preparation Example 86: Preparation of 3,5-dimethyl-2-((S)-pyrrolidin-3-yloxy)pyridine

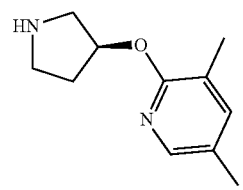

To a solution of (S)-1-(tert-butoxycarbonyl)-3-hydroxypyrrolidine (2.26 g) and 2,3,5-trichloropyridine (2.2 g) in N,N-dimethylformamide (20 mL) was added under ice-cooling sodium hydride (60% in oil) (507 mg) and the mixture was stirred at room temperature. After completion of the reaction, water was added and the mixture was extracted with ethyl acetate. The solvent was evaporated and the obtained residue was purified by column chromatography (hexane:ethyl acetate) to give (S)-3-(3,5-dichloropyridin-2-yloxy)pyrrolidine-1-carboxylic acid tert-butyl ester (3.74 g).

To the obtained (S)-3-(3,5-dichloropyridin-2-yloxy)pyrrolidine-1-carboxylic acid tert-butyl ester (3.74 g) were added 2,4,6-trimethylboroxine (4.7 mL), palladium(II) acetate (252 mg), potassium fluoride (5.21 g), 2-dicyclohexylphosphino-2',6'-dimethoxybiphenyl (922 mg) and 1,4-dioxane (38 mL) and the mixture was refluxed with stirring for 4 hr. The reaction mixture was filtered through celite and the filtrate was concentrated under reduced pressure. The obtained residue was purified by column chromatography (hexane:ethyl acetate) to give (S)-3-(3,5-dimethylpyridin-2-yloxy)pyrrolidine-1-carboxylic acid tert-butyl ester (2.96 g).

The obtained (S)-3-(3,5-dimethylpyridin-2-yloxy)pyrrolidine-1-carboxylic acid tert-butyl ester (2.96 g) was dissolved in dichloromethane (15 mL), trifluoroacetic acid (7.6 mL) was added under ice-cooling, and the mixture was stirred at room temperature. After completion of the reaction, to the reaction mixture was added saturated aqueous sodium hydrogen carbonate solution, and the mixture was extracted with ethyl acetate. The solvent was evaporated to give the title compound (1.5 g).

MS (ESI) m/z: 193 (M+H)+

Preparation Example 87: Preparation of 5-methyl-1-pyrrolidin-3-yl-2,3-dihydro-1H-pyrrolo[2,3-b]pyridine

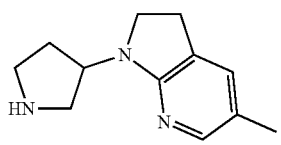

To a solution of 2,3-dihydro-7-azaindole (2.8 g) and 1-(tert-butoxycarbonyl)-3-oxopyrrolidine (5.44 g) in methanol (28 mL) were added under ice-cooling acetic acid (4.67 mL) and sodium cyanoborohydride (1.76 g) and the mixture was stirred at room temperature for 1.5 hr. 1-(tert-Butoxycarbonyl)-3-oxopyrrolidine (3 g) was added, and the mixture was stirred at room temperature for 1.5 hr. 2N aqueous sodium hydroxide solution (80 mL) was added and the mixture was concentrated under reduced pressure to evaporate methanol. The remaining aqueous solution was extracted with chloroform. The organic layer was dried over anhydrous magnesium sulfate and concentrated under reduced pressure. To the obtained residue was added ethyl acetate, and the mixture was back extracted with 1N hydrochloric acid. The aqueous layer was neutralized with aqueous sodium hydroxide solution and the mixture was extracted with ethyl acetate. The organic layer was washed with saturated brine, dried over anhydrous magnesium sulfate and concentrated under reduced pressure. The obtained residue was purified by column chromatography (hexane:ethyl acetate) to give 3-(2,3-dihydropyrrolo[2,3-b]pyridin-1-yl)pyrrolidine-1-carboxylic acid tert-butyl ester (2.96 g).

The obtained 3-(2,3-dihydropyrrolo[2,3-b]pyridin-1-yl)pyrrolidine-1-carboxylic acid tert-butyl ester (2 g) was dissolved in N,N-dimethylformamide (20 mL), N-bromosuccinimide (1.26 g) was added under ice-cooling, and the mixture was stirred for 2 hr. Water was added to the reaction mixture and the mixture was extracted with ethyl acetate. The organic layer was washed with saturated brine, dried over anhydrous magnesium sulfate and concentrated under reduced pressure to give 3-(5-bromo-2,3-dihydropyrrolo[2,3-b]pyridin-1-yl)pyrrolidine-1-carboxylic acid tert-butyl ester (2.77 g).

To the obtained 3-(5-bromo-2,3-dihydropyrrolo[2,3-b]pyridin-1-yl)pyrrolidine-1-carboxylic acid tert-butyl ester (1.2 g) were added 2,4,6-trimethylboroxine (4.24 mL), palladium(II) acetate (73.2 mg), potassium fluoride (757 mg), 2-dicyclohexylphosphino-2',6'-dimethoxybiphenyl (268 mg) and 1,4-dioxane (12 mL) and the mixture was refluxed with stirring for 1.5 hr. Water was added to the reaction mixture and the mixture was filtered through celite. The filtrate was extracted with ethyl acetate, and the extract was dried over anhydrous magnesium sulfate and concentrated under reduced pressure. The obtained residue was purified by column chromatography (hexane:ethyl acetate) to give 3-(5-methyl-2,3-dihydropyrrolo[2,3-b]pyridin-1-yl)pyrrolidine-1-carboxylic acid tert-butyl ester (792 mg).

To the obtained 3-(5-methyl-2,3-dihydropyrrolo[2,3-b]pyridin-1-yl)pyrrolidine-1-carboxylic acid tert-butyl ester (100 mg) were added ethyl acetate (0.5 mL), ethanol (0.5 mL) and 4N hydrogen chloride/ethyl acetate solution (1.6 mL) and the mixture was stirred at room temperature overnight. To the reaction mixture was added saturated aqueous sodium hydrogen carbonate solution, and the mixture was extracted with a mixed solvent of chloroform and methanol. The organic layer was dried over anhydrous sodium sulfate and concentrated under reduced pressure. The obtained residue was separated by HPLC using XBridge Prep C18 OBD (10 mmol/L aqueous ammonium carbonate solution, acetonitrile). The obtained solution was extracted with a mixed solvent of chloroform and methanol. The organic layer was dried over anhydrous sodium sulfate and concentrated under reduced pressure to give the title compound (22.1 mg).

MS(ESI) m/z: 204 (M+H)+

Preparation Example 88: Preparation of (3,5-dimethylpyridin-2-yl)-(S)-pyrrolidin-3-ylamine.2 hydrochloride

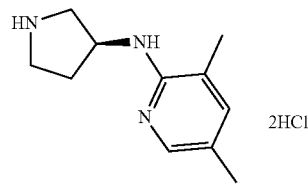

To 2-bromo-3,5-dimethylpyridine (10.26 g) were added (S)-1-(tert-butoxycarbonyl)-3-aminopyrrolidine (10.27 g), tris(dibenzylideneacetone)dipalladium(0) (505 mg), 2,2'-bis(diphenylphosphino)-1,1'-binaphthyl (1 g), sodium tert-butoxide (7.24 g) and toluene (180 mL) and the mixture was stirred at 80° C. for 3 hr. Water was added to the reaction mixture and the mixture was extracted with ethyl acetate. The organic layer was concentrated under reduced pressure and the obtained residue was purified by column chromatography (hexane:ethyl acetate). The solvent was evaporated, ethyl acetate (50 mL), 4N hydrogen chloride/1,4-dioxane solution (50 mL) and methanol (10 mL) were added to the obtained residue, and the mixture was stirred at room temperature for 2.5 hr. To the reaction mixture was added diethyl ether, and the supernatant was removed by decantation. To the obtained residue was added ethyl acetate/ethanol, and the precipitate was collected by filtration to give the title compound (11.9 g).
MS(ESI) m/z: 192 (M+H)+

Preparation Example 89: Preparation of 5-methyl-1-piperidin-4-yl-1H-pyrrolo[2,3-b]pyridine

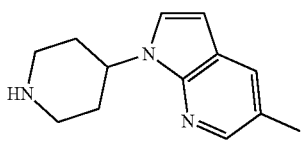 [SMILES: Cc1cnc2c(ccn2C2CCNCC2)c1]

To a solution of 4-(hydroxy)piperidine-1-carboxylic acid benzyl ester (2 g), 5-bromo-1H-pyrrolo[2,3-b]pyridine (1.12 g) and triphenylphosphine (2.97 g) in tetrahydrofuran (30 mL) was added under ice-cooling diisopropyl azodicarboxylate (2.2 mL). The mixture was stirred at room temperature overnight, water was added to the reaction mixture and the mixture was extracted with ethyl acetate. The organic layer was washed with saturated brine, dried over anhydrous magnesium sulfate and concentrated under reduced pressure. To the obtained residue was added hexane/ethyl acetate, and the mixture was filtered (precipitated triphenylphosphine oxide was removed). The filtrate was concentrated under reduced pressure and the obtained residue was purified by column chromatography (hexane:ethyl acetate) and NH column chromatography (hexane:ethyl acetate) to give 4-(5-bromopyrrolo[2,3-b]pyridin-1-yl)piperidine-1-carboxylic acid benzyl ester (650 mg).

To the obtained 4-(5-bromopyrrolo[2,3-b]pyridin-1-yl)piperidine-1-carboxylic acid benzyl ester (640 mg) were added 2,4,6-trimethylboroxine (504 mg), palladium(II) acetate (35 mg), potassium fluoride (359 mg), 2-dicyclohexylphosphino-2',6'-dimethoxybiphenyl (127 mg) and 1,4-dioxane (10 mL) and the mixture was stirred under reflux for 2 hr. 2,4,6-Trimethylboroxine (272 mg) was added, and the mixture was stirred under reflux for 2 hr. To the reaction mixture were added water and ethyl acetate, and the mixture was filtered through celite. The filtrate was extracted with ethyl acetate, and the organic layer was washed with saturated brine and dried over anhydrous magnesium sulfate. The solvent was evaporated and the obtained residue was purified by column chromatography (hexane:ethyl acetate) to give 4-(5-methylpyrrolo[2,3-b]pyridin-1-yl)piperidine-1-carboxylic acid benzyl ester (476 mg).

To a solution of the obtained 4-(5-methylpyrrolo[2,3-b]pyridin-1-yl)piperidine-1-carboxylic acid benzyl ester (380 mg) in ethanol (15 mL) was added 7.5% palladium carbon (114 mg) and the mixture was stirred under a hydrogen atmosphere at room temperature for 7 hr. The reaction mixture was filtered through celite and the filtrate was concentrated under reduced pressure. The obtained residue was purified by NH column chromatography (ethyl acetate:methanol) to give the title compound (207 mg).
MS(ESI) m/z: 216 (M+H)+

Preparation Example 90: Preparation of 5-methyl-1-(S)-pyrrolidin-3-yl-2,3-dihydro-1H-pyrrolo[2,3-b]pyridine

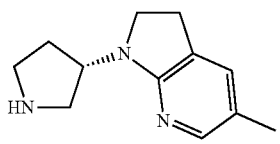

To a solution of (R)-3-hydroxypyrrolidine-1-carboxylic acid benzyl ester (2 g) and 5-bromo-1H-pyrrolo[2,3-b]pyridine (1.78 g) in toluene (25 mL) was added with heating at 80° C. a solution of cyanomethylenetributylphosphorane (4.364 g) in toluene (7 mL). The mixture was stirred at 110° C. for 5 hr and concentrated under reduced pressure. The obtained residue was purified by NH column chromatography (hexane:ethyl acetate) to give (S)-3-(5-bromopyrrolo[2,3-b]pyridin-1-yl)pyrrolidine-1-carboxylic acid benzyl ester (2.78 g).

To the obtained (S)-3-(5-bromopyrrolo[2,3-b]pyridin-1-yl)pyrrolidine-1-carboxylic acid benzyl ester (1.3 g) were added 2,4,6-trimethylboroxine (2.26 g), palladium(II) acetate (156 mg), potassium fluoride (1.61 g), 2-dicyclohexylphosphino-2',6'-dimethoxybiphenyl (570 mg) and 1,4-dioxane (40 mL) and the mixture was stirred under reflux for 1 hr. Water was added to the reaction mixture and the mixture was extracted with ethyl acetate. The organic layer was washed with saturated brine, dried over anhydrous magnesium sulfate and concentrated under reduced pressure. The obtained residue was purified by column chromatography (hexane:ethyl acetate) to give (S)-3-(5-methylpyrrolo[2,3-b]pyridin-1-yl)pyrrolidine-1-carboxylic acid benzyl ester (2.32 g).

The obtained (S)-3-(5-methylpyrrolo[2,3-b]pyridin-1-yl)pyrrolidine-1-carboxylic acid benzyl ester (1.3 g) was dissolved in acetic acid (12 mL), sodium cyanoborohydride (1.22 g) was added, and the mixture was stirred at room temperature overnight. Sodium cyanoborohydride (1.22 g) was added and the mixture was stirred at room temperature for 3 days. To the reaction mixture was added under ice-cooling 2N aqueous sodium hydroxide solution (50 mL). The mixture was basified with potassium carbonate and extracted with chloroform. The organic layer was dried over anhydrous magnesium sulfate and concentrated under reduced pressure. The obtained residue was purified by column chromatography (hexane:ethyl acetate) to give (S)-3-(5-methyl-2,3-dihydropyrrolo[2,3-b]pyridin-1-yl)pyrrolidine-1-carboxylic acid benzyl ester (2.78 g).

The obtained (S)-3-(5-methyl-2,3-dihydropyrrolo[2,3-b]pyridin-1-yl)pyrrolidine-1-carboxylic acid benzyl ester (1.12 g) was dissolved in ethanol (15 mL), 7.5% palladium carbon (336 mg) was added, and the mixture was stirred under a hydrogen atmosphere at room temperature for 2 days. The reaction mixture was filtered through celite and the filtrate was concentrated under reduced pressure. The obtained residue was dissolved in ethanol (20 mL), 7.5% palladium carbon (448 mg) was added, and the mixture was stirred under a hydrogen atmosphere at room temperature 4 days. The reaction mixture was filtered through celite and the filtrate was concentrated under reduced pressure. The obtained residue was purified by NH column chromatography (ethyl acetate:methanol) to give the title compound (479 mg).

MS(ESI) m/z: 204 (M+H)+

Preparation Example 91: Preparation of 5-methyl-1-(S)-pyrrolidin-3-yl-1H-pyrrolo[2,3-b]pyridine

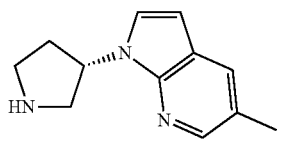

(S)-3-(5-methylpyrrolo[2,3-b]pyridin-1-yl)pyrrolidine-1-carboxylic acid benzyl ester (1.02 g) obtained by the synthesis method described in Preparation Example 90 was dissolved in ethanol (15 mL), 7.5% palladium carbon (306 mg) was added, and the mixture was stirred under a hydrogen atmosphere at room temperature for 8 hr. The reaction mixture was filtered through celite and the filtrate was concentrated under reduced pressure. The obtained residue was purified by NH column chromatography (ethyl acetate: methanol) to give the title compound (460 mg).

MS(ESI) m/z: 202 (M+H)+

Preparation Example 92: Preparation of 3-(3,5-dimethylpyridin-2-ylamino)azetidine-1-carboxylic acid tert-butyl ester

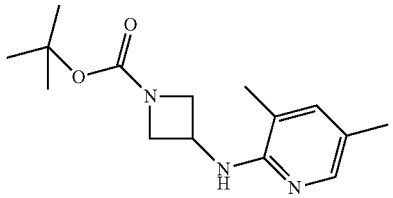 [SMILES: Cc1cnc(NC2CN(C(=O)OC(C)(C)C)C2)c(C)c1]

To 2-bromo-3,5-dimethylpyridine (1 g) were added 1-(tert-butoxycarbonyl)-3-aminoazetidine (1.11 g), tris(dibenzylideneacetone)dipalladium(0) (250 mg), 2,2'-bis(diphenylphosphino)-1,1'-binaphthyl (330 mg), sodium tert-butoxide (770 mg) and toluene (8 mL) and the mixture was stirred at 120° C. overnight. The reaction mixture was filtered through celite and the filtrate was concentrated under reduced pressure. The obtained residue was purified by NH column chromatography (hexane:ethyl acetate) to give the title compound (965 mg).

MS(APCI) m/z: 278 (M+H)+

Preparation Example 93: Preparation of (5-methylpyridin-2-yl)piperidin-4-ylmethanone.2 hydrochloride

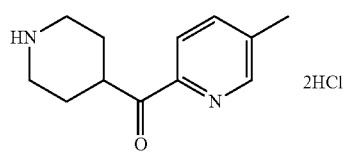

To a solution of 2-bromo-5-methylpyridine (4.04 g) in toluene (70 mL) was added at −78° C. n-butyllithium/hexane solution (1.6 M) (16.9 mL). The mixture was stirred at −78° C. for 10 min, and a solution of 4-(methoxymethylcarbamoyl)piperidine-1-carboxylic acid tert-butyl ester (6.4 g) in toluene (10 mL) was added. The mixture was stirred at −78° C. for 30 min, water was added to the reaction mixture and the mixture was extracted with ethyl acetate. The organic layer was dried over anhydrous magnesium sulfate and concentrated under reduced pressure. The obtained residue was purified by column chromatography (hexane:ethyl acetate) to give 4-(5-methylpyridine-2-carbonyl)piperidine-1-carboxylic acid tert-butyl ester (4.03 g).

To a solution of the obtained 4-(5-methylpyridine-2-carbonyl)piperidine-1-carboxylic acid tert-butyl ester (4.02 g) in chloroform (66 mL) was added 4N hydrogen chloride/ethyl acetate solution (33 mL) and the mixture was stirred at room temperature overnight. To the reaction mixture was added hexane, and the precipitate was collected by filtration to give the title compound (3.61 g).

MS(ESI) m/z: 205 (M+H)+

Preparation Example 94: Preparation of (3R,4R)-4-(3,5-dimethylpyridin-2-ylamino)pyrrolidin-3-ol.2 hydrochloride

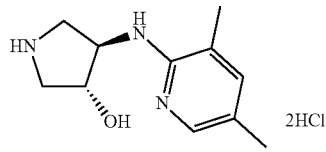

To (3R,4R)-3-amino-4-hydroxypyrrolidine-1-carboxylic acid tert-butyl ester (1.35 g) were added dichloromethane (67 mL), diisopropylethylamine (4.1 mL), 3,5-dimethylpyridine-N-oxide (986 mg) and bromotris(pyrrolidino)phosphonium hexafluorophosphate (3.73 g) and the mixture was stirred at room temperature for 6.5 hr. Water was added to the reaction mixture and the mixture was extracted with chloroform. The organic layer was concentrated under reduced pressure and the obtained residue was purified by column chromatography (hexane:ethyl acetate) to give (3R,4R)-3-(3,5-dimethylpyridin-2-ylamino)-4-hydroxypyrrolidine-1-carboxylic acid tert-butyl ester (1 g).

To the obtained (3R,4R)-3-(3,5-dimethylpyridin-2-ylamino)-4-hydroxypyrrolidine-1-carboxylic acid tert-butyl ester (1 g) were added chloroform (10 mL) and 4N hydrogen chloride/ethyl acetate solution (8.3 mL) and the mixture was stirred at room temperature overnight. The reaction mixture was concentrated under reduced pressure to give the title compound (1 g).

MS (ESI) m/z: 208 (M+H)+

Preparation Example 95: Preparation of 5,7-dimethyl-1-(R)-pyrrolidin-3-yl-1H-indazole

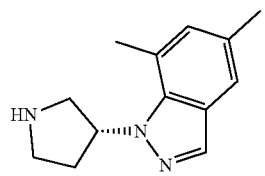 [SMILES: Cc1cc(C)c2c(cnn2[C@@H]2CCNC2)c1]

(S)-1-(tert-butoxycarbonyl)-3-hydroxypyrrolidine (853 mg), 3-iodo-5,7-dimethyl-1H-indazole (620 mg) and triphenylphosphine (1195 mg) were dissolved in tetrahydrofuran (12 mL), diisopropyl azodicarboxylate (0.897 mL) was added under ice-cooling, and the mixture was stirred at room temperature overnight. The reaction mixture was concentrated under reduced pressure, diisopropyl ether was added to the obtained residue, and the mixture was filtered (precipitate was removed). The filtrate was concentrated under reduced pressure and the obtained residue was purified by column chromatography (hexane:ethyl acetate) to give (R)-3-(3-iodo-5,7-dimethylindazol-1-yl)pyrrolidine-1-carboxylic acid tert-butyl ester (442 mg).

To a solution of the obtained (R)-3-(3-iodo-5,7-dimethylindazol-1-yl)pyrrolidine-1-carboxylic acid tert-butyl ester (435 mg) in ethanol (8.9 mL) was added 10% palladium carbon (44 mg) and the mixture was stirred under a hydrogen atmosphere at room temperature for 1.5 hr. To the reaction mixture was added 1N aqueous sodium hydroxide solution (1.97 mL) and the mixture was stirred at room temperature for 2 hr. The reaction mixture was filtered through celite and the filtrate was concentrated under reduced pressure. To the obtained residue were added water and ethyl acetate and the mixture was extracted with ethyl acetate. The organic layer was washed with saturated brine, dried over anhydrous sodium sulfate and concentrated under reduced pressure to give (R)-3-(5,7-dimethylindazol-1-yl)pyrrolidine-1-carboxylic acid tert-butyl ester (309 mg).

To (R)-3-(5,7-dimethylindazol-1-yl)pyrrolidine-1-carboxylic acid tert-butyl ester (361 mg) obtained by the above-mentioned method and a method similar to the above-mentioned method were added 1,4-dioxane (5.4 mL) and 4N hydrogen chloride/1,4-dioxane solution (2.86 mL) and the mixture was stirred at room temperature overnight. The reaction mixture was concentrated under reduced pressure, to the obtained residue was added saturated aqueous sodium hydrogen carbonate solution (about pH 8) under ice-cooling, and the mixture was extracted with ethyl acetate. The organic layer was washed with saturated brine, dried over anhydrous sodium sulfate, and concentrated under reduced pressure to give the title compound (239 mg).

MS(ESI) m/z: 216 (M+H)+

Preparation Example 96: Preparation of 5,7-dimethyl-2-piperidin-4-yl-2H-indazole.hydrochloride

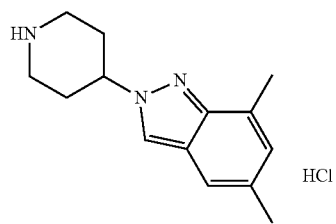 [SMILES: Cc1cc(C)c2nn(C3CCNCC3)cc2c1 ; Cl]

1) Preparation of 4-(3-iodo-5,7-dimethylindazol-2-yl)piperidine-1-carboxylic acid tert-butyl ester and 4-(3-iodo-5,7-dimethylindazol-1-yl)piperidine-1-carboxylic acid tert-butyl ester To a solution of 3-iodo-5,7-dimethyl-1H-indazole (300 mg), 1-(tert-butoxycarbonyl)-4-hydroxypiperidine (488 mg), triphenylphosphine (578 mg) in tetrahydrofuran (6 mL) was added under ice-cooling diethyl azodicarboxylate (40% toluene solution, about 2.2 mol/L) (1.002 mL) and the mixture was stirred at room temperature for 3.5 hr. The reaction mixture was concentrated under reduced pressure, diisopropyl ether was added to the obtained residue, and the mixture was filtered (precipitate was removed). The filtrate was concentrated under reduced pressure and the obtained residue was purified by column chromatography (hexane:ethyl acetate) to give 4-(3-iodo-5,7-dimethylindazol-2-yl)piperidine-1-carboxylic acid tert-butyl ester (226.5 mg) and 4-(3-iodo-5,7-dimethylindazol-1-yl)piperidine-1-carboxylic acid tert-butyl ester (227.4 mg).

In the analysis by Acqity UPLC BEH C18 (Waters) (2 mm×50 mm, mobile phase A: 0.05% formic acid/water, mobile phase B: 0.05% formic acid/acetonitrile, gradient: B 5%->98% 1 min, flow: 0.6 mL/min), the retention time was 1.38 min and 1.36 min, respectively.

2) Preparation of 5,7-dimethyl-2-piperidin-4-yl-2H-indazole.hydrochloride

To 4-(3-iodo-5,7-dimethylindazol-2-yl)piperidine-1-carboxylic acid tert-butyl ester (222 mg) described in the above-mentioned 1) were added methanol (4 mL), tetrahydrofuran (2 mL), 2N aqueous sodium hydroxide solution (0.488 mL) and 10% palladium carbon (22 mg) and the mixture was stirred under a hydrogen atmosphere at room temperature overnight. The reaction mixture was filtered, and the filtrate was concentrated under reduced pressure. To the obtained residue was added water and the mixture was extracted with ethyl acetate. The solvent was evaporated and the obtained residue was purified by column chromatography (hexane:ethyl acetate) to give 4-(5,7-dimethylindazol-2-yl)piperidine-1-carboxylic acid tert-butyl ester (154 mg).

To the obtained 4-(5,7-dimethylindazol-2-yl)piperidine-1-carboxylic acid tert-butyl ester (150 mg) were added 1,4-dioxane (2.2 mL) and 4N hydrogen chloride/1,4-dioxane solution (1.14 mL) and the mixture was stirred at room temperature for 1.5 hr. 4N hydrogen chloride/1,4-dioxane solution (2 mL) was added, and the mixture was stirred at room temperature overnight. The reaction mixture was concentrated under reduced pressure, diethyl ether was added to the obtained residue, and the precipitate was collected by filtration to give 5,7-dimethyl-2-piperidin-4-yl-2H-indazole.hydrochloride (150.7 mg).

MS(ESI) m/z: 230 (M+H)+

Preparation Example 97: Preparation of 5,7-dimethyl-1-piperidin-4-yl-1H-indazole.hydrochloride

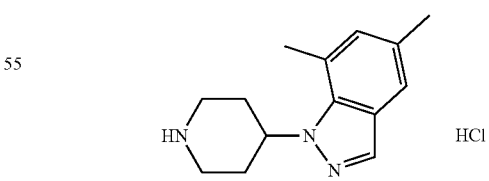

Using 4-(3-iodo-5,7-dimethylindazol-1-yl)piperidine-1-carboxylic acid tert-butyl ester (223 mg) described in Preparation Example 96, 1), reactions and treatments similar to those in Preparation Example 96, 2) were performed to give the title compound (116.5 mg).

MS(ESI) m/z: 230 (M+H)+

Preparation Example 98: Preparation of 4,6-dimethyl-3-piperidin-4-yl-1H-indazole

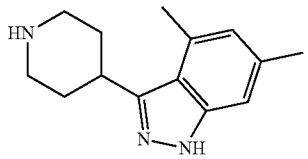 [SMILES: Cc1cc(C)c2c(C3CCNCC3)n[nH]c2c1]

1) Preparation of 4-[(2,4-dibromo-6-fluorophenyl)hydroxymethyl]piperidine-1-carboxylic acid tert-butyl ester To a solution of diisopropylamine (1.21 mL) in tetrahydrofuran (8 mL) was added at −78° C. n-butyllithium/hexane solution (2.65 mol/L, 3.33 mL). The mixture was stirred at 0° C. for 10 min, and at a solution of 1,3-dibromo-5-fluorobenzene (2 g) in tetrahydrofuran (25 mL) was added at −78° C. The mixture was stirred at −78° C. for 30 min, and a solution of 1-Boc-4-piperidinecarboxaldehyde (1.85 g) in tetrahydrofuran (32 mL) was added. The mixture was stirred at 0° C. for 6.5 hr, saturated aqueous ammonia chloride solution was added to the reaction mixture and the mixture was extracted with ethyl acetate. The organic layer was washed with saturated brine, dried over anhydrous magnesium sulfate and concentrated under reduced pressure. The obtained residue was purified by NH column chromatography (hexane:ethyl acetate) to give 4-[(2,4-dibromo-6-fluorophenyl)hydroxymethyl]piperidine-1-carboxylic acid tert-butyl ester (2.04 g).

2) Preparation of 4-(2,4-dibromo-6-fluorobenzoyl)piperidine-1-carboxylic acid tert-butyl ester To a solution of oxalyl chloride (0.63 mL) in dichloromethane (8 mL) was added under cooling at −78° C. a solution of dimethyl sulfoxide (0.785 mL) in dichloromethane (2 mL). The mixture was stirred at not more than −50° C. for 5 min, and a solution of 4-[(2,4-dibromo-6-fluorophenyl)hydroxymethyl]piperidine-1-carboxylic acid tert-butyl ester (1.72 g) in dichloromethane (10 mL) described in the above-mentioned 1) was added. The mixture was stirred at not more than −50° C. for 20 min, triethylamine (3.08 mL) was added, and the mixture was stirred at room temperature for 5 min. To the reaction mixture were added water and saturated aqueous sodium hydrogen carbonate solution and the mixture was extracted with chloroform. The organic layer was dried over anhydrous magnesium sulfate and concentrated under reduced pressure. The obtained residue was purified by column chromatography (hexane:ethyl acetate) to give 4-(2,4-dibromo-6-fluorobenzoyl)piperidine-1-carboxylic acid tert-butyl ester (1.714 g).

3) Preparation of 4-(4,6-dibromo-1H-indazol-3-yl)piperidine-1-carboxylic acid tert-butyl ester To 4-(2,4-dibromo-6-fluorobenzoyl)piperidine-1-carboxylic acid tert-butyl ester (3.74 g) obtained by a method similar to the above-mentioned 2) were added ethanol (74.8 mL) and hydrazine.1 hydrate (4.68 mL) and the mixture was stirred under reflux overnight. The reaction mixture was concentrated under reduced pressure, water was added to the obtained residue, and the precipitate was collected by filtration. The obtained precipitate was recrystallized from ethanol to give 4-(4,6-dibromo-1H-indazol-3-yl)piperidine-1-carboxylic acid tert-butyl ester (2.664 g).

4) Preparation of 4-[4,6-dibromo-1-(2-trimethylsilanylethoxymethyl)-1H-indazol-3-yl]piperidine-1-carboxylic acid tert-butyl ester To a solution of 4-(4,6-dibromo-1H-indazol-3-yl)piperidine-1-carboxylic acid tert-butyl ester (900 mg) obtained by a method similar to the above-mentioned 3) in N,N-dimethylformamide (18 mL) was added under ice-cooling sodium hydride (60% in oil) (102 mg). The mixture was stirred for 3 min and 2-(chloromethoxy)ethyltrimethylsilane (0.482 mL) was added. Under ice-cooling, the mixture was stirred for 1 hr, water was added to the reaction mixture, and the mixture was extracted with a mixed solvent of ethyl acetate and hexane. The organic layer was washed with saturated brine, dried over anhydrous magnesium sulfate and concentrated under reduced pressure. The obtained residue was purified by column chromatography (hexane:ethyl acetate) to give 4-[4,6-dibromo-1-(2-trimethylsilanylethoxymethyl)-1H-indazol-3-yl]piperidine-1-carboxylic acid tert-butyl ester (869 mg).

5) Preparation of 4-[4,6-dimethyl-1-(2-trimethylsilanylethoxymethyl)-1H-indazol-3-yl]piperidine-1-carboxylic acid tert-butyl ester 4-[4,6-Dibromo-1-(2-trimethylsilanylethoxymethyl)-1H-indazol-3-yl]piperidine-1-carboxylic acid tert-butyl ester (130 mg) described in the above-mentioned 4), methylboronic acid (52.8 mg) and palladium(II) acetate (5 mg) were dissolved in dry tetrahydrofuran (2.2 mL), potassium fluoride (102.5 mg) and 2-dicyclohexylphosphino-2',6'-dimethoxybiphenyl (18.1 mg) were added, and the mixture was stirred under a nitrogen atmosphere at 70° C. for 10 hr. Again, a similar reaction was performed using 4-[4,6-dibromo-1-(2-trimethylsilanylethoxymethyl)-1H-indazol-3-yl]piperidine-1-carboxylic acid tert-butyl ester (740 mg) described in the above-mentioned 4) and methylboronic acid (300.6 mg). These two reaction mixtures were combined and resulting solution was filtered through NH silica gel. The filtrate was concentrated under reduced pressure and the obtained residue was purified by column chromatography (hexane:ethyl acetate) to give 4-[4,6-dimethyl-1-(2-trimethylsilanylethoxymethyl)-1H-indazol-3-yl]piperidine-1-carboxylic acid tert-butyl ester (617 mg).

6) Preparation of 4,6-dimethyl-3-piperidin-4-yl-1H-indazole

4-[4,6-Dimethyl-1-(2-trimethylsilanylethoxymethyl)-1H-indazol-3-yl]piperidine-1-carboxylic acid tert-butyl ester (320 mg) described in the above-mentioned 5) was dissolved in 1,4-dioxane (6.4 mL), 4N hydrogen chloride/1,4-dioxane solution (1.7 mL) was added, and the mixture was stirred at 50° C. for 5.5 hr. 4N hydrogen chloride/1,4-dioxane solution (1.7 mL) was added, and the mixture was stirred at 80° C. for 26 hr. Furthermore, 4N hydrogen chloride/1,4-dioxane solution (1.7 mL) was added, and the mixture was stirred at 80° C. for 25 hr. The reaction mixture was concentrated under reduced pressure, ethyl acetate was added to the obtained residue, and the precipitate was collected by filtration. To the obtained solid was added 1N aqueous sodium hydroxide solution (5 mL) and the mixture was extracted with chloroform. The organic layer was concentrated under reduced pressure, diethyl ether was added to the obtained residue, and the precipitate was collected by filtration to give the title compound (150 mg).
MS(ESI) m/z: 230 (M+H)+

Preparation Example 99: Preparation of 1,4,6-trimethyl-3-piperidin-4-yl-1H-indazole.hydrochloride

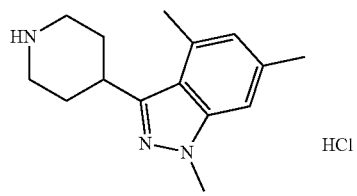 [SMILES: Cc1cc(C)c2c(C3CCNCC3)nn(C)c2c1 ; Cl]

To a solution of 4-(4,6-dibromo-1H-indazol-3-yl)piperidine-1-carboxylic acid tert-butyl ester (800 mg, see Preparation Example 98) in N,N-dimethylformamide (16 mL) was added under ice-cooling sodium hydride (60% in oil) (91 mg). Under ice-cooling, the mixture was stirred for 3 min, and methyl iodide (0.152 mL) was added. Under ice-cooling, the mixture was stirred for 1.5 hr, to the reaction mixture was added saturated aqueous sodium hydrogen carbonate solution and the mixture was extracted with ethyl acetate. The organic layer was washed with saturated brine, dried over anhydrous magnesium sulfate and concentrated under reduced pressure. The obtained residue was purified by column chromatography (hexane:ethyl acetate) to give 4-(4,6-dibromo-1-methyl-1H-indazol-3-yl)piperidine-1-carboxylic acid tert-butyl ester (748 mg).

To the obtained 4-(4,6-dibromo-1-methyl-1H-indazol-3-yl)piperidine-1-carboxylic acid tert-butyl ester (748 mg) were added methylboronic acid (377 mg), palladium(II) acetate (35 mg), dry tetrahydrofuran (16 mL), potassium fluoride (732 mg) and 2-dicyclohexylphosphino-2',6'-dimethoxybiphenyl (129 mg) and the mixture was stirred under a nitrogen atmosphere at 70° C. for 19 hr. The reaction mixture was purified by NH column chromatography (ethyl acetate) and column chromatography (hexane:ethyl acetate) to give 4-(1,4,6-trimethyl-1H-indazol-3-yl)piperidine-1-carboxylic acid tert-butyl ester (485.6 mg).

The obtained 4-(1,4,6-trimethyl-1H-indazol-3-yl)piperidine-1-carboxylic acid tert-butyl ester (481 mg) was dissolved in 1,4-dioxane (4.8 mL), 4N hydrogen chloride/1,4-dioxane solution (3.5 mL) was added, and the mixture was stirred at room temperature overnight. The reaction mixture was concentrated under reduced pressure, to the obtained residue was added diethyl ether, and the precipitate was collected by filtration to give the title compound (449 mg).
MS(ESI) m/z: 244 (M+H)+

Preparation Example 100: Preparation of 4-fluoro-6-methyl-3-piperidin-4-yl-1H-indazole

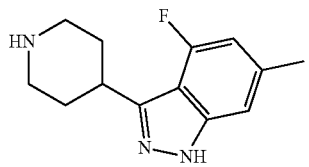 [SMILES: Cc1cc(F)c2c(C3CCNCC3)n[nH]c2c1]

To 4-(2,4-dibromo-6-fluorobenzoyl)piperidine-1-carboxylic acid tert-butyl ester (3.74 g, see Preparation Example 98) were added ethanol (75 mL) and hydrazine.1 hydrate (4.68 mL) and the mixture was stirred under reflux overnight. The reaction mixture was concentrated under reduced pressure, water was added to the obtained residue, and the precipitate was collected by filtration. The obtained precipitate was recrystallized from ethanol (35 mL) and the precipitate (4-(4,6-dibromo-1H-indazol-3-yl)piperidine-1-carboxylic acid tert-butyl ester) was collected by filtration. The filtrate was concentrated under reduced pressure and the obtained residue was purified by column chromatography (hexane:ethyl acetate) to give 4-(6-bromo-4-fluoro-1H-indazol-3-yl)piperidine-1-carboxylic acid tert-butyl ester (121 mg).

To a solution of 4-(6-bromo-4-fluoro-1H-indazol-3-yl)piperidine-1-carboxylic acid tert-butyl ester (170 mg) obtained by the above-mentioned method and a method similar to the above-mentioned method in N,N-dimethylformamide (3 mL) was added under ice-cooling sodium hydride (60% in oil) (20 mg). The mixture was stirred at 0° C. for 1 min and 2-(chloromethoxy)ethyltrimethylsilane (0.09 mL) was added. The mixture was stirred at 0° C. for 20 min, saturated aqueous ammonia chloride was added to the reaction mixture, and the mixture was extracted with ethyl acetate/diethyl ether. The organic layer was washed with saturated brine, dried over anhydrous magnesium sulfate and concentrated under reduced pressure. The obtained residue was purified by column chromatography (hexane:ethyl acetate) to give 4-[6-bromo-4-fluoro-1-(2-trimethylsilanylethoxymethyl)-1H-indazol-3-yl]piperidine-1-carboxylic acid tert-butyl ester (131 mg).

The obtained 4-[6-bromo-4-fluoro-1-(2-trimethylsilanylethoxymethyl)-1H-indazol-3-yl]piperidine-1-carboxylic acid tert-butyl ester (130 mg), methylboronic acid (37 mg) and palladium(II) acetate (6 mg) were dissolved in dry tetrahydrofuran (2 mL), potassium fluoride (71 mg) and 2-dicyclohexylphosphino-2',6'-dimethoxybiphenyl (20 mg) were added, and the mixture was stirred under a nitrogen atmosphere at 70° C. for 20 hr. The reaction mixture was filtered through NH silica gel. The filtrate was concentrated under reduced pressure and the obtained residue was purified by column chromatography (hexane:ethyl acetate) to give 4-[4-fluoro-6-methyl-1-(2-trimethylsilanylethoxymethyl)-1H-indazol-3-yl]piperidine-1-carboxylic acid tert-butyl ester (52.6 mg).

To the obtained 4-[4-fluoro-6-methyl-1-(2-trimethylsilanylethoxymethyl)-1H-indazol-3-yl]piperidine-1-carboxylic acid tert-butyl ester (52 mg) was added 4N hydrogen chloride/1,4-dioxane solution (5 mL) and the mixture was stirred at 70° C. for 4.5 hr. The reaction mixture was concentrated under reduced pressure, 1,4-dioxane (3 mL) and 28% aqueous ammonia (1 mL) were added to the obtained residue, and the mixture was stirred at 90° C. for 3 hr and at 70° C. overnight. To the reaction mixture was added 1N aqueous sodium hydroxide solution and the mixture was extracted with chloroform. The organic layer was concentrated under reduced pressure to give the title compound (32 mg).
MS(ESI) m/z: 234 (M+H)+

Preparation Example 101: Preparation of (2S,4S)-4-(3,5-dimethylpyridin-2-ylamino)pyrrolidine-2-carboxylic acid methyl ester.2 hydrochloride

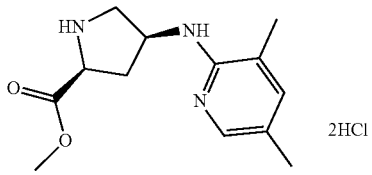 [SMILES: COC(=O)[C@@H]1C[C@H](Nc2ncc(C)cc2C)CN1]

(2S,4S)-4-aminopyrrolidine-1,2-dicarboxylic acid 1-tert-butyl ester 2-methyl ester (150 mg) was dissolved in dichloromethane (2.5 mL), diisopropylethylamine (0.32 mL), 3,5-dimethylpyridine-N-oxide (60.5 mg) and bromotris(pyrrolidino)phosphonium hexafluorophosphate (298 mg) were added, and the mixture was stirred at room temperature overnight. The reaction mixture was purified by NH column chromatography (hexane:ethyl acetate) to give (2S,4S)-4-(3,5-dimethylpyridin-2-ylamino)pyrrolidine-1,2-dicarboxylic acid 1-tert-butyl ester 2-methyl ester (74 mg).

To the obtained (2S,4S)-4-(3,5-dimethylpyridin-2-ylamino)pyrrolidine-1,2-dicarboxylic acid 1-tert-butyl ester 2-methyl ester (70 mg) were added 1,4-dioxane (0.7 mL) and 4N hydrogen chloride/1,4-dioxane solution (1.4 mL) and the mixture was stirred at room temperature for 3 hr. The reaction mixture was concentrated under reduced pressure to give the title compound (84 mg).

MS(ESI) m/z: 250 (M+H)$^+$

Preparation Example 102: Preparation of [(2S,4S)-4-(3,5-dimethylpyridin-2-ylamino)pyrrolidin-2-yl]methanol.2 hydrochloride

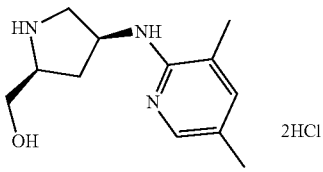 [SMILES: Cc1cnc(N[C@@H]2CN[C@H](CO)C2)c(C)c1]

(2S,4S)-4-(3,5-dimethylpyridin-2-ylamino)pyrrolidine-1,2-dicarboxylic acid 1-tertbutyl ester 2-methyl ester (310 mg, see Preparation Example 101) was dissolved in tetrahydrofuran (6.2 mL) and methanol (3.1 mL) and lithium chloride (113 mg) and sodium borohydride (104 mg) were added under ice-cooling. The mixture was stirred at room temperature overnight, and 1N hydrochloric acid (5 mL) was added to the reaction mixture. The mixture was concentrated under reduced pressure, water was added to the obtained residue and the mixture was extracted with ethyl acetate. The organic layer was dried over anhydrous sodium sulfate and concentrated under reduced pressure. The obtained residue was purified by column chromatography (hexane:ethyl acetate) to give (2S,4S)-4-(3,5-dimethylpyridin-2-ylamino)-2-hydroxymethylpyrrolidine-1-carboxylic acid tert-butyl ester (261 mg).

The obtained (2S,4S)-4-(3,5-dimethylpyridin-2-ylamino)-2-hydroxymethylpyrrolidine-1-carboxylic acid tert-butyl ester (150 mg) was dissolved in 1,4-dioxane (1.5 mL), 4N hydrogen chloride/1,4-dioxane solution (3 mL) was added, and the mixture was stirred at room temperature for 5 hr. The reaction mixture was concentrated under reduced pressure to give the title compound (133 mg).

MS(ESI) m/z: 222 (M+H)$^+$

Preparation Example 103: Preparation of (3,5-dimethylpyridin-2-yl) ((3S,5R)-5-methylpyrrolidin-3-yl)amine.2 hydrochloride

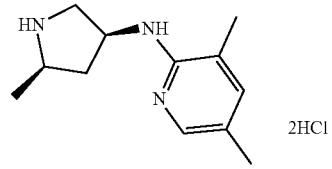

To (2R,4S)-4-amino-2-methylpyrrolidine-1-carboxylic acid tert-butyl ester (368 mg) were added dichloromethane (7 mL), diisopropylethylamine (1.2 mL), 3,5-dimethylpyridine-N-oxide (226 mg), bromotris(pyrrolidino)phosphonium hexafluorophosphate (1114 mg) and the mixture was stirred at room temperature overnight. The reaction mixture was concentrated under reduced pressure, the obtained residue was purified by NH column chromatography (hexane:ethyl acetate) to give (2R,4S)-4-(3,5-dimethylpyridin-2-ylamino)-2-methylpyrrolidine-1-carboxylic acid tert-butyl ester (298 mg).

The obtained (2R,4S)-4-(3,5-dimethylpyridin-2-ylamino)-2-methylpyrrolidine-1-carboxylic acid tert-butyl ester (295 mg) was dissolved in 1,4-dioxane (3 mL), 4N hydrogen chloride/1,4-dioxane solution (3 mL) was added, and the mixture was stirred at room temperature for 1.5 hr. The reaction mixture was concentrated under reduced pressure to give the title compound (264 mg).

Preparation Example 104: Preparation of (3,5-dimethylpyridin-2-yl) ((3S,5S)-5-methylpyrrolidin-3-yl)amine.2 hydrochloride

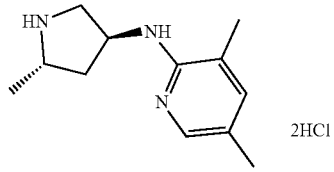

(2S,4S)-4-amino-2-methylpyrrolidine-1-carboxylic acid tert-butyl ester (280 mg) was dissolved in dichloromethane (6 mL), diisopropylethylamine (0.913 mL), 3,5-dimethylpyridine-N-oxide (172 mg) and bromotris(pyrrolidino)phosphonium hexafluorophosphate (847 mg) were added, and the mixture was stirred at room temperature overnight. 3,5-Dimethylpyridine-N-oxide (86 mg) and bromotris(pyrrolidino)phosphonium hexafluorophosphate (325 mg) were added, and the mixture was stirred at room temperature for 3 hr. The reaction mixture was concentrated under reduced pressure, and the obtained residue was purified by NH column chromatography (hexane:ethyl acetate) to give (2S,4S)-4-(3,5-dimethylpyridin-2-ylamino)-2-methylpyrrolidine-1-carboxylic acid tert-butyl ester (192 mg).

To the obtained (2S,4S)-4-(3,5-dimethylpyridin-2-ylamino)-2-methylpyrrolidine-1-carboxylic acid tert-butyl ester (190 mg) were added 1,4-dioxane (1.9 mL) and 4N hydrogen chloride/1,4-dioxane solution (1.9 mL) and the mixture was stirred at room temperature for 3.5 hr. The reaction mixture was concentrated under reduced pressure to give the title compound (182 mg).

Preparation Example 105: Preparation of (2S,3S)-3-(3,5-dimethylpyridin-2-ylamino)pyrrolidine-2-carboxylic acid methyl ester.2 hydrochloride

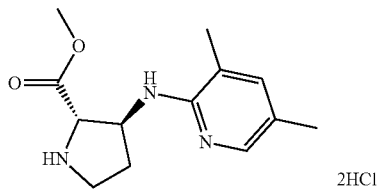 [SMILES: COC(=O)[C@H]1NCC[C@@H]1Nc1ncc(C)cc1C]

To a solution of (2S,3R)-3-hydroxypyrrolidine-1,2-dicarboxylic acid 1-tert-butyl ester 2-methyl ester (3.31 g) and triphenylphosphine (5.31 g) in tetrahydrofuran (48 mL) was added under ice-cooling a solution of diisopropyl azodicarboxylate (4.09 g) in tetrahydrofuran (10 mL). Then, under ice-cooling, a solution of diphenylphosphoryl azide (4.35 mL) in tetrahydrofuran (10 mL) was added and the mixture was stirred at room temperature for 6.5 hr. The reaction mixture was concentrated under reduced pressure and the obtained residue was purified by column chromatography (hexane:ethyl acetate) to give (2S,3S)-3-azidopyrrolidine-1,2-dicarboxylic acid 1-tert-butyl ester 2-methyl ester (3.31 g).

To a solution of the obtained (2S,3S)-3-azidopyrrolidine-1,2-dicarboxylic acid 1-tert-butyl ester 2-methyl ester (3.31 g) in methanol (33 mL) was added 10% palladium carbon (0.33 g) and the mixture was stirred under a hydrogen atmosphere at room temperature for 5.5 hr. The reaction mixture was filtered and the filtrate was concentrated under reduced pressure. The obtained residue was purified by NH column chromatography (hexane:ethyl acetate) to give (2S,3S)-3-aminopyrrolidine-1,2-dicarboxylic acid 1-tert-butyl ester 2-methyl ester (1.44 g).

To the obtained (2S,3S)-3-aminopyrrolidine-1,2-dicarboxylic acid 1-tert-butyl ester 2-methyl ester (450 mg) were added dichloromethane (7 mL), diisopropylethylamine (1.2 mL), 3,5-dimethylpyridine-N-oxide (250 mg) and bromotris(pyrrolidino)phosphonium hexafluorophosphate (1116 mg) and the mixture was stirred at room temperature overnight. The reaction mixture was concentrated under reduced pressure and the obtained residue was purified by NH column chromatography (hexane:ethyl acetate) to give (2S,3S)-3-(3,5-dimethylpyridin-2-ylamino)pyrrolidine-1,2-dicarboxylic acid 1-tert-butyl ester 2-methyl ester (215 mg).

The obtained (2S,3S)-3-(3,5-dimethylpyridin-2-ylamino)pyrrolidine-1,2-dicarboxylic acid 1-tert-butyl ester 2-methyl ester (215 mg) was dissolved in 1,4-dioxane (2.15 mL), 4N hydrogen chloride/1,4-dioxane solution (2.15 mL) was added, and the mixture was stirred at room temperature for 3 hr. The reaction mixture was concentrated under reduced pressure to give the title compound (213 mg).

MS(ESI) m/z: 250 (M+H)⁺

Preparation Example 106: Preparation of (2S,4S)-4-(3,5-dimethylpyridin-2-ylamino)pyrrolidine-2-carboxylic acid amide 2 hydrochloride

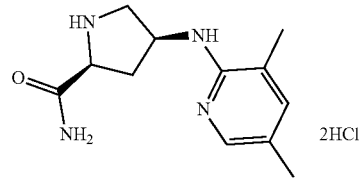 [SMILES: Cc1cnc(N[C@@H]2CN[C@H](C(N)=O)C2)c(C)c1 ; "2HCl"]

To (2S,4S)-4-(3,5-dimethylpyridin-2-ylamino)pyrrolidine-1,2-dicarboxylic acid 1-tert-butyl ester 2-methyl ester (480 mg, see Preparation Example 101) were added ethanol (4.8 mL) and 1N aqueous sodium hydroxide solution (2.75 mL) and the mixture was stirred at room temperature for 1 hr. To the reaction mixture was added 1N hydrochloric acid (2.75 mL) and the mixture was concentrated under reduced pressure to give (2S,4S)-4-(3,5-dimethylpyridin-2-ylamino)pyrrolidine-1,2-dicarboxylic acid 1-tert-butyl ester (640 mg).

To the obtained (2S,4S)-4-(3,5-dimethylpyridin-2-ylamino)pyrrolidine-1,2-dicarboxylic acid 1-tert-butyl ester (230 mg) were added ammonium chloride (183 mg), 1-hydroxybenzotriazole (140 mg), 1-ethyl-3-(3'-dimethylaminopropyl)carbodiimide.hydrochloride (200 mg), chloroform (5 mL) and triethylamine (0.67 mL) and the mixture was stirred at room temperature for 6 hr. To the reaction mixture was added saturated aqueous sodium hydrogen carbonate solution and the mixture was extracted with chloroform. The solvent was evaporated and the obtained residue was purified by column chromatography (hexane:ethyl acetate) to give (2S,4S)-2-carbamoyl-4-(3,5-dimethylpyridin-2-ylamino)pyrrolidine-1-carboxylic acid tert-butyl ester (172 mg).

To the obtained (2S,4S)-2-carbamoyl-4-(3,5-dimethylpyridin-2-ylamino)pyrrolidine-1-carboxylic acid tert-butyl ester (70 mg) were added 1,4-dioxane (0.7 mL) and 4N hydrogen chloride/1,4-dioxane solution (0.7 mL) and the mixture was stirred at room temperature for 6.5 hr. The reaction mixture was concentrated under reduced pressure to give the title compound (66 mg).

MS(ESI) m/z: 235 (M+H)⁺

Preparation Example 107: Preparation of (3,5-dimethylpyridin-2-yl) ((3S,5S)-5-methoxymethylpyrrolidin-3-yl)amine.2 hydrochloride

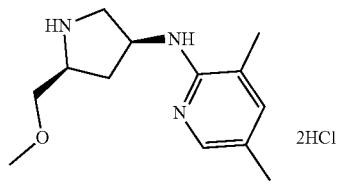

To (2S,4S)-4-amino-2-methoxymethylpyrrolidine-1-carboxylic acid tert-butyl ester (300 mg) were added 2-bromo-3,5-dimethylpyridine (291 mg), tris(dibenzylideneacetone)dipalladium(0) (30 mg), 2,2'-bis(diphenylphosphino)-1,1'-binaphthyl (41 mg), sodium tert-butoxide (188 mg) and toluene (6 mL) and the mixture was stirred at 80° C. for 6 hr. The reaction mixture was purified by column chromatography (hexane:ethyl acetate) to give (2S,4S)-4-(3,5-dimethylpyridin-2-ylamino)-2-methoxymethylpyrrolidine-1-carboxylic acid tert-butyl ester (489 mg).

The obtained (2S,4S)-4-(3,5-dimethylpyridin-2-ylamino)-2-methoxymethylpyrrolidine-1-carboxylic acid tert-butyl ester (435 mg) was dissolved in 1,4-dioxane (4.4 mL), 4N hydrogen chloride/1,4-dioxane solution (4.4 mL) was added, and the mixture was stirred at room temperature overnight. The reaction mixture was concentrated under reduced pressure to give the title compound (492 mg).

MS(ESI) m/z: 236 (M+H)+

Preparation Example 108: Preparation of 2-[(2S, 4S)-4-(3,5-dimethylpyridin-2-ylamino)pyrrolidin-2-yl]propan-2-ol.2 hydrochloride

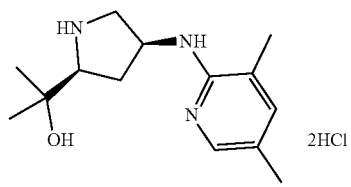 [SMILES: Cc1cnc(N[C@@H]2CN[C@H](C(C)(C)O)C2)c(C)c1 ; "2HCl"]

To a solution of (2S,4R)-4-hydroxypyrrolidine-1,2-dicarboxylic acid 1-tert-butyl ester 2-methyl ester (3 g) in tetrahydrofuran (40 mL) was added under ice-cooling 3 M methyl magnesium bromide/diethyl ether solution (14.3 mL). The mixture was stirred under ice-cooling for 15 min and at room temperature for 3 hr. To the reaction mixture was added saturated aqueous ammonia chloride solution and the mixture was extracted with ethyl acetate. The organic layer was washed with saturated brine, dried over anhydrous sodium sulfate and concentrated under reduced pressure. To the obtained residue was added hexane/diisopropyl ether, and the precipitate was collected by filtration to give (2S, 4R)-4-hydroxy-2-(1-hydroxy-1-methylethyl)pyrrolidine-1-carboxylic acid tert-butyl ester (2.68 g).

To a solution of the obtained (2S,4R)-4-hydroxy-2-(1-hydroxy-1-methylethyl)pyrrolidine-1-carboxylic acid tert-butyl ester (2.68 g), 4-(dimethylamino)pyridine (0.13 g) and triethylamine (3.05 mL) in dichloromethane (45 mL) was added under ice-cooling a solution of methanesulfonyl chloride (1.01 mL) in dichloromethane (10 mL). Under ice-cooling, the mixture was stirred for 1.5 hr, and the reaction mixture was concentrated under reduced pressure. The obtained residue was purified by column chromatography (hexane:ethyl acetate) to give (2S,4R)-2-(1-hydroxy-1-methylethyl)-4-methanesulfonyloxypyrrolidine-1-carboxylic acid tert-butyl ester (3.31 g).

The obtained (2S,4R)-2-(1-hydroxy-1-methylethyl)-4-methanesulfonyloxypyrrolidine-1-carboxylic acid tert-butyl ester (3.31 g) was dissolved in acetonitrile (37 mL), tetrabutylammonium azide (4.7 g) was added, and the mixture was stirred at 80° C. for 8.5 hr. The reaction mixture was concentrated under reduced pressure and the obtained residue was purified by column chromatography (hexane:ethyl acetate) to give (2S,4S)-4-azido-2-(1-hydroxy-1-methylethyl)pyrrolidine-1-carboxylic acid tert-butyl ester (1.73 g).

To a solution of the obtained (2S,4S)-4-azido-2-(1-hydroxy-1-methylethyl)pyrrolidine-1-carboxylic acid tert-butyl ester (1.73 g) in ethanol (32 mL) was added 10% palladium carbon (0.17 g) and the mixture was stirred under a hydrogen atmosphere at room temperature for 3.5 hr. The reaction mixture was filtered and the filtrate was concentrated under reduced pressure. The obtained residue was purified by column chromatography (hexane:ethyl acetate) to give (2S,4S)-4-amino-2-(1-hydroxy-1-methylethyl)pyrrolidine-1-carboxylic acid tert-butyl ester (1.324 g).

The obtained (2S,4S)-4-amino-2-(1-hydroxy-1-methylethyl)pyrrolidine-1-carboxylic acid tert-butyl ester (250 mg) was dissolved in dichloromethane (4 mL), diisopropylethylamine (0.67 mL), 3,5-dimethylpyridine-N-oxide (139 mg) and bromotris(pyrrolidino)phosphonium hexafluorophosphate (620 mg) were added, and the mixture was stirred at room temperature overnight. The reaction mixture was concentrated under reduced pressure and the obtained residue was purified by column chromatography (hexane:ethyl acetate) to give (2S,4S)-4-(3,5-dimethylpyridin-2-ylamino)-2-(1-hydroxy-1-methylethyl)pyrrolidine-1-carboxylic acid tert-butyl ester (265 mg).

The obtained (2S,4S)-4-(3,5-dimethylpyridin-2-ylamino)-2-(1-hydroxy-1-methylethyl)pyrrolidine-1-carboxylic acid tert-butyl ester (260 mg) was dissolved in 1,4-dioxane (3 mL) and 4N hydrogen chloride/1,4-dioxane solution (3 mL) was added under ice-cooling. Under ice-cooling, the mixture was stirred for 1 hr and at room temperature for 1 hr. The reaction mixture was concentrated under reduced pressure to give the title compound (265 mg).

MS(ESI) m/z: 250 (M+H)+

Preparation Example 109: Preparation of 4-(4-p-tolylpyrazol-1-yl)piperidine.hydrochloride

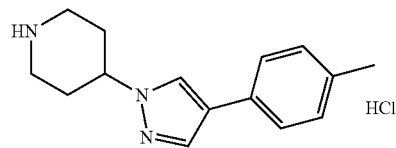 [SMILES: Cc1ccc(-c2cnn(C3CCNCC3)c2)cc1 ; Cl]

To 4-(4-bromopyrazol-1-yl)piperidine-1-carboxylic acid tert-butyl ester (208 mg) were added 4-methylphenylboronic acid (95 mg), N,N-dimethylformamide (3.2 mL), 2 M aqueous sodium carbonate solution (946 UL) and [1,1'-bis(diphenylphosphino)ferrocene]palladium(II) dichloride. dichloromethane complex (26 mg) and the mixture was stirred at 80° C. After completion of the reaction, saturated brine was added and the mixture was extracted with ethyl acetate. The solvent was evaporated and the obtained residue was purified by column chromatography (hexane:ethyl acetate) to give 4-[4-(p-tolyl)pyrazol-1-yl]piperidine-1-carboxylic acid tert-butyl ester (139 mg).

The obtained 4-[4-(p-tolyl)pyrazol-1-yl]piperidine-1-carboxylic acid tert-butyl ester (138 mg) was dissolved in 1,4-dioxane (2 mL), 4N hydrogen chloride/1,4-dioxane solution (1.01 mL) was added, and the mixture was stirred at room temperature overnight. The solvent was evaporated and ethyl acetate was added to the obtained residue, and the precipitate was collected by filtration to give the title compound (112.6 mg).

MS(ESI) m/z: 242 (M+H)+

Preparation Example 110: Preparation of 1-(3,5-dimethylpyridin-2-yl)-3-methylpiperazine

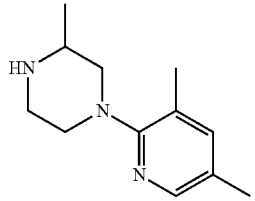

To a mixture of 2-methylpiperazine-1-carboxylic acid tert-butyl ester (2 g), 2-bromo-3,5-dimethylpyridine (1.95 g), tris(dibenzylideneacetone)dipalladium(0) (183 mg), rac-2,2'-bis(diphenylphosphino)-1,1'-binaphthyl (250 mg) and tert-butoxy sodium (1.3 g) was added toluene (33 mL) and the mixture was stirred with heating under reflux for 8 hr. The reaction mixture was cooled and filtered through celite. The filtrate was evaporated and the obtained residue was purified by column chromatography (hexane:ethyl acetate) to give 4-(3,5-dimethylpyridin-2-yl)-2-methylpiperazine-1-carboxylic acid tert-butyl ester (1.61 g). The obtained 4-(3,5-dimethylpyridin-2-yl)-2-methylpiperazine-1-carboxylic acid tert-butyl ester (1.61 g) was dissolved in ethyl acetate (10 mL), 4N hydrogen chloride/ethyl acetate solution (10 mL) and methanol (2 mL) were added, and the mixture was stirred at room temperature. After completion of the reaction, the solvent was evaporated, 1N aqueous sodium hydroxide solution was added to the obtained residue and the mixture was extracted with ethyl acetate. The solvent was evaporated to give the title compound (1.17 g).

MS(ESI) m/z: 206 (M+H)$^+$

Preparation Example 111: Preparation of (R)-1-(3,5-dimethylpyridin-2-yl)-2-methylpiperazine.2 hydrochloride

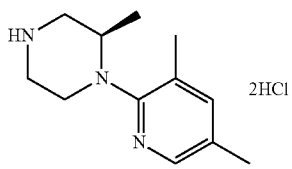

1) Preparation of (R)-4-(3,5-dimethylpyridin-2-yl)-3-methylpiperazine-1-carboxylic acid tert-butyl ester To a solution of (R)-3-methylpiperazine-1-carboxylic acid tert-butyl ester (500 mg), 3,5-dimethylpyridine-N-oxide (246 mg) and N,N-diisopropylethylamine (1.3 mL) in tetrahydrofuran (8 mL) was added bromotris(pyrrolidino)phosphonium hexafluorophosphate (1.21 g) and the mixture was stirred at room temperature overnight. To the reaction mixture was added saturated brine and the mixture was extracted with ethyl acetate. The solvent was evaporated and the obtained residue was purified by column chromatography (ethyl acetate:hexane) to give (R)-4-(3,5-dimethylpyridin-2-yl)-3-methylpiperazine-1-carboxylic acid tert-butyl ester (387 mg).

MS(ESI) m/z: 306 (M+H)$^+$

2) Preparation of (R)-1-(3,5-dimethylpyridin-2-yl)-2-methylpiperazine.2 hydrochloride (R)-4-(3,5-dimethylpyridin-2-yl)-3-methylpiperazine-1-carboxylic acid tert-butyl ester (197 mg, see the abovementioned 1)) was dissolved in ethyl acetate (1.3 mL), 4N hydrogen chloride/ethyl acetate solution (1.3 mL) and methanol (1.3 mL) were added, and the mixture was stirred at room temperature. After completion of the reaction, the solvent was evaporated to give the title compound (199 mg).

MS(ESI) m/z: 206 (M+H)$^+$

Preparation Example 112: Preparation of (R)-3-(3,5-dimethylpyridin-2-ylamino)pyrrolidine-1-carboxylic acid tert-butyl ester

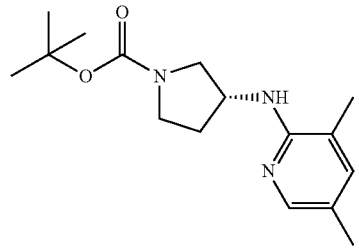 [SMILES: Cc1cnc(N[C@@H]2CCN(C(=O)OC(C)(C)C)C2)c(C)c1]

To 2-bromo-3,5-dimethylpyridine (204 μL) were added (R)-3-aminopyrrolidine-1-carboxylic acid tert-butyl ester (350 μL), a tris(dibenzylideneacetone)dipalladium(0) (73.8 mg), rac-2,2'-bis(diphenylphosphino)-1,1'-binaphthyl (100.4 mg), tert-butoxy sodium (232.4 mg) and toluene (4 mL) and the mixture was stirred at 120° C. for 7 hr. The reaction mixture was cooled and filtered through celite. The filtrate was concentrated and the obtained residue was purified by column chromatography (hexane:ethyl acetate) to give the title compound (459 mg).

MS(APCI) m/z: 292 (M+H)$^+$

Preparation Example 113: Preparation of (3,5-dimethylpyridin-2-yl)-(R)-pyrrolidin-3-ylamine

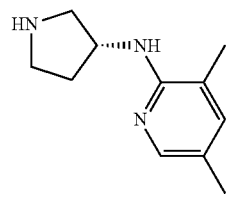

To a solution of (R)-3-(3,5-dimethylpyridin-2-ylamino)pyrrolidine-1-carboxylic acid tert-butyl ester (454 mg) described in Preparation Example 112 in chloroform (3 mL) was added trifluoroacetic acid (2.09 mL) and the mixture was stirred at room temperature. After completion of the reaction, the reaction mixture was diluted with methanol, charged for ion exchange chromatography, washed with methanol, and eluted with 1N ammonia/methanol solution to give the title compound (280 mg).

MS (APCI) m/z: 192 (M+H)$^+$

Preparation Example 114: Preparation of 4-((S)-4-isopropyl-2,5-dioxoimidazolidin-4-yl)benzoic acid

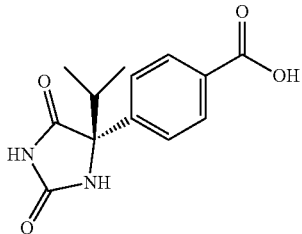 [SMILES: CC(C)[C@@]1(c2ccc(C(=O)O)cc2)NC(=O)NC1=O]

Using 4-(4-isopropyl-2,5-dioxo-imidazolidin-4-yl)benzoic acid (10.45 g) described in Preparation Example 5 and (S)-1-phenylethylamine (2.89 g), a method similar to Preparation Example 45 was performed to give 4-((S)-4-isopropyl-2,5-dioxoimidazolidin-4-yl)benzoic acid. (S)-1-phenylethylamine salt (2.15 g).

To the obtained 4-((S)-4-isopropyl-2,5-dioxoimidazolidin-4-yl)benzoic acid. (S)-1-phenylethylamine salt (1 g) were added water (10 mL) and 1N hydrochloric acid (10 mL). The precipitate was collected by filtration to give the title compound (635 mg).

MS(ESI) m/z: 263 (M+H)$^+$

Preparation Example 115: Preparation of (S)-4-(3,5-dimethylpyridin-2-yl)-3-methylpiperazine-1-carboxylic acid tert-butyl ester

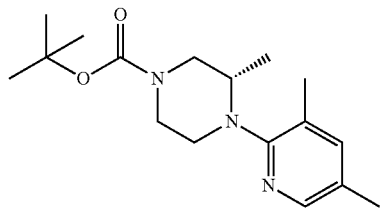 [SMILES: Cc1cnc(N2CCN(C(=O)OC(C)(C)C)C[C@@H]2C)c(C)c1]

To a solution of (S)-3-methylpiperazine-1-carboxylic acid tert-butyl ester (2.5 g), 3,5-dimethylpyridine-N-oxide (1.23 g) in tetrahydrofuran (40 mL) was added N,N-diisopropylethylamine (6.4 mL), bromotris(pyrrolidino)phosphonium hexafluorophosphate (6 g) and the mixture was stirred at room temperature overnight. To the reaction mixture was added aqueous sodium hydrogen carbonate solution and the mixture was extracted with ethyl acetate. The solvent was evaporated and the obtained residue was purified by column chromatography (ethyl acetate:hexane) to give (S)-4-(3,5-dimethylpyridin-2-yl)-3-methylpiperazine-1-carboxylic acid tert-butyl ester (1.27 g).

MS(ESI) m/z: 306 (M+H)$^+$

Preparation Example 116: Preparation of 1-(3,5-dimethylpyridin-2-yl)-3,3-dimethylpiperazine.2 hydrochloride

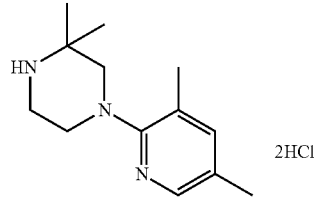 [SMILES: Cc1cnc(N2CCNC(C)(C)C2)c(C)c1]

Using 3,5-dimethylpyridine-N-oxide (574 mg) and 2,2-dimethylpiperazine-1-carboxylic acid tert-butyl ester (1 g), reactions and treatments similar to those in Preparation Example 115 were performed to give 4-(3,5-dimethylpyridin-2-yl)-2,2-dimethylpiperazine-1-carboxylic acid tert-butyl ester (1.11 g).

The obtained 4-(3,5-dimethylpyridin-2-yl)-2,2-dimethylpiperazine-1-carboxylic acid tert-butyl ester (1.1 g) was dissolved in ethyl acetate (7 mL), 4N hydrogen chloride/ethyl acetate solution (7 mL) and methanol (7 mL) were added, and the mixture was stirred at room temperature. After completion of the reaction, the solvent was evaporated to give the title compound (1.03 g).

MS(ESI) m/z: 220 (M+H)$^+$

Preparation Example 117: Preparation of (R)-4-(3,5-dimethylpyridin-2-yl)-2-methylpiperazine-1-carboxylic acid tert-butyl ester

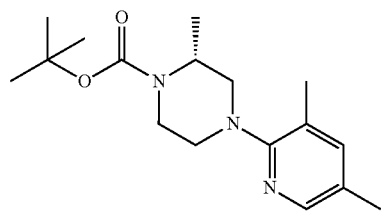 [SMILES: Cc1cnc(N2CCN(C(=O)OC(C)(C)C)[C@H](C)C2)c(C)c1]

To a mixture of (R)-2-methylpiperazine-1-carboxylic acid tert-butyl ester (1 g), 2-bromo-3,5-dimethylpyridine (975 mg), tris(dibenzylideneacetone)dipalladium(0) (92 mg), rac-2,2'-bis(diphenylphosphino)-1,1'-binaphthyl (125 mg) and tert-butoxy sodium (650 mg) was added toluene (17 mL) and the mixture was stirred under microwave irradiation at 130° C. for 2 hr. The reaction mixture was purified by column chromatography (hexane:ethyl acetate) to give the title compound (220 mg).

MS (ESI) m/z: 306 (M+H)$^+$

Preparation Example 118: Preparation of (R)-1-(3,5-dimethylpyridin-2-yl)-3-methylpiperazine. 2 hydrochloride

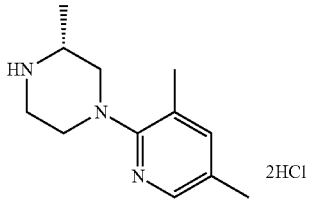

(R)-4-(3,5-dimethylpyridin-2-yl)-2-methylpiperazine-1-carboxylic acid tert-butyl ester (220 mg) described in Preparation Example 117 was dissolved in ethyl acetate (1.5 mL), 4N hydrogen chloride/ethyl acetate solution (1.5 mL) and methanol (1.5 mL) were added, and the mixture was stirred at room temperature. After completion of the reaction, the solvent was evaporated to give the title compound (198 mg).
MS(ESI) m/z: 206 (M+H)$^+$ Preparation Example 119: Preparation of (R)-1-(3,5-dimethylpyridin-2-yl)-3-methylpiperazine

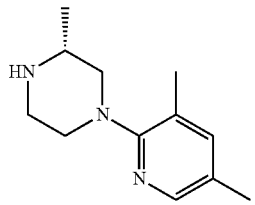

To (R)-4-(3,5-dimethylpyridin-2-yl)-2-methylpiperazine-1-carboxylic acid tert-butyl ester (2.4 g) described in Preparation Example 117 were added dichloromethane (50 mL) and trifluoroacetic acid (10 mL) and the mixture was stirred at room temperature. After completion of the reaction, the solvent was evaporated, aqueous sodium hydroxide solution was added to the obtained residue and the mixture was extracted with chloroform. The solvent was evaporated and the precipitated solid was filtered off. The filtrate was concentrated and the obtained residue was purified by NH coated silica gel column chromatography (ethyl acetate:hexane) to give the title compound (1.08 g).
MS(ESI) m/z: 206 (M+H)$^+$ Preparation Example 120: Preparation of 4-(3,5-dimethylpyridin-2-yl)-3-hydroxymethylpiperazine-1-carboxylic acid tert-butyl ester

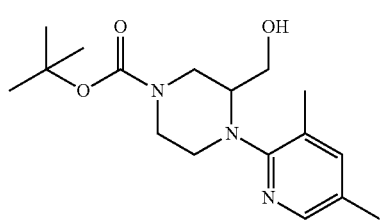 [SMILES: Cc1cnc(N2CCN(C(=O)OC(C)(C)C)CC2CO)c(C)c1]

To 3-hydroxymethylpiperazine-1-carboxylic acid tert-butyl ester (1.5 g) were added tetrahydrofuran (28 mL), bromotris(pyrrolidino)phosphonium hexafluorophosphate (3.4 g), 3,5-dimethylpyridine-N-oxide (690 mg) and N,N-diisopropylethylamine (3.58 mL) and the mixture was stirred at room temperature for 4.5 hr. Water was added to the reaction mixture, and the mixture was extracted with ethyl acetate and chloroform. The solvent was evaporated and the obtained residue was purified by column chromatography (ethyl acetate:hexane) to give the title compound (773 mg).
MS(ESI) m/z: 322 (M+H)$^+$ Preparation Example 121: Preparation of 1-(3,5-dimethylpyridin-2-yl)-2-methoxymethylpiperazine.2 hydrochloride

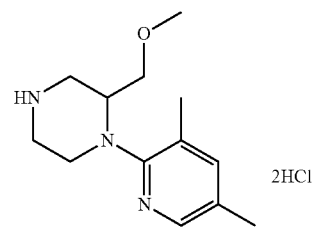 [SMILES: COCC1CNCCN1c1ncc(C)cc1C]

To a solution of 4-(3,5-dimethylpyridin-2-yl)-3-hydroxymethylpiperazine-1-carboxylic acid tert-butyl ester (440 mg) described in Preparation Example 120 and methyl iodide (96 μL) in N,N-dimethylformamide (7 mL) was added at 0° C. sodium hydride (60% in liquid paraffin dispersion) (62 mg) and the mixture was stirred at room temperature. After completion of the reaction, water was added to the reaction mixture, and the mixture was extracted with ethyl acetate and chloroform. The solvent was evaporated and the obtained residue was purified by column chromatography (ethyl acetate:hexane) to give 4-(3,5-dimethylpyridin-2-yl)-3-methoxymethylpiperazine-1-carboxylic acid tert-butyl ester (245 mg).
This compound (245 mg) was dissolved in methyl acetate (2 mL) and methanol (2 mL), 4N hydrogen chloride/ethyl acetate solution (2 mL) was added and the mixture was stirred at room temperature. After completion of the reaction, the solvent was evaporated to give the title compound (230 mg).
MS(ESI) m/z: 236 (M+H)$^+$ Preparation Example 122: Preparation of (R)-1-(3,5-dimethylpyridin-2-yl)-3-ethylpiperazine

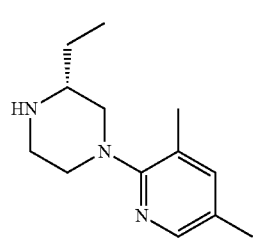 [SMILES: CC[C@@H]1CN(c2ncc(C)cc2C)CCN1]

To a solution of (R)-2-ethylpiperazine-1-carboxylic acid tert-butyl ester (1 g) and 3,5-dimethylpyridine-N-oxide (546 mg) in tetrahydrofuran (18 mL) were added N,N-diisopropylethylamine (3 mL) and bromotris(pyrrolidino)phosphonium hexafluorophosphate (2.8 g) and the mixture was stirred at room temperature overnight. Water was added to the reaction mixture, and the mixture was extracted with ethyl acetate and chloroform. The solvent was evaporated and the obtained residue was purified by column chromatography (ethyl acetate:hexane) to give (R)-4-(3,5-dimethylpyridin-2-yl)-2-ethylpiperazine-1-carboxylic acid tert-butyl ester (1.11 g).

The obtained (R)-4-(3,5-dimethylpyridin-2-yl)-2-ethylpiperazine-1-carboxylic acid tert-butyl ester (1.11 g) was dissolved in ethyl acetate (5 mL), 4N hydrogen chloride/ethyl acetate solution (5 mL) and methanol (5 mL) were added, and the mixture was stirred at room temperature. After completion of the reaction, aqueous sodium hydroxide solution was added, and the mixture was extracted with ethyl acetate and chloroform. The solvent was evaporated to give the title compound (735 mg).

MS (ESI) m/z: 220 (M+H)$^+$

Preparation Example 123: Preparation of (S)-4-(3,5-dimethylpyridin-2-yl)-2-hydroxymethylpiperazine-1-carboxylic acid tert-butyl ester

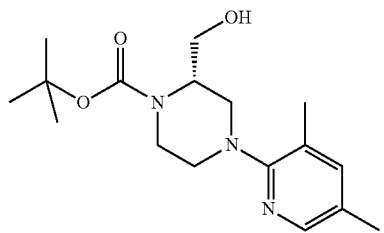 [SMILES: Cc1cnc(N2CCN(C(=O)OC(C)(C)C)[C@H](CO)C2)c(C)c1]

To (S)-2-hydroxymethylpiperazine-1-carboxylic acid tert-butyl ester (950 mg) were added tetrahydrofuran (17 mL), 3,5-dimethylpyridine-N-oxide (515 mg), N,N-diisopropylethylamine (2.8 mL) and bromotris(pyrrolidino)phosphonium hexafluorophosphate (2.67 g) and the mixture was stirred at room temperature for 5.5 hr. Water was added to the reaction mixture and the mixture was extracted with ethyl acetate. The solvent was evaporated and the obtained residue was purified by column chromatography (ethyl acetate:hexane) to give the title compound (640 mg).

MS(ESI) m/z: 322 (M+H)$^+$

Preparation Example 124: Preparation of (S)-4-(3,5-dimethylpyridin-2-yl)-2-methoxymethylpiperazine-1-carboxylic acid tert-butyl ester

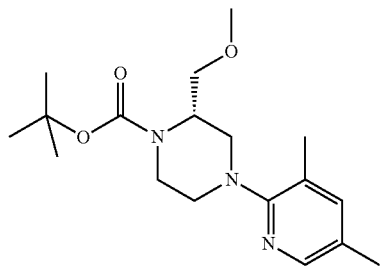 [SMILES: COC[C@@H]1CN(c2ncc(C)cc2C)CCN1C(=O)OC(C)(C)C]

1) To a solution of (S)-4-(3,5-dimethylpyridin-2-yl)-2-hydroxymethylpiperazine-1-carboxylic acid tert-butyl ester (83 mg) described in Preparation Example 123 and methyl iodide (20 µL) in N,N-dimethylformamide (1.3 mL) was added at 0° C. sodium hydride (60% in oil) (11.3 mg) and the mixture was stirred at room temperature for 3 hr. Water was added to the reaction mixture and the mixture was extracted with ethyl acetate. The solvent was evaporated to give a crude product.

2) Using (S)-4-(3,5-dimethylpyridin-2-yl)-2-hydroxymethylpiperazine-1-carboxylic acid tert-butyl ester (90 mg) described in Preparation Example 123, methyl iodide (18 µL), reactions and treatments similar to those in the above-mentioned 1) were performed to give a crude product.

The obtained crude products of 1) and 2) were combined and purified by column chromatography (ethyl acetate:hexane) to give the title compound (97 mg).

MS(ESI) m/z: 336 (M+H)$^+$

Preparation Example 125: Preparation of 8-(3,5-dimethylpyridin-2-yl)-5,8-diazaspiro[3.5]nonane

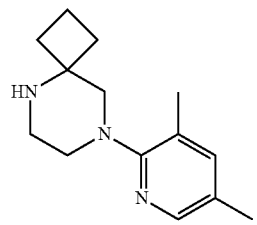 [SMILES: Cc1cnc(N2CCNC3(CCC3)C2)c(C)c1]

To a solution of 5,8-diazaspiro[3,5]nonane.2 hydrochloride (350 mg) and 3,5-dimethylpyridine-N-oxide (205 mg) in tetrahydrofuran (7 mL) were added N,N-diisopropylethylamine (1.73 mL) and bromotris(pyrrolidino)phosphonium hexafluorophosphate (1.07 g) and the mixture was stirred at room temperature for 5 hr. Water was added to the reaction mixture, and the mixture was extracted with ethyl acetate and chloroform. The solvent was evaporated and the obtained residue was purified by column chromatography (ethyl acetate:hexane) to give the title compound (176 mg).

MS(ESI) m/z: 232 (M+H)$^+$

Preparation Example 126: Preparation of (S)-1-(3,5-dimethylpyridin-2-yl)-3-methylpiperazine

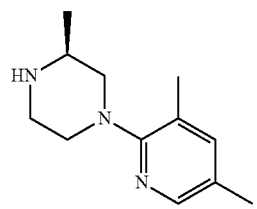

To a solution of (S)-2-methylpiperazine-1-carboxylic acid tert-butyl ester (2.0 g), 3,5-dimethylpyridine-N-oxide (1.2 g) in tetrahydrofuran (40 mL) were added N,N-diisopropylethylamine (6.4 mL) and bromotris(pyrrolidino)phosphonium hexafluorophosphate (6.06 g) and the mixture was stirred at room temperature overnight. Water was added to the reaction mixture and the mixture was extracted with ethyl acetate. The solvent was evaporated and the obtained residue was purified by column chromatography (ethyl acetate:hexane) to give (S)-4-(3,5-dimethylpyridin-2-yl)-2-methylpiperazine-1-carboxylic acid tert-butyl ester (2.49 g).

To the obtained (S)-4-(3,5-dimethylpyridin-2-yl)-2-methylpiperazine-1-carboxylic acid tert-butyl ester (2.49 g) were added ethyl acetate (15 mL), methanol (15 mL) and 4N hydrogen chloride/ethyl acetate solution (13 mL) and the mixture was stirred at room temperature. After completion of the reaction, 1N aqueous sodium hydroxide solution was added and the mixture was extracted with ethyl acetate. The solvent was evaporated and the obtained residue was purified by column chromatography (ethyl acetate:hexane) to give the title compound (1.31 g).

MS(ESI) m/z: 206 (M+H)+

Preparation Example 127: Preparation of [(R)-1-(3,5-dimethylpyridin-2-yl) piperazin-2-yl]methanol

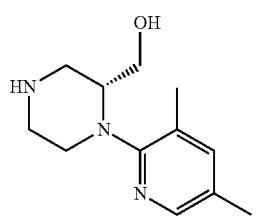 [SMILES: Cc1cnc(N2CCNC[C@@H]2CO)c(C)c1]

Using (R)-3-hydroxymethylpiperazine-1-carboxylic acid tert-butyl ester (5 g) and 3,5-dimethylpyridine-N-oxide (2.7 g), reactions and treatments similar to those in Preparation Example 126 were performed to give the title compound (1.16 g).

MS(ESI) m/z: 222 (M+H)+

Preparation Example 128: Preparation of [(S)-1-(3,5-dimethylpyridin-2-yl)piperazin-2-yl]methanol.2 hydrochloride

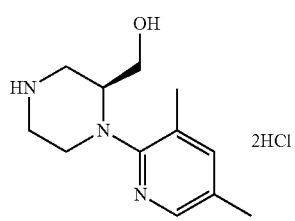 [SMILES: Cc1cnc(N2CCNC[C@H]2CO)c(C)c1]

Using (S)-3-hydroxymethylpiperazine-1-carboxylic acid tert-butyl ester (730 mg) and 3,5-dimethylpyridine-N-oxide (395 mg), reactions and treatments similar to those in Preparation Example 115 were performed to give the title compound (230 mg).

MS(ESI) m/z: 220 (M+H)+

Preparation Example 129: Preparation of (S)-4-(3,5-dimethylpyridin-2-yl)piperazine-1,2-dicarboxylic acid 1-tert-butyl ester 2-methyl ester

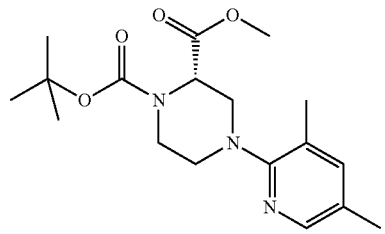 [SMILES: COC(=O)[C@@H]1CN(c2ncc(C)cc2C)CCN1C(=O)OC(C)(C)C]

To (S)-piperazine-1,2-dicarboxylic acid 1-tert-butyl ester 2-methyl ester (2.6 g) were added methylene chloride (42 mL), N,N-diisopropylethylamine (6.8 mL), 3,5-dimethylpyridine-N-oxide (1.24 g) and bromotris(pyrrolidino)phosphonium hexafluorophosphate (6.42 g) and the mixture was stirred at room temperature overnight. Bromotris(pyrrolidino)phosphonium hexafluorophosphate (676 mg) was added, and the mixture was stirred at room temperature overnight. Water was added to the reaction mixture and the mixture was extracted with chloroform. The solvent was evaporated and the obtained residue was purified by column chromatography (ethyl acetate:hexane) to give the title compound (1.52 g).

MS(ESI) m/z: 350 (M+H)+

Preparation Example 130: Preparation of (S)-4-(3,5-dimethylpyridin-2-yl)piperazine-2-carboxylic acid methyl ester

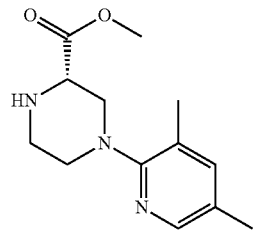 [SMILES: COC(=O)[C@@H]1CN(c2ncc(C)cc2C)CCN1]

Using (S)-piperazine-1,2-dicarboxylic acid 1-tert-butyl ester 2-methyl ester (2.4 g) and 3,5-dimethylpyridine-N-oxide (1.07 g), reactions and treatments similar to those in Preparation Example 126 were performed to give the title compound (620 mg).

MS(ESI) m/z: 250 (M+H)+

Preparation Example 131: Preparation of (S)-1-(3,5-dimethylpyridin-2-yl)-2-methylpiperazine.2 hydrochloride

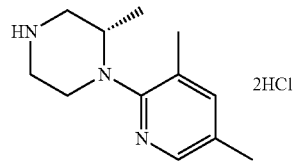

(S)-4-(3,5-dimethylpyridin-2-yl)-3-methylpiperazine-1-carboxylic acid tert-butyl ester (1.27 g) described in Preparation Example 115 was dissolved in ethyl acetate (8 mL), 4N hydrogen chloride/ethyl acetate solution (8 mL) and methanol (8 mL) were added, and the mixture was stirred at room temperature. After completion of the reaction, the solvent was evaporated to give the title compound (1.39 g).

MS(ESI) m/z: 206 (M+H)⁺

Preparation Example 132: Preparation of 4-((R)-4-isopropyl-2,5-dioxoimidazolidin-4-yl)benzoyl chloride

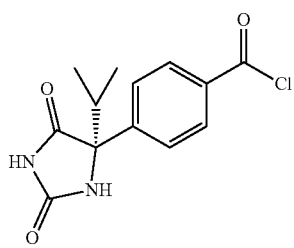 [SMILES: CC(C)[C@]1(c2ccc(C(=O)Cl)cc2)NC(=O)NC1=O]

To 4-((R)-4-isopropyl-2,5-dioxoimidazolidin-4-yl)benzoic acid (1.44 g) described in Preparation Example 45 were added 1,4-dioxane (11 mL) and thionyl chloride (1.16 mL) and the mixture was stirred at 80° C. for 3 hr. The solvent was evaporated to give the title compound (1.48 g).

Preparation Example 133: Preparation of (S)-2-carbamoyl-4-(3,5-dimethylpyridin-2-yl)piperazine-1-carboxylic acid tert-butyl ester

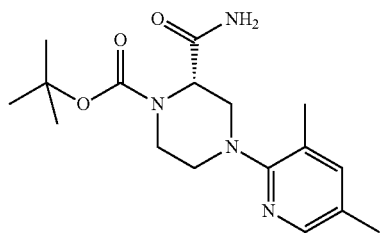 [SMILES: Cc1cnc(N2CCN(C(=O)OC(C)(C)C)[C@H](C(N)=O)C2)c(C)c1]

To (S)-4-(3,5-dimethylpyridin-2-yl)piperazine-2-carboxylic acid methyl ester (700 mg) described in Preparation Example 130 were added ethanol (4 mL) and 1N aqueous sodium hydroxide solution (4 mL). The mixture was stirred at room temperature for 4 hr, and 1N hydrochloric acid (4 mL) was added at 0° C. The solvent was evaporated, ammonium chloride (5 equivalents), chloroform (10 mL), 1-ethyl-3-(3'-dimethylaminopropyl)carbodiimide.hydrochloride (1.5 equivalents), 1-hydroxybenzotriazole (1.5 equivalents), and triethylamine (7 equivalents) were added to the obtained residue, and the mixture was stirred at room temperature. Water was added to the reaction mixture and the mixture was extracted with ethyl acetate. The solvent was evaporated and the obtained residue was purified by column chromatography (ethyl acetate:hexane) to give the title compound (420 mg).

MS(ESI) m/z: 335 (M+H)⁺

Preparation Example 134: Preparation of 4-[1-(p-tolyl)-1H-pyrazol-4-yl]piperidine

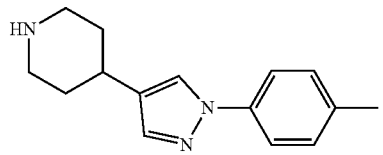 [SMILES: Cc1ccc(-n2cc(C3CCNCC3)cn2)cc1]

To N-Boc-1,2,5,6-tetrahydropyridine-4-boronic acid pinacol ester (927.6 mg) were added 1,2-dimethoxyethane (10 mL), water (5 mL), sodium carbonate (953.9 mg), 4-bromo-1-(p-tolyl)pyrazole (711.3 mg) and [1,1'-bis(diphenylphosphino)ferrocene]palladium(II) dichloride. dichloromethane complex (122.5 mg) and the mixture was stirred at 90° C. for 6 hr. To the reaction mixture were added water and ethyl acetate, and the mixture was filtered through celite and extracted with ethyl acetate. The solvent was evaporated and the obtained residue was purified by column chromatography (chloroform:methanol) to give 4-[1-(p-tolyl)-1H-pyrazol-4-yl]-3,6-dihydro-2H-pyridine-1-carboxylic acid tert-butyl ester (651.6 mg).

The obtained 4-[1-(p-tolyl)-1H-pyrazol-4-yl]-3,6-dihydro-2H-pyridine-1-carboxylic acid tert-butyl ester (300 mg) was dissolved in ethanol, and the mixture was reduced in H-cube (manufactured by ThalesNano) (catalyst: Pd—C, temperature: 60° C., flow rate: 1 mL/min). The solvent was evaporated to give 4-[1-(p-tolyl)-1H-pyrazol-4-yl]piperidine-1-carboxylic acid tert-butyl ester (297.8 mg).

To the obtained 4-[1-(p-tolyl)-1H-pyrazol-4-yl]piperidine-1-carboxylic acid tert-butyl ester (297.8 mg) were added methanol (2 mL) and 4N hydrogen chloride/1,4-dioxane solution (1.5 mL) and the mixture was stirred at room temperature overnight. After completion of the reaction, saturated aqueous sodium hydrogen carbonate solution was added and the mixture was extracted with ethyl acetate. The solvent was evaporated to give the title compound (193.1 mg).

MS(ESI) m/z: 242 (M+H)⁺

Preparation Example 135: Preparation of (1-benzoylpiperidin-4-yl)(2-hydroxy-4-methylphenyl)methanone

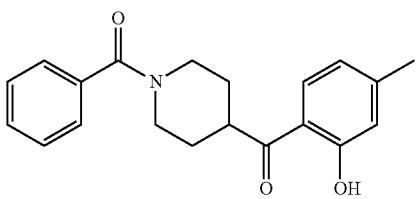 [SMILES: Cc1ccc(C(=O)C2CCN(C(=O)c3ccccc3)CC2)c(O)c1]

To a solution of 3-methylphenol (13 g), 1-benzoylpiperidine-4-carbonyl chloride (31 g) in 1,2-dichloroethane (250 mL) was added aluminum chloride (50 g) with stirring, and the mixture was heated under reflux for 1.5 hr. The reaction mixture was poured into ice water and the mixture was extracted with chloroform. The solvent was evaporated and the obtained residue was purified by column chromatography to give the title compound (18 g).

Preparation Example 136: Preparation of 4-(6-methylbenzofuran-3-yl)piperidine.hydrochloride

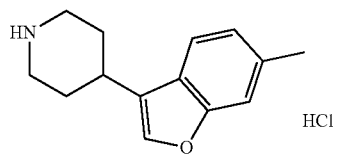 [SMILES: Cc1ccc2c(C3CCNCC3)coc2c1 ; Cl]

To (1-benzoylpiperidin-4-yl)(2-hydroxy-4-methylphenyl) methanone (18 g) described in Preparation Example 135 were added N,N-dimethylformamide (100 mL), sodium hydride (60% in liquid paraffin dispersion) (4.5 g) and ethyl bromoacetate (13 mL) and the mixture was stirred at 100° C. for 30 min and extracted with ethyl acetate. The solvent was evaporated and the obtained residue was purified by column chromatography to give 3-(1-benzoylpiperidin-4-yl)-6-methylbenzofuran-2-carboxylic acid ethyl ester (5 g).

To the obtained 3-(1-benzoylpiperidin-4-yl)-6-methylbenzofuran-2-carboxylic acid ethyl ester (5 g) were added ethanol (20 mL), sodium hydroxide (5 g) and water (30 mL) and the mixture was stirred with heating. The mixture was neutralized with hydrochloric acid and extracted with ethyl acetate. The solvent was evaporated, quinoline (50 mL) and copper (0.5 g) were added to the obtained residue (30 g) and the mixture was stirred at 180° C. for 3 hr. Hydrochloric acid was added and the mixture was extracted with ethyl acetate. The solvent was evaporated and the obtained residue was purified by column chromatography to give [4-(6-methylbenzofuran-3-yl)piperidin-1-yl)phenylmethanone (2 g).

To the obtained [4-(6-methylbenzofuran-3-yl)piperidin-1-yl)phenylmethanone (2 g) were added concentrated hydrochloric acid (25 mL) and acetic acid (25 mL) and the mixture was stirred with heating under reflux for 12 hr. The solvent was evaporated to give the title compound (1.1 g).

Preparation Example 137: Preparation of (1-benzoylpiperidin-4-yl)(2-hydroxy-3,5-dimethylphenyl) methanone

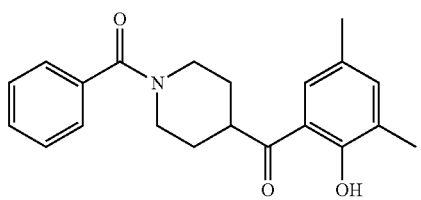 [SMILES: Cc1cc(C)c(O)c(C(=O)C2CCN(C(=O)c3ccccc3)CC2)c1]

2,4-Dimethylphenol (14 g) was dissolved in tetrahydrofuran (100 mL), triethylamine (30 mL) and 1-benzoylpiperidine-4-carbonyl chloride (30 g) were added, and the mixture was stirred at room temperature. After completion of the reaction, the mixture was extracted with ethyl acetate. The solvent was evaporated, aluminum chloride (40 g) was added to the obtained residue (24 g) and the mixture was stirred at 120° C. for 15 min. Under cooling, ice was added to the reaction mixture and the mixture was extracted with ethyl acetate. The solvent was evaporated and the obtained residue was purified by column chromatography to give the title compound (18 g).

Preparation Example 138: Preparation of 4-(5,7-dimethylbenzofuran-3-yl)piperidine.hydrochloride

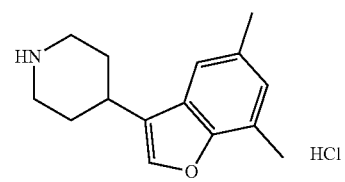 [SMILES: Cc1cc(C)c2occ(C3CCNCC3)c2c1 ; Cl]

Using (1-benzoylpiperidin-4-yl) (2-hydroxy-3,5-dimethylphenyl)methanone (18 g) described in Preparation Example 137 and ethyl bromoacetate (6 mL), reactions and treatments similar to those in Preparation Example 136 were performed to give the title compound (4.5 g).

Preparation Example 139: Preparation of (1-benzoylpiperidin-4-yl) (2-hydroxy-4,5-dimethylphenyl) methanone

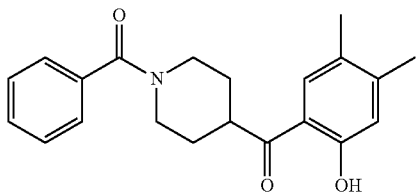 [SMILES: Cc1cc(O)c(C(=O)C2CCN(C(=O)c3ccccc3)CC2)cc1C]

Using 3,4-dimethylanisole (24 g) and 1-benzoylpiperidine-4-carbonyl chloride (46 g), reactions and treatments similar to those in Preparation Example 135 were performed to give the title compound (40 g).

Preparation Example 140: Preparation of 4-(5,6-dimethylbenzofuran-3-yl)piperidine.hydrochloride

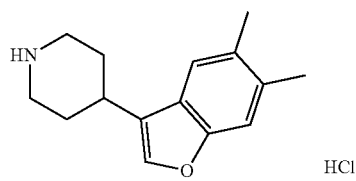 [SMILES: Cc1cc2occ(C3CCNCC3)c2cc1C ; Cl]

Using (1-benzoylpiperidin-4-yl) (2-hydroxy-4,5-dimethylphenyl)methanone (15 g) described in Preparation Example 139 and ethyl bromoacetate (5 mL), reactions and treatments similar to those in Preparation Example 136 were performed to give the title compound (2.7 g).

Preparation Example 141: Preparation of (1-benzoylpiperidin-4-yl) (2-hydroxy-4,6-dimethylphenyl)methanone

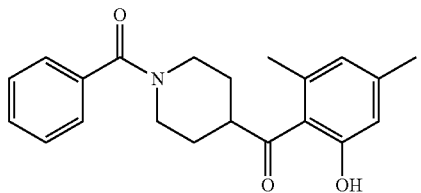 [SMILES: Cc1cc(C)c(C(=O)C2CCN(C(=O)c3ccccc3)CC2)c(O)c1]

Using 1-benzoylpiperidine-4-carbonyl chloride (50 g) and 3,5-dimethylphenol (25 g), reactions and treatments similar to those in Preparation Example 137 were performed to give the title compound (35 g).

Preparation Example 142: Preparation of 4-(4,6-dimethylbenzofuran-3-yl)piperidine.hydrochloride

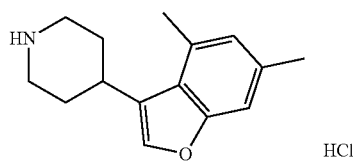 [SMILES: Cc1cc(C)c2c(C3CCNCC3)coc2c1 ; Cl]

Using (1-benzoylpiperidin-4-yl) (2-hydroxy-4,6-dimethylphenyl)methanone (35 g) described in Preparation Example 141 and ethyl bromoacetate (13 mL), reactions and treatments similar to those in Preparation Example 136 were performed to give the title compound (8 g).

Preparation Example 143: Preparation of 1-methyl-4-piperazin-1-yl-1H-indazole.2 hydrochloride

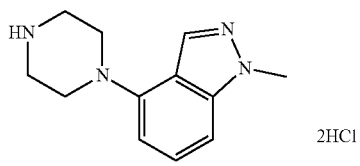 [SMILES: Cn1ncc2c(N3CCNCC3)cccc21]

To a mixture of piperazine-1-carboxylic acid tert-butyl ester (2.65 g), 4-((E)-1-bromopropenyl)-1-methyl-5-vinyl-1H-pyrazole (2 g), tris(dibenzylideneacetone)dipalladium (0) (86.8 mg), rac-2,2'-bis(diphenylphosphino)-1,1'-binaphthyl (88.5 mg) and tert-butoxy sodium (1.3 g) was added toluene (35 mL) and the mixture was stirred with heating under reflux. After completion of the reaction, saturated aqueous sodium hydrogen carbonate solution, and ethyl acetate were added. After filtration through celite, the filtrate was extracted with ethyl acetate. The solvent was evaporated and the obtained residue was purified by column chromatography (hexane:ethyl acetate) to give 4-(1-methyl-1H-indazol-4-yl)piperazine-1-carboxylic acid tert-butyl ester (2.46 g). To 4-(l-methyl-1H-indazol-4-yl)piperazine-1-carboxylic acid tert-butyl ester (2.46 g) were added ethyl acetate (16 mL), methanol (3.2 mL) and 4N hydrogen chloride/ethyl acetate solution (16.5 mL) and the mixture was stirred at room temperature. After completion of the reaction, the solvent was evaporated and ethyl acetate was added to the obtained residue. The precipitated solid was collected by filtration to give the title compound (2.24 g).
MS(ESI) m/z: 217 (M+H)$^+$

Preparation Example 144: Preparation of 5-methyl-2-(piperidin-4-yl)oxazolo[5,4-b]pyridine

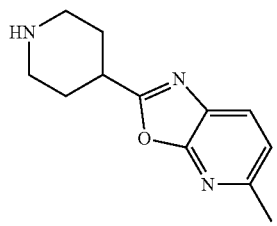 [SMILES: Cc1ccc2nc(C3CCNCC3)oc2n1]

To 1-[(benzyloxy)carbonyl]piperidine-4-carboxylic acid (2 g) were added methylene chloride (25 mL), pyridine (1.54 mL) and thionyl chloride (0.72 mL) and the mixture was stirred at room temperature for 1 hr. To the reaction mixture was added a solution of 3-amino-2-chloro-6-picoline (1.192 g), 4-(dimethylamino)pyridine (46 mg) and triethylamine (2.11 mL) in methylene chloride (15 mL) and the mixture was stirred at room temperature for 2.5 hr. The reaction mixture was concentrated under reduced pressure and the obtained residue was purified by column chromatography (chloroform:methanol) to give 4-(2-chloro-6-methylpyridin-3-ylcarbamoyl)piperidine-1-carboxylic acid benzyl ester (2.996 g).

To the obtained 4-(2-chloro-6-methylpyridin-3-ylcarbamoyl)piperidine-1-carboxylic acid benzyl ester (1.5 g) were added potassium carbonate (1.6 g) and N,N-dimethylformamide (30 mL) and the mixture was stirred under microwave irradiation at 200° C. for 20 min. The reaction mixture was filtered, the filtrate was concentrated under reduced pressure and the obtained residue was purified by column chromatography (hexane:ethyl acetate) to give 4-(5-methyloxazolo[5,4-b]pyridin-2-yl)piperidine-1-carboxylic acid benzyl ester (1.068 g).

To the obtained 4-(5-methyloxazolo[5,4-b]pyridin-2-yl)piperidine-1-carboxylic acid benzyl ester (1.06 g) were added ethanol (21 mL) and 10% palladium/carbon (wetted with 53.5% water) (530 mg) and the mixture was stirred under a hydrogen atmosphere at room temperature overnight. The reaction mixture was filtered, and the filtrate was concentrated under reduced pressure to give the title compound (582 mg).
MS(ESI) m/z: 218 (M+H)$^+$

Preparation Example 145: Preparation of 6-methyl-2-(piperidin-4-yl)thiazolo[4,5-b]pyridine

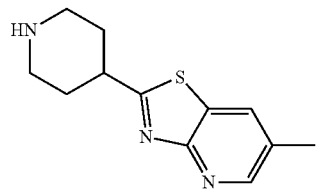 [SMILES: Cc1cnc2nc(C3CCNCC3)sc2c1]

To 1-[(benzyloxy)carbonyl]piperidine-4-carboxylic acid (3 g) were added methylene chloride (40 mL), pyridine (2.3 mL) and thionyl chloride (1.08 mL) and the mixture was stirred at room temperature for 1.5 hr. To the reaction mixture was added a solution of 2-amino-3-bromo-5-methylpyridine (2.13 g), 4-(dimethylamino)pyridine (69 mg) and triethylamine (3.2 mL) in methylene chloride (20 mL) and the mixture was stirred at room temperature for 5.5 hr. Water was added to the reaction mixture and the mixture was extracted with chloroform. The solvent was evaporated, diethyl ether was added to the obtained residue, and the precipitate was collected by filtration to give 4-(3-bromo-5-methylpyridin-2-ylcarbamoyl)piperidine-1-carboxylic acid benzyl ester (2.285 g).

To the obtained 4-(3-bromo-5-methylpyridin-2-ylcarbamoyl)piperidine-1-carboxylic acid benzyl ester (2.28 g) were added Lawesson reagent (3.21 g) and toluene (45 mL) and the mixture was stirred at 70° C. for 1 hr. The reaction mixture was purified by column chromatography (hexane:ethyl acetate) to give 4-(3-bromo-5-methylpyridin-2-ylthiocarbamoyl)piperidine-1-carboxylic acid benzyl ester. (1.774 g).

To the obtained 4-(3-bromo-5-methylpyridin-2-ylthiocarbamoyl)piperidine-1-carboxylic acid benzyl ester (1.7 g) were added cesium carbonate (2.48 g) and N,N-dimethylformamide (34 mL) and the mixture was stirred under microwave irradiation at 160° C. for 20 min. The reaction mixture was concentrated under reduced pressure and the obtained residue was purified by column chromatography (hexane:ethyl acetate) to give 4-(6-methylthiazolo[4,5-b]pyridin-2-yl)piperidine-1-carboxylic acid benzyl ester (1.291 g).

To the obtained 4-(6-methylthiazolo[4,5-b]pyridin-2-yl)piperidine-1-carboxylic acid benzyl ester (600 mg) were added trifluoroacetic acid (18 mL) and thioanisole (1.8 mL) and the mixture was stirred at room temperature for 3 hr. The reaction mixture was concentrated under reduced pressure, and the obtained residue was partitioned between water and diethyl ether. The aqueous layer was neutralized with saturated aqueous sodium hydrogen carbonate solution and the mixture was extracted with chloroform. The organic layer was dried over anhydrous sodium sulfate, and the solvent was evaporated to give the title compound as a crude product (821 mg).

Preparation Example 146: Preparation of 5-methyl-2-(piperidin-4-yl)thiazolo[5,4-b]pyridine.trifluoroacetate

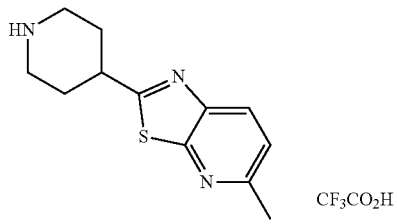

To 4-(2-chloro-6-methylpyridin-3-ylcarbamoyl)piperidine-1-carboxylic acid benzyl ester (1.42 g) were added Lawesson reagent (2.22 g) and toluene (30 mL) and the mixture was stirred at 70° C. for 3 hr. The reaction mixture was purified by column chromatography (hexane:ethyl acetate) to give 4-(5-methylthiazolo[5,4-b]pyridin-2-yl)piperidine-1-carboxylic acid benzyl ester (603 mg).

To the obtained 4-(5-methylthiazolo[5,4-b]pyridin-2-yl)piperidine-1-carboxylic acid benzyl ester (600 mg) were added trifluoroacetic acid (18 mL) and thioanisole (1.8 mL) and the mixture was stirred at room temperature for 3 hr. The reaction mixture was concentrated under reduced pressure to give the title compound as a crude product (2236 mg).

Preparation Example 147: Preparation of 1-(3,5-dicyclopropylpyridin-2-yl)piperazine.2 hydrochloride

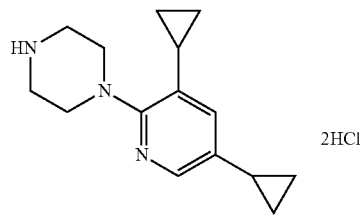 [SMILES: c1nc(N2CCNCC2)c(C2CC2)cc1C1CC1]

To a solution of 2,3,5-trichloropyridine (12.1 g), 1-Boc-piperazine (14.9 g) in toluene (80 mL) were added N,N-dimethylformamide (40 mL) and potassium carbonate (22 g) and the mixture was stirred at 120° C. for 7 hr. The reaction mixture was cooled, water was added and the mixture was extracted with ethyl acetate. The organic layer was washed with saturated brine, and the solvent was evaporated. The obtained residue was purified by column chromatography (hexane:ethyl acetate) to give 4-(3,5-dichloropyridin-2-yl)piperazine-1-carboxylic acid tert-butyl ester (13.08 g).

To the obtained 4-(3,5-dichloropyridin-2-yl)piperazine-1-carboxylic acid tert-butyl ester (5.3 g) were added toluene (160 mL), water (16 mL), bis(tricyclohexylphosphine)palladium(II) dichloride (0.59 g), tripotassium phosphate (16.9 g) and cyclopropylboronic acid (4.13 g) and the mixture was stirred at 100° C. After completion of the reaction, water was added and the mixture was extracted with ethyl acetate. The organic layer was washed with saturated brine, and the solvent was evaporated. The obtained residue was purified by column chromatography (hexane:ethyl acetate) to give 4-(3,5-dicyclopropylpyridin-2-yl)piperazine-1-carboxylic acid tert-butyl ester (3.12 g).

The obtained 4-(3,5-dicyclopropylpyridin-2-yl)piperazine-1-carboxylic acid tert-butyl ester (3.11 g) was dissolved in ethyl acetate (10 mL), 4N hydrogen chloride/ethyl acetate solution (10 mL) was added, and the mixture was stirred at room temperature overnight. The reaction mixture was concentrated under reduced pressure, saturated aqueous sodium hydrogen carbonate solution was added to the obtained residue and the mixture was extracted with ethyl acetate. The organic layer was washed with saturated brine, and the solvent was evaporated. The obtained residue was purified by column chromatography (hexane:ethyl acetate). The solvent was evaporated and the obtained residue was dissolved in ethyl acetate (20 mL) and 4N hydrogen chloride/ethyl acetate solution (4.5 mL) was added. The precipitate was collected by filtration to give the title compound (1.91 g).

Preparation Example 148: Preparation of 4-((R)-4-methyl-2,5-dioxoimidazolidin-4-yl)benzoic acid

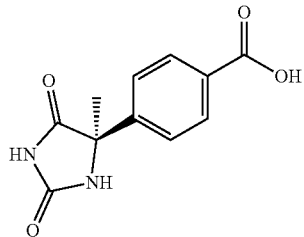

4-(4-Methyl-2,5-dioxoimidazolidin-4-yl)benzoic acid (24.4 g) was dissolved in tetrahydrofuran (488 mL), cinchonine (16.87 g) was added, and the mixture was stirred at room temperature for 8 hr. The precipitated solid was collected by filtration and dried under reduced pressure. To the obtained crude product (26.42 g) was added 1N hydrochloric acid (150 mL) and the mixture was stirred at room temperature for 6 hr. The precipitate was collected by filtration to give 4-((R)-4-methyl-2,5-dioxoimidazolidin-4-yl)benzoic acid (9.39 g, 99.6% ee).

Example 1: Synthesis of (R)-5-{4-[4-(3,5-dimethylpyridin-2-yl)piperazine-1-carbonyl]phenyl}-5-methylimidazolidine-2,4-dione

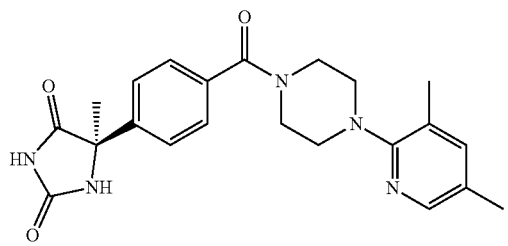 [SMILES: Cc1cnc(N2CCN(C(=O)c3ccc([C@@]4(C)NC(=O)NC4=O)cc3)CC2)c(C)c1]

4-((R)-4-methyl-2,5-dioxoimidazolidin-4-yl)benzoic acid (230 mg) described in Preparation Example 6, 1-(3,5-dimethylpyridin-2-yl)piperazine (188 mg) and 1-hydroxybenzotriazole (139 mg) were dissolved in N,N-dimethylformamide (3.3 mL), 1-ethyl-3-(3'-dimethylaminopropyl) carbodiimide.hydrochloride (200 mg) was added, and the mixture was stirred at room temperature overnight. To the reaction mixture was added saturated brine and the mixture was extracted with ethyl acetate. The solvent was evaporated and the obtained residue was purified by column chromatography (ethyl acetate:methanol). The solvent was evaporated and the obtained residue was recrystallized from a mixed solvent of ethanol and water to give the title compound (224.2 mg).

MS (APCI) m/z: 408 (M+H)$^+$

Example 2: Synthesis of (R)-5-{4-[4-(3,5-dicyclopropylpyridin-2-yl)piperazine-1-carbonyl]phenyl}-5-methylimidazolidine-2,4-dione

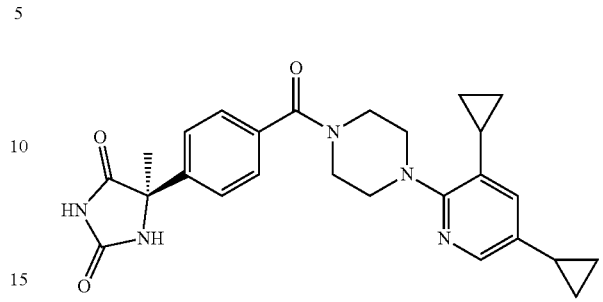

4-((R)-4-methyl-2,5-dioxoimidazolidin-4-yl)benzoic acid (80 mg) described in Preparation Example 6, 1-(3,5-dicyclopropylpyridin-2-yl)piperazine (83 mg) and 1-hydroxybenzotriazole (48.5 mg) were dissolved in N,N-dimethylformamide (1.2 mL), 1-ethyl-3-(3'-dimethylaminopropyl) carbodiimide.hydrochloride (68.8 mg) was added, and the mixture was stirred at room temperature overnight. Water was added to the reaction mixture and the mixture was extracted with ethyl acetate. The solvent was evaporated and the obtained residue was purified by column chromatography (ethyl acetate:methanol) to give the title compound (80.3 mg).

MS(APCI) m/z: 460 (M+H)$^+$

Example 3: Synthesis of (R)-5-{4-[4-(3,5-dimethylpyridin-2-yl)piperazine-1-carbonyl]-3-fluorophenyl}-5-methylimidazolidine-2,4-dione

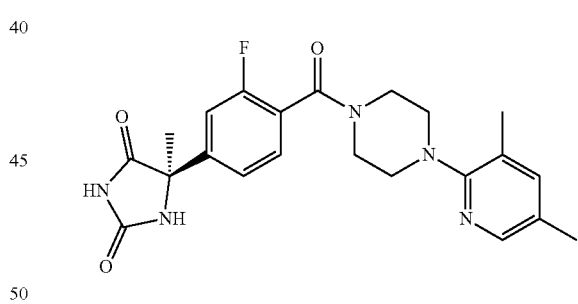

2-Fluoro-4-((R)-4-methyl-2,5-dioxoimidazolidin-4-yl)benzoic acid (790 mg) described in Preparation Example 29, 1-(3,5-dimethylpyridin-2-yl)piperazine (784.7 mg), 1-hydroxybenzotriazole (507.9 mg) and 1-ethyl-3-(3'-dimethylaminopropyl) carbodiimide.hydrochloride (780.7 mg) were dissolved in a mixed solvent of chloroform (23.7 mL) and N,N-dimethylformamide (7.9 mL), triethylamine (960.5 µL) was added, and the mixture was stirred at room temperature. To the reaction mixture was added saturated brine and the mixture was extracted with ethyl acetate. The solvent was evaporated and the obtained residue was purified by column chromatography (chloroform:methanol) to give the title compound (1210 mg).

MS (APCI) m/z: 426 (M+H)$^+$

Example 4: Synthesis of (R)-5-{4-[4-(5-ethyl-3-methylpyridin-2-yl)piperazine-1-carbonyl]phenyl}-5-methylimidazolidine-2,4-dione

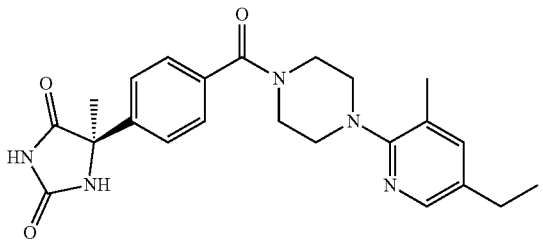 [SMILES: CCc1cnc(N2CCN(C(=O)c3ccc([C@@]4(C)NC(=O)NC4=O)cc3)CC2)c(C)c1]

4-((R)-4-methyl-2,5-dioxoimidazolidin-4-yl)benzoic acid (100 mg) described in Preparation Example 6, 1-(5-ethyl-3-methylpyridin-2-yl)piperazine (87.7 mg) and 1-hydroxybenzotriazole (60.6 mg) were dissolved in N,N-dimethylformamide (1.5 mL), 1-ethyl-3-(3'-dimethylaminopropyl)carbodiimide.hydrochloride (85.9 mg) was added, and the mixture was stirred at room temperature overnight. To the reaction mixture was added saturated brine and the mixture was extracted with ethyl acetate. The solvent was evaporated and the obtained residue was purified by column chromatography (ethyl acetate:methanol) to give the title compound (138 mg).

MS(APCI) m/z: 422 (M+H)$^+$

Example 5: Synthesis of (R)-5-{4-[4-(5-cyclopropyl-3-methylpyridin-2-yl)piperazine-1-carbonyl]phenyl}-5-methylimidazolidine-2,4-dione

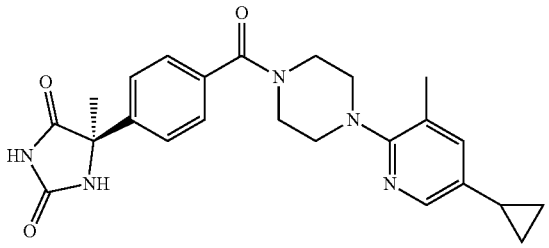 [SMILES: Cc1cc(C2CC2)cnc1N1CCN(C(=O)c2ccc([C@@]3(C)NC(=O)NC3=O)cc2)CC1]

4-((R)-4-methyl-2,5-dioxoimidazolidin-4-yl)benzoic acid (100 mg) described in Preparation Example 6, 1-(5-cyclopropyl-3-methylpyridin-2-yl)piperazine (92.8 mg) and 1-hydroxybenzotriazole (60.6 mg) were dissolved in N,N-dimethylformamide (1.5 mL), 1-ethyl-3-(3'-dimethylaminopropyl)carbodiimide.hydrochloride (85.9 mg) was added, and the mixture was stirred at room temperature overnight. To the reaction mixture was added saturated brine and the mixture was extracted with ethyl acetate. The solvent was evaporated and the obtained residue was purified by column chromatography (ethyl acetate:methanol) to give the title compound (152.3 mg).

MS(APCI) m/z: 434 (M+H)$^+$

Example 6: Synthesis of (R)-5-methyl-5-{4-[4-(3,5,6-trimethylpyridin-2-yl)piperazine-1-carbonyl]phenyl}imidazolidine-2,4-dione

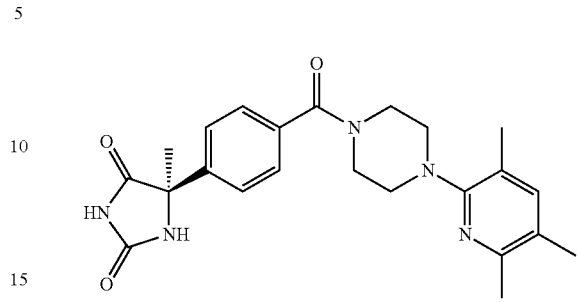

4-((R)-4-methyl-2,5-dioxoimidazolidin-4-yl)benzoic acid (100 mg) described in Preparation Example 6, 1-(3,5,6-trimethylpyridin-2-yl)piperazine (87.7 mg) and 1-hydroxybenzotriazole (60.6 mg) were dissolved in N,N-dimethylformamide (2.5 mL), 1-ethyl-3-(3'-dimethylaminopropyl)carbodiimide.hydrochloride (85.9 mg) was added, and the mixture was stirred at room temperature overnight. To the reaction mixture was added saturated brine and the mixture was extracted with ethyl acetate. The solvent was evaporated and the obtained residue was purified by column chromatography (ethyl acetate:hexane) to give the title compound (99.5 mg).

MS(APCI) m/z: 422 (M+H)$^+$

Example 7: Synthesis of (R)-5-{4-[4-(2,4-dimethylphenyl)piperazine-1-carbonyl]phenyl}-5-methylimidazolidine-2,4-dione

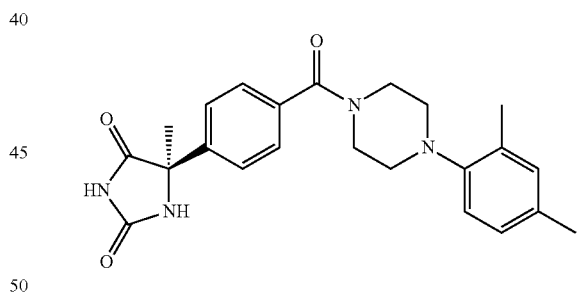

4-((R)-4-methyl-2,5-dioxoimidazolidin-4-yl)benzoic acid (100 mg) described in Preparation Example 6, 1-(2,4-dimethylphenyl)piperazine (81.2 mg) and 1-hydroxybenzotriazole (60.6 mg) were dissolved in N,N-dimethylformamide (1.5 mL), 1-ethyl-3-(3'-dimethylaminopropyl)carbodiimide.hydrochloride (85.9 mg) was added, and the mixture was stirred at room temperature overnight. To the reaction mixture was added saturated brine and the mixture was extracted with ethyl acetate. The solvent was evaporated and the obtained residue was purified by column chromatography (ethyl acetate:hexane) to give the title compound (130.5 mg).

MS(APCI) m/z: 407 (M+H)$^+$

Example 8: Synthesis of (R)-5-{4-[4-(3,5-dimethyl-pyridin-2-yl)piperazine-1-carbonyl]phenyl}-5-iso-propylimidazolidine-2,4-dione

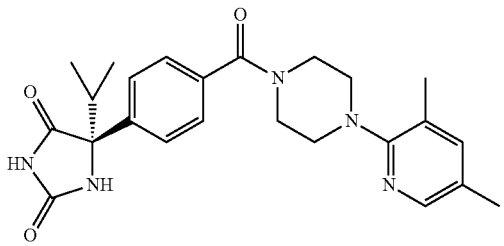

4-((R)-4-isopropyl-2,5-dioxoimidazolidin-4-yl)benzoic acid (2.88 g) described in Preparation Example 45 was dissolved in N,N-dimethylformamide (43.9 mL), 1-(3,5-dimethylpyridin-2-yl)piperazine.hydrochloride (2.75 g), 1-hydroxybenzotriazole (1.63 g), 1-ethyl-3-(3'-dimethylam-inopropyl)carbodiimide. hydrochloride (2.32 g) and N,N-diisopropylethylamine (4.21 mL) were added, and the mixture was stirred at room temperature overnight. Water was added to the reaction mixture, and the precipitate was collected by filtration. The obtained precipitate was recrystallized from a mixed solvent of ethanol and water to give the title compound (3.84 g).

MS(ESI) m/z: 436 (M+H)$^+$

Example 9: Synthesis of (R)-5-{4-[4-(3,5-dicyclo-propylpyridin-2-yl)piperazine-1-carbonyl]phenyl}-5-ethylimidazolidine-2,4-dione and (S)-5-{4-[4-(3,5-dicyclopropylpyridin-2-yl)piperazine-1-carbonyl]phenyl}-5-ethylimidazolidine-2,4-dione

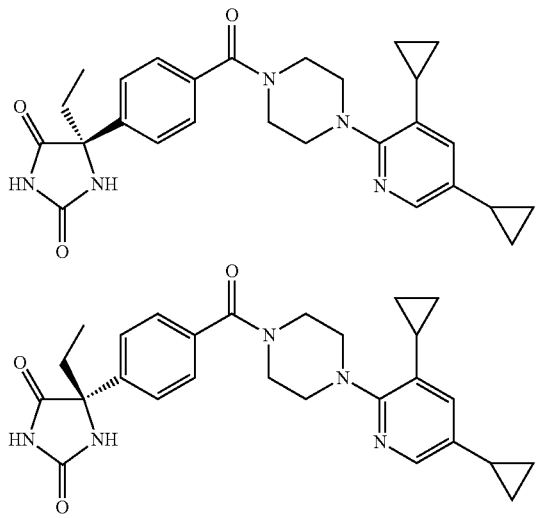

4-(4-Ethyl-2,5-dioxoimidazolidin-4-yl)benzoic acid (70 mg) described in Preparation Example 1, 1-(3,5-dicyclopropylpyridin-2-yl)piperazine (75 mg), 1-hydroxybenzotriazole (37.8 mg), 1-ethyl-3-(3'-dimethylaminopropyl)carbodiimide.hydrochloride (80 mg) and diisopropylethylamine (1 mL) were dissolved in N,N-dimethylformamide (5 mL) and the mixture was stirred at room temperature overnight. To the reaction mixture was added saturated aqueous sodium hydrogen carbonate solution and the mixture was extracted with ethyl acetate. The organic layer was washed with water and saturated brine, dried over anhydrous magnesium sulfate and concentrated under reduced pressure. The obtained residue was purified by NH column chromatography (chloroform:methanol) to give 5-{4-[4-(3,5-dicyclopropylpyridin-2-yl)piperazine-1-carbonyl]phenyl}-5-ethylimidazolidine-2,4-dione (78.6 mg).

The obtained 5-{4-[4-(3,5-dicyclopropylpyridin-2-yl)piperazine-1-carbonyl]phenyl}-5-ethylimidazolidine-2,4-dione (70 mg) was separated by HPLC using CHIRALPAK (Daicel) IC (tetrahydrofuran/ethanol/diethylamine) to give the both enantiomers indicated above (compound with short retention time 28.9 mg (MS(APCI) m/z: 474 (M+H)$^+$) and compound with long retention time 28.7 mg (MS(APCI) m/z: 474 (M+H)$^+$)).

In the analysis using CHIRALPAK (Daicel) IC-3 (4.6 mm×150 mm, tetrahydrofuran/ethanol/diethylamine=10/90/0.1, flow 0.5 mL/min), the retention time was respectively 5.5 min and 11.1 min.

Example 10: Synthesis of (R)-5-ethyl-5-{4-[4-(5-ethyl-3-methylpyridin-2-yl)piperazine-1-carbonyl]phenyl}imidazolidine-2,4-dione and (S)-5-ethyl-5-{4-[4-(5-ethyl-3-methylpyridin-2-yl)piperazine-1-carbonyl]phenyl}imidazolidine-2,4-dione

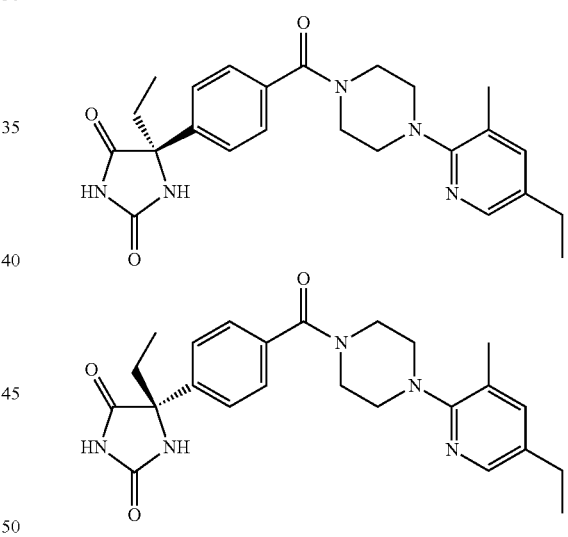

4-(4-Ethyl-2,5-dioxoimidazolidin-4-yl)benzoic acid (75 mg) described in Preparation Example 1, 1-(5-ethyl-3-methylpyridin-2-yl)piperazine (75 mg), 1-hydroxybenzotriazole (40 mg), 1-ethyl-3-(3'-dimethylaminopropyl)carbodiimide. hydrochloride (86 mg) and diisopropylethylamine (1 mL) were dissolved in N,N-dimethylformamide (4 mL) and the mixture was stirred at room temperature overnight. To the reaction mixture was added saturated aqueous sodium hydrogen carbonate solution and the mixture was extracted with ethyl acetate. The organic layer was washed with water and saturated brine, dried over anhydrous magnesium sulfate and concentrated under reduced pressure. The obtained residue was purified by NH column chromatography (chloroform:methanol) to give 5-ethyl-5-{4-[4-(5-ethyl-3-methylpyridin-2-yl)piperazine-1-carbonyl]phenyl}imidazolidine-2,4-dione (125 mg).

The obtained 5-ethyl-5-{4-[4-(5-ethyl-3-methylpyridin-2-yl)piperazine-1-carbonyl]phenyl}imidazolidine-2,4-dione (98 mg) was separated by HPLC using CHIRALPAK (Daicel) IC (tetrahydrofuran/ethanol/diethylamine) to give the both enantiomers indicated above (compound with short retention time 35.7 mg (MS(APCI) m/z: 436 (M+H)$^+$) and compound with long retention time 35.2 mg (MS(APCI) m/z: 436 (M+H)$^+$)).

In the analysis using CHIRALPAK (Daicel) IC-3 (4.6 mm×150 mm, tetrahydrofuran/ethanol/diethylamine=10/90/0.1, flow 0.5 mL/min), the retention time was respectively 5.4 min and 9.7 min.

Example 11: Synthesis of (R)-5-{4-[4-(5-cyclopropyl-3-methylpyridin-2-yl)piperazine-1-carbonyl]phenyl}-5-ethylimidazolidine-2,4-dione and (S)-5-{4-[4-(5-cyclopropyl-3-methylpyridin-2-yl)piperazine-1-carbonyl]phenyl}-5-ethylimidazolidine-2,4-dione

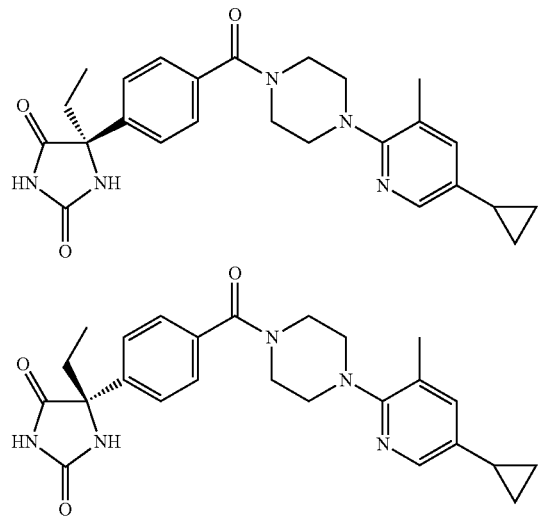

4-(4-Ethyl-2,5-dioxoimidazolidin-4-yl)benzoic acid (75 mg) described in Preparation Example 1, 1-(5-cyclopropyl-3-methylpyridin-2-yl)piperazine (80 mg), 1-hydroxybenzotriazole (40 mg), 1-ethyl-3-(3'-dimethylaminopropyl)carbodiimide.hydrochloride (86 mg) and diisopropylethylamine (1 mL) were dissolved in N,N-dimethylformamide (4 mL) and the mixture was stirred at room temperature overnight. To the reaction mixture was added saturated aqueous sodium hydrogen carbonate solution and the mixture was extracted with ethyl acetate. The organic layer was washed with water and saturated brine, dried over anhydrous magnesium sulfate and concentrated under reduced pressure. The obtained residue was purified by NH column chromatography (chloroform:methanol) to give 5-{4-[4-(5-cyclopropyl-3-methylpyridin-2-yl)piperazine-1-carbonyl]phenyl}-5-ethylimidazolidine-2,4-dione (103.6 mg).

The obtained 5-{4-[4-(5-cyclopropyl-3-methylpyridin-2-yl)piperazine-1-carbonyl]phenyl}-5-ethylimidazolidine-2,4-dione (98 mg) was separated by HPLC using CHIRALPAK (Daicel) IC (tetrahydrofuran/ethanol/diethylamine) to give the both enantiomers indicated above (compound with short retention time 34.4 mg (MS(APCI) m/z: 448 (M+H)$^+$) and compound with long retention time 19.9 mg (MS(APCI) m/z: 448 (M+H)$^+$)).

In the analysis using CHIRALPAK (Daicel) IC-3 (4.6 mm×150 mm, tetrahydrofuran/ethanol/diethylamine=10/90/0.1, flow 0.5 mL/min), the retention time was respectively 5.6 min and 10.8 min.

Example 12: Synthesis of (R)-5-{4-[4-(2,4-dimethylphenyl)piperazine-1-carbonyl]phenyl}-5-ethylimidazolidine-2,4-dione and (S)-5-{4-[4-(2,4-dimethylphenyl)piperazine-1-carbonyl]phenyl}-5-ethylimidazolidine-2,4-dione

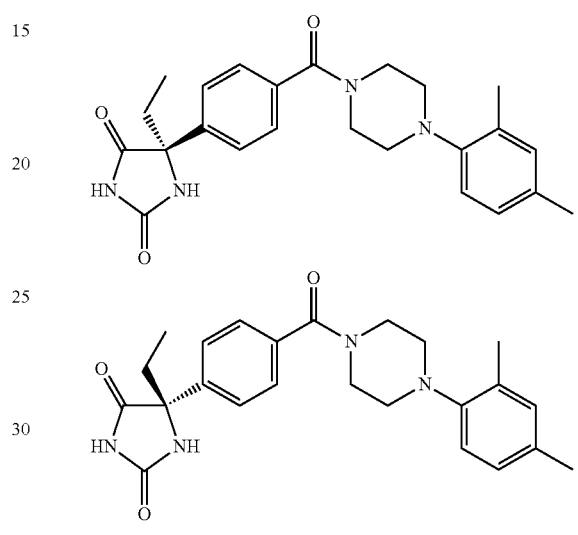

4-(4-Ethyl-2,5-dioxoimidazolidin-4-yl)benzoic acid (75 mg) described in Preparation Example 1, 1-(2,4-dimethylphenyl)piperazine (70 mg, CAS:1013-76-9), 1-hydroxybenzotriazole (40 mg), 1-ethyl-3-(3'-dimethylaminopropyl) carbodiimide.hydrochloride (86 mg) and diisopropylethylamine (1 mL) were dissolved in N,N-dimethylformamide (4 mL) and the mixture was stirred at room temperature overnight. To the reaction mixture was added saturated aqueous sodium hydrogen carbonate solution and the mixture was extracted with ethyl acetate. The organic layer was washed with water and saturated brine, dried over anhydrous magnesium sulfate and concentrated under reduced pressure. The obtained residue was purified by NH column chromatography (chloroform:methanol) to give 5-{4-[4-(2,4-dimethylphenyl)piperazine-1-carbonyl]phenyl}-5-ethylimidazolidine-2,4-dione (116.1 mg).

The obtained 5-{4-[4-(2,4-dimethylphenyl)piperazine-1-carbonyl]phenyl}-5-ethylimidazolidine-2,4-dione (106 mg) was separated by HPLC using CHIRALPAK (Daicel) IC (tetrahydrofuran/ethanol/diethylamine) to give the both enantiomers indicated above (compound with short retention time 36.8 mg (MS(APCI) m/z: 421 (M+H)$^+$) and compound with long retention time 37.8 mg (MS(APCI) m/z: 421 (M+H)$^+$)).

In the analysis using CHIRALPAK (Daicel) IC-3 (4.6 mm×150 mm, tetrahydrofuran/ethanol/diethylamine=1909/0.1, flow 0.5 mL/min), the retention time was respectively 5.3 min and 10.8 min.

Example 13: Synthesis of (R)-5-{4-[4-(3,5-dimethylpyridin-2-yl)piperazine-1-carbonyl]-2-fluorophenyl}-5-methylimidazolidine-2,4-dione and (S)-5-{4-[4-(3,5-dimethylpyridin-2-yl)piperazine-1-carbonyl]-2-fluorophenyl}-5-methylimidazolidine-2,4-dione

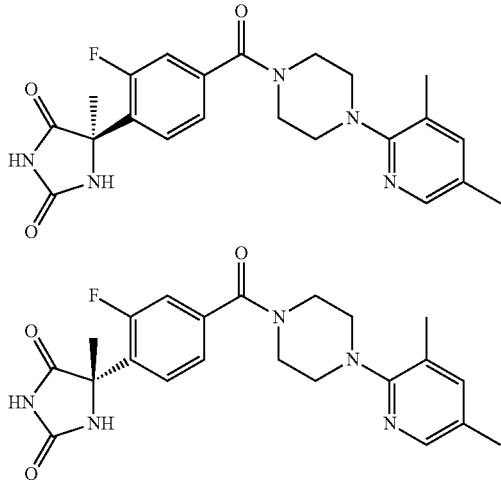

3-Fluoro-4-(4-methyl-2,5-dioxoimidazolidin-4-yl)benzoic acid (252 mg) described in Preparation Example 18 was dissolved in tetrahydrofuran (10 mL), 1-ethyl-3-(3'-dimethylaminopropyl)carbodiimide.hydrochloride (230 mg), 1-hydroxybenzotriazole (162 mg) and 1-(3,5-dimethylpyridin-2-yl)piperazine (230 mg) were added, and the mixture was stirred at room temperature overnight. Water was added to the reaction mixture and the mixture was extracted with ethyl acetate. The solvent was evaporated and the obtained residue was purified by column chromatography (ethyl acetate:hexane) to give 5-{4-[4-(3,5-dimethylpyridin-2-yl)piperazine-1-carbonyl]-2-fluorophenyl}-5-methylimidazolidine-2,4-dione (343 mg).

The obtained 5-{4-[4-(3,5-dimethylpyridin-2-yl)piperazine-1-carbonyl]-2-fluorophenyl}-5-methylimidazolidine-2,4-dione(racemate) (98 mg) was separated by HPLC using CHIRALPAK (Daicel) IA (tetrahydrofuran/ethanol/diethylamine) to give the both enantiomers indicated above (compound with short retention time 47.2 mg (MS(APCI) m/z: 426 (M+H)$^+$) and compound with long retention time 37.4 mg (MS(APCI) m/z: 426 (M+H)$^+$)).

In the analysis using CHIRALPAK (Daicel) IA-3 (4.6 mm×150 mm, tetrahydrofuran/ethanol/diethylamine=10/90/0.1, flow 0.5 mL/min), the retention time was respectively 5.8 min and 7.6 min.

Example 14: Synthesis of (R)-5-ethyl-5-{4-[4-(3,5,6-trimethylpyridin-2-yl)piperazine-1-carbonyl]phenyl}imidazolidine-2,4-dione and (S)-5-ethyl-5-{4-[4-(3,5,6-trimethylpyridin-2-yl)piperazine-1-carbonyl]phenyl}imidazolidine-2,4-dione

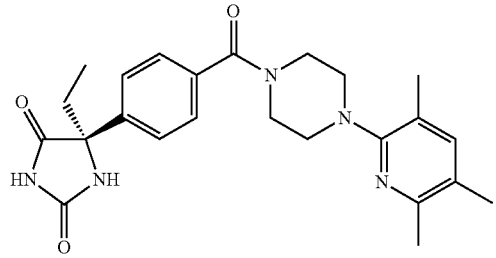

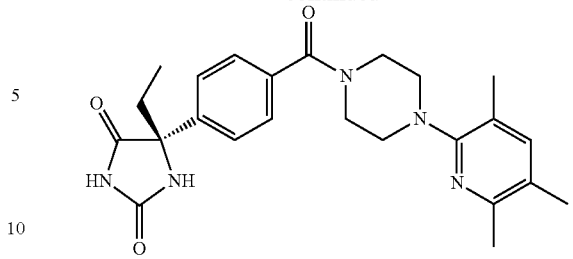

4-(4-Ethyl-2,5-dioxoimidazolidin-4-yl)benzoic acid (55 mg) described in Preparation Example 1, 1-(3,5,6-trimethylpyridin-2-yl)piperazine (58 mg) and 1-hydroxybenzotriazole (32 mg) were dissolved in N,N-dimethylformamide (2 mL), 1-ethyl-3-(3'-dimethylaminopropyl)carbodiimide.hydrochloride (45 mg) was added, and the mixture was stirred at room temperature overnight. To the reaction mixture was added saturated brine and the mixture was extracted with ethyl acetate. The solvent was evaporated and the obtained residue was purified by column chromatography (ethyl acetate:hexane) to give 5-ethyl-5-{4-[4-(3,5,6-trimethylpyridin-2-yl)piperazine-1-carbonyl]phenyl}imidazolidine-2,4-dione (85.4 mg).

The obtained 5-ethyl-5-{4-[4-(3,5,6-trimethylpyridin-2-yl)piperazine-1-carbonyl]phenyl}imidazolidine-2,4-dione (85.4 mg) was separated by moderate-pressure column using CHIRALFLASH (Daicel) IC (tetrahydrofuran/ethanol/diethylamine) to give the both enantiomers indicated above (compound with short retention time 42.5 mg (MS(APCI) m/z: 436 (M+H)$^+$) and compound with long retention time 37 mg (MS(APCI) m/z: 436 (M+H)$^+$)).

In the analysis using CHIRALPAK (Daicel) IC (4.6 mm×100 mm, tetrahydrofuran/ethanol/diethylamine=10/90/0.1, flow 0.3 mL/min), the retention time was respectively 6.8 min and 13.4 min.

Example 15: Synthesis of 5-{4-[4-(3,5-dimethylpyridin-2-yl)piperazine-1-carbonyl]-2-methoxyphenyl}-5-methylimidazolidine-2,4-dione

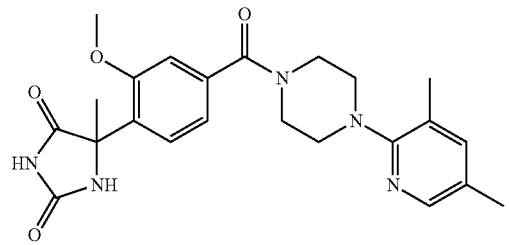 [SMILES: COc1cc(C(=O)N2CCN(c3ncc(C)cc3C)CC2)ccc1C1(C)NC(=O)NC1=O]

3-Methoxy-4-(4-methyl-2,5-dioxoimidazolidin-4-yl)benzoic acid (132 mg) described in Preparation Example 22, 1-(3,5-dimethylpyridin-2-yl)piperazine (105 mg) and 1-hydroxybenzotriazole (74 mg) were dissolved in N,N-dimethylformamide (1.7 mL), 1-ethyl-3-(3'-dimethylaminopropyl)carbodiimide.hydrochloride (105 mg) was added, and the mixture was stirred at room temperature overnight. Water was added to the reaction mixture and the mixture was extracted with ethyl acetate. The solvent was evaporated and the obtained residue was purified by column chromatography (ethyl acetate:methanol) to give the title compound (122.2 mg).

MS(APCI) m/z: 438 (M+H)$^+$

Example 16: Synthesis of 5-{4-[4-(3,5-dimethyl-pyridin-2-yl)piperazine-1-carbonyl]-2,3-difluorophenyl}-5-methylimidazolidine-2,4-dione

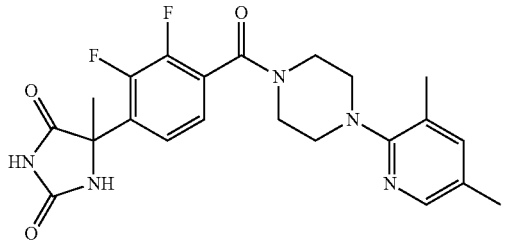 [SMILES: Cc1cnc(N2CCN(C(=O)c3ccc(C4(C)NC(=O)NC4=O)c(F)c3F)CC2)c(C)c1]

2,3-Difluoro-4-(4-methyl-2,5-dioxoimidazolidin-4-yl)benzoic acid (135 mg) described in Preparation Example 26, 1-(3,5-dimethylpyridin-2-yl)piperazine (105 mg) and 1-hydroxybenzotriazole (74 mg) were dissolved in N,N-dimethylformamide (1.7 mL), 1-ethyl-3-(3'-dimethylaminopropyl)carbodiimide.hydrochloride (105 mg) was added, and the mixture was stirred at room temperature overnight. Water was added to the reaction mixture and the mixture was extracted with ethyl acetate. The solvent was evaporated and the obtained residue was purified by column chromatography (ethyl acetate:methanol) to give the title compound (149 mg).

MS(APCI) m/z: 444 (M+H)$^+$

Example 17: Synthesis of 5-{4-[4-(3,5-dimethyl-pyridin-2-yl)piperazine-1-carbonyl]-2-methoxyphenyl}-5-isopropylimidazolidine-2,4-dione

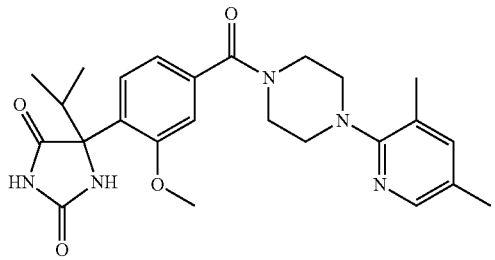 [SMILES: COc1cc(C(=O)N2CCN(c3ncc(C)cc3C)CC2)ccc1C1(C(C)C)NC(=O)NC1=O]

4-(4-Isopropyl-2,5-dioxoimidazolidin-4-yl)-3-methoxybenzoic acid (146 mg) described in Preparation Example 35, 1-(3,5-dimethylpyridin-2-yl)piperazine (105 mg) and 1-hydroxybenzotriazole (74 mg) were dissolved in N,N-dimethylformamide (1.7 mL), 1-ethyl-3-(3'-dimethylaminopropyl)carbodiimide.hydrochloride (105 mg) was added, and the mixture was stirred at room temperature overnight. To the reaction mixture was added saturated brine and the mixture was extracted with ethyl acetate. The solvent was evaporated and the obtained residue was purified by column chromatography (ethyl acetate:methanol) to give the title compound (152.9 mg).

MS(APCI) m/z: 466 (M+H)$^+$

Example 18: Synthesis of 5-{4-[4-(3,5-dimethyl-pyridin-2-yl)piperazine-1-carbonyl]-2-hydroxyphenyl}-5-methylimidazolidine-2,4-dione

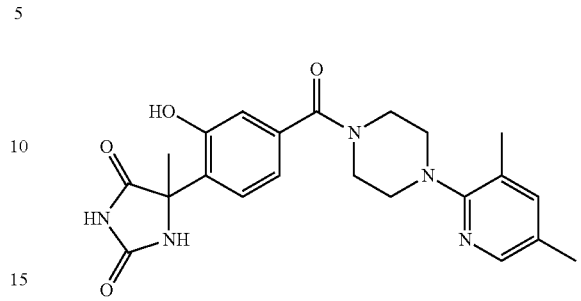

To 5-{4-[4-(3,5-dimethylpyridin-2-yl)piperazine-1-carbonyl]-2-methoxyphenyl}-5-methylimidazolidine-2,4-dione (100 mg) described in Example 15 was added dichloromethane (6 mL) and 1 mol/L boron tribromide dichloromethane solution (1.2 mL) was added while stirring with cooling at −78° C., and the mixture was stirred while raising the temperature to room temperature. The reaction mixture was poured into ice water, neutralized with sodium hydrogen carbonate and extracted with chloroform. The solvent was evaporated and the obtained residue was purified by column chromatography (ethyl acetate:methanol) to give the title compound as a crude product (54 mg). The obtained crude product (54 mg) was separated by HPLC using XBridge Prep C18 OBD (Waters) (10 mmol/L aqueous ammonium carbonate solution, acetonitrile). After extraction with ethyl acetate, the solvent was evaporated to give the title compound (20.8 mg).

MS(APCI) m/z: 424 (M+H)$^+$

Example 19: Synthesis of (R)-5-{4-[4-(3,5-dimethylpyridin-2-yl)piperazine-1-carbonyl]phenyl}-3-(2-hydroxyethyl)-5-methylimidazolidine-2,4-dione

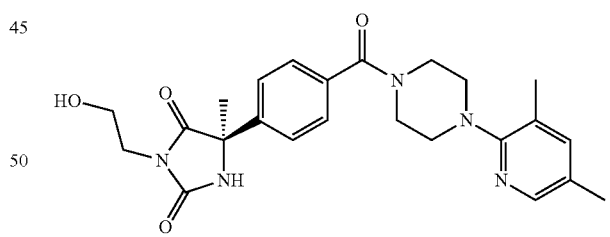

(R)-5-{4-[4-(3,5-dimethylpyridin-2-yl)piperazine-1-carbonyl]phenyl}-5-methylimidazolidine-2,4-dione (204 mg) described in Example 1 was dissolved in N,N-dimethylformamide (1 mL), 2-bromoethanol (43 μL) and potassium carbonate (90 mg) were added, and the mixture was stirred at room temperature overnight. To the reaction mixture was added saturated brine and the mixture was extracted with ethyl acetate. The solvent was evaporated and the obtained residue was purified by column chromatography (ethyl acetate:methanol) to give the title compound (74.6 mg).

MS(ESI) m/z: 452 (M+H)$^+$

Example 20: Synthesis of 5-{4-[4-(3,5-dimethylpyridin-2-yl)piperazine-1-carbonyl]-2-hydroxyphenyl}-5-isopropylimidazolidine-2,4-dione

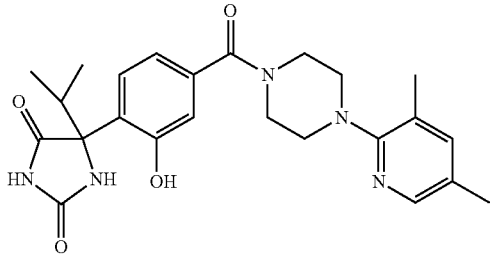 [SMILES: Cc1cnc(N2CCN(C(=O)c3ccc(C4(C(C)C)NC(=O)NC4=O)c(O)c3)CC2)c(C)c1]

To 5-{4-[4-(3,5-dimethylpyridin-2-yl)piperazine-1-carbonyl]-2-methoxyphenyl}-5-isopropylimidazolidine-2,4-dione (100 mg) described in Example 17 was added dichloromethane (6 mL) and 1 mol/L boron tribromide dichloromethane solution (2.2 mL) was added while stirring with cooling at −78° C., and the mixture was stirred while raising the temperature to room temperature. The reaction mixture was poured into ice water, neutralized with sodium hydrogen carbonate and extracted with chloroform. The solvent was evaporated and the obtained residue was purified by column chromatography (chloroform:methanol) to give the title compound (60.4 mg).

MS(APCI) m/z: 452 (M+H)$^+$

Example 21: Synthesis of 5-{4-[4-(5-cyclopropyl-3-methylpyridin-2-yl)piperazine-1-carbonyl]-2-methoxyphenyl}-5-isopropylimidazolidine-2,4-dione

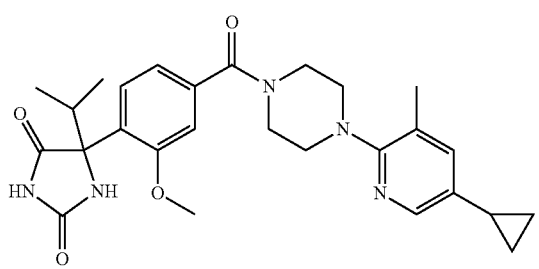 [SMILES: COc1cc(C(=O)N2CCN(c3ncc(C4CC4)cc3C)CC2)ccc1C1(C(C)C)NC(=O)NC1=O]

4-(4-Isopropyl-2,5-dioxoimidazolidin-4-yl)-3-methoxybenzoic acid (146 mg) described in Preparation Example 35, 1-(5-cyclopropyl-3-methylpyridin-2-yl)piperazine. hydrochloride (140 mg), 1-hydroxybenzotriazole (74 mg) and triethylamine (0.17 mL) were dissolved in N,N-dimethylformamide (1.7 mL), 1-ethyl-3-(3'-dimethylaminopropyl) carbodiimide. hydrochloride (105 mg) was added, and the mixture was stirred at room temperature overnight. To the reaction mixture was added saturated brine and the mixture was extracted with ethyl acetate. The solvent was evaporated and the obtained residue was purified by column chromatography (ethyl acetate:methanol) to give the title compound (205.1 mg).

MS(APCI) m/z: 492 (M+H)$^+$

Example 22: Synthesis of 5-isopropyl-5-{2-methoxy-4-[4-(3,5,6-trimethylpyridin-2-yl)piperazine-1-carbonyl]phenyl}imidazolidine-2,4-dione

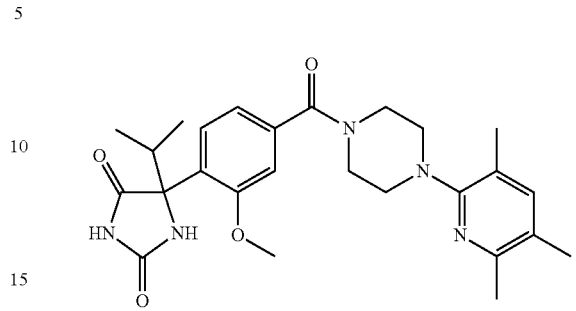

4-(4-Isopropyl-2,5-dioxoimidazolidin-4-yl)-3-methoxybenzoic acid (146 mg) described in Preparation Example 35, 1-(3,5,6-trimethylpyridin-2-yl)piperazine (113 mg) and 1-hydroxybenzotriazole (74 mg) were dissolved in N,N-dimethylformamide (1.7 mL), 1-ethyl-3-(3'-dimethylaminopropyl) carbodiimide.hydrochloride (105 mg) was added, and the mixture was stirred at room temperature overnight. To the reaction mixture was added saturated brine and the mixture was extracted with ethyl acetate. The solvent was evaporated and the obtained residue was purified by column chromatography (ethyl acetate:methanol) to give the title compound (190.7 mg).

MS(APCI) m/z: 480 (M+H)$^+$

Example 23: Synthesis of (R)-5-{4-[4-(3,5-dimethylpyridin-2-yl)piperazine-1-carbonyl]-2-methoxyphenyl}-5-isopropylimidazolidine-2,4-dione and (S)-5-{4-[4-(3,5-dimethylpyridin-2-yl)piperazine-1-carbonyl]-2-methoxyphenyl}-5-isopropylimidazolidine-2,4-dione

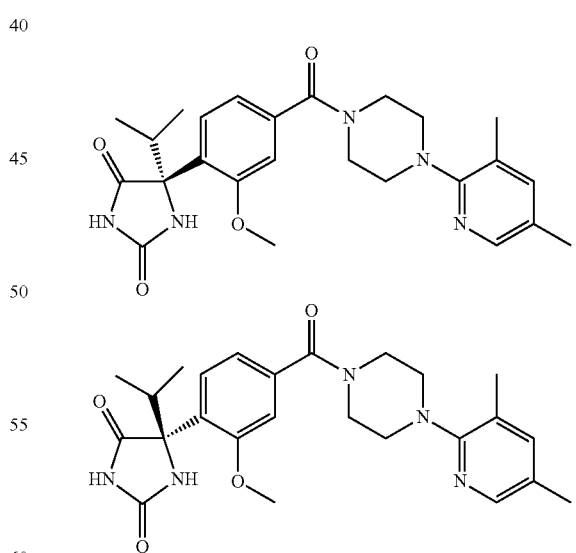

5-{4-[4-(3,5-Dimethylpyridin-2-yl)piperazine-1-carbonyl]-2-methoxyphenyl}-5-isopropylimidazolidine-2,4-dione (186 mg, see Example 17) was separated by HPLC using CHIRALPAK (Daicel) IC (hexane/chloroform/2-propanol) to give the both enantiomers indicated above (compound with short retention time 83.6 mg (MS(APCI) m/z:

466 (M+H)⁺) and compound with long retention time 82.2 mg (MS(APCI) m/z: 466 (M+H)⁺)).

In the analysis using CHIRALPAK (Daicel) IC-3 (4.6 mm×150 mm, hexane/2-propanol/tetrahydrofuran/diethylamine=60/20/20/0.1, flow 0.5 mL/min), the retention time was respectively 7.7 min and 9.7 min.

Example 24: Synthesis of (R)-5-{4-[4-(3,5-dimethylpyridin-2-yl) piperazine-1-carbonyl]phenyl}-1-(2-hydroxyethyl)-5-methylimidazolidine-2,4-dione

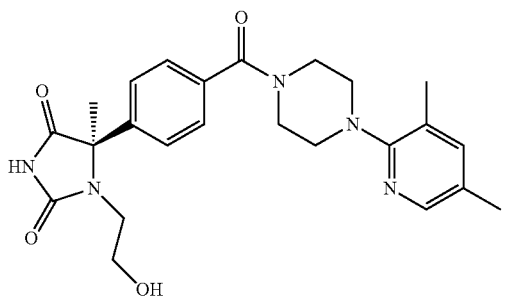 [SMILES: Cc1cnc(N2CCN(C(=O)c3ccc([C@]4(C)C(=O)NC(=O)N4CCO)cc3)CC2)c(C)c1]

(R)-5-{4-[4-(3,5-dimethylpyridin-2-yl)piperazine-1-carbonyl]phenyl}-5-methylimidazolidine-2,4-dione (300 mg) described in Example 1 was dissolved in N,N-dimethylformamide (1.5 mL), 4-methoxybenzyl chloride (0.12 mL), potassium carbonate (132 mg) and potassium iodide (12 mg) were added, and the mixture was stirred at room temperature overnight. To the reaction mixture was added saturated brine and the mixture was extracted with ethyl acetate. The solvent was evaporated and the obtained residue was purified by column chromatography (ethyl acetate:methanol) to give (R)-5-{4-[4-(3,5-dimethylpyridin-2-yl)piperazine-1-carbonyl]phenyl}-3-(4-methoxybenzyl)-5-methylimidazolidine-2,4-dione (242.1 mg).

The obtained (R)-5-{4-[4-(3,5-dimethylpyridin-2-yl)piperazine-1-carbonyl]phenyl}-3-(4-methoxybenzyl)-5-methylimidazolidine-2,4-dione (242.1 mg) and 2-(2-bromoethoxy)tetrahydropyran (152 μL) were dissolved in N,N-dimethylformamide (2 mL), sodium hydride (60% in liquid paraffin dispersion) (44 mg) was added under ice-cooling, and the mixture was stirred at room temperature overnight. To the reaction mixture was added saturated brine and the mixture was extracted with ethyl acetate. The solvent was evaporated and the obtained residue was purified by column chromatography (ethyl acetate:hexane) to give (R)-5-{4-[4-(3,5-dimethylpyridin-2-yl)piperazine-1-carbonyl]phenyl}-3-(4-methoxybenzyl)-5-methyl-1-[2-(tetrahydropyran-2-yloxy)ethyl]imidazolidine-2,4-dione (262 mg).

The obtained (R)-5-{4-[4-(3,5-dimethylpyridin-2-yl)piperazine-1-carbonyl]phenyl}-3-(4-methoxybenzyl)-5-methyl-1-[2-(tetrahydropyran-2-yloxy)ethyl]imidazolidine-2,4-dione (262 mg) was dissolved in 1,2-dichloroethane (7 mL), trifluoromethanesulfonic acid (0.5 mL) was added, and the mixture was stirred at 70° C. After completion of the reaction, saturated aqueous sodium hydrogen carbonate solution was added and the mixture was extracted with chloroform. The solvent was evaporated and the obtained residue was purified by column chromatography (chloroform:methanbl) to give the title compound (52.9 mg).

MS(APCI) m/z: 452 (M+H)⁺

Example 25: Synthesis of (R)-5-{4-[4-(6-fluorobenzo[d]isoxazol-3-yl)piperidine-1-carbonyl]phenyl}-5-fluoromethylimidazolidine-2,4-dione and (S)-5-{4-[4-(6-fluorobenzo[d]isoxazol-3-yl)piperidine-1-carbonyl]phenyl}-5-fluoromethylimidazolidine-2,4-dione

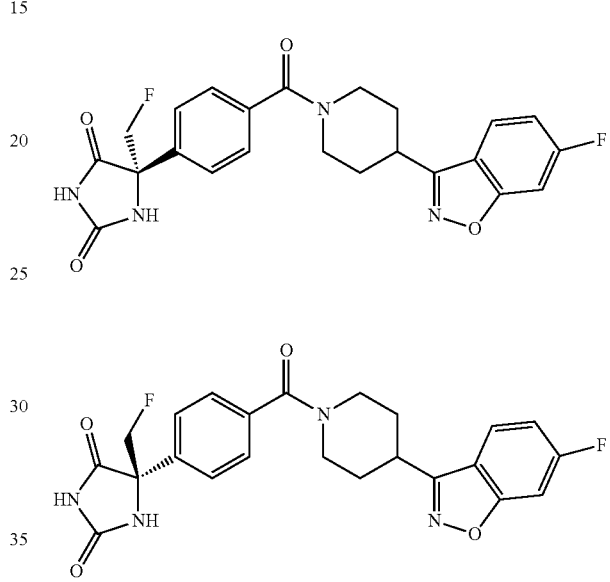

4-(4-Fluoromethyl-2,5-dioxoimidazolidin-4-yl)benzoic acid (168 mg) described in Preparation Example 63, 6-fluoro-3-(piperidin-4-yl)benzo[d]isoxazole (147 mg) and 1-hydroxybenzotriazole (99 mg) were dissolved in N,N-dimethylformamide (1 mL), 1-ethyl-3-(3'-dimethylaminopropyl)carbodiimide.hydrochloride (140 mg) was added, and the mixture was stirred at room temperature overnight. Water was added to the reaction mixture and the mixture was extracted with chloroform. The solvent was evaporated and the obtained residue was purified by column chromatography (chloroform:methanol) to give 5-{4-[4-(6-fluorobenzo[d]isoxazol-3-yl)piperidine-1-carbonyl]phenyl}-5-fluoromethylimidazolidine-2,4-dione (205.3 mg).

The obtained 5-{4-[4-(6-fluorobenzo[d]isoxazol-3-yl)piperidine-1-carbonyl]phenyl}-5-fluoromethylimidazolidine-2,4-dione (167 mg) was separated by HPLC using CHIRALPAK (Daicel) IC (hexane/methanol/tetrahydrofuran) to give the both enantiomers indicated above (compound with short retention time 62.8 mg (MS(APCI) m/z: 455 (M+H)⁺) and compound with long retention time 64.1 mg (MS(APCI) m/z: 455 (M+H)⁺)).

In the analysis using CHIRALPAK (Daicel) IC-3 (4.6 mm×150 mm, hexane/methanol/tetrahydrofuran=60/20/20, flow 0.5 mL/min), the retention time was respectively 6.6 min and 12.4 min.

Example 26: Synthesis of (R)-5-{4-[4-(6-fluorobenzo[d]isoxazol-3-yl)piperidine-1-carbonyl]phenyl}-5-methylimidazolidine-2,4-dione

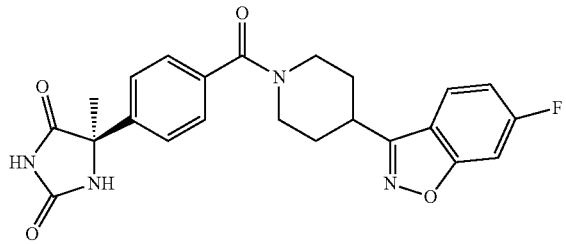 [SMILES: C[C@]1(c2ccc(C(=O)N3CCC(c4noc5cc(F)ccc45)CC3)cc2)NC(=O)NC1=O]

4-((R)-4-methyl-2,5-dioxoimidazolidin-4-yl)benzoic acid (117 mg) described in Preparation Example 6, 6-fluoro-3-(piperidin-4-yl)benzo[d]isoxazole (111 mg) and 1-hydroxybenzotriazole (74.3 mg) were dissolved in N,N-dimethylformamide (1 mL), 1-ethyl-3-(3'-dimethylaminopropyl)carbodiimide.hydrochloride (105 mg) was added, and the mixture was stirred at room temperature overnight. Water was added to the reaction mixture and the mixture was extracted with chloroform. The solvent was evaporated and the obtained residue was purified by column chromatography (chloroform:methanol) to give the title compound (196.3 mg).

MS(APCI) m/z: 437 (M+H)$^+$

Example 27: Synthesis of (R)-5-ethyl-5-{4-[4-(1-p-tolyl-1H-pyrazol-4-yl)piperidine-1-carbonyl]phenyl}imidazolidine-2,4-dione

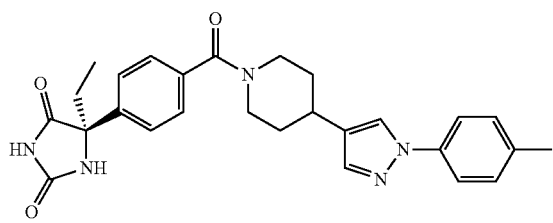 [SMILES: CC[C@]1(c2ccc(C(=O)N3CCC(c4cnn(-c5ccc(C)cc5)c4)CC3)cc2)NC(=O)NC1=O]

4-((R)-4-ethyl-2,5-dioxoimidazolidin-4-yl)benzoic acid (61.7 mg) described in Preparation Example 14, 4-[1-(p-tolyl)-1H-pyrazol-4-yl]piperidine (60 mg) described in Preparation Example 134, and 1-hydroxybenzotriazole (35.3 mg) were dissolved in N,N-dimethylformamide (1.5 mL), 1-ethyl-3-(3'-dimethylaminopropyl)carbodiimide.hydrochloride (50 mg) was added, and the mixture was stirred at room temperature overnight. To the reaction mixture was added saturated brine and the mixture was extracted with ethyl acetate. The solvent was evaporated and the obtained residue was purified by column chromatography (chloroform:methanol) to give the title compound (98 mg).

MS(APCI) m/z: 472 (M+H)$^+$

Example 28: Synthesis of (R)-5-methyl-5-{4-[4-(1-p-tolyl-1H-pyrazol-4-yl)piperidine-1-carbonyl]phenyl}imidazolidine-2,4-dione

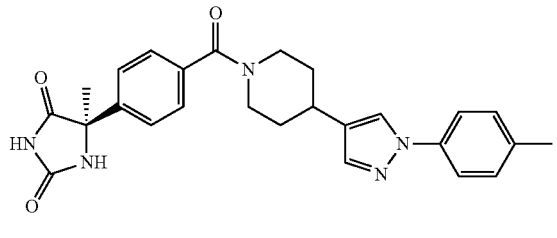 [SMILES: Cc1ccc(-n2cc(C3CCN(C(=O)c4ccc([C@@]5(C)NC(=O)NC5=O)cc4)CC3)cn2)cc1]

4-((R)-4-methyl-2,5-dioxoimidazolidin-4-yl)benzoic acid (58.2 mg) described in Preparation Example 6, 4-[1-(p-tolyl)-1H-pyrazol-4-yl]piperidine (60 mg) described in Preparation Example 134, and 1-hydroxybenzotriazole (35.3 mg) were dissolved in N,N-dimethylformamide (1.5 mL), 1-ethyl-3-(3'-dimethylaminopropyl)carbodiimide.hydrochloride (50 mg) was added, and the mixture was stirred at room temperature overnight. To the reaction mixture was added saturated brine and the mixture was extracted with ethyl acetate. The solvent was evaporated and the obtained residue was purified by column chromatography (chloroform:methanol) to give the title compound (92.8 mg).

MS(APCI) m/z: 458 (M+H)$^+$

Example 29: Synthesis of (R)-5-isopropyl-5-{4-[4-(1-p-tolyl-1H-pyrazol-4-yl)piperidine-1-carbonyl]phenyl}imidazolidine-2,4-dione

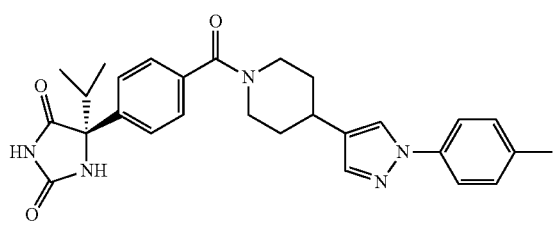 [SMILES: Cc1ccc(-n2cc(C3CCN(C(=O)c4ccc([C@@]5(C(C)C)NC(=O)NC5=O)cc4)CC3)cn2)cc1]

4-((R)-4-isopropyl-2,5-dioxoimidazolidin-4-yl)benzoic acid (79.4 mg) described in Preparation Example 45, 4-[1-(p-tolyl)-1H-pyrazol-4-yl]piperidine (73 mg) described in Preparation Example 134, and 1-hydroxybenzotriazole (42.9 mg) were dissolved in N,N-dimethylformamide (1.5 mL), 1-ethyl-3-(3'-dimethylaminopropyl)carbodiimide.hydrochloride (60.9 mg) was added, and the mixture was stirred at room temperature overnight. Water was added to the reaction mixture and the mixture was extracted with ethyl acetate. The solvent was evaporated and the obtained residue was purified by column chromatography (chloroform:methanol) to give the title compound (109.4 mg).

MS(APCI) m/z: 486 (M+H)$^+$

Example 30: Synthesis of 5-{3-bromo-4-[4-(3,5-dimethylpyridin-2-yl)piperazine-1-carbonyl]phenyl}-5-methylimidazolidine-2,4-dione

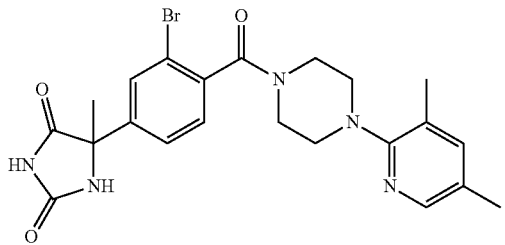 [SMILES: Cc1cnc(N2CCN(C(=O)c3ccc(C4(C)NC(=O)NC4=O)cc3Br)CC2)c(C)c1]

2-Bromo-4-(4-methyl-2,5-dioxoimidazolidin-4-yl)benzoic acid (118 mg) described in Preparation Example 3 was dissolved in tetrahydrofuran (2 mL), 1-ethyl-3-(3'-dimethylaminopropyl)carbodiimide.hydrochloride (76 mg), 1-hydroxybenzotriazole (108 mg) and 1-(3,5-dimethylpyridin-2-yl)piperazine (72 mg) were added, and the mixture was stirred at room temperature overnight. Water was added to the reaction mixture and the mixture was extracted with ethyl acetate. The solvent was evaporated and the obtained residue was purified by column chromatography (chloroform:methanol) to give the title compound (130 mg).

MS(ESI) m/z: 486 (M+H)$^+$

Example 31: Synthesis of 5-{4-[4-(3,5-dimethylpyridin-2-yl)piperazine-1-carbonyl]-3-methylphenyl}-5-methylimidazolidine-2,4-dione

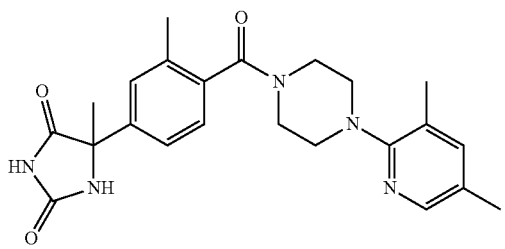 [SMILES: Cc1cnc(N2CCN(C(=O)c3ccc(C4(C)NC(=O)NC4=O)cc3C)CC2)c(C)c1]

To 2-methyl-4-(4-methyl-2,5-dioxoimidazolidin-4-yl)benzoic acid (150 mg) described in Preparation Example 8 were added 1-(3,5-dimethylpyridin-2-yl)piperazine (127.1 mg), 1-hydroxybenzotriazole (98 mg), 1-ethyl-3-(3'-dimethylaminopropyl)carbodiimide.hydrochloride (150.6 mg), chloroform (2 mL) and N,N-dimethylformamide (1 mL) and the mixture was stirred at room temperature overnight. Water was added to the reaction mixture and the mixture was extracted with ethyl acetate. The solvent was evaporated and the obtained residue was purified by column chromatography (chloroform:methanol) to give the title compound (191.3 mg).

MS(ESI) m/z: 422 (M+H)$^+$

Example 32: Synthesis of (R)-5-{2-fluoro-4-[4-(3,5,6-trimethylpyridin-2-yl)piperazine-1-carbonyl]phenyl}-5-methylimidazolidine-2,4-dione and (S)-5-{2-fluoro-4-[4-(3,5,6-trimethylpyridin-2-yl)piperazine-1-carbonyl]phenyl}-5-methylimidazolidine-2,4-dione

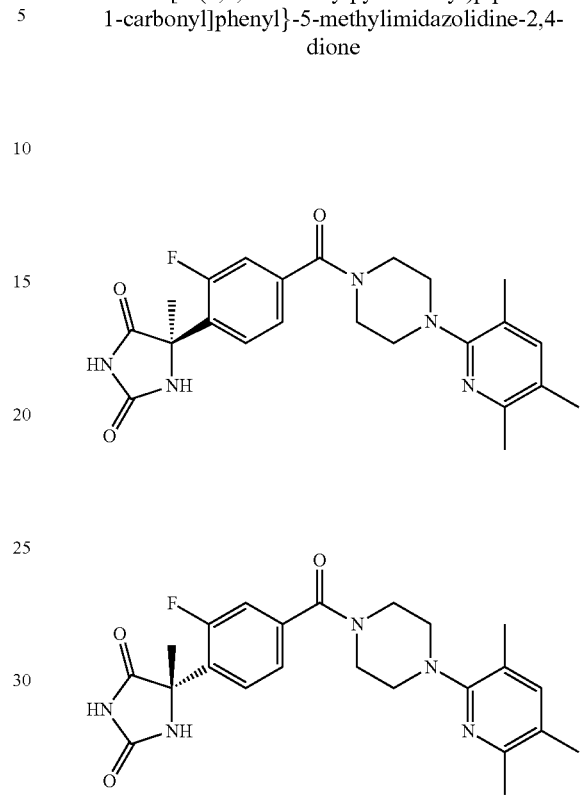

3-Fluoro-4-(4-methyl-2,5-dioxoimidazolidin-4-yl)benzoic acid (126 mg) described in Preparation Example 18 was dissolved in tetrahydrofuran (5 mL), 1-ethyl-3-(3'-dimethylaminopropyl) carbodiimide.hydrochloride (115 mg), 1-hydroxybenzotriazole (162 mg), 1-(3,5,6-trimethylpyridin-2-yl)piperazine (113 mg) and triethylamine (168 µL) were added, and the mixture was stirred at room temperature overnight. Water was added to the reaction mixture and the mixture was extracted with chloroform. The solvent was evaporated and the obtained residue was purified by column chromatography (chloroform:methanol) to give 5-{2-fluoro-4-[4-(3,5,6-trimethylpyridin-2-yl)piperazine-1-carbonyl]phenyl}-5-methylimidazolidine-2,4-dione (172 mg).

The obtained 5-{2-fluoro-4-[4-(3,5,6-trimethylpyridin-2-yl)piperazine-1-carbonyl]phenyl}-5-methylimidazolidine-2,4-dione (150 mg) was separated by moderate-pressure column using CHIRALFLASH (Daicel) IA (ethanol/diethylamine) to give the both enantiomers indicated above (compound with short retention time 51.5 mg (MS(ESI) m/z: 440 (M+H)$^+$) and compound with long retention time 34.6 mg (MS(ESI) m/z: 440 (M+H)$^+$)).

In the analysis using CHIRALPAK (Daicel) IA (4.6 mm×100 mm, ethanol/diethylamine=100/0.1, flow 0.5 mL/min), the retention time was respectively 4.6 min and 6.6 min.

Example 33: Synthesis of (R)-5-{4-[4-(5-cyclopropyl-3-methylpyridin-2-yl)piperazine-1-carbonyl]-2-fluorophenyl}-5-methylimidazolidine-2,4-dione and (S)-5-{4-[4-(5-cyclopropyl-3-methylpyridin-2-yl)piperazine-1-carbonyl]-2-fluorophenyl}-5-methyl-imidazolidine-2,4-dione

Example 34: Synthesis of (R)-5-{4-[4-(5-ethyl-3-methylpyridin-2-yl)piperazine-1-carbonyl]-2-fluorophenyl}-5-methylimidazolidine-2,4-dione and (S)-5-{4-[4-(5-ethyl-3-methylpyridin-2-yl)piperazine-1-carbonyl]-2-fluorophenyl}-5-methylimidazolidine-2,4-dione

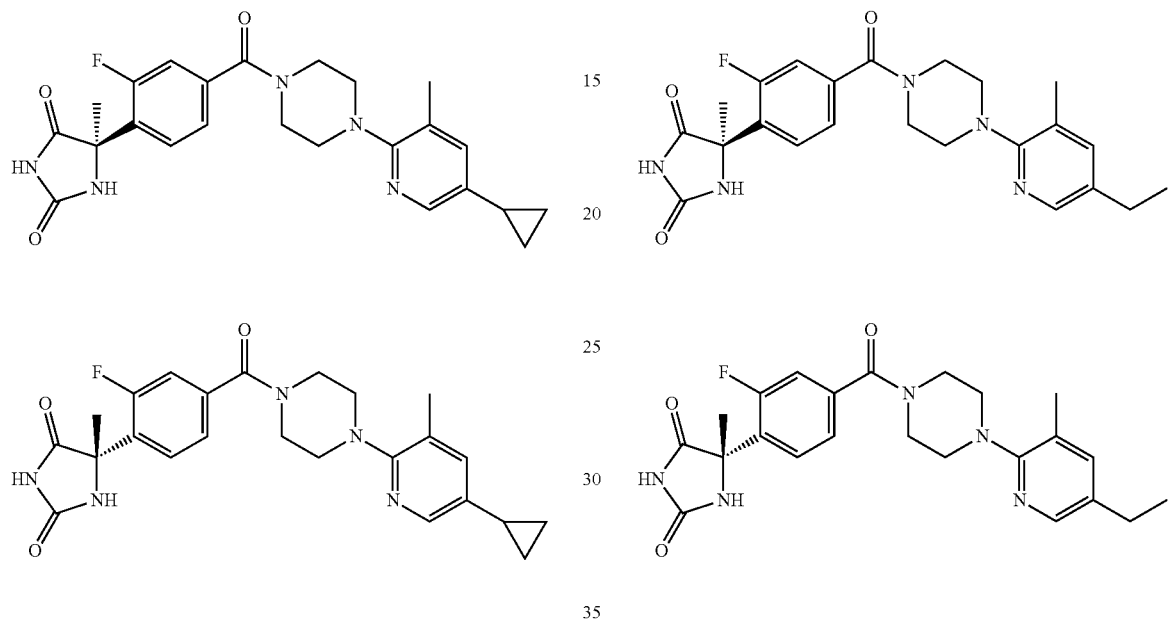

3-Fluoro-4-(4-methyl-2,5-dioxoimidazolidin-4-yl)benzoic acid (126 mg) described in Preparation Example 18 was dissolved in tetrahydrofuran (5 mL), 1-ethyl-3-(3'-dimethylaminopropyl)carbodiimide.hydrochloride (115 mg), 1-(5-cyclopropyl-3-methylpyridin-2-yl)piperazine (130 mg) and 1-hydroxybenzotriazole (162 mg) were added, and the mixture was stirred at room temperature overnight. Water was added to the reaction mixture and the mixture was extracted with chloroform. The solvent was evaporated and the obtained residue was purified by column chromatography (chloroform:methanol) to give 5-{4-[4-(5-cyclopropyl-3-methylpyridin-2-yl)piperazine-1-carbonyl]-2-fluorophenyl}-5-methylimidazolidine-2,4-dione (219 mg).

The obtained 5-{4-[4-(5-cyclopropyl-3-methylpyridin-2-yl)piperazine-1-carbonyl]-2-fluorophenyl}-5-methylimidazolidine-2,4-dione (150 mg) was separated by moderate-pressure column using CHIRALFLASH (Daicel) IA (ethanol/diethylamine/tetrahydrofuran) to give the both enantiomers indicated above (compound with short retention time 48.5 mg (MS(APCI) m/z: 452 (M+H)$^+$) and compound with long retention time 61 mg (MS(APCI) m/z: 452 (M+H)$^+$)).

In the analysis using CHIRALPAK (Daicel) IA (4.6 mm×100 mm, tetrahydrofuran/ethanol/diethylamine=10/90/0.1, flow 0.5 mL/min), the retention time was respectively 4.8 min and 7.8 min.

3-Fluoro-4-(4-methyl-2,5-dioxoimidazolidin-4-yl)benzoic acid (126 mg) described in Preparation Example 18 was dissolved in tetrahydrofuran (5 mL), 1-ethyl-3-(3'-dimethylaminopropyl)carbodiimide.hydrochloride (115 mg), 1-(5-ethyl-3-methylpyridin-2-yl)piperazine (130 mg) and 1-hydroxybenzotriazole (162 mg) were added, and the mixture was stirred at room temperature overnight. Water was added to the reaction mixture and the mixture was extracted with chloroform. The solvent was evaporated and the obtained residue was purified by column chromatography (chloroform:methanol) to give 5-{4-[4-(5-ethyl-3-methylpyridin-2-yl)piperazine-1-carbonyl]-2-fluorophenyl}-5-methylimidazolidine-2,4-dione (196 mg).

The obtained 5-{4-[4-(5-ethyl-3-methylpyridin-2-yl)piperazine-1-carbonyl]-2-fluorophenyl}-5-methylimidazolidine-2,4-dione (150 mg) was separated by moderate-pressure column using CHIRALFLASH (Daicel) IA (ethanol/diethylamine/tetrahydrofuran) to give the both enantiomers indicated above (compound with short retention time 37.5 mg (MS(APCI) m/z: 440 (M+H)$^+$) and compound with long retention time 34.5 mg (MS(APCI) m/z: 440 (M+H)$^+$)).

In the analysis using CHIRALPAK (Daicel) IA (4.6 mm×100 mm, tetrahydrofuran/ethanol/diethylamine=10/90/0.1, flow 0.5 mL/min), the retention time was respectively 4.1 min and 5.9 min.

Example 35: Synthesis of (R)-5-{4-[4-(3,5-dicyclopropylpyridin-2-yl)piperazine-1-carbonyl]-2-fluorophenyl}-5-methylimidazolidine-2,4-dione and (S)-5-{4-[4-(3,5-dicyclopropylpyridin-2-yl)piperazine-1-carbonyl]-2-fluorophenyl}-5-methylimidazolidine-2,4-dione

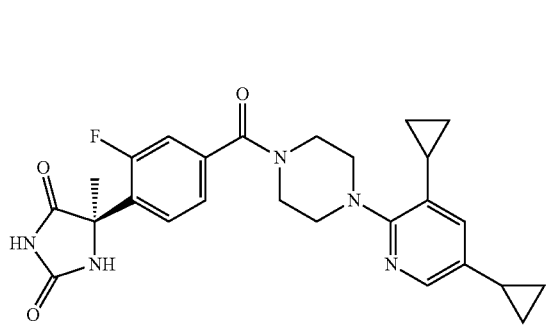

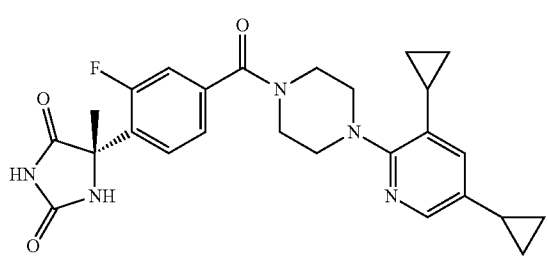

3-Fluoro-4-(4-methyl-2,5-dioxoimidazolidin-4-yl)benzoic acid (126 mg) described in Preparation Example 18 was dissolved in tetrahydrofuran (5 mL), 1-ethyl-3-(3'-dimethylaminopropyl)carbodiimide.hydrochloride (115 mg), 1-hydroxybenzotriazole (162 mg), 1-(3,5-dicyclopropylpyridin-2-yl)piperazine.2 hydrochloride (190 mg) and triethylamine (168 µL) were added, and the mixture was stirred at room temperature overnight. Water was added to the reaction mixture and the mixture was extracted with chloroform. The solvent was evaporated and the obtained residue was purified by column chromatography (chloroform:methanol) to give 5-{4-[4-(3,5-dicyclopropylpyridin-2-yl)piperazine-1-carbonyl]-2-fluorophenyl}-5-methylimidazolidine-2,4-dione (60 mg).

The obtained 5-{4-[4-(3,5-dicyclopropylpyridin-2-yl)piperazine-1-carbonyl]-2-fluorophenyl}-5-methylimidazolidine-2,4-dione (60 mg) was separated by moderate-pressure column using CHIRALFLASH (Daicel) IA (hexane/ethanol/diethylamine) to give the both enantiomers indicated above (compound with short retention time 18 mg (MS(ESI) m/z: 478 (M+H)$^+$) and compound with long retention time 16 mg (MS(ESI) m/z: 478 (M+H)$^+$)).

In the analysis using CHIRALPAK (Daicel) IA-3 (4.6 mm×150 mm, ethanol/diethylamine=100/0.1, flow 0.5 mL/min), the retention time was respectively 11.0 min and 25.9 min.

Example 36: Synthesis of (R)-5-{4-[4-(3,5-dimethylpyridin-2-yl)piperazine-1-carbonyl]-3-methylphenyl}-5-ethylimidazolidine-2,4-dione and (S)-5-{4-[4-(3,5-dimethylpyridin-2-yl)piperazine-1-carbonyl]-3-methylphenyl}-5-ethylimidazolidine-2,4-dione

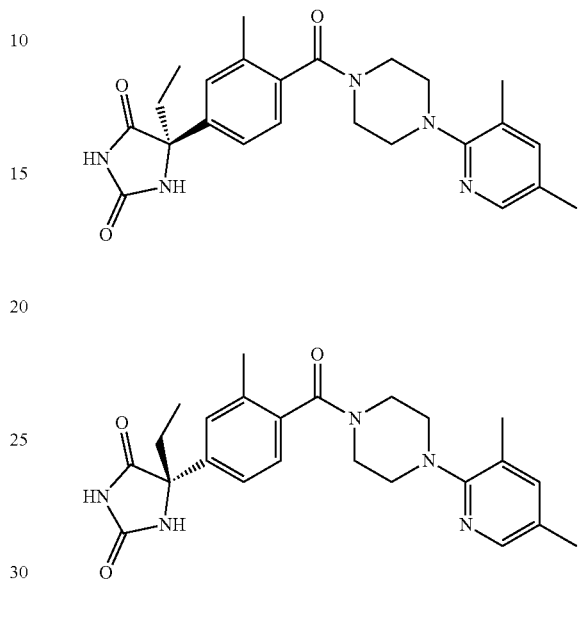

To 4-(4-ethyl-2,5-dioxoimidazolidin-4-yl)-2-methylbenzoic acid as a crude product (209 mg) described in Preparation Example 19 were added tetrahydrofuran (8 mL), N,N-dimethylformamide (1 mL), 1-ethyl-3-(3'-dimethylaminopropyl) carbodiimide.hydrochloride (183 mg), 1-hydroxybenzotriazole (129 mg), 1-(3,5-dimethylpyridin-2-yl)piperazine (190 mg) and triethylamine (278 µL) and the mixture was stirred at room temperature for 8 hr. Water was added to the reaction mixture, and the precipitated solid was collected by filtration. The obtained crude product was purified by column chromatography (chloroform:methanol) to give 5-{4-[4-(3,5-dimethylpyridin-2-yl)piperazine-1-carbonyl]-3-methylphenyl}-5-ethylimidazolidine-2,4-dione (130 mg).

The obtained 5-{4-[4-(3,5-dimethylpyridin-2-yl)piperazine-1-carbonyl]-3-methylphenyl}-5-ethylimidazolidine-2,4-dione (110 mg) was separated by moderate-pressure column using CHIRALFLASH (Daicel) IA (tetrahydrofuran/ethanol/diethylamine) to give the both enantiomers indicated above (compound with short retention time 34 mg (MS(ESI) m/z: 436 (M+H)$^+$) and compound with long retention time 45 mg (MS(ESI) m/z: 436 (M+H)$^+$)).

In the analysis using CHIRALPAK (Daicel) IC-3 (4.6 mm×150 mm, hexane/ethanol/diethylamine=10/90/0.1, flow 0.5 mL/min), the retention time was respectively 7.4 min and 15.9 min.

Example 37: Synthesis of (R)-5-{4-[4-(3,5-dimethylpyridin-2-yl)piperazine-1-carbonyl]-2-methylphenyl}-5-isopropylimidazolidine-2,4-dione and (S)-5-{4-[4-(3,5-dimethylpyridin-2-yl)piperazine-1-carbonyl]-2-methylphenyl}-5-isopropylimidazolidine-2,4-dione Example 38: Synthesis of (R)-5-{4-[4-(5-cyclopropyl-3-methylpyridin-2-yl)piperazine-1-carbonyl]-3-methylphenyl}-5-ethylimidazolidine-2,4-dione and (S)-5-{4-[4-(5-cyclopropyl-3-methylpyridin-2-yl)piperazine-1-carbonyl]-3-methylphenyl}-5-ethylimidazolidine-2,4-dione

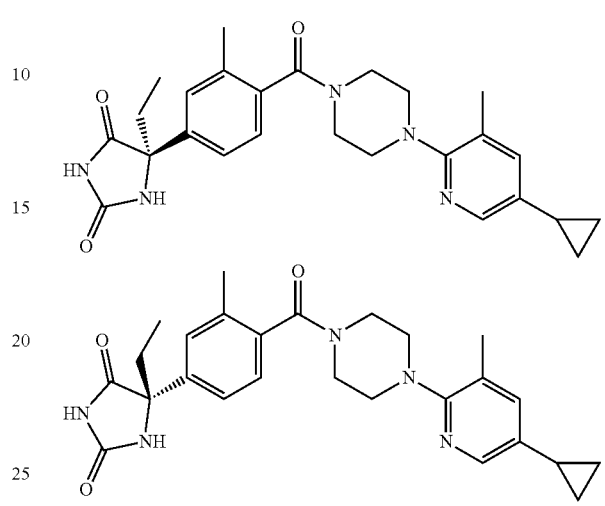

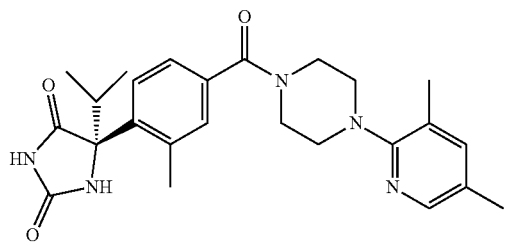

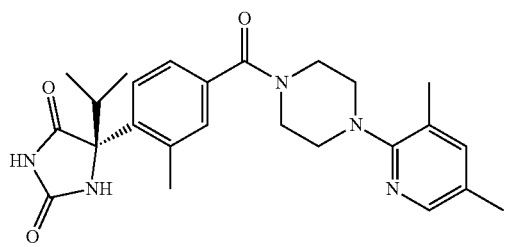

To 4-(4-isopropyl-2,5-dioxoimidazolidin-4-yl)-3-methylbenzoic acid as a crude product (138 mg) described in Preparation Example 39 were added tetrahydrofuran (5 mL), 1-hydroxybenzotriazole (81 mg), 1-ethyl-3-(3'-dimethylaminopropyl)carbodiimide.hydrochloride (115 mg), triethylamine (168 µL) and 1-(3,5-dimethylpyridin-2-yl)piperazine (115 mg) and the mixture was stirred at room temperature overnight. Water was added to the reaction mixture and the mixture was extracted with ethyl acetate. The solvent was evaporated and the obtained residue was purified by column chromatography (hexane:ethyl acetate:methanol) to give 5-{4-[4-(3,5-dimethylpyridin-2-yl)piperazine-1-carbonyl]-2-methylphenyl}-5-isopropylimidazolidine-2,4-dione (137 mg).

The obtained 5-{4-[4-(3,5-dimethylpyridin-2-yl)piperazine-1-carbonyl]-2-methylphenyl}-5-isopropylimidazolidine-2,4-dione (119 mg) was separated by HPLC using CHIRALPAK (Daicel) IF (tetrahydrofuran/ethanol/diethylamine) to give the both enantiomers indicated above (compound with short retention time 59.4 mg (MS(APCI) m/z: 450 (M+H)$^+$) and compound with long retention time 59 mg (MS(APCI) m/z: 450 (M+H)$^+$)).

In the analysis using CHIRALPAK (Daicel) IC-3 (4.6 mm×150 mm, tetrahydrofuran/ethanol/diethylamine=5/95/0.1, flow 0.5 mL/min), the retention time was respectively 8.0 min and 6.3 min.

To 4-(4-ethyl-2,5-dioxoimidazolidin-4-yl)-2-methylbenzoic acid as a crude product (131 mg) described in Preparation Example 19 were added tetrahydrofuran (5 mL), triethylamine (168 µL), 1-ethyl-3-(3'-dimethylaminopropyl)carbodiimide. hydrochloride (115 mg), 1-hydroxybenzotriazole (81 mg), 1-(5-cyclopropyl-3-methylpyridin-2-yl)piperazine (130 mg) and the mixture was stirred at room temperature overnight. The reaction mixture was purified by column chromatography (chloroform:methanol) to give 5-{4-[4-(5-cyclopropyl-3-methylpyridin-2-yl)piperazine-1-carbonyl]-3-methylphenyl}-5-ethylimidazolidine-2,4-dione. The obtained 5-{4-[4-(5-cyclopropyl-3-methylpyridin-2-yl)piperazine-1-carbonyl]-3-methylphenyl}-5-ethylimidazolidine-2,4-dione was separated by moderate-pressure column using CHIRALFLASH (Daicel) IC (ethanol/dimethylamine) to give the both enantiomers indicated above (compound with short retention time 18.5 mg (MS(ESI) m/z: 462 (M+H)$^+$) and compound with long retention time 17.8 mg (MS(ESI) m/z: 462 (M+H)$^+$)).

In the analysis using CHIRALPAK (Daicel) IC-3 (4.6 mm×150 mm, ethanol/diethylamine=100/0.1, flow 0.5 mL/min), the retention time was respectively 7.2 min and 14.5 min.

Example 39: Synthesis of (R)-5-{4-[4-(3,5-dimethylpyridin-2-yl)piperazine-1-carbonyl]-2-fluorophenyl}-5-ethylimidazolidine-2,4-dione and (S)-5-{4-[4-(3,5-dimethylpyridin-2-yl)piperazine-1-carbonyl]-2-fluorophenyl}-5-ethylimidazolidine-2,4-dione

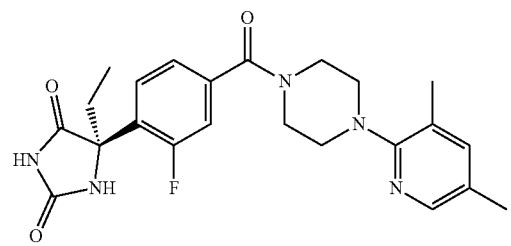

-continued

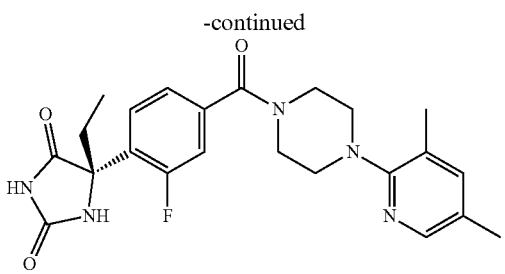

To 4-(4-ethyl-2,5-dioxoimidazolidin-4-yl)-3-fluorobenzoic acid (133 mg) described in Preparation Example 40 were added tetrahydrofuran (5 mL), triethylamine (168 μL), 1-ethyl-3-(3'-dimethylaminopropyl)carbodiimide.hydrochloride (115 mg), 1-hydroxybenzotriazole (81 mg), 1-(3,5-dimethylpyridin-2-yl)piperazine (115 mg) and the mixture was stirred at room temperature overnight. The reaction mixture was purified by column chromatography (chloroform:methanol) to give 5-{4-[4-(3,5-dimethylpyridin-2-yl)piperazine-1-carbonyl]-2-fluorophenyl}-5-ethylimidazolidine-2,4-dione (75 mg).

The obtained 5-{4-[4-(3,5-dimethylpyridin-2-yl)piperazine-1-carbonyl]-2-fluorophenyl}-5-ethylimidazolidine-2,4-dione (55 mg) was separated by HPLC using CHIRALPAK (Daicel) IF (hexane/ethanol/tetrahydrofuran/diethylamine) to give the both enantiomers indicated above (compound with short retention time 16.1 mg (MS(APCI) m/z: 440 (M+H)⁺) and compound with long retention time 16.1 mg (MS(APCI) m/z: 440 (M+H)⁺)).

In the analysis using CHIRALPAK (Daicel) IF-3 (4.6 mm×150 mm, hexane/ethanol/tetrahydrofuran/diethylamine=40/30/30/0.1, flow 0.5 mL/min), the retention time was respectively 7.0 min and 8.3 min.

Example 40: Synthesis of 5-{4-[4-(5-cyclopropyl-3-methylpyridin-2-yl)piperazine-1-carbonyl]-2-methylphenyl}-5-isopropylimidazolidine-2,4-dione

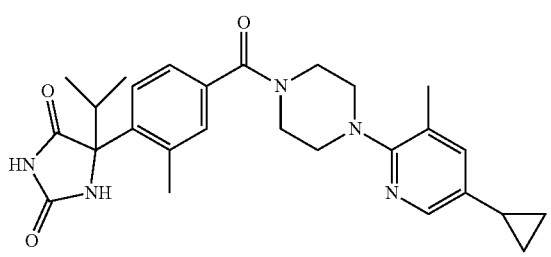 [SMILES: Cc1cc(C(=O)N2CCN(c3ncc(C4CC4)cc3C)CC2)ccc1C1(C(C)C)NC(=O)NC1=O]

To 4-(4-isopropyl-2,5-dioxoimidazolidin-4-yl)-3-methylbenzoic acid as a crude product (138 mg) described in Preparation Example 39 were added tetrahydrofuran (5 mL), 1-ethyl-3-(3'-dimethylaminopropyl)carbodiimide.hydrochloride (115 mg), 1-hydroxybenzotriazole (81 mg), triethylamine (168 μL), 1-(5-cyclopropyl-3-methylpyridin-2-yl)piperazine (123 mg) and the mixture was stirred at room temperature for 6.5 hr. The reaction mixture was purified by column chromatography (hexane:ethyl acetate) to give the title compound (118 mg).

MS(ESI) m/z: 476 (M+H)⁺

Example 41: Synthesis of 5-isopropyl-5-{2-methyl-4-[4-(3,5,6-trimethylpyridin-2-yl)piperazine-1-carbonyl]phenyl}imidazolidine-2,4-dione

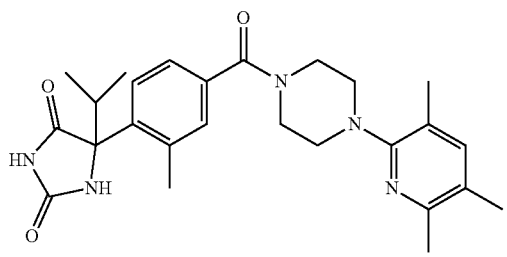 [SMILES: Cc1cc(C(=O)N2CCN(c3nc(C)c(C)cc3C)CC2)ccc1C1(C(C)C)NC(=O)NC1=O]

Using 4-(4-isopropyl-2,5-dioxoimidazolidin-4-yl)-3-methylbenzoic acid as a crude product (138 mg) described in Preparation Example 39, 1-(3,5,6-trimethylpyridin-2-yl)piperazine (130 mg), reactions and treatments similar to those in Example 40 were performed to give the title compound (85 mg).

MS(ESI) m/z: 464 (M+H)⁺

Example 42: Synthesis of 5-{4-[4-(5-cyclopropyl-3-methylpyridin-2-yl)piperazine-1-carbonyl]-2-fluorophenyl}-5-ethylimidazolidine-2,4-dione

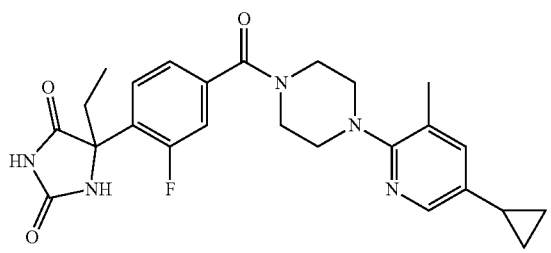 [SMILES: CCC1(c2ccc(C(=O)N3CCN(c4ncc(C5CC5)cc4C)CC3)cc2F)NC(=O)NC1=O]

To 4-(4-ethyl-2,5-dioxoimidazolidin-4-yl)-3-fluorobenzoic acid (67 mg) described in Preparation Example 40 were added tetrahydrofuran (2.5 mL), triethylamine (87 μL), 1-ethyl-3-(3'-dimethylaminopropyl)carbodiimide.hydrochloride (58 mg), 1-hydroxybenzotriazole (40 mg), 1-(5-cyclopropyl-3-methylpyridin-2-yl)piperazine.hydrochloride (76 mg) and the mixture was stirred at room temperature overnight. Water was added to the reaction mixture and the mixture was extracted with chloroform. The solvent was evaporated and the obtained residue was purified by column chromatography (hexane:ethyl acetate) to give the title compound (85 mg).

MS(ESI) m/z: 466 (M+H)⁺

Example 43: Synthesis of 5-ethyl-5-{2-fluoro-4-[4-(3,5,6-trimethylpyridin-2-yl)piperazine-1-carbonyl]phenyl}imidazolidine-2,4-dione

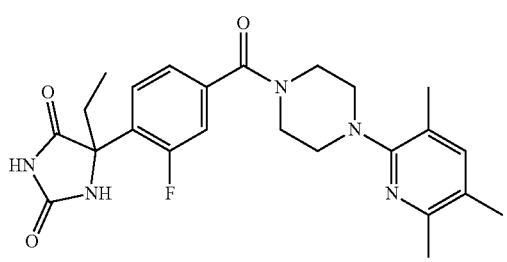 [SMILES: CCC1(c2ccc(C(=O)N3CCN(c4nc(C)c(C)cc4C)CC3)cc2F)NC(=O)NC1=O]

To 4-(4-ethyl-2,5-dioxoimidazolidin-4-yl)-3-fluorobenzoic acid (62 mg) described in Preparation Example 40 were added tetrahydrofuran (2.3 mL), N,N-dimethylformamide (3 mL), triethylamine (405 μL), 1-ethyl-3-(3'-dimethylaminopropyl)carbodiimide.hydrochloride (53 mg), 1-hydroxybenzotriazole (74 mg) and 1-(3,5,6-trimethylpyridin-2-yl)piperazine (60 mg) and the mixture was stirred at room temperature overnight. Water was added to the reaction mixture and the mixture was extracted with chloroform. The solvent was evaporated and the obtained residue was purified by column chromatography (hexane:ethyl acetate) to give the title compound (35 mg).

MS(ESI) m/z: 454 (M+H)+

Example 44: Synthesis of 5-{4-[4-(3,5-dimethyl-pyridin-2-yl)piperazine-1-carbonyl]-5-fluoro-2-methoxyphenyl}-5-isopropylimidazolidine-2,4-dione

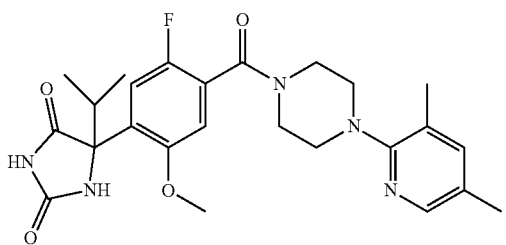 [SMILES: COc1cc(C(=O)N2CCN(c3ncc(C)cc3C)CC2)c(F)cc1C1(C(C)C)NC(=O)NC1=O]

To 2-fluoro-4-(4-isopropyl-2,5-dioxoimidazolidin-4-yl)-5-methoxybenzoic acid (310 mg) described in Preparation Example 59 were added tetrahydrofuran (10 mL), 1-ethyl-3-(3'-dimethylaminopropyl)carbodiimide.hydrochloride (230 mg), 1-hydroxybenzotriazole (162 mg), triethylamine (350 μL) and 1-(3,5-dimethylpyridin-2-yl)piperazine (230 mg) and the mixture was stirred at room temperature overnight. Water was added to the reaction mixture, and the precipitate was collected by filtration to give the title compound (380 mg).

MS(ESI) m/z: 484 (M+H)+

Example 45: Synthesis of 5-(1,1-difluoroethyl)-5-{4-[4-(3,5-dimethylpyridin-2-yl)piperazine-1-carbonyl]-2-methoxyphenyl}imidazolidine-2,4-dione

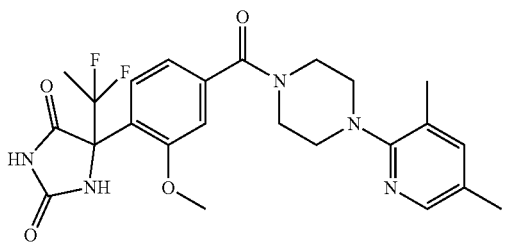 [SMILES: COc1cc(C(=O)N2CCN(c3ncc(C)cc3C)CC2)ccc1C1(C(C)(F)F)NC(=O)NC1=O]

To 4-[4-(1,1-difluoroethyl)-2,5-dioxo-imidazolidin-4-yl]-3-methoxybenzoic acid (157 mg) described in Preparation Example 60 were added tetrahydrofuran (5 mL), 1-ethyl-3-(3'-dimethylaminopropyl) carbodiimide.hydrochloride (115 mg), N,N-dimethylformamide (2 mL), 1-hydroxybenzotriazole (81 mg), triethylamine (175 μL) and 1-(3,5-dimethyl-pyridin-2-yl)piperazine (115 mg) and the mixture was stirred at room temperature overnight. Water was added to the reaction mixture and the mixture was extracted with chloroform. The solvent was evaporated and the obtained residue was purified by column chromatography (hexane:ethyl acetate) to give the title compound (77 mg).

MS(ESI) m/z: 488 (M+H)+

Example 46: Synthesis of 5-{4-[4-(3,5-dimethyl-pyridin-2-yl)piperazine-1-carbonyl]-5-fluoro-2-hydroxyphenyl}-5-isopropylimidazolidine-2,4-dione

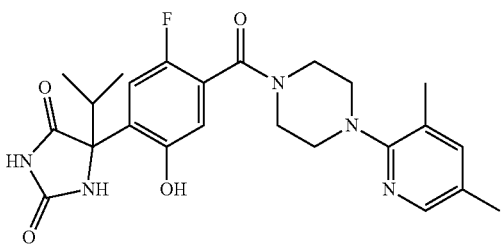 [SMILES: Cc1cnc(N2CCN(C(=O)c3cc(O)c(C4(C(C)C)NC(=O)NC4=O)cc3F)CC2)c(C)c1]

To 5-{4-[4-(3,5-dimethylpyridin-2-yl)piperazine-1-carbonyl]-5-fluoro-2-methoxyphenyl}-5-isopropylimidazolidine-2,4-dione (242 mg) described in Example 44 was added 1,2-dichloroethane (10 mL) and the mixture was cooled to 0° C. with stirring. A 1 mol/L boron tribromide dichloromethane solution (2.5 mL) was added, and the mixture was stirred at while raising the temperature to room temperature. Under microwave irradiation, the mixture was stirred at 40° C. for 1.5 hr and at 80° C. for 1.5 hr, toluene (2 mL) and 1 mol/L boron tribromide dichloromethane solution (2.5 mL) were added, and the mixture was stirred at 80° C. for 1.5 hr. After stirring at room temperature overnight, the reaction mixture was poured into aqueous sodium hydrogen carbonate solution and extracted with chloroform. The solvent was evaporated and the obtained residue was separated by HPLC using XBridge Phenyl (0.05% trifluoroacetic acid/water, 0.05% trifluoroacetic acid/acetonitrile). To the obtained solution was added aqueous sodium hydrogen carbonate solution and the mixture was extracted with ethyl acetate. The solvent was evaporated to give the title compound (21 mg).

MS(ESI) m/z: 470 (M+H)+

Example 47: Synthesis of 5-{4-[4-(3,5-dimethyl-pyridin-2-yl)piperazine-1-carbonyl]phenyl}-5-isopropyl-3-(4-methoxybenzyl) imidazolidine-2,4-dione

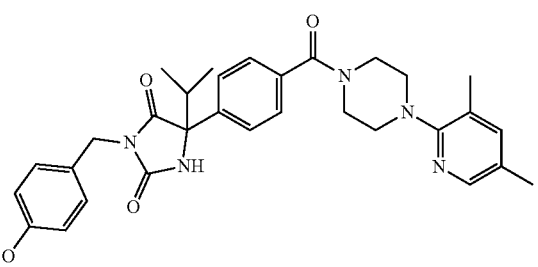

1) Synthesis of 5-{4-[4-(3,5-dimethylpyridin-2-yl)piperazine-1-carbonyl]phenyl}-5-isopropylimidazolidine-2,4-dione 4-(4-Isopropyl-2,5-dioxo-imidazolidin-4-yl)benzoic acid (180 mg) described in Preparation Example 5, 1-(3,5-dimethylpyridin-2-yl)piperazine (160 mg), 1-hydroxybenzotriazole (92 mg), 1-ethyl-3-(3'-dimethylaminopropyl)carbodiimide.hydrochloride (150 mg) and diisopropylethylamine (2.3 mL) were dissolved in N,N-dimethylformamide (7 mL) and the mixture was stirred at room temperature overnight. To the reaction mixture was added saturated aqueous sodium hydrogen carbonate solution and the mixture was extracted with ethyl acetate. The organic layer was washed with water and saturated brine, dried over anhydrous magnesium sulfate and concentrated under reduced pressure. The obtained residue was purified by NH column chromatography (chloroform:methanol) to give 5-{4-[4-(3,5-dimethylpyridin-2-yl)piperazine-1-carbonyl]phenyl}-5-isopropylimidazolidine-2,4-dione (240 mg).

MS (ESI) m/z: 436 (M+H)$^+$

2) Synthesis of 5-{4-[4-(3,5-dimethylpyridin-2-yl)piperazine-1-carbonyl]phenyl}-5-isopropyl-3-(4-methoxybenzyl)imidazolidine-2,4-dione To 5-{4-[4-(3,5-dimethylpyridin-2-yl)piperazine-1-carbonyl]phenyl}-5-isopropylimidazolidine-2,4-dione (217 mg, see the above-mentioned 1)) were added potassium carbonate (90 mg), N,N-dimethylformamide (5 mL), potassium iodide (8.3 mg) and 4-methoxybenzyl bromide (109 μL) and the mixture was stirred at room temperature. After completion of the reaction, water was added, and the precipitated solid was collected by filtration to give 5-{4-[4-(3,5-dimethylpyridin-2-yl)piperazine-1-carbonyl]phenyl}-5-isopropyl-3-(4-methoxybenzyl)imidazolidine-2,4-dione (278 mg).

MS(ESI) m/z: 556 (M+H)$^+$

Example 48: Synthesis of (R)-5-difluoromethyl-5-{4-[4-(3,5-dimethylpyridin-2-yl)piperazine-1-carbonyl]phenyl}imidazolidine-2,4-dione and (S)-5-difluoromethyl-5-{4-[4-(3,5-dimethylpyridin-2-yl)piperazine-1-carbonyl]phenyl}imidazolidine-2,4-dione

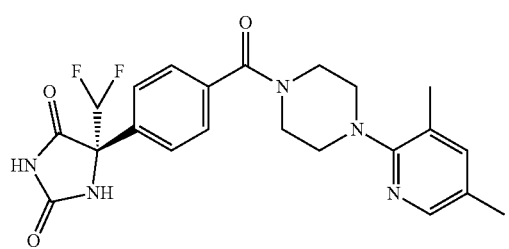

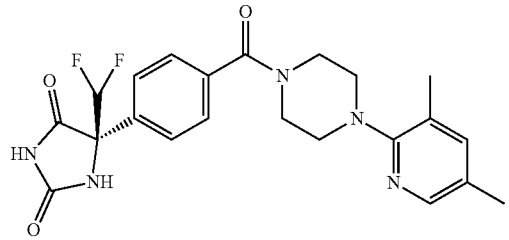

To 4-(4-difluoromethyl-2,5-dioxoimidazolidin-4-yl)benzoic acid (270 mg) described in Preparation Example 62 were added tetrahydrofuran (10 mL), 1-hydroxybenzotriazole (162 mg), 1-ethyl-3-(3'-dimethylaminopropyl)carbodiimide.hydrochloride (230 mg), triethylamine (350 μL), 1-(3,5-dimethylpyridin-2-yl)piperazine (230 mg) and N,N-dimethylformamide (3 mL) and the mixture was stirred at room temperature overnight. Water was added to the reaction mixture and the mixture was extracted with ethyl acetate. The solvent was evaporated and the obtained residue was purified by column chromatography (hexane:ethyl acetate) to give 5-difluoromethyl-5-{4-[4-(3,5-dimethylpyridin-2-yl)piperazine-1-carbonyl]phenyl}imidazolidine-2,4-dione (221 mg).

The obtained 5-difluoromethyl-5-{4-[4-(3,5-dimethylpyridin-2-yl)piperazine-1-carbonyl]phenyl}imidazolidine-2,4-dione (220 mg) was separated by HPLC using CHIRALPAK (Daicel) IF (2-propanol/tetrahydrofuran/diethylamine) to give the both enantiomers indicated above (compound with short retention time 57 mg (MS(ESI) m/z: 444 (M+H)$^+$) and compound with long retention time 94 mg (MS(ESI) m/z: 444 (M+H)$^+$).

In the analysis using CHIRALPAK (Daicel) IF-3 (4.6 mm×50 mm, 2-propanol/tetrahydrofuran/diethylamine=85/15/0.1, flow 0.5 mL/min), the retention time was respectively 5.6 min and 10.9 min.

Example 49: Synthesis of (R)-5-{4-[(S)-3-(3,5-dimethylpyridin-2-ylamino)pyrrolidine-1-carbonyl]phenyl}-5-isopropylimidazolidine-2,4-dione

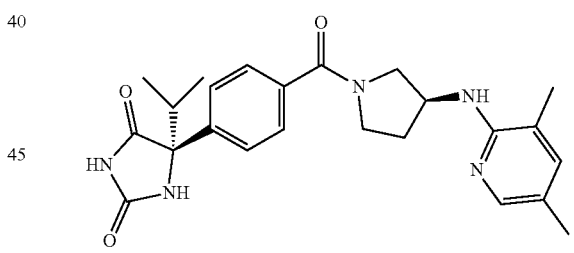

To 4-((R)-4-isopropyl-2,5-dioxoimidazolidin-4-yl)benzoic acid (136 mg) described in Preparation Example 45 were added tetrahydrofuran (5 mL), 1-ethyl-3-(3'-dimethylaminopropyl)carbodiimide.hydrochloride (115 mg), 1-hydroxybenzotriazole (81 mg), triethylamine (280 μL), (3,5-dimethyl-pyridin-2-yl)-(S)-pyrrolidin-3-ylamine.2 hydrochloride (158 mg) described in Preparation Example 88, and N,N-dimethylformamide (2 mL) and the mixture was stirred at room temperature overnight. Water was added to the reaction mixture and the mixture was extracted with ethyl acetate. The solvent was evaporated and the obtained residue was purified by column chromatography (chloroform:methanol) to give the title compound (131 mg).

MS(ESI) m/z: 436 (M+H)$^+$

Example 50: Synthesis of (R)-5-{4-[(S)-3-(3,5-dimethylpyridin-2-ylamino)pyrrolidine-1-carbonyl]phenyl}-5-ethylimidazolidine-2,4-dione

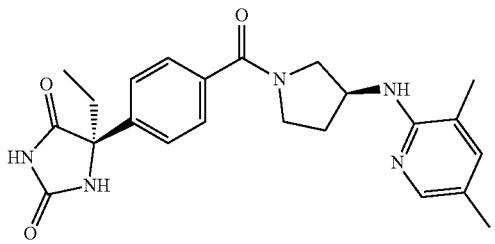 [SMILES: CC[C@]1(c2ccc(C(=O)N3CC[C@H](Nc4ncc(C)cc4C)C3)cc2)NC(=O)NC1=O]

Using 4-((R)-4-ethyl-2,5-dioxoimidazolidin-4-yl)benzoic acid (124 mg) described in Preparation Example 14 and (3,5-dimethyl-pyridin-2-yl)-(S)-pyrrolidin-3-ylamine.2 hydrochloride (158 mg) described in Preparation Example 88, reactions and treatments similar to those in Example 49 were performed to give the title compound (102 mg).
MS(ESI) m/z: 422 (M+H)+

Example 51: Synthesis of (R)-5-{4-[(S)-3-(3,5-dimethylpyridin-2-ylamino)pyrrolidine-1-carbonyl]phenyl}-5-methylimidazolidine-2,4-dione

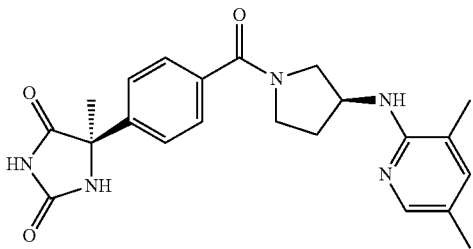 [SMILES: Cc1cnc(N[C@H]2CCN(C(=O)c3ccc([C@@]4(C)NC(=O)NC4=O)cc3)C2)c(C)c1]

Using 4-((R)-4-methyl-2,5-dioxoimidazolidin-4-yl)benzoic acid (117 mg) described in Preparation Example 6 and (3,5-dimethyl-pyridin-2-yl)-(S)-pyrrolidin-3-ylamine.2 hydrochloride (158 mg) described in Preparation Example 88, reactions and treatments similar to those in Example 49 were performed to give the title compound (45 mg).
MS(ESI) m/z: 408 (M+H)+

Example 52: Synthesis of (R)-5-{4-[(S)-4-(3,5-dimethylpyridin-2-yl)-2-methylpiperazine-1-carbonyl]phenyl}-5-isopropylimidazolidine-2,4-dione and (R)-5-{4-[(R)-4-(3,5-dimethylpyridin-2-yl)-2-methylpiperazine-1-carbonyl]phenyl}-5-isopropylimidazolidine-2,4-dione

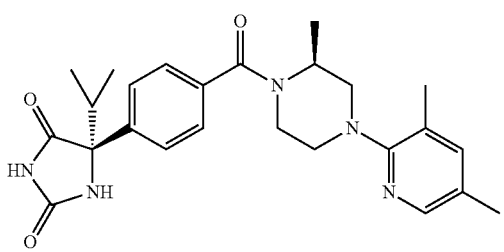

-continued

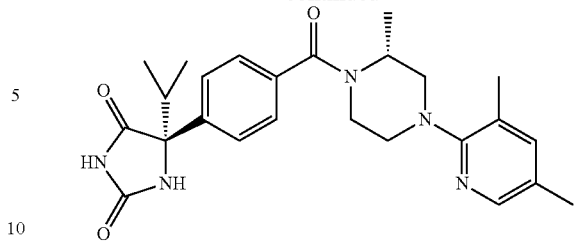

To 4-((R)-4-isopropyl-2,5-dioxoimidazolidin-4-yl)benzoic acid (262 mg) described in Preparation Example 45 were added tetrahydrofuran (10 mL), 1-ethyl-3-(3'-dimethylaminopropyl)carbodiimide.hydrochloride (230 mg), 1-hydroxybenzotriazole (162 mg), triethylamine (350 μL), 1-(3,5-dimethylpyridin-2-yl)-3-methylpiperazine (226 mg) described in Preparation Example 110 and N,N-dimethylformamide (3 mL) and the mixture was stirred at room temperature overnight. Water was added to the reaction mixture and the mixture was extracted with ethyl acetate. The solvent was evaporated and the obtained residue was purified by column chromatography (hexane:ethyl acetate) to give (R)-5-{4-[4-(3,5-dimethylpyridin-2-yl)-2-methylpiperazine-1-carbonyl]phenyl}-5-isopropylimidazolidine-2,4-dione (339 mg).

The obtained (R)-5-{4-[4-(3,5-dimethylpyridin-2-yl)-2-methylpiperazine-1-carbonyl]phenyl}-5-isopropylimidazolidine-2,4-dione (150 mg) was separated by HPLC using CHIRALPAK (Daicel) IF (ethanol/tetrahydrofuran/diethylamine) to give the both diastereomers indicated above (compound with short retention time 71.8 mg (MS(ESI) m/z: 450 (M+H)+) and compound with long retention time 63.8 mg (MS(ESI) m/z: 450 (M+H)+).

In the analysis using CHIRALPAK (Daicel) IF-3 (4.6 mm×150 mm, ethanol/tetrahydrofuran/diethylamine=90/10/0.1, flow 0.5 mL/min), the retention time was respectively 11.8 min and 13.5 min.

Example 53: Synthesis of (R)-5-{4-[(S)-3-(3,5-dimethylpyridin-2-ylamino)pyrrolidine-1-carbonyl]phenyl}-5-fluoromethylimidazolidine-2,4-dione and (S)-5-{4-[(S)-3-(3,5-dimethylpyridin-2-ylamino)pyrrolidine-1-carbonyl]phenyl}-5-fluoromethylimidazolidine-2,4-dione

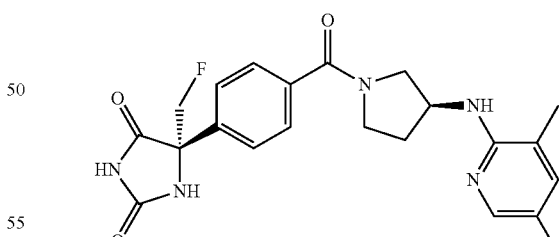

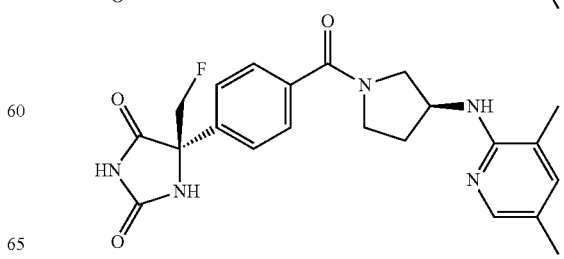

To 4-(4-fluoromethyl-2,5-dioxoimidazolidin-4-yl)benzoic acid (126 mg) described in Preparation Example 63 were added (3,5-dimethyl-pyridin-2-yl)-(S)-pyrrolidin-3-ylamine.2 hydrochloride (158.5 mg) described in Preparation Example 88, tetrahydrofuran (5 mL), 1-ethyl-3-(3'-dimethylaminopropyl)carbodiimide.hydrochloride (115 mg), 1-hydroxybenzotriazole (81 mg), triethylamine (315 μL) and N,N-dimethylformamide (1.5 mL) and the mixture was stirred at room temperature overnight. Water was added to the reaction mixture and the mixture was extracted with ethyl acetate. The solvent was evaporated and the obtained residue was purified by column chromatography (chloroform:methanol) to give 5-{4-[(S)-3-(3,5-dimethylpyridin-2-ylamino)pyrrolidine-1-carbonyl]phenyl}-5-fluoromethyl-imidazolidine-2,4-dione (95 mg).

The obtained 5-{4-[(S)-3-(3,5-dimethylpyridin-2-ylamino)pyrrolidine-1-carbonyl]phenyl}-5-fluoromethyl-imidazolidine-2,4-dione (55 mg) was separated by HPLC using CHIRALPAK (Daicel) IC (hexane/ethanol/diethylamine) to give the both diastereomers indicated above (compound with short retention time 13.5 mg (MS(ESI) m/z: 426 (M+H)$^+$) and compound with long retention time 14.1 mg (MS(ESI) m/z: 426 (M+H)$^+$)).

In the analysis using CHIRALPAK (Daicel) IC-3 (4.6 mm×150 mm, hexane/ethanol/diethylamine=10/90/0.1, flow 0.5 mL/min), the retention time was respectively 5.7 min and 10.1 min.

Example 54: Synthesis of (R)-5-{4-[(R)-4-(3,5-dimethylpyridin-2-yl)-3-methylpiperazine-1-carbonyl]phenyl}-5-isopropylimidazolidine-2,4-dione

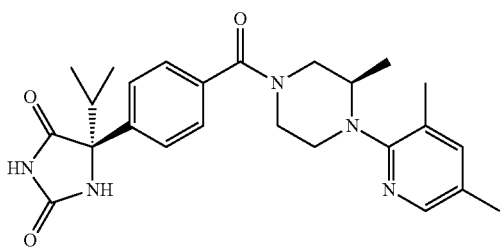 [SMILES: Cc1cnc(N2CCN(C(=O)c3ccc([C@@]4(C(C)C)NC(=O)NC4=O)cc3)C[C@H]2C)c(C)c1]

To 4-((R)-4-isopropyl-2,5-dioxoimidazolidin-4-yl)benzoic acid (186 mg) described in Preparation Example 45 were added (R)-1-(3,5-dimethylpyridin-2-yl)-2-methylpiperazine.2 hydrochloride (198 mg) described in Preparation Example 111, tetrahydrofuran (7 mL), 1-hydroxybenzotriazole (144 mg), 1-ethyl-3-(3'-dimethylaminopropyl) carbodiimide.hydrochloride (204 mg), triethylamine (446 μL) and N,N-dimethylformamide (1 mL) and the mixture was stirred at room temperature overnight. Water was added to the reaction mixture and the mixture was extracted with ethyl acetate. The solvent was evaporated and the obtained residue was purified by column chromatography (ethyl acetate:hexane) to give the title compound (220 mg).

MS(ESI) m/z: 450 (M+H)$^+$

Example 55: Synthesis of (R)-5-{4-[4-(3,5-dimethylpyridin-2-yl)piperazine-1-carbonyl]phenyl}-5-fluoromethylimidazolidine-2,4-dione and (S)-5-{4-[4-(3,5-dimethylpyridin-2-yl)piperazine-1-carbonyl]phenyl}-5-fluoromethylimidazolidine-2,4-dione

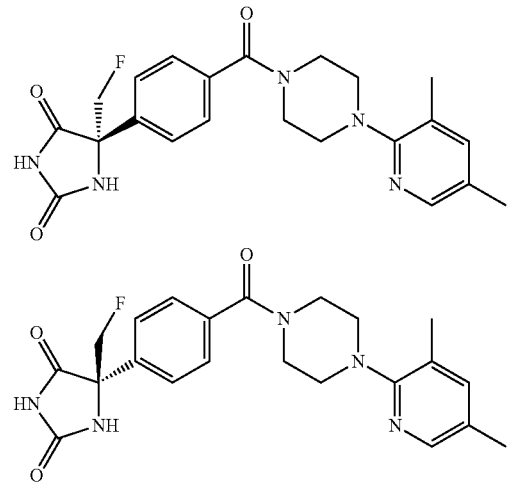

To 4-(4-fluoromethyl-2,5-dioxoimidazolidin-4-yl)benzoic acid (252 mg) described in Preparation Example 63 were added 1-(3,5-dimethylpyridin-2-yl)piperazine (230 mg), tetrahydrofuran (10 mL), 1-hydroxybenzotriazole (162 mg), 1-ethyl-3-(3'-dimethylaminopropyl)carbodiimide.hydrochloride (230 mg), triethylamine (350 μL) and N,N-dimethylformamide (1.5 mL) and the mixture was stirred at room temperature overnight. Water was added to the reaction mixture and the mixture was extracted with ethyl acetate. The solvent was evaporated and the obtained residue was purified by column chromatography (hexane:ethyl acetate) to give 5-{4-[4-(3,5-dimethylpyridin-2-yl)piperazine-1-carbonyl]phenyl}-5-fluoromethylimidazolidine-2,4-dione (288 mg).

The obtained 5-{4-[4-(3,5-dimethylpyridin-2-yl)piperazine-1-carbonyl]phenyl}-5-fluoromethylimidazolidine-2,4-dione (200 mg) was separated by HPLC using CHIRALPAK (Daicel) IF (2-propanol/tetrahydrofuran/diethylamine) to give the both enantiomers indicated above (compound with short retention time 85 mg (MS(ESI) m/z: 426 (M+H)$^+$) and compound with long retention time 80 mg (MS(ESI) m/z: 426 (M+H)$^+$).

In the analysis using CHIRALPAK (Daicel) IF-3 (4.6 mm×50 mm, 2-propanol/tetrahydrofuran/diethylamine=80/20/0.1, flow 0.5 mL/min), the retention time was respectively 5.5 min and 8.9 min.

Example 56: Synthesis of (R)-5-{4-[(R)-3-(3,5-dimethylpyridin-2-ylamino)pyrrolidine-1-carbonyl]phenyl}-5-isopropylimidazolidine-2,4-dione

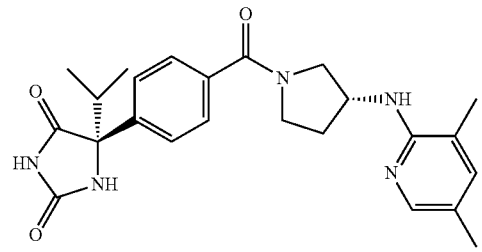 [SMILES: Cc1cnc(N[C@@H]2CCN(C(=O)c3ccc([C@@]4(C(C)C)NC(=O)NC4=O)cc3)C2)c(C)c1]

To 4-((R)-4-isopropyl-2,5-dioxoimidazolidin-4-yl)benzoic acid (131 mg) described in Preparation Example 45 were added (3,5-dimethylpyridin-2-yl)-(R)-pyrrolidin-3-ylamine (131 mg) described in Preparation Example 113, tetrahydrofuran (5 mL), 1-ethyl-3-(3'-dimethylaminopropyl)carbodiimide.hydrochloride (143 mg), 1-hydroxybenzotriazole (101 mg), triethylamine (174 µL) and N,N-dimethylformamide (0.5 mL) and the mixture was stirred at room temperature overnight. Water was added to the reaction mixture and the mixture was extracted with ethyl acetate. The solvent was evaporated and the obtained residue was purified by column chromatography (chloroform:methanol) to give the title compound as a crude product. The obtained crude product was separated by HPLC using Cosmosil Cholester (0.05% trifluoroacetic acid/water, 0.05% trifluoroacetic acid/acetonitrile). To the obtained solution was added saturated aqueous sodium hydrogen carbonate solution, and the mixture was extracted with chloroform. The solvent was evaporated to give the title compound (103 mg).
MS(ESI) m/z: 436 (M+H)+

Example 57: Synthesis of (S)-5-{4-[(S)-3-(3,5-dimethylpyridin-2-ylamino)pyrrolidine-1-carbonyl]phenyl}-5-isopropylimidazolidine-2,4-dione

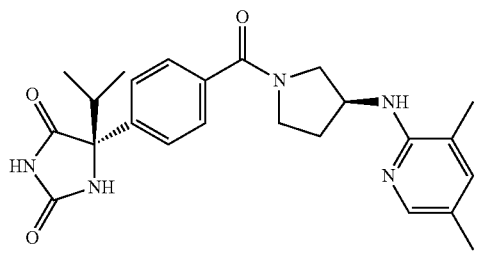 [SMILES: Cc1cnc(N[C@H]2CCN(C(=O)c3ccc([C@]4(C(C)C)NC(=O)NC4=O)cc3)C2)c(C)c1]

To 4-((S)-4-isopropyl-2,5-dioxoimidazolidin-4-yl)benzoic acid) (131 mg) described in Preparation Example 114 were added (3,5-dimethyl-pyridin-2-yl)-(S)-pyrrolidin-3-ylamine.2 hydrochloride (158 mg) described in Preparation Example 88, tetrahydrofuran (5 mL), 1-ethyl-3-(3'-dimethylaminopropyl)carbodiimide.hydrochloride (115 mg), 1-hydroxybenzotriazole (81 mg), triethylamine (315 µL) and N,N-dimethylformamide (1 mL) and the mixture was stirred at room temperature overnight. Water was added to the reaction mixture, and the mixture was extracted with ethyl acetate and chloroform. The solvent was evaporated and the obtained residue was purified by column chromatography (chloroform:methanol) to give the title compound (159 mg).
MS(ESI) m/z: 436 (M+H)+

Example 58: Synthesis of 5-{4-[(S)-4-(3,5-dimethylpyridin-2-yl)-3-methylpiperazine-1-carbonyl]phenyl}-5-fluoromethylimidazolidine-2,4-dione

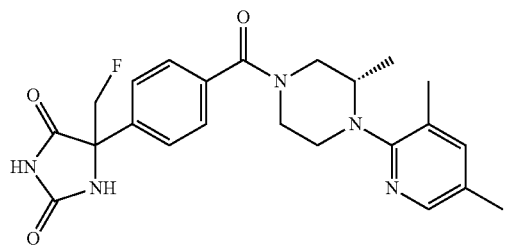 [SMILES: Cc1cnc(N2CCN(C(=O)c3ccc(C4(CF)NC(=O)NC4=O)cc3)C[C@@H]2C)c(C)c1]

To 4-(4-fluoromethyl-2,5-dioxoimidazolidin-4-yl)benzoic acid (76 mg) described in Preparation Example 63 were added (S)-1-(3,5-dimethylpyridin-2-yl)-2-methylpiperazine.2 hydrochloride (116 mg) described in Preparation Example 131, tetrahydrofuran (3 mL), 1-ethyl-3-(3'-dimethylaminopropyl)carbodiimide.hydrochloride (75 mg), 1-hydroxybenzotriazole (53 mg) and triethylamine (189 µL) and the mixture was stirred at room temperature overnight. Water was added to the reaction mixture, and the mixture was extracted with ethyl acetate and chloroform. The solvent was evaporated and the obtained residue was purified by column chromatography (hexane:ethyl acetate) to give the title compound (65 mg).
MS(ESI) m/z: 440 (M+H)+

Example 59: Synthesis of (R)-5-{4-[4-(3,5-dimethylpyridin-2-yl)-2,2-dimethylpiperazine-1-carbonyl]phenyl}-5-isopropylimidazolidine-2,4-dione

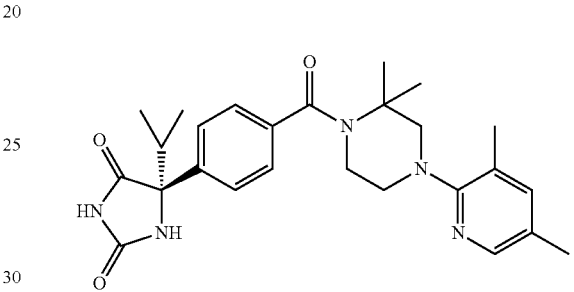

To 4-((R)-4-isopropyl-2,5-dioxoimidazolidin-4-yl)benzoic acid (169 mg) described in Preparation Example 45 were added 1-(3,5-dimethylpyridin-2-yl)-3,3-dimethylpiperazine.2 hydrochloride (198 mg) described in Preparation Example 116, tetrahydrofuran (6.4 mL), 1-ethyl-3-(3'-dimethylaminopropyl)carbodiimide.hydrochloride (160 mg), 1-hydroxybenzotriazole (105 mg), triethylamine (405 µL) and N,N-dimethylformamide (2 mL) and the mixture was stirred at room temperature overnight. Water was added to the reaction mixture, and the precipitate was collected by filtration to give the title compound (219 mg).
MS(ESI) m/z: 464 (M+H)+

Example 60: Synthesis of (R)-5-{4-[(S)-4-(3,5-dimethylpyridin-2-yl)-3-methylpiperazine-1-carbonyl]phenyl}-5-methylimidazolidine-2,4-dione

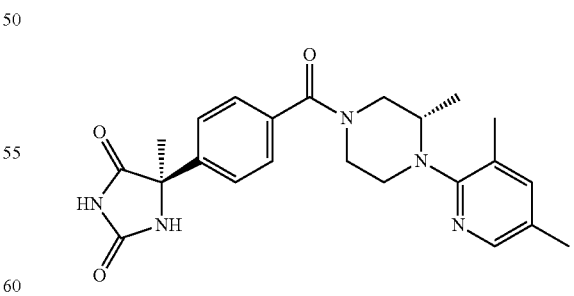

To 4-((R)-4-methyl-2,5-dioxoimidazolidin-4-yl)benzoic acid (70 mg) described in Preparation Example 6 were added (S)-1-(3,5-dimethylpyridin-2-yl)-2-methylpiperazine.2 hydrochloride (83 mg) described in Preparation Example 131, tetrahydrofuran (3 mL), 1-ethyl-3-(3'-dimethylaminopropyl)carbodiimide.hydrochloride (75 mg), 1-hydroxybenzotriazole (50 mg), triethylamine (189 µL) and N,N-dimethylformamide (2 mL) and the mixture was stirred at room temperature overnight. Water was added to the reaction mixture, and the mixture was extracted with ethyl acetate and chloroform. The solvent was evaporated and the obtained residue was purified by column chromatography (ethyl acetate:hexane) to give the title compound (30 mg).

MS(ESI) m/z: 422 (M+H)⁺

Example 61: Synthesis of (R)-5-{4-[(R)-4-(3,5-dimethylpyridin-2-yl)-2-methylpiperazine-1-carbonyl]phenyl}-5-methylimidazolidine-2,4-dione

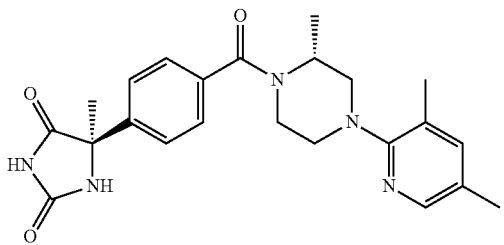 [SMILES: Cc1cnc(N2CCN(C(=O)c3ccc([C@@]4(C)NC(=O)NC4=O)cc3)[C@H](C)C2)c(C)c1]

To 4-((R)-4-methyl-2,5-dioxoimidazolidin-4-yl)benzoic acid (70 mg) described in Preparation Example 6 were added (R)-1-(3,5-dimethylpyridin-2-yl)-3-methylpiperazine.2 hydrochloride (87 mg) described in Preparation Example 118, N,N-dimethylformamide (4 mL), 1-ethyl-3-(3'-dimethylaminopropyl)carbodiimide.hydrochloride (75 mg), 1-hydroxybenzotriazole (53 mg) and triethylamine (189 µL) and the mixture was stirred at room temperature overnight. Water was added to the reaction mixture, and the mixture was extracted with ethyl acetate and chloroform. The solvent was evaporated and the obtained residue was purified by column chromatography (ethyl acetate:hexane) to give the title compound (46 mg).

MS(ESI) m/z: 422 (M+H)⁺

Example 62: Synthesis of (R)-5-fluoromethyl-5-{4-[4-(5-methylpyridin-2-ylamino)piperidine-1-carbonyl]phenyl}imidazolidine-2,4-dione and (S)-5-fluoromethyl-5-{4-[4-(5-methylpyridin-2-ylamino)piperidine-1-carbonyl]phenyl}imidazolidine-2,4-dione

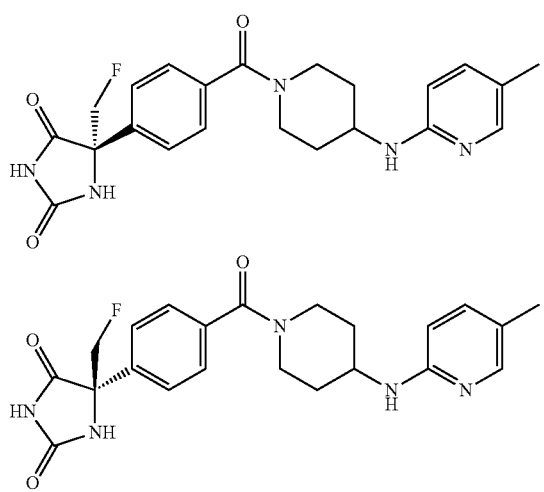

To 4-(4-fluoromethyl-2,5-dioxoimidazolidin-4-yl)benzoic acid (76 mg) described in Preparation Example 63 were added tetrahydrofuran (3 mL), (5-methylpyridin-2-yl)piperidin-4-ylamine (57 mg), 1-ethyl-3-(3'-dimethylaminopropyl) carbodiimide.hydrochloride (75 mg), 1-hydroxybenzotriazole (53 mg), triethylamine (105 µL) and N,N-dimethylformamide (1 mL) and the mixture was stirred at room temperature overnight. Water was added to the reaction mixture, and the mixture was extracted with ethyl acetate and chloroform. The solvent was evaporated and the obtained residue was purified by column chromatography (chloroform:methanol) to give 5-fluoromethyl-5-{4-[4-(5-methylpyridin-2-ylamino)piperidine-1-carbonyl]phenyl}imidazolidine-2,4-dione (62.2 mg).

The obtained 5-fluoromethyl-5-{4-[4-(5-methylpyridin-2-ylamino)piperidine-1-carbonyl]phenyl}imidazolidine-2,4-dione (40 mg) was separated by HPLC using CHIRALPAK (Daicel) IC (hexane/2-propanol/tetrahydrofuran/diethylamine) to give the both enantiomers indicated above (compound with short retention time 13.5 mg (MS(ESI) m/z: 426 (M+H)⁺) and compound with long retention time 12.7 mg (MS(ESI) m/z: 426 (M+H)⁺)).

In the analysis using CHIRALPAK (Daicel) IC-3 (4.6 mm×150 mm, hexane/2-propanol/tetrahydrofuran/diethylamine=60/20/20/0.1, flow 0.5 mL/min), the retention time was respectively 6.7 min and 11.6 min.

Example 63: Synthesis of 5-{4-[(R)-4-(3,5-dimethylpyridin-2-yl)-2-methylpiperazine-1-carbonyl]phenyl}-5-fluoromethylimidazolidine-2,4-dione

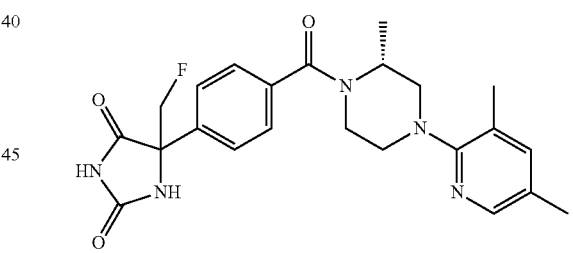

To 4-(4-fluoromethyl-2,5-dioxoimidazolidin-4-yl)benzoic acid (76 mg) described in Preparation Example 63 were added (R)-1-(3,5-dimethylpyridin-2-yl)-3-methylpiperazine (80 mg) described in Preparation Example 119, tetrahydrofuran (3 mL), 1-ethyl-3-(3'-dimethylaminopropyl) carbodiimide.hydrochloride (75 mg), 1-hydroxybenzotriazole (53 mg) and triethylamine (210 µL) and the mixture was stirred at room temperature overnight. Water was added to the reaction mixture, and the mixture was extracted with ethyl acetate and chloroform. The solvent was evaporated and the obtained residue was purified by column chromatography (ethyl acetate:hexane) to give the title compound (75 mg).

MS(ESI) m/z: 440 (M+H)⁺

Example 64: Synthesis of (S)-4-(3,5-dimethylpyridin-2-yl)-1-[4-((R)-4-isopropyl-2,5-dioxoimidazolidin-4-yl)benzoyl]piperazine-2-carboxylic acid methyl ester

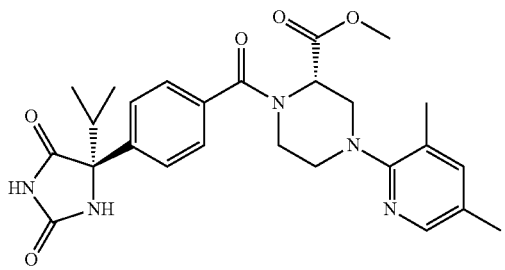 [SMILES: COC(=O)[C@@H]1CN(c2ncc(C)cc2C)CCN1C(=O)c1ccc([C@@]2(C(C)C)NC(=O)NC2=O)cc1]

To (S)-4-(3,5-dimethylpyridin-2-yl)piperazine-2-carboxylic acid methyl ester (620 mg) described in Preparation Example 130 were added 4-((R)-4-isopropyl-2,5-dioxoimidazolidin-4-yl)benzoic acid (465 mg) described in Preparation Example 45, tetrahydrofuran (18 mL), 1-ethyl-3-(3'-dimethylaminopropyl)carbodiimide.hydrochloride (440 mg), 1-hydroxybenzotriazole (310 mg) and triethylamine (620 μL) and the mixture was stirred at room temperature overnight. Water was added to the reaction mixture, and the mixture was extracted with ethyl acetate and chloroform. The solvent was evaporated and the obtained residue was purified by column chromatography (chloroform:methanol) to give the title compound (581 mg).

MS(ESI) m/z: 494 (M+H)$^+$

Example 65: Synthesis of (R)-5-{4-[8-(3,5-dimethylpyridin-2-yl)-5,8-diazaspiro[3.5]nonane-5-carbonyl]phenyl}-5-isopropylimidazolidine-2,4-dione

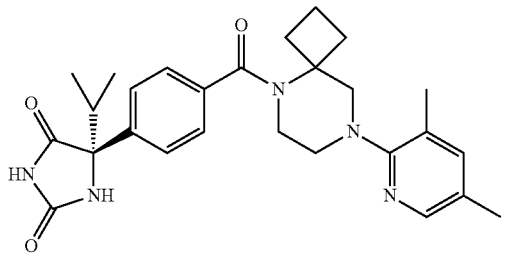 [SMILES: Cc1cnc(N2CCN(C(=O)c3ccc([C@@]4(C(C)C)NC(=O)NC4=O)cc3)C3(CCC3)C2)c(C)c1]

To a solution of 5,8-diazaspiro[3.5]nonane.2 hydrochloride (199 mg) and 3,5-dimethylpyridine-N-oxide (117 mg) in tetrahydrofuran (4 mL) were added N,N-diisopropylethylamine (980 μL) and bromotris(pyrrolidino)phosphonium hexafluorophosphate (606 mg) and the mixture was stirred at room temperature overnight. To the reaction mixture were added N,N-diisopropylethylamine (341 μL), 4-((R)-4-isopropyl-2,5-dioxoimidazolidin-4-yl)benzoic acid (262 mg) described in Preparation Example 45, and bromotris(pyrrolidino)phosphonium hexafluorophosphate (466 mg) and the mixture was stirred at room temperature for 8 hr. Water was added to the reaction mixture, and the mixture was extracted with ethyl acetate and chloroform. The solvent was evaporated and the obtained residue was purified by column chromatography (ethyl acetate:hexane) to give the title compound (89.2 mg).

MS(ESI) m/z: 476 (M+H)$^+$

Example 66: Synthesis of (R)-5-{4-[4-(3,5-dimethylpyridin-2-yl)-3-methoxymethylpiperazine-1-carbonyl]phenyl}-5-isopropylimidazolidine-2,4-dione

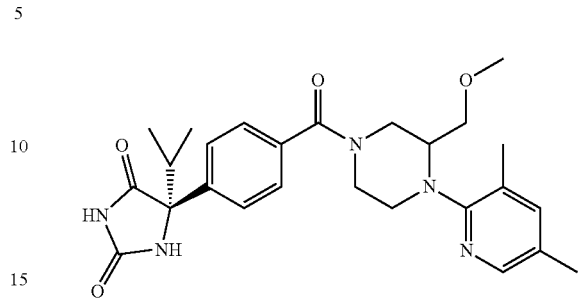

To 4-((R)-4-isopropyl-2,5-dioxoimidazolidin-4-yl)benzoic acid (52 mg) described in Preparation Example 45 were added 1-(3,5-dimethylpyridin-2-yl)-2-methoxymethylpiperazine.2 hydrochloride (62 mg) described in Preparation Example 121, tetrahydrofuran (2 mL), 1-ethyl-3-(3'-dimethylaminopropyl)carbodiimide.hydrochloride (50 mg), 1-hydroxybenzotriazole (35 mg) and triethylamine (126 μL) and the mixture was stirred at room temperature overnight. Water was added to the reaction mixture, and the mixture was extracted with ethyl acetate and chloroform. The solvent was evaporated and the obtained residue was purified by column chromatography (ethyl acetate:hexane) to give the title compound (53 mg).

MS (ESI) m/z: 480 (M+H)$^+$

Example 67: Synthesis of (R)-5-{4-[(R)-4-(3,5-dimethylpyridin-2-yl)-2-ethylpiperazine-1-carbonyl]phenyl}-5-isopropylimidazolidine-2,4-dione

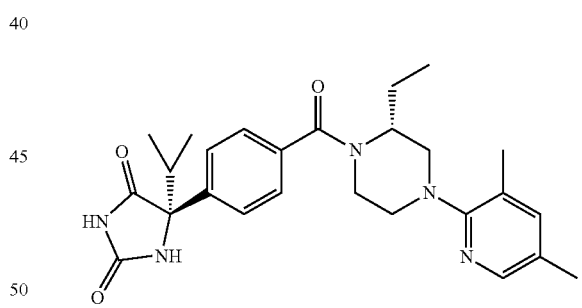

To 4-((R)-4-isopropyl-2,5-dioxoimidazolidin-4-yl)benzoic acid (131 mg) described in Preparation Example 45 were added (R)-1-(3,5-dimethylpyridin-2-yl)-3-ethylpiperazine (109 mg) described in Preparation Example 122, tetrahydrofuran (5 mL), 1-ethyl-3-(3'-dimethylaminopropyl)carbodiimide.hydrochloride (125 mg), 1-hydroxybenzotriazole (88 mg) and triethylamine (178 μL) and the mixture was stirred at room temperature for 5.5 hr. Water was added to the reaction mixture and the mixture was extracted with ethyl acetate. The solvent was evaporated and the obtained residue was purified by column chromatography (ethyl acetate:hexane) to give the title compound (132 mg).

MS (ESI) m/z: 464 (M+H)$^+$

Example 68: Synthesis of (R)-5-{4-[4-(3,5-dimethylpyridin-2-yl)-2,2-dimethylpiperazine-1-carbonyl]phenyl}-5-methylimidazolidine-2,4-dione

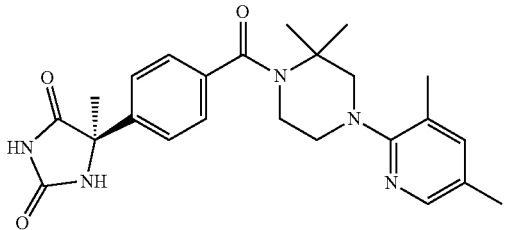 [SMILES: Cc1cnc(N2CCN(C(=O)c3ccc([C@@]4(C)NC(=O)NC4=O)cc3)C(C)(C)C2)c(C)c1]

To 1-(3,5-dimethylpyridin-2-yl)-3,3-dimethylpiperazine.2 hydrochloride (88 mg) described in Preparation Example 116 were added tetrahydrofuran (3 mL), 4-((R)-4-methyl-2,5-dioxoimidazolidin-4-yl)benzoic acid (70 mg) described in Preparation Example 6, triethylamine (189 μL), 1-ethyl-3-(3'-dimethylaminopropyl)carbodiimide.hydrochloride (75 mg) and 1-hydroxybenzotriazole (53 mg) and the mixture was stirred at room temperature overnight. Water was added to the reaction mixture and the mixture was extracted with ethyl acetate. The solvent was evaporated and the obtained residue was purified by column chromatography (ethyl acetate:hexane) to give the title compound (87 mg).

MS(ESI) m/z: 436 (M+H)$^+$

Example 69: Synthesis of 5-{4-[4-(3,5-dimethylpyridin-2-yl)-2,2-dimethylpiperazine-1-carbonyl]phenyl}-5-fluoromethylimidazolidine-2,4-dione

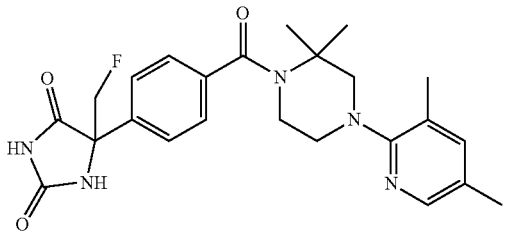 [SMILES: Cc1cnc(N2CCN(C(=O)c3ccc(C4(CF)NC(=O)NC4=O)cc3)C(C)(C)C2)c(C)c1]

To 1-(3,5-dimethylpyridin-2-yl)-3,3-dimethylpiperazine.2 hydrochloride (146 mg) described in Preparation Example 116 were added tetrahydrofuran (5 mL), 4-(4-fluoromethyl-2,5-dioxoimidazolidin-4-yl)benzoic acid (126 mg) described in Preparation Example 63, triethylamine (314 μL), 1-ethyl-3-(3'-dimethylaminopropyl)carbodiimide.hydrochloride (125 mg) and 1-hydroxybenzotriazole (88 mg) and the mixture was stirred at room temperature overnight. Water was added to the reaction mixture and the mixture was extracted with ethyl acetate. The solvent was evaporated and the obtained residue was purified by column chromatography (ethyl acetate:hexane) to give the title compound (112 mg).

MS(ESI) m/z: 454 (M+H)$^+$

Example 70: Synthesis of (R)-5-{4-[(S)-4-(3,5-dimethylpyridin-2-yl)-2-methoxymethylpiperazine-1-carbonyl]phenyl}-5-isopropylimidazolidine-2,4-dione

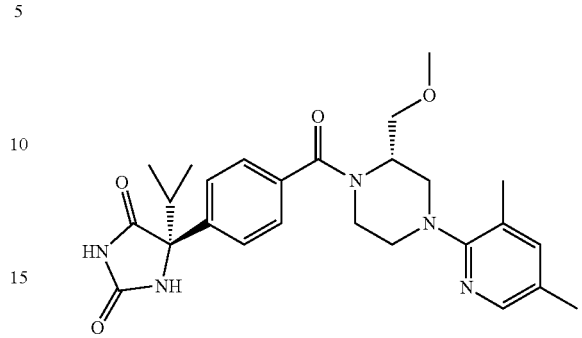

(S)-4-(3,5-dimethylpyridin-2-yl)-2-methoxymethylpiperazine-1-carboxylic acid tert-butyl ester (97 mg) described in Preparation Example 124 was dissolved in methyl acetate (1.5 mL) and methanol (1.5 mL) and 4N hydrogen chloride/ethyl acetate solution (1.5 mL) was added and the mixture was stirred at room temperature overnight. The solvent was evaporated, tetrahydrofuran (3 mL), triethylamine (182 μL), 4-((R)-4-isopropyl-2,5-dioxoimidazolidin-4-yl)benzoic acid (76 mg) described in Preparation Example 45, 1-ethyl-3-(3'-dimethylaminopropyl)carbodiimide.hydrochloride (72 mg) and 1-hydroxybenzotriazole (51 mg) were added to the obtained residue, and the mixture was stirred at room temperature overnight. Water was added to the reaction mixture and the mixture was extracted with ethyl acetate. The solvent was evaporated and the obtained residue was purified by column chromatography (ethyl acetate:hexane) to give the title compound (46 mg).

MS (ESI) m/z: 480 (M+H)$^+$

Example 71: Synthesis of (R)-5-{4-[8-(3,5-dimethylpyridin-2-yl)-5,8-diazaspiro[3.5]nonane-5-carbonyl]phenyl}-5-methylimidazolidine-2,4-dione

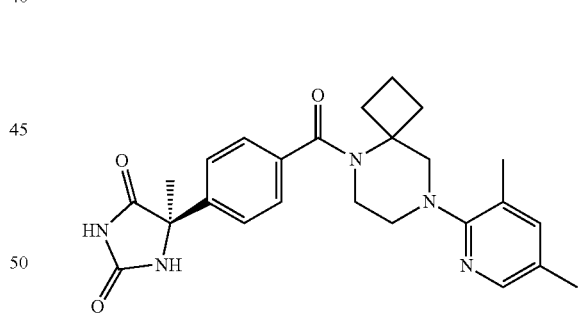

To 4-((R)-4-methyl-2,5-dioxoimidazolidin-4-yl)benzoic acid (70 mg) described in Preparation Example 6 were added tetrahydrofuran (3 mL), 8-(3,5-dimethylpyridin-2-yl)-5,8-diazaspiro[3.5]nonane (70 mg) described in Preparation Example 125, 1-ethyl-3-(3'-dimethylaminopropyl)carbodiimide.hydrochloride (75 mg), 1-hydroxybenzotriazole (53 mg) and triethylamine (105 μL) and the mixture was stirred at room temperature overnight. Water was added to the reaction mixture and the mixture was extracted with ethyl acetate. The solvent was evaporated and the obtained residue was purified by column chromatography (ethyl acetate:hexane) to give the title compound (76 mg).

MS(ESI) m/z: 448 (M+H)$^+$

Example 72: Synthesis of 5-{4-[(S)-4-(3,5-dimethylpyridin-2-yl)-2-methylpiperazine-1-carbonyl]phenyl}-5-fluoromethylimidazolidine-2,4-dione

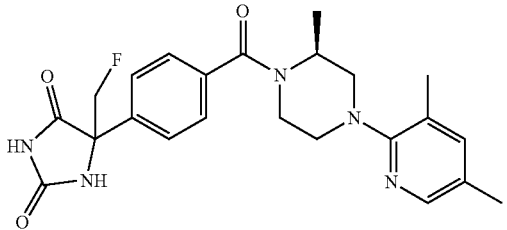 [SMILES: Cc1cnc(N2CCN(C(=O)c3ccc(C4(CF)NC(=O)NC4=O)cc3)[C@@H](C)C2)c(C)c1]

To 4-(4-fluoromethyl-2,5-dioxoimidazolidin-4-yl)benzoic acid (76 mg) described in Preparation Example 63 were added tetrahydrofuran (3 mL), (S)-1-(3,5-dimethylpyridin-2-yl)-3-methylpiperazine (62 mg) described in Preparation Example 126, triethylamine (105 µL), 1-ethyl-3-(3'-dimethylaminopropyl)carbodiimide.hydrochloride (75 mg) and 1-hydroxybenzotriazole (53 mg) and the mixture was stirred at room temperature overnight. Water was added to the reaction mixture and the mixture was extracted with ethyl acetate. The solvent was evaporated and the obtained residue was purified by column chromatography (ethyl acetate: methanol) to give the title compound (71 mg).

MS (ESI) m/z: 440 (M+H)$^+$

Example 73: Synthesis of (R)-5-{4-[(R)-4-(3,5-dimethylpyridin-2-yl)-3-hydroxymethylpiperazine-1-carbonyl]phenyl}-5-isopropylimidazolidine-2,4-dione

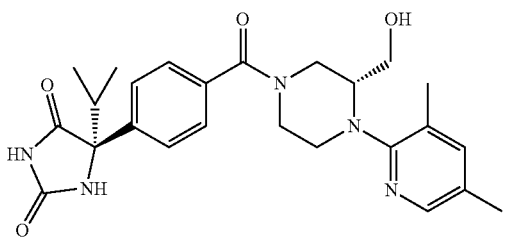 [SMILES: Cc1cnc(N2CCN(C(=O)c3ccc([C@@]4(C(C)C)NC(=O)NC4=O)cc3)C[C@@H]2CO)c(C)c1]

To [(R)-1-(3,5-dimethylpyridin-2-yl)piperazin-2-yl]methanol (110 mg) described in Preparation Example 127 were added 4-((R)-4-isopropyl-2,5-dioxoimidazolidin-4-yl)benzoic acid (130 mg) described in Preparation Example 45, tetrahydrofuran (5 mL), 1-ethyl-3-(3'-dimethylaminopropyl)carbodiimide.hydrochloride (125 mg), 1-hydroxybenzotriazole (90 mg) and triethylamine (175 µL) and the mixture was stirred at room temperature overnight. Water was added to the reaction mixture and the mixture was extracted with ethyl acetate. The solvent was evaporated and the obtained residue was purified by column chromatography (chloroform:methanol) to give the title compound (115 mg).

MS(ESI) m/z: 466 (M+H)$^+$

Example 74: Synthesis of (R)-5-{4-[(S)-4-(3,5-dimethylpyridin-2-yl)-3-hydroxymethylpiperazine-1-carbonyl]phenyl}-5-isopropylimidazolidine-2,4-dione

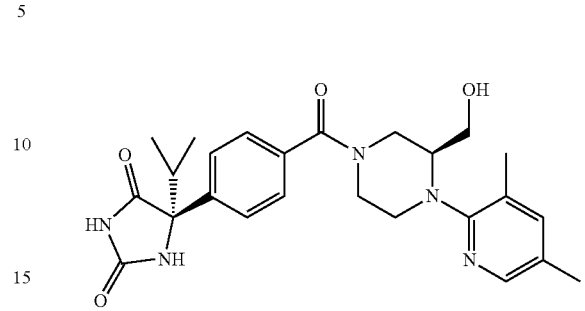

To [(S)-1-(3,5-dimethylpyridin-2-yl)piperazin-2-yl]methanol.2 hydrochloride (88 mg) described in Preparation Example 128 were added 4-((R)-4-isopropyl-2,5-dioxoimidazolidin-4-yl)benzoic acid (80 mg) described in Preparation Example 45, tetrahydrofuran (3 mL), 1-ethyl-3-(3'-dimethylaminopropyl) carbodiimide.hydrochloride (75 mg), 1-hydroxybenzotriazole (53 mg) and triethylamine (188 µL) and the mixture was stirred at room temperature overnight. Water was added to the reaction mixture, and the mixture was extracted with ethyl acetate and chloroform. The solvent was evaporated and the obtained residue was purified by column chromatography (ethyl acetate:methanol) to give the title compound (60 mg).

MS(ESI) m/z: 466 (M+H)$^+$

Example 75: Synthesis of (R)-5-isopropyl-5-{4-[4-(7-methylbenzoxazol-2-yl)piperidine-1-carbonyl]phenyl}imidazolidine-2,4-dione

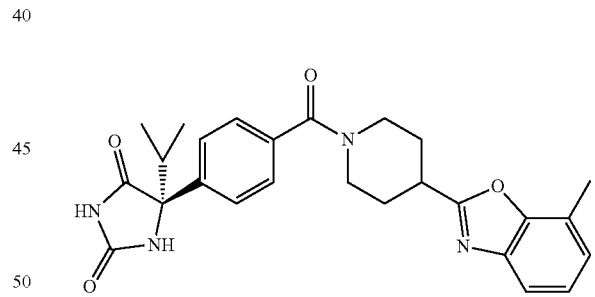

To 4-((R)-4-isopropyl-2,5-dioxoimidazolidin-4-yl)benzoic acid (79 mg) described in Preparation Example 45 were added 7-methyl-2-(piperidin-4-yl)-1,3-benzoxazole (65 mg), tetrahydrofuran (3 mL), 1-ethyl-3-(3'-dimethylaminopropyl)carbodiimide.hydrochloride (86 mg), 1-hydroxybenzotriazole (60 mg) and the mixture was stirred at room temperature overnight. Water was added to the reaction mixture, and the mixture was extracted with ethyl acetate and chloroform. The solvent was evaporated and the obtained residue was purified by column chromatography (ethyl acetate:hexane) to give the title compound (82 mg).

MS(ESI) m/z: 461 (M+H)$^+$

Example 76: Synthesis of (R)-5-methyl-5-{4-[4-(5-p-tolyl[1,3,4]oxadiazol-2-yl)piperidine-1-carbonyl]phenyl}imidazolidine-2,4-dione

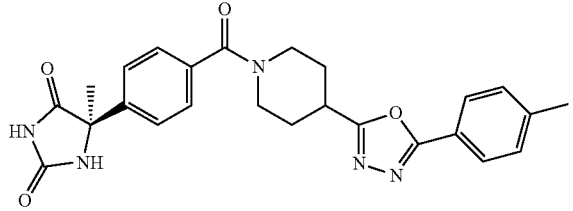 [SMILES: Cc1ccc(-c2nnc(C3CCN(C(=O)c4ccc([C@@]5(C)NC(=O)NC5=O)cc4)CC3)o2)cc1]

To 4-((R)-4-methyl-2,5-dioxoimidazolidin-4-yl)benzoic acid (117 mg) described in Preparation Example 6 were added 4-[5-(4-methylphenyl)-1,3,4-oxadiazol-2-yl]piperidine (73 mg), tetrahydrofuran (3 mL), 1-ethyl-3-(3'-dimethylaminopropyl)carbodiimide.hydrochloride (75 mg), 1-hydroxybenzotriazole (53 mg) and triethylamine (105 μL) and the mixture was stirred at room temperature. After completion of the reaction, water was added to the reaction mixture, and the mixture was extracted with ethyl acetate and chloroform. The solvent was evaporated and the obtained residue was purified by column chromatography (ethyl acetate:methanol) to give the title compound (85.3 mg).

MS (ESI) m/z: 460 (M+H)+

Example 77: Synthesis of (R)-5-ethyl-5-{4-[4-(5-o-tolyl[1,3,4]oxadiazol-2-yl)piperidine-1-carbonyl]phenyl}imidazolidine-2,4-dione

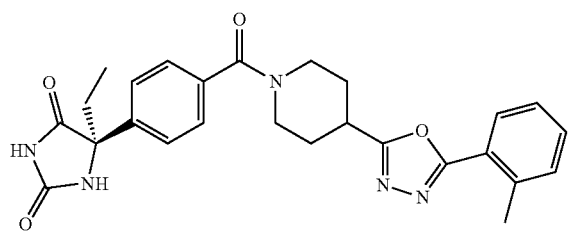 [SMILES: CC[C@]1(c2ccc(C(=O)N3CCC(c4nnc(-c5ccccc5C)o4)CC3)cc2)NC(=O)NC1=O]

To 4-((R)-4-ethyl-2,5-dioxo-imidazolidin-4-yl)benzoic acid (50 mg) described in Preparation Example 14 were added 4-[5-(2-methylphenyl)-1,3,4-oxadiazol-2-yl]piperidine (48 mg), tetrahydrofuran (2 mL), 1-ethyl-3-(3'-dimethylaminopropyl)carbodiimide.hydrochloride (58 mg), 1-hydroxybenzotriazole (40 mg) and triethylamine (70 UL) and the mixture was stirred at room temperature overnight. Water was added to the reaction mixture, and the mixture was extracted with ethyl acetate and chloroform. The solvent was evaporated and the obtained residue was purified by column chromatography (chloroform:methanol) to give the title compound (90 mg).

MS(ESI) m/z: 474 (M+H)+

Example 78: Synthesis of 5-fluoromethyl-5-{4-[4-(5-o-tolyl[1,3,4]oxadiazol-2-yl)piperidine-1-carbonyl]phenyl}imidazolidine-2,4-dione

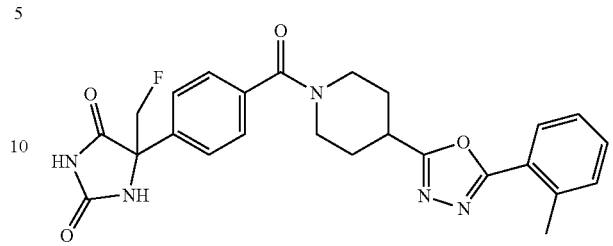

Using 4-[5-(2-methylphenyl)-1,3,4-oxadiazol-2-yl]piperidine (48 mg) and 4-(4-fluoromethyl-2,5-dioxo-imidazolidin-4-yl)benzoic acid (46 mg) described in Preparation Example 63, reactions and treatments similar to those in Example 77 were performed to give the title compound (67 mg).

MS(ESI) m/z: 478 (M+H)+

Example 79: Synthesis of (R)-5-isopropyl-5-{4-[4-(5-phenyl[1,3,4]oxadiazol-2-yl)piperidine-1-carbonyl]phenyl}imidazolidine-2,4-dione

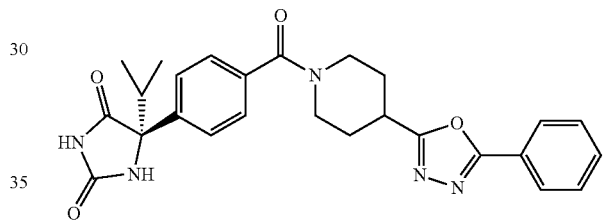

To 4-((R)-4-isopropyl-2,5-dioxoimidazolidin-4-yl)benzoic acid (79 mg) described in Preparation Example 45 were added 4-(5-phenyl-1,3,4-oxadiazol-2-yl)piperidine (70 mg), tetrahydrofuran (3 mL), 1-ethyl-3-(3'-dimethylaminopropyl)carbodiimide.hydrochloride (75 mg), 1-hydroxybenzotriazole (53 mg), triethylamine (105 μL) and N,N-dimethylformamide (0.3 mL) and the mixture was stirred at room temperature overnight. Water was added to the reaction mixture, and the mixture was extracted with ethyl acetate and chloroform. The solvent was evaporated and the obtained residue was purified by column chromatography (chloroform:methanol) to give the title compound (85 mg).

MS(ESI) m/z: 474 (M+H)+

Example 80: Synthesis of (R)-5-{4-[(S)-4-(3,5-dimethylpyridin-2-yl)-3-methylpiperazine-1-carbonyl]phenyl}-5-isopropylimidazolidine-2,4-dione

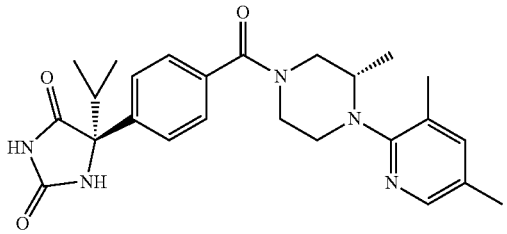

(S)-4-(3,5-dimethylpyridin-2-yl)-3-methylpiperazine-1-carboxylic acid tert-butyl ester (140 mg) described in Preparation Example 115 was dissolved in ethanol (2.5 mL), 4N hydrogen chloride/ethyl acetate solution (2.5 mL) was added, and the mixture was stirred at room temperature. After completion of the reaction, water and 1N aqueous sodium hydroxide solution were added, and the mixture was extracted with ethyl acetate. The solvent was evaporated to give (S)-1-(3,5-dimethylpyridin-2-yl)-2-methylpiperazine (103 mg).

To the obtained (S)-1-(3,5-dimethylpyridin-2-yl)-2-methylpiperazine (103 mg) were added 4-((R)-4-isopropyl-2,5-dioxoimidazolidin-4-yl)benzoic acid (128 mg) described in Preparation Example 45, tetrahydrofuran (5 mL), 1-ethyl-3-(3'-dimethylaminopropyl)carbodiimide.hydrochloride (115 mg), 1-hydroxybenzotriazole (81 mg), triethylamine (174 µL) and N,N-dimethylformamide (2 mL) and the mixture was stirred at room temperature overnight. Water was added to the reaction mixture and the mixture was extracted with ethyl acetate. The solvent was evaporated and the obtained residue was purified by column chromatography (hexane:ethyl acetate) to give the title compound (97 mg).

MS(ESI) m/z: 450 (M+H)$^+$

Example 81: Synthesis of (R)-5-isopropyl-5-{4-[4-(5-p-tolyl[1,3,4]oxadiazol-2-yl)piperidine-1-carbonyl]phenyl}imidazolidine-2,4-dione

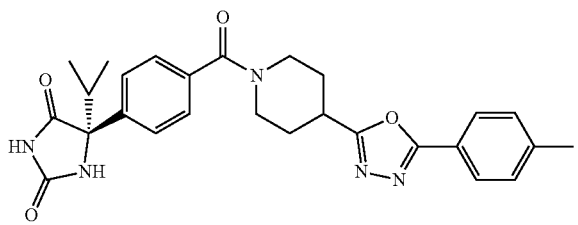 [SMILES: Cc1ccc(-c2nnc(C3CCN(C(=O)c4ccc([C@@]5(C(C)C)NC(=O)NC5=O)cc4)CC3)o2)cc1]

To 4-((R)-4-isopropyl-2,5-dioxoimidazolidin-4-yl)benzoyl chloride (126 mg) described in Preparation Example 132 were added pyridine (1.5 mL), 4-[5-(4-methylphenyl)-1,3,4-oxadiazol-2-yl]piperidine.trifluoroacetate (102 mg) and the mixture was stirred at 80° C. for 8 hr. Water was added to the reaction mixture, and the mixture was extracted with ethyl acetate and chloroform. The solvent was evaporated and the obtained residue was purified by column chromatography (ethyl acetate:methanol) to give the title compound (70 mg).

MS(ESI) m/z: 488 (M+H)$^+$

Example 82: Synthesis of (R)-5-isopropyl-5-{4-[4-(5-o-tolyl[1,3,4]oxadiazol-2-yl)piperidine-1-carbonyl]phenyl}imidazolidine-2,4-dione

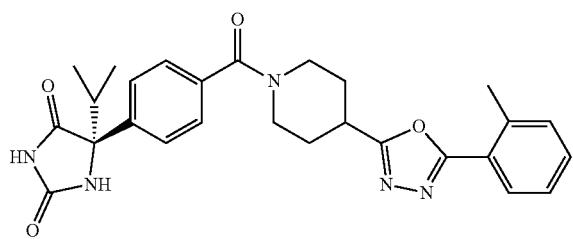 [SMILES: Cc1ccccc1-c1nnc(C2CCN(C(=O)c3ccc([C@@]4(C(C)C)NC(=O)NC4=O)cc3)CC2)o1]

Using 4-[5-(2-methylphenyl)-1,3,4-oxadiazol-2-yl]piperidine.trifluoroacetate (102 mg) and 4-((R)-4-isopropyl-2,5-dioxoimidazolidin-4-yl)benzoyl chloride (210 mg) described in Preparation Example 132, reactions and treatments similar to those in Example 81 were performed to give the title compound (65 mg).

MS(ESI) m/z: 488 (M+H)$^+$

Example 83: Synthesis of (S)-4-(3,5-dimethylpyridin-2-yl)-1-[4-((R)-4-isopropyl-2,5-dioxoimidazolidin-4-yl)benzoyl]piperazine-2-carbonitrile

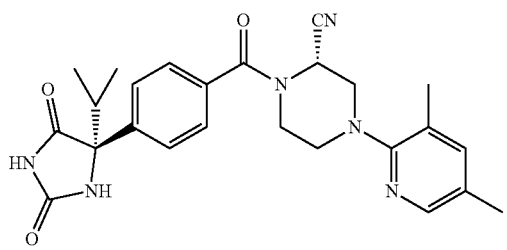 [SMILES: Cc1cnc(N2CCN(C(=O)c3ccc([C@@]4(C(C)C)NC(=O)NC4=O)cc3)[C@H](C#N)C2)c(C)c1]

Using (S)-2-carbamoyl-4-(3,5-dimethylpyridin-2-yl)piperazine-1-carboxylic acid tert-butyl ester (420 mg) described in Preparation Example 133 and 4-((R)-4-isopropyl-2,5-dioxoimidazolidin-4-yl)benzoic acid (328 mg) described in Preparation Example 45, reactions and treatments similar to those in Example 70 were performed to give (S)-4-(3,5-dimethylpyridin-2-yl)-1-[4-((R)-4-isopropyl-2,5-dioxoimidazolidin-4-yl)benzoyl]piperazine-2-carboxylic acid amide (390 mg) (MS(ESI) m/z: 479 (M+H)$^+$).

To a solution of the obtained (S)-4-(3,5-dimethylpyridin-2-yl)-1-[4-((R)-4-isopropyl-2,5-dioxoimidazolidin-4-yl)benzoyl]piperazine-2-carboxylic acid amide (300 mg) and triethylamine (524 µL) in tetrahydrofuran (3.1 mL) was added trifluoroacetic anhydride (260 µL) at 0° C. The mixture was stirred at room temperature overnight and triethylamine (262 µL) and trifluoroacetic anhydride (130 µL) were added, and the mixture was stirred at 0° C. for 2 hr. To the reaction mixture were added potassium carbonate (650 mg) and water (1 mL) and the mixture was stirred at 40° C. for 0.5 hr. Water was added to the reaction mixture and the mixture was extracted with chloroform. The solvent was evaporated and the obtained residue was purified by column chromatography (ethyl acetate:hexane) to give the title compound (162 mg).

MS(ESI) m/z: 461 (M+H)$^+$

Example 84: Synthesis of 5-{4-[4-(2,4-dimethylphenyl)piperidine-1-carbonyl]phenyl}-5-methylimidazolidine-2,4-dione

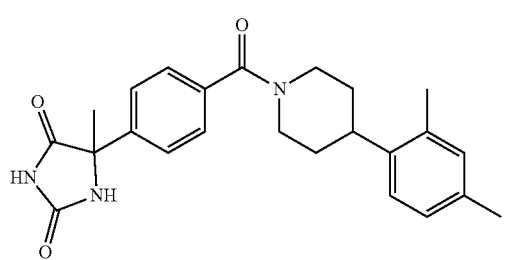 [SMILES: Cc1ccc(C2CCN(C(=O)c3ccc(C4(C)NC(=O)NC4=O)cc3)CC2)c(C)c1]

To a mixture of 4-(4-methyl-2,5-dioxoimidazolidin-4-yl)benzoic acid (70 mg), 4-(2,4-dimethylphenyl)piperidine.hydrochloride (68 mg) described in Preparation Example 82, 1-hydroxybenzotriazole (49 mg) and chloroform (2 ml) were added triethylamine (0.050 ml) and 1-ethyl-3-(3'-dimethylaminopropyl)carbodiimide.hydrochloride (75 mg) and the mixture was stirred at room temperature for 2 days. To the reaction mixture was added ethyl acetate, and the organic layer was washed with saturated brine and dried over sodium sulfate. The solvent was evaporated under reduced pressure. To the obtained residue was added hexane/ethyl acetate, and the precipitate was collected by filtration to give the title compound (83 mg).

MS(ESI) m/z: 406 (M+H)+

Example 85: Synthesis of 5-{4-[4-(3,5-dimethylpyridin-2-yl)piperazine-1-carbonyl]-3-fluorophenyl}-5-methylimidazolidine-2,4-dione

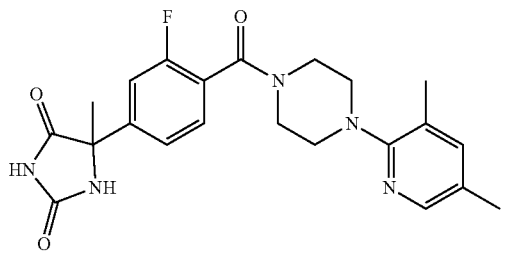 [SMILES: Cc1cnc(N2CCN(C(=O)c3ccc(C4(C)NC(=O)NC4=O)cc3F)CC2)c(C)c1]

To a mixture of 2-fluoro-4-(4-methyl-2,5-dioxoimidazolidin-4-yl)benzoic acid (93 mg) described in Preparation Example 2, 1-(3,5-dimethylpyridin-2-yl)piperazine (70 mg), 1-hydroxybenzotriazole (59 mg) and chloroform (2 ml) was added 1-ethyl-3-(3'-dimethylaminopropyl)carbodiimide.hydrochloride (91 mg) and the mixture was stirred at room temperature for 2 days. The reaction mixture was purified by NH column chromatography (chloroform:methanol) and column chromatography (chloroform:methanol) to give the title compound (105.9 mg).

MS(ESI) m/z: 426 (M+H)+

Example 86: Synthesis of (S)-5-{4-[4-(3,5-dimethylpyridin-2-yl) piperazine-1-carbonyl]phenyl}-5-methoxymethylimidazolidine-2,4-dione and (R)-5-{4-[4-(3,5-dimethylpyridin-2-yl)piperazine-1-carbonyl]phenyl}-5-methoxymethylimidazolidine-2,4-dione

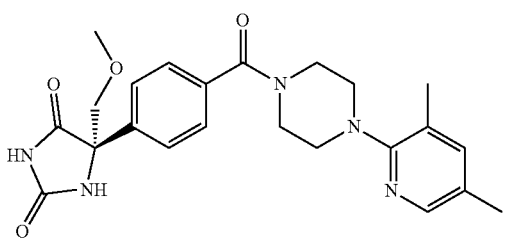

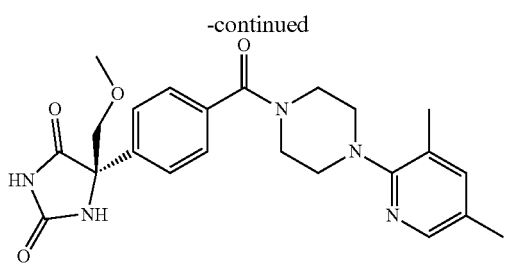

To a mixture of 4-(4-methoxymethyl-2,5-dioxoimidazolidin-4-yl)benzoic acid (113 mg) described in Preparation Example 9, 1-(3,5-dimethylpyridin-2-yl)piperazine (90 mg), 1-hydroxybenzotriazole (69 mg) and chloroform (3 ml) was added 1-ethyl-3-(3'-dimethylaminopropyl)carbodiimide.hydrochloride (123 mg) and the mixture was stirred at room temperature for 2 days. The reaction mixture was purified by NH column chromatography (chloroform:methanol) and column chromatography (chloroform:methanol) to give 5-{4-[4-(3,5-dimethylpyridin-2-yl)piperazine-1-carbonyl]phenyl}-5-methoxymethylimidazolidine-2,4-dione (129 mg).

The obtained 5-{4-[4-(3,5-dimethylpyridin-2-yl)piperazine-1-carbonyl]phenyl}-5-methoxymethylimidazolidine-2,4-dione (100 mg) was separated by HPLC using CHIRALPAK (Daicel) IC (ethanol/diethylamine) to give the both enantiomers indicated above (compound with short retention time 44 mg (MS(ESI) m/z: 438 (M+H)+) and compound with long retention time 44 mg (MS(ESI) m/z: 438 (M+H)+)).

In the analysis using CHIRALPAK (Daicel) IC-3 (4.6 mm×150 mm, ethanol/diethylamine=100/0.1, flow 0.5 mL/min), the retention time was respectively 9.3 min and 14.8 min.

Example 87: Synthesis of 5-{4-[4-(3,5-dimethylpyridin-2-yl)piperazine-1-carbonyl]phenyl}-5-trifluoromethylimidazolidine-2,4-dione

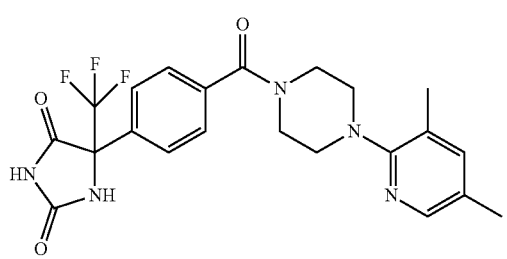 [SMILES: Cc1cnc(N2CCN(C(=O)c3ccc(C4(C(F)(F)F)NC(=O)NC4=O)cc3)CC2)c(C)c1]

To a mixture of 4-(2,5-dioxo-4-trifluoromethylimidazolidin-4-yl)benzoic acid (123 mg) described in Preparation Example 10, 1-(3,5-dimethylpyridin-2-yl)piperazine (90 mg), 1-hydroxybenzotriazole (69 mg) and chloroform (3 ml) was added 1-ethyl-3-(3'-dimethylaminopropyl)carbodiimide.hydrochloride (123 mg) and the mixture was stirred at room temperature for 2 days. The reaction mixture was purified by NH column chromatography (chloroform:methanol) and column chromatography (chloroform:methanol) to give the title compound (83 mg).

MS (ESI) m/z: 462 (M+H)+

Example 88: Synthesis of 5-cyclopropyl-5-{4-[4-(3,5-dimethylpyridin-2-yl)piperazine-1-carbonyl]phenyl}imidazolidine-2,4-dione

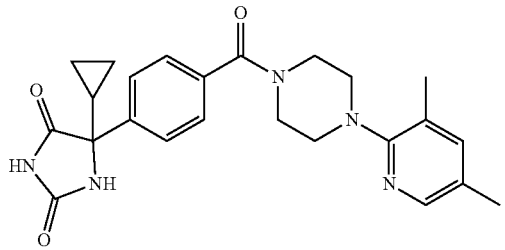 [SMILES: Cc1cnc(N2CCN(C(=O)c3ccc(C4(C5CC5)NC(=O)NC4=O)cc3)CC2)c(C)c1]

To a mixture of 4-(4-cyclopropyl-2,5-dioxoimidazolidin-4-yl)benzoic acid (111 mg) described in Preparation Example 11, 1-(3,5-dimethylpyridin-2-yl)piperazine (90 mg), 1-hydroxybenzotriazole (69 mg) and chloroform (3 ml) was added 1-ethyl-3-(3'-dimethylaminopropyl)carbodiimide.hydrochloride (123 mg) and the mixture was stirred at room temperature for 2 days. The reaction mixture was purified by NH column chromatography (chloroform:methanol) and column chromatography (chloroform:methanol) to give the title compound (102 mg).

MS(ESI) m/z: 434 (M+H)+

Example 89: Synthesis of 5-{4-[4-(5-cyclopropyl-3-methylpyridin-2-yl) piperazine-1-carbonyl]-3-fluorophenyl}-5-ethylimidazolidine-2,4-dione

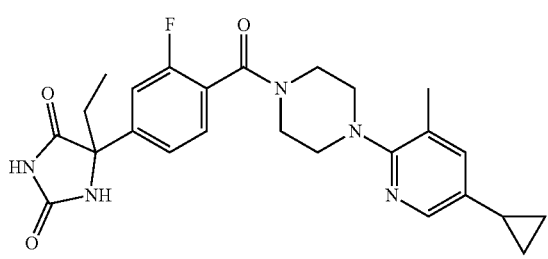 [SMILES: CCC1(c2ccc(C(=O)N3CCN(c4ncc(C5CC5)cc4C)CC3)c(F)c2)NC(=O)NC1=O]

To a mixture of 4-(4-ethyl-2,5-dioxoimidazolidin-4-yl)-2-fluorobenzoic acid (150 mg) described in Preparation Example 12, 1-(5-cyclopropyl-3-methylpyridin-2-yl)piperazine (246 mg), 1-hydroxybenzotriazole (114 mg), triethylamine (0.235 ml) and chloroform (3 ml) was added 1-ethyl-3-(3'-dimethylaminopropyl) carbodiimide.hydrochloride (216 mg) and the mixture was stirred at room temperature for 2 days. The reaction mixture was purified by NH column chromatography (chloroform:methanol) and column chromatography (chloroform:methanol) to give the title compound (115 mg).

MS(ESI) m/z: 466 (M+H)+

Example 90: Synthesis of 5-tert-butyl-5-{4-[4-(3,5,6-trimethylpyridin-2-yl)piperazine-1-carbonyl]phenyl}imidazolidine-2,4-dione

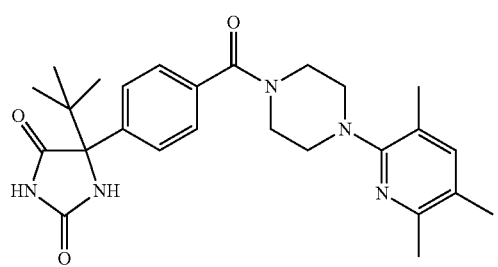 [SMILES: Cc1cc(C)c(N2CCN(C(=O)c3ccc(C4(C(C)(C)C)NC(=O)NC4=O)cc3)CC2)nc1C]

To a mixture of 4-(4-tert-butyl-2,5-dioxoimidazolidin-4-yl)benzoic acid (120 mg) described in Preparation Example 13, 1-(3,5,6-trimethylpyridin-2-yl)piperazine (134 mg), 1-hydroxybenzotriazole (76 mg), triethylamine (0.121 ml) and chloroform (3 ml) was added 1-ethyl-3-(3'-dimethylaminopropyl)carbodiimide.hydrochloride (125 mg) and the mixture was stirred at room temperature for 2 days. Water was added to the reaction mixture, and the mixture was extracted with ethyl acetate. The organic layer was washed with saturated brine, dried over sodium sulfate, and the solvent was evaporated. The obtained residue was purified by column chromatography (chloroform:methanol) and NH column chromatography (chloroform:methanol) to give the title compound (192 mg).

MS(ESI) m/z: 464 (M+H)+

Example 91: Synthesis of 5-tert-butyl-5-{4-[4-(5-cyclopropyl-3-methylpyridin-2-yl)piperazine-1-carbonyl]phenyl}imidazolidine-2,4-dione

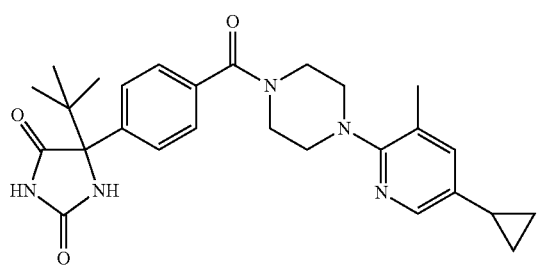 [SMILES: Cc1cc(C2CC2)cnc1N1CCN(C(=O)c2ccc(C3(C(C)(C)C)NC(=O)NC3=O)cc2)CC1]

Using 4-(4-tert-butyl-2,5-dioxoimidazolidin-4-yl)benzoic acid (120 mg) described in Preparation Example 13 and 1-(5-cyclopropyl-3-methylpyridin-2-yl)piperazine (142 mg), reactions and treatments similar to those in Example 90 were performed to give the title compound (160 mg).

MS(ESI) m/z: 476 (M+H)+

Example 92: Synthesis of 5-{4-[4-(3,5-dimethyl-pyridin-2-yl) piperazine-1-carbonyl]phenyl}-5-hydroxymethylimidazolidine-2,4-dione

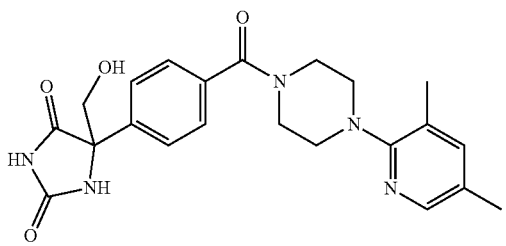 [SMILES: Cc1cnc(N2CCN(C(=O)c3ccc(C4(CO)NC(=O)NC4=O)cc3)CC2)c(C)c1]

To a mixture of 4-(4-hydroxymethyl-2,5-dioxoimidazolidin-4-yl)benzoic acid (125 mg) described in Preparation Example 23, 1-(3,5-dimethylpyridin-2-yl)piperazine.hydrochloride (228 mg), 1-hydroxybenzotriazole (101 mg), triethylamine (0.279 ml), chloroform (3 ml) and N,N-dimethylformamide (1 ml) was added 1-ethyl-3-(3'-dimethylaminopropyl)carbodiimide.hydrochloride (153 mg) and the mixture was stirred at room temperature for 16 hr. The reaction mixture was purified by NH column chromatography (chloroform:methanol) to give the title compound (89 mg).

MS(ESI) m/z: 424 (M+H)+

Example 93: Synthesis of 5-ethyl-5-{3-fluoro-4-[4-(3,5,6-trimethylpyridin-2-yl)piperazine-1-carbonyl]phenyl}imidazolidine-2,4-dione

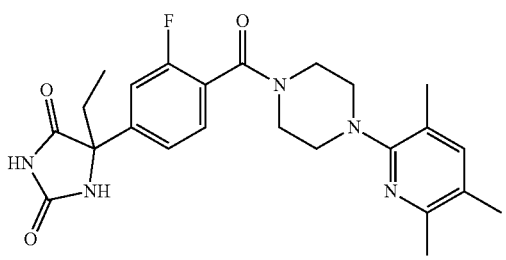 [SMILES: CCC1(c2ccc(C(=O)N3CCN(c4nc(C)c(C)cc4C)CC3)c(F)c2)NC(=O)NC1=O]

Using 4-(4-ethyl-2,5-dioxoimidazolidin-4-yl)-2-fluorobenzoic acid (150 mg) described in Preparation Example 12 and 1-(3,5,6-trimethylpyridin-2-yl)piperazine (232 mg), reactions and treatments similar to those in Example 89 were performed to give the title compound (183 mg).

MS(ESI) m/z: 454 (M+H)+

Example 94: Synthesis of 5-{4-[4-(3,5-dimethyl-pyridin-2-yl)piperazine-1-carbonyl]-3-fluorophenyl}-5-ethylimidazolidine-2,4-dione

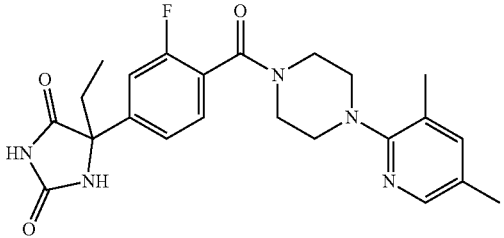 [SMILES: CCC1(c2ccc(C(=O)N3CCN(c4ncc(C)cc4C)CC3)c(F)c2)NC(=O)NC1=O]

Using 4-(4-ethyl-2,5-dioxoimidazolidin-4-yl)-2-fluorobenzoic acid (150 mg) described in Preparation Example 12 and 1-(3,5-dimethylpyridin-2-yl)piperazine (215 mg), reactions and treatments similar to those in Example 89 were performed to give the title compound (103 mg).

MS (ESI) m/z: 440 (M+H)+

Example 95: Synthesis of 5-tert-butyl-5-{4-[4-(3,5-dimethylpyridin-2-yl) piperazine-1-carbonyl]phenyl}imidazolidine-2,4-dione

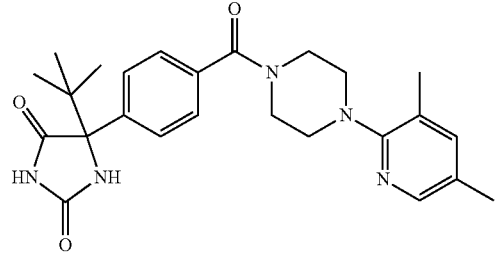 [SMILES: Cc1cnc(N2CCN(C(=O)c3ccc(C4(C(C)(C)C)NC(=O)NC4=O)cc3)CC2)c(C)c1]

To a mixture of 4-(4-tert-butyl-2,5-dioxoimidazolidin-4-yl)benzoic acid (120 mg) described in Preparation Example 13, 1-(3,5-dimethylpyridin-2-yl)piperazine (125 mg), 1-hydroxybenzotriazole (76 mg), triethylamine (0.121 ml) and chloroform (3 ml) was added 1-ethyl-3-(3'-dimethylaminopropyl)carbodiimide.hydrochloride (125 mg) and the mixture was stirred at room temperature for 2 days. The reaction mixture was purified by column chromatography (chloroform:methanol) and NH column chromatography (chloroform:methanol) to give the title compound (123 mg).

MS(ESI) m/z: 450 (M+H)+

Example 96: Synthesis of 5-{4-[4-(3,5-dimethyl-pyridin-2-yl)piperazine-1-carbonyl]phenyl}-5-(1-methoxy-1-methylethyl) imidazolidine-2,4-dione

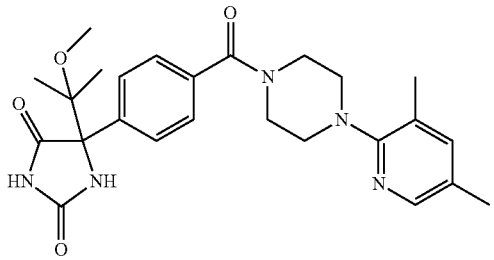 [SMILES: COC(C)(C)C1(c2ccc(C(=O)N3CCN(c4ncc(C)cc4C)CC3)cc2)NC(=O)NC1=O]

To a mixture of 4-[4-(1-methoxy-1-methylethyl)-2,5-dioxoimidazolidin-4-yl]benzoic acid (99 mg) described in Preparation Example 25, 1-(3,5-dimethylpyridin-2-yl)piperazine. hydrochloride (116 mg), 1-hydroxybenzotriazole (60 mg), triethylamine (0.142 ml) and chloroform (3 ml) was added 1-ethyl-3-(3'-dimethylaminopropyl)carbodiimide.hydrochloride (97 mg) and the mixture was stirred at room temperature for 3 hr. The reaction mixture was purified by column chromatography (chloroform:methanol) and NH column chromatography (chloroform:methanol) to give the title compound (133 mg).

MS(ESI) m/z: 466 (M+H)+

Example 97: Synthesis of 5-{4-[4-(3,5-dimethyl-pyridin-2-yl)piperazine-1-carbonyl]phenyl}-5-ethoxymethylimidazolidine-2,4-dione

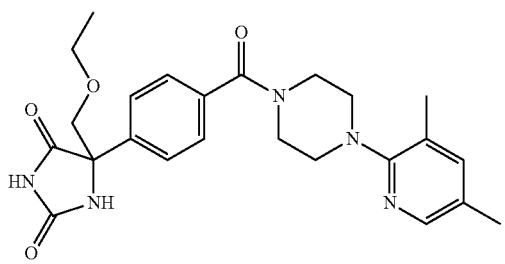 [SMILES: CCOCC1(c2ccc(C(=O)N3CCN(c4ncc(C)cc4C)CC3)cc2)NC(=O)NC1=O]

To 4-(4-ethoxymethyl-2,5-dioxoimidazolidin-4-yl)benzoic acid (150 mg) described in Preparation Example 24 were added 1-(3,5-dimethylpyridin-2-yl)piperazine.hydrochloride (160 mg), 1-hydroxybenzotriazole (87 mg), triethylamine (0.225 ml), chloroform (3 ml), and 1-ethyl-3-(3'-dimethylaminopropyl)carbodiimide.hydrochloride (155 mg) and the mixture was stirred at room temperature for 5 hr. The reaction mixture was purified by column chromatography (chloroform:methanol) and NH column chromatography (chloroform:methanol) to give the title compound (218 mg).

MS(ESI) m/z: 452 (M+H)+

Example 98: Synthesis of 5-ethoxymethyl-5-{4-[4-(3,5,6-trimethylpyridin-2-yl)piperazine-1-carbonyl]phenyl}imidazolidine-2,4-dione

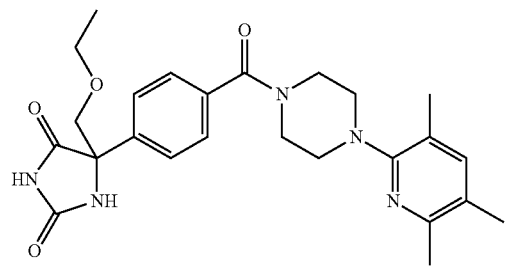 [SMILES: CCOCC1(c2ccc(C(=O)N3CCN(c4nc(C)c(C)cc4C)CC3)cc2)NC(=O)NC1=O]

To a mixture of 4-(4-ethoxymethyl-2,5-dioxoimidazolidin-4-yl)benzoic acid (150 mg) described in Preparation Example 24, 1-(3,5,6-trimethylpyridin-2-yl)piperazine (144 mg), 1-hydroxybenzotriazole (87 mg), triethylamine (0.151 ml) and chloroform (3 ml) were added 1-ethyl-3-(3'-dimethylaminopropyl) carbodiimide.hydrochloride (155 mg) and the mixture was stirred at room temperature for 5 hr. The reaction mixture was purified by NH column chromatography (chloroform:methanol) and column chromatography (chloroform:methanol) to give the title compound (197 mg).

MS(ESI) m/z: 466 (M+H)+

Example 99: Synthesis of 5-{4-[4-(5-cyclopropyl-3-methylpyridin-2-yl)piperazine-1-carbonyl]phenyl}-5-ethoxymethylimidazolidine-2,4-dione

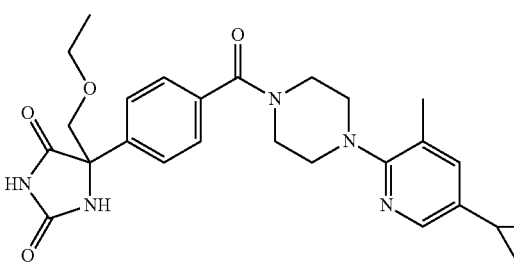

Using 4-(4-ethoxymethyl-2,5-dioxoimidazolidin-4-yl) benzoic acid (150 mg) described in Preparation Example 24 and 1-(5-cyclopropyl-3-methylpyridin-2-yl)piperazine (152 mg), reactions and treatments similar to those in Example 98 were performed to give the title compound (207 mg).

MS(ESI) m/z: 478 (M+H)+

Example 100: Synthesis of 5-trifluoromethyl-5-{4-[4-(3,5,6-trimethylpyridin-2-yl)piperazine-1-carbonyl]phenyl}imidazolidine-2,4-dione

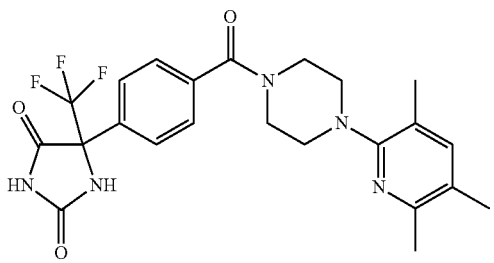 [SMILES: Cc1cc(C)c(N2CCN(C(=O)c3ccc(C4(C(F)(F)F)NC(=O)NC4=O)cc3)CC2)nc1C]

To a mixture of 4-(2,5-dioxo-4-trifluoromethylimidazolidin-4-yl)benzoic acid (150 mg) described in Preparation Example 10, 1-(3,5,6-trimethylpyridin-2-yl)piperazine (128 mg), 1-hydroxybenzotriazole (84 mg), triethylamine (0.145 ml) and chloroform (3 ml) was added 1-ethyl-3-(3'-dimethylaminopropyl) carbodiimide.hydrochloride (150 mg) and the mixture was stirred at room temperature for 18 hr. The reaction mixture was purified by column chromatography (chloroform:methanol) and NH column chromatography (chloroform:methanol) to give the title compound (72 mg).

MS(ESI) m/z: 476 (M+H)$^+$

Example 101: Synthesis of 5-{4-[4-(5-cyclopropyl-3-methylpyridin-2-yl) piperazine-1-carbonyl]phenyl}-5-trifluoromethylimidazolidine-2,4-dione

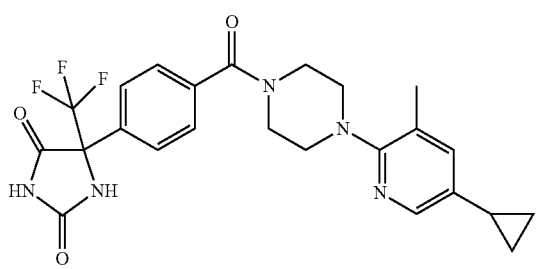 [SMILES: Cc1cc(C2CC2)cnc1N1CCN(C(=O)c2ccc(C3(C(F)(F)F)NC(=O)NC3=O)cc2)CC1]

Using 4-(2,5-dioxo-4-trifluoromethylimidazolidin-4-yl)benzoic acid (150 mg) described in Preparation Example 10 and 1-(5-cyclopropyl-3-methylpyridin-2-yl)piperazine (136 mg), reactions and treatments similar to those in Example 100 were performed to give the title compound (89 mg).

MS(ESI) m/z: 488 (M+H)$^+$

Example 102: Synthesis of 5-methoxymethyl-5-{4-[4-(3,5,6-trimethylpyridin-2-yl)piperazine-1-carbonyl]phenyl}imidazolidine-2,4-dione

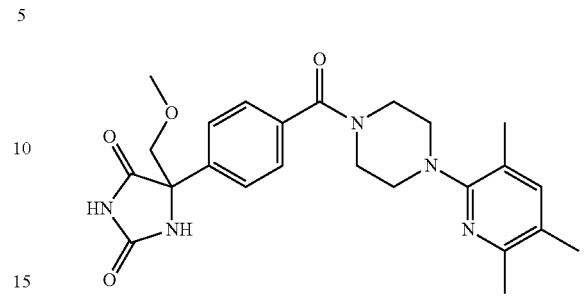

To a mixture of 4-(4-methoxymethyl-2,5-dioxoimidazolidin-4-yl)benzoic acid (145 mg) described in Preparation Example 9, 1-(3,5,6-trimethylpyridin-2-yl)piperazine (140 mg), 1-hydroxybenzotriazole (92 mg), triethylamine (0.158 ml) and chloroform (3 ml) was added 1-ethyl-3-(3'-dimethylaminopropyl)carbodiimide.hydrochloride (163 mg) and the mixture was stirred at room temperature for 20 hr. The reaction mixture was purified by column chromatography (chloroform:methanol) and NH column chromatography (chloroform:methanol) to give the title compound (149 mg).

MS(ESI) m/z: 452 (M+H)$^+$

Example 103: Synthesis of 5-{4-[4-(5-cyclopropyl-3-methylpyridin-2-yl)piperazine-1-carbonyl]phenyl}-5-methoxymethylimidazolidine-2,4-dione

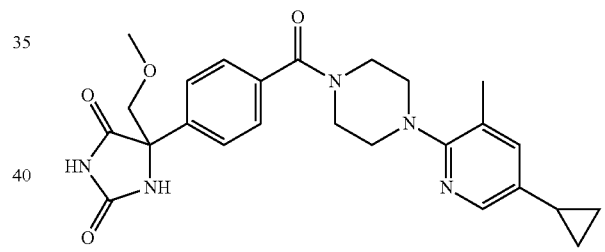

Using 4-(4-methoxymethyl-2,5-dioxoimidazolidin-4-yl) benzoic acid (145 mg) described in Preparation Example 9 and 1-(5-cyclopropyl-3-methylpyridin-2-yl)piperazine (148 mg), reactions and treatments similar to those in Example 102 were performed to give the title compound (148 mg).

MS(ESI) m/z: 464 (M+H)$^+$

Example 104: Synthesis of 5-cyclopropyl-5-{4-[4-(3,5,6-trimethylpyridin-2-yl)piperazine-1-carbonyl]phenyl}imidazolidine-2,4-dione

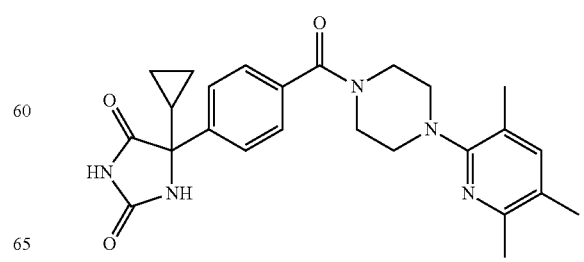

To a mixture of 4-(4-cyclopropyl-2,5-dioxoimidazolidin-4-yl)benzoic acid (130 mg) described in Preparation Example 11, 1-(3,5,6-trimethylpyridin-2-yl)piperazine (123 mg), 1-hydroxybenzotriazole (81 mg), triethylamine (0.139 ml) and chloroform (3 ml) was added 1-ethyl-3-(3'-dimethylaminopropyl) carbodiimide.hydrochloride (144 mg) and the mixture was stirred at room temperature for 5 hr. The reaction mixture was purified by column chromatography (chloroform:methanol) and NH column chromatography (chloroform:methanol) to give the title compound (167 mg).

MS(ESI) m/z: 448 (M+H)+

Example 105: Synthesis of 5-cyclopropyl-5-{4-[4-(5-cyclopropyl-3-methylpyridin-2-yl)piperazine-1-carbonyl]phenyl}imidazolidine-2,4-dione

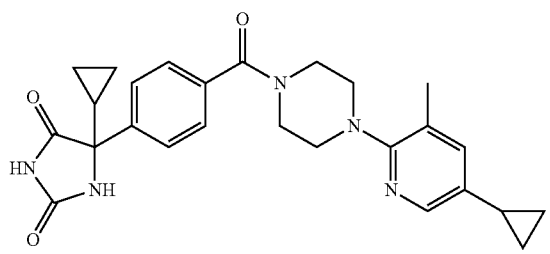 [SMILES: Cc1cc(C2CC2)cnc1N1CCN(C(=O)c2ccc(C3(C4CC4)NC(=O)NC3=O)cc2)CC1]

Using 4-(4-cyclopropyl-2,5-dioxoimidazolidin-4-yl)benzoic acid (130 mg) described in Preparation Example 11 and 1-(5-cyclopropyl-3-methylpyridin-2-yl)piperazine (130 mg), reactions and treatments similar to those in Example 104 were performed to give the title compound (168 mg).

MS(ESI) m/z: 460 (M+H)+

Example 106: Synthesis of 5-{4-[4-(5-cyclopropyl-3-methylpyridin-2-yl)piperazine-1-carbonyl]phenyl}-5-phenylimidazolidine-2,4-dione

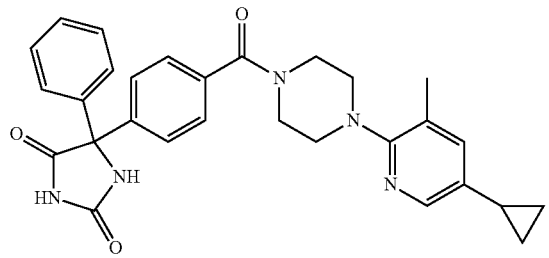 [SMILES: Cc1cc(C2CC2)cnc1N1CCN(C(=O)c2ccc(C3(c4ccccc4)NC(=O)NC3=O)cc2)CC1]

To a mixture of 4-(2,5-dioxo-4-phenylimidazolidin-4-yl)benzoic acid (150 mg) described in Preparation Example 37, 1-(5-cyclopropyl-3-methylpyridin-2-yl)piperazine (121 mg), 1-hydroxybenzotriazole (82 mg), triethylamine (0.155 ml) and chloroform (3 ml) was added 1-ethyl-3-(3'-dimethylaminopropyl)carbodiimide.hydrochloride (146 mg) and the mixture was stirred at room temperature for 2 days. The reaction mixture was purified by column chromatography (chloroform:methanol) and NH column chromatography (chloroform:methanol) to give the title compound (71 mg).

MS(ESI) m/z: 496 (M+H)+

Example 107: Synthesis of 5-{4-[4-(3,5-dimethyl-pyridin-2-yl)piperazine-1-carbonyl]phenyl}-5-phenylimidazolidine-2,4-dione

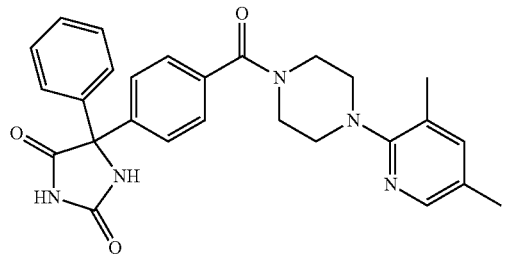 [SMILES: Cc1cnc(N2CCN(C(=O)c3ccc(C4(c5ccccc5)NC(=O)NC4=O)cc3)CC2)c(C)c1]

To a mixture of 4-(2,5-dioxo-4-phenylimidazolidin-4-yl)benzoic acid (150 mg) described in Preparation Example 37, 1-(3,5-dimethylpyridin-2-yl)piperazine.hydrochloride (127 mg), 1-hydroxybenzotriazole (82 mg), triethylamine (0.232 ml) and chloroform (3 ml) was added 1-ethyl-3-(3'-dimethylaminopropyl) carbodiimide.hydrochloride (146 mg) and the mixture was stirred at room temperature for 2 days. The reaction mixture was purified by NH coated silica gel column chromatography (chloroform:methanol) and silica gel column chromatography (chloroform:methanol) to give the title compound (63 mg).

MS(ESI) m/z: 470 (M+H)+

Example 108: Synthesis of 5-phenyl-5-{4-[4-(3,5,6-trimethylpyridin-2-yl)piperazine-1-carbonyl]phenyl}imidazolidine-2,4-dione

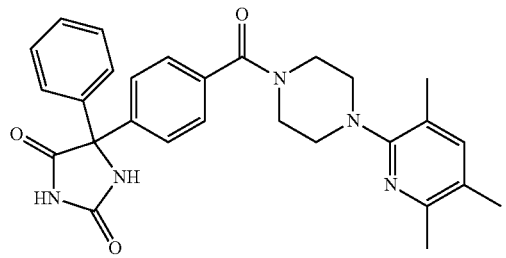 [SMILES: Cc1cc(C)c(N2CCN(C(=O)c3ccc(C4(c5ccccc5)NC(=O)NC4=O)cc3)CC2)nc1C]

Using 4-(2,5-dioxo-4-phenylimidazolidin-4-yl)benzoic acid (150 mg) described in Preparation Example 37 and 1-(3,5,6-trimethylpyridin-2-yl)piperazine (114 mg), reactions and treatments similar to those in Example 106 were performed to give the title compound (58 mg).

MS(ESI) m/z: 484 (M+H)+

Example 109: Synthesis of 5-{4-[4-(3,5-dimethyl-pyridin-2-yl)piperazine-1-carbonyl]phenyl}-5-(2-methoxy-1,1-dimethylethyl) imidazolidine-2,4-dione

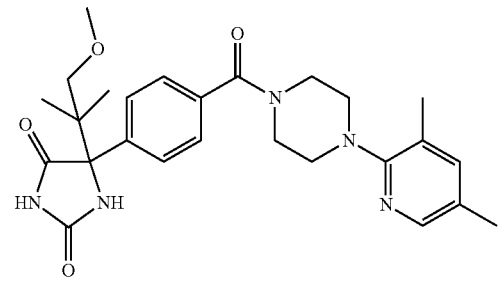 [SMILES: COCC(C)(C)C1(c2ccc(C(=O)N3CCN(c4ncc(C)cc4C)CC3)cc2)NC(=O)NC1=O]

To a mixture of 4-[4-(2-methoxy-1,1-dimethylethyl)-2,5-dioxoimidazolidin-4-yl]benzoic acid (120 mg) described in Preparation Example 38, 1-(3,5-dimethylpyridin-2-yl)piperazine. hydrochloride (107 mg), 1-hydroxybenzotriazole (64 mg), triethylamine (0.164 ml) and chloroform (3 ml) was added 1-ethyl-3-(3'-dimethylaminopropyl)carbodiimide.hydrochloride (90 mg) and the mixture was stirred at room temperature 4 days. The reaction mixture was purified by NH column chromatography (chloroform:methanol) and column chromatography (chloroform:methanol) to give the title compound (153 mg).

MS (ESI) m/z: 480 (M+H)+

Example 110: Synthesis of 5-{4-[4-(5-cyclopropyl-3-methylpyridin-2-yl)piperazine-1-carbonyl]phenyl}-5-(2-methoxy-1,1-dimethylethyl)imidazolidine-2,4-dione

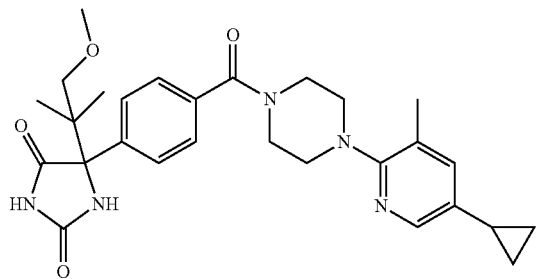 [SMILES: COCC(C)(C)C1(c2ccc(C(=O)N3CCN(c4ncc(C5CC5)cc4C)CC3)cc2)NC(=O)NC1=O]

To a mixture of 4-[4-(2-methoxy-1,1-dimethylethyl)-2,5-dioxoimidazolidin-4-yl]benzoic acid (120 mg) described in Preparation Example 38, 1-(5-cyclopropyl-3-methylpyridin-2-yl)piperazine (102 mg), 1-hydroxybenzotriazole (64 mg), triethylamine (0.109 ml) and chloroform (3 ml) was added 1-ethyl-3-(3'-dimethylaminopropyl)carbodiimide.hydrochloride (90 mg) and the mixture was stirred at room temperature for 4 days. The reaction mixture was purified by NH column chromatography (chloroform:methanol) and column chromatography (chloroform:methanol) to give the title compound (162 mg).

MS(ESI) m/z: 506 (M+H)+

Example 111: Synthesis of 5-(2-methoxy-1,1-dimethylethyl)-5-{4-[4-(3,5,6-trimethylpyridin-2-yl)piperazine-1-carbonyl]phenyl}imidazolidine-2,4-dione

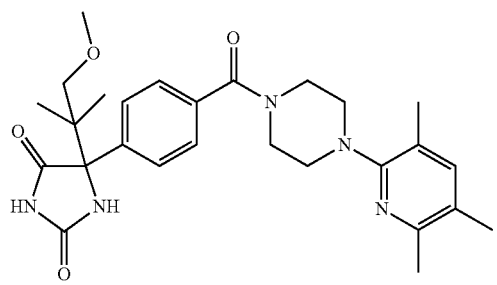 [SMILES: COCC(C)(C)C1(c2ccc(C(=O)N3CCN(c4nc(C)c(C)cc4C)CC3)cc2)NC(=O)NC1=O]

Using 4-[4-(2-methoxy-1,1-dimethylethyl)-2,5-dioxoimidazolidin-4-yl]benzoic acid (120 mg) described in Preparation Example 38 and 1-(3,5,6-trimethylpyridin-2-yl)piperazine (97 mg), reactions and treatments similar to those in Example 110 were performed to give the title compound (167 mg).

MS(ESI) m/z: 494 (M+H)+

Example 112: Synthesis of 5-{4-[4-(3,5-dimethylpyridin-2-yl)piperazine-1-carbonyl]phenyl}-5-(1-methoxycyclopropyl) imidazolidine-2,4-dione

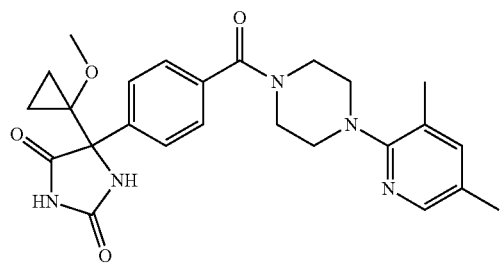 [SMILES: COC1(C2(c3ccc(C(=O)N4CCN(c5ncc(C)cc5C)CC4)cc3)NC(=O)NC2=O)CC1]

To a mixture of 4-[4-(1-methoxycyclopropyl)-2,5-dioxoimidazolidin-4-yl]benzoic acid (80 mg) described in Preparation Example 44, 1-(3,5-dimethylpyridin-2-yl)piperazine. hydrochloride (75 mg), 1-hydroxybenzotriazole (45 mg), triethylamine (58 mg) and chloroform (3 ml) was added 1-ethyl-3-(3'-dimethylaminopropyl) carbodiimide.hydrochloride (64 mg) and the mixture was stirred at room temperature for 18 hr. The reaction mixture was purified by column chromatography and NH column chromatography (chloroform:methanol) to give the title compound (92 mg).

MS(ESI) m/z: 464 (M+H)+

Example 113: Synthesis of 5-tert-butyl-5-{4-[4-(3,5-dimethylpyridin-2-yl)piperazine-1-carbonyl]-2-methoxyphenyl}imidazolidine-2,4-dione

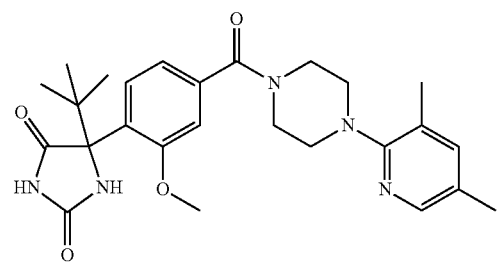 [SMILES: COc1cc(C(=O)N2CCN(c3ncc(C)cc3C)CC2)ccc1C1(C(C)(C)C)NC(=O)NC1=O]

To a mixture of 4-(4-tert-butyl-2,5-dioxoimidazolidin-4-yl)-3-methoxybenzoic acid (100 mg) described in Preparation Example 61, 1-(3,5-dimethylpyridin-2-yl)piperazine. hydrochloride (149 mg), 1-hydroxybenzotriazole (90.3 mg), diisopropylethylamine (0.142 ml) and chloroform (3 ml) was added 1-ethyl-3-(3'-dimethylaminopropyl)carbodiimide. hydrochloride (125 mg) and the mixture was stirred at room temperature for 20 hr. The reaction mixture was purified by NH column chromatography (chloroform:methanol) and column chromatography (chloroform:methanol) to give the title compound (94.6 mg).

MS(ESI) m/z: 480 (M+H)+

Example 114: Synthesis of 5-{5-[4-(3,5-dimethyl-pyridin-2-yl)piperazine-1-carbonyl]thiophen-2-yl}-5-isopropylimidazolidine-2,4-dione

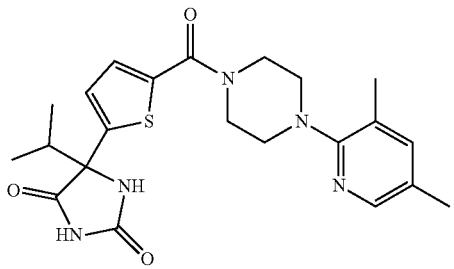 [SMILES: Cc1cnc(N2CCN(C(=O)c3ccc(C4(C(C)C)NC(=O)NC4=O)s3)CC2)c(C)c1]

To a mixture of 5-(4-isopropyl-2,5-dioxoimidazolidin-4-yl)thiophene-2-carboxylic acid (50 mg) described in Preparation Example 66, 1-(3,5-dimethylpyridin-2-yl)piperazine. hydrochloride (50.9 mg), 1-hydroxybenzotriazole (30 mg), triethylamine (0.052 ml) and chloroform (1.5 ml) was added 1-ethyl-3-(3'-dimethylaminopropyl)carbodiimide.hydrochloride (50 mg) and the mixture was stirred at room temperature for 24 hr. Water was added to the reaction mixture and the mixture was extracted with ethyl acetate. The organic layer was washed with saturated aqueous sodium hydrogen carbonate solution and saturated brine, dried over anhydrous sodium sulfate and concentrated under reduced pressure. To the obtained residue was added hexane/ethyl acetate, and the precipitate was collected by filtration to give the title compound (63.5 mg).

MS(ESI) m/z: 442 (M+H)$^+$, 440 (M−H)$^−$

Example 115: Synthesis of 5-{4-[4-(2,4-dimethyl-phenyl)piperazine-1-carbonyl]-3-fluorophenyl}-5-methylimidazolidine-2,4-dione

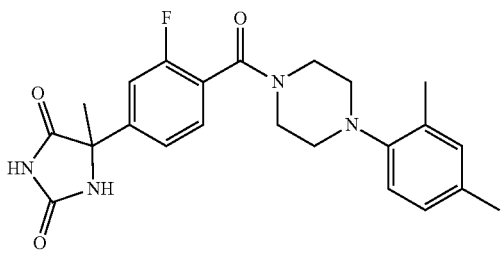 [SMILES: Cc1ccc(N2CCN(C(=O)c3ccc(C4(C)NC(=O)NC4=O)cc3F)CC2)c(C)c1]

To a solution of 1-(2,4-dimethylphenyl)piperazine (114 mg) in N,N-dimethylformamide (4 mL) were added 2-fluoro-4-(4-methyl-2,5-dioxoimidazolidin-4-yl)benzoic acid (126 mg) described in Preparation Example 2, 1-hydroxybenzotriazole (67 mg), 1-ethyl-3-(3'-dimethylaminopropyl)carbodiimide. hydrochloride (170 mg) and diisopropylethylamine (0.2 mL) and the mixture was stirred at room temperature overnight. To the reaction mixture was added saturated aqueous sodium hydrogen carbonate solution and the mixture was extracted with ethyl acetate. The organic layer was washed with water and saturated brine, dried over anhydrous magnesium sulfate and concentrated under reduced pressure. The obtained residue was purified by NH column chromatography (chloroform:methanol) to give the title compound (198 mg).

MS(ESI) m/z: 425 (M+H)$^+$

Example 116: Synthesis of 5-{4-[4-(3,5-dicyclopropylpyridin-2-yl)piperazine-1-carbonyl]-3-fluorophenyl}-5-methylimidazolidine-2,4-dione

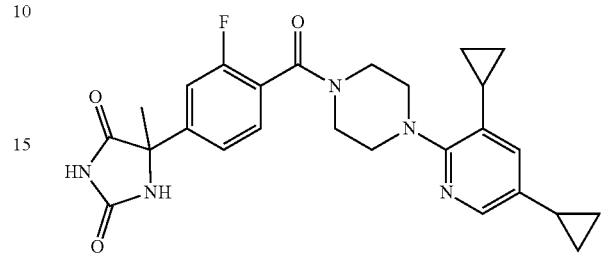

Using 2-fluoro-4-(4-methyl-2,5-dioxoimidazolidin-4-yl)benzoic acid (126 mg) described in Preparation Example 2 and 1-(3,5-dicyclopropylpyridin-2-yl)piperazine.2 hydrochloride (189 mg) described in Preparation Example 147, reactions and treatments similar to those in Example 115 were performed to give the title compound (183 mg).

MS(ESI) m/z: 478 (M+H)$^+$

Example 117: Synthesis of (R)-5-{3-fluoro-4-[4-(3,5,6-trimethylpyridin-2-yl)piperazine-1-carbonyl]phenyl}-5-methylimidazolidine-2,4-dione and (S)-5-{3-fluoro-4-[4-(3,5,6-trimethylpyridin-2-yl)piperazine-1-carbonyl]phenyl}-5-methylimidazolidine-2,4-dione

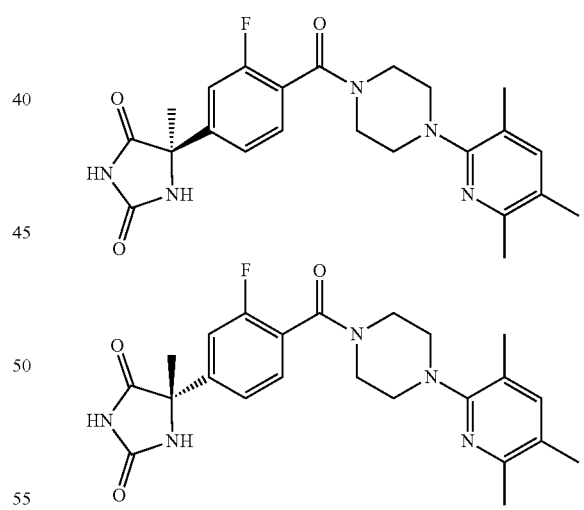

Using 2-fluoro-4-(4-methyl-2,5-dioxoimidazolidin-4-yl)benzoic acid (126 mg) described in Preparation Example 2 and 1-(3,5,6-trimethylpyridin-2-yl)piperazine (123 mg), reactions and treatments similar to those in Example 115 were performed to give 5-{3-fluoro-4-[4-(3,5,6-trimethylpyridin-2-yl)piperazine-1-carbonyl]phenyl}-5-methylimidazolidine-2,4-dione (183 mg).

The obtained 5-{3-fluoro-4-[4-(3,5,6-trimethylpyridin-2-yl)piperazine-1-carbonyl]phenyl}-5-methylimidazolidine-2,4-dione (120 mg) was separated by moderate-pressure column using CHIRALFLASH (Daicel) IA (hexane/ethanol/ diethylamine) to give the both enantiomers indicated above (compound with short retention time 52 mg (MS(ESI) m/z: 440 (M+H)+) and compound with long retention time 51 mg (MS(ESI) m/z: 440 (M+H)+)).

In the analysis using CHIRALPAK (Daicel) IA-3 (4.6 mm×150 mm, hexane/ethanol/diethylamine=10/90/0.1, flow 0.5 mL/min), the retention time was respectively 5.5 min and 7.7 min.

Example 118: Synthesis of (R)-5-{4-[4-(5-ethyl-3-methylpyridin-2-yl)piperazine-1-carbonyl]-3-fluorophenyl}-5-methylimidazolidine-2,4-dione and (S)-5-{4-[4-(5-ethyl-3-methylpyridin-2-yl)piperazine-1-carbonyl]-3-fluorophenyl}-5-methylimidazolidine-2,4-dione

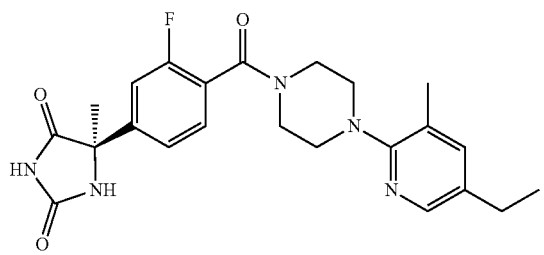

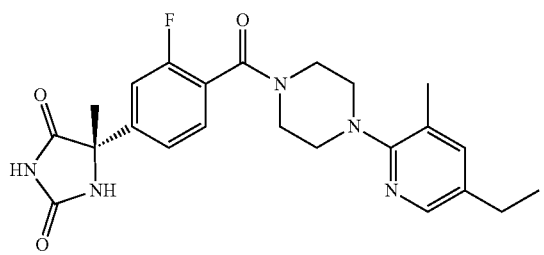

Using 2-fluoro-4-(4-methyl-2,5-dioxoimidazolidin-4-yl)benzoic acid (126 mg) described in Preparation Example 2 and 1-(5-ethyl-3-methylpyridin-2-yl)piperazine (123 mg), reactions and treatments similar to those in Example 115 were performed to give 5-{4-[4-(5-ethyl-3-methylpyridin-2-yl)piperazine-1-carbonyl]-3-fluorophenyl}-5-methylimidazolidine-2,4-dione (207 mg).

The obtained 5-{4-[4-(5-ethyl-3-methylpyridin-2-yl)piperazine-1-carbonyl]-3-fluorophenyl}-5-methylimidazolidine-2,4-dione (132 mg) was separated by moderate-pressure column using CHIRALFLASH (Daicel) IA (hexane/ethanol/diethylamine) to give the both enantiomers indicated above (compound with short retention time 38.7 mg (MS(ESI) m/z: 440 (M+H)+) and compound with long retention time 12.7 mg (MS(ESI) m/z: 440 (M+H)+)).

In the analysis using CHIRALPAK (Daicel) IA-3 (4.6 mm×150 mm, ethanol/diethylamine=100/0.1, flow 0.5 mL/min), the retention time was respectively 6.3 min and 12.4 min.

Example 119: Synthesis of (R)-5-{4-[4-(5-cyclopropyl-3-methylpyridin-2-yl)piperazine-1-carbonyl]-3-fluorophenyl}-5-methylimidazolidine-2,4-dione and (S)-5-{4-[4-(5-cyclopropyl-3-methylpyridin-2-yl)piperazine-1-carbonyl]-3-fluorophenyl}-5-methylimidazolidine-2,4-dione

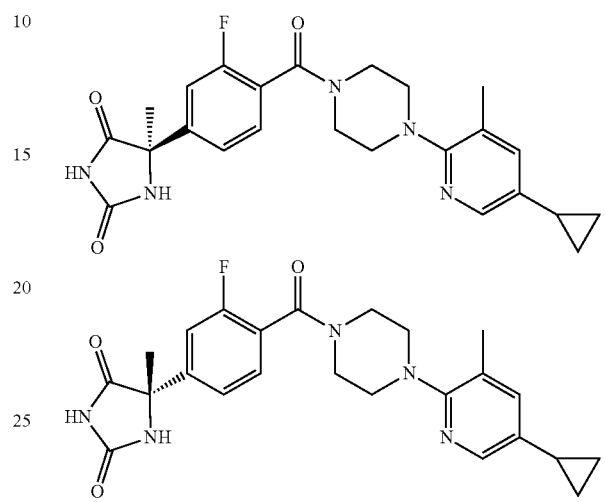

Using 2-fluoro-4-(4-methyl-2,5-dioxoimidazolidin-4-yl)benzoic acid (126 mg) described in Preparation Example 2 and 1-(5-cyclopropyl-3-methylpyridin-2-yl)piperazine (130 mg), reactions and treatments similar to those in Example 115 were performed to give 5-{4-[4-(5-cyclopropyl-3-methylpyridin-2-yl)piperazine-1-carbonyl]-3-fluorophenyl}-5-methylimidazolidine-2,4-dione (158 mg).

The obtained 5-{4-[4-(5-cyclopropyl-3-methylpyridin-2-yl)piperazine-1-carbonyl]-3-fluorophenyl}-5-methylimidazolidine-2,4-dione (106 mg) was separated by moderate-pressure column using CHIRALFLASH (Daicel) IA (hexane/ethanol/diethylamine=10/90/0.1) to give the both enantiomers indicated above (compound with short retention time 30.8 mg (MS(ESI) m/z: 452 (M+H)+) and compound with long retention time 31.5 mg (MS(ESI) m/z: 452 (M+H)+)).

In the analysis using CHIRALPAK (Daicel) IA-3 (4.6 mm×150 mm, ethanol/diethylamine=100/0.1, flow 0.5 mL/min), the retention time was respectively 10.4 min and 18.3 min.

Example 120: Synthesis of 5-{4-[4-(3,5-dimethylpyridin-2-yl)piperazine-1-carbonyl]-3-fluorophenyl}-5-isopropylimidazolidine-2,4-dione

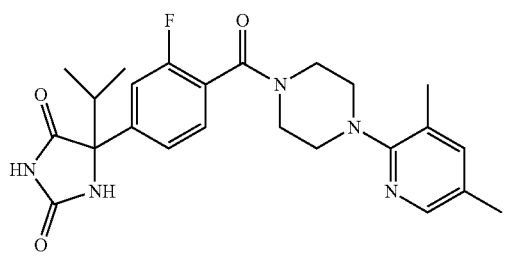 [SMILES: Cc1cnc(N2CCN(C(=O)c3ccc(C4(C(C)C)NC(=O)NC4=O)cc3F)CC2)c(C)c1]

To 2-fluoro-4-(4-isopropyl-2,5-dioxoimidazolidin-4-yl)benzoic acid (83 mg) described in Preparation Example 15 were added 1-(3,5-dimethylpyridin-2-yl)piperazine (68 mg), N,N-dimethylformamide (5 mL), 1-ethyl-3-(3'-dimethylaminopropyl)carbodiimide.hydrochloride (80 mg), 1-hydroxybenzotriazole (40 mg) and diisopropylethylamine (0.08 mL) and the mixture was stirred at room temperature overnight. To the reaction mixture was added saturated aqueous sodium hydrogen carbonate solution and the mixture was extracted with ethyl acetate. The organic layer was washed with water and saturated brine, dried over anhydrous magnesium sulfate and concentrated under reduced pressure. The obtained residue was purified by NH column chromatography (chloroform:methanol) to give the title compound (128 mg).

MS(ESI) m/z: 454 (M+H)$^+$

Example 121: Synthesis of 5-{4-[4-(3,5-dimethylpyridin-2-yl)piperazine-1-carbonyl]phenyl}-5-(3,3,3-trifluoropropyl) imidazolidine-2,4-dione

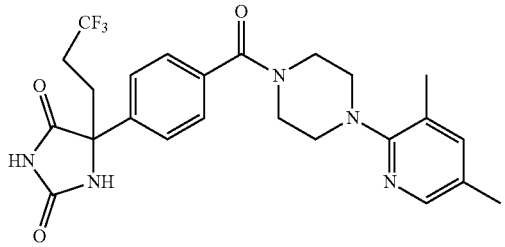 [SMILES: Cc1cnc(N2CCN(C(=O)c3ccc(C4(CCC(F)(F)F)NC(=O)NC4=O)cc3)CC2)c(C)c1]

To 4-[2,5-dioxo-4-(3,3,3-trifluoropropyl)imidazolidin-4-yl]benzoic acid (100 mg) described in Preparation Example 31 were added 1-(3,5-dimethylpyridin-2-yl)piperazine.hydrochloride (86 mg), N,N-dimethylformamide (3 mL), 1-ethyl-3-(3'-dimethylaminopropyl)carbodiimide.hydrochloride (90 mg), 1-hydroxybenzotriazole (43 mg) and diisopropylethylamine (0.13 mL) and the mixture was stirred at room temperature overnight. To the reaction mixture was added saturated aqueous sodium hydrogen carbonate solution and the mixture was extracted with ethyl acetate. The organic layer was washed with water and saturated brine, dried over anhydrous magnesium sulfate and concentrated under reduced pressure. The obtained residue was purified by NH column chromatography (chloroform:methanol) to give the title compound (49.3 mg).

MS(ESI) m/z: 490 (M+H)$^+$

Example 122: Synthesis of 5-{3-fluoro-4-[4-(3,5,6-trimethylpyridin-2-yl)piperazine-1-carbonyl]phenyl}-5-isopropylimidazolidine-2,4-dione

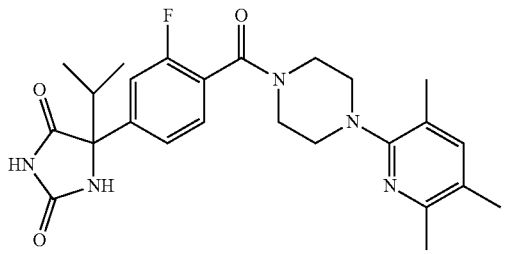 [SMILES: Cc1cc(C)c(N2CCN(C(=O)c3ccc(C4(C(C)C)NC(=O)NC4=O)cc3F)CC2)nc1C]

To 2-fluoro-4-(4-isopropyl-2,5-dioxoimidazolidin-4-yl)benzoic acid (47 mg) described in Preparation Example 15 were added 1-(3,5,6-trimethylpyridin-2-yl)piperazine (42 mg), N,N-dimethylformamide (3 mL), 1-ethyl-3-(3'-dimethylaminopropyl)carbodiimide.hydrochloride (48 mg), 1-hydroxybenzotriazole (22 mg) and diisopropylethylamine (0.06 mL) and the mixture was stirred at room temperature overnight. To the reaction mixture was added saturated aqueous sodium hydrogen carbonate solution and the mixture was extracted with ethyl acetate. The organic layer was washed with water and saturated brine, dried over anhydrous magnesium sulfate and concentrated under reduced pressure. The obtained residue was purified by NH column chromatography (chloroform:methanol) to give the title compound (46.6 mg).

MS(ESI) m/z: 468 (M+H)$^+$

Example 123: Synthesis of 5-{4-[4-(5-cyclopropyl-3-methylpyridin-2-yl)piperazine-1-carbonyl]-3-fluorophenyl}-5-isopropylimidazolidine-2,4-dione

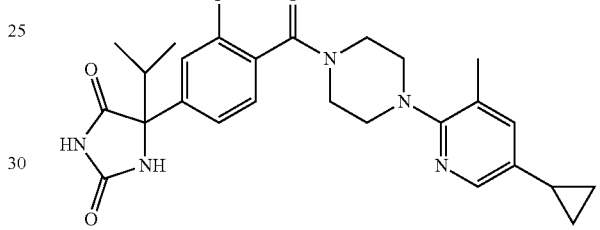

Using 2-fluoro-4-(4-isopropyl-2,5-dioxoimidazolidin-4-yl)benzoic acid (51 mg) described in Preparation Example 15 and 1-(5-cyclopropyl-3-methylpyridin-2-yl)piperazine (47 mg), reactions and treatments similar to those in Example 122 were performed to give the title compound (51.3 mg).

MS(ESI) m/z: 480 (M+H)$^+$

Example 124: Synthesis of (R)-5-{4-[4-(3,5-dimethylpyridin-2-yl)piperazine-1-carbonyl]phenyl}-5-ethylimidazolidine-2,4-dione

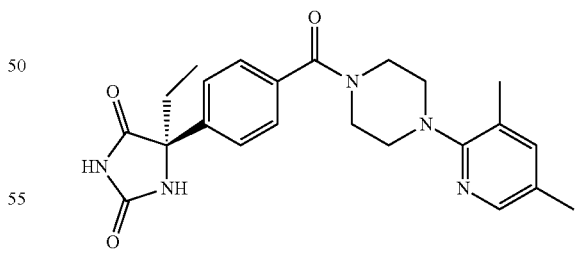

4-((R)-4-ethyl-2,5-dioxoimidazolidin-4-yl)benzoic acid (250 mg) described in Preparation Example 14, 1-(3,5-dimethylpyridin-2-yl)piperazine.hydrochloride (270 mg), 1-hydroxybenzotriazole (135 mg), 1-ethyl-3-(3'-dimethylaminopropyl)carbodiimide.hydrochloride (280 mg) and diisopropylethylamine (0.4 mL) were dissolved in N,N-dimethylformamide (10 mL) and the mixture was stirred at room temperature overnight. To the reaction mixture was added saturated aqueous sodium hydrogen carbonate solution and the mixture was extracted with ethyl acetate. The organic layer was washed with water and saturated brine, dried over anhydrous magnesium sulfate and concentrated under reduced pressure. The obtained residue was purified by NH column chromatography (chloroform:methanol) to give the title compound (367 mg).

MS(ESI) m/z: 422 (M+H)⁺

Example 125: Synthesis of (R)-5-{4-[4-(3,5-dimethylpyridin-2-yl)piperazine-1-carbonyl]-3-methylphenyl}-5-methylimidazolidine-2,4-dione and (S)-5-{4-[4-(3,5-dimethylpyridin-2-yl)piperazine-1-carbonyl]-3-methylphenyl}-5-methylimidazolidine-2,4-dione

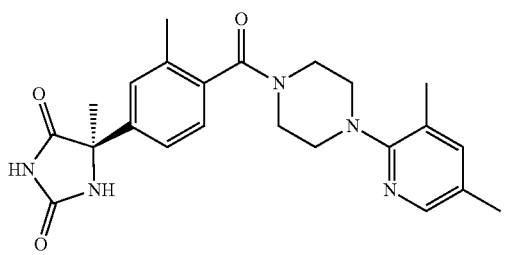

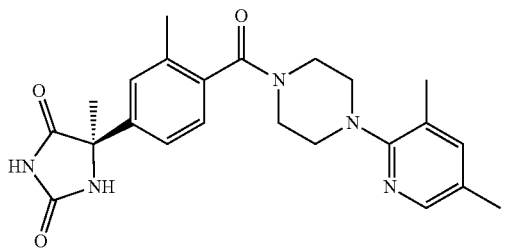 [SMILES: CC[C@]1(c2ccc(C(=O)N3CCN(c4ncc(C)cc4C)CC3)cc2)NC(=O)NC1=O]

To 2-methyl-4-(4-methyl-2,5-dioxoimidazolidin-4-yl)benzoic acid (150 mg) described in Preparation Example 8 were added 1-(3,5-dimethylpyridin-2-yl)piperazine (127 mg), 1-hydroxybenzotriazole (98 mg), 1-ethyl-3-(3'-dimethylaminopropyl)carbodiimide.hydrochloride (150 mg), chloroform (2 mL) and N,N-dimethylformamide (1 mL) and the mixture was stirred at room temperature overnight. Water was added to the reaction mixture, the mixture was extracted with ethyl acetate, and the solvent was evaporated. The obtained residue was purified by column chromatography (chloroform:methanol) to give 5-{4-[4-(3,5-dimethylpyridin-2-yl)piperazine-1-carbonyl]-3-methylphenyl}-5-methylimidazolidine-2,4-dione (191 mg).

The obtained 5-{4-[4-(3,5-dimethylpyridin-2-yl)piperazine-1-carbonyl]-3-methylphenyl}-5-methylimidazolidine-2,4-dione (100 mg) was separated by HPLC using CHIRALPAK (Daicel) IC (ethanol/diethylamine=100/0.1) to give the both enantiomers indicated above (compound with short retention time 49 mg (MS(ESI) m/z: 422 (M+H)⁺)) and compound with long retention time 50 mg (MS(ESI) m/z: 422 (M+H)⁺)).

In the analysis using CHIRALPAK (Daicel) IC-3 (4.6 mm×150 mm, ethanol/diethylamine=100/0.1, flow 0.5 mL/min), the retention time was respectively 7.3 min and 11.0 min.

Example 126: Synthesis of 5-methyl-5-{3-methyl-4-[4-(3,5,6-trimethylpyridin-2-yl)piperazine-1-carbonyl]phenyl}imidazolidine-2,4-dione

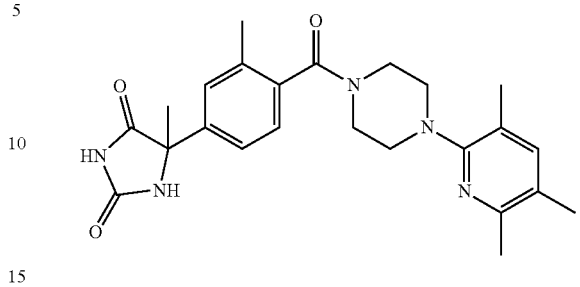

To 2-methyl-4-(4-methyl-2,5-dioxoimidazolidin-4-yl)benzoic acid (50 mg) described in Preparation Example 8 were added 1-(3,5,6-trimethylpyridin-2-yl)piperazine (45.5 mg), 1-hydroxybenzotriazole (33 mg), 1-ethyl-3-(3'-dimethylaminopropyl)carbodiimide.hydrochloride (50 mg), chloroform (1.5 mL) and N,N-dimethylformamide (0.5 mL) and the mixture was stirred at room temperature overnight. Water was added to the reaction mixture and the mixture was extracted with ethyl acetate, and the solvent was evaporated. The obtained residue was purified by column chromatography (hexane:ethyl acetate:methanol). The solvent was evaporated and hexane/ethyl acetate was added to the obtained residue. The precipitate was collected by filtration to give the title compound (48.6 mg).

MS(ESI) m/z: 436 (M+H)⁺

Example 127: Synthesis of 5-{4-[4-(5-cyclopropyl-3-methylpyridin-2-yl)piperazine-1-carbonyl]-3-methylphenyl}-5-methylimidazolidine-2,4-dione

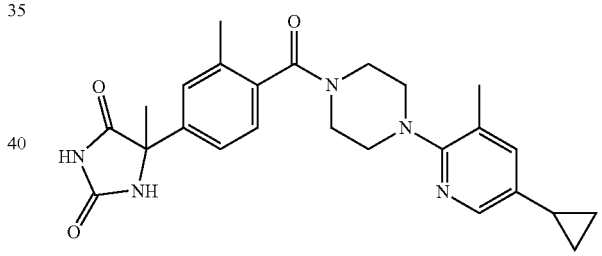

Using 2-methyl-4-(4-methyl-2,5-dioxoimidazolidin-4-yl)benzoic acid (50 mg) described in Preparation Example 8 and 1-(5-cyclopropyl-3-methylpyridin-2-yl)piperazine (48.1 mg), reactions and treatments similar to those in Example 126 were performed to give the title compound (56.4 mg).

MS (ESI) m/z: 448 (M+H)⁺

Example 128: Synthesis of 5-{4-[4-(5-ethyl-3-methyl-pyridin-2-yl)-piperazine-1-carbonyl]-3-methyl-phenyl}-5-methyl-imidazolidine-2,4-dione

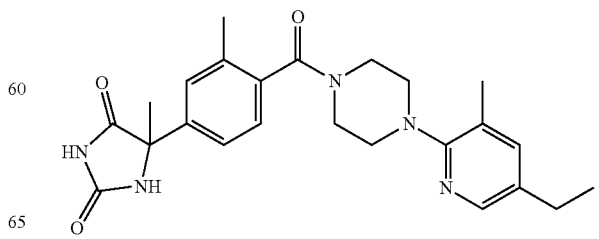

Using 2-methyl-4-(4-methyl-2,5-dioxoimidazolidin-4-yl)benzoic acid (50 mg) described in Preparation Example 8 and 1-(5-ethyl-3-methylpyridin-2-yl)piperazine (45.5 mg), reactions and treatments similar to those in Example 126 were performed to give the title compound (61.7 mg).

MS(ESI) m/z: 436 (M+H)+

Example 129: Synthesis of 5-{4-[4-(3,5-dicyclopropylpyridin-2-yl)piperazine-1-carbonyl]-3-methylphenyl}-5-methylimidazolidine-2,4-dione

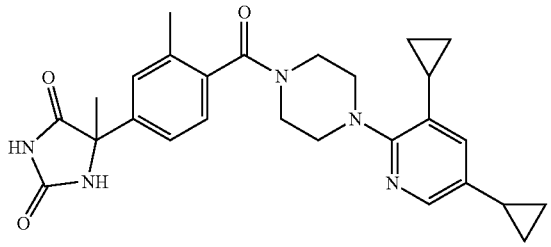 [SMILES: Cc1cc(C2(C)NC(=O)NC2=O)ccc1C(=O)N1CCN(c2ncc(C3CC3)cc2C2CC2)CC1]

To 2-methyl-4-(4-methyl-2,5-dioxoimidazolidin-4-yl)benzoic acid (50 mg) described in Preparation Example 8 were added 1-(3,5-dicyclopropylpyridin-2-yl)piperazine.2 hydrochloride (70 mg) described in Preparation Example 147, 1-hydroxybenzotriazole (33 mg), 1-ethyl-3-(3'-dimethylaminopropyl)carbodiimide.hydrochloride (50 mg), N,N-dimethylformamide (0.5 mL) and triethylamine (59 μL) and the mixture was stirred at room temperature overnight. Water was added to the reaction mixture, the mixture was extracted with ethyl acetate, and the solvent was evaporated. The obtained residue was purified by column chromatography (hexane:ethyl acetate:methanol). The solvent was evaporated and hexane/ethyl acetate was added to the obtained residue. The precipitate was collected by filtration to give the title compound (45.4 mg).

MS(ESI) m/z: 474 (M+H)+

Example 130: Synthesis of 5-{4-[4-(3,5-dimethylpyridin-2-yl)piperazine-1-carbonyl]phenyl}-5-isobutylimidazolidine-2,4-dione

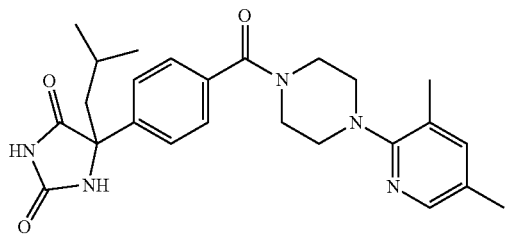 [SMILES: Cc1cnc(N2CCN(C(=O)c3ccc(C4(CC(C)C)NC(=O)NC4=O)cc3)CC2)c(C)c1]

To 4-(4-isobutyl-2,5-dioxoimidazolidin-4-yl)benzoic acid (80 mg) described in Preparation Example 27 were added 1-(3,5-dimethylpyridin-2-yl)piperazine (61 mg), 1-hydroxybenzotriazole (47 mg), 1-ethyl-3-(3'-dimethylaminopropyl)carbodiimide. hydrochloride (72 mg), chloroform (2.5 mL) and N,N-dimethylformamide (1 mL) and the mixture was stirred at room temperature overnight. Water was added to the reaction mixture, the mixture was extracted with ethyl acetate, and the solvent was evaporated. The obtained residue was purified by column chromatography (hexane:ethyl acetate:methanol). The solvent was evaporated and hexane/ethyl acetate was added to the obtained residue. The precipitate was collected by filtration to give the title compound (94 mg).

MS(ESI) m/z: 450 (M+H)+

Example 131: Synthesis of 5-isobutyl-5-{4-[4-(3,5,6-trimethylpyridin-2-yl)piperazine-1-carbonyl]phenyl}imidazolidine-2,4-dione

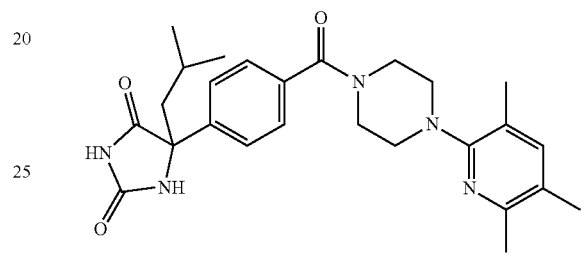

Using 4-(4-isobutyl-2,5-dioxoimidazolidin-4-yl)benzoic acid (80 mg) described in Preparation Example 27 and 1-(3,5,6-trimethylpyridin-2-yl)piperazine (89 mg), reactions and treatments similar to those in Example 130 were performed to give the title compound (73 mg).

MS (ESI) m/z: 464 (M+H)+

Example 132: Synthesis of 5-{4-[4-(2,4-dimethylphenyl)piperazine-1-carbonyl]phenyl}-5-isobutylimidazolidine-2,4-dione

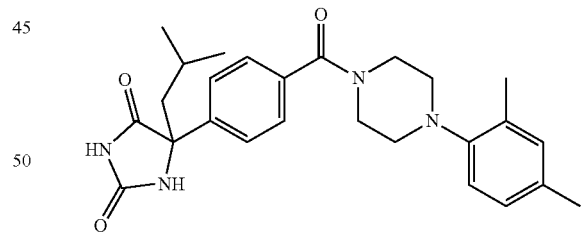

To 4-(4-isobutyl-2,5-dioxoimidazolidin-4-yl)benzoic acid (80 mg) described in Preparation Example 27 were added 1-(2,4-dimethylphenyl)piperazine (61 mg), 1-hydroxybenzotriazole (47 mg), 1-ethyl-3-(3'-dimethylaminopropyl)carbodiimide. hydrochloride (72 mg) and chloroform (2.5 mL) and the mixture was stirred at room temperature overnight. Water was added to the reaction mixture, the mixture was extracted with ethyl acetate, and the solvent was evaporated. The obtained residue was purified by column chromatography (hexane:ethyl acetate) to give the title compound (80 mg).

MS (ESI) m/z: 449 (M+H)+

Example 133: Synthesis of 5-{4-[4-(5-ethyl-3-methylpyridin-2-yl)piperazine-1-carbonyl]phenyl}-5-isobutylimidazolidine-2,4-dione

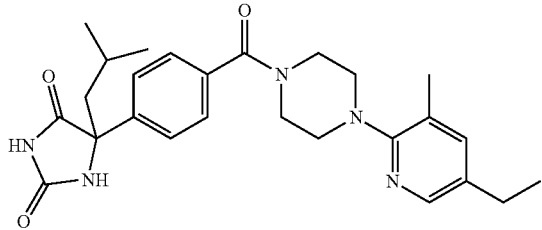 [SMILES: CCc1cnc(N2CCN(C(=O)c3ccc(C4(CC(C)C)NC(=O)NC4=O)cc3)CC2)c(C)c1]

To 4-(4-isobutyl-2,5-dioxoimidazolidin-4-yl)benzoic acid (80 mg) described in Preparation Example 27 were added 1-(5-ethyl-3-methylpyridin-2-yl)piperazine (65 mg), 1-hydroxybenzotriazole (47 mg), 1-ethyl-3-(3'-dimethylaminopropyl) carbodiimide.hydrochloride (72 mg), chloroform (2.5 mL) and N,N-dimethylformamide (0.5 mL) and the mixture was stirred at room temperature overnight. Water was added to the reaction mixture, the mixture was extracted with ethyl acetate, and the solvent was evaporated. The obtained residue was purified by column chromatography (hexane:ethyl acetate:methanol). The solvent was evaporated and hexane/ethyl acetate was added to the obtained residue. The precipitate was collected by filtration to give the title compound (95.8 mg).

MS(ESI) m/z: 464 (M+H)$^+$

Example 134: Synthesis of 5-{4-[4-(5-cyclopropyl-3-methylpyridin-2-yl)piperazine-1-carbonyl]phenyl}-5-isobutylimidazolidine-2,4-dione

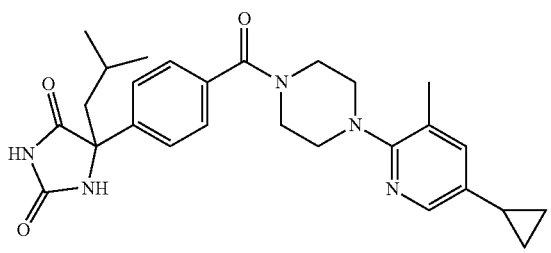 [SMILES: Cc1cc(C2CC2)cnc1N1CCN(C(=O)c2ccc(C3(CC(C)C)NC(=O)NC3=O)cc2)CC1]

Using 4-(4-isobutyl-2,5-dioxoimidazolidin-4-yl)benzoic acid (80 mg) described in Preparation Example 27 and 1-(5-cyclopropyl-3-methylpyridin-2-yl)piperazine (69 mg), reactions and treatments similar to those in Example 133 were performed to give the title compound (101 mg).

MS(ESI) m/z: 476 (M+H)$^+$

Example 135: Synthesis of 5-{4-[4-(3,5-dicyclopropylpyridin-2-yl)piperazine-1-carbonyl]phenyl}-5-isobutylimidazolidine-2,4-dione

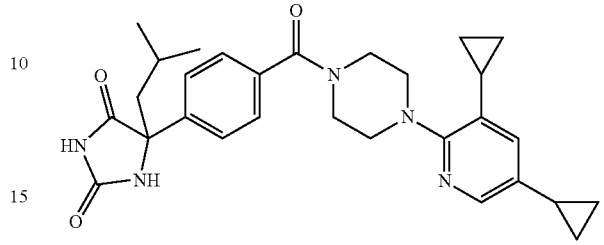

Using 4-(4-isobutyl-2,5-dioxoimidazolidin-4-yl)benzoic acid (80 mg) described in Preparation Example 27 and 1-(3,5-dicyclopropylpyridin-2-yl)piperazine.2 hydrochloride (101 mg) described in Preparation Example 147, reactions and treatments similar to those in Example 132 were performed to give the title compound (94.6 mg).

MS(ESI) m/z: 502 (M+H)$^+$

Example 136: Synthesis of 5-[4-(3',5'-dimethyl-2,3,5,6-tetrahydro[1,2']bipyrazinyl-4-carbonyl)phenyl]-5-isopropylimidazolidine-2,4-dione

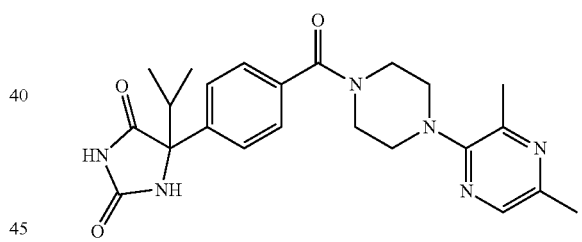

To 4-(4-isopropyl-2,5-dioxoimidazolidin-4-yl)benzoic acid (50 mg) described in Preparation Example 5 were added 3,5-dimethyl-3,4,5,6-tetrahydro-2H-[1,2']bipyrazinyl (40 mg) described in Preparation Example 83, 1-hydroxybenzotriazole (31 mg), 1-ethyl-3-(3'-dimethylaminopropyl) carbodiimide. hydrochloride (48 mg), chloroform (3 mL) and N,N-dimethylformamide (0.5 mL) and the mixture was stirred at room temperature overnight. Water was added to the reaction mixture, the mixture was extracted with chloroform, and the solvent was evaporated. The obtained residue was purified by column chromatography (chloroform:methanol). The solvent was evaporated and hexane/ethyl acetate was added to the obtained residue. The precipitate was collected by filtration to give the title compound (46 mg).

MS(ESI) m/z: 437 (M+H)$^+$

Example 137: Synthesis of 5-tert-butyl-5-[4-(3',5'-dimethyl-2,3,5,6-tetrahydro[1,2']bipyrazinyl-4-carbonyl)phenyl]imidazolidine-2,4-dione

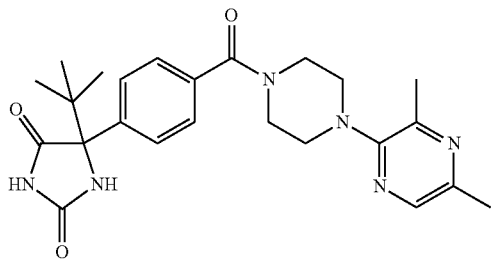 [SMILES: Cc1cnc(N2CCN(C(=O)c3ccc(C4(C(C)(C)C)NC(=O)NC4=O)cc3)CC2)c(C)n1]

Using 4-(4-tert-butyl-2,5-dioxo-imidazolidin-4-yl)benzoic acid (50 mg) described in Preparation Example 13 and 3,5-dimethyl-3,4,5,6-tetrahydro-2H-[1,2']bipyrazinyl (38 mg) described in Preparation Example 83, reactions and treatments similar to those in Example 136 were performed to give the title compound (55 mg).
MS(ESI) m/z: 451 (M+H)+

Example 138: Synthesis of 5-{4-[4-(3,5-dimethyl-pyridin-2-yl)piperazine-1-carbonyl]-2-methoxy-5-methylphenyl}-5-isopropylimidazolidine-2,4-dione

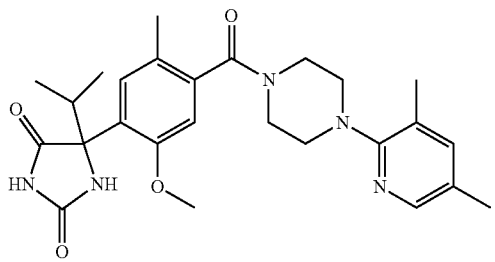 [SMILES: COc1cc(C(=O)N2CCN(c3ncc(C)cc3C)CC2)c(C)cc1C1(C(C)C)NC(=O)NC1=O]

To 4-(4-isopropyl-2,5-dioxoimidazolidin-4-yl)-5-methoxy-2-methylbenzoic acid (103 mg) described in Preparation Example 57 were added 1-(3,5-dimethylpyridin-2-yl)piperazine. hydrochloride (84.2 mg), 1-hydroxybenzotriazole (54.5 mg), 1-ethyl-3-(3'-dimethylaminopropyl) carbodiimide.hydrochloride (83.8 mg), tetrahydrofuran (3 mL) and triethylamine (0.056 mL) and the mixture was stirred at room temperature for 7 hr. Water was added to the reaction mixture, and the precipitate was collected by filtration. The obtained precipitate was suspended in hexane/ethyl acetate and collected by filtration to give the title compound (110.9 mg).
MS(ESI) m/z: 480 (M+H)+

Example 139: Synthesis of 5-{4-[4-(3,5-dimethyl-pyridin-2-yl)-piperazine-1-carbonyl]-2-hydroxy-5-methyl-phenyl}-5-isopropyl-imidazolidine-2,4-dione

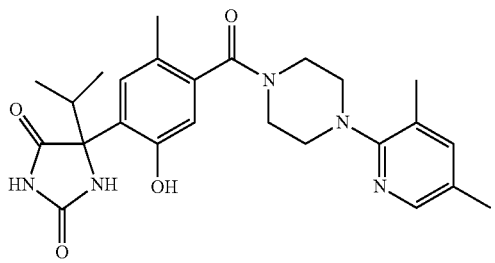 [SMILES: Cc1cnc(N2CCN(C(=O)c3cc(O)c(C4(C(C)C)NC(=O)NC4=O)cc3C)CC2)c(C)c1]

To 5-hydroxy-4-(4-isopropyl-2,5-dioxoimidazolidin-4-yl)-2-methylbenzoic acid (11 mg) described in Preparation Example 58 were added 1-(3,5-dimethylpyridin-2-yl)piperazine. hydrochloride (9.4 mg), 1-hydroxybenzotriazole (6.1 mg), 1-ethyl-3-(3'-dimethylaminopropyl)carbodiimide.hydrochloride (9.4 mg), tetrahydrofuran (2 mL) and triethylamine (6.3 µL) and the mixture was stirred at room temperature for 7 hr. Water was added to the reaction mixture and the mixture was extracted with ethyl acetate. The organic solvent was dried over anhydrous magnesium sulfate and concentrated under reduced pressure. The obtained residue was purified by column chromatography (chloroform:methanol) to give the title compound (13.4 mg).
MS(ESI) m/z: 466 (M+H)+

Example 140: Synthesis of (R)-5-ethyl-5-{4-[4-(4,5,6-trimethylpyridazin-3-yl)piperazine-1-carbonyl]phenyl}imidazolidine-2,4-dione

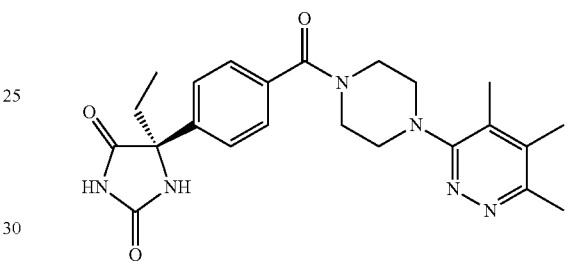

To 4-((R)-4-ethyl-2,5-dioxoimidazolidin-4-yl)benzoic acid (24 mg) described in Preparation Example 14 were added 3,4,5-trimethyl-6-(piperazin-1-yl)pyridazine (20 mg) described in Preparation Example 84, tetrahydrofuran (2 mL), 1-hydroxybenzotriazole (16 mg), 1-ethyl-3-(3'-dimethylaminopropyl)carbodiimide.hydrochloride (24 mg) and N,N-dimethylformamide (0.5 mL) and the mixture was stirred at room temperature overnight. To the reaction mixture was added saturated brine, and the mixture was extracted with ethyl acetate/methanol. The organic solvent was concentrated under reduced pressure and the obtained residue was purified by column chromatography (chloroform:methanol) to give the title compound (25.5 mg).
MS(ESI) m/z: 437 (M+H)+

Example 141: Synthesis of (R)-5-isopropyl-5-{4-[4-(4,5,6-trimethylpyridazin-3-yl)piperazine-1-carbonyl]phenyl}imidazolidine-2,4-dione

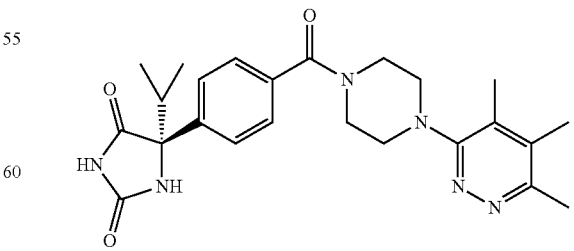

Using 4-((R)-4-isopropyl-2,5-dioxoimidazolidin-4-yl)benzoic acid (25.4 mg) described in Preparation Example 45 and 3,4,5-trimethyl-6-(piperazin-1-yl)pyridazine (20 mg)

described in Preparation Example 84, reactions and treatments similar to those in Example 140 were performed to give the title compound (25.1 mg).

MS(ESI) m/z: 451 (M+H)+

Example 142: Synthesis of (R)-5-isopropyl-5-{4-[4-(5-methylpyridin-2-yloxy)piperidine-1-carbonyl]phenyl}imidazolidine-2,4-dione

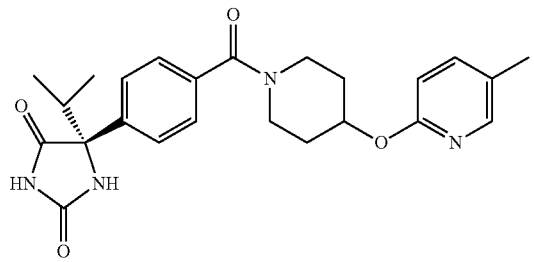

To 4-((R)-4-isopropyl-2,5-dioxoimidazolidin-4-yl)benzoic acid (50 mg) described in Preparation Example 45 were added 5-methyl-2-(piperidin-4-yloxy)pyridine (36.7 mg), tetrahydrofuran (1.5 mL), 1-hydroxybenzotriazole (31 mg) and 1-ethyl-3-(3'-dimethylaminopropyl)carbodiimide.hydrochloride (48 mg) and the mixture was stirred at room temperature overnight. Water was added to the reaction mixture, and the mixture was extracted with ethyl acetate/methanol. The organic solvent was dried over anhydrous magnesium sulfate, concentrated under reduced pressure and the obtained residue was purified by column chromatography (chloroform:methanol) to give the title compound (80.2 mg).

MS(ESI) m/z: 437 (M+H)+

Example 143: Synthesis of (R)-5-isopropyl-5-{4-[4-(5-methylpyridin-2-ylamino)piperidine-1-carbonyl]phenyl}imidazolidine-2,4-dione

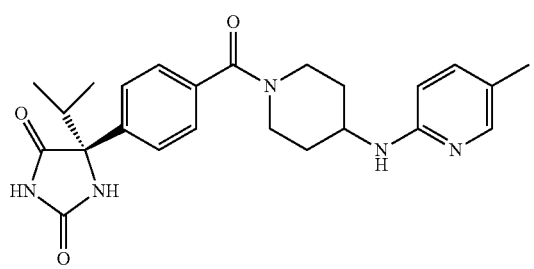 [SMILES: Cc1ccc(OC2CCN(C(=O)c3ccc([C@@]4(C(C)C)NC(=O)NC4=O)cc3)CC2)nc1]

Using 4-((R)-4-isopropyl-2,5-dioxoimidazolidin-4-yl)benzoic acid (50 mg) described in Preparation Example 45 and (5-methyl-pyridin-2-yl)-piperidin-4-yl-amine (36.5 mg), reactions and treatments similar to those in Example 142 were performed to give the title compound (60.4 mg).

MS(ESI) m/z: 436 (M+H)+

Example 144: Synthesis of (R)-5-{4-[4-(3,5-dimethylpyridin-2-ylamino)piperidine-1-carbonyl]phenyl}-5-isopropylimidazolidine-2,4-dione

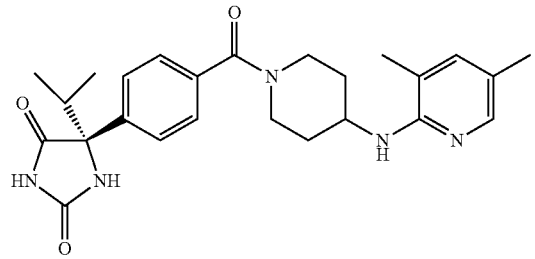 [SMILES: Cc1cnc(NC2CCN(C(=O)c3ccc([C@@]4(C(C)C)NC(=O)NC4=O)cc3)CC2)c(C)c1]

Using 4-((R)-4-isopropyl-2,5-dioxoimidazolidin-4-yl)benzoic acid (50 mg) described in Preparation Example 45 and (3,5-dimethylpyridin-2-yl)piperidin-4-ylamine (39 mg) described in Preparation Example 85, reactions and treatments similar to those in Example 142 were performed to give the title compound (84.5 mg).

MS(ESI) m/z: 450 (M+H)+

Example 145: Synthesis of (R)-5-isopropyl-5-{4-[4-(4-methylbenzoyl)piperidine-1-carbonyl]phenyl}imidazolidine-2,4-dione

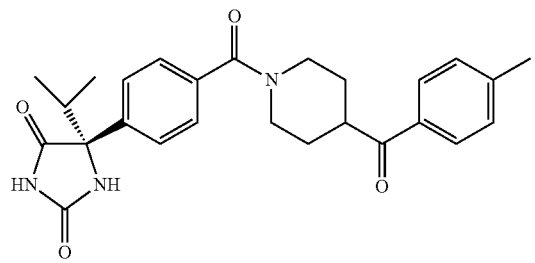 [SMILES: Cc1ccc(C(=O)C2CCN(C(=O)c3ccc([C@@]4(C(C)C)NC(=O)NC4=O)cc3)CC2)cc1]

Using 4-((R)-4-isopropyl-2,5-dioxoimidazolidin-4-yl)benzoic acid (50 mg) described in Preparation Example 45 and 4-(4-methylbenzoyl)piperidine (39 mg), reactions and treatments similar to those in Example 142 were performed to give the title compound (46.3 mg).

MS(ESI) m/z: 448 (M+H)+

Example 146: Synthesis of (R)-5-{4-[(S)-3-(3,5-dimethylpyridin-2-yloxy)pyrrolidine-1-carbonyl]phenyl}-5-isopropylimidazolidine-2,4-dione

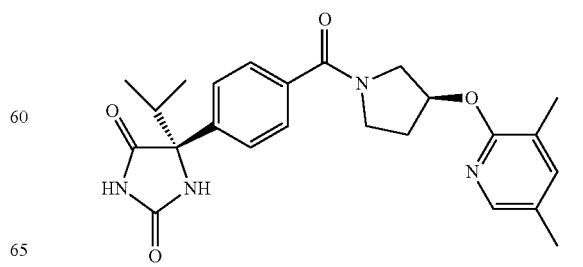

To 4-((R)-4-isopropyl-2,5-dioxoimidazolidin-4-yl)benzoic acid (50 mg) described in Preparation Example 45 were added 3,5-dimethyl-2-((S)-pyrrolidin-3-yloxy)pyridine (37 mg) described in Preparation Example 86, tetrahydrofuran (1.5 mL), 1-hydroxybenzotriazole (31 mg) and 1-ethyl-3-(3'-dimethylaminopropyl)carbodiimide.hydrochloride (48 mg) and the mixture was stirred at room temperature overnight. Water was added to the reaction mixture, and the precipitate was collected by filtration. The obtained precipitate was suspended in hexane/ethyl acetate and collected by filtration to give the title compound (79.8 mg).

MS(ESI) m/z: 437 (M+H)+

Example 147: Synthesis of (R)-5-isopropyl-5-{4-[3-(5-methyl-2,3-dihydropyrrolo[2,3-b]pyridin-1-yl)pyrrolidine-1-carbonyl]phenyl}imidazolidine-2,4-dione

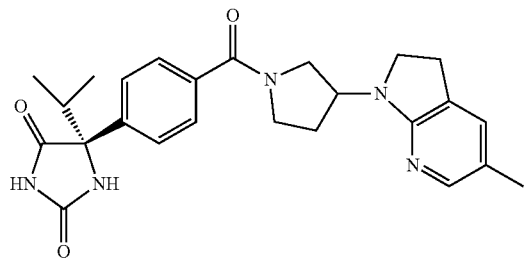 [SMILES: Cc1cnc2c(c1)CCN2C1CCN(C(=O)c2ccc([C@@]3(C(C)C)NC(=O)NC3=O)cc2)C1]

4-((R)-4-isopropyl-2,5-dioxoimidazolidin-4-yl)benzoic acid (32.3 mg) described in Preparation Example 45, 5-methyl-1-pyrrolidin-3-yl-2,3-dihydro-1H-pyrrolo[2,3-b]pyridine (25 mg) described in Preparation Example 87, tetrahydrofuran (1.5 mL), 1-hydroxybenzotriazole (20 mg) and 1-ethyl-3-(3'-dimethylaminopropyl)carbodiimide.hydrochloride (31 mg) were added, and the mixture was stirred at room temperature overnight. To the reaction mixture were added water and saturated aqueous sodium hydrogen carbonate solution and the mixture was extracted with chloroform. The organic layer was dried over anhydrous magnesium sulfate and concentrated under reduced pressure. The obtained residue was purified by column chromatography (chloroform:methanol). The solvent was evaporated and the obtained residue was separated by HPLC using XBridge Prep C18 OBD (Waters) (10 mmol/L aqueous ammonium carbonate solution, acetonitrile) to give the title compound (20.4 mg).

MS(ESI) m/z: 448 (M+H)+

Example 148: Synthesis of (R)-5-isopropyl-5-[4-(4-p-tolyloxypiperidine-1-carbonyl]phenyl}imidazolidine-2,4-dione

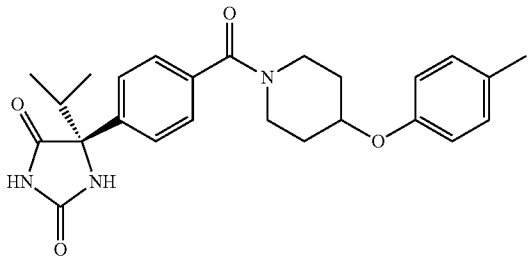 [SMILES: Cc1ccc(OC2CCN(C(=O)c3ccc([C@@]4(C(C)C)NC(=O)NC4=O)cc3)CC2)cc1]

Using 4-((R)-4-isopropyl-2,5-dioxoimidazolidin-4-yl)benzoic acid (50 mg) described in Preparation Example 45 and 4-(4-methylphenoxy)piperidine (36.5 mg), reactions and treatments similar to those in Example 146 were performed to give the title compound (70.7 mg).

MS(ESI) m/z: 436 (M+H)+

Example 149: Synthesis of (R)-5-methyl-5-{4-[4-(5-methylpyridin-2-ylamino)piperidine-1-carbonyl]phenyl}imidazolidine-2,4-dione

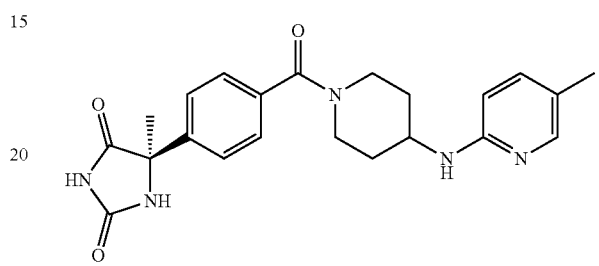

4-((R)-4-methyl-2,5-dioxoimidazolidin-4-yl)benzoic acid (30 mg) described in Preparation Example 6, (5-methylpyridin-2-yl) (piperidin-4-yl)amine (24.5 mg), 1-hydroxybenzotriazole (20.8 mg), 1-ethyl-3-(3'-dimethylaminopropyl)carbodiimide. hydrochloride (31.9 mg) and tetrahydrofuran (2 mL) were added, and the mixture was stirred at room temperature overnight. To the reaction mixture were added water and saturated aqueous sodium hydrogen carbonate solution and the mixture was extracted with ethyl acetate. The organic layer was dried over anhydrous magnesium sulfate and concentrated under reduced pressure. The obtained residue was purified by column chromatography (chloroform:methanol) to give the title compound (47.2 mg).

MS(ESI) m/z: 408 (M+H)+

Example 150: Synthesis of (R)-5-methyl-5-{4-[4-(4-methylbenzoyl)piperidine-1-carbonyl]phenyl}imidazolidine-2,4-dione

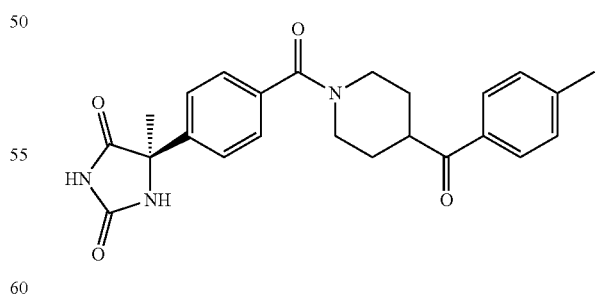

Using 4-((R)-4-methyl-2,5-dioxoimidazolidin-4-yl)benzoic acid (30 mg) described in Preparation Example 6 and 4-(4-methylbenzoyl)piperidine (26 mg), reactions and treatments similar to those in Example 149 were performed to give the title compound (33.5 mg).

MS(ESI) m/z: 420 (M+H)+

Example 151: Synthesis of 5-fluoromethyl-5-{4-[4-(4-methylbenzoyl)piperidine-1-carbonyl]phenyl}imidazolidine-2,4-dione

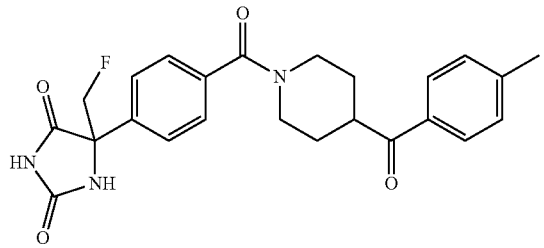 [SMILES: Cc1ccc(C(=O)C2CCN(C(=O)c3ccc(C4(CF)NC(=O)NC4=O)cc3)CC2)cc1]

To 4-(4-fluoromethyl-2,5-dioxoimidazolidin-4-yl)benzoic acid (50 mg) described in Preparation Example 63 were added 4-(4-methylbenzoyl)piperidine (40.3 mg), 1-hydroxybenzotriazole (32.1 mg), 1-ethyl-3-(3'-dimethylaminopropyl)carbodiimide. hydrochloride (49.4 mg) and tetrahydrofuran (2 mL) and the mixture was stirred at room temperature overnight. To the reaction mixture were added water and saturated aqueous sodium hydrogen carbonate solution and the mixture was extracted with ethyl acetate, dried over anhydrous magnesium sulfate and concentrated under reduced pressure. The obtained residue was purified by column chromatography (chloroform:methanol) to give the title compound (22.6 mg).

MS(ESI) m/z: 438 (M+H)$^+$

Example 152: Synthesis of (R)-5-methyl-5-[4-(4-p-tolyloxypiperidine-1-carbonyl]phenyl}imidazolidine-2,4-dione

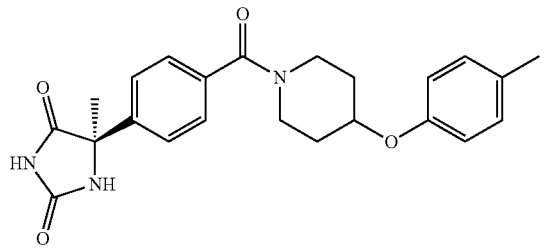 [SMILES: Cc1ccc(OC2CCN(C(=O)c3ccc([C@@]4(C)NC(=O)NC4=O)cc3)CC2)cc1]

Using 4-((R)-4-methyl-2,5-dioxoimidazolidin-4-yl)benzoic acid (30 mg) described in Preparation Example 6 and 4-(4-methylphenoxy)piperidine (24.5 mg), reactions and treatments similar to those in Example 149 were performed to give the title compound (46.9 mg).

MS(ESI) m/z: 408 (M+H)$^+$

Example 153: Synthesis of 5-fluoromethyl-5-[4-(4-p-tolyloxypiperidine-1-carbonyl]phenyl}imidazolidine-2,4-dione

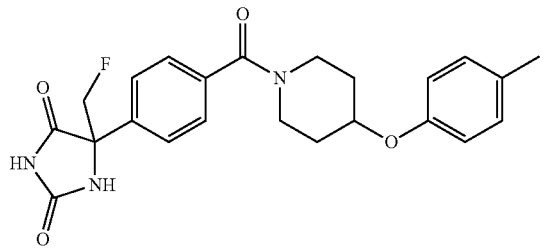 [SMILES: Cc1ccc(OC2CCN(C(=O)c3ccc(C4(CF)NC(=O)NC4=O)cc3)CC2)cc1]

Using 4-(4-fluoromethyl-2,5-dioxoimidazolidin-4-yl)benzoic acid (50 mg) described in Preparation Example 63 and 4-(4-methylphenoxy)piperidine (37.9 mg), reactions and treatments similar to those in Example 151 were performed to give the title compound (79.4 mg).

MS(ESI) m/z: 426 (M+H)$^+$

Example 154: Synthesis of 3-{4-[(S)-3-(3,5-dimethylpyridin-2-ylamino)pyrrolidine-1-carbonyl]phenyl}-3-ethylpyrrolidine-2,5-dione

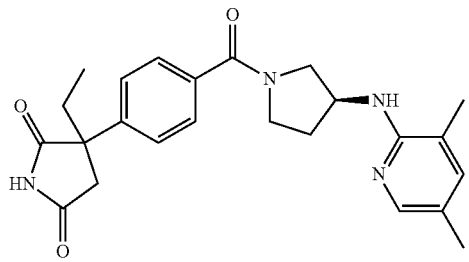 [SMILES: CCC1(c2ccc(C(=O)N3CC[C@H](Nc4ncc(C)cc4C)C3)cc2)CC(=O)NC1=O]

To 4-(3-ethyl-2,5-dioxopyrrolidin-3-yl)benzoic acid (100 mg) described in Preparation Example 20 were added (3,5-dimethylpyridin-2-yl)-(S)-pyrrolidin-3-ylamine.2 hydrochloride (106.9 mg) described in Preparation Example 88, 1-hydroxybenzotriazole (65.6 mg), 1-ethyl-3-(3'-dimethylaminopropyl)carbodiimide.hydrochloride (100.8 mg), tetrahydrofuran (4.5 mL) and triethylamine (0.118 mL) and the mixture was stirred at room temperature overnight. Water was added to the reaction mixture and the mixture was extracted with ethyl acetate, dried over anhydrous magnesium sulfate and concentrated under reduced pressure. The obtained residue was purified by column chromatography (chloroform:methanol). The solvent was evaporated and the obtained residue was separated by HPLC using Capcellpak C18 UG80 (0.05% trifluoroacetic acid/water, 0.05% trifluoroacetic acid/acetonitrile) to give the title compound (110.5 mg).

MS(ESI) m/z: 421 (M+H)$^+$

Example 155: Synthesis of (R)-5-isopropyl-5-{4-[(S)-3-(5-methylpyridin-2-ylamino)pyrrolidine-1-carbonyl]phenyl}imidazolidine-2,4-dione

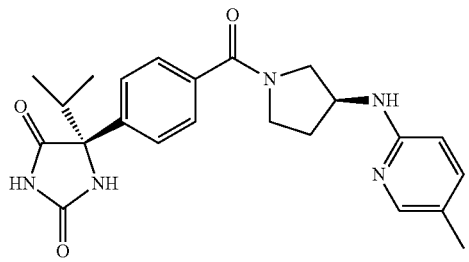 [SMILES: Cc1ccc(N[C@H]2CCN(C(=O)c3ccc([C@@]4(C(C)C)NC(=O)NC4=O)cc3)C2)nc1]

To 4-((R)-4-isopropyl-2,5-dioxoimidazolidin-4-yl)benzoic acid (30 mg) described in Preparation Example 45 were added (5-methylpyridin-2-yl)-(S)-pyrrolidin-3-ylamine (20.3 mg), 1-hydroxybenzotriazole (18.5 mg), 1-ethyl-3-(3'-dimethylaminopropyl)carbodiimide.hydrochloride (28.5 mg) and tetrahydrofuran (2.5 mL) and the mixture was stirred at room temperature overnight. Water was added to the reaction mixture and the mixture was extracted with ethyl acetate, dried over anhydrous magnesium sulfate and concentrated under reduced pressure. The obtained residue was purified by column chromatography (chloroform: methanol) to give the title compound (46.2 mg).
MS (ESI) m/z: 422 (M+H)+

Example 156: Synthesis of (R)-5-fluoromethyl-5-{4-[4-(5-methylpyridin-2-yloxy)piperidine-1-carbonyl]phenyl}imidazolidine-2,4-dione and (S)-5-fluoromethyl-5-{4-[4-(5-methylpyridin-2-yloxy)piperidine-1-carbonyl]phenyl}imidazolidine-2,4-dione

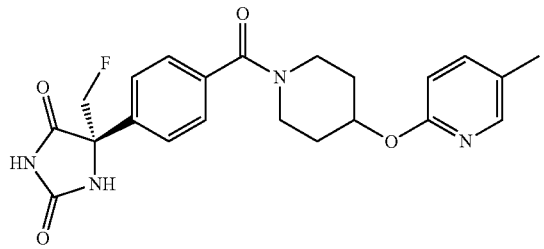

Using 4-(4-fluoromethyl-2,5-dioxoimidazolidin-4-yl)benzoic acid (100 mg) described in Preparation Example 63 and 5-methyl-2-(piperidin-4-yloxy)pyridine (76.2 mg), reactions and treatments similar to those in Example 151 were performed to give 5-fluoromethyl-5-{4-[4-(5-methylpyridin-2-yloxy)piperidine-1-carbonyl]phenyl}imidazolidine-2,4-dione (170 mg).

The obtained 5-fluoromethyl-5-{4-[4-(5-methyl-pyridin-2-yloxy)-piperidine-1-carbonyl]-phenyl}-imidazolidine-2,4-dione (170 mg) was separated by HPLC using CHIRALPAK (Daicel) IF (hexane/ethanol/tetrahydrofuran/diethylamine) to give the both enantiomers indicated above (compound with short retention time 77.4 mg (MS(ESI) m/z: 427 (M+H)+) and compound with long retention time 74.7 mg (MS(ESI) m/z: 427 (M+H)+)).

In the analysis using CHIRALPAK (Daicel) IF-3 (4.6 mm×150 mm, hexane/ethanol/tetrahydrofuran/diethylamine=50/30/20/0.1, flow 0.5 mL/min), the retention time was respectively 8.8 min and 10.9 min.

Example 157: Synthesis of (R)-5-isopropyl-5-{4-[4-(5-methylpyrrolo[2,3-b]pyridin-1-yl)piperidine-1-carbonyl]phenyl}imidazolidine-2,4-dione

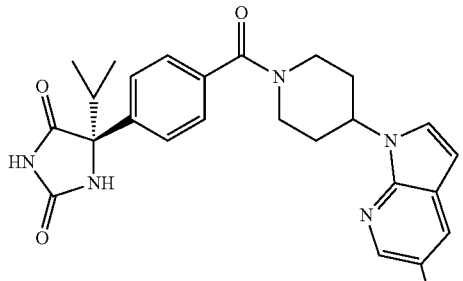

To 4-((R)-4-isopropyl-2,5-dioxoimidazolidin-4-yl)benzoic acid (50 mg) described in Preparation Example 45 were added 5-methyl-1-piperidin-4-yl-1H-indole (41 mg) described in Preparation Example 89, 1-hydroxybenzotriazole (31 mg), 1-ethyl-3-(3'-dimethylaminopropyl)carbodiimide.hydrochloride (48 mg) and tetrahydrofuran (2 mL) and the mixture was stirred at room temperature overnight. To the reaction mixture were added water and saturated aqueous sodium hydrogen carbonate solution and the mixture was extracted with ethyl acetate. The organic layer was concentrated under reduced pressure and the obtained residue was purified by column chromatography (chloroform: methanol). The solvent was evaporated and the obtained residue was separated by HPLC using XBridge Prep C18 OBD (Waters) (10 mmol/L aqueous ammonium carbonate solution, acetonitrile) to give the title compound (65.1 mg).
MS(ESI) m/z: 460 (M+H)+

Example 158: Synthesis of (R)-5-isopropyl-5-{4-[(S)-3-(5-methyl-2,3-dihydropyrrolo[2,3-b]pyridin-1-yl)pyrrolidine-1-carbonyl]phenyl}imidazolidine-2,4-dione

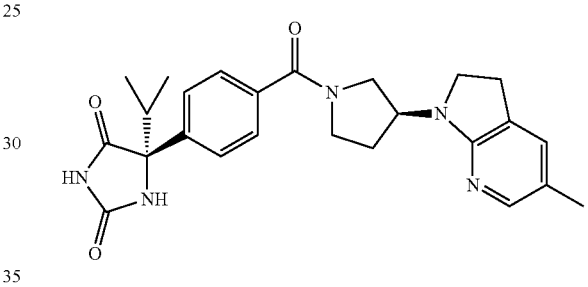

Using 4-((R)-4-isopropyl-2,5-dioxoimidazolidin-4-yl)benzoic acid (50 mg) described in Preparation Example 45 and 5-methyl-1-(S)-pyrrolidin-3-yl-2,3-dihydro-1H-pyrrolo[2,3-b]pyridine (39 mg) described in Preparation Example 90, reactions and treatments similar to those in Example 157 were performed to give the title compound (63.4 mg).
MS(ESI) m/z: 448 (M+H)+

Example 159: Synthesis of (R)-5-isopropyl-5-{4-[(S)-3-(5-methylpyrrolo[2,3-b]pyridin-1-yl)pyrrolidine-1-carbonyl]phenyl}imidazolidine-2,4-dione

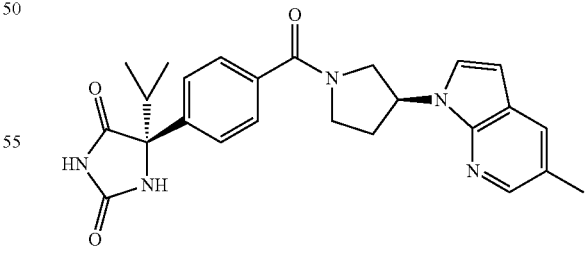

Using 4-((R)-4-isopropyl-2,5-dioxoimidazolidin-4-yl)benzoic acid (50 mg) described in Preparation Example 45 and 5-methyl-1-(S)-pyrrolidin-3-yl-1H-pyrrolo[2,3-b]pyridine (38 mg) described in Preparation Example 91, reactions and treatments similar to those in Example 157 were performed to give the title compound (72.3 mg).
MS(ESI) m/z: 446 (M+H)+

Example 160: Synthesis of (R)-5-methyl-5-{4-[(S)-3-(5-methyl-2,3-dihydropyrrolo[2,3-b]pyridin-1-yl)pyrrolidine-1-carbonyl]phenyl}imidazolidine-2,4-dione

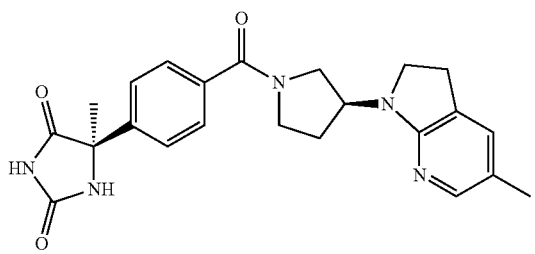 [SMILES: Cc1cnc2c(c1)CCN2[C@H]1CCN(C(=O)c2ccc([C@@]3(C)NC(=O)NC3=O)cc2)C1]

To 4-((R)-4-methyl-2,5-dioxoimidazolidin-4-yl)benzoic acid (50 mg) described in Preparation Example 6 were added 5-methyl-1-(S)-pyrrolidin-3-yl-2,3-dihydro-1H-pyrrolo[2,3-b]pyridine (43 mg) described in Preparation Example 90, tetrahydrofuran (2 mL), 1-hydroxybenzotriazole (35 mg), 1-ethyl-3-(3'-dimethylaminopropyl)carbodiimide.hydrochloride (53 mg) and triethylamine (0.06 mL) and the mixture was stirred at room temperature for 1.5 hr. To the reaction mixture were added water and saturated aqueous sodium hydrogen carbonate solution and the mixture was extracted with ethyl acetate. The organic layer was concentrated under reduced pressure and the obtained residue was purified by column chromatography (chloroform:methanol). The solvent was evaporated and the obtained residue was separated by HPLC using XBridge Prep C18 OBD (Waters) (10 mmol/L aqueous ammonium carbonate solution, acetonitrile) to give the title compound (39.6 mg).

MS(ESI) m/z: 420 (M+H)$^+$

Example 161: Synthesis of (R)-5-(4-{4-[5-(4-fluorophenyl)-[1,3,4]oxadiazol-2-yl]piperidine-1-carbonyl}phenyl)-5-isopropylimidazolidine-2,4-dione

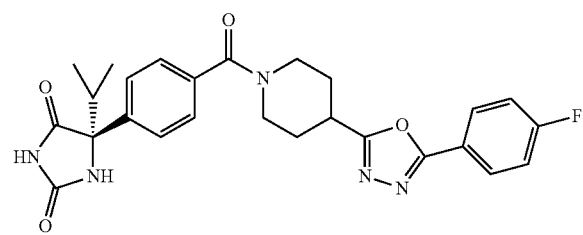 [SMILES: CC(C)[C@]1(c2ccc(C(=O)N3CCC(c4nnc(-c5ccc(F)cc5)o4)CC3)cc2)NC(=O)NC1=O]

4-((R)-4-isopropyl-2,5-dioxoimidazolidin-4-yl)benzoic acid (70 mg) described in Preparation Example 45, 2-(4-fluorophenyl)-5-(piperidin-4-yl)-1,3,4-oxadiazole (79 mg), 1-hydroxybenzotriazole (54 mg) and 1-ethyl-3-(3'-dimethylaminopropyl)carbodiimide.hydrochloride (79 mg) were dissolved in N,N-dimethylformamide (2 mL) and the mixture was stirred at room temperature overnight. Water was added to the reaction mixture and the mixture was extracted with ethyl acetate. The solvent was evaporated and the obtained residue was purified by column chromatography (hexane:ethyl acetate) to give the title compound (95 mg).

MS (APCI) m/z: 492 (M+H)$^+$

Example 162: Synthesis of (R)-5-(4-{4-[5-(2,4-dimethylphenyl)-[1,3,4]oxadiazol-2-yl]piperidine-1-carbonyl}phenyl)-5-methylimidazolidine-2,4-dione

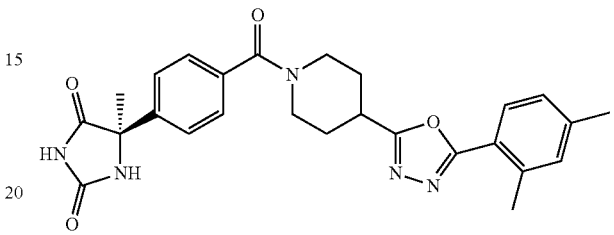

4-((R)-4-methyl-2,5-dioxoimidazolidin-4-yl)benzoic acid (80 mg) described in Preparation Example 6, 4-[5-(2,4-dimethylphenyl)-[1,3,4]oxadiazol-2-yl]piperidine.hydrochloride (131 mg) described in Preparation Example 75, 1-hydroxybenzotriazole (69 mg) and 1-ethyl-3-(3'-dimethylaminopropyl)carbodiimide.hydrochloride (98 mg) were dissolved in chloroform (3 mL), triethylamine (0.142 mL) was added, and the mixture was stirred at room temperature overnight. To the reaction mixture was added saturated aqueous sodium hydrogen carbonate solution, and the mixture was filtered by a phase separator. The filtrate was concentrated under reduced pressure and the obtained residue was purified by column chromatography (ethyl acetate:methanol) to give the title compound (70 mg).

MS(ESI) m/z: 474 (M+H)$^+$

Example 163: Synthesis of (R)-5-(4-{4-[5-(2,4-dimethylphenyl)-[1,3,4]oxadiazol-2-yl]piperidine-1-carbonyl}phenyl)-5-ethylimidazolidine-2,4-dione

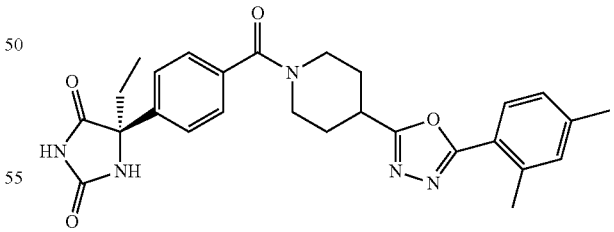

Using 4-((R)-4-ethyl-2,5-dioxoimidazolidin-4-yl)benzoic acid (80 mg) described in Preparation Example 14 and 4-[5-(2,4-dimethylphenyl)-[1,3,4]oxadiazol-2-yl]piperidine.hydrochloride (123 mg) described in Preparation Example 75, reactions and treatments similar to those in Example 162 were performed to give the title compound (104 mg).

MS(ESI) m/z: 488 (M+H)$^+$

Example 164: Synthesis of (R)-5-isopropyl-5-(4-{4-[5-(5-methylpyridyl-2-yl)-1H-pyrazol-3-yl]piperidine-1-carbonyl}phenyl)imidazolidine-2,4-dione

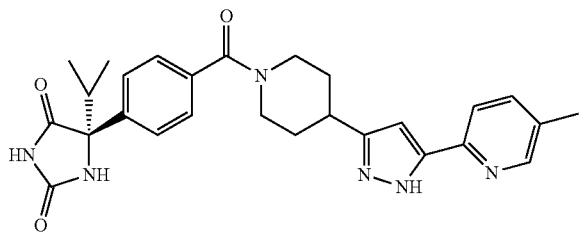 [SMILES: Cc1ccc(-c2cc(C3CCN(C(=O)c4ccc([C@@]5(C(C)C)NC(=O)NC5=O)cc4)CC3)n[nH]2)nc1]

4-((R)-4-isopropyl-2,5-dioxoimidazolidin-4-yl)benzoic acid (73 mg) described in Preparation Example 45, 5-methyl-2-(5-piperidin-4-yl-2H-pyrazol-3-yl)pyridine.2 hydrochloride (80 mg) described in Preparation Example 76, 1-hydroxybenzotriazole (51 mg) and 1-ethyl-3-(3'-dimethylaminopropyl)carbodiimide.hydrochloride (73 mg) were dissolved in chloroform (3 mL), triethylamine (0.106 mL) was added, and the mixture was stirred at room temperature overnight. To the reaction mixture was added saturated aqueous sodium hydrogen carbonate solution, and the mixture was filtered by a phase separator. The filtrate was concentrated under reduced pressure and the obtained residue was purified by column chromatography (ethyl acetate: methanol) to give the title compound (77 mg).

MS(ESI) m/z: 487 (M+H)$^+$

Example 165: Synthesis of 3-ethyl-3-{5-[4-(5-p-tolyl-1H-pyrazol-3-yl)piperidine-1-carbonyl}pyridin-2-yl}pyrrolidine-2,5-dione

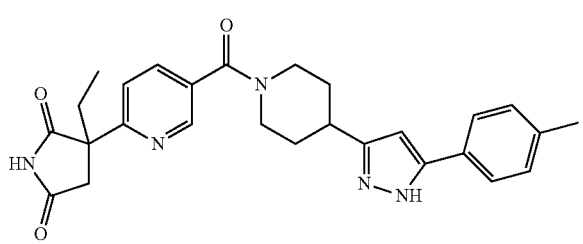 [SMILES: CCC1(c2ccc(C(=O)N3CCC(c4cc(-c5ccc(C)cc5)[nH]n4)CC3)cn2)CC(=O)NC1=O]

Using 6-(3-ethyl-2,5-dioxopyrrolidin-3-yl)nicotinic acid (64 mg) described in Preparation Example 51 and 4-[5-(p-tolyl)-1H-pyrazol-3-yl]piperidine (60 mg) described in Preparation Example 77, reactions and treatments similar to those in Example 164 were performed to give the title compound (61 mg).

MS(ESI) m/z: 472 (M+H)$^+$

Example 166: Synthesis of (R)-5-[4-(3,5-dimethyl-3',4',5',6'-tetrahydro-2'H-[2,4']bipyridinyl-1'-carbonyl)phenyl]-5-isopropylimidazolidine-2,4-dione

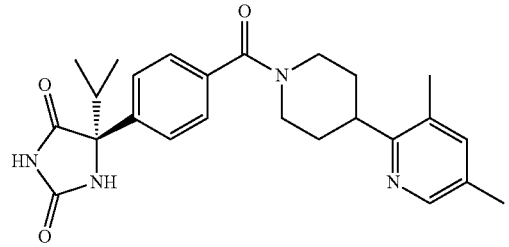 [SMILES: Cc1cnc(C2CCN(C(=O)c3ccc([C@@]4(C(C)C)NC(=O)NC4=O)cc3)CC2)c(C)c1]

4-((R)-4-isopropyl-2,5-dioxoimidazolidin-4-yl)benzoic acid (80 mg) described in Preparation Example 45, 3,5-dimethyl-1',2',3',4',5',6'-hexahydro-[2,4']bipyridinyl.2 hydrochloride (96 mg) described in Preparation Example 81, 1-hydroxy-7-azabenzotriazole (62 mg) and 1-ethyl-3-(3'-dimethylaminopropyl) carbodiimide.hydrochloride (88 mg) were dissolved in dichloromethane (3 mL), triethylamine (0.127 mL) was added, and the mixture was stirred at room temperature overnight. To the reaction mixture was added saturated aqueous sodium hydrogen carbonate solution, and the mixture was filtered by a phase separator. The filtrate was concentrated under reduced pressure and the obtained residue was purified by column chromatography (ethyl acetate: methanol) to give the title compound (101 mg).

MS (ESI) m/z: 435 (M+H)$^+$

Example 167: Synthesis of (R)-5-[4-(3,5-dimethyl-3',4',5',6'-tetrahydro-2'H-[2,4']bipyridinyl-1'-carbonyl)phenyl]-5-ethylimidazolidine-2,4-dione

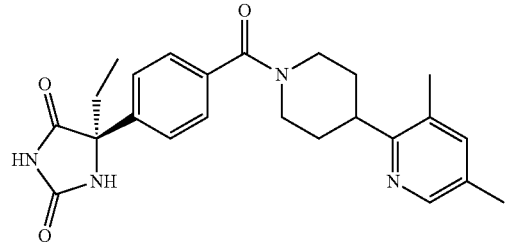 [SMILES: CC[C@]1(c2ccc(C(=O)N3CCC(c4ncc(C)cc4C)CC3)cc2)NC(=O)NC1=O]

Using 4-((R)-4-ethyl-2,5-dioxoimidazolidin-4-yl)benzoic acid (80 mg) described in Preparation Example 14 and 3,5-dimethyl-1',2',3',4',5',6'-hexahydro-[2,4']bipyridinyl.2 hydrochloride (102 mg) described in Preparation Example 81, reactions and treatments similar to those in Example 166 were performed to give the title compound (125 mg).

MS(ESI) m/z: 421 (M+H)$^+$

Example 168: Synthesis of 2,2-dimethylpropionic acid (R)-4-{4-[4-(5,7-dimethylindazol-2-yl)piperidine-1-carbonyl]phenyl}-4-methyl-2,5-dioxoimidazolidin-1-ylmethyl ester

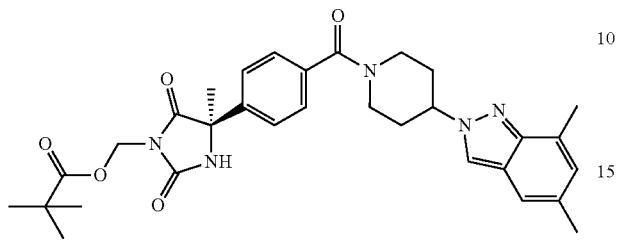

4-[(R)-1-(2,2-dimethylpropionyloxymethyl)-4-methyl-2,5-dioxoimidazolidin-4-yl]benzoic acid (80 mg) described in Preparation Example 65, 5,7-dimethyl-2-piperidin-4-yl-2H-indazole.hydrochloride (67 mg) described in Preparation Example 96, 1-hydroxy-7-azabenzotriazole (47 mg), 1-ethyl-3-(3'-dimethylaminopropyl) carbodiimide.hydrochloride (66 mg) were dissolved in dichloromethane (3 mL), triethylamine (0.096 mL) was added, and the mixture was stirred at room temperature overnight. To the reaction mixture was added saturated aqueous sodium hydrogen carbonate solution, and the mixture was filtered by a phase separator. The filtrate was concentrated under reduced pressure and the obtained residue was purified by column chromatography (ethyl acetate:methanol) to give the title compound (128 mg).

MS(ESI) m/z: 560 (M+H)$^+$

Example 169: Synthesis of (R)-5-methyl-5-{4-[4-(2-p-tolyl-2H-tetrazol-5-yl)piperidine-1-carbonyl]phenyl}imidazolidine-2,4-dione

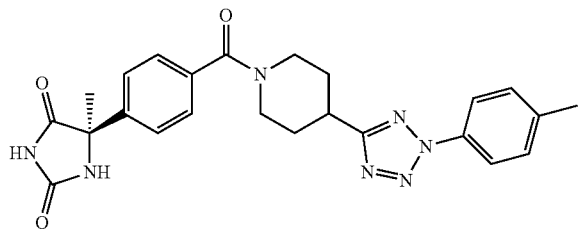 [SMILES: Cc1ccc(-n2nnc(C3CCN(C(=O)c4ccc([C@@]5(C)NC(=O)NC5=O)cc4)CC3)n2)cc1]

4-((R)-4-methyl-2,5-dioxoimidazolidin-4-yl)benzoic acid (80 mg) described in Preparation Example 6, 4-[2-(p-tolyl)-2H-tetrazol-5-yl]piperidine (100 mg) described in Preparation Example 78, 1-hydroxy-7-azabenzotriazole (70 mg) and 1-ethyl-3-(3'-dimethylaminopropyl)carbodiimide.hydrochloride (98 mg) were dissolved in dichloromethane (3 mL) and the mixture was stirred at room temperature overnight. To the reaction mixture was added saturated aqueous sodium hydrogen carbonate solution, and the mixture was filtered by a phase separator. The filtrate was concentrated under reduced pressure and the obtained residue was purified by column chromatography (ethyl acetate:methanol) to give the title compound (147 mg).

MS(ESI) m/z: 460 (M+H)$^+$

Example 170: Synthesis of (R)-5-ethyl-5-{4-[4-(2-p-tolyl-2H-tetrazol-5-yl)piperidine-1-carbonyl]phenyl}imidazolidine-2,4-dione

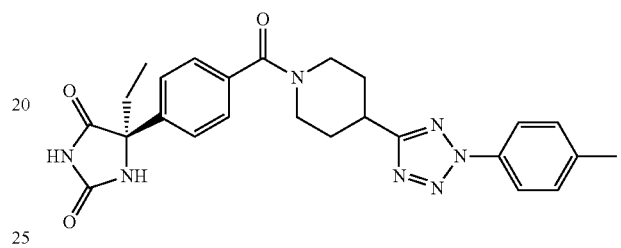

Using 4-((R)-4-ethyl-2,5-dioxoimidazolidin-4-yl)benzoic acid (80 mg) described in Preparation Example 14 and 4-[2-(p-tolyl)-2H-tetrazol-5-yl]piperidine (94 mg) described in Preparation Example 78, reactions and treatments similar to those in Example 169 were performed to give the title compound (137 mg).

MS(ESI) m/z: 474 (M+H)$^+$

Example 171: Synthesis of 3-methoxymethyl-3-{5-[4-(5-p-tolyl-1H-pyrazol-3-yl)piperidine-1-carbonyl]pyridin-2-yl}pyrrolidine-2,5-dione

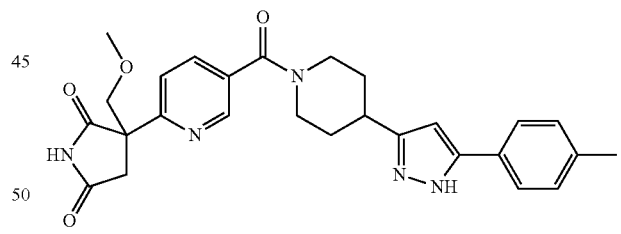

6-(3-Methoxymethyl-2,5-dioxopyrrolidin-3-yl)nicotinic acid (51 mg) described in Preparation Example 64, 4-[5-(p-tolyl)-1H-pyrazol-3-yl]piperidine (42 mg, see Preparation Example 77), 1-hydroxy-7-azabenzotriazole (36 mg) and 1-ethyl-3-(3'-dimethylaminopropyl)carbodiimide.hydrochloride (50 mg) were dissolved in dichloromethane (3 mL) and the mixture was stirred at room temperature for 4 hr. To the reaction mixture was added saturated aqueous sodium hydrogen carbonate solution, and the mixture was filtered by a phase separator. The filtrate was concentrated under reduced pressure and the obtained residue was purified by column chromatography (ethyl acetate:methanol) to give the title compound (12 mg).

MS(ESI) m/z: 488 (M+H)$^+$

Example 172: Synthesis of (R)-5-methyl-5-{4-[4-(1-p-tolyl-1H-[1,2,3]triazol-4-yl)piperidine-1-carbonyl]phenyl}imidazolidine-2,4-dione

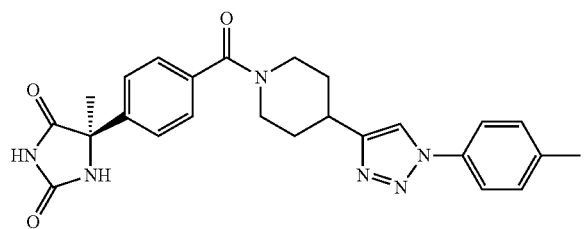 [SMILES: Cc1ccc(-n2cc(C3CCN(C(=O)c4ccc([C@@]5(C)NC(=O)NC5=O)cc4)CC3)nn2)cc1]

4-((R)-4-methyl-2,5-dioxoimidazolidin-4-yl)benzoic acid (80 mg) described in Preparation Example 6, 4-[1-(p-tolyl)-1H-[1,2,3]triazol-4-yl]piperidine.2 hydrochloride (118 mg) described in Preparation Example 79, 1-hydroxy-7-azabenzotriazole (70 mg) and 1-ethyl-3-(3'-dimethylaminopropyl)carbodiimide.hydrochloride (98 mg) were dissolved in dichloromethane (3 mL) and the mixture was stirred at room temperature overnight. To the reaction mixture was added saturated aqueous sodium hydrogen carbonate solution, and the mixture was filtered by a phase separator. The filtrate was concentrated under reduced pressure and the obtained residue was purified by column chromatography (ethyl acetate: methanol) to give the title compound (154 mg).

MS(ESI) m/z: 459 (M+H)+

Example 173: Synthesis of (R)-5-ethyl-5-{4-[4-(1-p-tolyl-1H-[1,2,3]triazol-4-yl)piperidine-1-carbonyl]phenyl}imidazolidine-2,4-dione

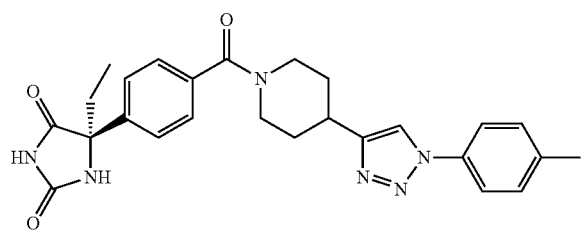 [SMILES: CC[C@]1(c2ccc(C(=O)N3CCC(c4cn(-c5ccc(C)cc5)nn4)CC3)cc2)NC(=O)NC1=O]

Using 4-((R)-4-ethyl-2,5-dioxoimidazolidin-4-yl)benzoic acid (80 mg) described in Preparation Example 14 and 4-[1-(p-tolyl)-1H-[1,2,3]triazol-4-yl]piperidine.2 hydrochloride (112 mg) described in Preparation Example 79, reactions and treatments similar to those in Example 172 were performed to give the title compound (149 mg).

MS(ESI) m/z: 473 (M+H)+

Example 174: Synthesis of (R)-5-methyl-5-{4-[4-(1-p-tolyl-1H-imidazol-4-yl)piperidine-1-carbonyl]phenyl}imidazolidine-2,4-dione

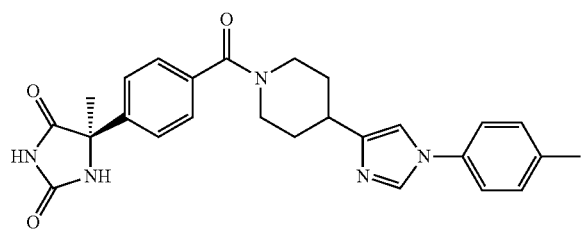 [SMILES: Cc1ccc(-n2cnc(C3CCN(C(=O)c4ccc([C@@]5(C)NC(=O)NC5=O)cc4)CC3)c2)cc1]

4-((R)-4-methyl-2,5-dioxoimidazolidin-4-yl)benzoic acid (72 mg) described in Preparation Example 6, 4-[1-(p-tolyl)-1H-imidazol-4-yl]piperidine.2 hydrochloride (80 mg) described in Preparation Example 80, 1-hydroxy-7-azabenzotriazole (52 mg) and 1-ethyl-3-(3'-dimethylaminopropyl)carbodiimide. hydrochloride (73 mg) were dissolved in dichloromethane (3 mL), triethylamine (0.106 mL) was added, and the mixture was stirred at room temperature overnight. To the reaction mixture was added saturated aqueous sodium hydrogen carbonate solution, and the mixture was filtered by a phase separator. The filtrate was concentrated under reduced pressure and the obtained residue was purified by column chromatography (ethyl acetate: methanol) to give the title compound (109 mg).

MS(ESI) m/z: 458 (M+H)+

Example 175: Synthesis of (R)-5-ethyl-5-{4-[4-(1-p-tolyl-1H-imidazol-4-yl)piperidine-1-carbonyl]phenyl}imidazolidine-2,4-dione

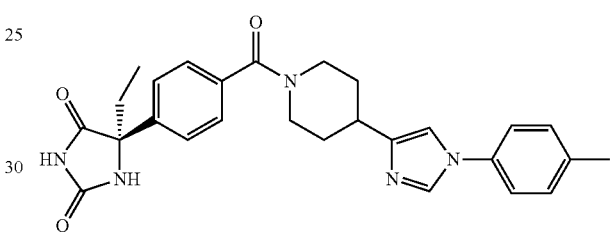

Using 4-((R)-4-ethyl-2,5-dioxoimidazolidin-4-yl)benzoic acid (76 mg) described in Preparation Example 14 and 4-[1-(p-tolyl)-1H-imidazol-4-yl]piperidine.2 hydrochloride (80 mg) described in Preparation Example 80, reactions and treatments similar to those in Example 174 were performed to give the title compound (115 mg).

MS(ESI) m/z: 472 (M+H)+

Example 176: Synthesis of (R)-5-[4-(3,5-dimethyl-3',4',5',6'-tetrahydro-2'H-[2,4']bipyridinyl-1'-carbonyl)phenyl]-5-methylimidazolidine-2,4-dione

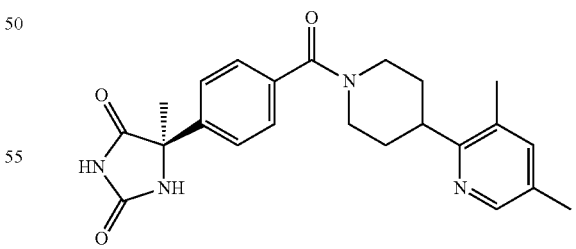

Using 4-((R)-4-methyl-2,5-dioxoimidazolidin-4-yl)benzoic acid (80 mg) described in Preparation Example 6 and 3,5-dimethyl-1',2',3',4',5',6'-hexahydro-[2,4']bipyridinyl.2 hydrochloride (108 mg) described in Preparation Example 81, reactions and treatments similar to those in Example 166 were performed to give the title compound (139 mg).

MS(ESI) m/z: 407 (M+H)+

Example 177: Synthesis of 5-[4-(3,5-dimethyl-3',4', 5',6'-tetrahydro-2'H-[2,4']bipyridinyl-1'-carbonyl)-2-fluorophenyl]-5-ethylimidazolidine-2,4-dione

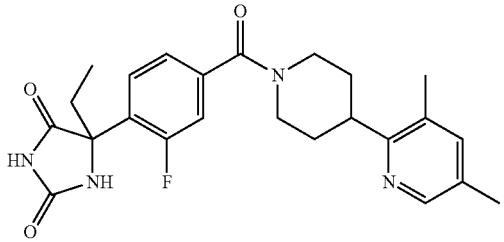 [SMILES: CCC1(c2ccc(C(=O)N3CCC(c4ncc(C)cc4C)CC3)cc2F)NC(=O)NC1=O]

4-(4-Ethyl-2,5-dioxoimidazolidin-4-yl)-3-fluorobenzoic acid (150 mg) described in Preparation Example 40, 3,5-dimethyl-1',2',3',4',5',6'-hexahydro-[2,4']bipyridinyl.2 hydrochloride (178 mg) described in Preparation Example 81, 1-hydroxy-7-azabenzotriazole (115 mg) and 1-ethyl-3-(3'-dimethylaminopropyl)carbodiimide.hydrochloride (162 mg) were dissolved in dichloromethane (3 mL), triethylamine (0.235 mL) was added, and the mixture was stirred at room temperature overnight. To the reaction mixture was added saturated aqueous sodium hydrogen carbonate solution, and the mixture was filtered by a phase separator. The filtrate was concentrated under reduced pressure and the obtained residue was purified by column chromatography (ethyl acetate:methanol) to give the title compound (247 mg).
MS(ESI) m/z: 439 (M+H)+

Example 178: Synthesis of 5-ethyl-5-{2-fluoro-4-[4-(1-p-tolyl-1H-[1,2,3]triazol-4-yl)piperidine-1-carbonyl]phenyl}imidazolidine-2,4-dione

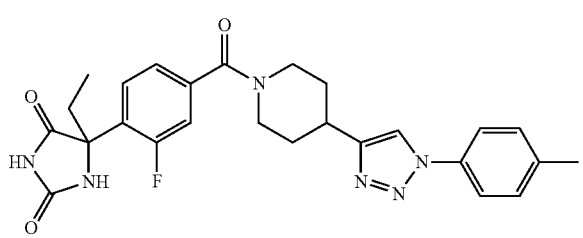 [SMILES: CCC1(c2ccc(C(=O)N3CCC(c4cn(-c5ccc(C)cc5)nn4)CC3)cc2F)NC(=O)NC1=O]

Using 4-(4-ethyl-2,5-dioxoimidazolidin-4-yl)-3-fluorobenzoic acid (150 mg) described in Preparation Example 40 and 4-[1-(p-tolyl)-1H-[1,2,3]triazol-4-yl]piperidine.2 hydrochloride (195 mg) described in Preparation Example 79, reactions and treatments similar to those in Example 177 were performed to give the title compound (265 mg).
MS(ESI) m/z: 491 (M+H)+

Example 179: Synthesis of 3-[5-(3,5-dimethyl-3',4', 5',6'-tetrahydro-2'H-[2,4']bipyridinyl-1'-carbonyl) pyridin-2-yl]-3-ethylpyrrolidine-2,5-dione

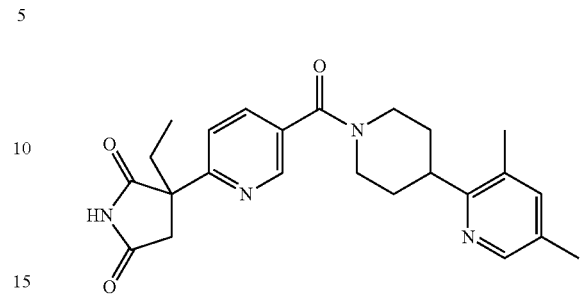

Using 6-(3-ethyl-2,5-dioxopyrrolidin-3-yl)nicotinic acid (170 mg) described in Preparation Example 51 and 3,5-dimethyl-1',2',3',4',5',6'-hexahydro-[2,4']bipyridinyl.2 hydrochloride (216 mg) described in Preparation Example 81, reactions and treatments similar to those in Example 166 were performed to give the title compound (266 mg).
MS(ESI) m/z: 421 (M+H)+

Example 180: Synthesis of 5-{4-[4-(3,5-dimethyl-pyridin-2-yl)piperazine-1-carbonyl]-3-hydroxyphenyl}-5-methylimidazolidine-2,4-dione

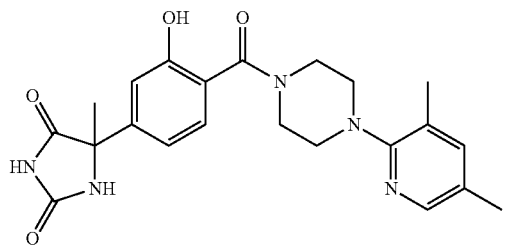 [SMILES: Cc1cnc(N2CCN(C(=O)c3ccc(C4(C)NC(=O)NC4=O)cc3O)CC2)c(C)c1]

Using 2-hydroxy-4-(4-methyl-2,5-dioxoimidazolidin-4-yl)benzoic acid (123 mg) described in Preparation Example 48 and 1-(3,5-dimethylpyridin-2-yl)piperazine (113 mg), reactions and treatments similar to those in Example 42 were performed to give the title compound (92 mg).
MS(ESI) m/z: 424 (M+H)+

Example 181: Synthesis of 5-{4-[4-(3,5-dimethyl-pyridin-2-yl)piperazine-1-carbonyl]phenyl}-5-(2-methoxyethyl) imidazolidine-2,4-dione

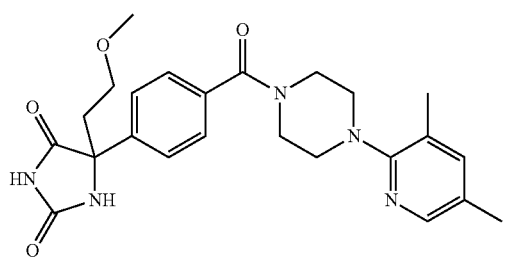 [SMILES: COCCC1(c2ccc(C(=O)N3CCN(c4ncc(C)cc4C)CC3)cc2)NC(=O)NC1=O]

To 4-[4-(2-methoxyethyl)-2,5-dioxoimidazolidin-4-yl] benzoic acid as a crude product (280 mg) described in Preparation Example 36 were added 1-(3,5-dimethylpyridin-2-yl)piperazine.hydrochloride (145.7 mg), chloroform (8.4 mL), N,N-dimethylformamide (2.8 mL), 1-hydroxybenzotriazole (93.7 mg), 1-ethyl-3-(3'-dimethylaminopropyl)carbodiimide. hydrochloride (143.1 mg) and triethylamine (178.4 µL) and the mixture was stirred at room temperature for 4 hr. Water was added to the reaction mixture and the mixture was extracted with ethyl acetate. The organic layer was washed with saturated brine, dried over anhydrous magnesium sulfate, and the solvent was evaporated. The obtained residue was purified by column chromatography (ethyl acetate:methanol) to give the title compound (135 mg).

MS(ESI) m/z: 452 (M+H)+

Example 182: Synthesis of 5-{4-[4-(3,5-dimethylpyridin-2-yl) piperazine-1-carbonyl]phenyl}-5-isopropyl-1-methylimidazolidine-2,4-dione

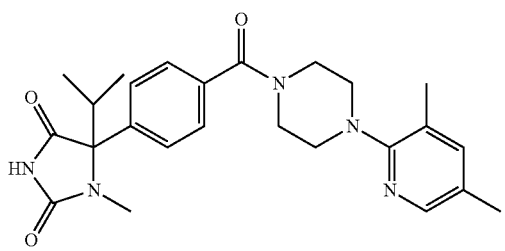 [SMILES: Cc1cnc(N2CCN(C(=O)c3ccc(C4(C(C)C)C(=O)NC(=O)N4C)cc3)CC2)c(C)c1]

5-{4-[4-(3,5-Dimethylpyridin-2-yl)piperazine-1-carbonyl]phenyl}-5-isopropyl-3-(4-methoxybenzyl)imidazolidine-2,4-dione (260 mg, see Example 47) was dissolved in N,N-dimethylformamide (4.7 mL), sodium hydride (60% in liquid paraffin dispersion) (23 mg) and methyl iodide (35 µL) were added under a nitrogen atmosphere, and the mixture was stirred at room temperature. After completion of the reaction, water was added to the reaction mixture and the mixture was extracted with ethyl acetate. The solvent was evaporated to give 5-{4-[4-(3,5-dimethylpyridin-2-yl)piperazine-1-carbonyl]phenyl}-5-isopropyl-3-(4-methoxybenzyl)-1-methylimidazolidine-2,4-dione (256 mg).

The obtained 5-{4-[4-(3,5-dimethylpyridin-2-yl)piperazine-1-carbonyl]phenyl}-5-isopropyl-3-(4-methoxybenzyl)-1-methylimidazolidine-2,4-dione (256 mg) was dissolved in 1,2-dichloroethane (4.7 mL), trifluoromethanesulfonic anhydride (366 µL) was added, and the mixture was stirred at 70° C. After completion of the reaction, aqueous sodium hydrogen carbonate solution was added under ice-cooling and the mixture was extracted with chloroform. The solvent was evaporated, hexane was added to the obtained residue, and the precipitate was collected by filtration to give the title compound (67 mg).

MS (ESI) m/z: 450 (M+H)+

Example 183: Synthesis of 5-[4-(3,5-dimethyl-3',4',5',6'-tetrahydro-2'H-[2,4']bipyridinyl-1'-carbonyl)phenyl]-5-fluoromethylimidazolidine-2,4-dione

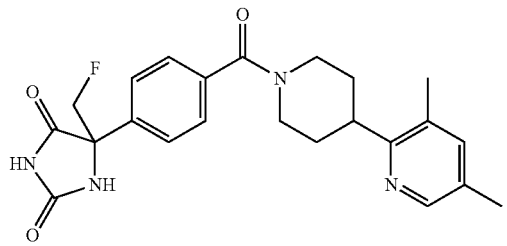 [SMILES: Cc1cnc(C2CCN(C(=O)c3ccc(C4(CF)NC(=O)NC4=O)cc3)CC2)c(C)c1]

Using 4-(4-fluoromethyl-2,5-dioxoimidazolidin-4-yl)benzoic acid (150 mg) described in Preparation Example 63 and 3,5-dimethyl-1',2',3',4',5',6'-hexahydro-[2,4']bipyridinyl. 2 hydrochloride (188 mg) described in Preparation Example 81, reactions and treatments similar to those in Example 166 were performed to give the title compound (202 mg).

MS(ESI) m/z: 425 (M+H)+

Example 184: Synthesis of 3-[5-(3,5-dimethyl-3',4',5',6'-tetrahydro-2'H-[2,4']bipyridinyl-1'-carbonyl)pyridin-2-yl]-3-isopropylpyrrolidine-2,5-dione

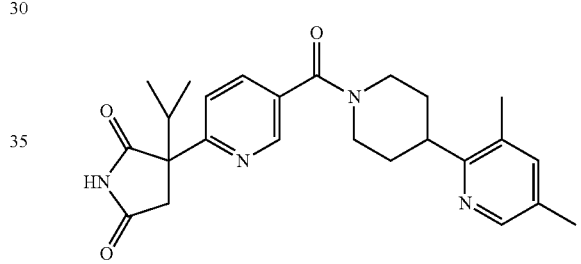

Using 6-(3-isopropyl-2,5-dioxopyrrolidin-3-yl) nicotinic acid (90 mg) described in Preparation Example 52 and 3,5-dimethyl-1',2',3',4',5',6'-hexahydro-[2,4']bipyridinyl.2 hydrochloride (108 mg) described in Preparation Example 81, reactions and treatments similar to those in Example 166 were performed to give the title compound (149 mg).

MS(ESI) m/z: 435 (M+H)+

Example 185: Synthesis of (R)-5-{4-[3-(3,5-dimethylpyridin-2-ylamino)azetidine-1-carbonyl]phenyl}-5-isopropylimidazolidine-2,4-dione.hydrochloride

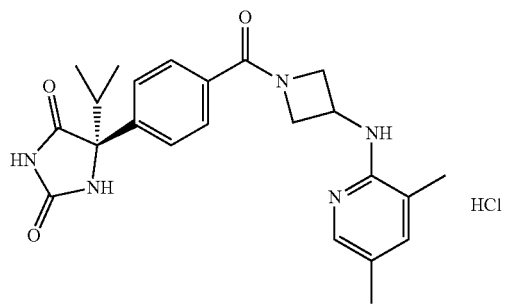 [SMILES: Cc1cnc(NC2CN(C(=O)c3ccc([C@@]4(C(C)C)NC(=O)NC4=O)cc3)C2)c(C)c1 ; Cl]

3-(3,5-Dimethylpyridin-2-ylamino)azetidine-1-carboxylic acid tert-butyl ester (122 mg) described in Preparation Example 92 was dissolved in chloroform (3 mL), 4N hydrogen chloride/ethyl acetate solution (1.1 mL) was added, and the mixture was stirred at room temperature overnight. The reaction mixture was concentrated under reduced pressure, 4-((R)-4-isopropyl-2,5-dioxoimidazolidin-4-yl)benzoic acid (105 mg) described in Preparation Example 45, 1-hydroxybenzotriazole (65 mg), 1-ethyl-3-(3'-dimethylaminopropyl) carbodiimide. hydrochloride (92 mg), N,N-dimethylformamide (4 mL) and triethylamine (0.223 mL) were added to the obtained residue, and the mixture was stirred at room temperature overnight. Water was added to the reaction mixture and the mixture was extracted with ethyl acetate. The organic layer was dried over anhydrous magnesium sulfate, and the solvent was evaporated. The obtained residue was purified by column chromatography (hexane:ethyl acetate) to give an oil. The obtained oil was dissolved in ethyl acetate and 4N hydrogen chloride/ethyl acetate solution (0.2 mL) was added. The solvent was evaporated to give the title compound (90 mg).

MS(APCI) m/z: 422 (M+H)⁺

Example 186: Synthesis of (R)-5-isopropyl-5-{4-[4-(5-methylpyridine-2-carbonyl)piperidine-1-carbonyl]phenyl]imidazolidine-2,4-dione

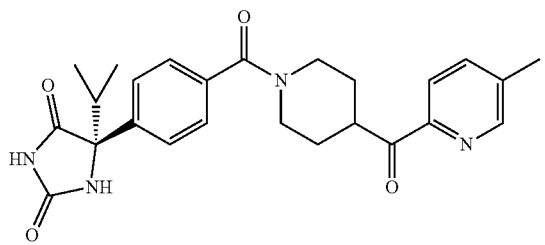 [SMILES: Cc1ccc(C(=O)C2CCN(C(=O)c3ccc([C@@]4(C(C)C)NC(=O)NC4=O)cc3)CC2)nc1]

4-((R)-4-isopropyl-2,5-dioxoimidazolidin-4-yl)benzoic acid (105 mg) described in Preparation Example 45, (5-methylpyridin-2-yl)piperidin-4-ylmethanone.2 hydrochloride (122 mg) described in Preparation Example 93, 1-hydroxybenzotriazole (81 mg) and 1-ethyl-3-(3'-dimethylaminopropyl)carbodiimide.hydrochloride (115 mg) were dissolved in tetrahydrofuran (4 mL), triethylamine (0.233 mL) was added, and the mixture was stirred at room temperature overnight. Water was added to the reaction mixture and the mixture was extracted with chloroform. The solvent was evaporated and the obtained residue was purified by column chromatography (hexane:ethyl acetate) to give the title compound (101 mg).

MS(ESI) m/z: 449 (M+H)⁺

Example 187: Synthesis of (R)-5-{4-[(3R,4R)-3-(3,5-dimethylpyridin-2-ylamino)-4-hydroxypyrrolidine-1-carbonyl]phenyl}-5-isopropylimidazolidine-2,4-dione

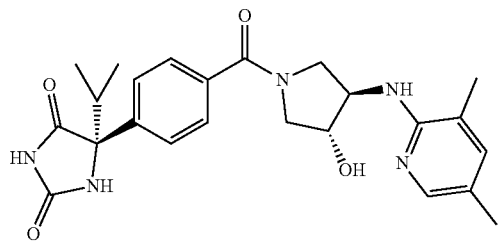 [SMILES: Cc1cnc(N[C@@H]2CN(C(=O)c3ccc([C@@]4(C(C)C)NC(=O)NC4=O)cc3)C[C@H]2O)c(C)c1]

Using 4-((R)-4-isopropyl-2,5-dioxoimidazolidin-4-yl)benzoic acid (105 mg) described in Preparation Example 45 and (3R,4R)-4-(3,5-dimethylpyridin-2-ylamino)pyrrolidin-3-ol.2 hydrochloride (134 mg) described in Preparation Example 94, reactions and treatments similar to those in Example 186 were performed to give the title compound (85 mg).

MS(ESI) m/z: 452 (M+H)⁺

Example 188: Synthesis of (R)-5-ethyl-5-{4-[4-(5-p-toluyl-1H-pyrazol-3-yl)piperidine-1-carbonyl]phenyl}imidazolidine-2,4-dione

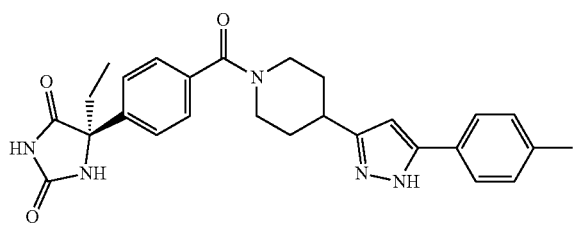 [SMILES: CC[C@]1(c2ccc(C(=O)N3CCC(c4cc(-c5ccc(C)cc5)[nH]n4)CC3)cc2)NC(=O)NC1=O]

Using 4-((R)-4-ethyl-2,5-dioxoimidazolidin-4-yl)benzoic acid (75 mg) described in Preparation Example 14 and 4-[5-(p-tolyl)-1H-pyrazol-3-yl]piperidine (101 mg) described in Preparation Example 77, reactions and treatments similar to those in Example 186 were performed to give the title compound (34 mg).

MS(ESI) m/z: 472 (M+H)⁺

Example 189: Synthesis of (2S,4S)-4-(3,5-dimethylpyridin-2-ylamino)-1-[4-((R)-4-isopropyl-2,5-dioxoimidazolidin-4-yl)benzoyl]pyrrolidine-2-carboxylic acid methyl ester

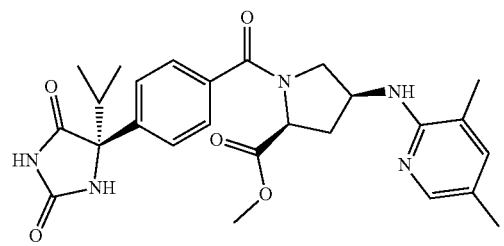 [SMILES: COC(=O)[C@@H]1C[C@H](Nc2ncc(C)cc2C)CN1C(=O)c1ccc([C@@]2(C(C)C)NC(=O)NC2=O)cc1]

A mixture of 4-((R)-4-isopropyl-2,5-dioxoimidazolidin-4-yl)benzoic acid (48.8 mg) described in Preparation Example 45, (2S,4S)-4-(3,5-dimethylpyridin-2-ylamino)pyrrolidine-2-carboxylic acid methyl ester.2 hydrochloride (60 mg) described in Preparation Example 101, 1-hydroxybenzotriazole (37.7 mg), 1-ethyl-3-(3'-dimethylaminopropyl) carbodiimide.hydrochloride (53.5 mg), triethylamine (0.104 mL) and N,N-dimethylformamide (1.2 mL) was stirred at room temperature for 7.5 hr. To the reaction mixture was added saturated aqueous sodium hydrogen carbonate solution and the mixture was extracted with chloroform. The solvent was evaporated and the obtained residue was purified by column chromatography (hexane: ethyl acetate) to give the title compound (73 mg).

MS(APCI) m/z: 494.6 (M+H)⁺

Example 190: Synthesis of (R)-5-{4-[(2S,4S)-4-(3,5-dimethylpyridin-2-ylamino)-2-hydroxymethylpyrrolidine-1-carbonyl]phenyl}-5-isopropylimidazolidine-2,4-dione

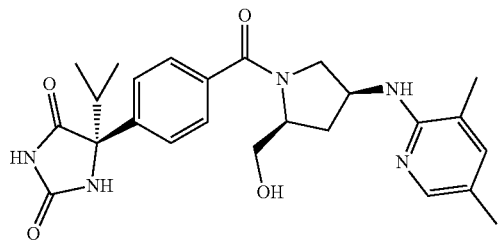 [SMILES: Cc1cnc(N[C@H]2C[C@@H](CO)N(C(=O)c3ccc([C@@]4(C(C)C)NC(=O)NC4=O)cc3)C2)c(C)c1]

[(2S,4S)-4-(3,5-dimethylpyridin-2-ylamino)pyrrolidin-2-yl]methanol.2 hydrochloride described in Preparation Example 102 was dissolved in N,N-dimethylformamide (1.8 mL), N,O-bis(trimethylsilyl)acetamide (76.3 mg) and triethylamine (0.175 mL) were added, and the mixture was stirred at room temperature for 3 hr. To the reaction mixture were added 4-((R)-4-isopropyl-2,5-dioxoimidazolidin-4-yl)benzoic acid (82 mg) described in Preparation Example 45, 1-hydroxybenzotriazole (65 mg) and 1-ethyl-3-(3'-dimethylaminopropyl)carbodiimide. hydrochloride (90 mg) and the mixture was stirred at room temperature for 2.5 hr. To the reaction mixture was added saturated aqueous sodium hydrogen carbonate solution and the mixture was extracted with chloroform. The solvent was evaporated and the obtained residue was purified by column chromatography (chloroform:methanol) to give the title compound (63 mg).

MS(APCI) m/z: 466 (M+H)+

Example 191: Synthesis of (R)-5-{4-[(2R,4S)-4-(3,5-dimethylpyridin-2-ylamino)-2-methylpyrrolidine-1-carbonyl]phenyl}-5-isopropylimidazolidine-2,4-dione

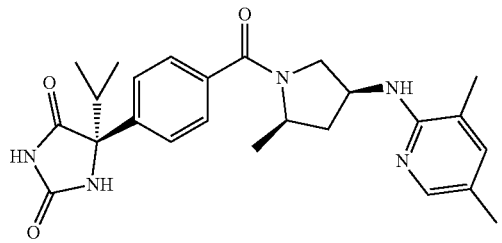 [SMILES: Cc1cnc(N[C@H]2C[C@@H](C)N(C(=O)c3ccc([C@@]4(C(C)C)NC(=O)NC4=O)cc3)C2)c(C)c1]

Using 4-((R)-4-isopropyl-2,5-dioxoimidazolidin-4-yl) benzoic acid (75.4 mg) described in Preparation Example 45 and (3,5-dimethylpyridin-2-yl) ((3S,5R)-5-methylpyrrolidin-3-yl)amine.2 hydrochloride (80 mg) described in Preparation Example 103, reactions and treatments similar to those in Example 189 were performed to give the title compound (68 mg).

MS(APCI) m/z: 450 (M+H)+

Example 192: Synthesis of 3-{5-[4-(3,5-dimethylpyridin-2-yl)piperazine-1-carbonyl]pyridin-2-yl}-3-methoxymethylpyrrolidine-2,5-dione

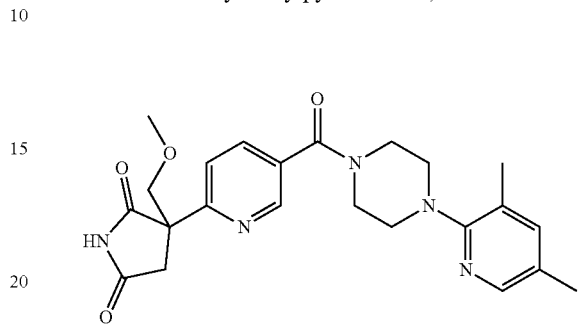

To 6-(3-methoxymethyl-2,5-dioxopyrrolidin-3-yl)nicotinic acid (83 mg) described in Preparation Example 64 were added 1-(3,5-dimethylpyridin-2-yl)piperazine (78.8 mg), N,N-dimethylformamide (5 mL), 1-ethyl-3-(3'-dimethylaminopropyl)carbodiimide.hydrochloride (66.3 mg), 1-hydroxybenzotriazole.1 hydrate (46.8 mg) and triethylamine (0.087 mL) and the mixture was stirred at room temperature overnight. The reaction mixture was concentrated under reduced pressure and the obtained residue was purified by column chromatography (chloroform:methanol) to give the title compound (75 mg).

MS (ESI) m/z: 438 (M+H)+

Example 193: Synthesis of (R)-5-{4-[(2S,4S)-4-(3,5-dimethylpyridin-2-ylamino)-2-methylpyrrolidine-1-carbonyl]phenyl}-5-isopropylimidazolidine-2,4-dione

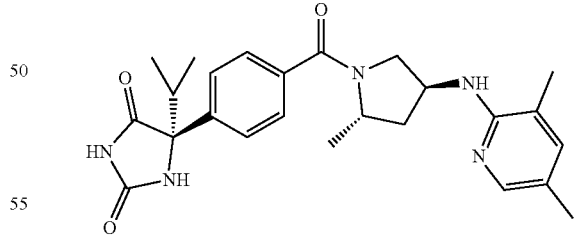

Using 4-((R)-4-isopropyl-2,5-dioxoimidazolidin-4-yl) benzoic acid (75.4 mg) described in Preparation Example 45 and (3,5-dimethylpyridin-2-yl) ((3S,5S)-5-methylpyrrolidin-3-yl)amine.2 hydrochloride (80 mg) described in Preparation Example 104, reactions and treatments similar to those in Example 189 were performed to give the title compound (61 mg).

MS (APCI) m/z: 450 (M+H)+

Example 194: Synthesis of 3-{5-[(S)-3-(3,5-dimethylpyridin-2-ylamino)pyrrolidine-1-carbonyl]pyridin-2-yl}-3-methoxymethylpyrrolidine-2,5-dione

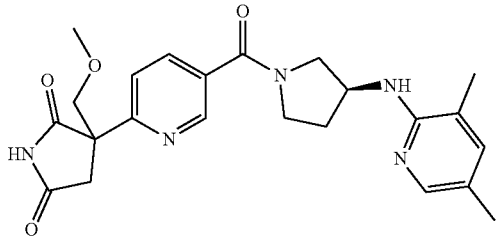 [SMILES: COCC1(c2ccc(C(=O)N3CC[C@H](Nc4ncc(C)cc4C)C3)cn2)CC(=O)NC1=O]

Using 6-(3-methoxymethyl-2,5-dioxopyrrolidin-3-yl) nicotinic acid (200 mg) described in Preparation Example 64 and (3,5-dimethylpyridin-2-yl) ((S)-pyrrolidin-3-yl)amine.2 hydrochloride (220 mg) described in Preparation Example 88, reactions and treatments similar to those in Example 189 were performed to give the title compound (268 mg).
MS(ESI) m/z: 438 (M+H)+

Example 195: Synthesis of (2S,3S)-3-(3,5-dimethylpyridin-2-ylamino)-1-[4-((R)-4-isopropyl-2,5-dioxoimidazolidin-4-yl)benzoyl]pyrrolidine-2-carboxylic acid methyl ester

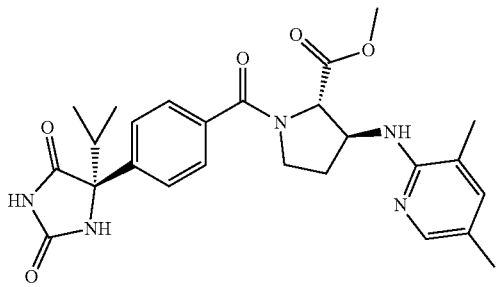 [SMILES: COC(=O)[C@@H]1[C@@H](Nc2ncc(C)cc2C)CCN1C(=O)c1ccc([C@@]2(C(C)C)NC(=O)NC2=O)cc1]

Using 4-((R)-4-isopropyl-2,5-dioxoimidazolidin-4-yl) benzoic acid (75.4 mg) described in Preparation Example 45 and (2S,3S)-3-(3,5-dimethylpyridin-2-ylamino)pyrrolidine-2-carboxylic acid methyl ester.2 hydrochloride (80 mg) described in Preparation Example 105, reactions and treatments similar to those in Example 189 were performed to give the title compound (36 mg).
MS(ESI) m/z: 494 (M+H)+

Example 196: Synthesis of (R)-5-{4-[(2S,4S)-4-(3,5-dimethylpyridin-2-ylamino)-2-hydroxymethylpyrrolidine-1-carbonyl]phenyl}-5-methylimidazolidine-2,4-dione

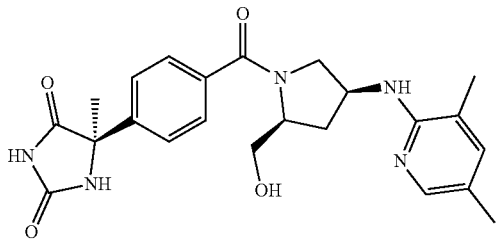 [SMILES: Cc1cnc(N[C@H]2C[C@@H](CO)N(C(=O)c3ccc([C@@]4(C)NC(=O)NC4=O)cc3)C2)c(C)c1]

[(2S,4S)-4-(3,5-dimethylpyridin-2-ylamino)pyrrolidin-2-yl]methanol.2 hydrochloride (100 mg) described in Preparation Example 102 was dissolved in N,N-dimethylformamide (2 mL), N,O-bis(trimethylsilyl)acetamide (90 mg) and triethylamine (0.190 mL) were added, and the mixture was stirred at room temperature for 2 hr. To the reaction mixture were added 4-((R)-4-methyl-2,5-dioxoimidazolidin-4-yl) benzoic acid (96 mg) described in Preparation Example 6, 1-hydroxybenzotriazole (69 mg) and 1-ethyl-3-(3'-dimethylaminopropyl)carbodiimide.hydrochloride (98 mg) and the mixture was stirred at room temperature overnight. To the reaction mixture were added 1N aqueous sodium hydroxide solution and saturated aqueous sodium hydrogen carbonate solution and the mixture was extracted with chloroform. The solvent was evaporated and the obtained residue was purified by column chromatography (chloroform:methanol) to give the title compound (58 mg).
MS(APCI) m/z: 438 (M+H)+

Example 197: Synthesis of (2S,4S)-4-(3,5-dimethylpyridin-2-ylamino)-1-[4-((R)-4-isopropyl-2,5-dioxoimidazolidin-4-yl)benzoyl]pyrrolidine-2-carboxylic acid amide

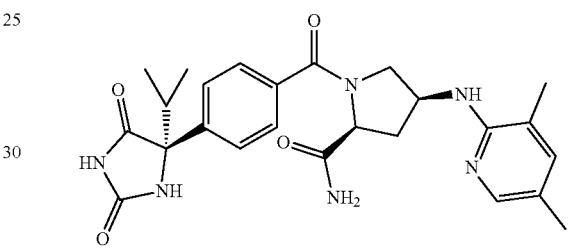

To (2S,4S)-4-(3,5-dimethylpyridin-2-ylamino)pyrrolidine-2-carboxylic acid amide.2 hydrochloride (64 mg) described in Preparation Example 106 were added 4-((R)-4-isopropyl-2,5-dioxoimidazolidin-4-yl)benzoic acid (60 mg) described in Preparation Example 45, 1-ethyl-3-(3'-dimethylaminopropyl)carbodiimide.hydrochloride (60 mg), 1-hydroxybenzotriazole (42 mg), N,N-dimethylformamide (1.3 mL) and triethylamine (0.12 mL) and the mixture was stirred at room temperature overnight. To the reaction mixture was added saturated aqueous sodium hydrogen carbonate solution and the mixture was extracted with chloroform. The solvent was evaporated and the obtained residue was purified by column chromatography (chloroform:methanol) to give the title compound (79 mg).
MS(ESI) m/z: 479 (M+H)+

Example 198: Synthesis of (2S,4S)-4-(3,5-dimethylpyridin-2-ylamino)-1-[4-((R)-4-isopropyl-2,5-dioxoimidazolidin-4-yl)benzoyl]pyrrolidine-2-carbonitrile

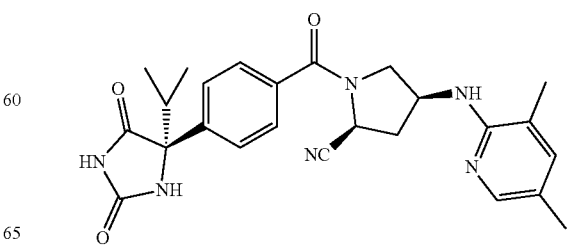

(2S,4S)-4-(3,5-dimethylpyridin-2-ylamino)-1-[4-((R)-4-isopropyl-2,5-dioxoimidazolidin-4-yl)benzoyl]pyrrolidine-2-carboxylic acid amide (60 mg) described in Example 197 was dissolved in tetrahydrofuran (2.4 mL), triethylamine (0.055 mL) and trifluoroacetic anhydride (0.035 mL) were added under ice-cooling, and the mixture was stirred for 5.5 hr while raising the temperature to room temperature. To the reaction mixture was added trifluoroacetic anhydride (0.035 mL) and the mixture was stirred at room temperature overnight. To the reaction mixture was added saturated aqueous sodium hydrogen carbonate solution and the mixture was extracted with chloroform. The solvent was evaporated and the obtained residue was purified by column chromatography (hexane:ethyl acetate) to give the title compound (32 mg).

MS(ESI) m/z: 461 (M+H)+

Example 199: Synthesis of (R)-5-{4-[(2R,4S)-4-(3,5-dimethylpyridin-2-ylamino)-2-methylpyrrolidine-1-carbonyl]phenyl}-5-methylimidazolidine-2,4-dione

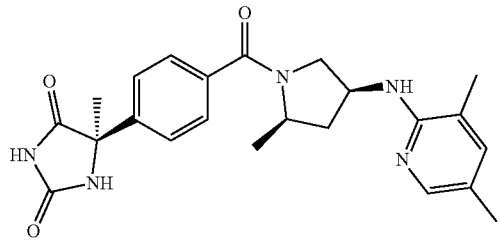 [SMILES: Cc1cnc(N[C@H]2C[C@@H](C)N(C(=O)c3ccc([C@@]4(C)NC(=O)NC4=O)cc3)C2)c(C)c1]

To (3,5-dimethylpyridin-2-yl) ((3S,5R)-5-methylpyrrolidin-3-yl)amine.2 hydrochloride (60 mg) described in Preparation Example 103 were added 4-((R)-4-methyl-2,5-dioxoimidazolidin-4-yl)benzoic acid (61 mg) described in Preparation Example 6, 1-ethyl-3-(3'-dimethylaminopropyl)carbodiimide.hydrochloride (62 mg), 1-hydroxybenzotriazole (44 mg), chloroform (0.6 mL), tetrahydrofuran (0.6 mL) and triethylamine (0.12 mL) and the mixture was stirred at room temperature overnight. To the reaction mixture was added saturated aqueous sodium hydrogen carbonate solution and the mixture was extracted with chloroform. The solvent was evaporated and the obtained residue was purified by column chromatography (chloroform:methanol) to give the title compound (42 mg).

MS(ESI) m/z: 422 (M+H)+

Example 200: Synthesis of (R)-5-{4-[(2S,4S)-4-(3,5-dimethylpyridin-2-ylamino)-2-methoxymethylpyrrolidine-1-carbonyl]phenyl}-5-isopropylimidazolidine-2,4-dione

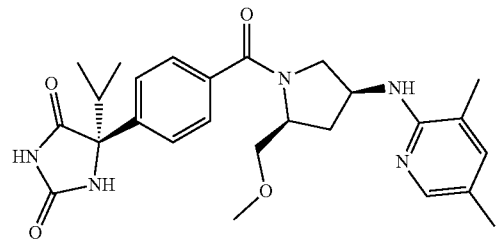 [SMILES: COC[C@@H]1C[C@H](Nc2ncc(C)cc2C)CN1C(=O)c1ccc([C@@]2(C(C)C)NC(=O)NC2=O)cc1]

To (3,5-dimethylpyridin-2-yl) ((3S,5S)-5-methoxymethylpyrrolidin-3-yl)amine.2 hydrochloride (80 mg) described in Preparation Example 107 were added 4-((R)-4-isopropyl-2,5-dioxoimidazolidin-4-yl)benzoic acid (75 mg) described in Preparation Example 45, 1-ethyl-3-(3'-dimethylaminopropyl)carbodiimide.hydrochloride (75 mg), 1-hydroxybenzotriazole (53 mg), chloroform (1.2 mL), tetrahydrofuran (1.2 mL) and triethylamine (0.145 mL) and the mixture was stirred at room temperature overnight. To the reaction mixture was added saturated aqueous sodium hydrogen carbonate solution and the mixture was extracted with chloroform. The solvent was evaporated and the obtained residue was purified by column chromatography (chloroform:methanol) to give the title compound (91 mg).

MS(ESI) m/z: 480 (M+H)+

Example 201: Synthesis of (R)-5-{4-[(2S,4S)-4-(3,5-dimethylpyridin-2-ylamino)-2-methoxymethylpyrrolidine-1-carbonyl]phenyl}-5-methylimidazolidine-2,4-dione

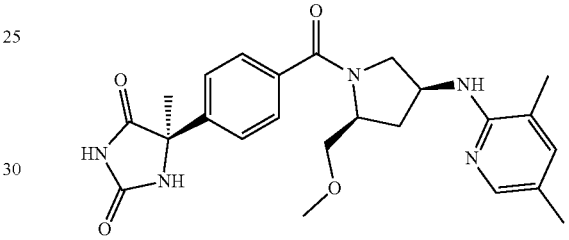

Using 4-((R)-4-methyl-2,5-dioxoimidazolidin-4-yl)benzoic acid (67 mg) described in Preparation Example 6 and (3,5-dimethylpyridin-2-yl) ((3S,5S)-5-methoxymethylpyrrolidin-3-yl)amine.2 hydrochloride (80 mg) described in Preparation Example 107, reactions and treatments similar to those in Example 200 were performed to give the title compound (90 mg).

MS(ESI) m/z: 452 (M+H)+

Example 202: Synthesis of (R)-5-{4-[(2S,4S)-4-(2,4-dimethylphenylamino)-2-hydroxymethylpyrrolidine-1-carbonyl]phenyl}-5-isopropylimidazolidine-2,4-dione

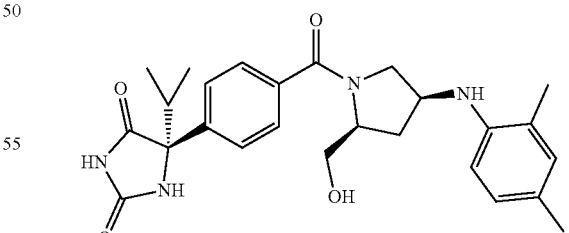

To (2S,4S)-2-(tert-butyldimethylsilanyloxymethyl)-4-(2,4-dimethylphenylamino)pyrrolidine-1-carboxylic acid tert-butyl ester (220 mg) described in Preparation Example 73 were added 1,4-dioxane (2.2 mL) and 4N hydrogen chloride/1,4-dioxane solution (2.2 mL). The mixture was stirred at room temperature for 2.5 hr and concentrated under reduced pressure. To the obtained residue (60 mg) were added 4-((R)-4-isopropyl-2,5-dioxoimidazolidin-4-yl)benzoic acid (61 mg) described in Preparation Example 45, 1-ethyl-3-(3'-dimethylaminopropyl)carbodiimide.hydrochloride (67 mg), 1-hydroxybenzotriazole (47 mg), chloroform (0.6 mL), tetrahydrofuran (0.6 mL) and triethylamine (0.098 mL) and the mixture was stirred at room temperature overnight. To the reaction mixture was added saturated aqueous sodium hydrogen carbonate solution and the mixture was extracted with chloroform. The solvent was evaporated and the obtained residue was purified by column chromatography (chloroform:methanol) to give the title compound (23 mg).

MS(ESI) m/z: 465 (M+H)+

Example 203: Synthesis of (R)-5-{4-[(2S,4S)-4-(3,5-dimethylpyridin-2-ylamino)-2-(1-hydroxy-1-methylethyl)pyrrolidine-1-carbonyl)phenyl]-5-isopropylimidazolidine-2,4-dione

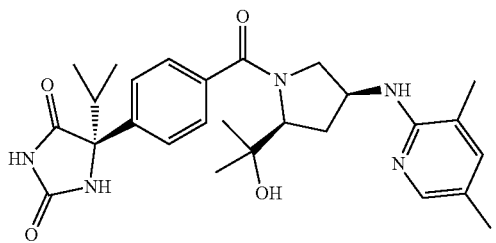 [SMILES: Cc1cnc(N[C@H]2C[C@@H](C(C)(C)O)N(C(=O)c3ccc([C@@]4(C(C)C)NC(=O)NC4=O)cc3)C2)c(C)c1]

Using 4-((R)-4-isopropyl-2,5-dioxoimidazolidin-4-yl) benzoic acid (49 mg) described in Preparation Example 45 and 2-[(2S,4S)-4-(3,5-dimethylpyridin-2-ylamino)pyrrolidin-2-yl]propan-2-ol.2 hydrochloride (60 mg) described in Preparation Example 108, reactions and treatments similar to those in Example 200 were performed to give the title compound (60 mg).

MS(ESI) m/z: 494 (M+H)+

Example 204: Synthesis of 3-{5-[(2R,4S)-4-(3,5-dimethylpyridin-2-ylamino)-2-methylpyrrolidine-1-carbonyl]pyridin-2-yl}-3-methoxymethylpyrrolidine-2,5-dione.2 hydrochloride

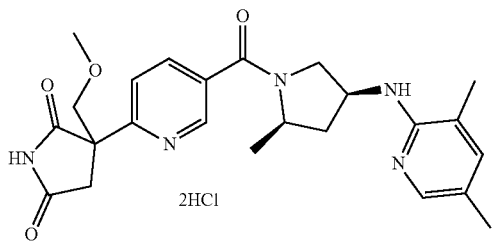 [SMILES: COCC1(c2ccc(C(=O)N3C[C@@H](Nc4ncc(C)cc4C)C[C@H]3C)cn2)CC(=O)NC1=O]

To (3,5-dimethylpyridin-2-yl) ((3S,5R)-5-methylpyrrolidin-3-yl)amine.2 hydrochloride (80 mg) described in Preparation Example 103 were added 6-(3-methoxymethyl-2,5-dioxopyrrolidin-3-yl)nicotinic acid (84 mg) described in Preparation Example 64, 1-ethyl-3-(3'-dimethylaminopropyl) carbodiimide.hydrochloride (83 mg), 1-hydroxybenzotriazole (58 mg), chloroform (1.2 mL), tetrahydrofuran (1.2 mL) and triethylamine (0.16 mL) and the mixture was stirred at room temperature for 8 hr. To the reaction mixture was added saturated aqueous sodium hydrogen carbonate solution and the mixture was extracted with chloroform. The solvent was evaporated and the obtained residue was purified by column chromatography (chloroform:methanol). The solvent was evaporated, the obtained residue was dissolved in ethyl acetate, and 4N hydrogen chloride/ethyl acetate solution was added. The precipitate was collected by filtration to give the title compound (100 mg).

MS (ESI) m/z: 452 (M+H)+

Example 205: Synthesis of (R)-5-{4-[3-(2,4-dimethylbenzyl)pyrrolidine-1-carbonyl]phenyl}-5-isopropylimidazolidine-2,4-dione

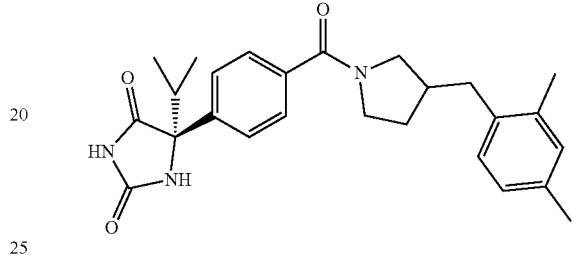

To 3-(2,4-dimethylbenzyl)pyrrolidine (100 mg) were added chloroform (2 mL), triethylamine (0.295 mL), 4-((R)-4-isopropyl-2,5-dioxoimidazolidin-4-yl)benzoic acid (140 mg) described in Preparation Example 45, 1-ethyl-3-(3'-dimethylaminopropyl)carbodiimide.hydrochloride (150 mg) and 1-hydroxybenzotriazole (107 mg) and the mixture was stirred at room temperature overnight. To the reaction mixture was added saturated aqueous sodium hydrogen carbonate solution and the mixture was extracted with chloroform. The solvent was evaporated and the obtained residue was purified by column chromatography (hexane:ethyl acetate) to give the title compound (104 mg).

MS(ESI) m/z: 434 (M+H)+

Example 206: Synthesis of (R)-5-{4-[(2S,4S)-4-(3,5-dimethylpyridin-2-ylamino)-2-(1-hydroxy-1-methylethyl)pyrrolidine-1-carbonyl)phenyl]-5-methylimidazolidine-2,4-dione

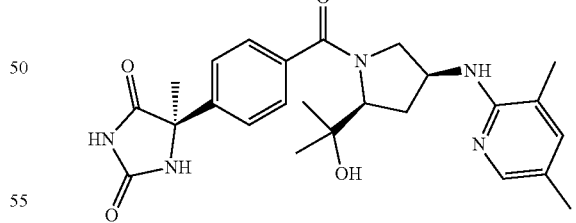

To 2-[(2S,4S)-4-(3,5-dimethylpyridin-2-ylamino)pyrrolidin-2-yl]propan-2-ol.2 hydrochloride (80 mg) described in Preparation Example 108 were added 4-((R)-4-methyl-2,5-dioxoimidazolidin-4-yl)benzoic acid (64 mg) described in Preparation Example 6, 1-ethyl-3-(3'-dimethylaminopropyl) carbodiimide.hydrochloride (72 mg), 1-hydroxybenzotriazole (50 mg), chloroform (1.6 mL) and triethylamine (0.14 mL) and the mixture was stirred at room temperature overnight. To the reaction mixture was added saturated aqueous sodium hydrogen carbonate solution and the mixture was extracted with chloroform. The solvent was evaporated and the obtained residue was purified by column chromatography (chloroform:methanol) to give the title compound (78 mg).

MS(ESI) m/z: 466 (M+H)⁺

Example 207: Synthesis of (R)-5-[4-(4-indazol-2-ylpiperidine-1-carbonyl)phenyl]-5-isopropylimidazolidine-2,4-dione

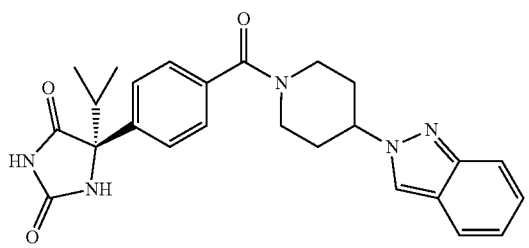 [SMILES: CC(C)[C@]1(c2ccc(C(=O)N3CCC(n4cc5ccccc5n4)CC3)cc2)NC(=O)NC1=O]

To 2-(piperidin-4-yl)-2H-indazole.2 hydrochloride (80 mg) described in Preparation Example 67 were added 4-((R)-4-isopropyl-2,5-dioxoimidazolidin-4-yl)benzoic acid (98 mg) described in Preparation Example 45, 1-ethyl-3-(3'-dimethylaminopropyl)carbodiimide.hydrochloride (97 mg), 1-hydroxybenzotriazole (70 mg), chloroform (1.6 mL) and triethylamine (190 μL) and the mixture was stirred at room temperature. After completion of the reaction, saturated aqueous sodium hydrogen carbonate solution and chloroform were added, and the precipitate was collected by filtration. The obtained precipitate was suspended in ethanol/water and collected by filtration to give the title compound (110 mg).

MS(ESI) m/z: 446 (M+H)⁺

Example 208: Synthesis of (R)-5-{4-[4-(5-chloroindazol-2-yl)piperidine-1-carbonyl]phenyl}-5-isopropylimidazolidine-2,4-dione

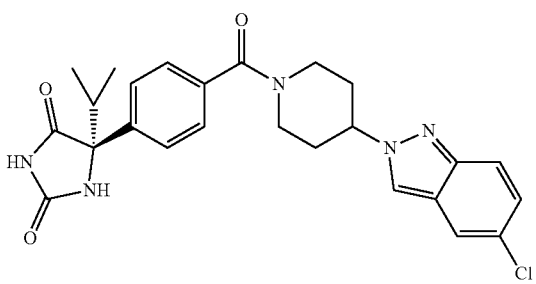 [SMILES: CC(C)[C@]1(c2ccc(C(=O)N3CCC(n4cc5cc(Br)ccc5n4)CC3)cc2)NC(=O)NC1=O]

Using 4-((R)-4-isopropyl-2,5-dioxoimidazolidin-4-yl)benzoic acid (85 mg) described in Preparation Example 45 and 5-chloro-2-(piperidin-4-yl)-2H-indazole.2 hydrochloride (80 mg) described in Preparation Example 68, reactions and treatments similar to those in Example 207 were performed to give the title compound (105 mg).

MS(ESI) m/z: 480 (M+H)⁺

Example 209: Synthesis of (R)-5-{4-[4-(5-bromoindazol-2-yl)piperidine-1-carbonyl]phenyl}-5-isopropylimidazolidine-2,4-dione

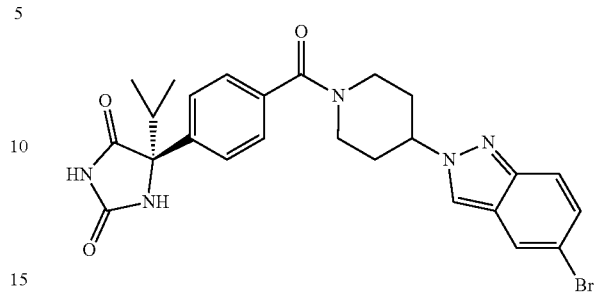

Using 4-((R)-4-isopropyl-2,5-dioxoimidazolidin-4-yl)benzoic acid (73 mg) described in Preparation Example 45 and 5-bromo-2-(piperidin-4-yl)-2H-indazole.2 hydrochloride (80 mg) described in Preparation Example 69, reactions and treatments similar to those in Example 207 were performed to give the title compound (78 mg).

MS(ESI) m/z: 524 (M+H)⁺

Example 210: Synthesis of (R)-5-{4-[4-(5-bromoindazol-2-yl)piperidine-1-carbonyl]phenyl}-5-isopropylimidazolidine-2,4-dione

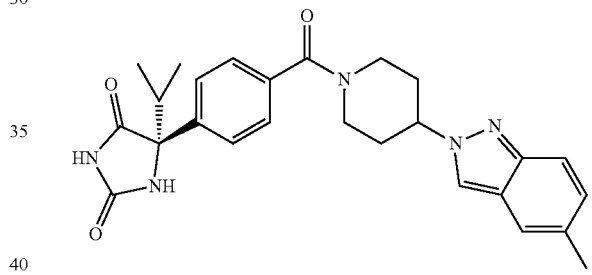

Using 4-((R)-4-isopropyl-2,5-dioxoimidazolidin-4-yl)benzoic acid (70 mg) described in Preparation Example 45 and 5-methyl-2-(piperidin-4-yl)-2H-indazole.2 hydrochloride as a crude product (60 mg) described in Preparation Example 70, reactions and treatments similar to those in Example 207 were performed to give the title compound (65 mg).

MS(ESI) m/z: 460 (M+H)⁺

Example 211: Synthesis of (R)-5-methyl-5-{4-[4-(5-methylindazol-2-yl)piperidine-1-carbonyl]phenyl}imidazolidine-2,4-dione

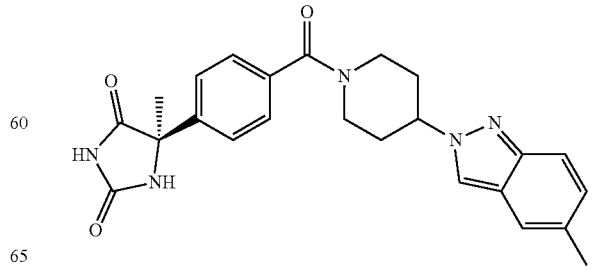

Using 4-((R)-4-methyl-2,5-dioxoimidazolidin-4-yl)benzoic acid (61 mg) described in Preparation Example 6 and 5-methyl-2-(piperidin-4-yl)-2H-indazole.2 hydrochloride as a crude product (60 mg) described in Preparation Example 70, reactions and treatments similar to those in Example 206 were performed to give the title compound (67 mg).

MS(ESI) m/z: 432 (M+H)+

Example 212: Synthesis of (R)-5-isopropyl-5-{4-[4-(2-methylbenzoyl)piperidine-1-carbonyl]phenyl}imidazolidine-2,4-dione

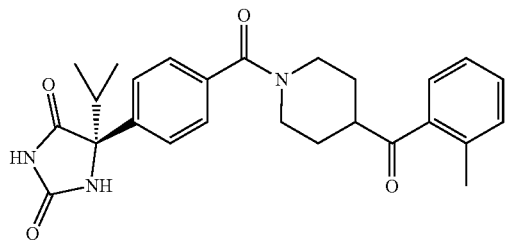 [SMILES: Cc1ccccc1C(=O)C1CCN(C(=O)c2ccc([C@@]3(C(C)C)NC(=O)NC3=O)cc2)CC1]

Using 4-((R)-4-isopropyl-2,5-dioxoimidazolidin-4-yl)benzoic acid (97 mg) described in Preparation Example 45 and (piperidin-4-yl) (o-tolyl)methanone (81 mg), reactions and treatments similar to those in Example 205 were performed to give the title compound (84 mg).

MS(ESI) m/z: 448 (M+H)+

Example 213: Synthesis of (R)-5-(4-{4-[5-(3,5-dichloropyridin-2-yl) [1,3,4]oxadiazol-2-yl]piperidine-1-carbonyl}phenyl)-5-isopropylimidazolidine-2,4-dione

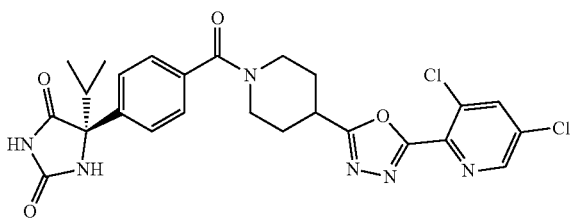 [SMILES: CC(C)[C@]1(c2ccc(C(=O)N3CCC(c4nnc(-c5ncc(Cl)cc5Cl)o4)CC3)cc2)NC(=O)NC1=O]

Using 4-((R)-4-isopropyl-2,5-dioxoimidazolidin-4-yl)benzoic acid (62 mg) described in Preparation Example 45 and 3,5-dichloro-2-(5-piperidin-4-yl[1,3,4]oxadiazol-2-yl)pyridine. 2 hydrochloride (80 mg) described in Preparation Example 71, reactions and treatments similar to those in Example 206 were performed to give the title compound (59 mg).

MS(ESI) m/z: 543 (M+H)+

Example 214: Synthesis of (R)-5-ethyl-5-{4-[4-(5-methylbenzothiazol-2-yl)piperidine-1-carbonyl]phenyl}imidazolidine-2,4-dione

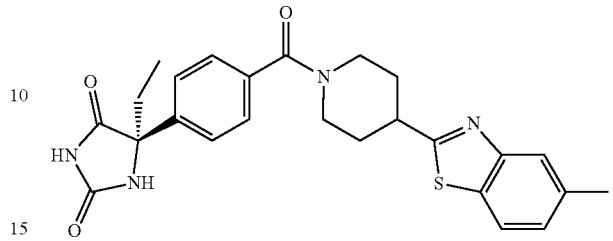

To 4-((R)-4-ethyl-2,5-dioxoimidazolidin-4-yl)benzoic acid (72 mg) described in Preparation Example 14 were added 5-methyl-2-(piperidin-4-yl)-1,3-benzothiazole (80 mg), 1-hydroxybenzotriazole (70 mg), 1-ethyl-3-(3'-dimethylaminopropyl)carbodiimide.hydrochloride (100 mg), triethylamine (145 μL) and chloroform (1.6 mL) and the mixture was stirred at room temperature. After completion of the reaction, saturated aqueous sodium hydrogen carbonate solution was added and the mixture was extracted with chloroform. The solvent was evaporated and the obtained residue was purified by column chromatography (chloroform:methanol) to give the title compound (91 mg).

MS(ESI) m/z: 463 (M+H)+

Example 215: Synthesis of (R)-5-methyl-5-(4-{4-[5-(5-methylpyridin-2-yl)thiazol-2-yl]piperidine-1-carbonyl}phenyl)imidazolidine-2,4-dione

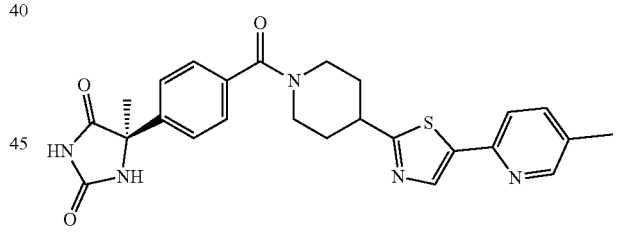

To 4-((R)-4-methyl-2,5-dioxoimidazolidin-4-yl)benzoic acid (42 mg) described in Preparation Example 6 were added 5-methyl-2-(2-piperidin-4-ylthiazol-5-yl)pyridine.hydrochloride (55 mg) described in Preparation Example 72, 1-hydroxybenzotriazole (34 mg), 1-ethyl-3-(3'-dimethylaminopropyl)carbodiimide.hydrochloride (48 mg), triethylamine (70 μL) and chloroform (1.1 mL) and the mixture was stirred at room temperature overnight. Saturated aqueous sodium hydrogen carbonate solution was added and the mixture was extracted with chloroform. The solvent was evaporated and the obtained residue was purified by column chromatography (chloroform:methanol) to give the title compound (49 mg).

MS(ESI) m/z: 476 (M+H)+

Example 216: Synthesis of (R)-5-ethyl-5-(4-{4-[5-(5-methylpyridin-2-yl)thiazol-2-yl]piperidine-1-carbonyl}phenyl) imidazolidine-2,4-dione

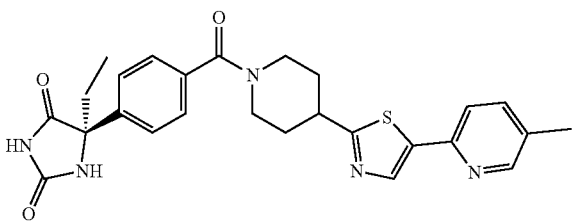 [SMILES: CC[C@]1(c2ccc(C(=O)N3CCC(c4ncc(-c5ccc(C)cn5)s4)CC3)cc2)NC(=O)NC1=O]

Using 4-((R)-4-ethyl-2,5-dioxoimidazolidin-4-yl)benzoic acid (42 mg) described in Preparation Example 14 and 5-methyl-2-(2-piperidin-4-ylthiazol-5-yl)pyridine.hydrochloride (55 mg) described in Preparation Example 72, reactions and treatments similar to those in Example 215 were performed to give the title compound (46 mg).
MS (APCI) m/z: 490 (M+H)$^+$

Example 217: Synthesis of (R)-5-{3-fluoro-4-[4-(6-methylbenzoxazol-2-yl)piperidine-1-carbonyl]phenyl}-5-methylimidazolidine-2,4-dione

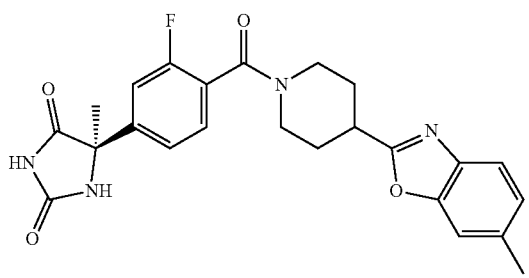 [SMILES: Cc1ccc2nc(C3CCN(C(=O)c4ccc([C@@]5(C)NC(=O)NC5=O)cc4F)CC3)oc2c1]

Using 2-fluoro-4-((R)-4-methyl-2,5-dioxoimidazolidin-4-yl)benzoic acid (93 mg) described in Preparation Example 29 and 6-methyl-2-(piperidin-4-yl)-1,3-benzoxazole (80 mg), reactions and treatments similar to those in Example 214 were performed to give the title compound (46 mg).
MS(ESI) m/z: 451 (M+H)$^+$

Example 218: Synthesis of (R)-5-ethyl-5-{4-[4-(5-methyloxazolo[5,4-b]pyridin-2-yl)piperidine-1-carbonyl]phenyl}imidazolidine-2,4-dione

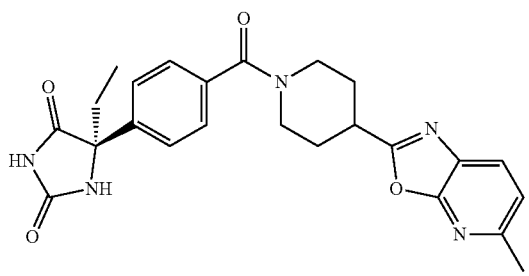

Using 4-((R)-4-ethyl-2,5-dioxoimidazolidin-4-yl)benzoic acid (95 mg) described in Preparation Example 14 and 5-methyl-2-(piperidin-4-yl)oxazolo[5,4-b]pyridine (81 mg) described in Preparation Example 144, reactions and treatments similar to those in Example 214 were performed to give the title compound (110 mg).
MS (ESI) m/z: 448 (M+H)$^+$

Example 219: Synthesis of (R)-5-ethyl-5-{4-[4-(6-methylthiazolo[4,5-b]pyridin-2-yl)piperidine-1-carbonyl]phenyl}imidazolidine-2,4-dione

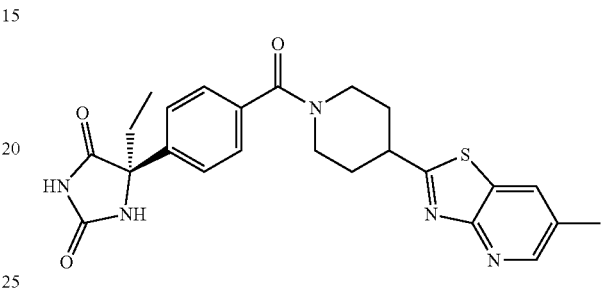

Using 4-((R)-4-ethyl-2,5-dioxoimidazolidin-4-yl)benzoic acid (89 mg) described in Preparation Example 14 and 6-methyl-2-(piperidin-4-yl)thiazolo[4,5-b]pyridine as a crude product (152 mg) described in Preparation Example 145, reactions and treatments similar to those in Example 214 were performed to give the title compound (59 mg).
MS(ESI) m/z: 464 (M+H)$^+$

Example 220: Synthesis of (R)-5-isopropyl-5-{4-[4-(6-methylthiazolo[4,5-b]pyridin-2-yl)piperidine-1-carbonyl]phenyl}imidazolidine-2,4-dione

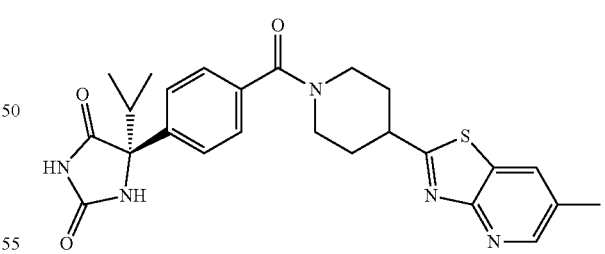

Using 4-((R)-4-isopropyl-2,5-dioxoimidazolidin-4-yl)benzoic acid (135 mg) described in Preparation Example 45 and 6-methyl-2-(piperidin-4-yl)thiazolo[4,5-b]pyridine as a crude product (200 mg) described in Preparation Example 145, reactions and treatments similar to those in Example 214 were performed to give the title compound (112 mg).
MS(ESI) m/z: 478 (M+H)$^+$ Example 221: Synthesis of (R)-5-isopropyl-5-{4-[4-(5-methyloxazolo[5,4-b]pyridin-2-yl)piperidine-1-carbonyl]phenyl}imidazolidine-2,4-dione

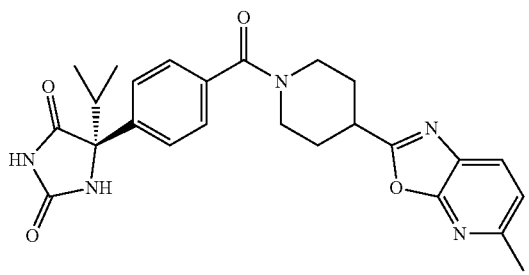 [SMILES: Cc1ccc2nc(C3CCN(C(=O)c4ccc([C@@]5(C(C)C)NC(=O)NC5=O)cc4)CC3)oc2n1]

To 4-((R)-4-isopropyl-2,5-dioxoimidazolidin-4-yl)benzoic acid (105 mg) described in Preparation Example 45 were added 5-methyl-2-(piperidin-4-yl)oxazolo[5,4-b]pyridine (80 mg) described in Preparation Example 144, 1-hydroxybenzotriazole (75 mg), 1-ethyl-3-(3'-dimethylaminopropyl)carbodiimide. hydrochloride (105 mg), triethylamine (155 μL) and chloroform (1.6 mL) and the mixture was stirred at room temperature. After completion of the reaction, saturated aqueous sodium hydrogen carbonate solution was added, and the precipitate was collected by filtration. The obtained precipitate was suspended in ethanol/water and collected by filtration to give the title compound (117 mg).

MS(ESI) m/z: 462 (M+H)$^+$

Example 222: Synthesis of (R)-5-isopropyl-5-{4-[4-(5-methylthiazolo[5,4-b]pyridin-2-yl)piperidine-1-carbonyl]phenyl}imidazolidine-2,4-dione

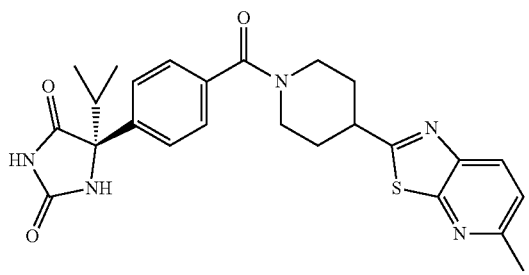 [SMILES: Cc1ccc2nc(C3CCN(C(=O)c4ccc([C@@]5(C(C)C)NC(=O)NC5=O)cc4)CC3)sc2n1]

Using 4-((R)-4-isopropyl-2,5-dioxoimidazolidin-4-yl)benzoic acid (115 mg) described in Preparation Example 45 and 5-methyl-2-(piperidin-4-yl)thiazolo[5,4-b]pyridine. trifluoroacetate as a crude product (500 mg) described in Preparation Example 146, reactions and treatments similar to those in Example 221 were performed to give the title compound (114 mg).

MS(ESI) m/z: 478 (M+H)$^+$

Example 223: Synthesis of (R)-5-methyl-5-{4-[4-(6-methylbenzothiazol-2-yl)piperidine-1-carbonyl]phenyl}imidazolidine-2,4-dione

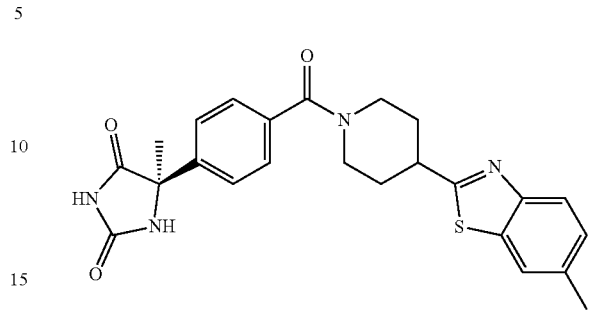

Using 4-((R)-4-methyl-2,5-dioxoimidazolidin-4-yl)benzoic acid (78 mg) described in Preparation Example 6 and 6-methyl-2-(piperidin-4-yl)-1,3-benzothiazole.hydrochloride (80 mg), reactions and treatments similar to those in Example 214 were performed to give the title compound (100 mg).

MS(ESI) m/z: 449 (M+H)$^+$

Example 224: Synthesis of (R)-5-ethyl-5-{4-[4-(6-methylbenzothiazol-2-yl)piperidine-1-carbonyl]phenyl}imidazolidine-2,4-dione

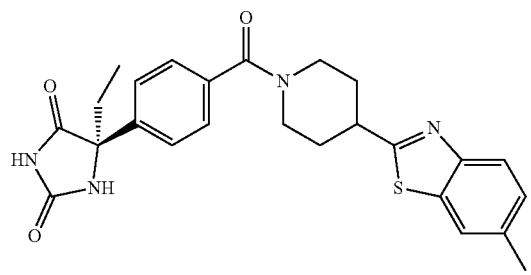 [SMILES: CC[C@]1(c2ccc(C(=O)N3CCC(c4nc5ccc(C)cc5s4)CC3)cc2)NC(=O)NC1=O]

Using 4-((R)-4-ethyl-2,5-dioxoimidazolidin-4-yl)benzoic acid (81 mg) described in Preparation Example 14 and 6-methyl-2-(piperidin-4-yl)-1,3-benzothiazole.hydrochloride (80 mg), reactions and treatments similar to those in Example 214 were performed to give the title compound (107 mg).

MS (ESI) m/z: 463 (M+H)$^+$

Example 225: Synthesis of (R)-5-isopropyl-5-{4-[4-(6-methylbenzothiazol-2-yl)piperidine-1-carbonyl]phenyl}imidazolidine-2,4-dione

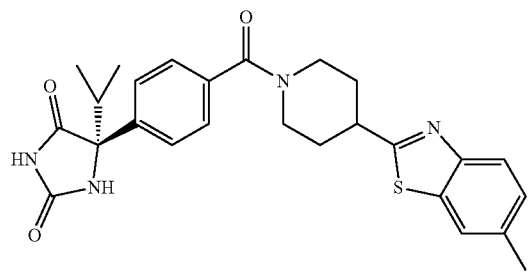

Using 4-((R)-4-isopropyl-2,5-dioxoimidazolidin-4-yl)benzoic acid (105 mg) described in Preparation Example 45 and 6-methyl-2-(piperidin-4-yl)-1,3-benzothiazole. hydrochloride (80 mg), reactions and treatments similar to those in Example 221 were performed to give the title compound (103 mg).

MS(ESI) m/z: 477 (M+H)+

Example 226: Synthesis of 3-methoxymethyl-3-{5-[4-(6-methylbenzothiazol-2-yl)piperidine-1-carbonyl]pyridin-2-yl}pyrrolidine-2,5-dione

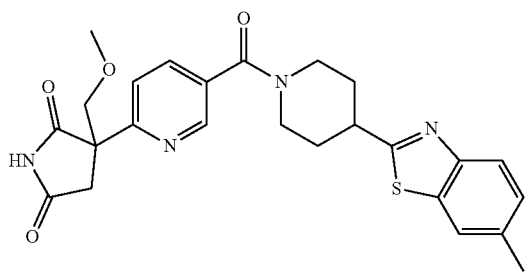 [SMILES: COCC1(c2ccc(C(=O)N3CCC(c4nc5ccc(C)cc5s4)CC3)cn2)CC(=O)NC1=O]

Using 6-(3-methoxymethyl-2,5-dioxopyrrolidin-3-yl)nicotinic acid (87 mg) described in Preparation Example 64 and 6-methyl-2-(piperidin-4-yl)-1,3-benzothiazole. hydrochloride (80 mg), reactions and treatments similar to those in Example 214 were performed to give the title compound (101 mg).

MS (ESI) m/z: 479 (M+H)+

Example 227: Synthesis of (R)-5-isopropyl-5-{4-[4-(5-phenyl[1,3,4]thiadiazol-2-yl)piperidine-1-carbonyl]phenyl}imidazolidine-2,4-dione

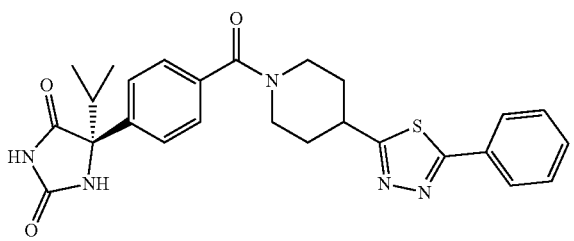 [SMILES: CC(C)[C@]1(c2ccc(C(=O)N3CCC(c4nnc(-c5ccccc5)s4)CC3)cc2)NC(=O)NC1=O]

To 4-((R)-4-isopropyl-2,5-dioxoimidazolidin-4-yl)benzoic acid (52.5 mg) described in Preparation Example 45 were added 4-(5-phenyl[1,3,4]thiadiazol-2-yl)piperidine.hydrochloride (56.4 mg), 1-hydroxybenzotriazole (28.4 mg), 1-ethyl-3-(3'-dimethylaminopropyl) carbodiimide.hydrochloride (40.3 mg) and N,N-dimethylformamide (1 mL) and the mixture was stirred at room temperature overnight. To the reaction mixture was added saturated brine and the mixture was extracted with ethyl acetate. The organic layer was washed with saturated aqueous sodium hydrogen carbonate solution and water, and concentrated under reduced pressure. The obtained residue was purified by column chromatography (chloroform:methanol) to give the title compound (92 mg).

MS(APCI) m/z: 490 (M+H)+

Example 228: Synthesis of (R)-5-[4-(4-benzoxazol-2-ylpiperidine-1-carbonyl)phenyl]-5-isopropylimidazolidine-2,4-dione

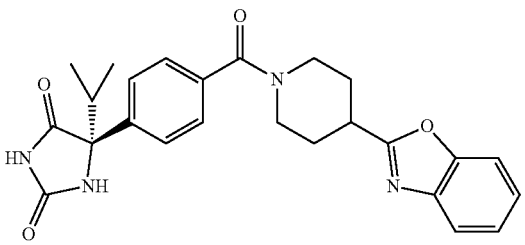 [SMILES: CC(C)[C@]1(c2ccc(C(=O)N3CCC(c4nc5ccccc5o4)CC3)cc2)NC(=O)NC1=O]

Using 4-((R)-4-isopropyl-2,5-dioxoimidazolidin-4-yl)benzoic acid (52.5 mg) described in Preparation Example 45 and 2-piperidin-4-ylbenzoxazole (40.5 mg), reactions and treatments similar to those in Example 227 were performed to give the title compound (78 mg).

MS (APCI) m/z: 447 (M+H)+

Example 229: Synthesis of (R)-5-isopropyl-5-{4-[4-(4-methylbenzyl)piperidine-1-carbonyl]phenyl}imidazolidine-2,4-dione

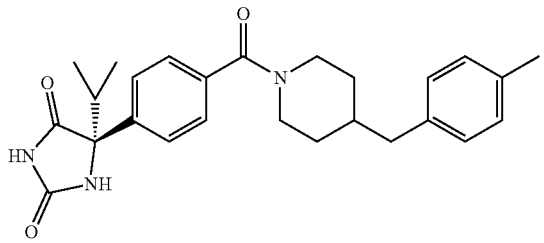 [SMILES: Cc1ccc(CC2CCN(C(=O)c3ccc([C@@]4(C(C)C)NC(=O)NC4=O)cc3)CC2)cc1]

To 4-((R)-4-isopropyl-2,5-dioxoimidazolidin-4-yl)benzoic acid (100 mg) described in Preparation Example 45 were added 4-(4-methylbenzyl)piperidine (95 mg), 1-hydroxybenzotriazole (51 mg), 1-ethyl-3-(3'-dimethylaminopropyl)carbodiimide. hydrochloride (110 mg), triethylamine (0.064 mL) and N,N-dimethylformamide (2 mL) and the mixture was stirred at room temperature overnight. To the reaction mixture was added saturated aqueous sodium hydrogen carbonate solution, and the mixture was extracted with ethyl acetate/hexane. The organic layer was washed with 10% aqueous citric acid solution and saturated brine, dried over anhydrous sodium sulfate and concentrated under reduced pressure. The obtained residue was purified by column chromatography (chloroform:methanol) to give the title compound (117 mg).

MS(ESI) m/z: 434 (M+H)+

Example 230: Synthesis of (R)-5-isopropyl-5-{4-[4-(5-methoxybenzo[d]isoxazol-3-yl)piperidine-1-carbonyl]phenyl}imidazolidine-2,4-dione

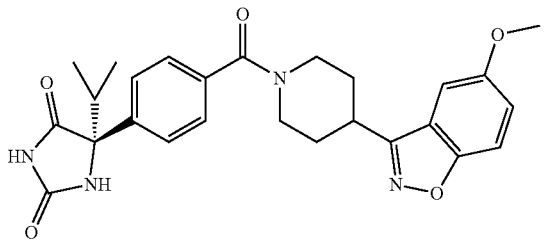 [SMILES: COc1ccc2onc(C3CCN(C(=O)c4ccc([C@@]5(C(C)C)NC(=O)NC5=O)cc4)CC3)c2c1]

Using 4-((R)-4-isopropyl-2,5-dioxoimidazolidin-4-yl)benzoic acid (52.5 mg) described in Preparation Example 45 and 5-methoxy-3-(4-piperidyl)-1,2-benzisoxazole.hydrochloride (28.4 mg), reactions and treatments similar to those in Example 227 were performed to give the title compound (64 mg).

MS (APCI) m/z: 477 (M+H)+

Example 231: Synthesis of (R)-5-{4-[4-(4,6-dimethylbenzofuran-3-yl)piperidine-1-carbonyl]phenyl}-5-isopropylimidazolidine-2,4-dione

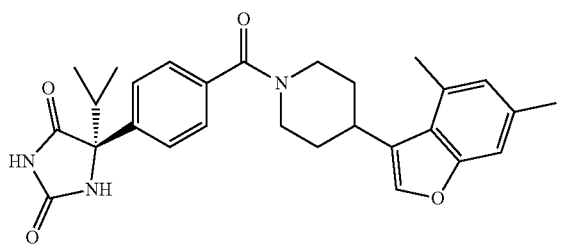 [SMILES: Cc1cc(C)c2c(C3CCN(C(=O)c4ccc([C@@]5(C(C)C)NC(=O)NC5=O)cc4)CC3)coc2c1]

To 4-((R)-4-isopropyl-2,5-dioxoimidazolidin-4-yl)benzoic acid (52.5 mg) described in Preparation Example 45 were added 4-(4,6-dimethylbenzofuran-3-yl)piperidine.hydrochloride (53.2 mg, see Preparation Example 142), 1-hydroxybenzotriazole (28.4 mg), 1-ethyl-3-(3'-dimethylaminopropyl)carbodiimide. hydrochloride (40.3 mg) and N,N-dimethylformamide (1 mL) and the mixture was stirred at room temperature overnight. To the reaction mixture was added saturated brine and the mixture was extracted with ethyl acetate. The organic layer was washed with water and saturated brine, and concentrated under reduced pressure. The obtained residue was purified by column chromatography (chloroform:ethyl acetate) to give the title compound (90 mg).

MS(APCI) m/z: 474 (M+H)+

Example 232: Synthesis of (R)-5-{4-[4-(5,6-dimethylbenzofuran-3-yl)piperidine-1-carbonyl]phenyl}-5-isopropylimidazolidine-2,4-dione

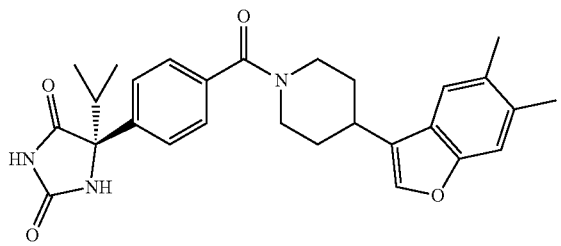 [SMILES: Cc1cc2occ(C3CCN(C(=O)c4ccc([C@@]5(C(C)C)NC(=O)NC5=O)cc4)CC3)c2cc1C]

Using 4-((R)-4-isopropyl-2,5-dioxoimidazolidin-4-yl)benzoic acid (52.5 mg) described in Preparation Example 45 and 4-(5,6-dimethylbenzofuran-3-yl)piperidine.hydrochloride (53.2 mg, see Preparation Example 140), reactions and treatments similar to those in Example 231 were performed to give the title compound (92 mg).

MS(APCI) m/z: 474 (M+H)+

Example 233: Synthesis of (R)-5-{4-[4-(5,7-dimethyl-benzofuran-3-yl)-piperidine-1-carbonyl]-phenyl}-5-isopropyl-imidazolidine-2,4-dione

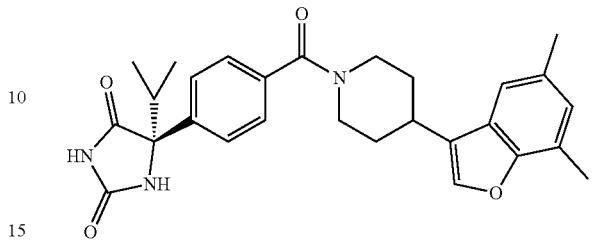

Using 4-((R)-4-isopropyl-2,5-dioxoimidazolidin-4-yl)benzoic acid (52.5 mg) described in Preparation Example 45 and 4-(5,7-dimethyl-benzofuran-3-yl)piperidine.hydrochloride (53.2 mg, see Preparation Example 138), reactions and treatments similar to those in Example 227 were performed to give the title compound (73 mg).

MS (APCI) m/z: 474 (M+H)+

Example 234: Synthesis of (R)-5-{4-[4-(6-fluorobenzofuran-3-yl)piperidine-1-carbonyl]phenyl}-5-isopropylimidazolidine-2,4-dione

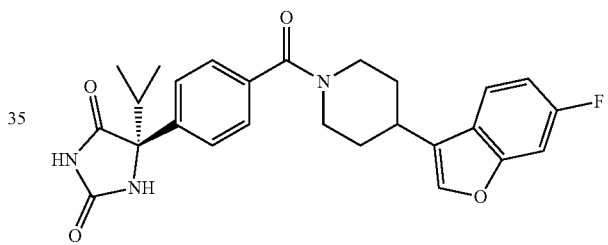

Using 4-((R)-4-isopropyl-2,5-dioxoimidazolidin-4-yl)benzoic acid (52.5 mg) described in Preparation Example 45 and 4-(6-fluoro-1-benzofuran-3-yl)piperidine (43.9 mg), reactions and treatments similar to those in Example 227 were performed to give the title compound (47 mg).

MS (APCI) m/z: 464 (M+H)+

Example 235: Synthesis of (R)-5-{4-[4-(5-fluorobenzo[d]isoxazol-3-yl)piperidine-1-carbonyl]phenyl}-5-isopropylimidazolidine-2,4-dione

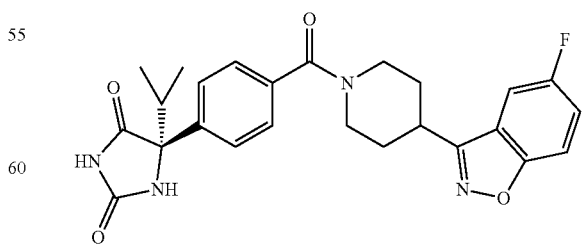

Using 4-((R)-4-isopropyl-2,5-dioxoimidazolidin-4-yl)benzoic acid (52.5 mg) described in Preparation Example 45 and 5-fluoro-3-(4-piperidinyl)-1,2-benzisoxazole (44 mg),

Example 236: Synthesis of (R)-5-{4-[4-(5-chlorobenzo[d]isoxazol-3-yl)piperidine-1-carbonyl]phenyl}-5-isopropylimidazolidine-2,4-dione

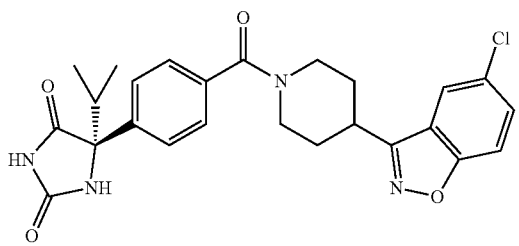 [SMILES: Cc1ccc2occ(C3CCN(C(=O)c4ccc([C@@]5(C(C)C)NC(=O)NC5=O)cc4)CC3)c2c1]

Using 4-((R)-4-isopropyl-2,5-dioxoimidazolidin-4-yl)benzoic acid (52.5 mg) described in Preparation Example 45 and 5-chloro-3-(piperidin-4-yl)benzo[d]isoxazole (47.3 mg), reactions and treatments similar to those in Example 227 were performed to give the title compound (67 mg).

MS (APCI) m/z: 481 (M+H)$^+$

Example 237: Synthesis of (R)-5-{4-[4-(5-chlorobenzofuran-3-yl)piperidine-1-carbonyl]phenyl}-5-isopropylimidazolidine-2,4-dione

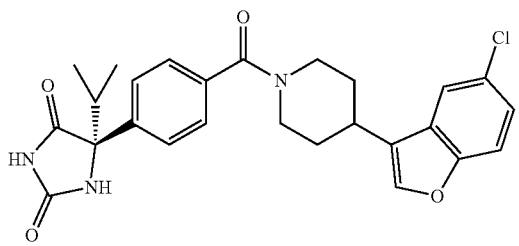

To 4-((R)-4-isopropyl-2,5-dioxoimidazolidin-4-yl)benzoic acid (52.5 mg) described in Preparation Example 45 were added 4-(5-chlorobenzofuran-3-yl)piperidine (47.1 mg), 1-hydroxybenzotriazole (28.4 mg), 1-ethyl-3-(3'-dimethylaminopropyl)carbodiimide.hydrochloride (40.3 mg) and N,N-dimethylformamide (1 mL) and the mixture was stirred at room temperature overnight. To the reaction mixture was added saturated brine and the mixture was extracted with ethyl acetate. The organic layer was washed with water and saturated brine, and concentrated under reduced pressure. The obtained residue was purified by column chromatography (hexane:ethyl acetate) to give the title compound (59 mg).

MS(APCI) m/z: 480 (M+H)$^+$

Example 238: Synthesis of (R)-5-{4-[4-(6-fluorobenzo[d]isoxazol-3-yl)piperidine-1-carbonyl]phenyl}-5-isopropylimidazolidine-2,4-dione

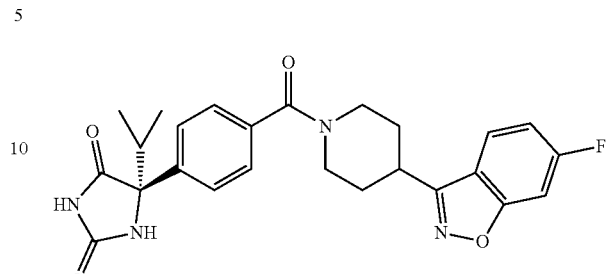

Using 4-((R)-4-isopropyl-2,5-dioxoimidazolidin-4-yl)benzoic acid (52.5 mg) described in Preparation Example 45 and 6-fluoro-3-(4-piperidinyl)-1,2-benzisoxazole (44 mg), reactions and treatments similar to those in Example 227 were performed to give the title compound (60 mg).

MS(APCI) m/z: 465 (M+H)$^+$

Example 239: Synthesis of (R)-5-isopropyl-5-{4-[4-(5-methylbenzofuran-3-yl)piperidine-1-carbonyl]phenyl}imidazolidine-2,4-dione

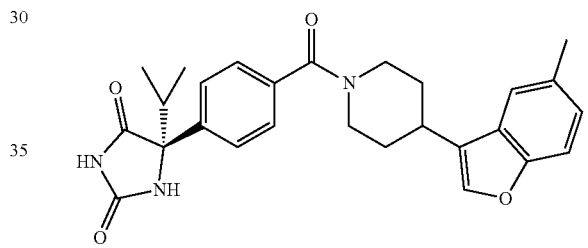

Using 4-((R)-4-isopropyl-2,5-dioxoimidazolidin-4-yl)benzoic acid (52.5 mg) described in Preparation Example 45 and 4-(5-methyl-1-benzofuran-3-yl)piperidine (43.1 mg), reactions and treatments similar to those in Example 237 were performed to give the title compound (56 mg).

MS (APCI) m/z: 460 (M+H)$^+$

Example 240: Synthesis of (R)-5-isopropyl-5-{4-[4-(6-methylbenzofuran-3-yl)piperidine-1-carbonyl]phenyl}imidazolidine-2,4-dione

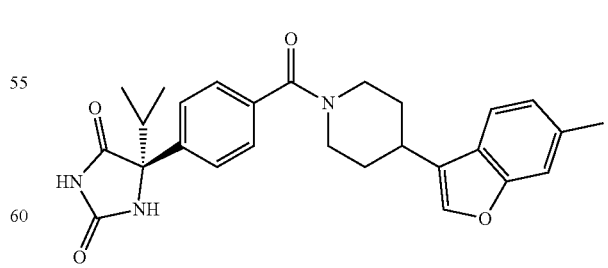

Using 4-((R)-4-isopropyl-2,5-dioxoimidazolidin-4-yl)benzoic acid (52.5 mg) described in Preparation Example 45 and 4-(6-methylbenzofuran-3-yl)piperidine.hydrochloride (43.1 mg, see Preparation Example 136), reactions and treatments similar to those in Example 227 were performed to give the title compound (60 mg).
MS(APCI) m/z: 460 (M+H)+

Example 241: Synthesis of (R)-5-(4-{4-[5-(4-chlorophenyl) [1,3,4]oxadiazol-2-yl]piperidine-1-carbonyl}phenyl)-5-isopropylimidazolidine-2,4-dione

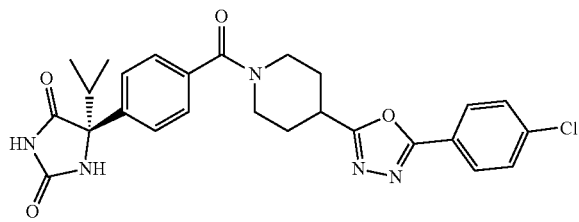 [SMILES: CC(C)[C@]1(c2ccc(C(=O)N3CCC(c4nnc(-c5ccc(Cl)cc5)o4)CC3)cc2)NC(=O)NC1=O]

Using 4-((R)-4-isopropyl-2,5-dioxoimidazolidin-4-yl)benzoic acid (52.5 mg) described in Preparation Example 45 and 4-[5-(4-chlorophenyl)-1,3,4-oxadiazol-2-yl]piperidine.hydrobromide (68.9 mg), reactions and treatments similar to those in Example 227 were performed to give the title compound (9 mg).
MS(APCI) m/z: 508 (M+H)+

Example 242: Synthesis of (R)-5-isopropyl-5-[4-(4-naphthalen-2-ylpiperidine-1-carbonyl)phenyl]imidazolidine-2,4-dione

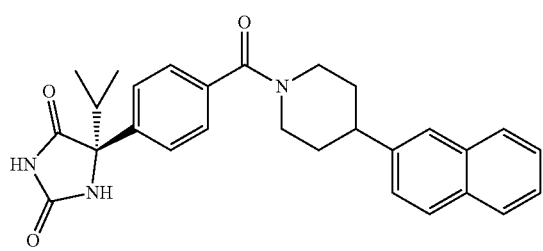 [SMILES: CC(C)[C@]1(c2ccc(C(=O)N3CCC(c4ccc5ccccc5c4)CC3)cc2)NC(=O)NC1=O]

Using 4-((R)-4-isopropyl-2,5-dioxoimidazolidin-4-yl)benzoic acid (52.5 mg) described in Preparation Example 45 and 4-(2-naphthyl)piperidine.hydrochloride (49.6 mg), reactions and treatments similar to those in Example 227 were performed to give the title compound (86 mg).
MS(APCI) m/z: 456 (M+H)+

Example 243: Synthesis of (R)-5-isopropyl-5-{4-[4-(1-methyl-1H-benzimidazol-2-yl) piperazine-1-carbonyl]phenyl}imidazolidine-2,4-dione

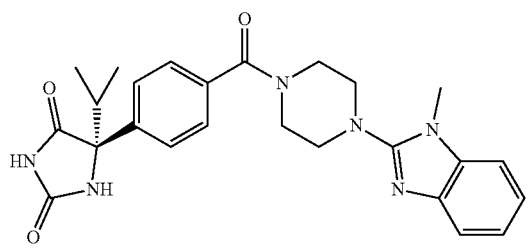 [SMILES: CC(C)[C@]1(c2ccc(C(=O)N3CCN(c4nc5ccccc5n4C)CC3)cc2)NC(=O)NC1=O]

To 4-((R)-4-isopropyl-2,5-dioxoimidazolidin-4-yl)benzoic acid (52.5 mg) described in Preparation Example 45 were added 1-methyl-2-(piperazin-1-yl)-1H-benzimidazole.2 hydrochloride (57.8 mg), 1-hydroxybenzotriazole (28.4 mg), 1-ethyl-3-(3'-dimethylaminopropyl)carbodiimide.hydrochloride (40.3 mg) and N,N-dimethylformamide (1 mL) and the mixture was stirred at room temperature overnight. To the reaction mixture was added saturated brine and the mixture was extracted with ethyl acetate. The organic layer was washed with water and saturated brine, and concentrated under reduced pressure. The obtained residue was purified by column chromatography (ethyl acetate:methanol) to give the title compound (70 mg).
MS(APCI) m/z: 461 (M+H)+

Example 244: Synthesis of (R)-5-[4-(4-benzothiazol-2-ylpiperidine-1-carbonyl)phenyl]-5-isopropylimidazolidine-2,4-dione

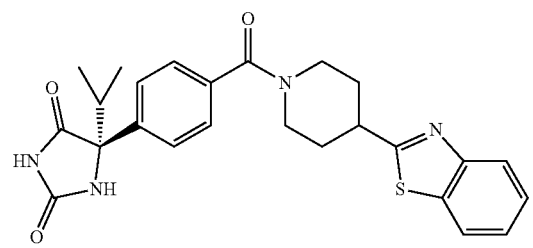 [SMILES: CC(C)[C@]1(c2ccc(C(=O)N3CCC(c4nc5ccccc5s4)CC3)cc2)NC(=O)NC1=O]

Using 4-((R)-4-isopropyl-2,5-dioxoimidazolidin-4-yl)benzoic acid (52.5 mg) described in Preparation Example 45 and 2-(4-piperidinyl)-1,3-benzothiazole (43.7 mg), reactions and treatments similar to those in Example 227 were performed to give the title compound (70 mg).
MS(APCI) m/z: 463 (M+H)+

Example 245: Synthesis of (R)-5-{4-[4-(4,6-dimethylbenzofuran-3-yl)piperidine-1-carbonyl]phenyl}-5-methylimidazolidine-2,4-dione

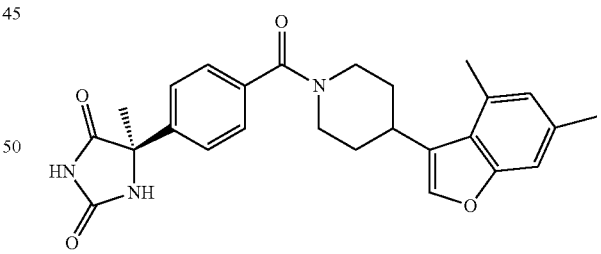

To 4-((R)-4-methyl-2,5-dioxoimidazolidin-4-yl)benzoic acid (50 mg) described in Preparation Example 6 were added 4-(4,6-dimethylbenzofuran-3-yl)piperidine.hydrochloride (57 mg, see Preparation Example 142), 1-hydroxybenzotriazole (29 mg), 1-ethyl-3-(3'-dimethylaminopropyl) carbodiimide.hydrochloride (53 mg), triethylamine (59 µL) and dichloromethane (2 mL) and the mixture was stirred at room temperature overnight. To the reaction mixture was added saturated aqueous sodium hydrogen carbonate solution and the mixture was extracted with ethyl acetate. The organic layer was washed with water and saturated brine, dried over anhydrous sodium sulfate and concentrated under reduced pressure. The obtained residue was purified by column chromatography (chloroform:methanol) to give the title compound (54 mg).

MS(ESI) m/z: 446 (M+H)⁺

Example 246: Synthesis of (R)-5-methyl-5-{4-[4-(6-methylbenzofuran-3-yl)piperidine-1-carbonyl]phenyl}imidazolidine-2,4-dione

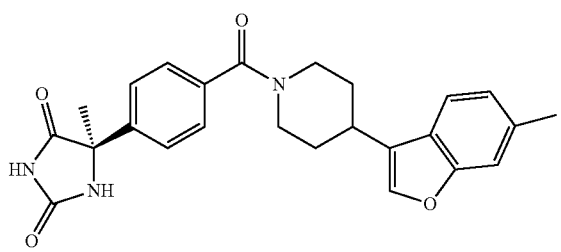 [SMILES: Cc1ccc2c(C3CCN(C(=O)c4ccc([C@@]5(C)NC(=O)NC5=O)cc4)CC3)coc2c1]

To 4-((R)-4-methyl-2,5-dioxoimidazolidin-4-yl)benzoic acid (50 mg) described in Preparation Example 6 were added 4-(6-methylbenzofuran-3-yl)piperidine.hydrochloride (46 mg, see Preparation Example 136), 1-hydroxybenzotriazole (29 mg), 1-ethyl-3-(3'-dimethylaminopropyl) carbodiimide.hydrochloride (53 mg), triethylamine (0.03 mL) and dichloromethane (2 mL) and the mixture was stirred at room temperature overnight. To the reaction mixture was added saturated aqueous sodium hydrogen carbonate solution and the mixture was extracted with ethyl acetate. The organic layer was washed with water and saturated brine, dried over anhydrous sodium sulfate and concentrated under reduced pressure. The obtained residue was purified by column chromatography (chloroform:methanol) to give the title compound (33 mg).

MS (ESI) m/z: 432 (M+H)⁺

Example 247: Synthesis of (R)-5-isopropyl-5-{4-[4-(1-methyl-1H-indazol-4-yl)piperazine-1-carbonyl]phenyl) imidazolidine-2,4-dione

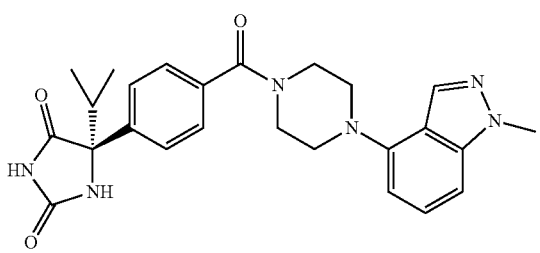 [SMILES: CC(C)[C@]1(c2ccc(C(=O)N3CCN(c4cccc5c4cnn5C)CC3)cc2)NC(=O)NC1=O]

To 4-((R)-4-isopropyl-2,5-dioxoimidazolidin-4-yl)benzoic acid (52.5 mg) described in Preparation Example 45 were added 1-methyl-4-piperazin-1-yl-1H-indazole.2 hydrochloride (57.8 mg) described in Preparation Example 143, 1-hydroxybenzotriazole (28 mg), 1-ethyl-3-(3'-dimethylaminopropyl)carbodiimide.hydrochloride (40 mg), triethylamine (0.056 mL) and N,N-dimethylformamide (1 mL) and the mixture was stirred at room temperature overnight. To the reaction mixture was added saturated brine and the mixture was extracted with ethyl acetate. The organic layer was washed with water and saturated aqueous sodium hydrogen carbonate solution, and concentrated under reduced pressure. The obtained residue was purified by column chromatography (hexane:ethyl acetate) to give the title compound (85 mg).

MS(APCI) m/z: 461 (M+H)⁺

Example 248: Synthesis of (R)-5-{4-[4-(5-fluoro-1-methyl-1H-indol-3-yl)piperidine-1-carbonyl]phenyl}-5-isopropylimidazolidine-2,4-dione

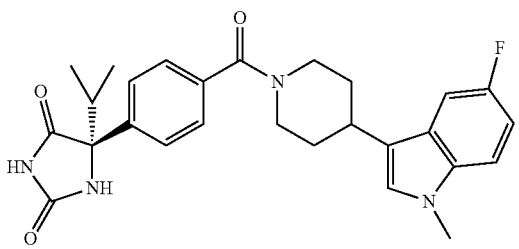 [SMILES: CC(C)[C@]1(c2ccc(C(=O)N3CCC(c4cn(C)c5ccc(F)cc45)CC3)cc2)NC(=O)NC1=O]

Using 4-((R)-4-isopropyl-2,5-dioxoimidazolidin-4-yl) benzoic acid (52.5 mg) described in Preparation Example 45 and 5-fluoro-1-methyl-3-piperidin-4-yl-1H-indole (46.5 mg), reactions and treatments similar to those in Example 231 were performed to give the title compound (79 mg).

MS (APCI) m/z: 477 (M+H)⁺

Example 249: Synthesis of (R)-5-{4-[4-(6-fluorobenzo[d]isothiazol-3-yl)piperidine-1-carbonyl]phenyl}-5-isopropylimidazolidine-2,4-dione

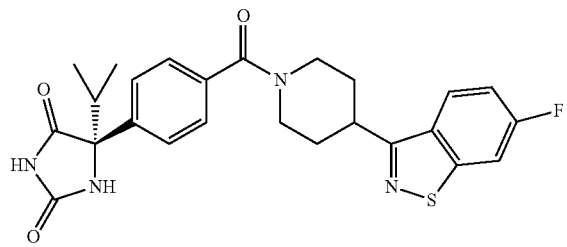 [SMILES: CC(C)[C@]1(c2ccc(C(=O)N3CCC(c4nsc5cc(F)ccc45)CC3)cc2)NC(=O)NC1=O]

Using 4-((R)-4-isopropyl-2,5-dioxoimidazolidin-4-yl) benzoic acid (52.5 mg) described in Preparation Example 45 and 6-fluoro-3-(piperidin-4-yl)benzo[d]isothiazole (47.3 mg), reactions and treatments similar to those in Example 231 were performed to give the title compound (43 mg).

MS (APCI) m/z: 481 (M+H)⁺

Example 250: Synthesis of (R)-5-{4-[4-(6-fluoro-1-methyl-1H-indazol-3-yl)piperidine-1-carbonyl]phenyl}-5-isopropylimidazolidine-2,4-dione

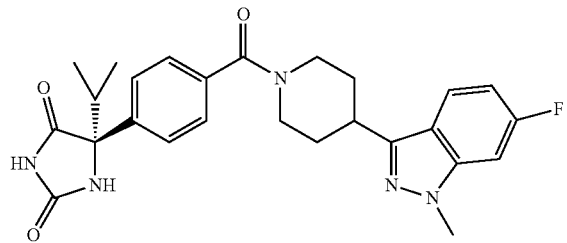 [SMILES: CC(C)[C@]1(c2ccc(C(=O)N3CCC(c4nn(C)c5cc(F)ccc45)CC3)cc2)NC(=O)NC1=O]

Using 4-((R)-4-isopropyl-2,5-dioxoimidazolidin-4-yl) benzoic acid (52.5 mg) described in Preparation Example 45 and 6-fluoro-1-methyl-3-(piperidin-4-yl)-1H-indazole (47.7 mg), reactions and treatments similar to those in Example 243 were performed to give the title compound (72 mg).
MS(APCI) m/z: 478 (M+H)+

Example 251: Synthesis of (R)-5-{4-[4-(6-fluoro-1H-indazol-3-yl)piperidine-1-carbonyl]phenyl}-5-isopropylimidazolidine-2,4-dione

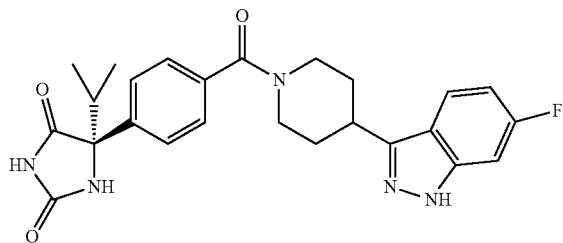 [SMILES: CC(C)[C@]1(c2ccc(C(=O)N3CCC(c4n[nH]c5cc(F)ccc45)CC3)cc2)NC(=O)NC1=O]

Using 4-((R)-4-isopropyl-2,5-dioxoimidazolidin-4-yl)benzoic acid (52.5 mg) described in Preparation Example 45 and 6-fluoro-3-(piperidin-4-yl)-1H-indazole (43.9 mg), reactions and treatments similar to those in Example 243 were performed to give the title compound (72 mg).
MS (APCI) m/z: 464 (M+H)+

Example 252: Synthesis of (R)-5-[4-(4-benzo[d]isoxazol-3-ylpiperazine-1-carbonyl)phenyl]-5-isopropylimidazolidine-2,4-dione

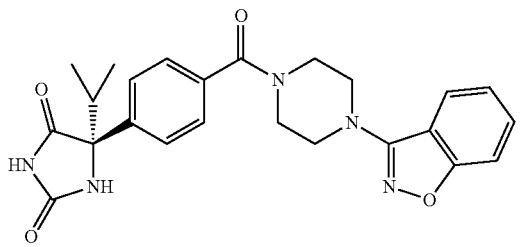 [SMILES: CC(C)[C@]1(c2ccc(C(=O)N3CCN(c4noc5ccccc45)CC3)cc2)NC(=O)NC1=O]

Using 4-((R)-4-isopropyl-2,5-dioxoimidazolidin-4-yl)benzoic acid (52.5 mg) described in Preparation Example 45 and 3-piperazin-1-yl-1,2-benzisoxazole (40.6 mg), reactions and treatments similar to those in Example 231 were performed to give the title compound (75 mg).
MS(APCI) m/z: 448 (M+H)+

Example 253: Synthesis of (R)-5-{4-[4-(6-chlorobenzo[d]isothiazol-3-yl)piperazine-1-carbonyl)phenyl]-5-isopropylimidazolidine-2,4-dione

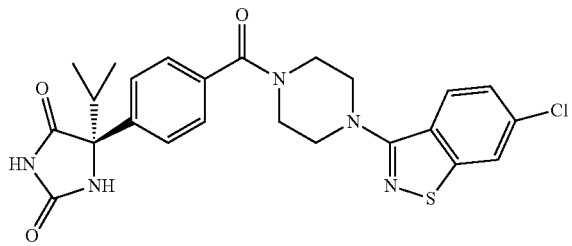 [SMILES: CC(C)[C@]1(c2ccc(C(=O)N3CCN(c4nsc5cc(Cl)ccc45)CC3)cc2)NC(=O)NC1=O]

Using 4-((R)-4-isopropyl-2,5-dioxoimidazolidin-4-yl)benzoic acid (52.5 mg) described in Preparation Example 45 and 6-chloro-3-(piperazin-1-yl)benzo[d]isothiazole (50.8 mg), reactions and treatments similar to those in Example 231 were performed to give the title compound (99 mg).
MS(APCI) m/z: 498 (M+H)+

Example 254: Synthesis of (R)-5-isopropyl-5-{4-[4-(4-phenylthiazol-2-yl)piperidine-1-carbonyl]phenyl}imidazolidine-2,4-dione

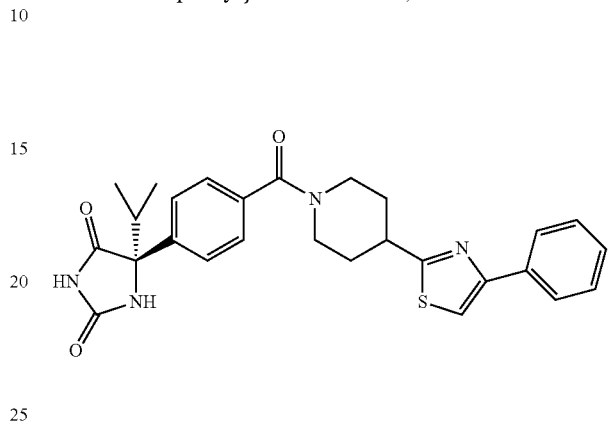

To 4-((R)-4-isopropyl-2,5-dioxoimidazolidin-4-yl)benzoic acid (52.5 mg) described in Preparation Example 45 were added 4-(4-phenyl-1,3-thiazol-2-yl)piperidine (48.9 mg), 1-hydroxybenzotriazole (28.4 mg), 1-ethyl-3-(3'-dimethylaminopropyl)carbodiimide.hydrochloride (40.3 mg) and N,N-dimethylformamide (1 mL) and the mixture was stirred at room temperature overnight. To the reaction mixture was added saturated brine and the mixture was extracted with ethyl acetate. The organic layer was washed with water and saturated brine, dried over anhydrous sodium sulfate and concentrated under reduced pressure. The obtained residue was purified by NH column chromatography (chloroform:methanol) to give the title compound (15 mg).
MS(APCI) m/z: 489 (M+H)+

Example 255: Synthesis of (R)-5-isopropyl-5-[4-(4-quinolin-2-ylpiperazine-1-carbonyl)phenyl]imidazolidine-2,4-dione

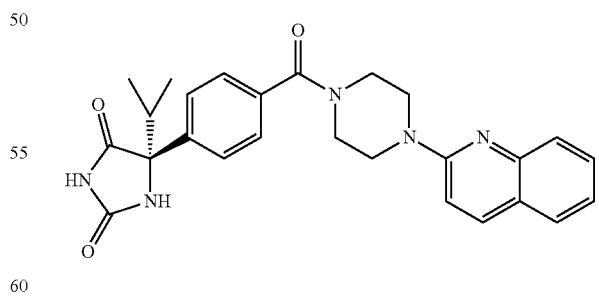

Using 4-((R)-4-isopropyl-2,5-dioxoimidazolidin-4-yl)benzoic acid (52.5 mg) described in Preparation Example 45 and 2-(piperazin-1-yl)quinoline (42.7 mg), reactions and treatments similar to those in Example 227 were performed to give the title compound (74 mg).
MS(APCI) m/z: 458 (M+H)+

Example 256: Synthesis of (R)-5-{4-[4-(6-chloro-5-methylbenzoxazol-2-yl)piperidine-1-carbonyl]phenyl}-5-isopropylimidazolidine-2,4-dione

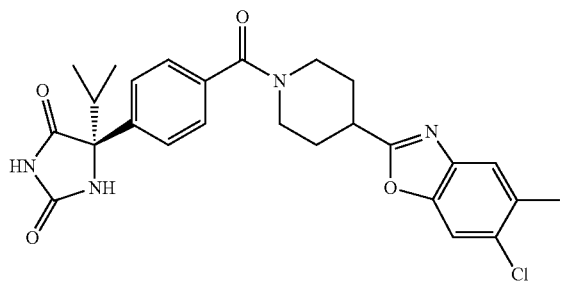 [SMILES: Cc1cc2nc(C3CCN(C(=O)c4ccc([C@@]5(C(C)C)NC(=O)NC5=O)cc4)CC3)oc2cc1Cl]

Using 4-((R)-4-isopropyl-2,5-dioxoimidazolidin-4-yl)benzoic acid (52.5 mg) described in Preparation Example 45 and 6-chloro-5-methyl-2-piperidin-4-yl-1,3-benzoxazole (50.1 mg), reactions and treatments similar to those in Example 227 were performed to give the title compound (79 mg).
MS(APCI) m/z: 495 (M+H)$^+$ Example 257: Synthesis of (R)-5-isopropyl-5-{4-[4-(6-methylbenzoxazol-2-yl)piperidine-1-carbonyl]phenyl}imidazolidine-2,4-dione

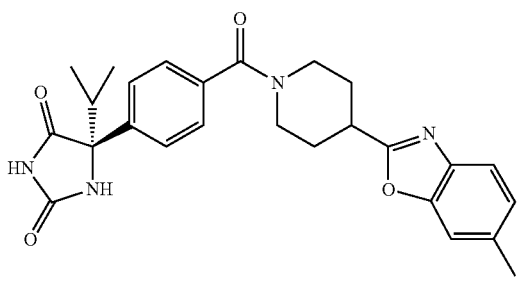 [SMILES: Cc1ccc2nc(C3CCN(C(=O)c4ccc([C@@]5(C(C)C)NC(=O)NC5=O)cc4)CC3)oc2c1]

Using 4-((R)-4-isopropyl-2,5-dioxoimidazolidin-4-yl)benzoic acid (52.5 mg) described in Preparation Example 45 and 6-methyl-2-(piperidin-4-yl)-1,3-benzoxazole (43.3 mg), reactions and treatments similar to those in Example 227 were performed to give the title compound (76 mg).
MS(APCI) m/z: 461 (M+H)$^+$ Example 258: Synthesis of (R)-5-isopropyl-5-{4-[4-(4-methylbenzoxazol-2-yl)piperidine-1-carbonyl]phenyl}-imidazolidine-2,4-dione

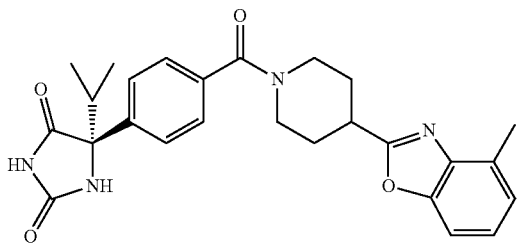 [SMILES: Cc1cccc2oc(C3CCN(C(=O)c4ccc([C@@]5(C(C)C)NC(=O)NC5=O)cc4)CC3)nc12]

Using 4-((R)-4-isopropyl-2,5-dioxoimidazolidin-4-yl)benzoic acid (52.5 mg) described in Preparation Example 45 and 4-methyl-2-piperidin-4-yl-1,3-benzoxazole (43.3 mg), reactions and treatments similar to those in Example 231 were performed to give the title compound (79 mg).
MS(APCI) m/z: 461 (M+H)$^+$ Example 259: Synthesis of (R)-5-isopropyl-5-{4-[4-(5-phenylthiazol-2-yl)piperidine-1-carbonyl]phenyl}imidazolidine-2,4-dione

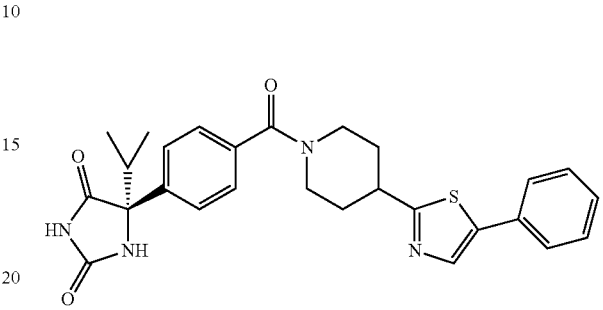

Using 4-((R)-4-isopropyl-2,5-dioxoimidazolidin-4-yl)benzoic acid (52.5 mg) described in Preparation Example 45 and 4-(5-phenylthiazol-2-yl)piperidine (48.9 mg), reactions and treatments similar to those in Example 227 were performed to give the title compound (94 mg).
MS(APCI) m/z: 489 (M+H)$^+$ Example 260: Synthesis of (R)-5-isopropyl-5-{4-[4-(3-phenylisoxazol-5-yl)piperidine-1-carbonyl]phenyl}imidazolidine-2,4-dione

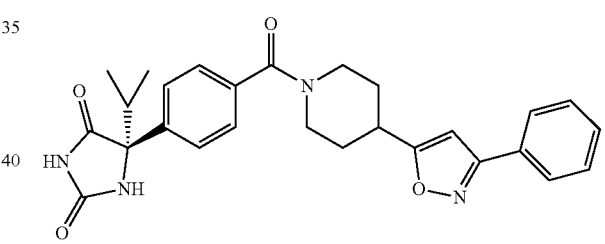

Using 4-((R)-4-isopropyl-2,5-dioxoimidazolidin-4-yl)benzoic acid (52.5 mg) described in Preparation Example 45 and 4-(3-phenylisoxazol-5-yl)piperidine (45.7 mg), reactions and treatments similar to those in Example 237 were performed to give the title compound (39 mg).
MS(APCI) m/z: 473 (M+H)$^+$ Example 261: Synthesis of (R)-5-{4-[4-(1H-indol-2-yl)piperidine-1-carbonyl]phenyl}-5-isopropylimidazolidine-2,4-dione

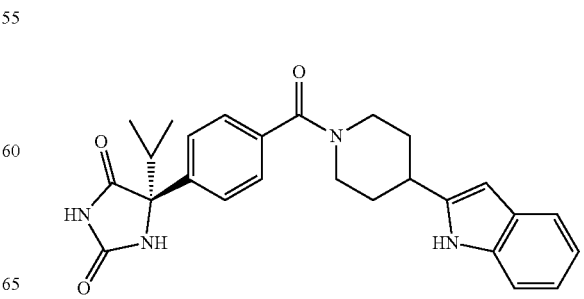

Using 4-((R)-4-isopropyl-2,5-dioxoimidazolidin-4-yl)benzoic acid (52.5 mg) described in Preparation Example 45 and 2-(piperidin-4-yl)-1H-indole (40.1 mg), reactions and treatments similar to those in Example 237 were performed to give the title compound (74 mg).

MS (APCI) m/z: 445 (M+H)$^+$

Example 262: Synthesis of (R)-5-isopropyl-5-{4-[4-(5-trifluoromethylbenzothiazol-2-yl)piperidine-1-carbonyl]phenyl}imidazolidine-2,4-dione

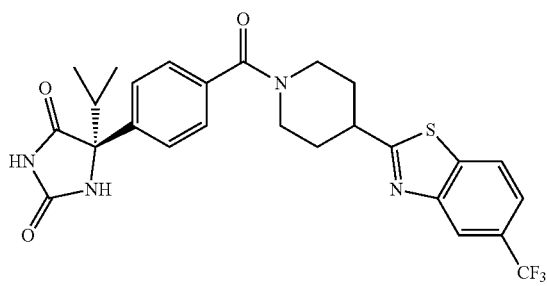 [SMILES: CC(C)[C@]1(c2ccc(C(=O)N3CCC(c4nc5cc(C(F)(F)F)ccc5s4)CC3)cc2)NC(=O)NC1=O]

Using 4-((R)-4-isopropyl-2,5-dioxoimidazolidin-4-yl)benzoic acid (52.5 mg) described in Preparation Example 45 and 2-(piperidin-4-yl)-5-(trifluoromethyl)-1,3-benzothiazole (57.1 mg), reactions and treatments similar to those in Example 237 were performed to give the title compound (97 mg).

MS(APCI) m/z: 531 (M+H)$^+$

Example 263: Synthesis of (R)-5-{4-[4-(5-chlorobenzoxazol-2-yl)piperidine-1-carbonyl]phenyl}-5-isopropylimidazolidine-2,4-dione

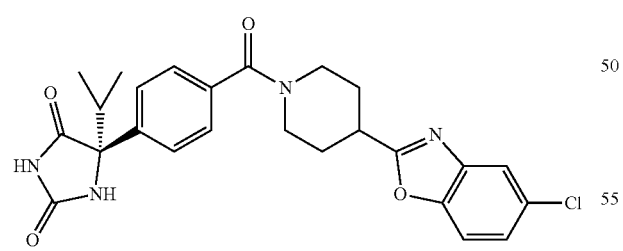

Using 4-((R)-4-isopropyl-2,5-dioxoimidazolidin-4-yl)benzoic acid (52.5 mg) described in Preparation Example 45 and 5-chloro-2-(piperidin-4-yl)-1,3-benzoxazole (47.3 mg), reactions and treatments similar to those in Example 237 were performed to give the title compound (77 mg).

MS (APCI) m/z: 481 (M+H)$^+$

Example 264: Synthesis of (R)-5-isopropyl-5-{4-[4-(5-methylbenzothiazol-2-yl)piperidine-1-carbonyl]phenyl}imidazolidine-2,4-dione

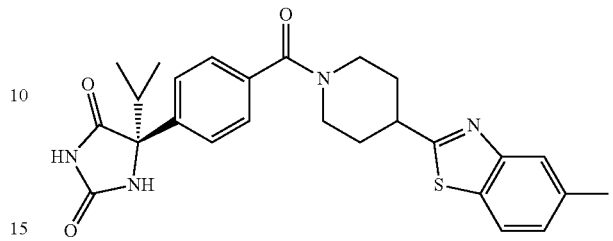

Using 4-((R)-4-isopropyl-2,5-dioxoimidazolidin-4-yl)benzoic acid (52.5 mg) described in Preparation Example 45 and 5-methyl-2-(piperidin-4-yl)-1,3-benzothiazole (46.5 mg), reactions and treatments similar to those in Example 237 were performed to give the title compound (84 mg).

MS(APCI) m/z: 477 (M+H)$^+$

Example 265: Synthesis of (R)-5-(4-{4-[5-(4-chlorophenyl)-1H-pyrazol-3-yl]piperidine-1-carbonyl}phenyl)-5-isopropylimidazolidine-2,4-dione

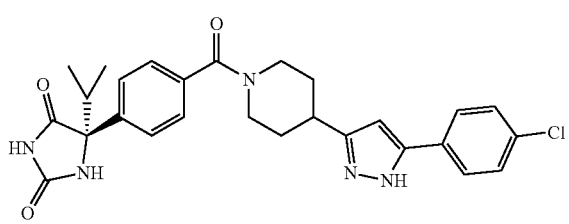 [SMILES: CC(C)[C@]1(c2ccc(C(=O)N3CCC(c4cc(-c5ccc(Cl)cc5)[nH]n4)CC3)cc2)NC(=O)NC1=O]

Using 4-((R)-4-isopropyl-2,5-dioxoimidazolidin-4-yl)benzoic acid (52.5 mg) described in Preparation Example 45 and 4-[5-(4-chlorophenyl)-1H-pyrazol-3-yl]piperidine (52.4 mg), reactions and treatments similar to those in Example 243 were performed to give the title compound (97 mg).

MS(APCI) m/z: 506 (M+H)$^+$

Example 266: Synthesis of (R)-5-isopropyl-5-[4-(4-naphthalen-2-ylpiperazine-1-carbonyl)phenyl]imidazolidine-2,4-dione To 4-((R)-4-isopropyl-2,5-dioxoimidazolidin-4-yl)benzoic acid (52.5 mg) described in Preparation Example 45 were added 1-(naphthalen-2-yl)piperazine.hydrochloride (52.4 mg), 1-hydroxybenzotriazole (28.4 mg), 1-ethyl-3-(3'- dimethylaminopropyl)carbodiimide.hydrochloride (40.3 mg), triethylamine (0.028 mL) and N,N-dimethylformamide (1 mL) and the mixture was stirred at room temperature overnight. To the reaction mixture was added saturated brine and the mixture was extracted with ethyl acetate. The organic layer was washed with water and saturated brine, dried over anhydrous sodium sulfate and concentrated under reduced pressure. The obtained residue was purified by column chromatography (ethyl acetate:methanol) to give the title compound (97 mg).

MS(APCI) m/z: 457 (M+H)+

Example 267: Synthesis of (R)-5-methyl-5-{4-[4-(6-methylbenzoxazol-2-yl)piperidine-1-carbonyl]phenyl}imidazolidine-2,4-dione

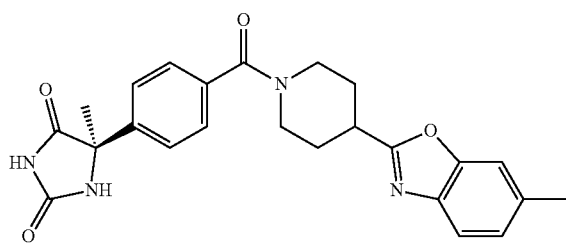 [SMILES: Cc1ccc2nc(C3CCN(C(=O)c4ccc([C@@]5(C)NC(=O)NC5=O)cc4)CC3)oc2c1]

Using 4-((R)-4-methyl-2,5-dioxoimidazolidin-4-yl)benzoic acid (46.8 mg) described in Preparation Example 6 and 6-methyl-2-piperidin-4-yl-1,3-benzoxazole (43.3 mg), reactions and treatments similar to those in Example 254 were performed to give the title compound (58 mg).

MS (APCI) m/z: 433 (M+H)+

Example 268: Synthesis of (R)-5-methyl-5-{4-[4-(5-trifluoromethylbenzothiazol-2-yl)piperidine-1-carbonyl]phenyl}imidazolidine-2,4-dione

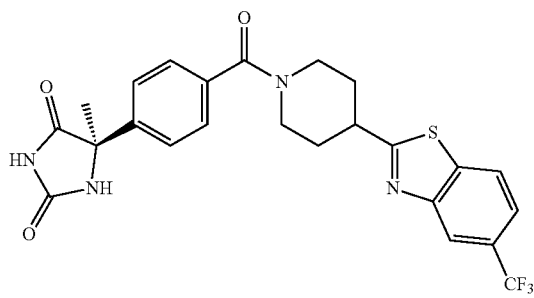 [SMILES: C[C@]1(c2ccc(C(=O)N3CCC(c4nc5cc(C(F)(F)F)ccc5s4)CC3)cc2)NC(=O)NC1=O]

Using 4-((R)-4-methyl-2,5-dioxoimidazolidin-4-yl)benzoic acid (46.8 mg) described in Preparation Example 6 and 2-(piperidin-4-yl)-5-(trifluoromethyl)-1,3-benzothiazole (57.3 mg), reactions and treatments similar to those in Example 227 were performed to give the title compound (67 mg).

MS(APCI) m/z: 503 (M+H)+

Example 269: Synthesis of (R)-5-(4-{4-[5-(4-chlorophenyl)-1H-pyrazol-3-yl]piperidine-1-carbonyl}phenyl)-5-methylimidazolidine-2,4-dione

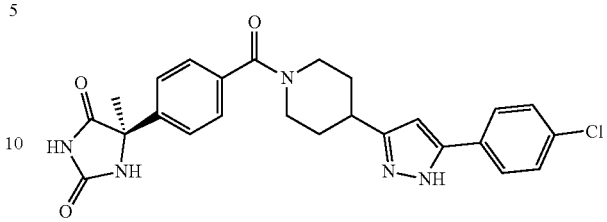

Using 4-((R)-4-methyl-2,5-dioxoimidazolidin-4-yl)benzoic acid (46.8 mg) described in Preparation Example 6 and 4-[5-(4-chlorophenyl)-1H-pyrazol-3-yl]piperidine (52.4 mg), reactions and treatments similar to those in Example 227 were performed to give the title compound (91 mg).

MS(APCI) m/z: 478 (M+H)+

Example 270: Synthesis of (R)-5-isopropyl-5-{4-[4-(1-methyl-1H-benzimidazol-2-yl)piperidine-1-carbonyl]phenyl}imidazolidine-2,4-dione

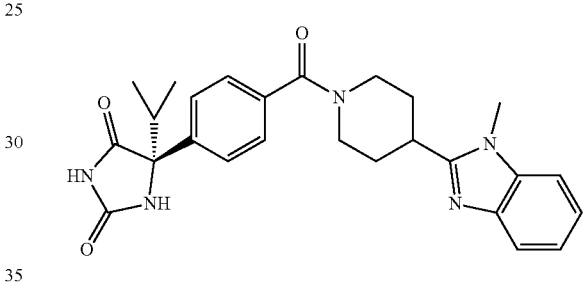

To a mixture of 4-((R)-4-isopropyl-2,5-dioxoimidazolidin-4-yl)benzoic acid (67 mg) described in Preparation Example 45, 1-methyl-2-piperidin-4-yl-1H-benzoimidazole.2 hydrochloride (70 mg), 1-hydroxybenzotriazole (39 mg), 1-ethyl-3-(3'-dimethylaminopropyl)carbodiimide.hydrochloride (56 mg) and chloroform (3 mL) was added triethylamine (0.102 mL) and the mixture was stirred at room temperature for 3.5 hr. To the reaction mixture was added saturated aqueous sodium hydrogen carbonate solution, and the mixture was filtered by a phase separator. The filtrate was concentrated under reduced pressure and the obtained residue was purified by column chromatography (chloroform:methanol) to give the title compound (71.3 mg).

MS(ESI) m/z: 460 (M+H)+

Example 271: Synthesis of (R)-5-{4-[4-(5,7-dimethylindazol-2-yl)piperidine-1-carbonyl]phenyl}-5-isopropylimidazolidine-2,4-dione

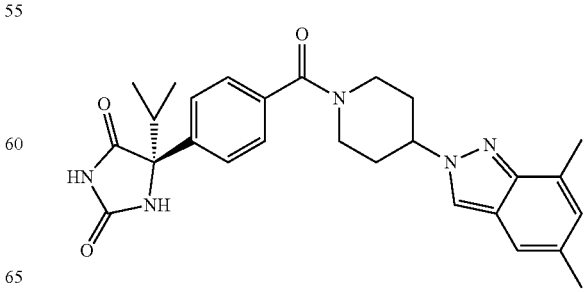

To a mixture of 4-((R)-4-isopropyl-2,5-dioxoimidazolidin-4-yl)benzoic acid (52 mg) described in Preparation Example 45, 5,7-dimethyl-2-piperidin-4-yl-2H-indazole.hydrochloride (50 mg) described in Preparation Example 96, 1-hydroxybenzotriazole (31 mg), 1-ethyl-3-(3'-dimethylaminopropyl)carbodiimide. hydrochloride (43 mg) and chloroform (1 mL) was added triethylamine (0.058 mL) and the mixture was stirred at room temperature for 3.5 hr. To the reaction mixture was added saturated aqueous sodium hydrogen carbonate solution, and the mixture was filtered by a phase separator. The filtrate was concentrated under reduced pressure and the obtained residue was purified by column chromatography (chloroform:methanol) to give the title compound (51.2 mg).

MS(ESI) m/z: 474 (M+H)+

Example 272: Synthesis of (R)-5-{4-[4-(5,7-dimethylindazol-1-yl)piperidine-1-carbonyl]phenyl}-5-isopropylimidazolidine-2,4-dione

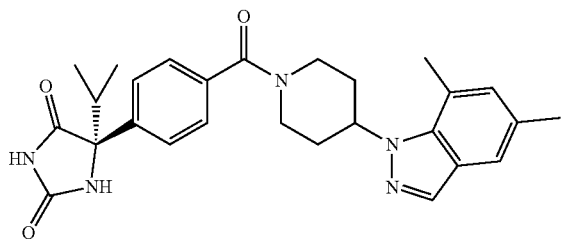 [SMILES: Cc1cc(C)c2c(cnn2C2CCN(C(=O)c3ccc([C@@]4(C(C)C)NC(=O)NC4=O)cc3)CC2)c1]

Using 4-((R)-4-isopropyl-2,5-dioxoimidazolidin-4-yl)benzoic acid (52 mg) described in Preparation Example 45 and 5,7-dimethyl-1-piperidin-4-yl-1H-indazole.hydrochloride (50 mg) described in Preparation Example 97, reactions and treatments similar to those in Example 271 were performed to give the title compound (73.4 mg).

MS(ESI) m/z: 474 (M+H)+

Example 273: Synthesis of (R)-5-{4-[4-(5,7-dimethylindazol-2-yl)piperidine-1-carbonyl]phenyl}-5-methylimidazolidine-2,4-dione

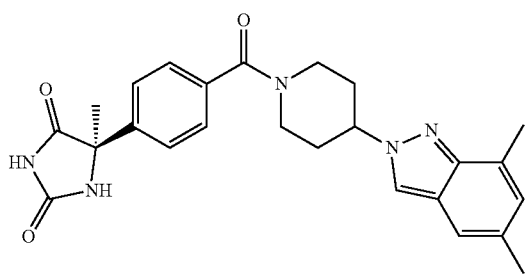 [SMILES: Cc1cc(C)c2nn(C3CCN(C(=O)c4ccc([C@@]5(C)NC(=O)NC5=O)cc4)CC3)cc2c1]

Using 4-((R)-4-methyl-2,5-dioxoimidazolidin-4-yl)benzoic acid (46 mg) described in Preparation Example 6 and 5,7-dimethyl-2-piperidin-4-yl-2H-indazole.hydrochloride (50 mg) described in Preparation Example 96, reactions and treatments similar to those in Example 271 were performed to give the title compound (43.3 mg).

MS(ESI) m/z: 446 (M+H)+

Example 274: Synthesis of (R)-5-{4-[4-(5,7-dimethylindazol-1-yl)piperidine-1-carbonyl]phenyl}-5-methylimidazolidine-2,4-dione

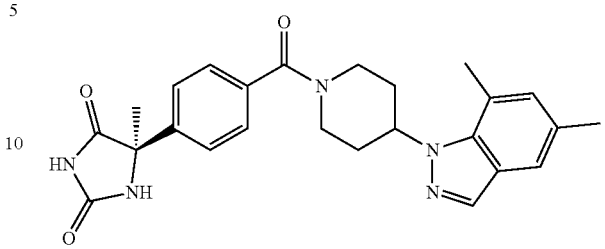

Using 4-((R)-4-methyl-2,5-dioxoimidazolidin-4-yl)benzoic acid (46 mg) described in Preparation Example 6 and 5,7-dimethyl-1-piperidin-4-yl-1H-indazole.hydrochloride (50 mg) described in Preparation Example 97, reactions and treatments similar to those in Example 271 were performed to give the title compound (59.3 mg).

MS(ESI) m/z: 446 (M+H)+

Example 275: Synthesis of (R)-5-{4-[4-(4,6-dimethyl-1H-indazol-3-yl)piperidine-1-carbonyl]phenyl}-5-isopropylimidazolidine-2,4-dione

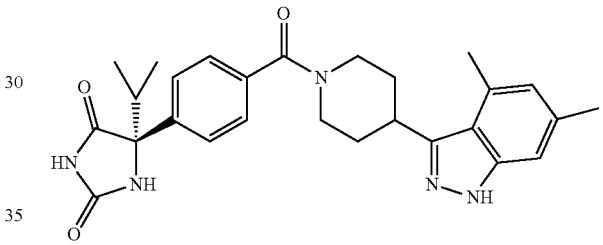

A mixture of 4-((R)-4-isopropyl-2,5-dioxoimidazolidin-4-yl)benzoic acid (14.4 mg) described in Preparation Example 45, 4,6-dimethyl-3-piperidin-4-yl-1H-indazole (12 mg) described in Preparation Example 98, 1-hydroxybenzotriazole (8.5 mg), 1-ethyl-3-(3'-dimethylaminopropyl)carbodiimide.hydrochloride (12 mg), triethylamine (0.01 mL) and chloroform (0.2 mL) was stirred at room temperature for 6 hr. To the reaction mixture was added saturated aqueous sodium hydrogen carbonate solution, and the mixture was filtered by a phase separator. The filtrate was concentrated under reduced pressure and the obtained residue was purified by column chromatography (chloroform:methanol) to give the title compound (18.0 mg).

MS(ESI) m/z: 474 (M+H)+

Example 276: Synthesis of (R)-5-{4-[4-(4,6-dimethyl-1H-indazol-3-yl)piperidine-1-carbonyl]phenyl}-5-methyl-imidazolidine-2,4-dione

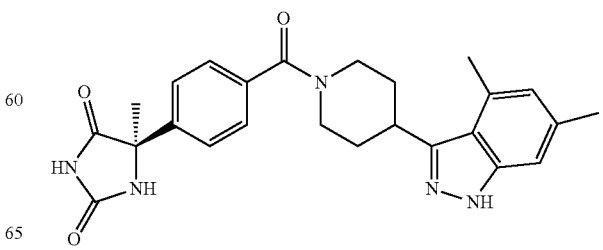

To a mixture of 4-((R)-4-methyl-2,5-dioxoimidazolidin-4-yl)benzoic acid (46 mg) described in Preparation Example 6, 4,6-dimethyl-3-piperidin-4-yl-1H-indazole (50 mg) described in Preparation Example 98, 1-hydroxybenzotriazole (31 mg), 1-ethyl-3-(3'-dimethylaminopropyl)carbodiimide.hydrochloride (43 mg), chloroform (1 mL) was added triethylamine (0.029 mL) and the mixture was stirred at room temperature overnight. To the reaction mixture was added saturated aqueous sodium hydrogen carbonate solution, and the mixture was filtered by a phase separator. The filtrate was concentrated under reduced pressure and the obtained residue was purified by column chromatography (chloroform:methanol) to give the title compound (72.3 mg).

MS(ESI) m/z: 446 (M+H)$^+$

Example 277: Synthesis of (R)-5-isopropyl-5-{4-[4-(1,4,6-trimethyl-1H-indazol-3-yl)piperidine-1-carbonyl]phenyl}imidazolidine-2,4-dione

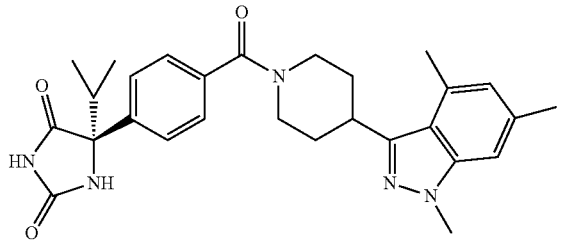 [SMILES: Cc1cc(C)c2c(C3CCN(C(=O)c4ccc([C@@]5(C(C)C)NC(=O)NC5=O)cc4)CC3)nn(C)c2c1]

A mixture of 4-((R)-4-isopropyl-2,5-dioxoimidazolidin-4-yl)benzoic acid (52.2 mg) described in Preparation Example 45, 1,4,6-trimethyl-3-piperidin-4-yl-1H-indazole.hydrochloride (60 mg) described in Preparation Example 99, 1-hydroxybenzotriazole (30.8 mg), 1-ethyl-3-(3'-dimethylaminopropyl)carbodiimide. hydrochloride (43.6 mg), triethylamine (0.085 mL) and chloroform (1.2 mL) was stirred at room temperature for 3 hr. To the reaction mixture was added saturated aqueous sodium hydrogen carbonate solution, and the mixture was filtered by a phase separator. The filtrate was concentrated under reduced pressure and the obtained residue was purified by column chromatography (chloroform:methanol) to give the title compound (50.9 mg).

MS (ESI) m/z: 488 (M+H)$^+$

Example 278: Synthesis of (R)-5-methyl-5-{4-[4-(1,4,6-trimethyl-1H-indazol-3-yl)piperidine-1-carbonyl]phenyl}imidazolidine-2,4-dione

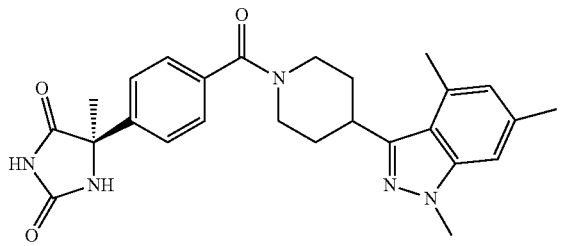 [SMILES: Cc1cc(F)c2c(C3CCN(C(=O)c4ccc([C@@]5(C)NC(=O)NC5=O)cc4)CC3)n[nH]c2c1]

Using 4-((R)-4-methyl-2,5-dioxoimidazolidin-4-yl)benzoic acid (46.7 mg) described in Preparation Example 6 and 1,4,6-trimethyl-3-piperidin-4-yl-1H-indazole.hydrochloride (60 mg) described in Preparation Example 99, reactions and treatments similar to those in Example 277 were performed to give the title compound (49 mg).

MS(ESI) m/z: 460 (M+H)$^+$

Example 279: Synthesis of (R)-5-{4-[4-(5-chlorobenzothiazol-2-yl)piperidine-1-carbonyl]phenyl}-5-methylimidazolidine-2,4-dione

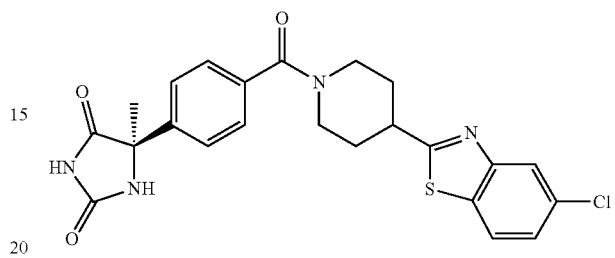

A mixture of 4-((R)-4-methyl-2,5-dioxoimidazolidin-4-yl)benzoic acid (50 mg) described in Preparation Example 6, 5-chloro-2-piperidin-4-yl-1,3-benzothiazole (51 mg), 1-hydroxybenzotriazole (33 mg), 1-ethyl-3-(3'-dimethylaminopropyl)carbodiimide.hydrochloride (47 mg), triethylamine (0.037 mL) and chloroform (1 mL) was stirred at room temperature for 5 hr. To the reaction mixture was added saturated aqueous sodium hydrogen carbonate solution, and the mixture was filtered by a phase separator. The filtrate was concentrated under reduced pressure and the obtained residue was purified by column chromatography (chloroform:methanol) to give the title compound (49.7 mg).

MS(ESI) m/z: 469 (M+H)$^+$

Example 280: Synthesis of (R)-5-{4-[4-(4-fluoro-6-methyl-1H-indazol-3-yl)piperidine-1-carbonyl]phenyl}-5-methylimidazolidine-2,4-dione

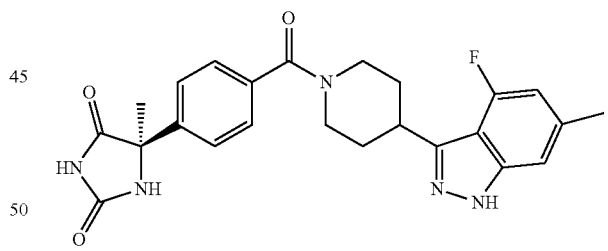

To a mixture of 4-((R)-4-methyl-2,5-dioxoimidazolidin-4-yl)benzoic acid (28 mg) described in Preparation Example 6, 4-fluoro-6-methyl-3-piperidin-4-yl-1H-indazole (32 mg) described in Preparation Example 100, 1-hydroxybenzotriazole (18 mg), 1-ethyl-3-(3'-dimethylaminopropyl)carbodiimide.hydrochloride (26 mg) and chloroform (1 mL) was added triethylamine (0.034 mL) and the mixture was stirred at room temperature for 5 hr. To the reaction mixture was added saturated aqueous sodium hydrogen carbonate solution, and the mixture was filtered by a phase separator. The filtrate was concentrated under reduced pressure and the obtained residue was purified by column chromatography (chloroform:methanol) to give the title compound (18 mg).

MS (ESI) m/z: 450 (M+H)$^+$

Example 281: Synthesis of (R)-5-methyl-5-{4-[4-(5-p-toluyl-1H-pyrazol-3-yl)piperidine-1-carbonyl]phenyl}imidazolidine-2,4-dione

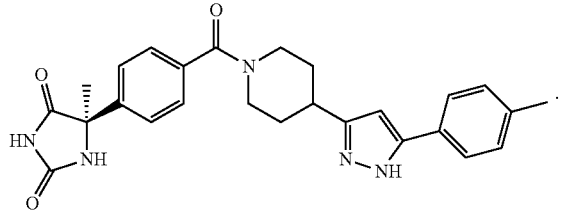 [SMILES: Cc1ccc(-c2cc(C3CCN(C(=O)c4ccc([C@@]5(C)NC(=O)NC5=O)cc4)CC3)n[nH]2)cc1]

A mixture of 4-((R)-4-methyl-2,5-dioxoimidazolidin-4-yl)benzoic acid (102 mg) described in Preparation Example 6, 4-(5-p-tolyl-1H-pyrazol-3-yl)piperidine (96 mg) described in Preparation Example 77, 1-hydroxybenzotriazole (67 mg), 1-ethyl-3-(3'-dimethylaminopropyl)carbodiimide.hydrochloride (96 mg), triethylamine (69 μL) and chloroform (1 mL) was stirred at room temperature overnight. To the reaction mixture were added saturated aqueous sodium hydrogen carbonate solution and chloroform, and the mixture was decanted. The precipitate was washed with water, ethanol was added, and the obtained ethanol solution was concentrated under reduced pressure. The organic layer of the supernatant was also concentrated under reduced pressure. The obtained residue was combined, and the mixture was purified by column chromatography (chloroform:methanol) to give the title compound (125 mg).

MS(ESI) m/z: 458 (M+H)+

Example 282: Synthesis of (R)-5-{4-[4-(2,3-dimethylphenyl)piperazine-1-carbonyl]phenyl}-5-isopropylimidazolidine-2,4-dione

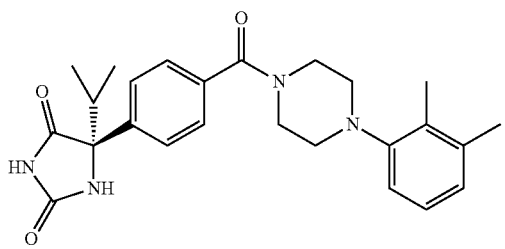 [SMILES: Cc1cccc(N2CCN(C(=O)c3ccc([C@@]4(C(C)C)NC(=O)NC4=O)cc3)CC2)c1C]

To 4-((R)-4-isopropyl-2,5-dioxo-imidazolidin-4-yl)benzoic acid (76 mg) described in Preparation Example 45 were added 1-(2,3-dimethylphenyl)piperazine.hydrochloride (63.5 mg), 1-hydroxybenzotriazole (37.3 mg), 1-ethyl-3-(3'-dimethylaminopropyl)carbodiimide.hydrochloride (52.9 mg), triethylamine (39 μL) and N,N-dimethylformamide (1 mL) and the mixture was stirred at room temperature for 3 hr. To the reaction mixture was added saturated brine and the mixture was extracted with ethyl acetate. The organic layer was concentrated under reduced pressure and the obtained residue was purified by column chromatography (hexane:ethyl acetate) to give the title compound (94 mg).

MS(APCI) m/z: 435 (M+H)+

Example 283: Synthesis of (R)-5-{4-[4-(3,4-dimethylphenyl)piperazine-1-carbonyl]phenyl}-5-isopropylimidazolidine-2,4-dione

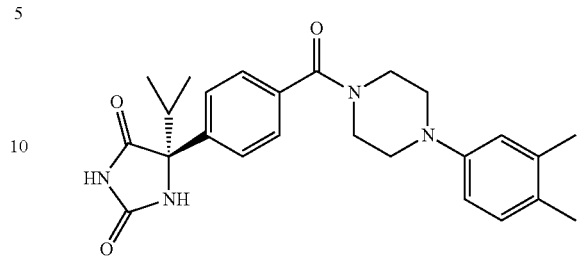

To 4-((R)-4-isopropyl-2,5-dioxo-imidazolidin-4-yl)benzoic acid (76 mg) described in Preparation Example 45 were added 1-(3,4-dimethylphenyl)piperazine (53.3 mg), 1-hydroxybenzotriazole (37.3 mg), 1-ethyl-3-(3'-dimethylaminopropyl)carbodiimide.hydrochloride (52.9 mg) and N,N-dimethylformamide (1 mL) and the mixture was stirred at room temperature for 3 hr. To the reaction mixture was added saturated brine and the mixture was extracted with ethyl acetate. The organic layer was concentrated under reduced pressure and the obtained residue was purified by column chromatography (hexane:ethyl acetate) to give the title compound (91 mg).

MS (APCI) m/z: 435 (M+H)+

Example 284: Synthesis of (R)-5-isopropyl-5-{4-[4-(3-methylpyridin-2-yl)piperazine-1-carbonyl]phenyl}imidazolidine-2,4-dione

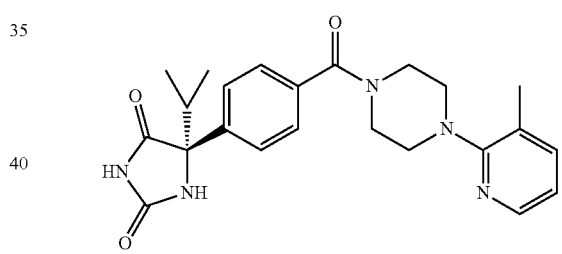

Using 4-((R)-4-isopropyl-2,5-dioxo-imidazolidin-4-yl)benzoic acid (76 mg) described in Preparation Example 45 and 1-(3-methylpyridin-2-yl)piperazine (49.6 mg), reactions and treatments similar to those in Example 283 were performed to give the title compound (83 mg).

MS(APCI) m/z: 422 (M+H)+

Example 285: Synthesis of (R)-5-{4-[4-(2,6-dimethylphenyl)piperazine-1-carbonyl]phenyl}-5-isopropylimidazolidine-2,4-dione

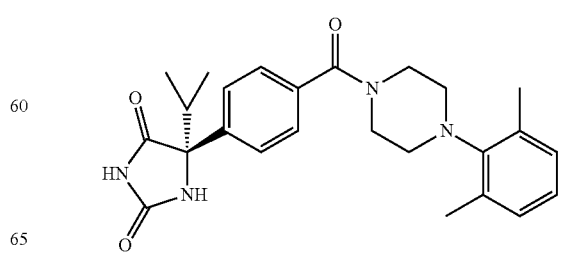

Using 4-((R)-4-isopropyl-2,5-dioxo-imidazolidin-4-yl)benzoic acid (79 mg) described in Preparation Example 45 and 1-(2,6-dimethylphenyl)piperazine (68.9 mg), reactions and treatments similar to those in Example 283 were performed to give the title compound (68 mg).

MS(ESI) m/z: 435 (M+H)+

Example 286: Synthesis of 5-{4-[4-(2,4-dimethylphenyl)piperazine-1-carbonyl]phenyl}-5-propylimidazolidine-2,4-dione

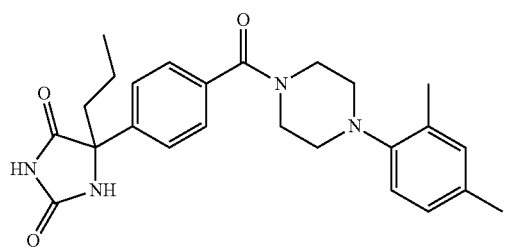 [SMILES: CCCC1(c2ccc(C(=O)N3CCN(c4ccc(C)cc4C)CC3)cc2)NC(=O)NC1=O]

To 4-(2,5-dioxo-4-propylimidazolidin-4-yl)benzoic acid (200 mg) described in Preparation Example 16 were added 1-(2,4-dimethylphenyl)piperazine (145 mg), 1-ethyl-3-(3'-dimethylaminopropyl)carbodiimide.hydrochloride (176 mg), 1-hydroxybenzotriazole.1 hydrate (103 mg), N,N-dimethylformamide (5 mL) and triethylamine (0.213 mL) and the mixture was stirred at room temperature overnight. The reaction mixture was concentrated under reduced pressure, to the obtained residue was added water, and the mixture was extracted with chloroform. The obtained organic layer was washed with saturated brine and dried over anhydrous sodium sulfate. The solvent was evaporated under reduced pressure and the obtained residue was purified by column chromatography (chloroform:methanol) to give the title compound (241 mg).

MS(ESI) m/z: 435 (M+H)+

Example 287: Synthesis of 5-propyl-5-{4-[4-(3,5,6-trimethylpyridin-2-yl)piperazine-1-carbonyl]phenyl}imidazolidine-2,4-dione

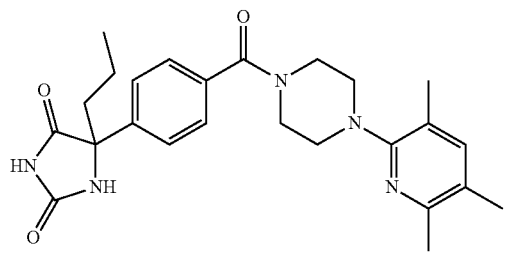 [SMILES: CCCC1(c2ccc(C(=O)N3CCN(c4nc(C)c(C)cc4C)CC3)cc2)NC(=O)NC1=O]

Using 4-(2,5-dioxo-4-propylimidazolidin-4-yl)benzoic acid (200 mg) described in Preparation Example 16 and 1-(3,5,6-trimethylpyridin-2-yl)piperazine (157 mg), reactions and treatments similar to those in Example 286 were performed to give the title compound (163 mg).

MS(ESI) m/z: 450 (M+H)+

Example 288: Synthesis of 5-{4-[4-(3,5-dicyclopropylpyridin-2-yl)piperazine-1-carbonyl]phenyl}-5-propylimidazolidine-2,4-dione

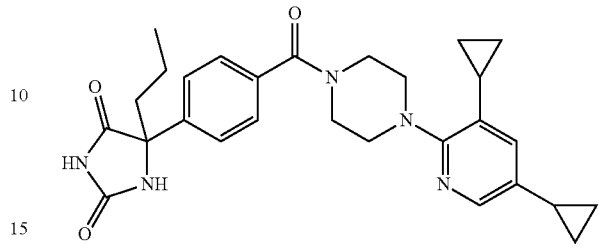

To 4-(2,5-dioxo-4-propylimidazolidin-4-yl)benzoic acid (200 mg) described in Preparation Example 16 were added 1-(3,5-dicyclopropylpyridin-2-yl)piperazine.2 hydrochloride (213 mg) described in Preparation Example 147, 1-ethyl-3-(3'-dimethylaminopropyl)carbodiimide.hydrochloride (176 mg), 1-hydroxybenzotriazole.1 hydrate (103 mg), N,N-dimethylformamide (5 mL) and triethylamine (0.426 mL) and the mixture was stirred at room temperature overnight. The reaction mixture was concentrated under reduced pressure, to the obtained residue was added water, and the mixture was extracted with chloroform. The obtained organic layer was dried over anhydrous sodium sulfate and concentrated under reduced pressure. The obtained residue was purified by column chromatography (chloroform:methanol) to give the title compound (157 mg).

MS(ESI) m/z: 488 (M+H)+

Example 289: Synthesis of 5-{4-[4-(5-cyclopropyl-3-methylpyridin-2-yl)piperazine-1-carbonyl]phenyl}-5-propylimidazolidine-2,4-dione

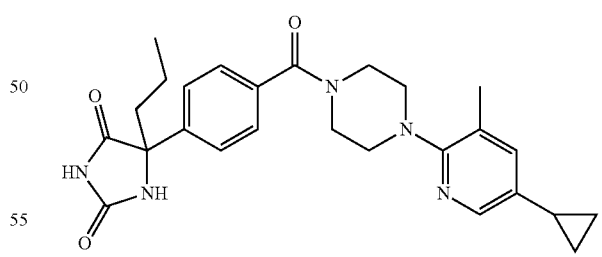

Using 4-(2,5-dioxo-4-propylimidazolidin-4-yl)benzoic acid (100 mg) described in Preparation Example 16 and 1-(5-cyclopropyl-3-methylpyridin-2-yl)piperazine (83 mg), reactions and treatments similar to those in Example 286 were performed to give the title compound (132 mg).

MS(ESI) m/z: 462 (M+H)+

Example 290: Synthesis of 5-{4-[4-(5-ethyl-3-methylpyridin-2-yl)piperazine-1-carbonyl]phenyl}-5-propylimidazolidine-2,4-dione

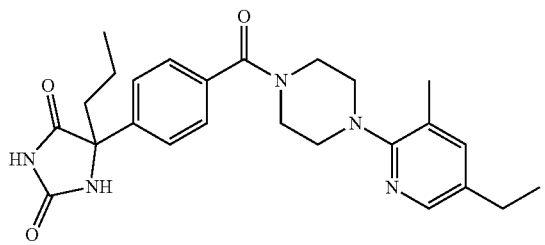 [SMILES: CCCC1(c2ccc(C(=O)N3CCN(c4ncc(CC)cc4C)CC3)cc2)NC(=O)NC1=O]

Using 4-(2,5-dioxo-4-propylimidazolidin-4-yl)benzoic acid (100 mg) described in Preparation Example 16 and 1-(5-ethyl-3-methylpyridin-2-yl)piperazine (79 mg), reactions and treatments similar to those in Example 286 were performed to give the title compound (131 mg).
MS(ESI) m/z: 450 (M+H)+

Example 291: Synthesis of 3-{4-[4-(3,5-dimethylpyridin-2-yl) piperazine-1-carbonyl]phenyl}-3-methylpyrrolidine-2,5-dione

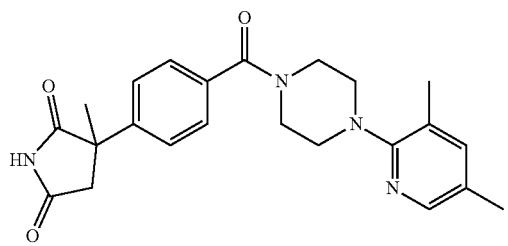 [SMILES: Cc1cnc(N2CCN(C(=O)c3ccc(C4(C)CC(=O)NC4=O)cc3)CC2)c(C)c1]

To 4-(3-methyl-2,5-dioxopyrrolidin-3-yl)benzoic acid (209 mg) described in Preparation Example 41 were added 1-(3,5-dimethylpyridin-2-yl)piperazine (256 mg), 1-ethyl-3-(3'-dimethylaminopropyl)carbodiimide.hydrochloride (257 mg), 1-hydroxybenzotriazole.1 hydrate (181 mg), N,N-dimethylformamide (10 mL) and triethylamine (0.375 mL) and the mixture was stirred at room temperature overnight. Water was added to the reaction mixture and the mixture was extracted with chloroform. The obtained organic layer was washed with saturated brine and dried over anhydrous sodium sulfate. The solvent was evaporated under reduced pressure and the obtained residue was purified by column chromatography (hexane:ethyl acetate) to give the title compound (183 mg).
MS(ESI) m/z: 407 (M+H)+

Example 292: Synthesis of 5-{4-[4-(3,5-dimethylpyridin-2-yl)piperazine-1-carbonyl]-3-fluorophenyl}-5-propylimidazolidine-2,4-dione

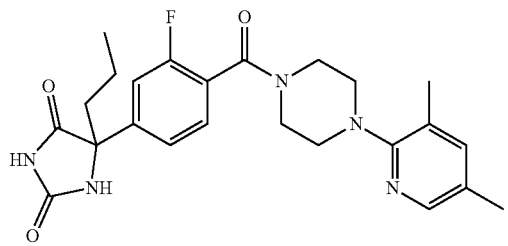 [SMILES: CCCC1(c2ccc(C(=O)N3CCN(c4ncc(C)cc4C)CC3)c(F)c2)NC(=O)NC1=O]

To 4-(2,5-dioxo-4-propylimidazolidin-4-yl)-2-fluorobenzoic acid (100 mg) described in Preparation Example 17 were added 1-(3,5-dimethylpyridin-2-yl)piperazine (68.3 mg), 1-ethyl-3-(3'-dimethylaminopropyl)carbodiimide.hydrochloride (82.1 mg), 1-hydroxybenzotriazole.1 hydrate (48.2 mg), N,N-dimethylformamide (5 mL) and triethylamine (0.1 mL) and the mixture was stirred at room temperature overnight. The reaction mixture was concentrated under reduced pressure and the obtained residue was purified by column chromatography (chloroform:methanol) to give the title compound (136 mg).
MS(ESI) m/z: 454 (M+H)+

Example 293: Synthesis of 5-{4-[4-(5-cyclopropyl-3-methylpyridin-2-yl)piperazine-1-carbonyl]-3-fluorophenyl}-5-propylimidazolidine-2,4-dione

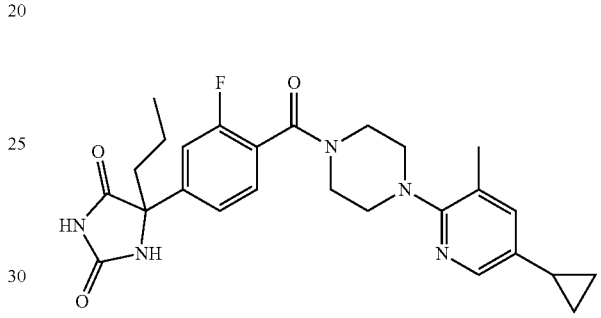

Using 4-(2,5-dioxo-4-propylimidazolidin-4-yl)-2-fluorobenzoic acid (100 mg) described in Preparation Example 17 and 1-(5-cyclopropyl-3-methylpyridin-2-yl)piperazine (77.6 mg), reactions and treatments similar to those in Example 292 were performed to give the title compound (143 mg).
MS(ESI) m/z: 480 (M+H)+

Example 294: Synthesis of 5-{3-fluoro-4-[4-(3,5,6-trimethylpyridin-2-yl)piperazine-1-carbonyl]phenyl}-5-propylimidazolidine-2,4-dione

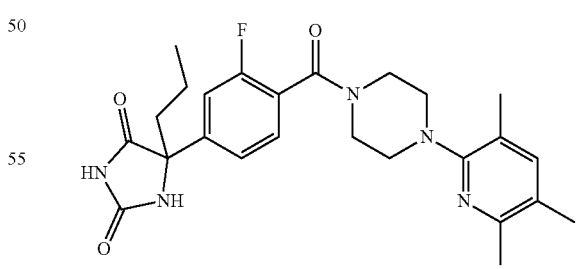

Using 4-(2,5-dioxo-4-propylimidazolidin-4-yl)-2-fluorobenzoic acid (100 mg) described in Preparation Example 17 and 1-(3,5,6-trimethylpyridin-2-yl)piperazine (73.3 mg), reactions and treatments similar to those in Example 292 were performed to give the title compound (79 mg).
MS(ESI) m/z: 468 (M+H)+

Example 295: Synthesis of (R)-5-propyl-5-{4-[4-(3,5,6-trimethylpyridin-2-yl)piperazine-1-carbonyl]phenyl}imidazolidine-2,4-dione and (S)-5-propyl-5-{4-[4-(3,5,6-trimethylpyridin-2-yl)piperazine-1-carbonyl]phenyl}imidazolidine-2,4-dione

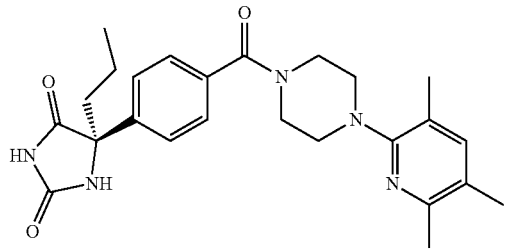

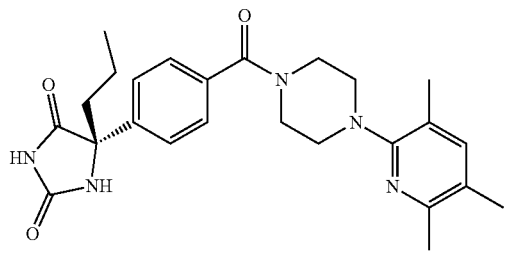 [SMILES: CCCC1(c2ccc(C(=O)N3CCN(c4nc(C)c(C)cc4C)CC3)c(F)c2)NC(=O)NC1=O]

5-Propyl-5-{4-[4-(3,5,6-trimethylpyridin-2-yl)piperazine-1-carbonyl]phenyl}imidazolidine-2,4-dione (122 mg, see Example 287) was separated by moderate-pressure column using CHIRALFLASH (Daicel) IC (hexane/ethanol/diethylamine) to give the both enantiomers indicated above (compound with short retention time 28 mg (MS(ESI) m/z: 450 (M+H)$^+$) and compound with long retention time 32 mg (MS(ESI) m/z: 450 (M+H)$^+$)).

In the analysis using CHIRALPAK (Daicel) IC-3 (4.6 mm×150 mm, hexane/ethanol/diethylamine=10/90/0.1, flow 0.5 mL/min), the retention time was respectively 7.9 min and 13.9 min.

Example 296: Synthesis of (R)-5-{4-[4-(3,5-dimethylpyridin-2-yl)piperazine-1-carbonyl]phenyl}-5-propylimidazolidine-2,4-dione and (S)-5-{4-[4-(3,5-dimethylpyridin-2-yl)piperazine-1-carbonyl]phenyl}-5-propylimidazolidine-2,4-dione

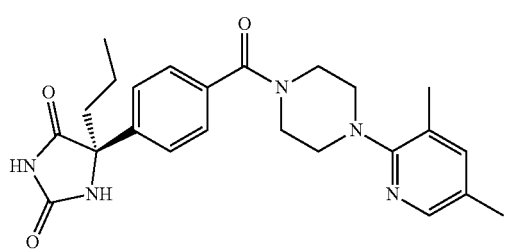

-continued

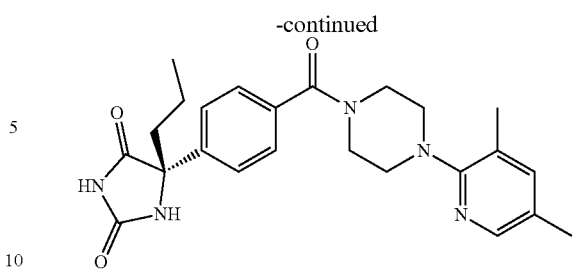

To 4-(2,5-dioxo-4-propylimidazolidin-4-yl)benzoic acid (400 mg) described in Preparation Example 16 were added 1-(3,5-dimethylpyridin-2-yl)piperazine (293 mg), 1-ethyl-3-(3'-dimethylaminopropyl)carbodiimide.hydrochloride (353 mg), 1-hydroxybenzotriazole.1 hydrate (207 mg), N,N-dimethylformamide (10 mL) and triethylamine (0.43 mL) and the mixture was stirred at room temperature overnight. The reaction mixture was concentrated under reduced pressure, water was added to the obtained residue and the mixture was extracted with ethyl acetate. The obtained organic layer was washed with saturated brine and dried over anhydrous sodium sulfate. The solvent was evaporated under reduced pressure and the obtained residue was purified by column chromatography (chloroform:methanol) to give 5-{4-[4-(3,5-dimethylpyridin-2-yl)piperazine-1-carbonyl]phenyl}-5-propylimidazolidine-2,4-dione (484 mg).

The obtained 5-{4-[4-(3,5-dimethylpyridin-2-yl)piperazine-1-carbonyl]phenyl}-5-propylimidazolidine-2,4-dione (300 mg) was separated by moderate-pressure column using CHIRALFLASH (Daicel) IC (hexane/ethanol/diethylamine) to give the both enantiomers indicated above (compound with short retention time 149 mg (MS(ESI) m/z: 436 (M+H)$^+$) and compound with long retention time 143 mg (MS(ESI) m/z: 436 (M+H)$^+$)).

In the analysis using CHIRALPAK (Daicel) IC-3 (4.6 mm×150 mm, hexane/ethanol/diethylamine=10/90/0.1, flow 0.5 mL/min), the retention time was respectively 8.8 min and 16.6 min.

Example 297: Synthesis of 5-{4-[4-(3,5-dimethylpyridin-2-yl)piperazine-1-carbonyl]-2-fluorophenyl}-5-propylimidazolidine-2,4-dione

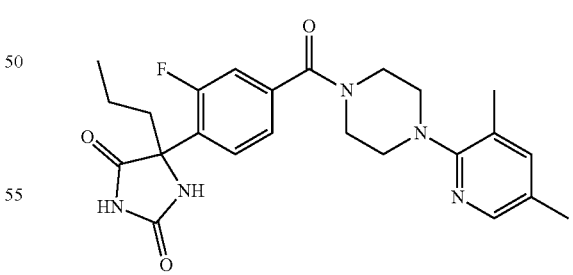

To 4-(2,5-dioxo-4-propylimidazolidin-4-yl)-3-fluorobenzoic acid (120 mg) described in Preparation Example 30 were added 1-(3,5-dimethylpyridin-2-yl)piperazine (90 mg), 1-ethyl-3-(3'-dimethylaminopropyl)carbodiimide.hydrochloride (90.3 mg), 1-hydroxybenzotriazole.1 hydrate (63.6 mg), N,N-dimethylformamide (5 mL) and triethylamine (0.12 mL) and the mixture was stirred at room temperature overnight. The reaction mixture was concentrated under reduced pressure and the obtained residue was purified by column chromatography (chloroform:methanol) to give the title compound (166 mg).

MS(ESI) m/z: 454 (M+H)⁺

Example 298: Synthesis of 5-{4-[4-(5-cyclopropyl-3-methylpyridin-2-yl) piperazine-1-carbonyl]-2-fluorophenyl}-5-propylimidazolidine-2,4-dione

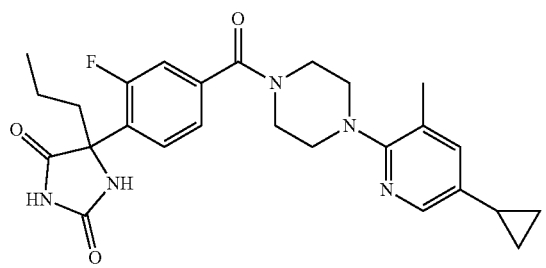 [SMILES: CCCC1(c2ccc(C(=O)N3CCN(c4ncc(C5CC5)cc4C)CC3)cc2F)NC(=O)NC1=O]

Using 4-(2,5-dioxo-4-propylimidazolidin-4-yl)-3-fluorobenzoic acid (120 mg) described in Preparation Example 30 and 1-(5-cyclopropyl-3-methylpyridin-2-yl)piperazine (102 mg), reactions and treatments similar to those in Example 297 were performed to give the title compound (174 mg).

MS(ESI) m/z: 480 (M+H)⁺

Example 299: Synthesis of 5-{2-fluoro-4-[4-(3,5,6-trimethylpyridin-2-yl)piperazine-1-carbonyl]phenyl}-5-propylimidazolidine-2,4-dione

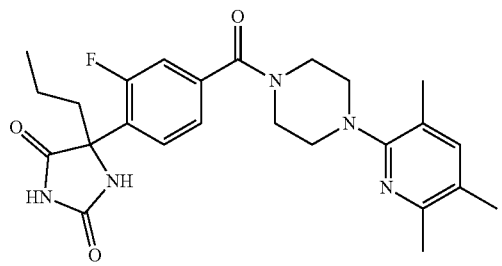 [SMILES: CCCC1(c2ccc(C(=O)N3CCN(c4nc(C)c(C)cc4C)CC3)cc2F)NC(=O)NC1=O]

To 4-(2,5-dioxo-4-propylimidazolidin-4-yl)-3-fluorobenzoic acid (101 mg) described in Preparation Example 30 were added 1-(3,5,6-trimethylpyridin-2-yl)piperazine (96.7 mg), 1-ethyl-3-(3'-dimethylaminopropyl)carbodiimide.hydrochloride (90 mg), 1-hydroxybenzotriazole.1 hydrate (63.6 mg), N,N-dimethylformamide (5 mL) and triethylamine (0.12 mL) and the mixture was stirred at room temperature overnight. The reaction mixture was concentrated under reduced pressure and the obtained residue was purified by column chromatography (chloroform:methanol) to give the title compound (130 mg).

MS(ESI) m/z: 468 (M+H)⁺

Example 300: Synthesis of 5-cyclopropyl-5-{4-[4-(5-cyclopropyl-3-methylpyridin-2-yl)piperazine-1-carbonyl]-3-fluorophenyl}imidazolidine-2,4-dione

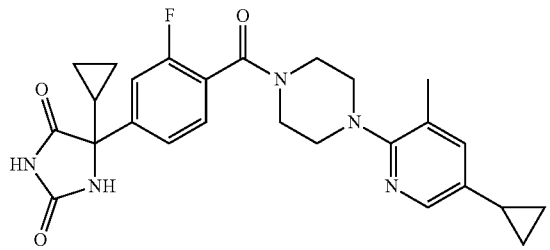 [SMILES: Cc1cc(C2CC2)cnc1N1CCN(C(=O)c2ccc(C3(C4CC4)NC(=O)NC3=O)cc2F)CC1]

Using 4-(4-cyclopropyl-2,5-dioxoimidazolidin-4-yl)-2-fluorobenzoic acid (150 mg) described in Preparation Example 34 and 1-(5-cyclopropyl-3-methylpyridin-2-yl) piperazine (129 mg), reactions and treatments similar to those in Example 297 were performed to give the title compound (207 mg).

MS(ESI) m/z: 478 (M+H)⁺

Example 301: Synthesis of 5-cyclopropyl-5-{3-fluoro-4-[4-(3,5,6-trimethylpyridin-2-yl)piperazine-1-carbonyl]phenyl}imidazolidine-2,4-dione

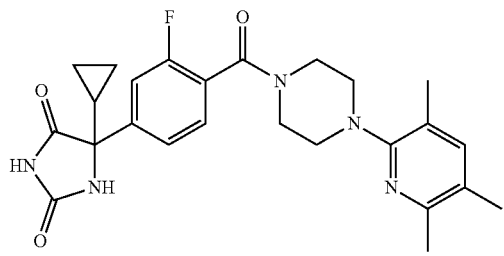 [SMILES: Cc1cc(C)c(N2CCN(C(=O)c3ccc(C4(C5CC5)NC(=O)NC4=O)cc3F)CC2)nc1C]

Using 4-(4-cyclopropyl-2,5-dioxoimidazolidin-4-yl)-2-fluorobenzoic acid (150 mg) described in Preparation Example 34 and 1-(3,5,6-trimethylpyridin-2-yl)piperazine (122 mg), reactions and treatments similar to those in Example 297 were performed to give the title compound (205 mg).

MS(ESI) m/z: 466 (M+H)⁺

Example 302: Synthesis of 3-{4-[4-(5-cyclopropyl-3-methylpyridin-2-yl)piperazine-1-carbonyl]phenyl}-3-methylpyrrolidine-2,5-dione

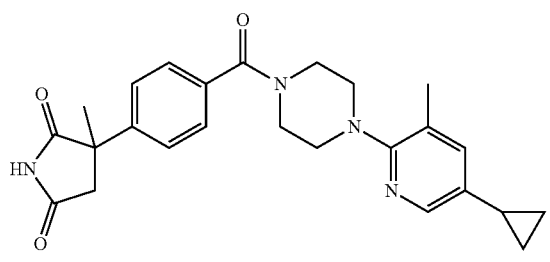 [SMILES: Cc1cc(C2CC2)cnc1N1CCN(C(=O)c2ccc(C3(C)CC(=O)NC3=O)cc2)CC1]

Using 4-(3-methyl-2,5-dioxopyrrolidin-3-yl)benzoic acid (150 mg) described in Preparation Example 41 and 1-(5-cyclopropyl-3-methylpyridin-2-yl)piperazine.hydrochloride (245 mg), reactions and treatments similar to those in Example 291 were performed to give the title compound (151 mg).

MS(ESI) m/z: 433 (M+H)⁺

Example 303: Synthesis of 3-methyl-3-{4-[4-(3,5,6-trimethylpyridin-2-yl)piperazine-1-carbonyl]phenyl}pyrrolidine-2,5-dione

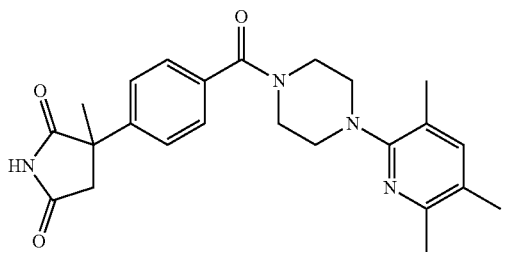 [SMILES: Cc1cc(C)c(N2CCN(C(=O)c3ccc(C4(C)CC(=O)NC4=O)cc3)CC2)nc1C]

Using 4-(3-methyl-2,5-dioxopyrrolidin-3-yl)benzoic acid (150 mg) described in Preparation Example 41 and 1-(3,5,6-trimethylpyridin-2-yl)piperazine (198 mg), reactions and treatments similar to those in Example 291 were performed to give the title compound (134 mg).

MS(ESI) m/z: 421 (M+H)⁺

Example 304: Synthesis of 5-cyclopropyl-5-{4-[4-(3,5-dimethylpyridin-2-yl)piperazine-1-carbonyl]-3-fluorophenyl}imidazolidine-2,4-dione

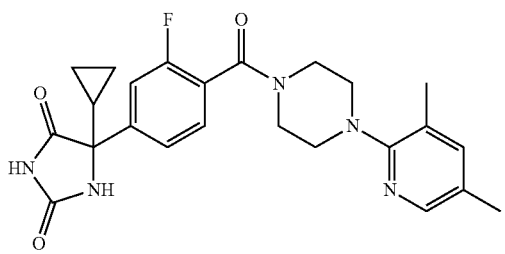 [SMILES: Cc1cnc(N2CCN(C(=O)c3ccc(C4(C5CC5)NC(=O)NC4=O)cc3F)CC2)c(C)c1]

Using 4-(4-cyclopropyl-2,5-dioxoimidazolidin-4-yl)-2-fluorobenzoic acid (150 mg) described in Preparation Example 34 and 1-(3,5-dimethylpyridin-2-yl)piperazine (113 mg), reactions and treatments similar to those in Example 297 were performed to give the title compound (133 mg).

MS(ESI) m/z: 452 (M+H)⁺

Example 305: Synthesis of (R)-5-{4-[4-(5-cyclopropyl-3-methylpyridin-2-yl)piperazine-1-carbonyl]phenyl}-5-propylimidazolidine-2,4-dione and (S)-5-{4-[4-(5-cyclopropyl-3-methylpyridin-2-yl)piperazine-1-carbonyl]phenyl}-5-propylimidazolidine-2,4-dione

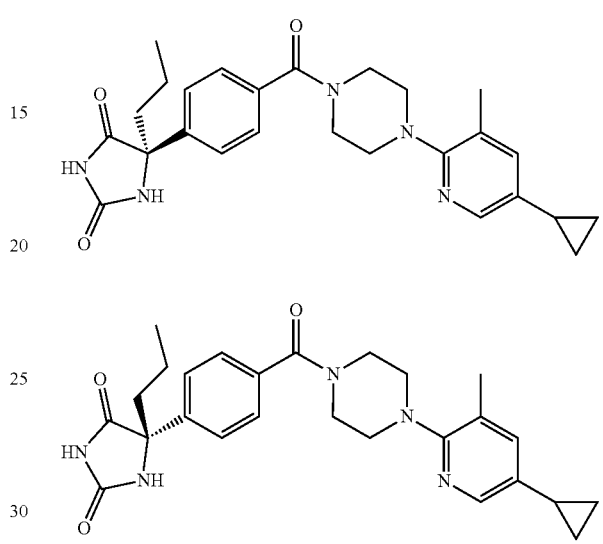

5-{4-[4-(5-Cyclopropyl-3-methylpyridin-2-yl)piperazine-1-carbonyl]phenyl}-5-propylimidazolidine-2,4-dione (90 mg, see Example 289) was separated by moderate-pressure column using CHIRALFLASH (Daicel) IC (ethanol/hexane/diethylamine) to give the both enantiomers indicated above (compound with short retention time 30 mg (MS(ESI) m/z: 462 (M+H)⁺) and compound with long retention time 32 mg (MS(ESI) m/z: 462 (M+H)⁺)).

In the analysis using CHIRALPAK (Daicel) IC-3 (4.6 mm×150 mm, ethanol/diethylamine=100/0.1, flow 0.5 mL/min), the retention time was respectively 8.5 min and 15.0 min.

Example 306: Synthesis of (R)-3-{4-[4-(3,5-dimethylpyridin-2-yl)piperazine-1-carbonyl]phenyl}-3-methylpyrrolidine-2,5-dione and (S)-3-{4-[4-(3,5-dimethylpyridin-2-yl)piperazine-1-carbonyl]phenyl}-3-methylpyrrolidine-2,5-dione

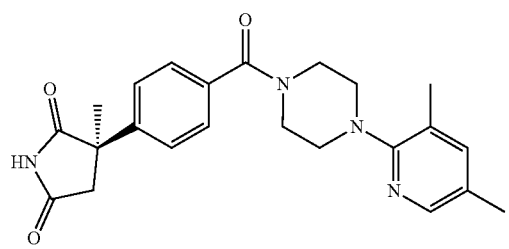

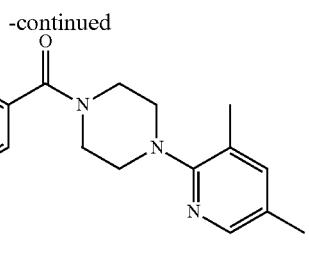

3-{4-[4-(3,5-Dimethylpyridin-2-yl)piperazine-1-carbonyl]phenyl}-3-methylpyrrolidine-2,5-dione (168 mg, see Example 291) was separated by HPLC using CHIRALPAK (Daicel) ID (tetrahydrofuran/ethanol/diethylamine) to give the both enantiomers indicated above (compound with short retention time 79.3 mg (MS(ESI) m/z: 407 (M+H)$^+$) and compound with long retention time 78.6 mg (MS(ESI) m/z: 407 (M+H)$^+$)).

In the analysis using CHIRALPAK (Daicel) ID-3 (4.6 mm×150 mm, tetrahydrofuran/ethanol/diethylamine=20/80/0.1, flow 0.5 mL/min), the retention time was respectively 7.6 min and 10.0 min.

Example 307: Synthesis of 3-{5-[4-(3,5-dimethylpyridin-2-yl)piperazine-1-carbonyl]pyridin-2-yl}-3-methylpyrrolidine-2,5-dione

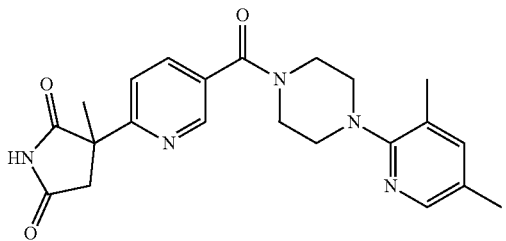

To 6-(3-methyl-2,5-dioxopyrrolidin-3-yl)nicotinic acid (40 mg) described in Preparation Example 50 were added 1-(3,5-dimethylpyridin-2-yl)piperazine (42.8 mg), 1-ethyl-3-(3'-dimethylaminopropyl)carbodiimide.hydrochloride (36 mg), 1-hydroxybenzotriazole.1 hydrate (25.4 mg), N,N-dimethylformamide (3 mL) and triethylamine (0.048 mL) and the mixture was stirred at room temperature overnight. The reaction mixture was concentrated under reduced pressure and the obtained residue was purified by column chromatography (chloroform:methanol) to give the title compound (58 mg).

MS(ESI) m/z: 408 (M+H)$^+$

Example 308: Synthesis of 3-{5-[4-(3,5-dimethylpyridin-2-yl)piperazine-1-carbonyl]pyridin-2-yl}-3-isopropylpyrrolidine-2,5-dione

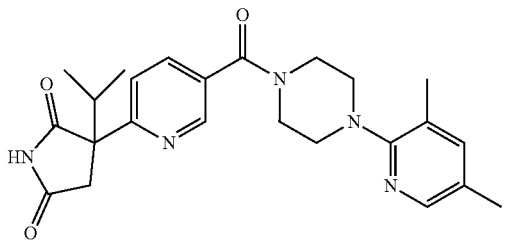

To 6-(3-isopropyl-2,5-dioxopyrrolidin-3-yl)nicotinic acid (52.7 mg) described in Preparation Example 52 were added 1-(3,5-dimethylpyridin-2-yl)piperazine (50.3 mg), 1-ethyl-3-(3'-dimethylaminopropyl) carbodiimide.hydrochloride (42.4 mg), 1-hydroxybenzotriazole.1 hydrate (30 mg), N,N-dimethylformamide (3 mL) and triethylamine (0.056 mL) and the mixture was stirred at room temperature overnight. The reaction mixture was concentrated under reduced pressure and the obtained residue was purified by column chromatography (chloroform:methanol) to give the title compound (75 mg).

MS(ESI) m/z: 436 (M+H)$^+$

Example 309: Synthesis of 5-[4-(4'-hydroxy-3,5-dimethyl-3',4',5',6'-tetrahydro-2'H-[2,4']bipyridinyl-1'-carbonyl)phenyl]-5-isopropylimidazolidine-2,4-dione

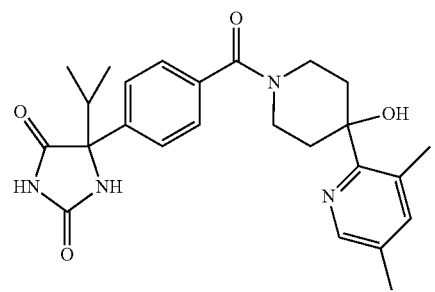 [SMILES: Cc1cnc(C2(O)CCN(C(=O)c3ccc(C4(C(C)C)NC(=O)NC4=O)cc3)CC2)c(C)c1]

4-((R)-4-isopropyl-2,5-dioxoimidazolidin-4-yl)benzoic acid (52.7 mg) described in Preparation Example 45, 3,5-dimethyl-2',3',5',6'-tetrahydro-1'H-[2,4']bipyridinyl-4'-ol.2 hydrochloride (58.9 mg) described in Preparation Example 74, 1-hydroxybenzotriazole.1 hydrate (28.5 mg), 1-ethyl-3-(3'-dimethylaminopropyl)carbodiimide.hydrochloride (40.5 mg) and triethylamine (0.084 mL) were dissolved in N,N-dimethylformamide (3 mL) and the mixture was stirred at room temperature overnight. The reaction mixture was concentrated under reduced pressure and the obtained residue was purified by column chromatography (chloroform:methanol) to give the title compound (74 mg).

MS(ESI) m/z: 451 (M+H)$^+$

Example 310: Synthesis of (R)-3-{5-[4-(3,5-dimethylpyridin-2-yl)piperazine-1-carbonyl]pyridin-2-yl}-3-methoxymethylpyrrolidine-2,5-dione and (S)-3-{5-[4-(3,5-dimethylpyridin-2-yl)piperazine-1-carbonyl]pyridin-2-yl}-3-methoxymethylpyrrolidine-2,5-dione

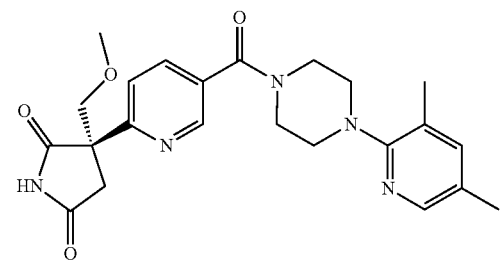

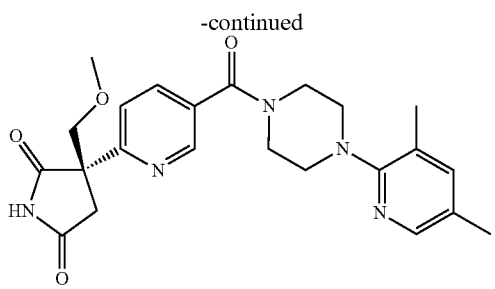

3-{5-[4-(3,5-Dimethylpyridin-2-yl)piperazine-1-carbonyl]pyridin-2-yl}-3-methoxymethylpyrrolidine-2,5-dione (397 mg, see Example 192) was separated by HPLC using CHIRALPAK (Daicel) IA (2-propanol/tetrahydrofuran/acetic acid) to give the both enantiomers indicated above (compound with short retention time 186 mg (MS(ESI) m/z: 438 (M+H)$^+$) and compound with long retention time 188 mg (MS(ESI) m/z: 438 (M+H)$^+$)).

In the analysis using CHIRALPAK (Daicel) IA-3 (4.6 mm×150 mm, 2-propanol/tetrahydrofuran/acetic acid=90/10/0.5, flow 0.5 mL/min), the retention time was respectively 6.6 min and 8.5 min.

Example 311: Synthesis of (R)-3-{5-[4-(3,5-dimethylpyridin-2-yl)piperazine-1-carbonyl]pyridin-2-yl}-3-ethylpyrrolidine-2,5-dione and (S)-3-{5-[4-(3,5-dimethylpyridin-2-yl)piperazine-1-carbonyl]pyridin-2-yl}-3-ethylpyrrolidine-2,5-dione

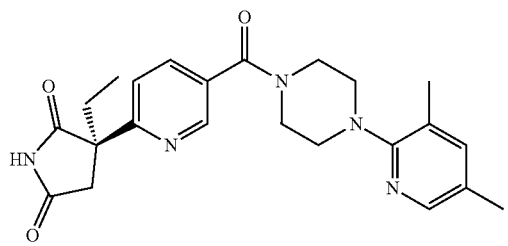

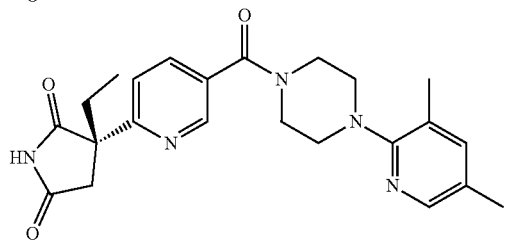

6-(3-Ethyl-2,5-dioxopyrrolidin-3-yl)nicotinic acid (500 mg, see Preparation Example 51), 1-(3,5-dimethylpyridin-2-yl)piperazine (425 mg), 1-hydroxybenzotriazole.1 hydrate (300 mg) and 1-ethyl-3-(3'-dimethylaminopropyl)carbodiimide. hydrochloride (425 mg) were dissolved in N,N-dimethylformamide (30 mL), triethylamine (0.56 mL) was added, and the mixture was stirred at room temperature overnight. The reaction mixture was concentrated under reduced pressure and the obtained residue was purified by column chromatography (chloroform:methanol) to give 3-{5-[4-(3,5-dimethylpyridin-2-yl)piperazine-1-carbonyl]pyridin-2-yl}-3-ethylpyrrolidine-2,5-dione (868 mg).

The obtained 3-{5-[4-(3,5-dimethylpyridin-2-yl)piperazine-1-carbonyl]pyridin-2-yl}-3-ethylpyrrolidine-2,5-dione (862 mg) was separated by HPLC using CHIRALPAK (Daicel) IA (2-propanol/tetrahydrofuran/diethylamine) to give the both enantiomers indicated above (compound with short retention time 449 mg (MS(ESI) m/z: 422 (M+H)$^+$) and compound with long retention time 446 mg (MS(ESI) m/z: 422 (M+H)$^+$)).

In the analysis using CHIRALPAK (Daicel) IA-3 (4.6 mm×50 mm, 2-propanol/tetrahydrofuran/diethylamine=70/30/0.1, flow 0.5 mL/min), the retention time was respectively 5.1 min and 11.1 min.

Example 312: Synthesis of 5-butyl-5-{4-[4-(3,5-dimethylpyridin-2-yl)piperazine-1-carbonyl]phenyl}imidazolidine-2,4-dione

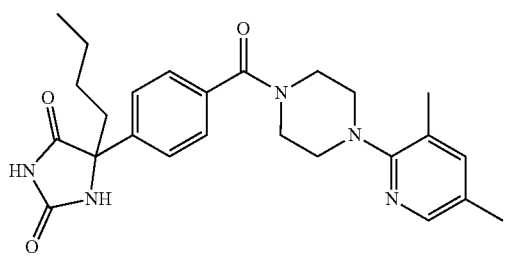 [SMILES: CCCCC1(c2ccc(C(=O)N3CCN(c4ncc(C)cc4C)CC3)cc2)NC(=O)NC1=O]

To a solution of 1-(3,5-dimethylpyridin-2-yl)piperazine (48 mg) in N,N-dimethylformamide (0.5 mL) were added 4-(4-butyl-2,5-dioxoimidazolidin-4-yl)benzoic acid (69 mg) described in Preparation Example 7, 1-hydroxybenzotriazole (37 mg), 1-ethyl-3-(3'-dimethylaminopropyl)carbodiimide.hydrochloride (53 mg) and diisopropylethylamine (0.049 mL) and the mixture was stirred at room temperature overnight. The reaction mixture was purified by column chromatography (hexane:ethyl acetate) to give the title compound (55 mg).

MS(APCI) m/z: 450 (M+H)$^+$

Example 313: Synthesis of 5-butyl-5-{4-[4-(5-cyclopropyl-3-methylpyridin-2-yl)piperazine-1-carbonyl]phenyl}imidazolidine-2,4-dione

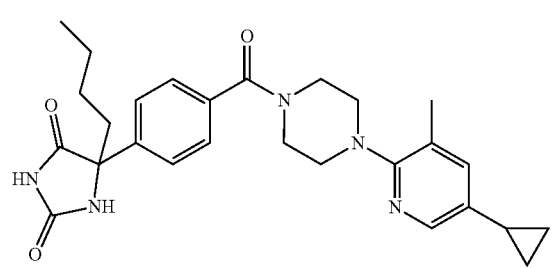 [SMILES: CCCCC1(c2ccc(C(=O)N3CCN(c4ncc(C5CC5)cc4C)CC3)cc2)NC(=O)NC1=O]

To a solution of 1-(5-cyclopropyl-3-methylpyridin-2-yl)piperazine (54 mg) in N,N-dimethylformamide (0.5 mL) were added 4-(4-butyl-2,5-dioxoimidazolidin-4-yl)benzoic acid (69 mg) described in Preparation Example 7, 1-hydroxybenzotriazole (37 mg), 1-ethyl-3-(3'-dimethylaminopropyl)carbodiimide. hydrochloride (53 mg) and diisopropylethylamine (0.049 mL) and the mixture was stirred at room temperature overnight. Water was added to the reaction mixture and the mixture was extracted with ethyl acetate. The organic layer was dried over anhydrous sodium sulfate, and the solvent was evaporated. The obtained residue was purified by column chromatography (hexane:ethyl acetate and chloroform:methanol) to give the title compound (73 mg).

MS(ESI) m/z: 476 (M+H)⁺

Example 314: Synthesis of 5-butyl-5-{4-[4-(5-ethyl-3-methylpyridin-2-yl) piperazine-1-carbonyl]phenyl}imidazolidine-2,4-dione

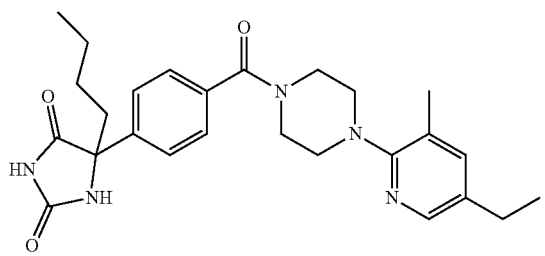 [SMILES: CCCCC1(c2ccc(C(=O)N3CCN(c4ncc(CC)cc4C)CC3)cc2)NC(=O)NC1=O]

Using 4-(4-butyl-2,5-dioxoimidazolidin-4-yl)benzoic acid (69 mg) described in Preparation Example 7 and 1-(5-ethyl-3-methylpyridin-2-yl)piperazine (51 mg), reactions and treatments similar to those in Example 313 were performed to give the title compound (77 mg).

MS(ESI) m/z: 464 (M+H)⁺

Example 315: Synthesis of 5-butyl-5-{4-[4-(3,5,6-trimethylpyridin-2-yl)piperazine-1-carbonyl]phenyl}imidazolidine-2,4-dione

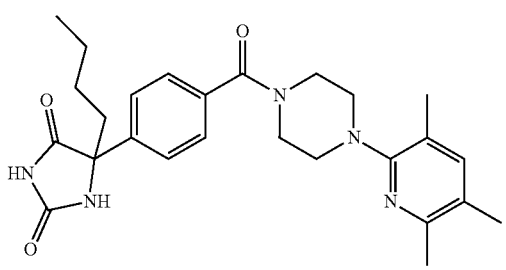 [SMILES: CCCCC1(c2ccc(C(=O)N3CCN(c4nc(C)c(C)cc4C)CC3)cc2)NC(=O)NC1=O]

Using 4-(4-butyl-2,5-dioxoimidazolidin-4-yl)benzoic acid (69 mg) described in Preparation Example 7 and 1-(3,5,6-trimethylpyridin-2-yl)piperazine (51 mg), reactions and treatments similar to those in Example 313 were performed to give the title compound (43 mg).

MS(ESI) m/z: 464 (M+H)⁺

Example 316: Synthesis of 5-butyl-5-{4-[4-(3,5-dicyclopropylpyridin-2-yl)piperazine-1-carbonyl]phenyl}imidazolidine-2,4-dione

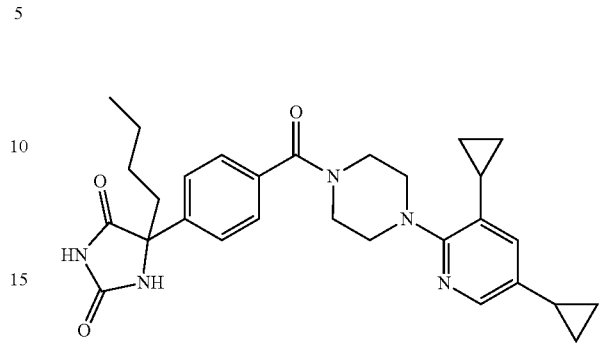

Using 4-(4-butyl-2,5-dioxoimidazolidin-4-yl)benzoic acid (69 mg) described in Preparation Example 7 and 1-(3,5-dicyclopropylpyridin-2-yl)piperazine.2 hydrochloride (79 mg) described in Preparation Example 147, reactions and treatments similar to those in Example 313 were performed to give the title compound (67 mg).

MS(ESI) m/z: 502 (M+H)⁺

Example 317: Synthesis of 5-butyl-5-{4-[4-(2,4-dimethylphenyl)piperazine-1-carbonyl]phenyl}imidazolidine-2,4-dione

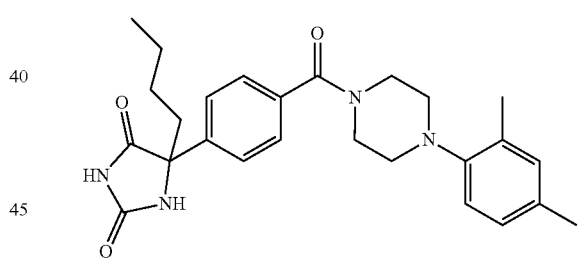

To 4-(4-butyl-2,5-dioxoimidazolidin-4-yl)benzoic acid (111 mg) described in Preparation Example 7 were added 1-(2,4-dimethylphenyl)piperazine (76 mg), N,N-dimethylformamide (0.8 mL), 1-hydroxybenzotriazole (59 mg), 1-ethyl-3-(3'-dimethylaminopropyl)carbodiimide.hydrochloride (84 mg) and diisopropylethylamine (0.077 mL) and the mixture was stirred at room temperature overnight. Water was added to the reaction mixture and the mixture was extracted with ethyl acetate. The organic layer was dried over anhydrous sodium sulfate, and the solvent was evaporated. To the obtained residue was added ethyl acetate, and the precipitate was collected by filtration to give the title compound (93 mg).

MS(ESI) m/z: 449 (M+H)⁺

Example 318: Synthesis of 3-{4-[4-(3,5-dimethyl-pyridin-2-yl)piperazine-1-carbonyl]phenyl}-3-ethyl-pyrrolidine-2,5-dione

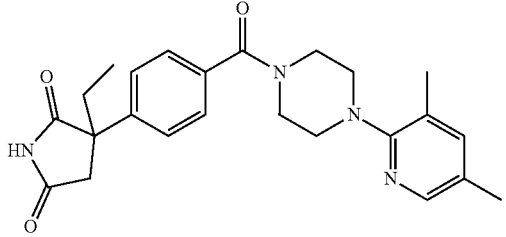 [SMILES: CCC1(c2ccc(C(=O)N3CCN(c4ncc(C)cc4C)CC3)cc2)CC(=O)NC1=O]

To 4-(3-ethyl-2,5-dioxopyrrolidin-3-yl)benzoic acid (240 mg) described in Preparation Example 20 were added N,N-dimethylformamide (2 mL), 1-(3,5-dimethylpyridin-2-yl)piperazine.hydrochloride (251 mg), 1-hydroxybenzotriazole (149 mg), 1-ethyl-3-(3'-dimethylaminopropyl)carbodiimide.hydrochloride (211 mg) and diisopropylethylamine (0.383 mL) and the mixture was stirred at room temperature overnight. Water was added to the reaction mixture and the mixture was extracted with ethyl acetate. The organic layer was washed with saturated brine, dried over anhydrous sodium sulfate, and the solvent was evaporated. To the obtained residue was added ethanol/water, and the precipitate was collected by filtration to give the title compound (229 mg).

MS(ESI) m/z: 419 (M−H)⁻

Example 319: Synthesis of 3-{4-[4-(3,5-dimethyl-pyridin-2-yl) piperazine-1-carbonyl]phenyl}-3-ethyl-1-methylpyrrolidine-2,5-dione

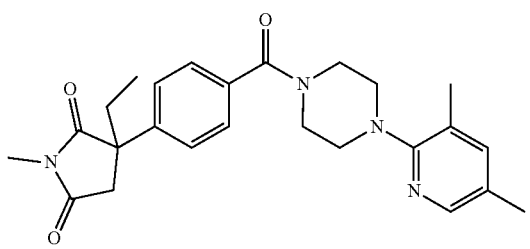

To 3-{4-[4-(3,5-dimethylpyridin-2-yl)piperazine-1-carbonyl]phenyl}-3-ethylpyrrolidine-2,5-dione (25 mg) described in Example 318 were added N,N-dimethylformamide (0.25 mL), potassium carbonate (24 mg) and methyl iodide (8.4 mg) and the mixture was stirred at room temperature for 1.5 hr. To the reaction mixture was added ethyl acetate, and the mixture was filtered. The filtrate was concentrated under reduced pressure and the obtained residue was purified by column chromatography (hexane:ethyl acetate) to give the title compound (23 mg).

MS (ESI) m/z: 435 (M+H)⁺

Example 320: Synthesis of 5-{4-[4-(3,5-dimethyl-pyridin-2-yl)piperazine-1-carbonyl]phenyl}-5-(tetra-hydropyran-4-yl)imidazolidine-2,4-dione

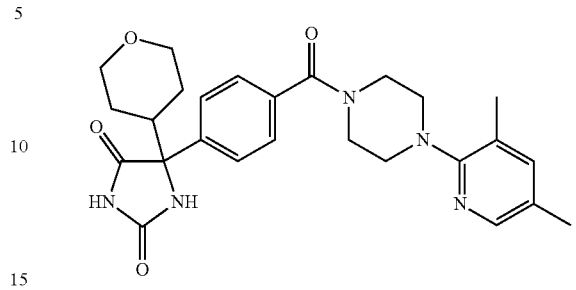

To 4-[2,5-dioxo-4-(tetrahydropyran-4-yl)imidazolidin-4-yl]benzoic acid (183 mg) described in Preparation Example 32 were added N,N-dimethylformamide (1.32 mL), 1-(3,5-dimethylpyridin-2-yl)piperazine.hydrochloride (165 mg), 1-hydroxybenzotriazole (99 mg), 1-ethyl-3-(3'-dimethylaminopropyl)carbodiimide.hydrochloride (140 mg) and diisopropylethylamine (0.253 mL) and the mixture was stirred at room temperature overnight. Water was added to the reaction mixture and the mixture was extracted with ethyl acetate. The organic layer was washed with saturated aqueous sodium chloride solution and dried over anhydrous sodium sulfate. The solvent was evaporated and the obtained residue was purified by column chromatography (chloroform:methanol) to give the title compound (107 mg).

MS (ESI) m/z: 476 (M−H)⁻

Example 321: Synthesis of 5-cyclobutyl-5-{4-[4-(3,5-dimethylpyridin-2-yl)piperazine-1-carbonyl]phenyl}imidazolidine-2,4-dione

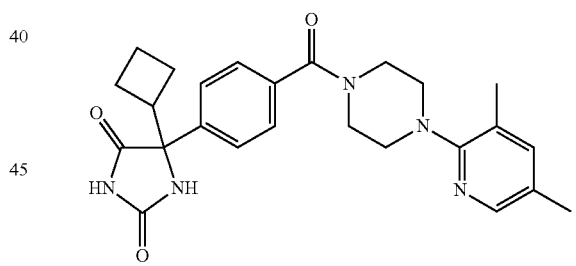

4-(4-Cyclobutyl-2,5-dioxoimidazolidin-4-yl)benzoic acid (247 mg) described in Preparation Example 33, 1-(3,5-dimethylpyridin-2-yl)piperazine (251 mg), 1-hydroxybenzotriazole (149 mg) and 1-ethyl-3-(3'-dimethylaminopropyl)carbodiimide.hydrochloride (211 mg) were dissolved in N,N-dimethylformamide (4.0 mL), diisopropylethylamine (0.383 mL) was added, and the mixture was stirred at room temperature overnight. Water was added to the reaction mixture, and the precipitate was collected by filtration. The obtained precipitate was dissolved in ethyl acetate, dried over anhydrous sodium sulfate, and the solvent was evaporated. To the obtained residue was added ethyl acetate, and the precipitate was collected by filtration to give the title compound (312 mg).

MS(ESI) m/z: 446 (M−H)⁻

Example 322: Synthesis of 5-cyclobutyl-5-{4-[4-(5-cyclopropyl-3-methylpyridin-2-yl)piperazine-1-carbonyl]phenyl}imidazolidine-2,4-dione

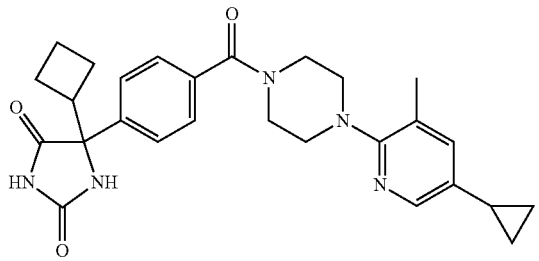

Using 4-(4-cyclobutyl-2,5-dioxoimidazolidin-4-yl)benzoic acid (247 mg) described in Preparation Example 33 and 1-(5-cyclopropyl-3-methylpyridin-2-yl)piperazine (239 mg), reactions and treatments similar to those in Example 321 were performed to give the title compound (255 mg).
MS(ESI) m/z: 472 (M−H)⁻

Example 323: Synthesis of 5-cyclobutyl-5-{4-[4-(3,5,6-trimethylpyridin-2-yl)piperazine-1-carbonyl]phenyl}imidazolidine-2,4-dione

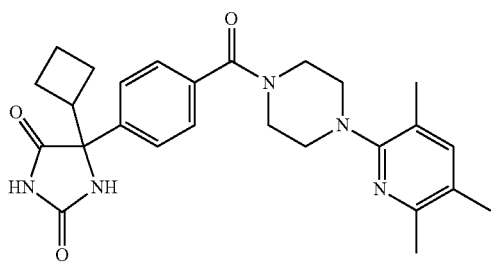

Using 4-(4-cyclobutyl-2,5-dioxoimidazolidin-4-yl)benzoic acid (247 mg) described in Preparation Example 33 and 1-(3,5,6-trimethylpyridin-2-yl)piperazine (226 mg), reactions and treatments similar to those in Example 321 were performed to give the title compound (315 mg).
MS(ESI) m/z: 460 (M−H)⁻

Example 324: Synthesis of (R)-3-{4-[4-(3,5-dimethylpyridin-2-yl)piperazine-1-carbonyl]phenyl}-3-ethylpyrrolidine-2,5-dione and (S)-3-{4-[4-(3,5-dimethylpyridin-2-yl)piperazine-1-carbonyl]phenyl}-3-ethylpyrrolidine-2,5-dione

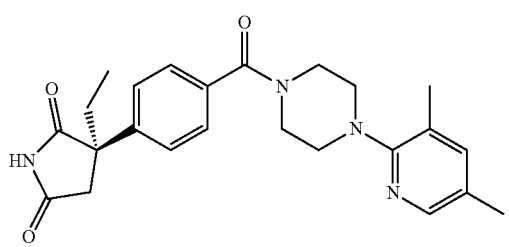

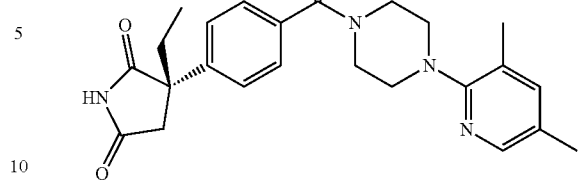

3-{4-[4-(3,5-Dimethylpyridin-2-yl)piperazine-1-carbonyl]phenyl}-3-ethylpyrrolidine-2,5-dione (169 mg) described in Example 318 was separated by HPLC using CHIRALPAK (Daicel) IC (tetrahydrofuran/ethanol/diethylamine) to give the both enantiomers indicated above (compound with short retention time 76 mg (MS(ESI) m/z: 419 (M−H)⁻ and compound with long retention time 74 mg (MS(ESI) m/z: 419 (M−H)⁻). In the analysis using CHIRALPAK (Daicel) IC-3 (4.6 mm×150 mm, tetrahydrofuran/ethanol/diethylamine=15/85/0.1, flow 0.5 mL/min), the retention time was respectively 7.3 min and 8.6 min.

Example 325: Synthesis of 5-{4-[4-(5-cyclopropyl-3-methylpyridin-2-yl)piperazine-1-carbonyl]phenyl}-5-(tetrahydropyran-4-yl)imidazolidine-2,4-dione

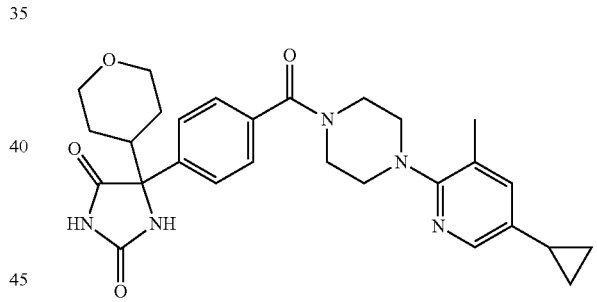

To 1-(5-cyclopropyl-3-methylpyridin-2-yl)piperazine (172 mg) were added N,N-dimethylformamide (3.2 mL), 4-[2,5-dioxo-4-(tetrahydropyran-4-yl)imidazolidin-4-yl]benzoic acid (239 mg) described in Preparation Example 32, 1-hydroxybenzotriazole (107 mg), 1-ethyl-3-(3'-dimethylaminopropyl)carbodiimide. hydrochloride (151 mg) and diisopropylethylamine (0.138 mL) and the mixture was stirred at room temperature overnight. Water was added to the reaction mixture and the mixture was extracted with ethyl acetate. The organic layer was washed with saturated brine and dried over anhydrous sodium sulfate. The solvent was evaporated and hexane/ethyl acetate was added to the obtained residue. The precipitate was collected by filtration to give the title compound (186 mg).
MS(ESI) m/z: 502 (M−H)⁻

Example 326: Synthesis of 5-(tetrahydropyran-4-yl)-5-{4-[4-(3,5,6-trimethylpyridin-2-yl)piperazine-1-carbonyl]phenyl}imidazolidine-2,4-dione

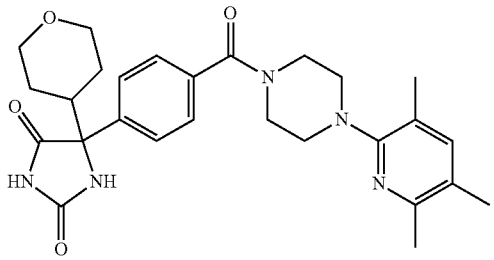 [SMILES: Cc1cnc(N2CCN(C(=O)c3ccc(C4(C5CCOCC5)NC(=O)NC4=O)cc3)CC2)c(C)c1]

Using 4-[2,5-dioxo-4-(tetrahydropyran-4-yl)imidazolidin-4-yl]benzoic acid (239 mg) described in Preparation Example 32 and 1-(3,5,6-trimethylpyridin-2-yl)piperazine (162 mg), reactions and treatments similar to those in Example 325 were performed to give the title compound (180 mg).

MS(ESI) m/z: 490 (M−H)⁻

Example 327: Synthesis of 5-tert-butyl-5-{5-[4-(3,5-dimethylpyridin-2-yl)piperazine-1-carbonyl]pyridin-2-yl}imidazolidine-2,4-dione

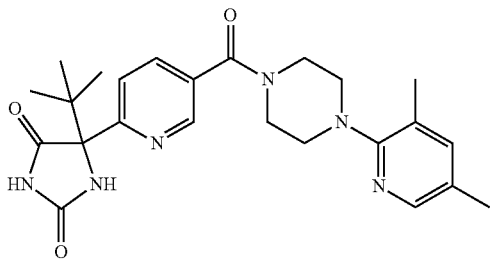 [SMILES: Cc1cnc(N2CCN(C(=O)c3ccc(C4(C(C)(C)C)NC(=O)NC4=O)nc3)CC2)c(C)c1]

Using 6-(4-tert-butyl-2,5-dioxoimidazolidin-4-yl)nicotinic acid as a crude product (119 mg, see Preparation Example 46) and 1-(3,5-dimethylpyridin-2-yl)piperazine (108 mg), reactions and treatments similar to those in Example 321 were performed to give the title compound (88 mg).

MS (ESI) m/z: 451 (M+H)⁺

Example 328: Synthesis of 5-isopropyl-5-{4-[4-(3,5,6-trimethylpyridin-2-yl) piperazine-1-carbonyl]phenyl}imidazolidine-2,4-dione

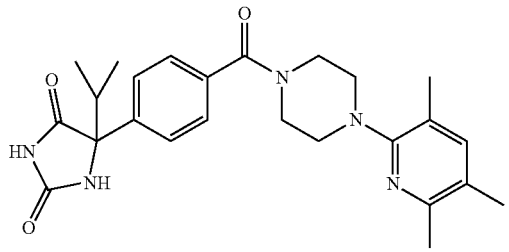 [SMILES: Cc1cc(C)c(N2CCN(C(=O)c3ccc(C4(C(C)C)NC(=O)NC4=O)cc3)CC2)nc1C]

A mixture of 4-(4-isopropyl-2,5-dioxoimidazolidin-4-yl)benzoic acid (100 mg) described in Preparation Example 5, 1-(3,5,6-trimethylpyridin-2-yl)piperazine (86.1 mg), 1-hydroxybenzotriazole (61.8 mg), 1-ethyl-3-(3'-dimethylaminopropyl)carbodiimide.hydrochloride (95 mg), chloroform (3 mL) and N,N-dimethylformamide (1 mL) was stirred at room temperature overnight. Water was added to the reaction mixture and the mixture was extracted with ethyl acetate. The solvent was evaporated and the obtained residue was purified by column chromatography (hexane:ethyl acetate) to give the title compound (131.5 mg).

MS(ESI) m/z: 450 (M+H)⁺

Example 329: Synthesis of 5-{4-[4-(5-cyclopropyl-3-methylpyridin-2-yl)piperazine-1-carbonyl]phenyl}-5-isopropylimidazolidine-2,4-dione

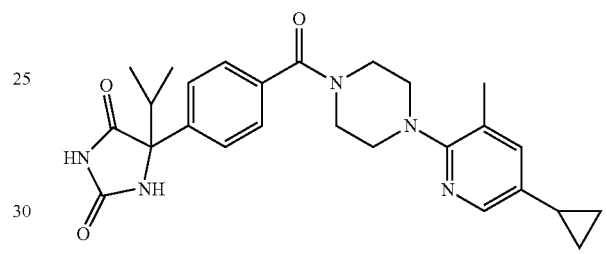

Using 4-(4-isopropyl-2,5-dioxoimidazolidin-4-yl)benzoic acid (100 mg) described in Preparation Example 5 and 1-(5-cyclopropyl-3-methylpyridin-2-yl)piperazine (91.1 mg), reactions and treatments similar to those in Example 328 were performed to give the title compound (102.9 mg).

MS(ESI) m/z: 462 (M+H)⁺

Example 330: Synthesis of 3-ethyl-3-{4-[4-(3,5,6-trimethylpyridin-2-yl) piperazine-1-carbonyl]phenyl}pyrrolidine-2,4-dione

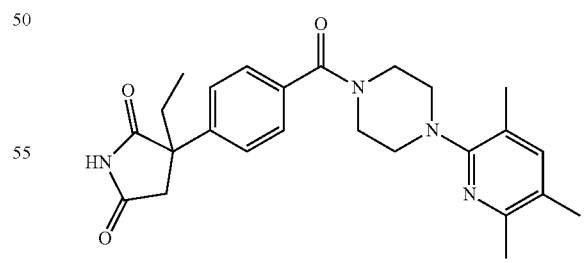

Using 4-(3-ethyl-2,5-dioxopyrrolidin-3-yl)benzoic acid (150 mg) described in Preparation Example 20 and 1-(3,5,6-trimethylpyridin-2-yl)piperazine (137 mg), reactions and treatments similar to those in Example 328 were performed to give the title compound (106 mg).

MS (ESI) m/z: 435 (M+H)⁺

Example 331: Synthesis of 3-{4-[4-(5-cyclopropyl-3-methylpyridin-2-yl)piperazine-1-carbonyl]phenyl}-3-ethylpyrrolidine-2,4-dione

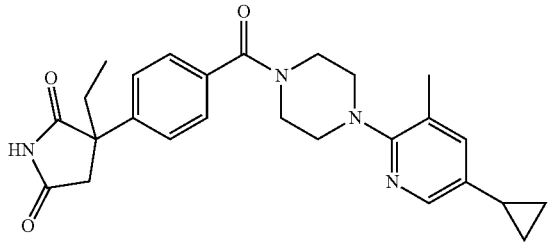 [SMILES: CCC1(c2ccc(C(=O)N3CCN(c4ncc(C5CC5)cc4C)CC3)cc2)CC(=O)NC1=O]

Using 4-(3-ethyl-2,5-dioxopyrrolidin-3-yl)benzoic acid (150 mg) described in Preparation Example 20 and 1-(5-cyclopropyl-3-methylpyridin-2-yl)piperazine (145 mg), reactions and treatments similar to those in Example 328 were performed to give the title compound (101.6 mg).
MS (ESI) m/z: 447 (M+H)+

Example 332: Synthesis of 5-{4-[4-(3,5-dimethylpyridin-2-yl)piperazine-1-carbonyl]-3-fluorophenyl}-5-methoxymethylimidazolidine-2,4-dione

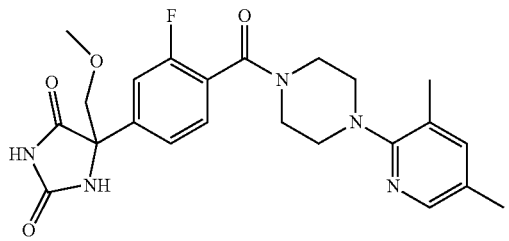 [SMILES: COCC1(c2ccc(C(=O)N3CCN(c4ncc(C)cc4C)CC3)c(F)c2)NC(=O)NC1=O]

To 2-fluoro-4-(4-methoxymethyl-2,5-dioxoimidazolidin-4-yl)benzoic acid (95 mg) described in Preparation Example 28 were added 1-(3,5-dimethylpyridin-2-yl)piperazine.hydrochloride (84.3 mg), chloroform (2.8 mL), N,N-dimethylformamide (1 mL), 1-hydroxybenzotriazole (54.6 mg), 1-ethyl-3-(3'-dimethylaminopropyl)carbodiimide.hydrochloride (83.9 mg) and triethylamine (0.103 mL) and the mixture was stirred at room temperature for 3 hr. Water was added to the reaction mixture and the mixture was extracted with ethyl acetate. The organic layer was washed with saturated brine, dried over anhydrous magnesium sulfate, and the solvent was evaporated. The obtained residue was purified by column chromatography (chloroform:methanol) to give the title compound (60.3 mg).
MS (ESI) m/z: 456 (M+H)+

Example 333: Synthesis of 5-{3-fluoro-4-[4-(3,5,6-trimethylpyridin-2-yl)piperazine-1-carbonyl]phenyl}-5-methoxymethylimidazolidine-2,4-dione

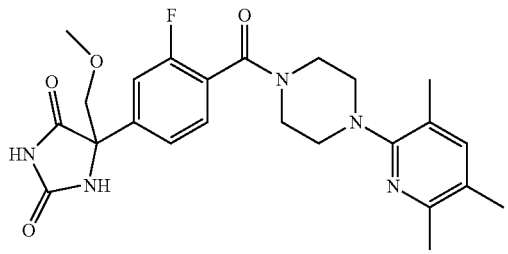 [SMILES: COCC1(c2ccc(C(=O)N3CCN(c4nc(C)c(C)cc4C)CC3)c(F)c2)NC(=O)NC1=O]

A mixture of 2-fluoro-4-(4-methoxymethyl-2,5-dioxoimidazolidin-4-yl)benzoic acid (85 mg) described in Preparation Example 28, 1-(3,5,6-trimethylpyridin-2-yl)piperazine (68 mg), 1-hydroxybenzotriazole (48.8 mg), 1-ethyl-3-(3'-dimethylaminopropyl)carbodiimide.hydrochloride (75.1 mg), chloroform (2.6 mL) and N,N-dimethylformamide (0.8 mL) was stirred at room temperature for 4 hr. Water was added to the reaction mixture and the mixture was extracted with ethyl acetate. The organic layer was washed with saturated brine, dried over anhydrous magnesium sulfate, and the solvent was evaporated. The obtained residue was purified by column chromatography (chloroform:methanol) to give the title compound (75.6 mg).
MS(ESI) m/z: 470 (M+H)+

Example 334: Synthesis of 5-{4-[4-(5-cyclopropyl-3-methylpyridin-2-yl)piperazine-1-carbonyl]-3-fluorophenyl}-5-methoxymethylimidazolidine-2,4-dione

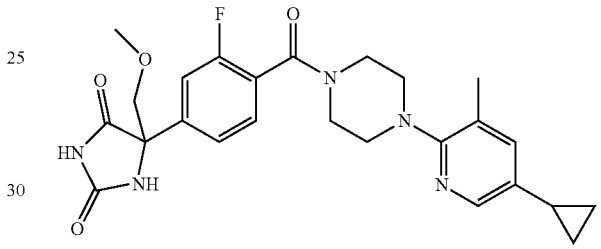

Using 2-fluoro-4-(4-methoxymethyl-2,5-dioxoimidazolidin-4-yl)benzoic acid (85 mg) described in Preparation Example 28 and 1-(5-cyclopropyl-3-methylpyridin-2-yl)piperazine (72 mg), reactions and treatments similar to those in Example 333 were performed to give the title compound (74.9 mg).
MS(ESI) m/z: 482 (M+H)+

Example 335: Synthesis of 5-tert-butyl-5-{6-[4-(3,5-dimethylpyridin-2-yl)piperazine-1-carbonyl]pyridin-3-yl}imidazolidine-2,4-dione

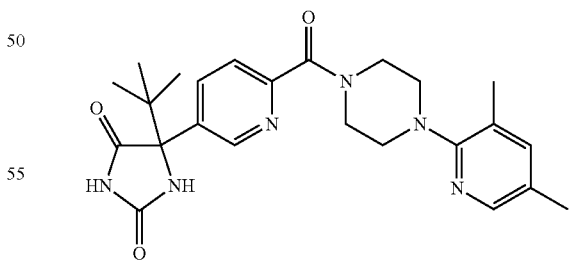

Using 5-(4-tert-butyl-2,5-dioxoimidazolidin-4-yl)pyridine-2-carboxylic acid (240 mg) described in Preparation Example 43 and 1-(3,5-dimethylpyridin-2-yl)piperazine.hydrochloride (216.8 mg), reactions and treatments similar to those in Example 332 were performed to give the title compound (256.7 mg).
MS(ESI) m/z: 451 (M+H)+

Example 336: Synthesis of 3-{4-[4-(3,5-dimethyl-pyridin-2-yl)piperazine-1-carbonyl]phenyl}-3-isopropylpyrrolidine-2,5-dione

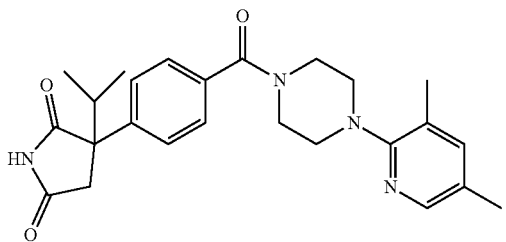 [SMILES: Cc1cnc(N2CCN(C(=O)c3ccc(C4(C(C)C)CC(=O)NC4=O)cc3)CC2)c(C)c1]

Using 4-(3-isopropyl-2,5-dioxopyrrolidin-3-yl)benzoic acid (120 mg) described in Preparation Example 49 and 1-(3,5-dimethylpyridin-2-yl)piperazine.hydrochloride (112.8 mg), reactions and treatments similar to those in Example 332 were performed to give the title compound (156 mg).
MS(ESI) m/z: 435 (M+H)+

Example 337: Synthesis of 3-isopropyl-3-{4-[4-(3,5,6-trimethylpyridin-2-yl) piperazine-1-carbonyl]phenyl}pyrrolidine-2,5-dione

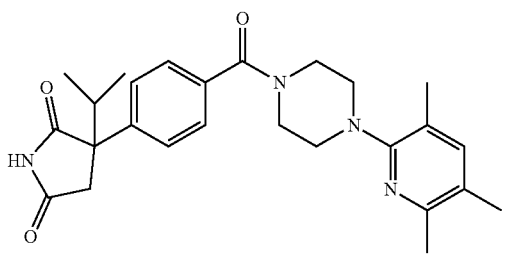 [SMILES: Cc1cc(C)c(N2CCN(C(=O)c3ccc(C4(C(C)C)CC(=O)NC4=O)cc3)CC2)nc1C]

Using 4-(3-isopropyl-2,5-dioxopyrrolidin-3-yl)benzoic acid (120 mg) described in Preparation Example 49 and 1-(3,5,6-trimethylpyridin-2-yl)piperazine (101.6 mg), reactions and treatments similar to those in Example 333 were performed to give the title compound (140 mg).
MS(ESI) m/z: 449 (M+H)+

Example 338: Synthesis of 3-{4-[4-(5-cyclopropyl-3-methylpyridin-2-yl)piperazine-1-carbonyl]phenyl}-3-isopropylpyrrolidine-2,5-dione

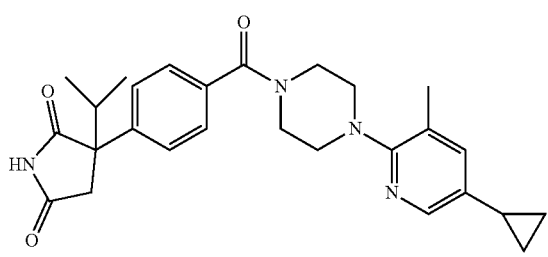 [SMILES: Cc1cc(C2CC2)cnc1N1CCN(C(=O)c2ccc(C3(C(C)C)CC(=O)NC3=O)cc2)CC1]

Using 4-(3-isopropyl-2,5-dioxopyrrolidin-3-yl)benzoic acid (120 mg) described in Preparation Example 49 and 1-(5-cyclopropyl-3-methylpyridin-2-yl)piperazine.hydrochloride (125.6 mg), reactions and treatments similar to those in Example 332 were performed to give the title compound (146 mg).
MS (ESI) m/z: 461 (M+H)+

Example 339: Synthesis of 5-{4-[4-(3,5-dimethyl-pyridin-2-yl)piperazine-1-carbonyl]-2-methoxyphenyl}-5-ethylimidazolidine-2,4-dione

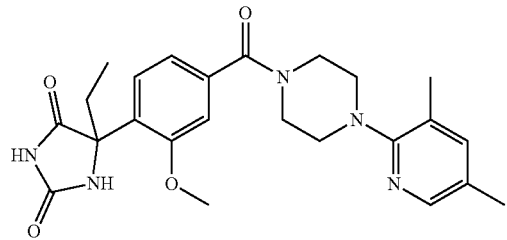 [SMILES: CCC1(c2ccc(C(=O)N3CCN(c4ncc(C)cc4C)CC3)cc2OC)NC(=O)NC1=O]

Using 4-(4-ethyl-2,5-dioxoimidazolidin-4-yl)-3-methoxybenzoic acid (220 mg) described in Preparation Example 53 and 1-(3,5-dimethylpyridin-2-yl)piperazine.hydrochloride (198.1 mg), reactions and treatments similar to those in Example 332 were performed to give the title compound (157 mg).
MS(ESI) m/z: 452 (M+H)+

Example 340: Synthesis of 5-{4-[4-(3,5-dimethyl-pyridin-2-yl)piperazine-1-carbonyl]-2-methoxyphenyl}-5-propylimidazolidine-2,4-dione

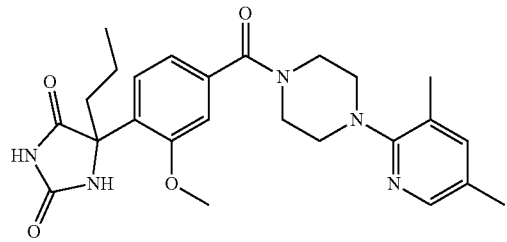 [SMILES: CCCC1(c2ccc(C(=O)N3CCN(c4ncc(C)cc4C)CC3)cc2OC)NC(=O)NC1=O]

Using 4-(2,5-dioxo-4-propylimidazolidin-4-yl)-3-methoxybenzoic acid (220 mg) described in Preparation Example 54 and 1-(3,5-dimethylpyridin-2-yl)piperazine.hydrochloride (188.5 mg), reactions and treatments similar to those in Example 332 were performed to give the title compound (289 mg).
MS (ESI) m/z: 466 (M+H)+

Example 341: Synthesis of 5-difluoromethyl-5-{4-[4-(3,5-dimethylpyridin-2-yl)piperazine-1-carbonyl]-2-methoxyphenyl}imidazolidine-2,4-dione

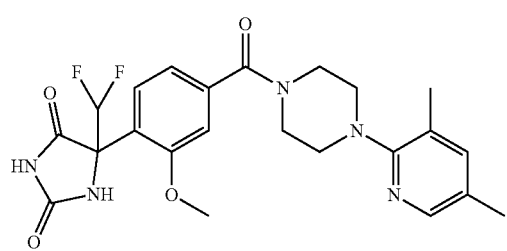 [SMILES: COc1cc(C(=O)N2CCN(c3ncc(C)cc3C)CC2)ccc1C1(C(F)F)NC(=O)NC1=O]

Using 4-(4-difluoromethyl-2,5-dioxoimidazolidin-4-yl)-3-methoxybenzoic acid (150 mg) described in Preparation Example 55 and 1-(3,5-dimethylpyridin-2-yl)piperazine.hydrochloride (125.2 mg), reactions and treatments similar to those in Example 332 were performed to give the title compound (199 mg).

MS(ESI) m/z: 474 (M+H)$^+$

Example 342: Synthesis of 5-{4-[4-(3,5-dimethyl-pyridin-2-yl)piperazine-1-carbonyl]-2-ethoxyphenyl}-5-isopropylimidazolidine-2,4-dione

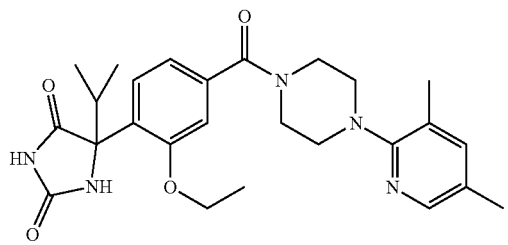 [SMILES: CCOc1cc(C(=O)N2CCN(c3ncc(C)cc3C)CC2)ccc1C1(C(C)C)NC(=O)NC1=O]

Using 3-ethoxy-4-(4-isopropyl-2,5-dioxoimidazolidin-4-yl)benzoic acid (180 mg) described in Preparation Example 56 and 1-(3,5-dimethylpyridin-2-yl)piperazine.hydrochloride (147.2 mg), reactions and treatments similar to those in Example 332 were performed to give the title compound (127.3 mg).

MS(ESI) m/z: 480 (M+H)$^+$

Example 343: Synthesis of 3-{5-[4-(4,6-dimethyl-benzofuran-3-yl)piperidine-1-carbonyl]pyridin-2-yl}-3-methoxymethyl-pyrrolidine-2,5-dione

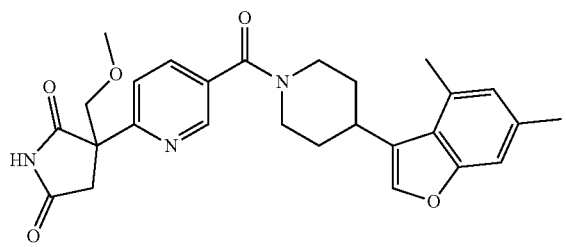 [SMILES: COCC1(c2ccc(C(=O)N3CCC(c4coc5cc(C)cc(C)c45)CC3)cn2)CC(=O)NC1=O]

To 6-(3-methoxymethyl-2,5-dioxopyrrolidin-3-yl)nicotinic acid (55 mg) described in Preparation Example 64 were added 4-(4,6-dimethylbenzofuran-3-yl)piperidine.hydrochloride (55 mg, see Preparation Example 142), 1-hydroxy-benzotriazole (28 mg), dichloromethane (2 mL), triethylamine (0.058 mL) and 1-ethyl-3-(3'-dimethylaminopropyl) carbodiimide.hydrochloride (52 mg) and the mixture was stirred at room temperature for 3 hr. To the reaction mixture was added saturated aqueous sodium hydrogen carbonate solution, and the mixture was filtered by a phase separator. The filtrate was concentrated under reduced pressure and the obtained residue was purified by column chromatography (hexane:ethyl acetate) to give the title compound (77.3 mg).

MS(ESI) m/z: 476 (M+H)$^+$

Example 344: Synthesis of (R)-5-{4-[(R)-3-(5,7-dimethylindazol-1-yl)pyrrolidine-1-carbonyl]phenyl}-5-methylimidazolidine-2,4 dione

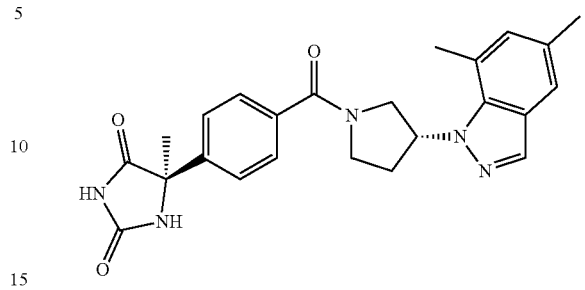

To 4-((R)-4-methyl-2,5-dioxoimidazolidin-4-yl)benzoic acid (73 mg) described in Preparation Example 6 were added 5,7-dimethyl-1-(R)-pyrrolidin-3-yl-1H-indazole (67 mg) described in Preparation Example 95, 1-hydroxybenzotriazole (42 mg), dichloromethane (1.4 mL), triethylamine (0.044 mL) and 1-ethyl-3-(3'-dimethylaminopropyl) carbodiimide.hydrochloride (78 mg) and the mixture was stirred at room temperature. After completion of the reaction, to the reaction mixture was added saturated aqueous sodium hydrogen carbonate solution, and the mixture was filtered by a phase separator. The filtrate was concentrated under reduced pressure and the obtained residue was purified by column chromatography (chloroform:methanol) to give the title compound (95.5 mg).

MS (ESI) m/z: 432 (M+H)$^+$

Example 345: Synthesis of (R)-5-methyl-5-{4-[4-(6-methyl-1H-indol-3-yl)piperidine-1-carbonyl]phenyl}imidazolidine-2,4-dione

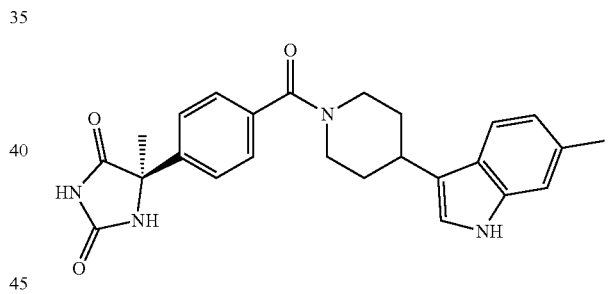

Using 4-((R)-4-methyl-2,5-dioxoimidazolidin-4-yl)benzoic acid (56 mg) described in Preparation Example 6 and 6-methyl-3-piperidin-4-yl-1H-indole (52 mg), reactions and treatments similar to those in Example 344 were performed to give the title compound (34 mg).

MS (ESI) m/z: 431 (M+H)$^+$

Example 346: Synthesis of (R)-5-methyl-5-{4-[4-(4-p-toluylpyrazol-1-yl)piperidine-1-carbonyl]phenyl}imidazolidine-2,4-dione

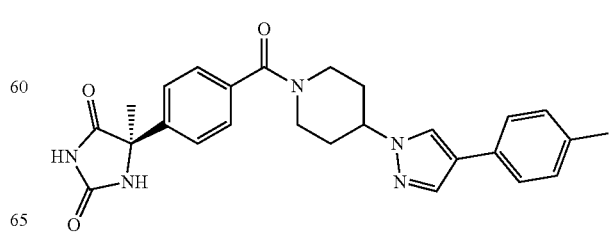

To 4-((R)-4-methyl-2,5-dioxoimidazolidin-4-yl)benzoic acid (59.6 mg) described in Preparation Example 6 were added 4-(4-p-toluylpyrazol-1-yl)piperidine.hydrochloride (71 mg) described in Preparation Example 109, 1-hydroxybenzotriazole (34 mg), dichloromethane (1.2 mL), triethylamine (89 µL) and 1-ethyl-3-(3'-dimethylaminopropyl)carbodiimide.hydrochloride (63 mg) and the mixture was stirred at room temperature overnight. To the reaction mixture was added saturated aqueous sodium hydrogen carbonate solution, and the mixture was filtered by a phase separator. The filtrate was concentrated under reduced pressure and the obtained residue was purified by column chromatography (chloroform:methanol) to give the title compound (71.9 mg).

MS (ESI) m/z: 458 (M+H)+

Example 347: Synthesis of (R)-5-{4-[4-(5,7-dimethylindazol-2-yl)piperidine-1-carbonyl]phenyl}-5-ethylimidazolidine-2,4-dione

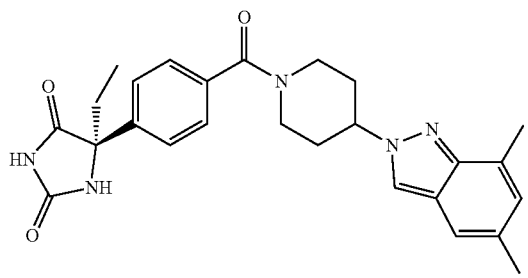 [SMILES: CC[C@]1(c2ccc(C(=O)N3CCC(n4cc5cc(C)cc(C)c5n4)CC3)cc2)NC(=O)NC1=O]

Using 4-((R)-4-ethyl-2,5-dioxoimidazolidin-4-yl)benzoic acid (57.4 mg) described in Preparation Example 14, 5,7-dimethyl-2-piperidin-4-yl-2H-indazole.hydrochloride (61 mg) described in Preparation Example 96 and dichloromethane (2 mL), reactions and treatments similar to those in Example 346 were performed to give the title compound (82.6 mg).

MS(ESI) m/z: 460 (M+H)+

Example 348: Synthesis of (R)-5-{4-[4-(5,7-dimethylindazol-2-yl)piperidine-1-carbonyl]phenyl}-5-fluoromethylimidazolidine-2,4-dione

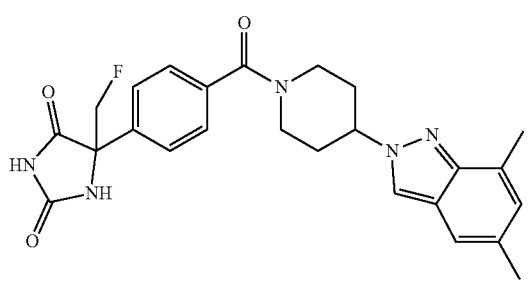 [SMILES: Cc1cc(C)c2nn(C3CCN(C(=O)c4ccc(C5(CF)NC(=O)NC5=O)cc4)CC3)cc2c1]

Using 4-(4-fluoromethyl-2,5-dioxoimidazolidin-4-yl)benzoic acid (55 mg) described in Preparation Example 63, 5,7-dimethyl-2-piperidin-4-yl-2H-indazole hydrochloride (58 mg) described in Preparation Example 96 and dichloromethane (2 mL), reactions and treatments similar to those in Example 346 were performed to give the title compound (57.5 mg).

MS (ESI) m/z: 464 (M+H)+

Example 349: Synthesis of 5-{4-[4-(3,5-dimethylpyridin-2-yl)piperazine-1-carbonyl]-3-trifluoromethylphenyl}-5-methylimidazolidine-2,4-dione

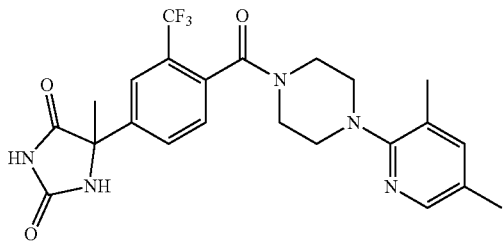 [SMILES: Cc1cnc(N2CCN(C(=O)c3ccc(C4(C)NC(=O)NC4=O)cc3C(F)(F)F)CC2)c(C)c1]

Using 4-(4-methyl-2,5-dioxoimidazolidin-4-yl)-2-trifluoromethylbenzoic acid as a crude product (150 mg) described in Preparation Example 47 and 1-(3,5-dimethylpyridin-2-yl)piperazine (115 mg), reactions and treatments similar to those in Example 42 were performed to give the title compound (52 mg).

MS(ESI) m/z: 476 (M+H)+

Example 350: Synthesis of acetic acid (R)-4-{4-[4-(5,7-dimethylindazol-2-yl)piperidine-1-carbonyl]phenyl]-4-methyl-2,5-dioxoimidazolidin-1-ylmethyl ester

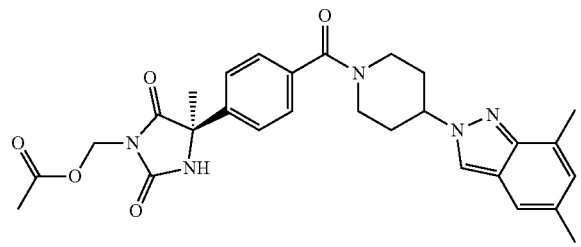 [SMILES: CC(=O)OCN1C(=O)N[C@](C)(c2ccc(C(=O)N3CCC(n4cc5cc(C)cc(C)c5n4)CC3)cc2)C1=O]

(R)-5-{4-[4-(5,7-dimethylindazol-2-yl)piperidine-1-carbonyl]phenyl}-5-methylimidazolidine-2,4-dione (120 mg, see Example 273), and potassium carbonate (45 mg) were dissolved in N,N-dimethylformamide (2 mL), chloromethyl acetate (31 mg) was added, and the mixture was stirred at room temperature overnight. Water was added to the reaction mixture and the mixture was extracted with ethyl acetate. The organic layer was washed with saturated brine, and the solvent was evaporated. The obtained residue was purified by column chromatography (ethyl acetate:methanol) to give the title compound (39 mg).

MS(ESI) m/z: 518 (M+H)+

Example 351: Synthesis of butyric acid (R)-4-{4-[4-(5,7-dimethylindazol-2-yl)piperidine-1-carbonyl]phenyl}-4-methyl-2,5-dioxoimidazolidin-1-ylmethyl ester

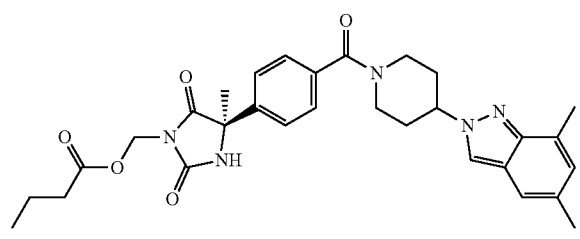 [SMILES: CCCC(=O)OCN1C(=O)N[C@](C)(c2ccc(C(=O)N3CCC(n4cc5cc(C)cc(C)c5n4)CC3)cc2)C1=O]

Using (R)-5-{4-[4-(5,7-dimethylindazol-2-yl)piperidine-1-carbonyl]phenyl}-5-methylimidazolidine-2,4-dione (120 mg, see Example 273) and chloromethyl butyrate (39 mg), reactions and treatments similar to those in Example 350 were performed to give the title compound (54 mg).

MS(ESI) m/z: 546 (M+H)+

Example 352: Synthesis of (R)-5-isopropyl-5-{4-[4-(6-methyl-1H-indol-3-yl)piperidine-1-carbonyl]phenyl}imidazolidine-2,4-dione

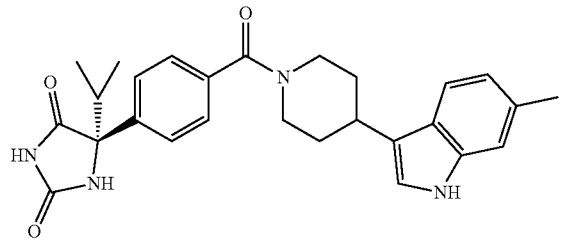 [SMILES: Cc1ccc2c(C3CCN(C(=O)c4ccc([C@@]5(C(C)C)NC(=O)NC5=O)cc4)CC3)c[nH]c2c1]

Using 4-((R)-4-isopropyl-2,5-dioxo-imidazolidin-4-yl)benzoic acid (53 mg) described in Preparation Example 45 and 6-methyl-3-piperidin-4-yl-1H-indole (43 mg), reactions and treatments similar to those in Example 344 were performed to give the title compound (54.5 mg).

MS(ESI) m/z: 459 (M+H)+

Example 353: Synthesis of 5-{4-[4-(3,5-dimethylpyridin-2-yl)piperazine-1-carbonyl]phenyl}-5-isopropyl-3-methylimidazolidine-2,4-dione

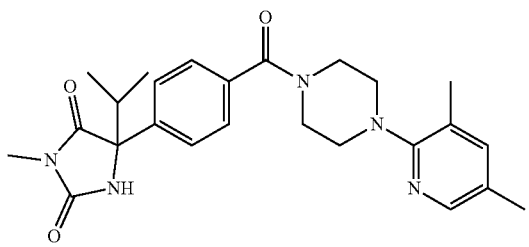

To 5-{4-[4-(3,5-dimethylpyridin-2-yl)piperazine-1-carbonyl]phenyl}-5-isopropylimidazolidine-2,4-dione (435 mg, see Example 47, 1)) were added potassium carbonate (180 mg), N,N-dimethylformamide (10 mL) and methyl iodide (75 µL) and the mixture was stirred at room temperature for 7 hr. After completion of the reaction, water was added, and the precipitate was collected by filtration to give the title compound (382 mg).

MS(ESI) m/z: 450 (M+H)+

Example 354: Synthesis of 5-{4-[4-(3,5-dimethylpyridin-2-yl)piperazine-1-carbonyl]phenyl}-5-isopropyl-1,3-dimethylimidazolidine-2,4-dione

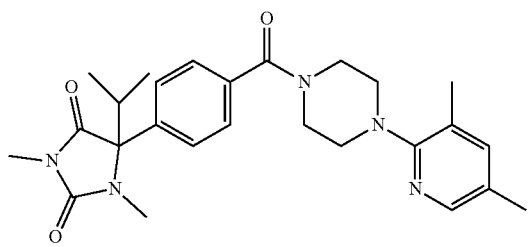

To 5-{4-[4-(3,5-dimethylpyridin-2-yl)piperazine-1-carbonyl]phenyl}-5-isopropyl-3-methylimidazolidine-2,4-dione (225 mg) described in Example 353 were added under a nitrogen atmosphere N,N-dimethylformamide (5 mL), sodium hydride (60% in liquid paraffin dispersion) (24 mg) and methyl iodide (37 µL) and the mixture was stirred at room temperature. After completion of the reaction, water was added to the reaction mixture and the mixture was extracted with ethyl acetate. The solvent was evaporated under reduced pressure, to the obtained residue was added ethyl acetate/hexane, and the precipitate was collected by filtration to give the title compound (206 mg).

MS(ESI) m/z: 464 (M+H)+

Example 355: Synthesis of 2,2-dimethylpropionic acid (R)-4-methyl-2,5-dioxo-4-{4-[4-(5-p-tolyl-[1,3,4]oxadiazol-2-yl)piperidine-1-carbonyl]phenyl}imidazolidin-1-ylmethyl ester

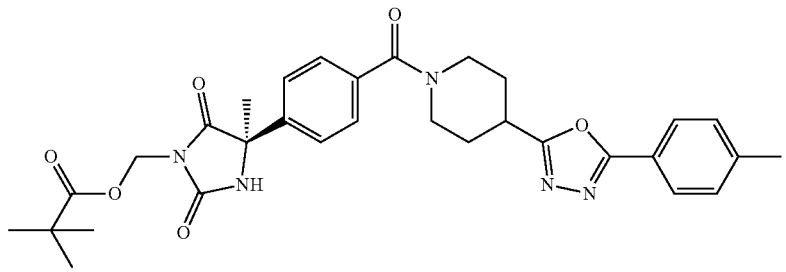 [SMILES: Cc1ccc(-c2nnc(C3CCN(C(=O)c4ccc([C@@]5(C)NC(=O)N(COC(=O)C(C)(C)C)C5=O)cc4)CC3)o2)cc1]

Using (R)-5-methyl-5-{4-[4-(5-p-tolyl[1,3,4]oxadiazol-2-yl)piperidine-1-carbonyl]phenyl}imidazolidine-2,4-dione (80 mg) described in Example 76 and chloromethyl 2,2- dimethylpropionate (28 mg), reactions and treatments similar to those in Example 350 were performed to give the title compound (66 mg).

MS(ESI) m/z: 574 (M+H)$^+$

Experimental Example 1: Action of Human TNFα Stimulated THP-1 Cell on proMMP-9 Production THP-1 cell (human monocytic leukemia cell line) was adjusted to 1×10$^7$ cells/mL in a culture medium (10% fetal bovine serum/RPMI1640 medium), and dispensed to a 96 well multiplate. This was equilibrated under the conditions of 37° C./5% $CO_2$, and a culture medium containing human TNFα (final concentration 10 ng/mL) and a test compound was dissolved therein. After incubation under the conditions of 37° C./5% $CO_2$ for 24 hr, the culture medium was centrifuged and the culture supernatant was collected, which was subjected to the following measurement.

Quantification of proMMP-9 in Culture Supernatant

The proMMP-9 concentration of the collected culture supernatant was quantified using a commercially available measurement reagent (manufactured by GE Healthcare, MMP-9, Human, Biotrak ELISA System).

Calculation of proMMP-9 Suppression Rate

The proMMP-9 suppression rate of the test compound was calculated from the following formula:

% suppression=100−((Test−Min)/(Max−Min)×100)

wherein Max is proMMP-9 concentration of culture supernatant induced by stimulation with human TNFα, without addition of a test compound (added with solvent alone) Min is proMMP-9 concentration of culture supernatant without addition of a test compound (added with solvent alone) and without stimulation with human TNFα, and Test is proMMP-9 concentration of culture supernatant induced by stimulation with human TNFα when a test compound is added.

Furthermore, the concentration of the test compound necessary for suppressing proMMP-9 production by human TNFα stimulated THP-1 cell by 50% (IC$_{50}$ value) was calculated from 3 points of proMMP-9 suppression rate at test compound concentrations of 5, 50 and 500 nmol/L or 1, 10 and 100 nmol/L.

Experimental Example 2: Action of THP-1 Cell on Hemostatic Type proMMP-2 Production THP-1 cell (human monocytic leukemia cell line) was adjusted to 1×10$^7$ cells/mL in a culture medium (10% fetal bovine serum/RPMI1640 medium), and dispensed to a 96 well multiplate. This was equilibrated under the conditions of 37° C./5% $CO_2$, and a culture medium dissolving a test compound was added thereto. After incubation under the conditions of 37° C./5% $CO_2$ for 24 hr, the culture medium was centrifuged and the culture supernatant was collected, which was subjected to the following measurement.

Quantification of proMMP-2 in Culture Supernatant

The proMMP-2 concentration of the collected culture supernatant was quantified using a commercially available measurement reagent (manufactured by GE Healthcare, MMP-2, Human, Biotrak ELISA System).

Calculation of proMMP-2 Suppression Rate

The proMMP-2 suppression rate of the test compound was calculated from the following formula:

% suppress=100−((Test/Cont)×100).

wherein Cont is proMMP-2 concentration of culture supernatant without addition of a test compound (added with solvent alone) and Test is proMMP-2 concentration of culture supernatant with addition of a test compound.

Furthermore, the concentration of the test compound necessary for suppressing proMMP-2 production by 50% (IC$_{50}$ value) was calculated from 3 points of proMMP-2 suppression rate at test compound concentrations of 0.1, 1 and 10 μmol/L.

The results of the Example compounds of the present invention in Experimental Example 1 are shown in Table 1 and the results of Experimental Example 2 are shown in Table 2.

TABLE 1

| Example | proMMP-9 suppression rate IC$_{50}$ (nM) |
|---|---|
| 1 | 27 |
| 20 | 6 |
| 27 | 16 |
| 64 | 64 |
| 65 | 9 |
| 66 | <5 |
| 69 | 11 |
| 108 | 11 |
| 112 | 11 |
| 114 | 82 |
| 124 | 1 |
| 126 | 8 |
| 137 | 14 |
| 141 | 70 |
| 150 | 25 |
| 152 | 14 |
| 158 | 49 |
| 165 | 90 |
| 170 | 60 |
| 175 | 88 |
| 178 | 34 |
| 182 | 67 |
| 185 | 82 |
| 187 | 19 |
| 198 | 2 |
| 220 | 55 |
| 221 | 72 |
| 222 | 76 |
| 227 | 84 |
| 243 | 27 |
| 259 | 60 |
| 262 | 13 |
| 267 | 5 |
| 272 | <5 |
| 280 | <5 |
| 322 | <1 |
| 335 | 1 |
| 343 | <3 |
| 345 | 15 |
| 346 | 88 |
| 350 | 115 |

TABLE 2

| Example | IC$_{50}$ value (μmol/L) |
|---|---|
| 1 | >10 |

MMP-9 is produced as a precursor proMMP-9 by the stimulated cells, extracellularly activated and expresses the physiological activity as MMP-9. That is, evaluation of the suppression of proMMP-9 produced by the cell means evaluation of the suppression of production of MMP-9. The same applies to MMP-2, and evaluation of the suppression of proMMP-2 produced by the cell means evaluation of the suppression of production of MMP-2.

Experimental Example 3 Suppressive Action on Articular Joints Injury Marker Free of Rat Monoiodoacetic Acid-Induced Osteoarthritis Model Monoiodoacetic acid solution (0.3 mg/25 μL) was injected into the right hindpaw knee joint cavity of anesthetized rats (LEW, male, 7-week-old). A test compound was orally administered once a day from immediately after monoiodoacetic acid injection to day 4 at a dose of 1 mg/kg. On day 5, cold phosphate buffer (20 μL) was injected into the right hindpaw knee joint cavity of the euthanized rats, and the joint cavity washing was collected. The joints injury marker COMP (Cartilage Oligomeric Matrix Protein) concentration of the joint cavity washing was quantified using a commercially available measurement reagent (Animal COMP ELISA Kit manufactured by Anamer Medical).

Calculation of Joints Injury Marker COMP Suppression Rate

The COMP suppression rate of the test compound was calculated from the following formula:

% suppression=100−((Test−Min)/(Max−Min)×100)

wherein Max is a COMP concentration of the joint cavity washing of the pathology group administered with a monoiodoacetic acid solution (oral administration of solvent alone), Min is a COMP concentration of the joint cavity washing of the non-treatment normal group (oral administration of solvent alone), and Test is a COMP concentration of the joint cavity washing of the test compound administration group.

The results of the Example compounds of the present invention in Experimental Example 3 are shown in Table 3 below.

TABLE 3

| compound administered | administration dose | Joints injury marker COMP suppression rate (%) |
|---|---|---|
| Example 1 | 1 mg/kg once per day | 80.9 |
| Example 8 | 0.1 mg/kg once per day | 84.3 |

The results of Experimental Example 3 of the compounds described in patent document 3 (WO 2011/136292) are shown in the following Table 4.

TABLE 4

| compound administered | administration dose | Joints injury marker COMP suppression rate (%) |
|---|---|---|
| Example 450 | 1 mg/kg once per day | 14.4 |
| Example 571 | 3 mg/kg once per day | 55.3 |

The upper panel shows the structures of the compounds of the present invention, and the lower panel shows the structures of the compounds described in patent document 3, as shown below. By comparison of the structures of the compounds of the present invention and those of compounds described in patent document 3, they are different in that the left-most heterocycle and the rest are bonded via a carbon atom in the compound of the present invention, whereas they are bonded via a nitrogen atom in the compounds described in patent document 3. By comparison of the structures of Example 1 which is the compound of the present invention and Example 450 described in patent document 3, they are completely the same except that the binding position of the remaining part to the left-most heterocycle is different. The same applies to the structures of Example 8, which is the compound of the present invention, and Example 571 described in patent document 3. By comparison of the joints injury marker COMP suppression rates of Example 1, which is the compound of the present invention, and that of Example 450 described in patent document 3, the compound of the present invention was at least 5-fold superior. By comparison of the joints injury marker COMP suppression rates of Example 8, which is the compound of the present invention, and that of Example 571 described in patent document 3, the compound of the present invention was at least 30-fold superior. Being 10-fold superior to Example 571 described in patent document 3 means 55.3% suppression at 0.3 mg/kg and being 30-fold superior means 55.3% suppression at 0.1 mg/kg. However, Example 8, which is the compound of the present invention, showed 84.3% suppression at 0.1 mg/kg.

Example 1

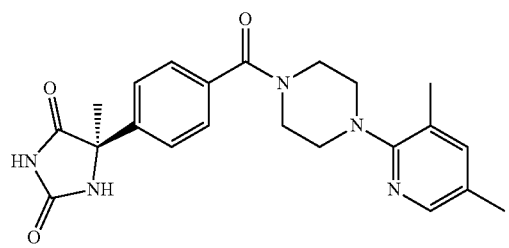

Example 8

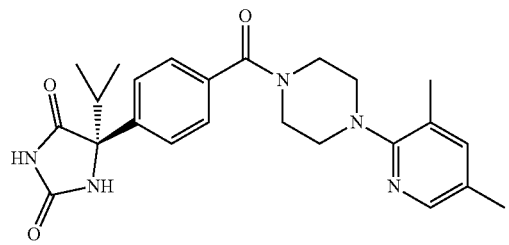

Example 450

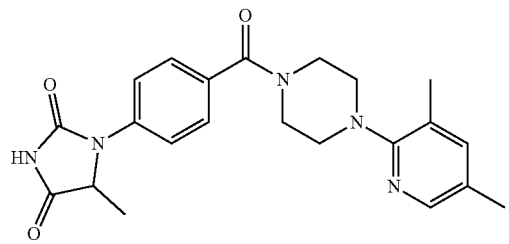

Example 571

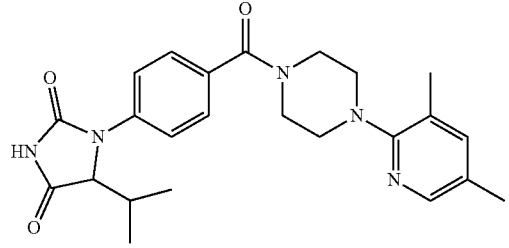

Experimental Example 4 Suppressive Action on Enteritis Score (Disease Activity Index, DAI) of Mouse Dextran Sulfuric Acid Induced Colitis Model Mice (C57BL/6J, male, 6-week-old) were allowed to freely ingest 2.0% (w/v) dextran sulfuric acid solution for 5 days, the solution was exchanged with water, and pathology was evaluated on day 10. The test compound was orally administered twice per day at a dose of 30 mg/kg for 5 days of dextran sulfuric acid solution ingestion and thereafter until day 10. On days 3, 5, 7 and 10 from the start of the test, the body weight decrease, stool consistency, and the state of occult blood or gross bleeding were respectively scored in 0-4 points, and the mean of the total score was taken as Disease Activity Index (DAI), an index of enteritis pathology. The diagnostic criteria of the stool consistency score and occult blood or gross bleeding score were as follows.

TABLE 5

| score | Stool consistency score | Occult blood or gross bleeding score |
|---|---|---|
| 0 | normal stool | hemoccult negative |
| 1 | loose stool | hemoccult slight positive |
| 2 | severe loose stool | hemoccult positive |
| 3 | diarrhea | hemoccult strong positive |
| 4 | severe diarrhea | gross bleeding |

The evaluation results are shown by the area under the curve (AUC) calculated using DAI on days 3, 5, 7 and 10.

The results of the Example compounds of the present invention in Experimental Example 4 are shown in Table 6 below.

TABLE 6

| test group | dose | DAI (AUC) |
|---|---|---|
| pathology group | | 11.75 ± 1.18 |
| Example 1 | 30 mg/kg twice per day | 9.78 ± 0.80 |

As is clear from the results of Experimental Examples 1 and 2, the compound of the present invention has a selective MMP-9 production suppressive action, and is a highly safe compound showing suppressed expression of side effects caused by the suppression of MMP-2 production. Furthermore, the compound of the present invention has a suppressive action on articular joint injury marker free of monoiodoacetic acid-induced osteoarthritis models (Experimental Example 3) and therefore, it is useful as a prophylactic and/or therapeutic drug for osteoarthritis. In view of the suppressive action on the enteritis score of the dextran sulfuric acid induced colitis model (Experimental Example 4), moreover, the compound is useful as a drug for the prophylaxis and/or treatment of inflammatory bowel diseases (ulcerative colitis, Crohn's disease).

INDUSTRIAL APPLICABILITY

The compound of the present invention selectively suppresses production of induction type MMPs, particularly MMP-9, rather than production of hemostatic type MMP-2. Therefore, it is useful as a drug for the prophylaxis and/or treatment of autoimmune diseases such as rheumatoid arthritis and the like, inflammatory bowel diseases (ulcerative colitis, Crohn's disease) or osteoarthritis.

This application is based on patent application No. 2015-138105 filed in Japan, the contents of which are encompassed in full herein.

The invention claimed is:

1. An imide derivative represented by the following formula (I)

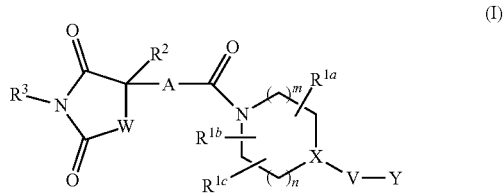

(I)

wherein
A is a 6-membered ring of the structure

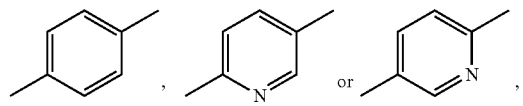

each of which is optionally substituted by one or the same or different 2 or 3 substituents selected from a halogen atom; hydroxyl group;
nitro; cyano; $C_1$-$C_6$ alkyl optionally substituted by amino optionally mono- or di-substituted by $C_1$-$C_6$ alkyl, a halogen atom, a hydroxyl group or $C_1$-$C_6$ alkoxy; $C_3$-$C_6$ cycloalkyl optionally substituted by amino optionally mono- or di-substituted by $C_1$-$C_6$ alkyl, a halogen atom, a hydroxyl group or $C_1$-$C_6$ alkoxy; amino optionally mono- or di-substituted by $C_1$-$C_6$ alkyl; and $C_1$-$C_6$ alkoxy optionally substituted by amino optionally mono- or di-substituted by $C_1$-$C_6$ alkyl, a halogen atom, a hydroxyl group or $C_1$-$C_6$ alkoxy, the right bond is linked to carbonyl and the left bond is linked to quaternary carbon bonded to $R^2$,
$R^{1a}$, $R^{1b}$ and $R^{1c}$ are the same or different and each is a hydrogen atom; a halogen atom; a hydroxyl group; cyano; oxo; carboxy; $C_1$-$C_6$ alkyl optionally substituted by amino optionally mono- or di-substituted by $C_1$-$C_6$ alkyl, a halogen atom, a hydroxyl group or $C_1$-$C_6$ alkoxy; $C_1$-$C_6$ alkoxy optionally substituted by amino optionally mono- or di-substituted by $C_1$-$C_6$ alkyl, a halogen atom, a hydroxyl group or $C_1$-$C_6$ alkoxy; $C_2$-$C_7$ alkoxycarbonyl; or aminocarbonyl optionally mono- or di-substituted by $C_1$-$C_6$ alkyl; or two of $R^{1a}$, $R^{1b}$ and $R^{1c}$ are joined to show $C_3$-$C_6$ cycloalkyl; or two of $R^{1a}$, $R^{1b}$ and $R^{1c}$ are joined to show a saturated nonaromatic heterocyclic group containing 1-4 atoms selected from a nitrogen atom, an oxygen atom and a sulfur atom and having 3-7 ring-constituting atoms,
$R^2$ is $C_1$-$C_6$ alkyl optionally substituted by amino optionally mono- or di-substituted by $C_1$-$C_6$ alkyl, $C_3$-$C_6$ cycloalkyl, a halogen atom, a hydroxyl group or $C_1$-$C_6$ alkoxy; $C_3$-$C_6$ cycloalkyl optionally substituted by a halogen atom, a hydroxyl group, $C_1$-$C_6$ alkoxy or amino; a saturated nonaromatic heterocyclic group containing 1-4 atoms selected from a nitrogen atom, an oxygen atom and a sulfur atom and having 3-7 ring-constituting atoms; $C_6$-$C_{10}$ aryl optionally substituted by substituent B shown below; or heteroaryl containing 1-6 atoms selected from a nitrogen atom, an oxygen atom and a sulfur atom, having 5-10 ring-constituting atoms, and optionally substituted by substituent B shown below, $R^3$ is a hydrogen atom; $C_1$-$C_6$ alkyl optionally substituted by amino optionally mono- or di-substituted by $C_1$-$C_6$ alkyl, a halogen atom, a hydroxyl group, $C_1$-$C_6$ alkoxy or $C_2$-$C_7$ acyloxy; $C_3$-$C_6$ cycloalkyl; arylalkyl wherein the $C_6$-$C_{10}$ aryl moiety is optionally substituted by a halogen atom, a hydroxyl group, $C_1$-$C_6$ alkoxy, $C_1$-$C_6$ alkyl or amino, and the alkyl moiety has a carbon number of 1-6; or heteroarylalkyl wherein the heteroaryl moiety containing 1-6 atoms selected from a nitrogen atom, an oxygen atom and a sulfur atom and having 5 to 10 ring-constituting atoms is optionally substituted by a halogen atom, a hydroxyl group, $C_1$-$C_6$ alkoxy, $C_1$-$C_6$ alkyl or amino and the alkyl moiety has a carbon number of 1-6, W is —N($R^x$)— wherein $R^x$ is a hydrogen atom or $C_1$-$C_6$ alkyl optionally substituted by a halogen atom, a hydroxyl group, $C_1$-$C_6$ alkoxy or $C_2$-$C_7$ acyloxy or methylene optionally substituted by a halogen atom, a hydroxyl group, $C_1$-$C_6$ alkyl or $C_1$-$C_6$ alkoxy, m+n is 0, 1, 2 or 3, X is a carbon atom (any one of $R^{1a}$, $R^{1b}$ and $R^{1c}$ may be bonded to the carbon atom but the carbon atom is not substituted by oxo) or a nitrogen atom (when V is a bond, the nitrogen atom may be oxidized to form N-oxide), V is a bond; carbonyl; $C_1$-$C_6$ alkylene optionally substituted by a halogen atom, a hydroxyl group or $C_1$-$C_6$ alkoxy; an oxygen atom; or —N($R^Y$)— wherein $R^Y$ is a hydrogen atom, $C_1$-$C_6$ alkyl or $C_2$-$C_7$ acyl, Y is a 5-membered ring group, a 6-membered ring group, a 5-membered ring group substituted by a 5-membered ring group, a 5-membered ring group substituted by a 6-membered ring group, a 6-membered ring group substituted by a 5-membered ring group, a 6-membered ring group substituted by a 6-membered ring group, a fused ring group of a 5-membered ring and a 5-membered ring, a fused ring group of a 5-membered ring and a 6-membered ring or a fused ring group of a 6-membered ring and a 6-membered ring (wherein the 5-membered ring and the 5-membered ring group contain 0-4 atoms selected from a nitrogen atom, an oxygen atom and a sulfur atom, and the rest is constituted of a carbon atom, the 6-membered ring and the 6-membered ring group contain 0-4 atoms selected from a nitrogen atom, an oxygen atom and a sulfur atom, and the rest is constituted of a carbon atom), and these ring groups are optionally substituted by a halogen atom; a hydroxyl group; $C_1$-$C_6$ alkyl optionally substituted by amino optionally mono- or di-substituted by $C_1$-$C_6$ alkyl, a halogen atom, a hydroxyl group or $C_1$-$C_6$ alkoxy; $C_3$-$C_6$ cycloalkyl optionally substituted by a halogen atom, a hydroxyl group, amino or $C_1$-$C_6$ alkyl; or $C_1$-$C_6$ alkoxy optionally substituted by amino optionally mono- or di-substituted by $C_1$-$C_6$ alkyl, a halogen atom, a hydroxyl group, $C_1$-$C_6$ alkyl or $C_1$-$C_6$ alkoxy, and substituent B is a halogen atom; a hydroxyl group; cyano; $C_1$-$C_6$ alkyl optionally substituted by amino optionally mono- or di-substituted by $C_1$-$C_6$ alkyl, a halogen atom, a hydroxyl group or $C_1$-$C_6$ alkoxy; $C_3$-$C_6$ cycloalkyl optionally substituted by a halogen atom, a hydroxyl group or amino; $C_1$-$C_6$ alkoxy optionally substituted by amino optionally mono- or di-substituted by $C_1$-$C_6$ alkyl, a halogen atom, a hydroxyl group or $C_1$-$C_6$ alkoxy; amino optionally mono- or di-substituted by $C_1$-$C_6$ alkyl or $C_3$-$C_6$ cycloalkyl, or a pharmacologically acceptable salt thereof.

2. The imide derivative according to claim 1 wherein Y is phenyl, pyridyl, pyrazinyl, pyridazinyl, naphthyl, quinolyl or a ring group shown below

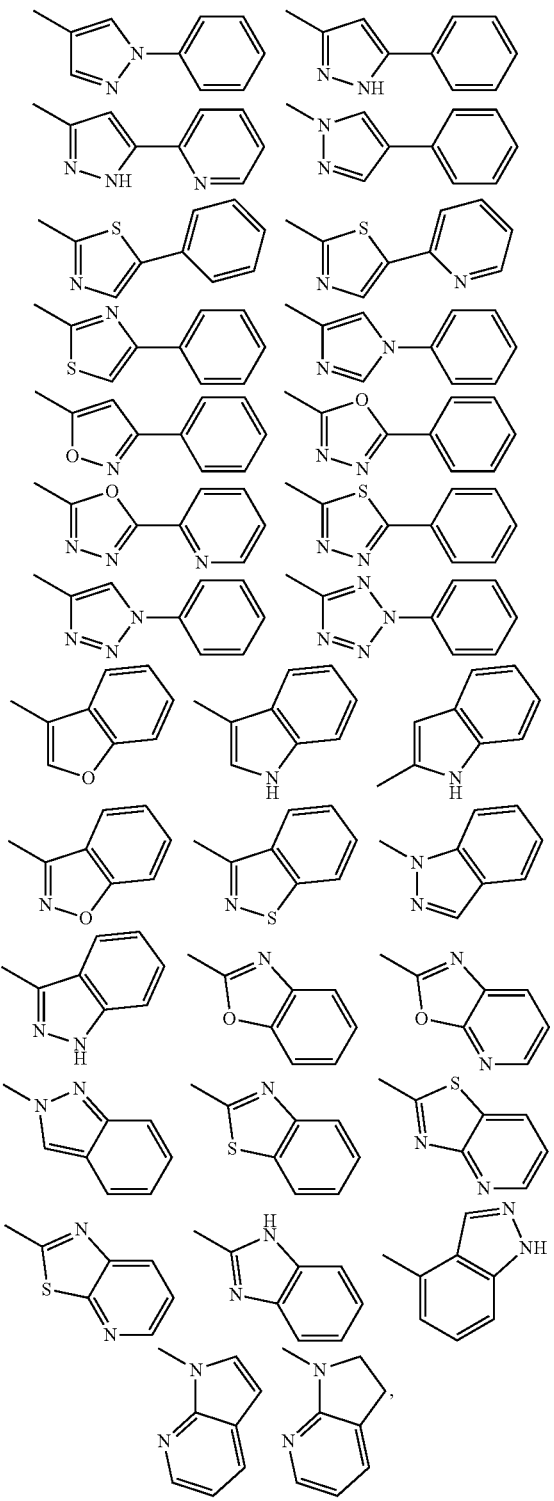

and these ring groups are optionally substituted by a halogen atom; a hydroxyl group; $C_1$-$C_6$ alkyl optionally substituted by amino optionally mono- or di-substituted by $C_1$-$C_6$ alkyl, a halogen atom, a hydroxyl group or $C_1$-$C_6$ alkoxy; $C_3$-$C_6$ cycloalkyl optionally substituted by a halogen atom, a hydroxyl group, amino or $C_1$-$C_6$ alkyl; or $C_1$-$C_6$ alkoxy optionally substituted by amino optionally mono- or di-substituted by $C_1$-$C_6$ alkyl, a halogen atom, a hydroxyl group, $C_1$-$C_6$ alkyl or $C_1$-$C_6$ alkoxy, or a pharmacologically acceptable salt thereof.

3. The imide derivative according to claim 1 wherein Y is phenyl or pyridyl represented by the following formula

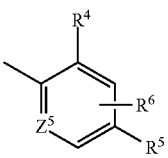

wherein $Z^5$ is a carbon atom or a nitrogen atom, $R^4$ and $R^5$ are the same or different and each is $C_1$-$C_6$ alkyl optionally substituted by a halogen atom; or $C_3$-$C_6$ cycloalkyl optionally substituted by a halogen atom, and $R^6$ is a hydrogen atom; $C_1$-$C_6$ alkyl optionally substituted by a halogen atom; or $C_3$-$C_6$ cycloalkyl optionally substituted by a halogen atom, or a ring group represented by the following formula

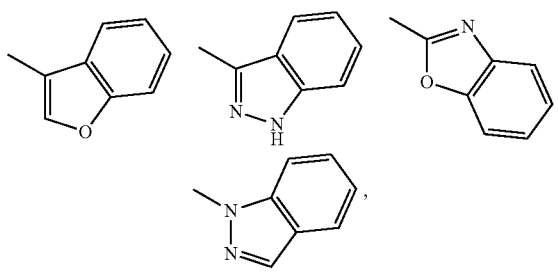

these ring groups being optionally substituted by a halogen atom or $C_1$-$C_6$ alkyl, or a pharmacologically acceptable salt thereof.

4. The imide derivative according to claim 1 wherein Y is phenyl or pyridyl represented by the following formula

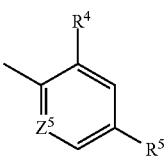

wherein $Z^5$ is a carbon atom or a nitrogen atom, and $R^4$ and $R^5$ are the same or different and each is $C_1$-$C_6$ alkyl; or $C_3$-$C_6$ cycloalkyl, or a pharmacologically acceptable salt thereof.

5. The imide derivative according to claim 1 wherein Y is pyridyl represented by the following formula

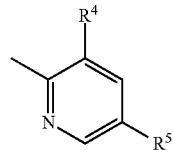

wherein $R^4$ and $R^5$ are the same or different and each is $C_1$-$C_6$ alkyl; or $C_3$-$C_6$ cycloalkyl, or a pharmacologically acceptable salt thereof.

6. The imide derivative according to claim 1 wherein V is a bond, or a pharmacologically acceptable salt thereof.

7. The imide derivative according to claim 1 wherein X is a nitrogen atom, or a pharmacologically acceptable salt thereof.

8. The imide derivative according to claim 1 wherein $R^{1a}$, $R^{1b}$ and $R^{1c}$ are each a hydrogen atom, or a pharmacologically acceptable salt thereof.

9. The imide derivative according to claim 1 wherein $R^2$ is $C_1$-$C_6$ alkyl and $R^3$ is a hydrogen atom, or a pharmacologically acceptable salt thereof.

10. The imide derivative according to claim 1 wherein W is —NH— or methylene, or a pharmacologically acceptable salt thereof.

11. The imide derivative according to claim 1 wherein W is —NH—, or a pharmacologically acceptable salt thereof.

12. (R)-5-{4-[4-(3,5-dimethylpyridin-2-yl)piperazine-1-carbonyl]phenyl}-5-methylimidazolidine-2,4-dione, (R)-5-{4-[4-(3,5-dimethylpyridin-2-yl)piperazine-1-carbonyl]-3-fluorophenyl}-5-methylimidazolidine-2,4-dione, (R)-5-{4-[4-(5-cyclopropyl-3-methylpyridin-2-yl)piperazine-1-carbonyl]phenyl}-5-methylimidazolidine-2,4-dione, (R)-5-methyl-5-{4-[4-(3,5,6-trimethylpyridin-2-yl)piperazine-1-carbonyl]phenyl}imidazolidine-2,4-dione, (R)-5-{4-[4-(3,5-dimethylpyridin-2-yl)piperazine-1-carbonyl]phenyl}-5-isopropylimidazolidine-2,4-dione, 5-isopropyl-5-{2-methoxy-4-[4-(3,5,6-trimethylpyridin-2-yl)piperazine-1-carbonyl]phenyl}imidazolidine-2,4-dione, (R)-5-{4-[(S)-3-(3,5-dimethylpyridin-2-ylamino)pyrrolidine-1-carbonyl]phenyl}-5-isopropylimidazolidine-2,4-dione, (R)-5-{4-[(S)-3-(3,5-dimethylpyridin-2-ylamino)pyrrolidine-1-carbonyl]phenyl}-5-ethylimidazolidine-2,4-dione, (R)-5-{4-[4-(3,5-dimethylpyridin-2-yl)-2,2-dimethylpiperazine-1-carbonyl]phenyl}-5-isopropylimidazolidine-2,4-dione, (R)-5-{4-[(S)-4-(3,5-dimethylpyridin-2-yl)-3-methylpiperazine-1-carbonyl]phenyl}-5-isopropylimidazolidine-2,4-dione, 5-tert-butyl-5-{4-[4-(5-cyclopropyl-3-methylpyridin-2-yl)piperazine-1-carbonyl]phenyl}imidazolidine-2,4-dione, (R)-5-{4-[4-(3,5-dimethylpyridin-2-yl)piperazine-1-carbonyl]phenyl}-5-ethylimidazolidine-2,4-dione, (R)-5-methyl-5-{4-[4-(4-methylbenzoyl)piperidine-1-carbonyl]phenyl}imidazolidine-2,4-dione, (R)-5-methyl-5-[4-[4-(4-p-tolyloxypiperidine-1-carbonyl]phenyl}imidazolidine-2,4-dione, (R)-5-isopropyl-5-{4-[4-(5-methylpyridine-2-carbonyl)piperidine-1-carbonyl]phenyl]imidazolidine-2,4-dione, (R)-5-isopropyl-5-{4-[4-(6-methylbenzofuran-3-yl)piperidine-1-carbonyl]phenyl}imidazolidine-2,4-dione, (R)-5-{4-[4-(4,6-dimethylbenzofuran-3-yl)piperidine-1-carbonyl]phenyl}-5-methylimidazolidine-2,4-dione, (R)-5-isopropyl-5-{4-[4-(6-methylbenzoxazol-2-yl)piperidine-1-carbonyl]phenyl}imidazolidine-2,4-dione, (R)-5-{4-[4-(5,7-dimethylindazol-1-yl)piperidine-1-carbonyl]phenyl}-5-isopropylimidazolidine-2,4-dione, (R)-5-{4-[4-(4,6-dimethyl-1H-indazol-3-yl)piperidine-1-carbonyl]phenyl}-5-methyl-imidazolidine-2,4-dione, (R)-5-methyl-5-{4-[4-(1,4,6-trimethyl-1H-indazol-3-yl)piperidine-1-carbonyl]phenyl}imidazolidine-2,4-dione, (R)-5-{4-[4-(4-fluoro-6-methyl-1H-indazol-3-yl)piperidine-1-carbonyl]phenyl}-5-methylimidazolidine-2,4-dione, 5-{4-[4-(5-cyclopropyl-3-methylpyridin-2-yl)piperazine-1-carbonyl]phenyl}-5-(tetrahydropyran-4-yl)imidazolidine-2,4-dione, 5-{4-[4-(5-cyclopropyl-3-methylpyridin-2-yl)piperazine-1-carbonyl]phenyl}-5-isopropylimidazolidine-2,4-dione, or a pharmacologically acceptable salt of any of the foregoing compounds.

13. A pharmaceutical composition comprising the imide derivative according to claim 1, or a pharmacologically acceptable salt thereof, and a pharmaceutically acceptable additive.

14. An agent for suppressing MMP-9 production, comprising the imide derivative according to claim 1, or a pharmacologically acceptable salt thereof.

15. A method of treating an autoimmune disease or an inflammatory bowel disease, comprising administering the imide derivative according to claim 1, or a pharmacologically acceptable salt thereof, wherein the autoimmune disease is rheumatoid arthritis, multiple sclerosis, or systemic lupus erythematosus.

16. The method according to claim 15 wherein the inflammatory bowel disease is Crohn's disease or ulcerative colitis.

17. A method of treating osteoarthritis, comprising administering the imide derivative according to claim 1, or a pharmacologically acceptable salt thereof.

18. A method of treating an autoimmune disease or an inflammatory bowel disease, comprising administering the imide derivative according to claim 12, or a pharmacologically acceptable salt thereof, wherein the autoimmune disease is rheumatoid arthritis, multiple sclerosis, or systemic lupus erythematosus.

19. The method according to claim 18 wherein the inflammatory bowel disease is Crohn's disease or ulcerative colitis.

20. A method of treating osteoarthritis, comprising administering the imide derivative according to claim 12, or a pharmacologically acceptable salt thereof.

21. A pharmaceutical composition comprising the imide derivative according to claim 12, or a pharmacologically acceptable salt thereof, and a pharmaceutically acceptable additive.

* * * * *